US011919948B2

(12) United States Patent
Liang et al.

(10) Patent No.: US 11,919,948 B2

(45) Date of Patent: Mar. 5, 2024

(54) ISOFORM-SELECTIVE ANTI-TGFβ ANTIBODIES AND METHODS OF USE

(71) Applicant: Genentech, Inc., South San Francisco, CA (US)

(72) Inventors: Wei-Ching Liang, South San Francisco, CA (US); Joseph R. Arron, South San Francisco, CA (US); Daryle Depianto, South San Francisco, CA (US); Wendy Green Halpern, South San Francisco, CA (US); WeiYu Lin, South San Francisco, CA (US); Patrick J. Lupardus, South San Francisco, CA (US); Thirumalai Rajan Ramalingam, South San Francisco, CA (US); Dhaya Seshasayee, South San Francisco, CA (US); Tianhe Sun, South San Francisco, CA (US); Tulika Tyagi, South San Francisco, CA (US); Jia Wu, South San Francisco, CA (US); Yan Wu, South San Francisco, CA (US); Jian Ping Yin, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 20 days.

(21) Appl. No.: 17/205,663

(22) Filed: Mar. 18, 2021

(65) Prior Publication Data

US 2021/0301005 A1 Sep. 30, 2021

Related U.S. Application Data

(60) Provisional application No. 63/044,478, filed on Jun. 26, 2020, provisional application No. 62/991,806, filed on Mar. 19, 2020.

(51) Int. Cl.

| | |
|---|---|
| *C07K 16/22* | (2006.01) |
| *A61K 39/00* | (2006.01) |
| *A61K 39/395* | (2006.01) |
| *A61P 11/00* | (2006.01) |
| *C07K 16/46* | (2006.01) |

(52) U.S. Cl.

CPC .............. *C07K 16/22* (2013.01); *A61P 11/00* (2018.01); *C07K 16/464* (2013.01); *A61K 39/39533* (2013.01); *A61K 39/39566* (2013.01); *A61K 2039/505* (2013.01); *C07K 2317/24* (2013.01); *C07K 2317/31* (2013.01); *C07K 2317/41* (2013.01); *C07K 2317/565* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,747,035 A * | 5/1998 | Presta | ................ | C07K 16/2845 424/153.1 |
| 7,527,791 B2 | 5/2009 | Adams et al. | | |
| 8,012,482 B2 | 6/2011 | Adams et al. | | |
| 8,198,412 B2 | 6/2012 | Kojima et al. | | |
| 9,090,685 B2 | 7/2015 | Ledbetter et al. | | |
| 9,085,625 B2 | 12/2015 | Labrijn et al. | | |
| 10,723,793 B2 | 7/2020 | Van Snick et al. | | |
| 10,738,110 B2 * | 8/2020 | Agrawal | ............ | C07K 16/2869 |
| 2018/0148501 A1 | 5/2018 | VanSnick et al. | | |
| 2019/0092846 A1 | 3/2019 | Ibebunjo et al. | | |
| 2020/0079840 A1 | 12/2020 | Datta et al. | | |
| 2020/0392221 A1 | 12/2020 | Van Snick et al. | | |

FOREIGN PATENT DOCUMENTS

| | | | |
|---|---|---|---|
| WO | 92/00330 | A1 | 9/1992 |
| WO | 2014/132647 | A1 | 4/2014 |
| WO | 2016/201282 | A2 | 10/2016 |
| WO | WO 2021/188749 | * | 9/2021 |

OTHER PUBLICATIONS

"International Search Report and Written Opinion—PCT/US2021/022870":27 (dated Aug. 26, 2021).

Sun et al., "TGFβ2 and TGFβ3 isoforms drive fibrotic disease pathogenesis" Science Translational Medicine (including Supplementary Materials), 13:1-59 (Aug. 4, 2021).

Anderton, M., et al., "Induction of heart valve lesions by small-molecule ALK5 inhibitors" Toxicol Pathol 39(6):916-924 (Oct. 1, 2011).

Bahn, R.,, "Graves' Ophthalmopathy" N Engl J Med 362(8):726-738 (Feb. 25, 2010).

Bertoli-Avella, A., et al., "Mutations in a TGF-β ligand, TGFB3, cause syndromic aortic aneurysms and dissections" J Am Coll Cardiol 65(13):1324-1336 (Apr. 7, 2015).

Brioschi, M., et al., "Humanization and characterization of novel, best in class isoforrn specific anti-TGF β monoclonal antibodies" Abstract (P482, J Immuno Ther Cancer, 6:(Suppl 1)) 33rd Annual Meeting & Pre-Conference Programs of the Society for Imrnunotherapy of Cancer (SITC 2018), Washington, D.C.—USA, pp. 251 (Nov. 7-11, 2018).

Brioschi, M., et al., "Isoform-specific blockade of active TGFb1 with mAb 13A1 enhances the efficacy of PD-L1 checkpoint therapy in a EMT6 mouse tumor model" Abstract (P477; J Immuno Ther Cancer 7:Suppl 1) 34th Annual Meeting & Pre-Conference Programs of the Society for Immunotherapy of Cancer (SITC 2019), National Harbor, MD—USA, pp. 260 (Nov. 6-10, 2019).

(Continued)

*Primary Examiner* — Marianne P Allen

(74) *Attorney, Agent, or Firm* — HALEY GUILIANO LLP; Karen Mangasarian; Stacey W. Chung

(57) ABSTRACT

The invention provides isoform-selective anti-TGFβ antibodies and methods of using the same. In particular, isoform-selective anti-TGFβ2, anti-TGFβ3, and anti-TGFβ2/3 monoclonal antibodies are provided, e.g., for the treatment of fibrosis and other TGFβ-related disorders.

27 Claims, 49 Drawing Sheets

Specification includes a Sequence Listing.

(56) References Cited

OTHER PUBLICATIONS

Carthy, J., et al., "Wnt3a Induces Myofibroblast Differentiation by Upregulating TGF-β Signaling Through SMAD2 in a β-Catenin-Dependent Manner" PLOS ONE 6(5 Suppl 619809):1-10 (May 18, 2011).
Dasch, J.R., et al., "Monoclonal Antibodies Recognizing Transforming Growth Factor-β" J Immunol 142(5):1536-1541 (Mar. 1, 1989).
Del Re, E., et al., "In the absence of type III receptor, the transforming growth factor (TGF)-beta type II-B receptor requires the type I receptor to bind TGF-beta2" J Biol Chem 279(21):22765-22772 (May 21, 2004).
Denton, C., et al., "Recombinant human anti-transforming growth factor beta1 antibody therapy in systemic sclerosis: a multicenter, randomized, placebo-controlled phase I/II trial of CAT-192" Arthritis Rheum 56(1):323-333 (Jan. 1, 2007).
Derynck, R., et al., "Specificity, versatility, and control of TGF-β family signaling" Sci Signal 12(570):eaav5183 (1-25) (Feb. 26, 2019).
Du Bois, R., et al., "Strategies for treating idiopathic pulmonary fibrosis" Nat Rev Drug Discov 9(2):129-140 (Feb. 1, 2010).
Frazier, K., et al., "Inhibition of ALKS signaling induces physeal dysplasia in rats" Toxicol Pathol 35(2):284-295 (Feb. 1, 2007).
Friedlander, M.,, "Fibrosis and diseases of the eye" J Clin Invest 117(3):576-586 (Mar. 1, 2007).
Gabrielli, A., et al., "Scleroderma" N Engl J Med 360(19):1989-2003 (May 7, 2009).
Gauglitz, G., et al., "Hypertrophie scarring and keloids: pathomechanisms and current and emerging treatment strategies" Mol Med 17(1-2):113-125 (Jan. 31, 2011).
Greene, R., et al., "Intracellular dynamics of Smad-mediated TGFβ signaling" J Cell Physiol 197(2):261-271 (Nov. 1, 2003).
Gu, L., et al., "Effect of TGF-beta/Smad signaling pathway on lung myofibroblast differentiation" Acta Pharmacol Sin 28(3):382-391 (Mar. 1, 2007).
Hinck, A.P., et al., "Structural Biology and Evolution of the TGF-β Family" Cold Spring Harb Perspect Biol 8(12 Suppl a022103):1-49 (Dec. 1, 2016).
Hinz, B., "Formation and function of the myofibroblast duting tissue repair" J Invest Dermatol 127(3):526-537 (Mar. 1, 2007).
Khanna, D., et al., "Safety and efficacy of subcutaneous tocilizumab in adults with systemic sclerosis (faSScinate): a phase 2, randomised, controlled trial" Lancet 387(10038):2630-2640 (Jun. 25, 2016).
Kullberg, M., et al., "Helicobacter hepaticus Triggers Colitis in Specific-Pathogen-Free Interleukin-10 (IL-10)-Deficient Mice through an IL-12- and Gamma Interferon-Dependent Mechanism" Infect Immun 66(11):5157-5166 (Nov. 1, 1998).
Kullberg, M., et al., "Helicobacter hepaticus-Induced Colitis in Interleukin-10-Deficient Mice: Cytokine Requirements for the Induction and Maintenance of Intestinal Inflammation" Infect Immun 69(7):4232-4241 (Jul. 1, 2001).
Kullberg, M., et al., "IL-23 plays a key role in Helicobacter hepaticus-induced T cell-dependent colitis" J Exp Med 203(11):2485-2494 (Oct. 30, 2006).
Kuriyan, A., et al., "The myofibroblast in pulmonary fibrosis" Curr Opin Ophthalmol 19(6):499-506 (Nov. 1, 2008).
Lacouture, M., et al., "Cutaneous keratoacanthomas/squamous cell carcinomas associated with neutralization of transforming growth factor β by the monoclonal antibody fresolimumab (GC1008)" Cancer Immunol Immunother 64(4):437-446 (Apr. 1, 2015).
Lafyatis, R., "Transforming growth factor β—at the centre of systemic sclerosis" Nat Rev Rheumatol 10(12):706-719 (Dec. 1, 2014).
Lebrin, F., et al., "Endoglin promotes endothelial cell proliferation and TGF-β/ALK1 signal transduction" Embo J 23(20):4018-4028 (Oct. 13, 2004).
Lehmann, G., et al., "Immune mechanisms in thyroid eye disease" Thyroid 18(9):959-965 (Sep. 1, 2008).
Li, M.O., et al., "Transforming Growth Factor-β Controls Development, Homeostasis, and Tolerance of T Cells by Regulatory T Cell-Dependent and -Independent Mechanisms" Immunity 25(3):455-471 (Sep. 1, 2006).
Lindsay, M., et al., "Loss-of-function mutations in TGFB2 cause a syndromic presentation of thoracic aortic aneurysm" Nat Genet 44(8):922-927 (Jul. 8, 2012).
Lo, M., et al., "Effector-attenuating Substitutions That Maintain Antibody Stability and Reduce Toxicity in Mice" J Biol Chem 292(9):3900-3908 (Mar. 3, 2017).
Lonning, S., et al., "Antibody targeting of TGF-β in cancer patients" Curr Pharm Biotechnol 12(12):2176-2189 (Dec. 1, 2011).
Marie, J.C., et al., "Cellular Mechanisms of Fatal Early-Onset Autoimmunity in Mice with the T Cell-Specific Targeting of Transforming Growth Factor-β Receptor" Immunity 25(3):441-454 (Sep. 1, 2006).
Masi, A, et al., "Preliminary criteria for the classification of systemic sclerosis (scleroderma)" Arthritis Rheum 23(5):581-590 (May 1, 1980).
Mitra, M., et al., "A Potent Pan-TGFβ Neutralizing Monoclonal Antibody Elicits Cardiovascular Toxicity in Mice and Cynomolgus Monkeys" Toxicol Sci 175(1):24-34 (May 1, 2020).
Moylan, C., et al., "Hepatic gene expression profiles differentiate presymptomatic patients with mild versus severe nonalcoholic fatty liver disease" Hepatology 59(2):471-482 (Feb. 1, 2014).
Murphy, S., et al., "Relationship Between Methylome and Transcriptome in Patients With Nonalcoholic Fatty Liver Disease" Gastroenterology 145(5):1076-1087 (Nov. 1, 2013).
Niessen, F.B., et al., "On the nature of hypertrophic scars and keloids: a review" Plast Reconstr Surg 104(5):1435-1458 (Oct. 1, 1999).
Noble, P., et al., "Pulmonary fibrosis: patterns and perpetrators" J Clin Invest 122(8):2756-2762 (Aug. 1, 2012).
Phan, S.,, "The myofibroblast in pulmonary fibrosis" Chest 122(6):286S-289S (Dec. 1, 2002).
Radaev, S., et al., "Ternary complex of transforming growth factor-beta1 reveals isoform-specific ligand recognition and receptor recruitment in the superfamily" J Biol Chem 285(19):14806-14814 (May 7 , 2010).
Raghu, G. et al., "An official ATS/ERS/JRS/ALAT statement: Idiopathic pulmonary fibrosis: Evidence-based guidelines for diagnosis and management" Am J Respir Crit Care Med 183(6):788-824 (Mar. 15, 2011).
Raghu, G., et al., "Incidence and Prevalence of Idiopathic Pulmonary Fibrosis" Am J Respir Crit Care Med 174(7):810-816 (Oct. 1, 2006).
Rice, L., et al, "Fresolimumab treatment decreases biomarkers and improves clinical symptoms in systemic sclerosis patients" J Clin Invest 125(7):2795-2807 (Jul. 1, 2015).
Ryu, J., et al., "Idiopathic Pulmonary Fibrosis: Current Concepts" Mayo Clin Proc 73(11):1085-1101 (Nov. 1, 1998).
Schepers, D., et al., "A mutation update on the LDS-associated genes TGFB2/3 and SMAD2/3" Hum Mutat 39(5):621-634 (May 1, 2018).
Schlothauer, T., et al., "Novel human IgG1 and IgG4 Fc-engineered antibodies with completely abolished immune effector functions" Protein Eng Des Sel 29(10):457-466 (Oct. 1, 2016).
Shi, M, et al., "Latent TGF-B structure and activation" Nature 474(7351):343-349 (Jun. 16, 2011).
Usuki, J ., et al., "Sequential analysis of myofibroblast differentiation and transforming growth -factor-β/Smad pathway activation in murine pulmonary fibrosis" J Nippon Med Sch 79(1):46-59 (2012).
Weiss, A., et al., "The TGFbeta superfamily signaling pathway" Wiley Interdiscip Rev Dev Biol 2(1):47-63 (Jan. 31, 2013).
Zhao, X., et al., "Newly proposed fibrosis staging criterion for assessing carbon tetrachloride- and albumin complex-induced liver fibrosis in rodents" Pathol Int 58(9):580-588 (Sep. 1, 2008).

* cited by examiner intercorrelations with skin TGFβ gene signature

| variable | Spearman ρ | p-value |
| --- | --- | --- |
| TGFβ1 expression | 0.03 | 0.8 |
| TGFβ2 expression | -0.1 | 0.4 |
| TGFβ3 expression | 0.92 | $<10^{-4}$ |
| POSTN expression | 0.76 | $<10^{-4}$ |
| COMP expression | 0.89 | $<10^{-4}$ |
| serum periostin | 0.55 | $<10^{-4}$ |
| serum COMP | 0.39 | 0.002 | intercorrelations with baseline MRSS

| | | |
| --- | --- | --- |
| serum periostin | 0.76 | $<10^{-4}$ |
| serum COMP | 0.70 | $<10^{-4}$ |

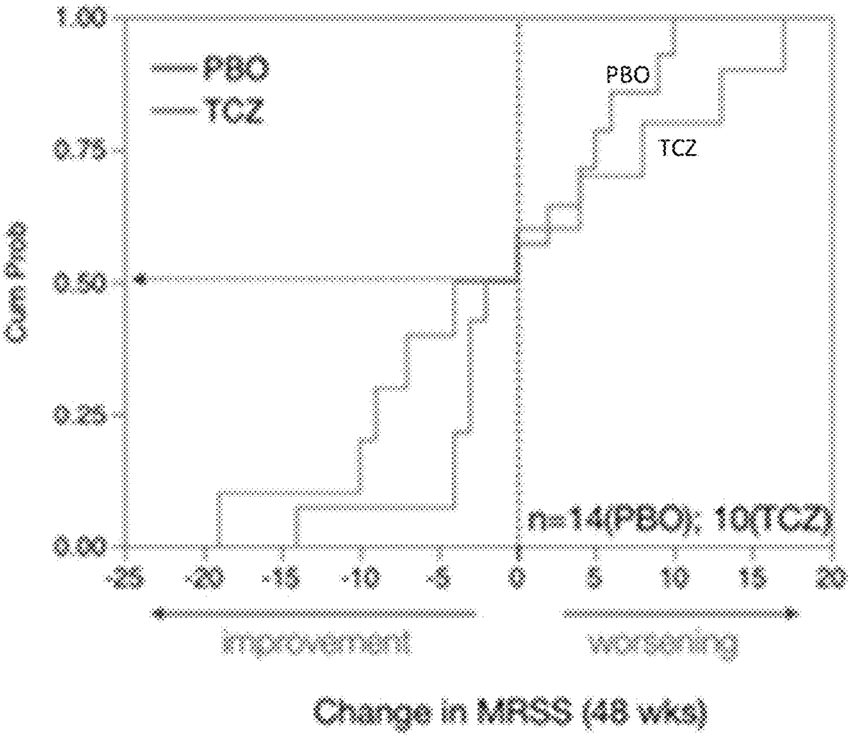
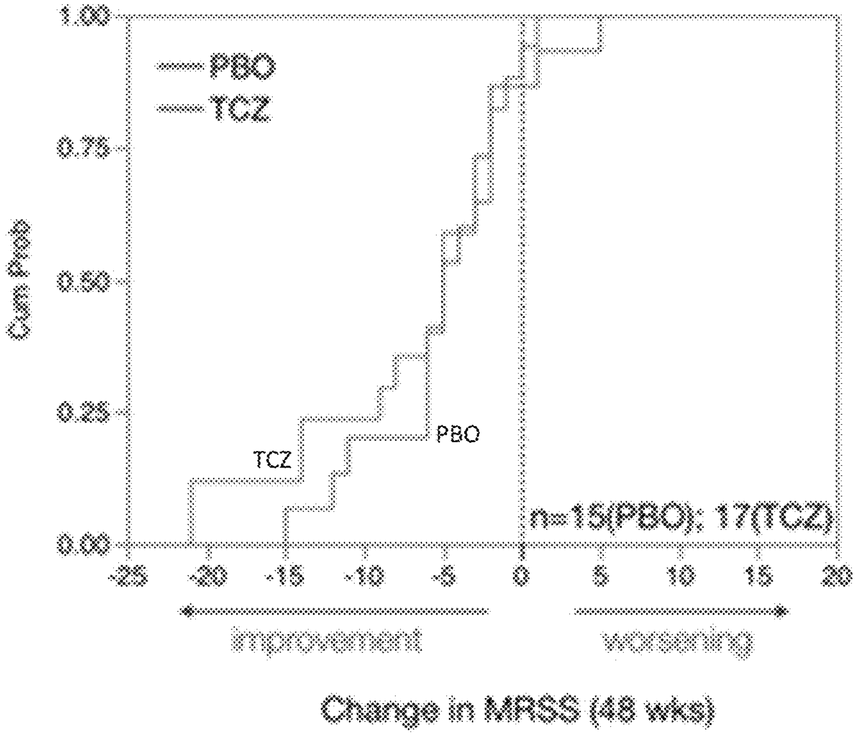
FIG. 7

| 2A10 variants | Human Framework | Framework mutation | BIAcore (pM) | | | HEKBlue TGFβ blocking IC50 (nM) | | | SEC |
|---|---|---|---|---|---|---|---|---|---|
| | | | TGFβ1 | TGFβ2 | TGFβ3 | TGFβ1 | TGFβ2 | TGFβ3 | Monomer (%) |
| Rat 2A10 | - | - | - | 62.8 | 1.2 | >200 | 70 | 0.01 | - |
| h2A10.v1 | $K_{LO-39}H_{3-49}$ | - | - | - | 4.4 | - | - | - | 88.97 |
| h2A10.v1.1 | $K_{LO-39}H_{3-49}$ | LC: L4M | No expression | | | - | - | - | - |
| h2A10.v1.2 | $K_{LO-39}H_{3-49}$ | LC: H38Q | - | - | 2.8 | - | - | - | 97.7 |
| h2A10.v1.3 | $K_{LO-39}H_{3-49}$ | LC: Q43A | - | - | 3.3 | - | - | - | 92.0 |
| h2A10.v1.4 | $K_{LO-39}H_{3-49}$ | LC: I58V | - | - | 3.0 | - | - | - | 90.1 |
| h2A10.v1.5 | $K_{LO-39}H_{3-49}$ | HC: L47W | - | - | 493 | - | - | - | 98.6 |
| h2A10.v1.6 | $K_{LO-39}H_{3-49}$ | HC: A49G | - | - | 5.3 | - | - | - | 94.0 |
| h2A10.v1.7 | $K_{LO-39}H_{3-49}$ | HC: V78A | - | - | 3.9 | - | - | - | 96.5 |
| h2A10.v1.N54S | $K_{LO-39}H_{3-49}$ | - | No expression | | | - | - | - | - |
| h2A10.v1.N54Q | $K_{LO-39}H_{3-49}$ | - | No expression | | | - | - | - | - |
| h2A10.v1.T56A | $K_{LO-39}H_{3-49}$ | - | - | - | 2.3 | - | - | - | 72.3 |
| h2A10.v2 | $K_{LO-39}H_{3-23}$ | - | - | 314 | 1.3 | >200 | >200 | 0.01 | 99.6 |
| h2A10.v2.1 | $K_{LO-39}H_{3-23}$ | LC: L4M | - | 238 | 3.1 | >200 | >200 | 0.01 | 99.4 |
| h2A10.v2.2 | $K_{LO-39}H_{3-23}$ | LC: H38Q | - | 124 | 1.2 | >200 | >200 | 0.01 | 99.5 |
| h2A10.v2.3 | $K_{LO-39}H_{3-23}$ | LC: Q43A | - | 242 | 1.5 | >200 | >200 | 0.01 | 99.5 |
| h2A10.v2.4 | $K_{LO-39}H_{3-23}$ | LC: I58V | - | 190 | 2.1 | >200 | >200 | 0.01 | 99.5 |
| h2A10.v2.5 | $K_{LO-39}H_{3-23}$ | HC: L47W | - | 2820 | 500 | >200 | >200 | 27.4 | 99.6 |
| h2A10.v2.6 | $K_{LO-39}H_{3-23}$ | HC: A49S | - | 249 | 1.5 | >200 | >200 | 0.01 | 99.8 |
| h2A10.v2.7 | $K_{LO-39}H_{3-23}$ | HC: D73N | - | 921 | 1.2 | >200 | >200 | 0.12 | 99.5 |
| h2A10.v2.8 | $K_{LO-39}H_{3-23}$ | HC: S76N | - | 365 | 1.2 | >200 | >200 | 0.01 | 99.6 |
| h2A10.v2.9 | $K_{LO-39}H_{3-23}$ | HC: V78L | - | 768 | 0.7 | >200 | >200 | 0.01 | 99.6 |
| h2A10.v2.N54S | $K_{LO-39}H_{3-23}$ | - | - | 425 | 2.4 | >200 | >200 | 0.01 | 99.5 |
| h2A10.v2.N54Q | $K_{LO-39}H_{3-23}$ | - | - | 378 | 2.5 | >200 | >200 | 0.01 | 99.6 |
| h2A10.v2.T56A | $K_{LO-39}H_{3-23}$ | - | - | 347 | 1.0 | >200 | >200 | 0.01 | 99.6 |

Detrimental mutation
(>2 fold drop compared to h2A10.v1)
- L47W (HC FW2)

✓ No expression for some variants
✓ Potential aggregation (6-28%)

Detrimental mutation
(>2 fold drop compared to h2A10.v2)
- L4M (LC FW1)
- L47W (HC FW2)
- D73N (HC FW3)

✓ No aggregation observed

Final humanized polished versions based on h2A10.v2
- h2A10.v3: Keep L4, L47, D73 + CDRH2:N54S (NYT -> SYT)
- h2A10.v4: Keep L4, L47, D73 + CDRH2:T56A (NYT -> NYA)

FIG. 11

\* Vernier zone
Light chain variable region

| Kabat number | | | | | | | | | | | | | | | | | | | | | | | | |
|---|---|---|---|---|---|---|---|---|---|---|---|---|---|---|---|---|---|---|---|---|---|---|---|---|
| Rat 2A10 | D I V L T Q S P A . L A V S L G Q R A T I S C R A S Q S V S I S R F N L M H W Y Q H |
| h2A10.v1 | D I Q L T Q S P S S L S A S V G D R V T I T C R A S Q S V S I S R F N L M H W Y Q H |
| h2A10.v2 | D I Q L T Q S P S S L S A S V G D R V T I T C R A S Q S V S I S R F N L M H W Y Q H |
| h2A10.v3 | D I Q L T Q S P S S L S A S V G D R V T I T C R A S Q S V S I S R F N L M H W Y Q Q |
| h2A10.v4 | D I Q L T Q S P S S L S A S V G D R V T I T C R A S Q S V S I S R F N L M H W Y Q Q |

| Rat 2A10 | K P G Q Q P K L L I Y R A S N L A S G I P A R F S G S G S G T D F T L T I N P V Q A |
| h2A10.v1 | K P G K Q P K L L I Y R A S N L A S G I P S R F S G S G S G T D F T L T I S S L Q P |
| h2A10.v2 | K P G K Q P K L L I Y R A S N L A S G I P S R F S G S G S G T D F T L T I S S L Q P |
| h2A10.v3 | K P G K A P K L L I Y R A S N L A S G V P S R F S G S G S G T D F T L T I S S L Q P |
| h2A10.v4 | K P G K A P K L L I Y R A S N L A S G V P S R F S G S G S G T D F T L T I S S L Q P |

| Rat 2A10 | D D L A T Y Y C Q H S R E S P W T F G G G T K L E I K |
| h2A10.v1 | E D F A T Y Y C Q H S R E S P W T F G G G T K V E I K |
| h2A10.v2 | E D F A T Y Y C Q H S R E S P W T F G G G T K V E I K |
| h2A10.v3 | E D F A T Y Y C Q H S R E S P W T F G G G T K V E I K |
| h2A10.v4 | E D F A T Y Y C Q H S R E S P W T F G G G T K V E I K |

Heavy chain variable region

| Rat 2A10 | E V Q L V E S G G G L V Q P K G S L K L S C A A S G F D F N S Y G M S W V R Q A P G |
| h2A10.v1 | E V Q L V E S G G G L V Q P G P S L R L S C T A S G F D F N S Y G M S W V R Q A P G |
| h2A10.v2 | E V Q L L E S G G G L V Q P G G S L R L S C A A S G F D F N S Y G M S W V R Q A P G |
| h2A10.v3 | E V Q L L E S G G G L V Q P G G S L R L S C A A S G F D F N S Y G M S W V R Q A P G |
| h2A10.v4 | E V Q L L E S G G G L V Q P G G S L R L S C A A S G F D F N S Y G M S W V R Q A P G |

| Rat 2A10 | K G L D L V A D I V S K T Y N Y T T Y Y S D S V K D R F T I S R D D S Q S M V Y L Q |
| h2A10.v1 | K G L E L V A D I V S K T Y N Y T T Y Y S D S V K D R F T I S R D D S K S I V Y L Q |
| h2A10.v2 | K G L E L V A D I V S K T Y S Y T T Y Y S D S V K D R F T I S R D D S K S T V Y L Q |
| h2A10.v3 | K G L E L V S D I V S K T Y S Y T T Y Y S D S V K D R F T I S R D D S K N T L Y L Q |
| h2A10.v4 | K G L E L V S D I V S K T Y N Y A T Y Y S D S V K D R F T I S R D D S K N T L Y L Q |

| Rat 2A10 | M D N L K T E D T A L Y Y C T V A P G G S F D Y W G Q G V M V T V S S |
| h2A10.v1 | M N S L K T E D T A V Y Y C T V A P G G S F D Y W G Q G T L V T V S S |
| h2A10.v2 | M N S L R A E D T A V Y Y C T V A P G G S F D Y W G Q G T L V T V S S |
| h2A10.v3 | M N S L R A E D T A V Y Y C T V A P G G S F D Y W G Q G T L V T V S S |
| h2A10.v4 | M N S L R A E D T A V Y Y C T V A P G G S F D Y W G Q G T L V T V S S |

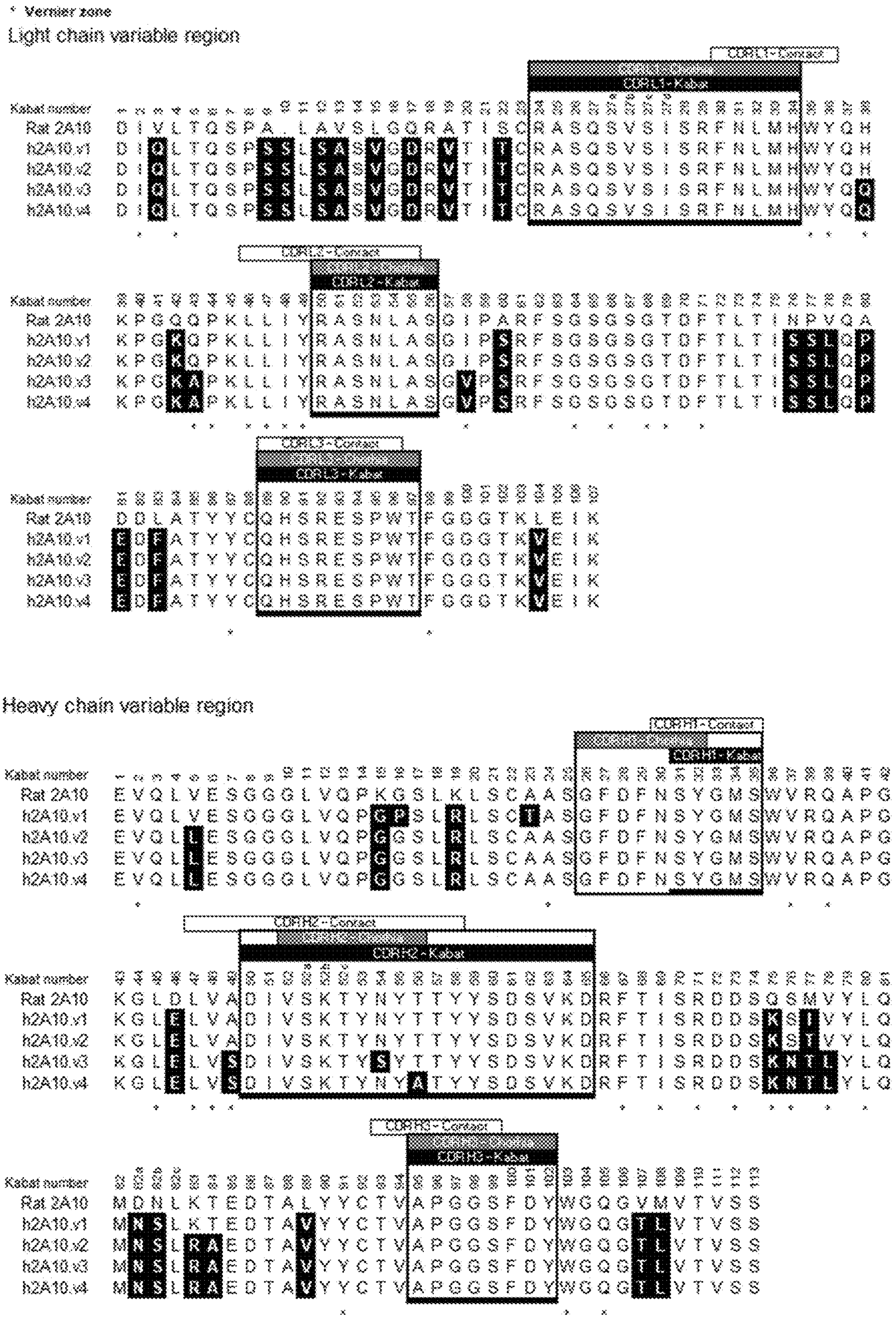

FIG. 12

Heavy chain variable region

[Sequence alignment of heavy chain variable region showing Rat 2A10 and humanized variants h2A10.v2 through h2A10.v2.9, with CDR H1, CDR H2, and CDR H3 regions (Kabat and Contact definitions) highlighted]

\* Vernier zone
Light chain variable region

```
Kabat number              1                                                    20                      30
Rat 2A10       D I V L T Q S P A  L A V S L G Q R A T I S C R A S Q S V S I S R F N L M H W Y Q H
h2A10.v2       D I Q L T Q S P S S L S A S V G D R V T I T C R A S Q S V S I S R F N L M H W Y Q H
h2A10.v2.N54S  D I Q L T Q S P S S L S A S V G D R V T I T C R A S Q S V S I S R F N L M H W Y Q H
h2A10.v2.N54Q  D I Q L T Q S P S S L S A S V G D R V T I T C R A S Q S V S I S R F N L M H W Y Q H
h2A10.v2.T56A  D I Q L T Q S P S S L S A S V G D R V T I T C R A S Q S V S I S R F N L M H W Y Q H
```

```
Kabat number
Rat 2A10       K P G Q Q P K L L I Y R A S N L A S G I P A R F S G S G S G T D F T L T I N P V Q A
h2A10.v2       K P G K Q P K L L I Y R A S N L A S G I P S R F S G S G S G T D F T L T I S S L Q P
h2A10.v2.N54S  K P G K Q P K L L I Y R A S N L A S G I P S R F S G S G S G T D F T L T I S S L Q P
h2A10.v2.N54Q  K P G K Q P K L L I Y R A S N L A S G I P S R F S G S G S G T D F T L T I S S L Q P
h2A10.v2.T56A  K P G K Q P K L L I Y R A S N L A S G I P S R F S G S G S G T D F T L T I S S L Q P
```

```
Kabat number
Rat 2A10       D D L A T Y Y C Q H S R E S P W T F G G G T K L E I K
h2A10.v2       E D F A T Y Y C Q H S R E S P W T F G G G T K V E I K
h2A10.v2.N54S  E D F A T Y Y C Q H S R E S P W T F G G G T K V E I K
h2A10.v2.N54Q  E D F A T Y Y C Q H S R E S P W T F G G G T K V E I K
h2A10.v2.T56A  E D F A T Y Y C Q H S R E S P W T F G G G T K V E I K
```

Heavy chain variable region

```
Kabat number
Rat 2A10       E V Q L V E S G G G L V Q P K G S L K L S C A A S G F D F N S Y G M S W V R Q A P G
h2A10.v2       E V Q L L E S G G G L V Q P G G S L R L S C A A S G F D F N S Y G M S W V R Q A P G
h2A10.v2.N54S  E V Q L L E S G G G L V Q P G G S L R L S C A A S G F D F N S Y G M S W V R Q A P G
h2A10.v2.N54Q  E V Q L L E S G G G L V Q P G G S L R L S C A A S G F D F N S Y G M S W V R Q A P G
h2A10.v2.T56A  E V Q L L E S G G G L V Q P G G S L R L S C A A S G F D F N S Y G M S W V R Q A P G
```

```
Kabat number
Rat 2A10       K G L D L V A D I V S K T Y N Y T T Y Y S D S V K D R F T I S R D D S Q S M V Y L Q
h2A10.v2       K G L E L V A D I V S K T Y N Y T T Y Y S D S V K D R F T I S R D D S K S T V Y L Q
h2A10.v2.N54S  K G L E L V A D I V S K T Y S Y T T Y Y S D S V K D R F T I S R D D S K S T V Y L Q
h2A10.v2.N54Q  K G L E L V A D I V S K T Y Q Y T T Y Y S D S V K D R F T I S R D D S K S T V Y L Q
h2A10.v2.T56A  K G L E L V A D I V S K T Y N Y A T Y Y S D S V K D R F T I S R D D S K S T V Y L Q
```

```
Kabat number
Rat 2A10       M D N L K T E D T A L Y Y C T V A P G G S F D Y W G Q G V M V T V S S
h2A10.v2       M N S L R A E D T A V Y Y C T V A P G G S F D Y W G Q G T L V T V S S
h2A10.v2.N54S  M N S L R A E D T A V Y Y C T V A P G G S F D Y W G Q G T L V T V S S
h2A10.v2.N54Q  M N S L R A E D T A V Y Y C T V A P G G S F D Y W G Q G T L V T V S S
h2A10.v2.T56A  M N S L R A E D T A V Y Y C T V A P G G S F D Y W G Q G T L V T V S S
```

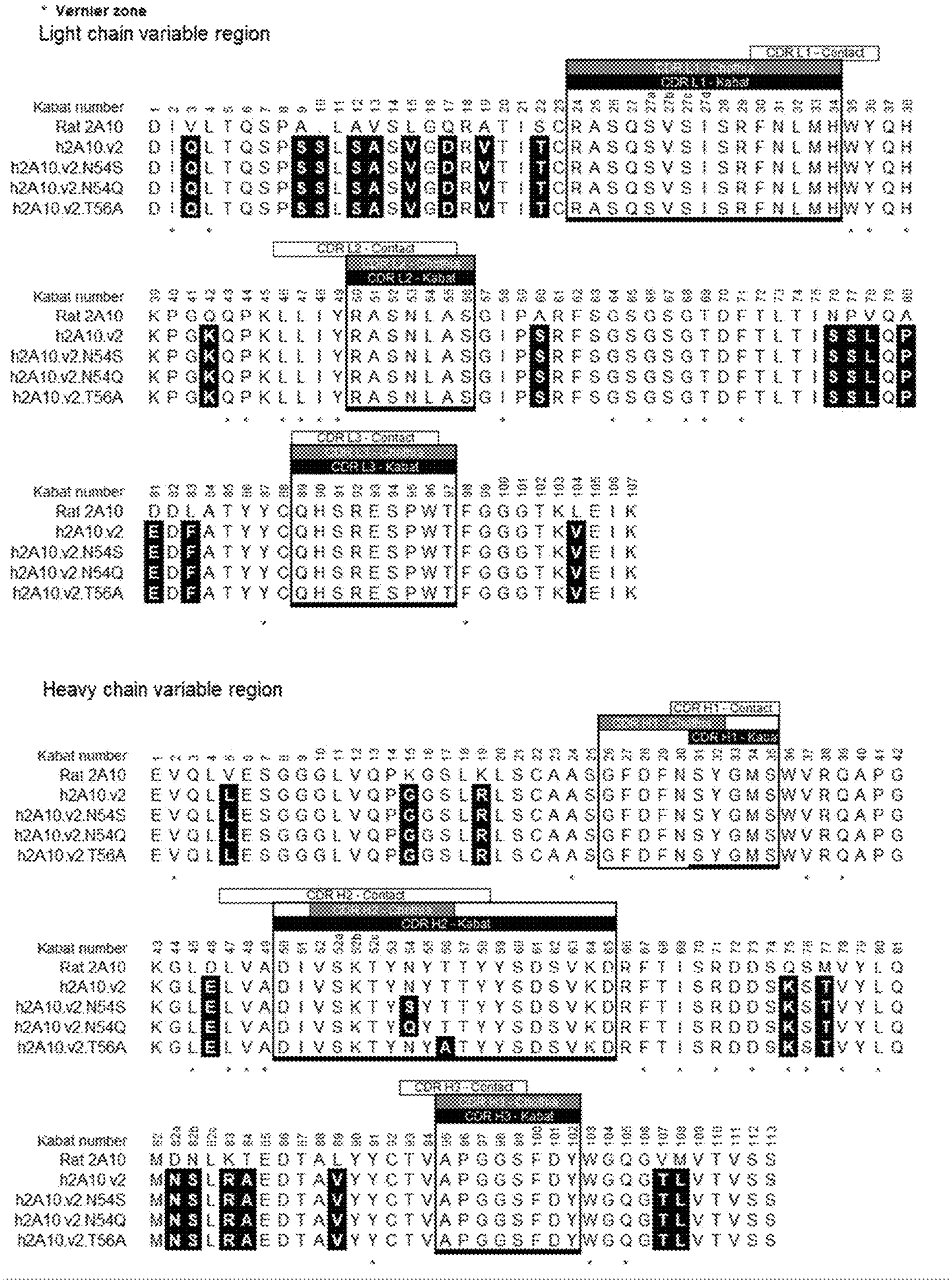

FIG. 15

\* Vernier zone
Light chain variable region

```
Kabat number     1 2 3 4 5 6 7 8 9 10 11 12 13 14 15 16 17 18 19 20 21 22 23 24 25 26 27 28 29 30 31 32 33 34 35 36 37 38
Rat 2A10         D I V L T Q S P A . L A V S L G Q R A T I S C R A S Q S V S I S R F N L M H W Y Q H
h2A10.v4         D I Q L T Q S P S S L S A S V G D R V T I T C R A S Q S V S I S R F N L M H W Y Q Q
```
CDRL1-Kabat / CDRL1-Contact

```
Kabat number     39 40 41 42 43 44 45 46 47 48 49 50 51 52 53 54 55 56 57 58 59 60 61 62 63 64 65 66 67 68 69 70 71 72 73 74 75 76 77 78 79 80
Rat 2A10         K P G Q Q P K L L I Y R A S N L A S G I P A R F S G S G S G T D F T L T I N P V Q A
h2A10.v4         K P G K A P K L L I Y R A S N L A S G V P S R F S G S G S G T D F T L T I S S L Q P
```
CDRL2-Kabat / CDRL2-Contact

```
Kabat number     81 82 83 84 85 86 87 88 89 90 91 92 93 94 95 96 97 98 99 100 101 102 103 104 105 106 107
Rat 2A10         D D L A T Y Y C Q H S R E S P W T F G G G T K L E I K
h2A10.v4         E D F A T Y Y C Q H S R E S P W T F G G G T K V E I K
```
CDRL3-Kabat / CDRL3-Contact Heavy chain variable region

```
Kabat number     1 2 3 4 5 6 7 8 9 10 11 12 13 14 15 16 17 18 19 20 21 22 23 24 25 26 27 28 29 30 31 32 33 34 35 36 37 38
Rat 2A10         E V Q L V E S G G G L V Q P K G S L K L S C A A S G F D F N S Y G M S W V R Q A P G
h2A10.v4         E V Q L L E S G G G L V Q P G G S L R L S C A A S G F D F N S Y G M S W V R Q A P G
```
CDRH1-Kabat / CDRH1-Contact

```
Kabat number     39 40 41 42 43 44 45 46 47 48 49 50 51 52 53 54 55 56 57 58 59 60 61 62 63 64 65 66 67 68 69 70 71 72 73 74 75 76 77 78 79 80 81 82
Rat 2A10         K G L D L V A D I V S K T Y N Y T T Y Y S D S V K D R F T I S R D D S Q S M V Y L Q
h2A10.v4         K G L E L V S D I V S K T Y N Y A T Y Y S D S V K D R F T I S R D D S K N T L Y L Q
```
CDRH2-Kabat / CDRH2-Contact

```
Kabat number     83 84 85 86 87 88 89 90 91 92 93 94 95 96 97 98 99 100 101 102 103 104 105 106 107 108 109 110 111 112 113
Rat 2A10         M D N L K T E D T A L Y Y C T V A P G G S F D Y W G Q G V M V T V S S
h2A10.v4         M N S L R A E D T A V Y Y C T V A P G G S F D Y W G Q G T L V T V S S
```
CDRH3-Kabat / CDRH3-Contact

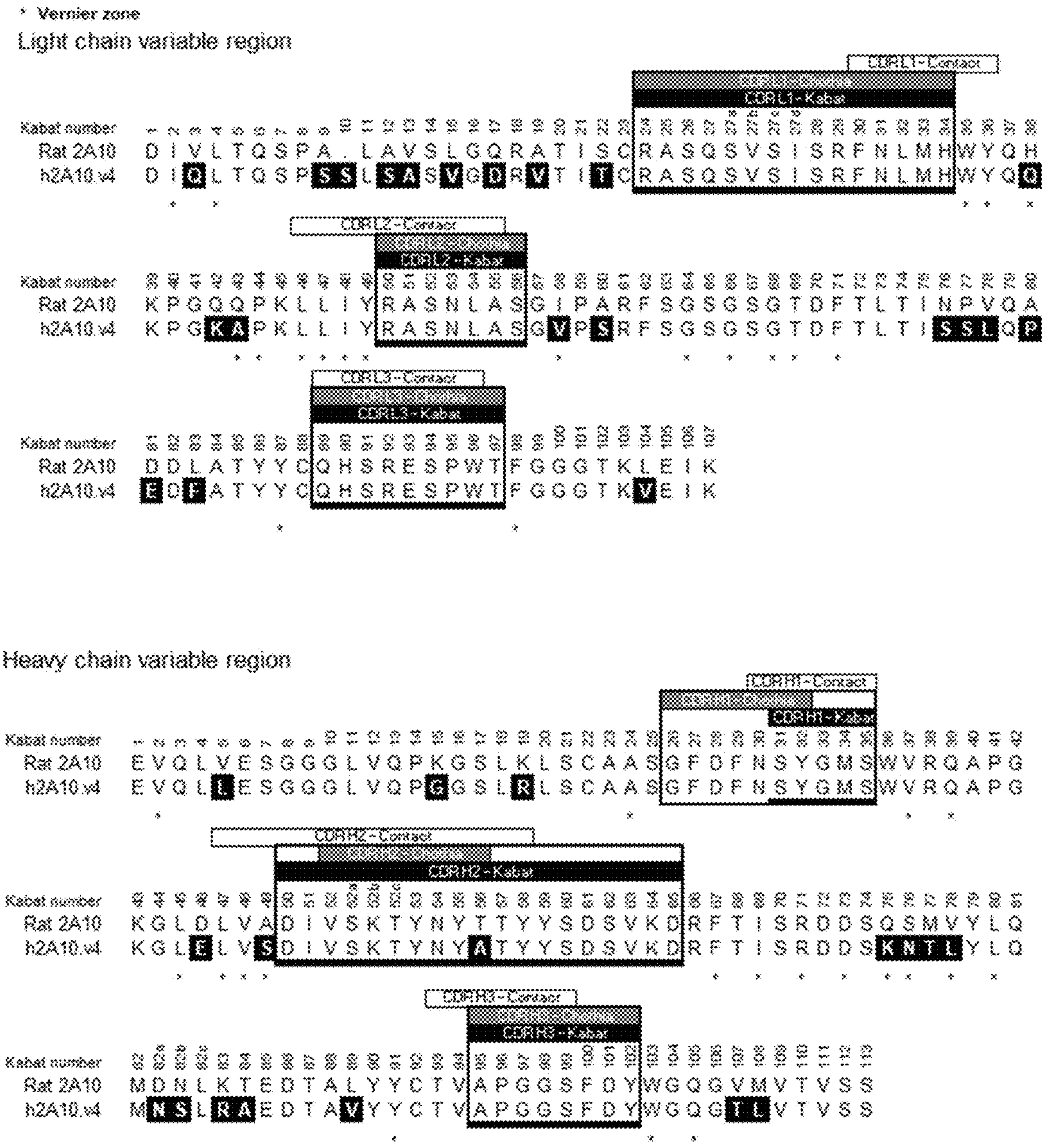

FIG. 16

Heavy chain variable region

| Kabat number | | | | |
|---|---|---|---|---|
| Rbt 4A11  | QSLEESGGRLVTPGTPLTLTCTVSGFSLSSYTVNWVRQAPG |
| h4A11.v1  | EQLVESGGGLVQPGGSLRLSCAVSGFSLSSYTVNWVRQAPG |
| h4A11.v2  | EQLVESGGGLVQPGGSLRLSCAVSGFSLSSYTVNWVRQAPG |
| h4A11.v3  | EQLQESGPGLVKPSETLSLTCTVTGFSLSSYTVNWVRQPAG |
| h4A11.v4  | EQLQESGPGLVKPSETLSLTCTVTGFSLSSYTVNWVRQPAG |
| h4A11.v5  | EQLVESGGGLVQPGGSLRLSCAVSGFSLSSYTVNWVRQAPG |
| h4A11.v6  | EQLVESGGGLVQPGGSLRLSCAVSGFSLSSYTVNWVRQAPG |
| h4A11.v7  | EQLQESGPGLVKPSETLSLTCTVTGFSLSSYTVNWVRQPAG |
| h4A11.v8  | EQLQESGPGLVKPSETLSLTCTVTGFSLSSYTVNWVRQPAG |

| Kabat number | | | | |
|---|---|---|---|---|
| Rbt 4A11  | KGLEWIGYISYGGSAYYASWANGRFTISKTSA..TVDLKITS |
| h4A11.v1  | KGLEWIGYISYGGSAYYASWANGRFTISKDSAKNSVYLQMNS |
| h4A11.v2  | KGLEWIGYISYGGSAYYASWANGRFTISKDSAKNSVYLQMNS |
| h4A11.v3  | KGLEWIGYISYGGSAYYASWANGRFTISKDSSKNQVSLKLSS |
| h4A11.v4  | KGLEWIGYISYGGSAYYASWANGRFTISKDSSKNQVSLKLSS |
| h4A11.v5  | KGLEWIGYISYGGSAYYASWANGRFTISKDSAKNSVYLQMNS |
| h4A11.v6  | KGLEWIGYISYGGSAYYASWANGRFTISKDSAKNSVYLQMNS |
| h4A11.v7  | KGLEWIGYISYGGSAYYASWANGRFTISKDSSKNQVSLKLSS |
| h4A11.v8  | KGLEWIGYISYGGSAYYASWANGRFTISKDSSKNQVSLKLSS |

| Kabat number | | | | |
|---|---|---|---|---|
| Rbt 4A11  | PTTEDTATYFCARHMQVGGAPTGSMAAFDPWGPGTLVTVSS |
| h4A11.v1  | LRAEDTAVYFCARHMQVGGAPTGSMAAFDPWGPGTLVTVSS |
| h4A11.v2  | LRAEDTAVYFCARHMQVGGAPTGSMAAFDPWGPGTLVTVSS |
| h4A11.v3  | VTAADTAVYFCARHMQVGGAPTGSMAAFDPWGPGTLVTVSS |
| h4A11.v4  | VTAADTAVYFCARHMQVGGAPTGSMAAFDPWGPGTLVTVSS |
| h4A11.v5  | LRAEDTAVYFCARHMQVGGAPTGSMAAFDPWGPGTLVTVSS |
| h4A11.v6  | LRAEDTAVYFCARHMQVGGAPTGSMAAFDPWGPGTLVTVSS |
| h4A11.v7  | VTAADTAVYFCARHMQVGGAPTGSMAAFDPWGPGTLVTVSS |
| h4A11.v8  | VTAADTAVYFCARHMQVGGAPTGSMAAFDPWGPGTLVTVSS |

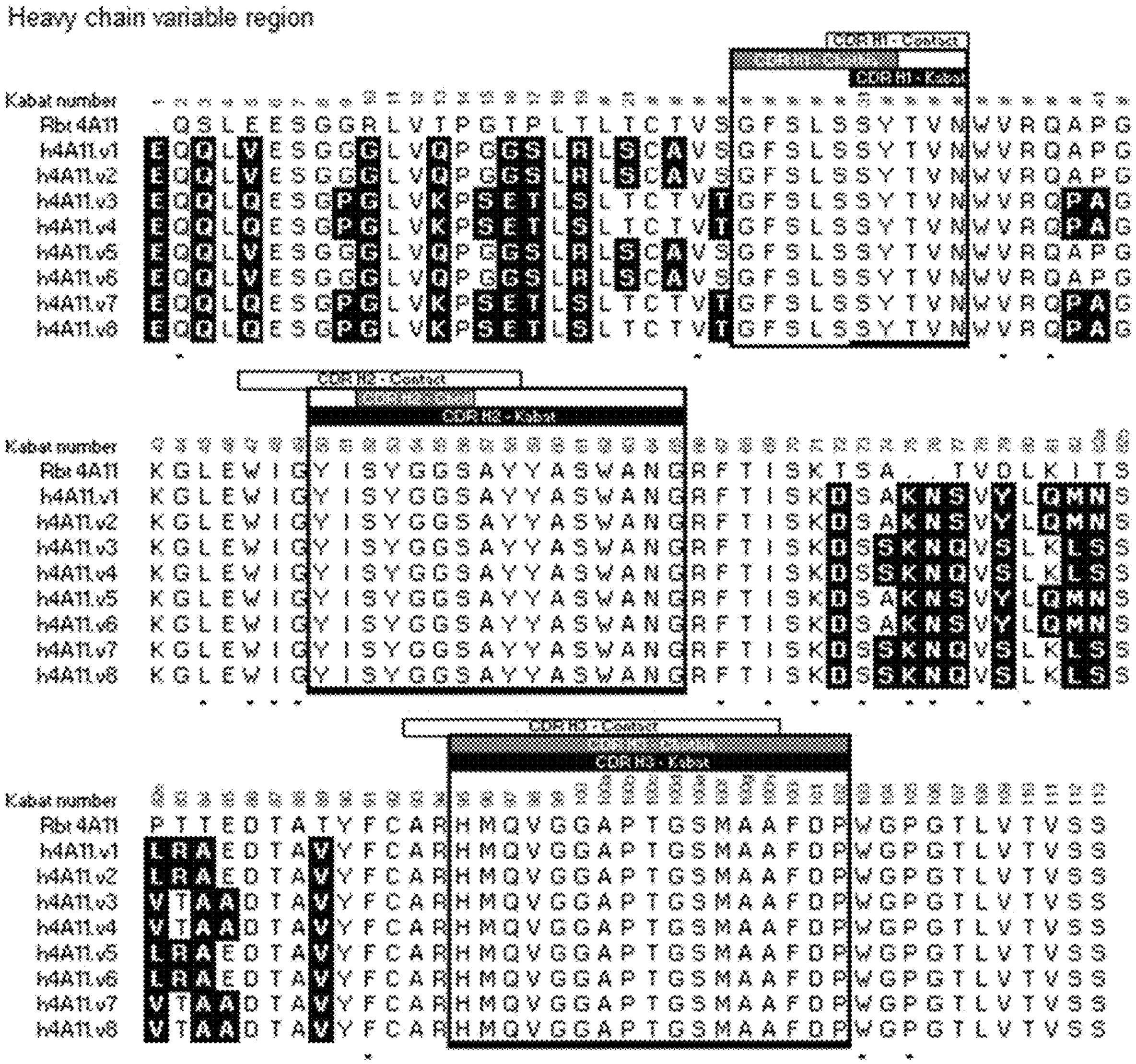

FIG. 19

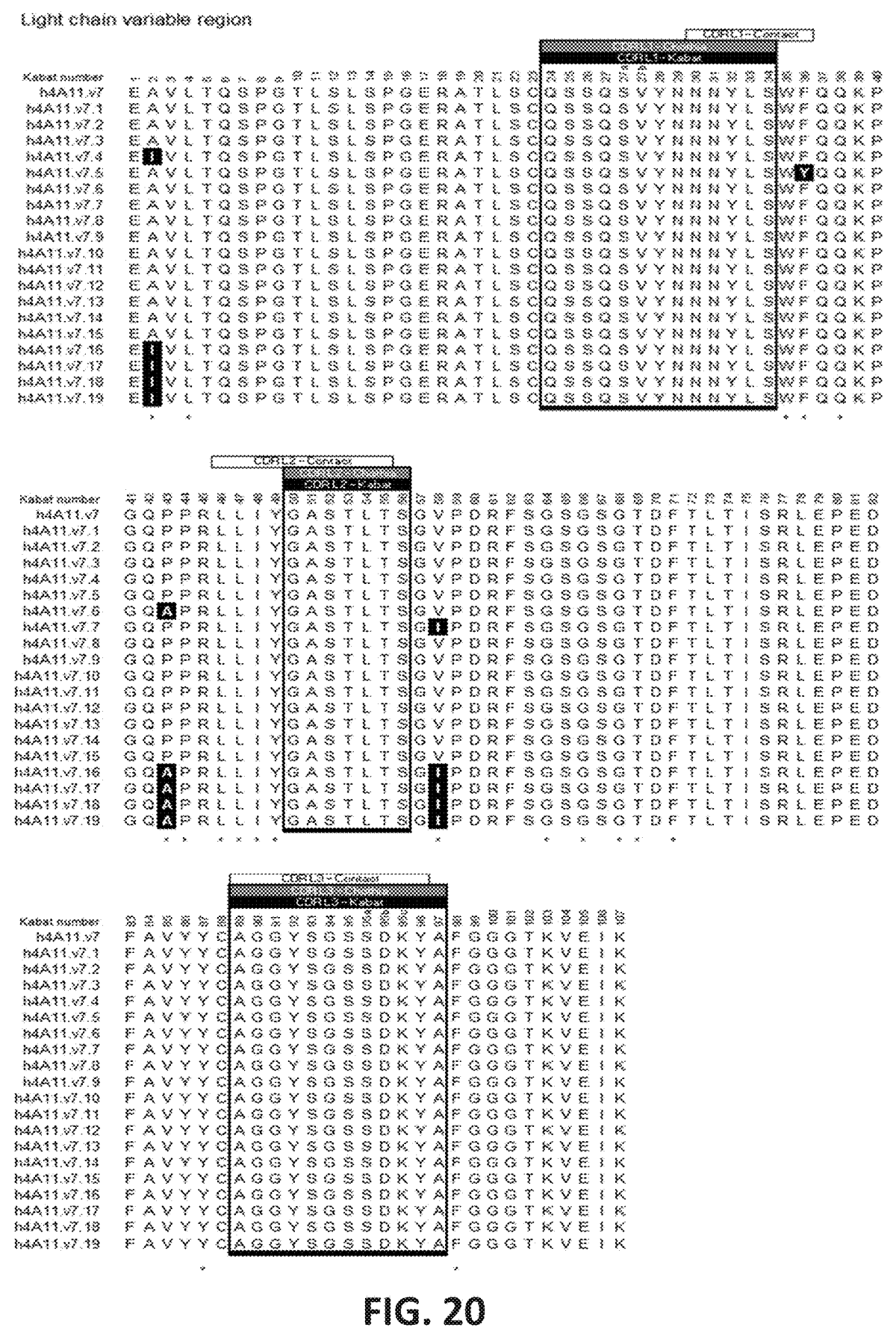

Light chain variable region

| Kabat number | [illegible] | CDR L1 - Contact / CDR L1 - Kabat | [illegible] |
|---|---|---|---|
| h4A11.v7 | E A V L T Q S P G T L S L S P G E R A T L S C | Q S S Q S V Y N N N Y L S | W F Q Q K P |
| h4A11.v7.1 | E A V L T Q S P G T L S L S P G E R A T L S C | Q S S Q S V Y N N N Y L S | W F Q Q K P |
| h4A11.v7.2 | E A V L T Q S P G T L S L S P G E R A T L S C | Q S S Q S V Y N N N Y L S | W F Q Q K P |
| h4A11.v7.3 | E A V L T Q S P G T L S L S P G E R A T L S C | Q S S Q S V Y N N N Y L S | W F Q Q K P |
| h4A11.v7.4 | E I V L T Q S P G T L S L S P G E R A T L S C | Q S S Q S V Y N N N Y L S | W F Q Q K P |
| h4A11.v7.5 | E A V L T Q S P G T L S L S P G E R A T L S C | Q S S Q S V Y N N N Y L S | W Y Q Q K P |
| h4A11.v7.6 | E A V L T Q S P G T L S L S P G E R A T L S C | Q S S Q S V Y N N N Y L S | W F Q Q K P |
| h4A11.v7.7 | E A V L T Q S P G T L S L S P G E R A T L S C | Q S S Q S V Y N N N Y L S | W F Q Q K P |
| h4A11.v7.8 | E A V L T Q S P G T L S L S P G E R A T L S C | Q S S Q S V Y N N N Y L S | W F Q Q K P |
| h4A11.v7.9 | E A V L T Q S P G T L S L S P G E R A T L S C | Q S S Q S V Y N N N Y L S | W F Q Q K P |
| h4A11.v7.10 | E A V L T Q S P G T L S L S P G E R A T L S C | Q S S Q S V Y N N N Y L S | W F Q Q K P |
| h4A11.v7.11 | E A V L T Q S P G T L S L S P G E R A T L S C | Q S S Q S V Y N N N Y L S | W F Q Q K P |
| h4A11.v7.12 | E A V L T Q S P G T L S L S P G E R A T L S C | Q S S Q S V Y N N N Y L S | W F Q Q K P |
| h4A11.v7.13 | E A V L T Q S P G T L S L S P G E R A T L S C | Q S S Q S V Y N N N Y L S | W F Q Q K P |
| h4A11.v7.14 | E A V L T Q S P G T L S L S P G E R A T L S C | Q S S Q S V Y N N N Y L S | W F Q Q K P |
| h4A11.v7.15 | E A V L T Q S P G T L S L S P G E R A T L S C | Q S S Q S V Y N N N Y L S | W F Q Q K P |
| h4A11.v7.16 | E I V L T Q S P G T L S L S P G E R A T L S C | Q S S Q S V Y N N N Y L S | W F Q Q K P |
| h4A11.v7.17 | E I V L T Q S P G T L S L S P G E R A T L S C | Q S S Q S V Y N N N Y L S | W F Q Q K P |
| h4A11.v7.18 | E I V L T Q S P G T L S L S P G E R A T L S C | Q S S Q S V Y N N N Y L S | W F Q Q K P |
| h4A11.v7.19 | E I V L T Q S P G T L S L S P G E R A T L S C | Q S S Q S V Y N N N Y L S | W F Q Q K P |

| Kabat number | [illegible] | CDR L2 - Contact / CDR L2 - Kabat | [illegible] |
|---|---|---|---|
| h4A11.v7 | G Q P P R L L I Y | G A S T L T S | G V P D R F S G S G S G T D F T L T I S R L E P E D |
| h4A11.v7.1 | G Q P P R L L I Y | G A S T L T S | G V P D R F S G S G S G T D F T L T I S R L E P E D |
| h4A11.v7.2 | G Q P P R L L I Y | G A S T L T S | G V P D R F S G S G S G T D F T L T I S R L E P E D |
| h4A11.v7.3 | G Q P P R L L I Y | G A S T L T S | G V P D R F S G S G S G T D F T L T I S R L E P E D |
| h4A11.v7.4 | G Q P P R L L I Y | G A S T L T S | G V P D R F S G S G S G T D F T L T I S R L E P E D |
| h4A11.v7.5 | G Q P P R L L I Y | G A S T L T S | G V P D R F S G S G S G T D F T L T I S R L E P E D |
| h4A11.v7.6 | G Q A P R L L I Y | G A S T L T S | G V P D R F S G S G S G T D F T L T I S R L E P E D |
| h4A11.v7.7 | G Q P P R L L I Y | G A S T L T S | G I P D R F S G S G S G T D F T L T I S R L E P E D |
| h4A11.v7.8 | G Q P P R L L I Y | G A S T L T S | G V P D R F S G S G S G T D F T L T I S R L E P E D |
| h4A11.v7.9 | G Q P P R L L I Y | G A S T L T S | G V P D R F S G S G S G T D F T L T I S R L E P E D |
| h4A11.v7.10 | G Q P P R L L I Y | G A S T L T S | G V P D R F S G S G S G T D F T L T I S R L E P E D |
| h4A11.v7.11 | G Q P P R L L I Y | G A S T L T S | G V P D R F S G S G S G T D F T L T I S R L E P E D |
| h4A11.v7.12 | G Q P P R L L I Y | G A S T L T S | G V P D R F S G S G S G T D F T L T I S R L E P E D |
| h4A11.v7.13 | G Q P P R L L I Y | G A S T L T S | G V P D R F S G S G S G T D F T L T I S R L E P E D |
| h4A11.v7.14 | G Q P P R L L I Y | G A S T L T S | G V P D R F S G S G S G T D F T L T I S R L E P E D |
| h4A11.v7.15 | G Q P P R L L I Y | G A S T L T S | G V P D R F S G S G S G T D F T L T I S R L E P E D |
| h4A11.v7.16 | G Q A P R L L I Y | G A S T L T S | G I P D R F S G S G S G T D F T L T I S R L E P E D |
| h4A11.v7.17 | G Q A P R L L I Y | G A S T L T S | G I P D R F S G S G S G T D F T L T I S R L E P E D |
| h4A11.v7.18 | G Q A P R L L I Y | G A S T L T S | G I P D R F S G S G S G T D F T L T I S R L E P E D |
| h4A11.v7.19 | G Q A P R L L I Y | G A S T L T S | G I P D R F S G S G S G T D F T L T I S R L E P E D |

| Kabat number | [illegible] | CDR L3 - Contact / CDR L3 - Kabat | [illegible] |
|---|---|---|---|
| h4A11.v7 | F A V Y Y C | A G G Y S G S S D K Y A | F G G G T K V E I K |
| h4A11.v7.1 | F A V Y Y C | A G G Y S G S S D K Y A | F G G G T K V E I K |
| h4A11.v7.2 | F A V Y Y C | A G G Y S G S S D K Y A | F G G G T K V E I K |
| h4A11.v7.3 | F A V Y Y C | A G G Y S G S S D K Y A | F G G G T K V E I K |
| h4A11.v7.4 | F A V Y Y C | A G G Y S G S S D K Y A | F G G G T K V E I K |
| h4A11.v7.5 | F A V Y Y C | A G G Y S G S S D K Y A | F G G G T K V E I K |
| h4A11.v7.6 | F A V Y Y C | A G G Y S G S S D K Y A | F G G G T K V E I K |
| h4A11.v7.7 | F A V Y Y C | A G G Y S G S S D K Y A | F G G G T K V E I K |
| h4A11.v7.8 | F A V Y Y C | A G G Y S G S S D K Y A | F G G G T K V E I K |
| h4A11.v7.9 | F A V Y Y C | A G G Y S G S S D K Y A | F G G G T K V E I K |
| h4A11.v7.10 | F A V Y Y C | A G G Y S G S S D K Y A | F G G G T K V E I K |
| h4A11.v7.11 | F A V Y Y C | A G G Y S G S S D K Y A | F G G G T K V E I K |
| h4A11.v7.12 | F A V Y Y C | A G G Y S G S S D K Y A | F G G G T K V E I K |
| h4A11.v7.13 | F A V Y Y C | A G G Y S G S S D K Y A | F G G G T K V E I K |
| h4A11.v7.14 | F A V Y Y C | A G G Y S G S S D K Y A | F G G G T K V E I K |
| h4A11.v7.15 | F A V Y Y C | A G G Y S G S S D K Y A | F G G G T K V E I K |
| h4A11.v7.16 | F A V Y Y C | A G G Y S G S S D K Y A | F G G G T K V E I K |
| h4A11.v7.17 | F A V Y Y C | A G G Y S G S S D K Y A | F G G G T K V E I K |
| h4A11.v7.18 | F A V Y Y C | A G G Y S G S S D K Y A | F G G G T K V E I K |
| h4A11.v7.19 | F A V Y Y C | A G G Y S G S S D K Y A | F G G G T K V E I K |

FIG. 20

Heavy chain variable region

| Kabat number | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| h4A11.v7   | E Q Q L Q E S G P G L V K P S E T L S L T C T V T | G F S L S S Y T V N | W V R Q P A G |
| h4A11.v7.1 | . Q Q L Q E S G P G L V K P S E T L S L T C T V T | G F S L S S Y T V N | W V R Q P A G |
| h4A11.v7.2 | E Q Q L Q E S G P G L V K P S E T L S L T C T V T | G F S L S S Y T V N | W V R Q P A G |
| h4A11.v7.3 | . Q Q L Q E S G P G L V K P S E T L S L T C T V T | G F S L S S Y T V N | W V R Q P A G |
| h4A11.v7.4 | E Q Q L Q E S G P G L V K P S E T L S L T C T V T | G F S L S S Y T V N | W V R Q P A G |
| h4A11.v7.5 | E Q Q L Q E S G P G L V K P S E T L S L T C T V T | G F S L S S Y T V N | W V R Q P A G |
| h4A11.v7.6 | E Q Q L Q E S G P G L V K P S E T L S L T C T V T | G F S L S S Y T V N | W V R Q P A G |
| h4A11.v7.7 | E Q Q L Q E S G P G L V K P S E T L S L T C T V T | G F S L S S Y T V N | W V R Q P A G |
| h4A11.v7.8 | E **V** Q L Q E S G P G L V K P S E T L S L T C T V T | G F S L S S Y T V N | W V R Q P A G |
| h4A11.v7.9 | E Q Q L Q E S G P G L V K P S E T L S L T C T V T | G F S L S S Y T V N | **F** R Q P A G |
| h4A11.v7.10 | E Q Q L Q E S G P G L V K P S E T L S L T C T V T | G F S L S S Y T V N | W V R Q P A G |
| h4A11.v7.11 | E Q Q L Q E S G P G L V K P S E T L S L T C T V T | G F S L S S Y T V N | W V R Q P A G |
| h4A11.v7.12 | E Q Q L Q E S G P G L V K P S E T L S L T C T V T | G F S L S S Y T V N | W V R Q P A G |
| h4A11.v7.13 | E Q Q L Q E S G P G L V K P S E T L S L T C T V T | G F S L S S Y T V N | W V R Q P A G |
| h4A11.v7.14 | E Q Q L Q E S G P G L V K P S E T L S L T C T V T | G F S L S S Y T V N | W V R Q P A G |
| h4A11.v7.15 | E Q Q L Q E S G P G L V K P S E T L S L T C T V T | G F S L S S Y T V N | W V R Q P A G |
| h4A11.v7.16 | E **V** Q L Q E S G P G L V K P S E T L S L T C T V T | G F S L S S Y T V N | W **F** R Q P A G |
| h4A11.v7.17 | E **V** Q L Q E S G P G L V K P S E T L S L T C T V T | G F S L S S Y T V N | W **F** R Q P A G |
| h4A11.v7.18 | E **V** Q L Q E S G P G L V K P S E T L S L T C T V T | G F S L S S Y T V N | W **F** R Q P A G |
| h4A11.v7.19 | E **V** Q L Q E S G P G L V K P S E T L S L T C T V T | G F S L S S Y T V N | W **F** R Q P A G |

| h4A11.v7    | K G L E W I G | Y I S Y G G S A Y Y A S W A N G | R F T I S K D S S K N Q V S L K L S S |
|---|---|---|---|
| h4A11.v7.1  | K G L E W I G | Y I S Y G G S A Y Y A S W A N G | R F T I S K D S S K N Q V S L K L S S |
| h4A11.v7.2  | K G L E W I G | Y I S Y G G S A Y Y A S W A N G | R F T I S K D S S . . Q V S L K L S S |
| h4A11.v7.3  | K G L E W I G | Y I S Y G G S A Y Y A S W A N G | R F T I S K D S S . . Q V S L K L S S |
| h4A11.v7.4  | K G L E W I G | Y I S Y G G S A Y Y A S W A N G | R F T I S K D S S K N Q V S L K L S S |
| h4A11.v7.5  | K G L E W I G | Y I S Y G G S A Y Y A S W A N G | R F T I S K D S S K N Q V S L K L S S |
| h4A11.v7.6  | K G L E W I G | Y I S Y G G S A Y Y A S W A N G | R F T I S K D S S K N Q V S L K L S S |
| h4A11.v7.7  | K G L E W I G | Y I S Y G G S A Y Y A S W A N G | R F T I S K D S S K N Q V S L K L S S |
| h4A11.v7.8  | K G L E W I G | Y I S Y G G S A Y Y A S W A N G | R F T I S K D S S K N Q V S L K L S S |
| h4A11.v7.9  | K G L E W I G | Y I S Y G G S A Y Y A S W A N G | R F T I S K D S S K N Q V S L K L S S |
| h4A11.v7.10 | K G L E W I G | Y I S Y G G S A Y Y A S W A N G | **V** T I S K D S S K N Q V S L K L S S |
| h4A11.v7.11 | K G L E W I G | Y I S Y G G S A Y Y A S W A N G | R F T I S **V** D S S K N Q V S L K L S S |
| h4A11.v7.12 | K G L E W I G | Y I S Y G G S A Y Y A S W A N G | R F T I S K D **T** S K N Q V S L K L S S |
| h4A11.v7.13 | K G L E W I G | Y I S Y G G S A Y Y A S W A N G | R F T I S K D S S K N Q **F** S L K L S S |
| h4A11.v7.14 | K G L E W I G | Y I S Y G G S A Y Y A S W A N G | R F T I S K D S S K N Q V S L K L S S |
| h4A11.v7.15 | K G L E W I G | Y I S Y G G S A Y Y A S W A N G | R F T I S K D S S K N Q V S L K L S S |
| h4A11.v7.16 | K G L E W I G | Y I S Y G G S A Y Y A S W A N G | **V** T I S K D **T** S K N Q **F** S L K L S S |
| h4A11.v7.17 | K G L E W I G | Y I S Y G G S A Y Y A S W A N G | **V** T I S K D **T** S K N Q V S L K L S S |
| h4A11.v7.18 | K G L E W I G | Y I S Y G G S A Y Y A S W A N G | **V** T I S K D **T** S K N Q V S L K L S S |
| h4A11.v7.19 | K G L E W I G | Y I S Y G G S A Y Y A S W A N G | **V** T I S K D **T** S . . Q V S L K L S S |

| h4A11.v7    | V T A A D T A V Y F C A R | H M Q V G G A P T G S M A A F D P | W G P G T L V T V S S |
|---|---|---|---|
| h4A11.v7.1  | V T A A D T A V Y F C A R | H M Q V G G A P T G S M A A F D P | W G P G T L V T V S S |
| h4A11.v7.2  | V T A A D T A V Y F C A R | H M Q V G G A P T G S M A A F D P | W G P G T L V T V S S |
| h4A11.v7.3  | V T A A D T A V Y F C A R | H M Q V G G A P T G S M A A F D P | W G P G T L V T V S S |
| h4A11.v7.4  | V T A A D T A V Y F C A R | H M Q V G G A P T G S M A A F D P | W G P G T L V T V S S |
| h4A11.v7.5  | V T A A D T A V Y F C A R | H M Q V G G A P T G S M A A F D P | W G P G T L V T V S S |
| h4A11.v7.6  | V T A A D T A V Y F C A R | H M Q V G G A P T G S M A A F D P | W G P G T L V T V S S |
| h4A11.v7.7  | V T A A D T A V Y F C A R | H M Q V G G A P T G S M A A F D P | W G P G T L V T V S S |
| h4A11.v7.8  | V T A A D T A V Y F C A R | H M Q V G G A P T G S M A A F D P | W G P G T L V T V S S |
| h4A11.v7.9  | V T A A D T A V Y F C A R | H M Q V G G A P T G S M A A F D P | W G P G T L V T V S S |
| h4A11.v7.10 | V T A A D T A V Y F C A R | H M Q V G G A P T G S M A A F D P | W G P G T L V T V S S |
| h4A11.v7.11 | V T A A D T A V Y F C A R | H M Q V G G A P T G S M A A F D P | W G P G T L V T V S S |
| h4A11.v7.12 | V T A A D T A V Y F C A R | H M Q V G G A P T G S M A A F D P | W G P G T L V T V S S |
| h4A11.v7.13 | V T A A D T A V Y F C A R | H M Q V G G A P T G S M A A F D P | W G P G T L V T V S S |
| h4A11.v7.14 | V T A A D T A V **Y** C A R | H M Q V G G A P T G S M A A F D P | W G P G T L V T V S S |
| h4A11.v7.15 | V T A A D T A V Y F C A R | H M Q V G G A P T G S M A A F D P | W **Q** G T L V T V S S |
| h4A11.v7.16 | V T A A D T A V Y F C A R | H M Q V G G A P T G S M A A F D P | W **Q** G T L V T V S S |
| h4A11.v7.17 | V T A A D T A V **Y** C A R | H M Q V G G A P T G S M A A F D P | W G P G T L V T V S S |
| h4A11.v7.18 | V T A A D T A V Y F C A R | H M Q V G G A P T G S M A A F D P | W **Q** G T L V T V S S |
| h4A11.v7.19 | V T A A D T A V Y F C A R | H M Q V G G A P T G S M A A F D P | W **Q** G T L V T V S S |

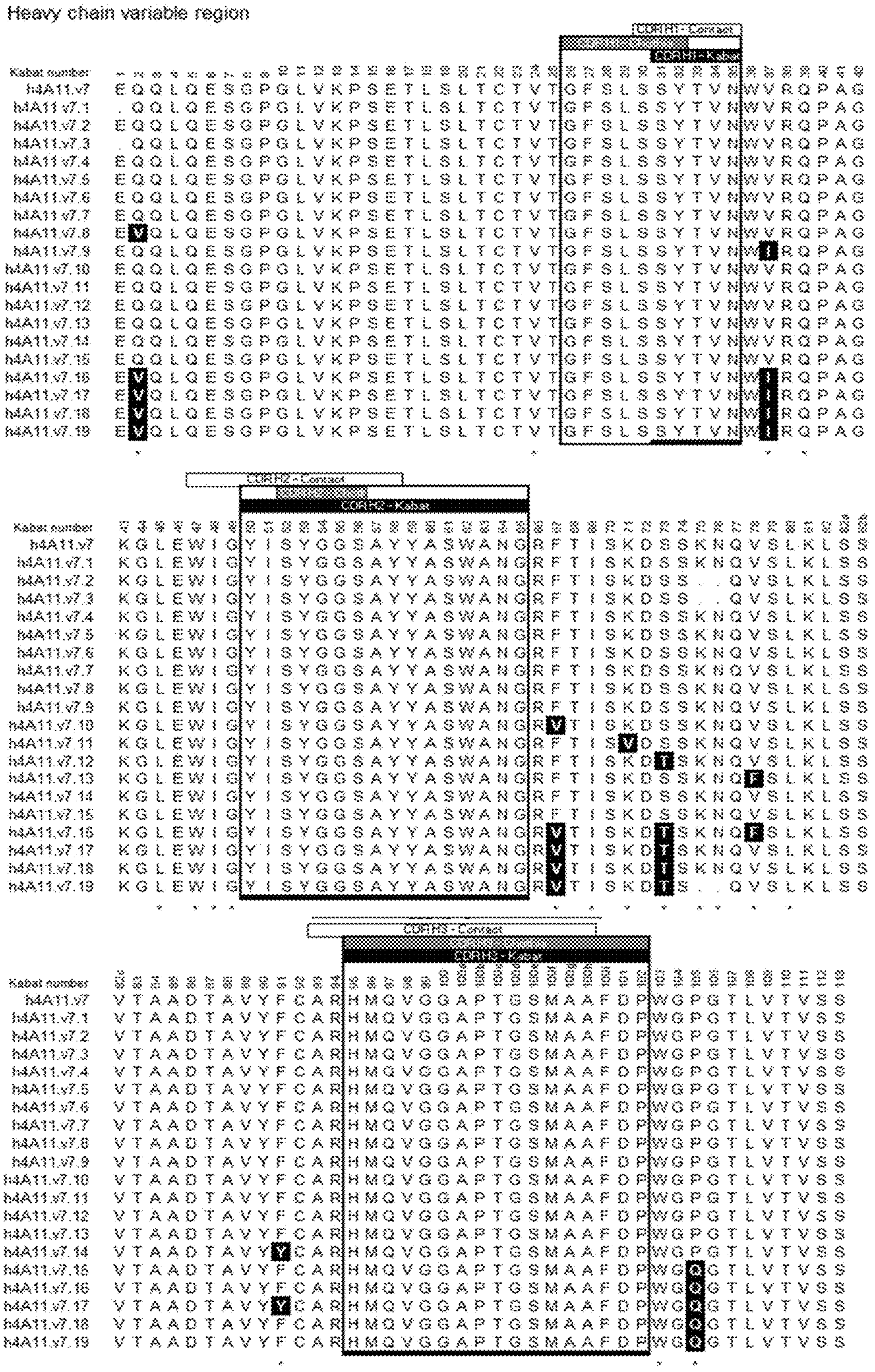

FIG. 21

Light chain variable region

| Kabat number | | CDR L1 - Kabat | |
|---|---|---|---|
| h6F12.v1 | D I Q M T Q S P S T L S A S V G D R V T I T C | L A S E D I Y S N L A | W Y Q Q K P G K |
| h6F12.v1.1 | D I Q M T Q S P S T L S A S V G D R V T I T C | L A S E D I Y S N L A | W Y Q Q K P G K |
| h6F12.v1.2 | D I Q M T Q S P S T L S A S V G D R V T I T C | L A S E D I Y S N L A | W Y Q Q K P G K |
| h6F12.v1.3 | D I Q M T Q S P S T L S A S V G D R V T I T C | L A S E D I Y S N L A | W Y Q Q K P G K |
| h6F12.v1.4 | D I Q M T Q S P S T L S A S V G D R V T I T C | L A S E D I Y S N L A | W Y Q Q K P G K |
| h6F12.v1.5 | D I Q M T Q S P S T L S A S V G D R V T I T C | L A S E D I Y S N L A | W Y Q Q K P G K |
| h6F12.v1.6 | D I Q M T Q S P S T L S A S V G D R V T I T C | L A S E D I Y S N L A | W Y Q Q K P G K |
| h6F12.v1.7 | D I Q M T Q S P S T L S A S V G D R V T I T C | L A S E D I Y S N L A | W Y Q Q K P G K |
| h6F12.v1.8 | D I Q M T Q S P S T L S A S V G D R V T I T C | L A S E D I Y S N L A | W Y Q Q K P G K |
| h6F12.v1.9 | D I Q M T Q S P S T L S A S V G D R V T I T C | L A S E D I Y S N L A | W Y Q Q K P G K |

CDR L1 - Contact

| Kabat number | | CDR L2 - Kabat | |
|---|---|---|---|
| h6F12.v1 | S P K L L I Y | D A R S L Q D | G V P S R F S G S E S G P E Y T L T I S S L Q P D D F A |
| h6F12.v1.1 | **A** P K L L I Y | D A R S L Q D | G V P S R F S G S E S G P E Y T L T I S S L Q P D D F A |
| h6F12.v1.2 | S P K L L I Y | D A R S L Q D | G V P S R F S G S **G** S G P E Y T L T I S S L Q P D D F A |
| h6F12.v1.3 | S P K L L I Y | D A R S L Q D | G V P S R F S G S E S G **T** E Y T L T I S S L Q P D D F A |
| h6F12.v1.4 | S P K L L I Y | D A R S L Q D | G V P S R F S G S E S G P E **F** T L T I S S L Q P D D F A |
| h6F12.v1.5 | S P K L L I Y | D A R S L Q D | G V P S R F S G S E S G P E Y T L T I S S L Q P D D F A |
| h6F12.v1.6 | S P K L L I Y | D A R S L Q D | G V P S R F S G S E S G P E Y T L T I S S L Q P D D F A |
| h6F12.v1.7 | S P K L L I Y | D A R S L Q D | G V P S R F S G S E S G P E Y T L T I S S L Q P D D F A |
| h6F12.v1.8 | S P K L L I Y | D A R S L Q D | G V P S R F S G S E S G P E Y T L T I S S L Q P D D F A |
| h6F12.v1.9 | S P K L L I Y | D A R S L Q D | G V P S R F S G S E S G P E Y T L T I S S L Q P D D F A |

CDR L2 - Contact

| Kabat number | | CDR L3 - Kabat | |
|---|---|---|---|
| h6F12.v1 | T Y F C | Q Q H H A Y P F T | F G Q G T K V E I K |
| h6F12.v1.1 | T Y F C | Q Q H H A Y P F T | F G Q G T K V E I K |
| h6F12.v1.2 | T Y F C | Q Q H H A Y P F T | F G Q G T K V E I K |
| h6F12.v1.3 | T Y F C | Q Q H H A Y P F T | F G Q G T K V E I K |
| h6F12.v1.4 | T Y F C | Q Q H H A Y P F T | F G Q G T K V E I K |
| h6F12.v1.5 | T Y **Y** C | Q Q H H A Y P F T | F G Q G T K V E I K |
| h6F12.v1.6 | T Y F C | Q Q H H A Y P F T | F G Q G T K V E I K |
| h6F12.v1.7 | T Y F C | Q Q H H A Y P F T | F G Q G T K V E I K |
| h6F12.v1.8 | T Y F C | Q Q H H A Y P F T | F G Q G T K V E I K |
| h6F12.v1.9 | T Y F C | Q Q H H A Y P F T | F G Q G T K V E I K |

CDR L3 - Contact

FIG. 23

Heavy chain variable region

| Kabat number | 1...30 |
|---|---|
| h6F12.v1   | E V T L K E S G P V L V K P T E T L T L T C T V S G F S L T T Y N V H W V R Q P P G |
| h6F12.v1.1 | E V T L K E S G P V L V K P T E T L T L T C T V S G F S L T T Y N V H W V R Q P P G |
| h6F12.v1.2 | E V T L K E S G P V L V K P T E T L T L T C T V S G F S L T T Y N V H W V R Q P P G |
| h6F12.v1.3 | E V T L K E S G P V L V K P T E T L T L T C T V S G F S L T T Y N V H W V R Q P P G |
| h6F12.v1.4 | E V T L K E S G P V L V K P T E T L T L T C T V S G F S L T T Y N V H W V R Q P P G |
| h6F12.v1.5 | E V T L K E S G P V L V K P T E T L T L T C T V S G F S L T T Y N V H W V R Q P P G |
| h6F12.v1.6 | E V T L K E S G P V L V K P T E T L T L T C T V S G F S L T T Y N V H W I R Q P P G |
| h6F12.v1.7 | E V T L K E S G P V L V K P T E T L T L T C T V S G F S L T T Y N V H W V R Q P P G |
| h6F12.v1.8 | E V T L K E S G P V L V K P T E T L T L T C T V S G F S L T T Y N V H W V R Q P P G |
| h6F12.v1.9 | E V T L K E S G P V L V K P T E T L T L T C T V S G F S L T T Y N V H W V R Q P P G |

| Kabat number | |
|---|---|
| h6F12.v1   | K A L E W M G L I W N T G G T R Y N S A L K S R L T I S K D T S K S Q V V L T M T N |
| h6F12.v1.1 | K A L E W M G L I W N T G G T R Y N S A L K S R L T I S K D T S K S Q V V L T M T N |
| h6F12.v1.2 | K A L E W M G L I W N T G G T R Y N S A L K S R L T I S K D T S K S Q V V L T M T N |
| h6F12.v1.3 | K A L E W M G L I W N T G G T R Y N S A L K S R L T I S K D T S K S Q V V L T M T N |
| h6F12.v1.4 | K A L E W M G L I W N T G G T R Y N S A L K S R L T I S K D T S K S Q V V L T M T N |
| h6F12.v1.5 | K A L E W M G L I W N T G G T R Y N S A L K S R L T I S K D T S K S Q V V L T M T N |
| h6F12.v1.6 | K A L E W M G L I W N T G G T R Y N S A L K S R L T I S K D T S K S Q V V L T M T N |
| h6F12.v1.7 | K A L E W L G L I W N T G G T R Y N S A L K S R L T I S K D T S K S Q V V L T M T N |
| h6F12.v1.8 | K A L E W M A L I W N T G G T R Y N S A L K S R L T I S K D T S K S Q V V L T M T N |
| h6F12.v1.9 | K A L E W M G L I W N T G G T R Y N S A L K S R L T I S K D T S K S Q V V L T M T N |

| Kabat number | |
|---|---|
| h6F12.v1   | M D P V D T A T Y Y C A R D P V P N K W H F D F W G P G T L V T V S S |
| h6F12.v1.1 | M D P V D T A T Y Y C A R D P V P N K W H F D F W G P G T L V T V S S |
| h6F12.v1.2 | M D P V D T A T Y Y C A R D P V P N K W H F D F W G P G T L V T V S S |
| h6F12.v1.3 | M D P V D T A T Y Y C A R D P V P N K W H F D F W G P G T L V T V S S |
| h6F12.v1.4 | M D P V D T A T Y Y C A R D P V P N K W H F D F W G P G T L V T V S S |
| h6F12.v1.5 | M D P V D T A T Y Y C A R D P V P N K W H F D F W G P G T L V T V S S |
| h6F12.v1.6 | M D P V D T A T Y Y C A R D P V P N K W H F D F W G P G T L V T V S S |
| h6F12.v1.7 | M D P V D T A T Y Y C A R D P V P N K W H F D F W G P G T L V T V S S |
| h6F12.v1.8 | M D P V D T A T Y Y C A R D P V P N K W H F D F W G P G T L V T V S S |
| h6F12.v1.9 | M D P V D T A T Y Y C A R D P V P N K W H F D F R G P G T L V T V S S |

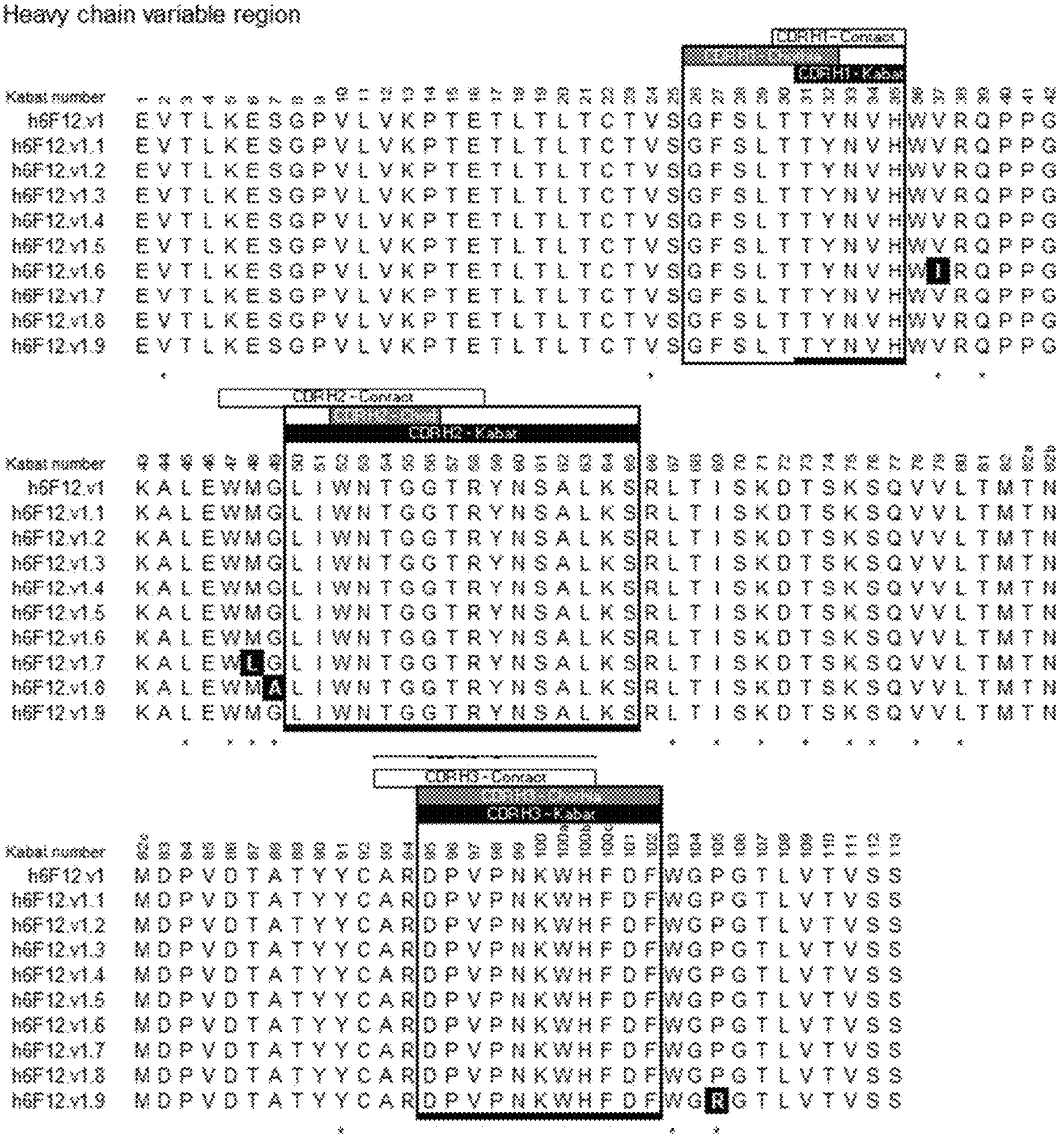

FIG. 24

| % | LAP1 | LAP2 | LAP3 |
|---|---|---|---|
| LAP1 | --- | 42 | 45 |
| LAP2 | | --- | 56 |
| LAP3 | | | --- |

| % | mature β1 | mature β2 | mature β3 |
|---|---|---|---|
| mature β1 | --- | 85 | 83 |
| mature β2 | | --- | 90 |
| mature β3 | | | --- |

| $IC_{50}$ (nM) | TGFβ1 | TGFβ2 | TGFβ3 |
|---|---|---|---|
| Fc-LAP1 | 96 | 64 | 43 |
| Fc-LAP2 | 10,143 | 548 | 525 |
| Fc-LAP3 | no inhibition | 12,446 | 2,924 |
FIG. 51
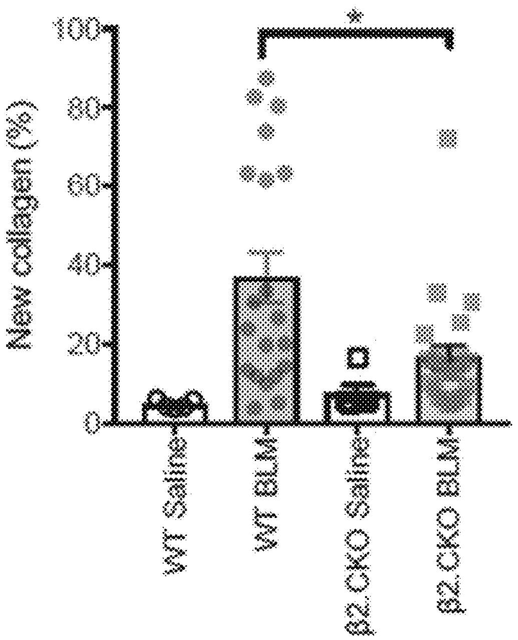
FIG. 52A
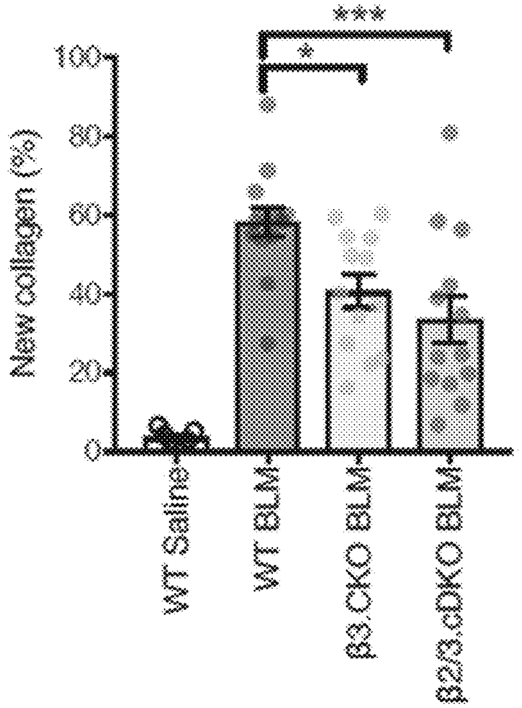
FIG. 52B

| $K_D$ (nM) | Human β2 | mouse β2 |
|---|---|---|
| 6F12 | <0.001 | <0.001 |
| 4A11 | 0.008 | <0.002 |

SEQUENCE LISTING

```
<160> NUMBER OF SEQ ID NOS: 188

<210> SEQ ID NO 1
<211> LENGTH: 390
<212> TYPE: PRT
<213> ORGANISM: Homo sapiens

<400> SEQUENCE: 1

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190
```

```
Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390


<210> SEQ ID NO 2
<211> LENGTH: 414
<212> TYPE: PRT
<213> ORGANISM: Homo sapiens

<400> SEQUENCE: 2

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175
```

```
Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
        275                 280                 285

Tyr Arg Leu Glu Ser Gln Gln Thr Asn Arg Arg Lys Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
        355                 360                 365

Thr Ile Asn Pro Glu Ala Ser Ala Ser Pro Cys Cys Val Ser Gln Asp
    370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410


<210> SEQ ID NO 3
<211> LENGTH: 412
<212> TYPE: PRT
<213> ORGANISM: Homo sapiens

<400> SEQUENCE: 3

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
```

-continued

```
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

His His Asn Pro His Leu Ile Leu Met Met Ile Pro Pro His Arg Leu
        275                 280                 285

Asp Asn Pro Gly Gln Gly Gly Gln Arg Lys Lys Arg Ala Leu Asp Thr
    290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Tyr Gly Met Ser
1               5


<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ile Val Ser Lys Thr Tyr Asn Tyr Thr Thr Tyr Tyr Ser Asp Ser
```

1 5 10 15

Val Lys Asp

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Ala Pro Gly Gly Ser Phe Asp Tyr
1 5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Arg Ala Ser Gln Ser Val Ser Ile Ser Arg Phe Asn Leu Met His
1 5 10 15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Arg Ala Ser Asn Leu Ala Ser
1 5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gln His Ser Arg Glu Ser Pro Trp Thr
1 5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ser Tyr Thr Val Asn
1 5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Tyr Ile Ser Tyr Gly Gly Ser Ala Tyr Tyr Ala Ser Trp Ala Asn Gly
1 5 10 15

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

His Met Gln Val Gly Gly Ala Pro Thr Gly Ser Met Ala Ala Phe Asp
1 5 10 15

Pro

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Gln Ser Ser Gln Ser Val Tyr Asn Asn Asn Tyr Leu Ser
1 5 10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gly Ala Ser Thr Leu Thr Ser
1 5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Ala Gly Gly Tyr Ser Gly Ser Ser Asp Lys Tyr Ala
1 5 10

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Thr Tyr Asn Val His 1 5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Leu Ile Trp Asn Thr Gly Gly Thr Arg Tyr Asn Ser Ala Leu Lys Ser
1 5 10 15

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Asp Pro Val Pro Asn Lys Trp His Phe Asp Phe
1 5 10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Leu Ala Ser Glu Asp Ile Tyr Ser Asn Leu Ala
1 5 10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Asp Ala Arg Ser Leu Gln Asp
1 5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Gln Gln His His Ala Tyr Pro Phe Thr
1 5

<210> SEQ ID NO 22
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Asp Ile Val Leu Thr Gln Ser Pro Ala Leu Ala Val Ser Leu Gly Gln
1 5 10 15

Arg Ala Thr Ile Ser Cys Arg Ala Ser Gln Ser Val Ser Ile Ser Arg
20 25 30

Phe Asn Leu Met His Trp Tyr Gln His Lys Pro Gly Gln Gln Pro Lys
35 40 45

Leu Leu Ile Tyr Arg Ala Ser Asn Leu Ala Ser Gly Ile Pro Ala Arg
50 55 60

Phe Ser Gly Ser Gly Ser Gly Thr Asp Phe Thr Leu Thr Ile Asn Pro
65 70 75 80

Val Gln Ala Asp Asp Leu Ala Thr Tyr Tyr Cys Gln His Ser Arg Glu
85 90 95

Ser Pro Trp Thr Phe Gly Gly Gly Thr Lys Leu Glu Ile Lys
100 105 110

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

Glu Val Gln Leu Val Glu Ser Gly Gly Gly Leu Val Gln Pro Lys Gly
1 5 10 15

Ser Leu Lys Leu Ser Cys Ala Ala Ser Gly Phe Asp Phe Asn Ser Tyr
20 25 30

Gly Met Ser Trp Val Arg Gln Ala Pro Gly Lys Gly Leu Asp Leu Val
35 40 45

Ala Asp Ile Val Ser Lys Thr Tyr Asn Tyr Thr Thr Tyr Tyr Ser Asp
50 55 60

Ser Val Lys Asp Arg Phe Thr Ile Ser Arg Asp Asp Ser Gln Ser Met
65 70 75 80

Val Tyr Leu Gln Met Asp Asn Leu Lys Thr Glu Asp Thr Ala Leu Tyr
85 90 95

Tyr Cys Thr Val Ala Pro Gly Gly Ser Phe Asp Tyr Trp Gly Gln Gly
100 105 110

Val Met Val Thr Val Ser Ser
115

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

Asp Ile Gln Met Thr Gln Ser Pro Ala Ser Leu Ser Ala Ser Leu Gly
1 5 10 15

Glu Thr Val Thr Ile Glu Cys Leu Ala Ser Glu Asp Ile Tyr Ser Asn
20 25 30

Leu Ala Trp Tyr Gln Gln Lys Pro Gly Lys Ser Pro Gln Leu Leu Ile
35 40 45

```
Tyr Asp Ala Arg Ser Leu Gln Asp Gly Val Pro Ser Arg Phe Ser Gly
    50                  55                  60

Ser Glu Ser Gly Pro Gln Tyr Ser Leu Glu Ile Asn Ser Leu Gln Ser
65                  70                  75                  80

Glu Asp Ala Val Thr Tyr Phe Cys Gln Gln His His Ala Tyr Pro Phe
                85                  90                  95

Thr Phe Gly Ser Gly Thr Lys Leu Glu Ile Lys
            100                 105
```

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Leu Ile Trp Asn Thr Gly Gly Thr Arg Tyr Asn Ser Ala Leu Lys
    50                  55                  60

Ser Arg Leu Ser Ile Ser Lys Asp Thr Ser Lys Ser Gln Val Phe Leu
65                  70                  75                  80

Arg Met Asn Ser Leu Gln Thr Glu Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Met Val Thr Val Ser Ser
        115
```

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Tyr Asn Asn
            20                  25                  30

Asn Tyr Leu Ser Trp Phe Gln Gln Lys Pro Gly Gln Pro Pro Lys Leu
        35                  40                  45

Leu Ile Tyr Gly Ala Ser Thr Leu Thr Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ser Gly
                85                  90                  95

Ser Ser Asp Lys Tyr Ala Phe Gly Gly Gly Thr Glu Val Val Val Lys
            100                 105                 110
```

<210> SEQ ID NO 27
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Thr
            20                  25                  30

Val Asn Trp Val Arg Gln Ala Pro Gly Lys Gly Leu Glu Trp Ile Gly
        35                  40                  45

Tyr Ile Ser Tyr Gly Gly Ser Ala Tyr Tyr Ala Ser Trp Ala Asn Gly
    50                  55                  60

Arg Phe Thr Ile Ser Lys Thr Ser Ala Thr Val Asp Leu Lys Ile Thr
65                  70                  75                  80

Ser Pro Thr Thr Glu Asp Thr Ala Thr Tyr Phe Cys Ala Arg His Met
                85                  90                  95

Gln Val Gly Gly Ala Pro Thr Gly Ser Met Ala Ala Phe Asp Pro Trp
            100                 105                 110

Gly Pro Gly Thr Leu Val Thr Val Ser Ser
        115                 120
```

<210> SEQ ID NO 28
<211> LENGTH: 217
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Asp Ile Val Leu Thr Gln Ser Pro Ala Leu Ala Val Ser Leu Gly Gln
1               5                   10                  15

Arg Ala Thr Ile Ser Cys Arg Ala Ser Gln Ser Val Ser Ile Ser Arg
            20                  25                  30

Phe Asn Leu Met His Trp Tyr Gln His Lys Pro Gly Gln Gln Pro Lys
        35                  40                  45

Leu Leu Ile Tyr Arg Ala Ser Asn Leu Ala Ser Gly Ile Pro Ala Arg
    50                  55                  60

Phe Ser Gly Ser Gly Ser Gly Thr Asp Phe Thr Leu Thr Ile Asn Pro
65                  70                  75                  80

Val Gln Ala Asp Asp Leu Ala Thr Tyr Tyr Cys Gln His Ser Arg Glu
                85                  90                  95

Ser Pro Trp Thr Phe Gly Gly Gly Thr Lys Leu Glu Ile Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175
```

```
Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215


<210> SEQ ID NO 29
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Asp Phe Asn Ser Tyr
            20                  25                  30

Gly Met Ser Trp Val Arg Gln Ala Pro Gly Lys Gly Leu Asp Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Gln Ser Met
65                  70                  75                  80

Val Tyr Leu Gln Met Asp Asn Leu Lys Thr Glu Asp Thr Ala Leu Tyr
                85                  90                  95

Tyr Cys Thr Val Ala Pro Gly Gly Ser Phe Asp Tyr Trp Gly Gln Gly
            100                 105                 110

Val Met Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Ala Ala Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
```

-continued 305 310 315 320

Phe Lys Cys Lys Val Asn Asn Lys Asp Leu Gly Ala Pro Ile Glu Arg
325 330 335

Thr Ile Ser Lys Pro Lys Gly Ser Val Arg Ala Pro Gln Val Tyr Val
340 345 350

Leu Pro Pro Pro Glu Glu Glu Met Thr Lys Lys Gln Val Thr Leu Thr
355 360 365

Cys Met Val Thr Asp Phe Met Pro Glu Asp Ile Tyr Val Glu Trp Thr
370 375 380

Asn Asn Gly Lys Thr Glu Leu Asn Tyr Lys Asn Thr Glu Pro Val Leu
385 390 395 400

Asp Ser Asp Gly Ser Tyr Phe Met Tyr Ser Lys Leu Arg Val Glu Lys
405 410 415

Lys Asn Trp Val Glu Arg Asn Ser Tyr Ser Cys Ser Val Val His Glu
420 425 430

Gly Leu His Asn His His Thr Thr Lys Ser Phe Ser Arg Thr Pro Gly
435 440 445

Lys

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Asp Ile Gln Met Thr Gln Ser Pro Ala Ser Leu Ser Ala Ser Leu Gly
1 5 10 15

Glu Thr Val Thr Ile Glu Cys Leu Ala Ser Glu Asp Ile Tyr Ser Asn
20 25 30

Leu Ala Trp Tyr Gln Gln Lys Pro Gly Lys Ser Pro Gln Leu Leu Ile
35 40 45

Tyr Asp Ala Arg Ser Leu Gln Asp Gly Val Pro Ser Arg Phe Ser Gly
50 55 60

Ser Glu Ser Gly Pro Gln Tyr Ser Leu Glu Ile Asn Ser Leu Gln Ser
65 70 75 80

Glu Asp Ala Val Thr Tyr Phe Cys Gln Gln His His Ala Tyr Pro Phe
85 90 95

Thr Phe Gly Ser Gly Thr Lys Leu Glu Ile Lys Arg Ala Asp Ala Ala
100 105 110

Pro Thr Val Ser Ile Phe Pro Pro Ser Ser Glu Gln Leu Thr Ser Gly
115 120 125

Gly Ala Ser Val Val Cys Phe Leu Asn Asn Phe Tyr Pro Lys Asp Ile
130 135 140

Asn Val Lys Trp Lys Ile Asp Gly Ser Glu Arg Gln Asn Gly Val Leu
145 150 155 160

Asn Ser Trp Thr Asp Gln Asp Ser Lys Asp Ser Thr Tyr Ser Met Ser
165 170 175

Ser Thr Leu Thr Leu Thr Lys Asp Glu Tyr Glu Arg His Asn Ser Tyr
180 185 190

Thr Cys Glu Ala Thr His Lys Thr Ser Thr Ser Pro Ile Val Lys Ser
195 200 205

Phe Asn Arg Asn Glu Cys
210

210

<210> SEQ ID NO 31
<211> LENGTH: 449
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

Gln Val Gln Leu Lys Glu Ser Gly Pro Gly Leu Val Gln Pro Ser Gln
1 5 10 15

Thr Leu Ser Leu Thr Cys Thr Val Ser Gly Phe Ser Leu Thr Thr Tyr
20 25 30

Asn Val His Trp Val Arg Gln Pro Pro Gly Lys Gly Leu Glu Trp Met
35 40 45

Gly Leu Ile Trp Asn Thr Gly Gly Thr Arg Tyr Asn Ser Ala Leu Lys
50 55 60

Ser Arg Leu Ser Ile Ser Lys Asp Thr Ser Lys Ser Gln Val Phe Leu
65 70 75 80

Arg Met Asn Ser Leu Gln Thr Glu Asp Thr Ala Thr Tyr Tyr Cys Ala
85 90 95

Arg Asp Pro Val Pro Asn Lys Trp His Phe Asp Phe Trp Gly Pro Gly
100 105 110

Thr Met Val Thr Val Ser Ser Ala Lys Thr Thr Ala Pro Ser Val Tyr
115 120 125

Pro Leu Ala Pro Val Cys Gly Asp Thr Thr Gly Ser Ser Val Thr Leu
130 135 140

Gly Cys Leu Val Lys Gly Tyr Phe Pro Glu Pro Val Thr Leu Thr Trp
145 150 155 160

Asn Ser Gly Ser Leu Ser Ser Gly Val His Thr Phe Pro Ala Val Leu
165 170 175

Gln Ser Asp Leu Tyr Thr Leu Ser Ser Ser Val Thr Val Thr Ser Ser
180 185 190

Thr Trp Pro Ser Gln Ser Ile Thr Cys Asn Val Ala His Pro Ala Ser
195 200 205

Ser Thr Lys Val Asp Lys Lys Ile Glu Pro Arg Gly Pro Thr Ile Lys
210 215 220

Pro Cys Pro Pro Cys Lys Cys Pro Ala Pro Asn Ala Ala Gly Gly Pro
225 230 235 240

Ser Val Phe Ile Phe Pro Pro Lys Ile Lys Asp Val Leu Met Ile Ser
245 250 255

Leu Ser Pro Ile Val Thr Cys Val Val Val Asp Val Ser Glu Asp Asp
260 265 270

Pro Asp Val Gln Ile Ser Trp Phe Val Asn Asn Val Glu Val His Thr
275 280 285

Ala Gln Thr Gln Thr His Arg Glu Asp Tyr Asn Ser Thr Leu Arg Val
290 295 300

Val Ser Ala Leu Pro Ile Gln His Gln Asp Trp Met Ser Gly Lys Glu
305 310 315 320

Phe Lys Cys Lys Val Asn Asn Lys Asp Leu Gly Ala Pro Ile Glu Arg
325 330 335

Thr Ile Ser Lys Pro Lys Gly Ser Val Arg Ala Pro Gln Val Tyr Val
340 345 350

```
Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys


<210> SEQ ID NO 32
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Tyr Asn Asn
            20                  25                  30

Asn Tyr Leu Ser Trp Phe Gln Gln Lys Pro Gly Gln Pro Pro Lys Leu
        35                  40                  45

Leu Ile Tyr Gly Ala Ser Thr Leu Thr Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ser Gly
                85                  90                  95

Ser Ser Asp Lys Tyr Ala Phe Gly Gly Gly Thr Glu Val Val Val Lys
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215


<210> SEQ ID NO 33
<211> LENGTH: 445
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 33

Gln Ser Leu Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Thr
20 25 30

Val Asn Trp Val Arg Gln Ala Pro Gly Lys Gly Leu Glu Trp Ile Gly
35 40 45

Tyr Ile Ser Tyr Gly Gly Ser Ala Tyr Tyr Ala Ser Trp Ala Asn Gly
50 55 60

Arg Phe Thr Ile Ser Lys Thr Ser Ala Thr Val Asp Leu Lys Ile Thr
65 70 75 80

Ser Pro Thr Thr Glu Asp Thr Ala Thr Tyr Phe Cys Ala Arg His Met
85 90 95

Gln Val Gly Gly Ala Pro Thr Gly Ser Met Ala Ala Phe Asp Pro Trp
100 105 110

Gly Pro Gly Thr Leu Val Thr Val Ser Ser Gly Gln Pro Lys Ala Pro
115 120 125

Ser Val Phe Pro Leu Ala Pro Cys Cys Gly Asp Thr Pro Ser Ser Thr
130 135 140

Val Thr Leu Gly Cys Leu Val Lys Gly Tyr Leu Pro Glu Pro Val Thr
145 150 155 160

Val Thr Trp Asn Ser Gly Thr Leu Thr Asn Gly Val Arg Thr Phe Pro
165 170 175

Ser Val Arg Gln Ser Ser Gly Leu Tyr Ser Leu Ser Ser Val Val Ser
180 185 190

Val Thr Ser Ser Ser Gln Pro Val Thr Cys Asn Val Ala His Pro Ala
195 200 205

Thr Asn Thr Lys Val Asp Lys Thr Val Ala Pro Ser Thr Cys Ser Lys
210 215 220

Pro Thr Cys Pro Pro Pro Glu Leu Leu Gly Gly Pro Ser Val Phe Ile
225 230 235 240

Phe Pro Pro Lys Pro Lys Asp Thr Leu Met Ile Ser Arg Thr Pro Glu
245 250 255

Val Thr Cys Val Val Val Asp Val Ser Gln Asp Asp Pro Glu Val Gln
260 265 270

Phe Thr Trp Tyr Ile Asn Asn Glu Gln Val Arg Thr Ala Arg Pro Pro
275 280 285

Leu Arg Glu Gln Gln Phe Asn Ser Thr Ile Arg Val Val Ser Thr Leu
290 295 300

Pro Ile Ala His Gln Asp Trp Leu Arg Gly Lys Glu Phe Lys Cys Lys
305 310 315 320

Val His Asn Lys Ala Leu Pro Ala Pro Ile Glu Lys Thr Ile Ser Lys
325 330 335

Ala Arg Gly Gln Pro Leu Glu Pro Lys Val Tyr Thr Met Gly Pro Pro
340 345 350

Arg Glu Glu Leu Ser Ser Arg Ser Val Ser Leu Thr Cys Met Ile Asn
355 360 365

Gly Phe Tyr Pro Ser Asp Ile Ser Val Glu Trp Glu Lys Asn Gly Lys
370 375 380

Ala Glu Asp Asn Tyr Lys Thr Thr Pro Ala Val Leu Asp Ser Asp Gly
385 390 395 400

```
Ser Tyr Phe Leu Tyr Asn Lys Leu Ser Val Pro Thr Ser Glu Trp Gln
                405                 410                 415

Arg Gly Asp Val Phe Thr Cys Ser Val Met His Glu Ala Leu His Asn
            420                 425                 430

His Tyr Thr Gln Lys Ser Ile Ser Arg Ser Pro Gly Lys
        435                 440                 445


<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Ile Val Ser Lys Thr Tyr Ser Tyr Thr Thr Tyr Tyr Ser Asp Ser
1               5                   10                  15

Val Lys Asp


<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ile Val Ser Lys Thr Tyr Asn Tyr Ala Thr Tyr Tyr Ser Asp Ser
1               5                   10                  15

Val Lys Asp


<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Gln Pro
        35                  40                  45

Lys Leu Leu Ile Tyr Arg Ala Ser Asn Leu Ala Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys
            100                 105                 110


<210> SEQ ID NO 37
<211> LENGTH: 119
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 37

```
Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115
```

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Gln Pro
        35                  40                  45

Lys Leu Leu Ile Tyr Arg Ala Ser Asn Leu Ala Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys
            100                 105                 110
```

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30
```

```
Arg Phe Asn Leu Met His Trp Tyr Gln Gln Lys Pro Gly Lys Gln Pro
        35                  40                  45

Lys Leu Leu Ile Tyr Arg Ala Ser Asn Leu Ala Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys
            100                 105                 110


<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Ala Pro
        35                  40                  45

Lys Leu Leu Ile Tyr Arg Ala Ser Asn Leu Ala Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys
            100                 105                 110


<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Gln Pro
        35                  40                  45

Lys Leu Leu Ile Tyr Arg Ala Ser Asn Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys
            100                 105                 110
```

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

```
Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Trp Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115
```

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

```
Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Gly Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115
```

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Glu Val Gln Leu Val Glu Ser Gly Gly Gly Leu Val Gln Pro Gly Pro
1 5 10 15

Ser Leu Arg Leu Ser Cys Thr Ala Ser Gly Phe Asp Phe Asn Ser Tyr
20 25 30

Gly Met Ser Trp Val Arg Gln Ala Pro Gly Lys Gly Leu Glu Leu Val
35 40 45

Ala Asp Ile Val Ser Lys Thr Tyr Asn Tyr Thr Thr Tyr Tyr Ser Asp
50 55 60

Ser Val Lys Asp Arg Phe Thr Ile Ser Arg Asp Asp Ser Lys Ser Ile
65 70 75 80

Ala Tyr Leu Gln Met Asn Ser Leu Lys Thr Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser
115

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ala Asp Ile Val Ser Lys Thr Tyr Asn Tyr Thr Thr Tyr Tyr Ser Asp
50 55 60

Ser Val Lys Asp Arg Phe Thr Ile Ser Arg Asp Asp Ser Lys Ser Thr
65 70 75 80

Val Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser
115

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Trp Val

```
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115


<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ser Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115


<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asn Ser Lys Ser Thr
65                  70                  75                  80

Val Tyr Leu Gln Met Asn Ser Leu Arg Ala Glu Asp Thr Ala Val Tyr
```

```
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115


<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115


<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115
```

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ala Asp Ile Val Ser Lys Thr Tyr Ser Tyr Thr Thr Tyr Tyr Ser Asp
50 55 60

Ser Val Lys Asp Arg Phe Thr Ile Ser Arg Asp Asp Ser Lys Ser Thr
65 70 75 80

Val Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser
115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ala Asp Ile Val Ser Lys Thr Tyr Gln Tyr Thr Thr Tyr Tyr Ser Asp
50 55 60

Ser Val Lys Asp Arg Phe Thr Ile Ser Arg Asp Asp Ser Lys Ser Thr
65 70 75 80

Val Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser
115

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Ala Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser
        115


<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln Gln Lys Pro Gly Lys Ala Pro
        35                  40                  45

Lys Leu Leu Ile Tyr Arg Ala Ser Asn Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys
            100                 105                 110


<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ser Asp Ile Val Ser Lys Thr Tyr Ser Tyr Thr Thr Tyr Tyr Ser Asp
    50                  55                  60
```

Ser Val Lys Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser
115

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Val Ser Ile Ser
20 25 30

Arg Phe Asn Leu Met His Trp Tyr Gln Gln Lys Pro Gly Lys Ala Pro
35 40 45

Lys Leu Leu Ile Tyr Arg Ala Ser Asn Leu Ala Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln His Ser Arg
85 90 95

Glu Ser Pro Trp Thr Phe Gly Gly Gly Thr Lys Val Glu Ile Lys
100 105 110

<210> SEQ ID NO 57
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ser Asp Ile Val Ser Lys Thr Tyr Asn Tyr Ala Thr Tyr Tyr Ser Asp
50 55 60

Ser Val Lys Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser
115

<210> SEQ ID NO 58
<211> LENGTH: 218
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 58

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Gln Pro
        35                  40                  45

Lys Leu Leu Ile Tyr Arg Ala Ser Asn Leu Ala Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 59
<211> LENGTH: 449
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

```
Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80
```

```
Val Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 60
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Val Ser Ile Ser
20 25 30

Arg Phe Asn Leu Met His Trp Tyr Gln His Lys Pro Gly Lys Gln Pro
35 40 45

Lys Leu Leu Ile Tyr Arg Ala Ser Asn Leu Ala Ser Gly Ile Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln His Ser Arg
85 90 95

Glu Ser Pro Trp Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 61
<211> LENGTH: 218
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Val Ser Ile Ser
20 25 30

Arg Phe Asn Leu Met His Trp Tyr Gln Gln Lys Pro Gly Lys Gln Pro
35 40 45

Lys Leu Leu Ile Tyr Arg Ala Ser Asn Leu Ala Ser Gly Ile Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln His Ser Arg
85 90 95

Glu Ser Pro Trp Thr Phe Gly Gly Gly Thr Lys Val Glu Ile Lys Arg
100 105 110

Thr Val Ala Ala Pro Ser Val Phe Ile Phe Pro Pro Ser Asp Glu Gln

```
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 62
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Ala Pro
        35                  40                  45

Lys Leu Leu Ile Tyr Arg Ala Ser Asn Leu Ala Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 63
<211> LENGTH: 218
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 63

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln His Lys Pro Gly Lys Gln Pro
        35                  40                  45

Lys Leu Leu Ile Tyr Arg Ala Ser Asn Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 64

Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Trp Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 65
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Glu Val Gln Leu Val Glu Ser Gly Gly Gly Leu Val Gln Pro Gly Pro
1 5 10 15

-continued

```
Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Gly Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

```
        435                 440                 445

Lys


<210> SEQ ID NO 66
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Leu Val Gln Pro Gly Pro
1               5                   10                  15

Ser Leu Arg Leu Ser Cys Thr Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 67
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 68
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Trp Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 69
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ser Asp Ile Val Ser Lys Thr Tyr Asn Tyr Thr Thr Tyr Tyr Ser Asp

```
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 70
<211> LENGTH: 449

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 70

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ala Asp Ile Val Ser Lys Thr Tyr Asn Tyr Thr Thr Tyr Tyr Ser Asp
50 55 60

Ser Val Lys Asp Arg Phe Thr Ile Ser Arg Asp Asn Ser Lys Ser Thr
65 70 75 80

Val Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 71
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ala Asp Ile Val Ser Lys Thr Tyr Asn Tyr Thr Thr Tyr Tyr Ser Asp
50 55 60

Ser Val Lys Asp Arg Phe Thr Ile Ser Arg Asp Asp Ser Lys Asn Thr
65 70 75 80

Val Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 72
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Leu Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 73
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Ser Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95
```

```
Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 74
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

-continued

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Gln Tyr Thr Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 75
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ala Asp Ile Val Ser Lys Thr Tyr Asn Tyr Ala Thr Tyr Tyr Ser Asp
    50                  55                  60

Ser Val Lys Asp Arg Phe Thr Ile Ser Arg Asp Asp Ser Lys Ser Thr
65                  70                  75                  80

Val Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 76
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln Gln Lys Pro Gly Lys Ala Pro
        35                  40                  45

Lys Leu Leu Ile Tyr Arg Ala Ser Asn Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 77
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asn Ser Tyr
            20                  25                  30

Gly Met Ser Trp Val Arg Gln Ala Pro Gly Lys Gly Leu Glu Leu Val
        35                  40                  45

Ser Asp Ile Val Ser Lys Thr Tyr Ser Tyr Thr Thr Tyr Tyr Ser Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Thr Val Ala Pro Gly Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 78
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Arg Phe Asn Leu Met His Trp Tyr Gln Gln Lys Pro Gly Lys Ala Pro
        35                  40                  45

Lys Leu Leu Ile Tyr Arg Ala Ser Asn Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 79
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 79

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Asn Ser Tyr
20 25 30

Gly Met Ser Trp Val Arg Gln Ala Pro Gly Lys Gly Leu Glu Leu Val
35 40 45

Ser Asp Ile Val Ser Lys Thr Tyr Asn Tyr Ala Thr Tyr Tyr Ser Asp
50 55 60

Ser Val Lys Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Thr Val Ala Pro Gly Gly Ser Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys

-continued

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 80
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ala Val Leu Thr Gln Ser Pro Asp Ser Leu Ala Val Ser Leu Gly
1               5                   10                  15

Glu Arg Ala Thr Ile Asn Cys Gln Ser Ser Gln Ser Val Tyr Asn Asn
            20                  25                  30

Asn Tyr Leu Ser Trp Phe Gln Gln Lys Pro Gly Gln Pro Pro Lys Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Ser Leu
65                  70                  75                  80

Gln Ala Glu Asp Val Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 81
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Gln Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Thr Val Asn Trp Val Arg Gln Ala Pro Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ala Lys Asn Ser Val Tyr Leu
65                  70                  75                  80

Gln Met Asn Ser Leu Arg Ala Glu Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
        115                 120                 125


<210> SEQ ID NO 82
```

<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Asp Ala Gln Leu Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Tyr Leu Ser Trp Phe Gln Gln Lys Pro Gly Lys Pro Pro Lys Leu
        35                  40                  45

Leu Ile Tyr Gly Ala Ser Thr Leu Thr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110
```

<210> SEQ ID NO 83
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
        115                 120                 125
```

<210> SEQ ID NO 84
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Glu Ala Val Leu Thr Gln Ser Pro Gly Thr Leu Ser Leu Ser Pro Gly
1               5                   10                  15
```

```
Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 85
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ala Val Leu Thr Gln Thr Pro Leu Ser Ser Pro Val Thr Leu Gly
1               5                   10                  15

Gln Pro Ala Ser Ile Ser Cys Gln Ser Ser Gln Ser Val Tyr Asn Asn
            20                  25                  30

Asn Tyr Leu Ser Trp Phe Gln Gln Arg Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ala Gly Thr Asp Phe Thr Leu Lys Ile Ser Arg Val
65                  70                  75                  80

Glu Ala Glu Asp Val Gly Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 86
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Gln Leu Gln Glu Ser Gly Pro Gly Leu Val Lys Pro Ser Glu Thr
1               5                   10                  15

Leu Ser Leu Thr Cys Thr Val Thr Gly Phe Ser Leu Ser Ser Tyr Thr
            20                  25                  30

Val Asn Trp Val Arg Gln Pro Ala Gly Lys Gly Leu Glu Trp Ile Gly
        35                  40                  45

Tyr Ile Ser Tyr Gly Gly Ser Ala Tyr Tyr Ala Ser Trp Ala Asn Gly
    50                  55                  60

Arg Phe Thr Ile Ser Lys Asp Ser Ser Lys Asn Gln Val Ser Leu Lys
65                  70                  75                  80

Leu Ser Ser Val Thr Ala Ala Asp Thr Ala Val Tyr Phe Cys Ala Arg
                85                  90                  95
```

His Met Gln Val Gly Gly Ala Pro Thr Gly Ser Met Ala Ala Phe Asp
100 105 110

Pro Trp Gly Pro Gly Thr Leu Val Thr Val Ser Ser
115 120

<210> SEQ ID NO 87
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Glu Gln Gln Leu Gln Glu Ser Gly Pro Gly Leu Val Lys Pro Ser Glu
1 5 10 15

Thr Leu Ser Leu Thr Cys Thr Val Thr Gly Phe Ser Leu Ser Ser Tyr
20 25 30

Thr Val Asn Trp Val Arg Gln Pro Ala Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Phe Thr Ile Ser Lys Asp Ser Ser Gln Val Ser Leu Lys Leu
65 70 75 80

Ser Ser Val Thr Ala Ala Asp Thr Ala Val Tyr Phe Cys Ala Arg His
85 90 95

Met Gln Val Gly Gly Ala Pro Thr Gly Ser Met Ala Ala Phe Asp Pro
100 105 110

Trp Gly Pro Gly Thr Leu Val Thr Val Ser Ser
115 120

<210> SEQ ID NO 88
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

Gln Gln Leu Gln Glu Ser Gly Pro Gly Leu Val Lys Pro Ser Glu Thr
1 5 10 15

Leu Ser Leu Thr Cys Thr Val Thr Gly Phe Ser Leu Ser Ser Tyr Thr
20 25 30

Val Asn Trp Val Arg Gln Pro Ala Gly Lys Gly Leu Glu Trp Ile Gly
35 40 45

Tyr Ile Ser Tyr Gly Gly Ser Ala Tyr Tyr Ala Ser Trp Ala Asn Gly
50 55 60

Arg Phe Thr Ile Ser Lys Asp Ser Ser Gln Val Ser Leu Lys Leu Ser
65 70 75 80

Ser Val Thr Ala Ala Asp Thr Ala Val Tyr Phe Cys Ala Arg His Met
85 90 95

Gln Val Gly Gly Ala Pro Thr Gly Ser Met Ala Ala Phe Asp Pro Trp
100 105 110

Gly Pro Gly Thr Leu Val Thr Val Ser Ser
115 120

<210> SEQ ID NO 89
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Ile Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 90
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Ala Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Tyr Gln Gln Lys Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 91
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ala Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Ala Pro Arg Leu
```

```
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 92
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ala Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Pro Pro Arg Leu
        35                  40                  45

Leu Ile Tyr Gly Ala Ser Thr Leu Thr Ser Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 93
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
```

```
        115                 120                 125


<210> SEQ ID NO 94
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
        115                 120                 125


<210> SEQ ID NO 95
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
        115                 120                 125


<210> SEQ ID NO 96
<211> LENGTH: 125
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 96

Glu Gln Gln Leu Gln Glu Ser Gly Pro Gly Leu Val Lys Pro Ser Glu
1 5 10 15

Thr Leu Ser Leu Thr Cys Thr Val Thr Gly Phe Ser Leu Ser Ser Tyr
20 25 30

Thr Val Asn Trp Val Arg Gln Pro Ala Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Phe Thr Ile Ser Val Asp Ser Ser Lys Asn Gln Val Ser Leu
65 70 75 80

Lys Leu Ser Ser Val Thr Ala Ala Asp Thr Ala Val Tyr Phe Cys Ala
85 90 95

Arg His Met Gln Val Gly Gly Ala Pro Thr Gly Ser Met Ala Ala Phe
100 105 110

Asp Pro Trp Gly Pro Gly Thr Leu Val Thr Val Ser Ser
115 120 125

<210> SEQ ID NO 97
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Glu Gln Gln Leu Gln Glu Ser Gly Pro Gly Leu Val Lys Pro Ser Glu
1 5 10 15

Thr Leu Ser Leu Thr Cys Thr Val Thr Gly Phe Ser Leu Ser Ser Tyr
20 25 30

Thr Val Asn Trp Val Arg Gln Pro Ala Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Phe Thr Ile Ser Lys Asp Thr Ser Lys Asn Gln Val Ser Leu
65 70 75 80

Lys Leu Ser Ser Val Thr Ala Ala Asp Thr Ala Val Tyr Phe Cys Ala
85 90 95

Arg His Met Gln Val Gly Gly Ala Pro Thr Gly Ser Met Ala Ala Phe
100 105 110

Asp Pro Trp Gly Pro Gly Thr Leu Val Thr Val Ser Ser
115 120 125

<210> SEQ ID NO 98
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Glu Gln Gln Leu Gln Glu Ser Gly Pro Gly Leu Val Lys Pro Ser Glu
1 5 10 15

Thr Leu Ser Leu Thr Cys Thr Val Thr Gly Phe Ser Leu Ser Ser Tyr
20 25 30

```
Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
        115                 120                 125


<210> SEQ ID NO 99
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser
        115                 120                 125


<210> SEQ ID NO 100
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80
```

```
Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Gln Gly Thr Leu Val Thr Val Ser Ser
        115                 120                 125


<210> SEQ ID NO 101
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Ile Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Ala Pro Arg Leu
        35                  40                  45

Leu Ile Tyr Gly Ala Ser Thr Leu Thr Ser Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110


<210> SEQ ID NO 102
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Gln Gly Thr Leu Val Thr Val Ser Ser
        115                 120                 125


<210> SEQ ID NO 103
```

<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

Glu Val Gln Leu Gln Glu Ser Gly Pro Gly Leu Val Lys Pro Ser Glu
1 5 10 15

Thr Leu Ser Leu Thr Cys Thr Val Thr Gly Phe Ser Leu Ser Ser Tyr
20 25 30

Thr Val Asn Trp Ile Arg Gln Pro Ala Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Val Thr Ile Ser Lys Asp Thr Ser Lys Asn Gln Val Ser Leu
65 70 75 80

Lys Leu Ser Ser Val Thr Ala Ala Asp Thr Ala Val Tyr Tyr Cys Ala
85 90 95

Arg His Met Gln Val Gly Gly Ala Pro Thr Gly Ser Met Ala Ala Phe
100 105 110

Asp Pro Trp Gly Gln Gly Thr Leu Val Thr Val Ser Ser
115 120 125

<210> SEQ ID NO 104
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Glu Val Gln Leu Gln Glu Ser Gly Pro Gly Leu Val Lys Pro Ser Glu
1 5 10 15

Thr Leu Ser Leu Thr Cys Thr Val Thr Gly Phe Ser Leu Ser Ser Tyr
20 25 30

Thr Val Asn Trp Ile Arg Gln Pro Ala Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Val Thr Ile Ser Lys Asp Thr Ser Lys Asn Gln Val Ser Leu
65 70 75 80

Lys Leu Ser Ser Val Thr Ala Ala Asp Thr Ala Val Tyr Phe Cys Ala
85 90 95

Arg His Met Gln Val Gly Gly Ala Pro Thr Gly Ser Met Ala Ala Phe
100 105 110

Asp Pro Trp Gly Gln Gly Thr Leu Val Thr Val Ser Ser
115 120 125

<210> SEQ ID NO 105
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Thr Ser Gln Val Ser Leu Lys Leu
65                  70                  75                  80

Ser Ser Val Thr Ala Ala Asp Thr Ala Val Tyr Phe Cys Ala Arg His
                85                  90                  95

Met Gln Val Gly Gly Ala Pro Thr Gly Ser Met Ala Ala Phe Asp Pro
            100                 105                 110

Trp Gly Gln Gly Thr Leu Val Thr Val Ser Ser
        115                 120


<210> SEQ ID NO 106
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ala Val Leu Thr Gln Ser Pro Asp Ser Leu Ala Val Ser Leu Gly
1               5                   10                  15

Glu Arg Ala Thr Ile Asn Cys Gln Ser Ser Gln Ser Val Tyr Asn Asn
            20                  25                  30

Asn Tyr Leu Ser Trp Phe Gln Gln Lys Pro Gly Gln Pro Pro Lys Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Ser Leu
65                  70                  75                  80

Gln Ala Glu Asp Val Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 107
```

<211> LENGTH: 455
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

Glu Gln Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Thr Val Asn Trp Val Arg Gln Ala Pro Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Phe Thr Ile Ser Lys Asp Ser Ala Lys Asn Ser Val Tyr Leu
65 70 75 80

Gln Met Asn Ser Leu Arg Ala Glu Asp Thr Ala Val Tyr Phe Cys Ala
85 90 95

Arg His Met Gln Val Gly Gly Ala Pro Thr Gly Ser Met Ala Ala Phe
100 105 110

Asp Pro Trp Gly Pro Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys Asp Lys Thr His Thr Cys Pro Pro Cys Pro Ala Pro
225 230 235 240

Glu Leu Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Gly Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp

```
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 108
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Asp Ala Gln Leu Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Tyr Leu Ser Trp Phe Gln Gln Lys Pro Gly Lys Pro Pro Lys Leu
        35                  40                  45

Leu Ile Tyr Gly Ala Ser Thr Leu Thr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 109
<211> LENGTH: 455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

```
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 110
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Ala Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 111
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ala Val Leu Thr Gln Thr Pro Leu Ser Ser Pro Val Thr Leu Gly
1               5                   10                  15

Gln Pro Ala Ser Ile Ser Cys Gln Ser Ser Gln Ser Val Tyr Asn Asn
            20                  25                  30
```

```
Asn Tyr Leu Ser Trp Phe Gln Gln Arg Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ala Gly Thr Asp Phe Thr Leu Lys Ile Ser Arg Val
65                  70                  75                  80

Glu Ala Glu Asp Val Gly Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 112
<211> LENGTH: 454
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Gln Gln Leu Gln Glu Ser Gly Pro Gly Leu Val Lys Pro Ser Glu Thr
1               5                   10                  15

Leu Ser Leu Thr Cys Thr Val Thr Gly Phe Ser Leu Ser Ser Tyr Thr
            20                  25                  30

Val Asn Trp Val Arg Gln Pro Ala Gly Lys Gly Leu Glu Trp Ile Gly
        35                  40                  45

Tyr Ile Ser Tyr Gly Gly Ser Ala Tyr Tyr Ala Ser Trp Ala Asn Gly
    50                  55                  60

Arg Phe Thr Ile Ser Lys Asp Ser Ser Lys Asn Gln Val Ser Leu Lys
65                  70                  75                  80

Leu Ser Ser Val Thr Ala Ala Asp Thr Ala Val Tyr Phe Cys Ala Arg
                85                  90                  95

His Met Gln Val Gly Gly Ala Pro Thr Gly Ser Met Ala Ala Phe Asp
            100                 105                 110

Pro Trp Gly Pro Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
```

```
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Gly
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 113
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60
```

```
Gly Arg Phe Thr Ile Ser Lys Asp Ser Ser Gln Val Ser Leu Lys Leu
65                  70                  75                  80

Ser Ser Val Thr Ala Ala Asp Thr Ala Val Tyr Phe Cys Ala Arg His
                85                  90                  95

Met Gln Val Gly Gly Ala Pro Thr Gly Ser Met Ala Ala Phe Asp Pro
            100                 105                 110

Trp Gly Pro Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Gly Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 114
<211> LENGTH: 452
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 114

Gln Gln Leu Gln Glu Ser Gly Pro Gly Leu Val Lys Pro Ser Glu Thr
1               5                   10                  15

Leu Ser Leu Thr Cys Thr Val Thr Gly Phe Ser Leu Ser Ser Tyr Thr
            20                  25                  30

Val Asn Trp Val Arg Gln Pro Ala Gly Lys Gly Leu Glu Trp Ile Gly
        35                  40                  45

Tyr Ile Ser Tyr Gly Gly Ser Ala Tyr Tyr Ala Ser Trp Ala Asn Gly
    50                  55                  60

Arg Phe Thr Ile Ser Lys Asp Ser Ser Gln Val Ser Leu Lys Leu Ser
65                  70                  75                  80

Ser Val Thr Ala Ala Asp Thr Ala Val Tyr Phe Cys Ala Arg His Met
                85                  90                  95

Gln Val Gly Gly Ala Pro Thr Gly Ser Met Ala Ala Phe Asp Pro Trp
            100                 105                 110

Gly Pro Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gly Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

```
Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 115
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ile Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 116
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116
```

-continued

```
Glu Ala Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Tyr Gln Gln Lys Pro Gly Gln Pro Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 117
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Glu Ala Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Ala Pro Arg Leu
        35                  40                  45

Leu Ile Tyr Gly Ala Ser Thr Leu Thr Ser Gly Val Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 118
<211> LENGTH: 219
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 118

Glu Ala Val Leu Thr Gln Ser Pro Gly Thr Leu Ser Leu Ser Pro Gly
1 5 10 15

Glu Arg Ala Thr Leu Ser Cys Gln Ser Ser Gln Ser Val Tyr Asn Asn
20 25 30

Asn Tyr Leu Ser Trp Phe Gln Gln Lys Pro Gly Gln Pro Pro Arg Leu
35 40 45

Leu Ile Tyr Gly Ala Ser Thr Leu Thr Ser Gly Ile Pro Asp Arg Phe
50 55 60

Ser Gly Ser Gly Ser Gly Thr Asp Phe Thr Leu Thr Ile Ser Arg Leu
65 70 75 80

Glu Pro Glu Asp Phe Ala Val Tyr Tyr Cys Ala Gly Gly Tyr Ser Gly
85 90 95

Ser Ser Asp Lys Tyr Ala Phe Gly Gly Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 119
<211> LENGTH: 455
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 119

```
Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

```
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 120
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320
```

```
Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 121
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
```

```
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 122
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Val Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110
```

```
Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455
```

<210> SEQ ID NO 123
<211> LENGTH: 455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

```
Glu Gln Gln Leu Gln Glu Ser Gly Pro Gly Leu Val Lys Pro Ser Glu
1               5                   10                  15
```

Thr Leu Ser Leu Thr Cys Thr Val Thr Gly Phe Ser Leu Ser Ser Tyr
20 25 30

Thr Val Asn Trp Val Arg Gln Pro Ala Gly Lys Gly Leu Glu Trp Ile
35 40 45

Gly Tyr Ile Ser Tyr Gly Gly Ser Ala Tyr Tyr Ala Ser Trp Ala Asn
50 55 60

Gly Arg Phe Thr Ile Ser Lys Asp Thr Ser Lys Asn Gln Val Ser Leu
65 70 75 80

Lys Leu Ser Ser Val Thr Ala Ala Asp Thr Ala Val Tyr Phe Cys Ala
85 90 95

Arg His Met Gln Val Gly Gly Ala Pro Thr Gly Ser Met Ala Ala Phe
100 105 110

Asp Pro Trp Gly Pro Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys Asp Lys Thr His Thr Cys Pro Pro Cys Pro Ala Pro
225 230 235 240

Glu Leu Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Gly Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Glu Glu Met Thr Lys
355 360 365

Asn Gln Val Ser Leu Thr Cys Leu Val Lys Gly Phe Tyr Pro Ser Asp
370 375 380

Ile Ala Val Glu Trp Glu Ser Asn Gly Gln Pro Glu Asn Asn Tyr Lys
385 390 395 400

Thr Thr Pro Pro Val Leu Asp Ser Asp Gly Ser Phe Phe Leu Tyr Ser
405 410 415

Lys Leu Thr Val Asp Lys Ser Arg Trp Gln Gln Gly Asn Val Phe Ser
420 425 430

```
Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 124
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335
```

```
Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 125
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Met Gln Val Gly Gly Ala Pro Thr Gly Ser Met Ala Ala Phe
            100                 105                 110

Asp Pro Trp Gly Pro Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
```

```
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 126
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Gln Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Val Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Phe Thr Ile Ser Lys Asp Ser Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Gln Gly Thr Leu Val Thr Val Ser Ser Ala Ser Thr
        115                 120                 125
```

-continued

```
Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 127
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30
```

-continued

```
Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445
```

```
Leu Ser Leu Ser Pro Gly Lys
    450                 455


<210> SEQ ID NO 128
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Met Gln Val Gly Gly Ala Pro Thr Gly Ser Met Ala Ala Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350
```

```
Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 129
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg His Met Gln Val Gly Gly Ala Pro Thr Gly Ser Met Ala Ala Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
```

```
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Gly Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 130
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Gln Glu Ser Gly Pro Gly Leu Val Lys Pro Ser Glu
1               5                   10                  15

Thr Leu Ser Leu Thr Cys Thr Val Thr Gly Phe Ser Leu Ser Ser Tyr
            20                  25                  30

Thr Val Asn Trp Ile Arg Gln Pro Ala Gly Lys Gly Leu Glu Trp Ile
        35                  40                  45

Gly Tyr Ile Ser Tyr Gly Gly Ser Ala Tyr Tyr Ala Ser Trp Ala Asn
    50                  55                  60

Gly Arg Val Thr Ile Ser Lys Asp Thr Ser Gln Val Ser Leu Lys Leu
65                  70                  75                  80

Ser Ser Val Thr Ala Ala Asp Thr Ala Val Tyr Phe Cys Ala Arg His
                85                  90                  95

Met Gln Val Gly Gly Ala Pro Thr Gly Ser Met Ala Ala Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Gly Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45
```

```
Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys
            100                 105
```

<210> SEQ ID NO 132
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

```
Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Val Arg Gln Pro Pro Gly Lys Ala Leu Glu Trp Met
        35                  40                  45

Gly Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser
        115
```

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

```
Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys
            100                 105
```

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 134

```
Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Gly Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys
            100                 105
```

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 135

```
Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Thr Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys
            100                 105
```

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 136

```
Asp Ile Gln Met Thr Gln Ser Pro Ser Thr Leu Ser Ala Ser Val Gly
1               5                   10                  15
```

```
Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Phe Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys
            100                 105


<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Tyr Cys Gln Gln His His Ala Tyr Pro Phe
                85                  90                  95

Thr Phe Gly Gln Gly Thr Lys Val Glu Ile Lys
            100                 105


<210> SEQ ID NO 138
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Ile Arg Gln Pro Pro Gly Lys Ala Leu Glu Trp Met
        35                  40                  45

Gly Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95
```

```
Arg Asp Pro Val Pro Asn Lys Trp His Phe Asp Phe Trp Gly Pro Gly
            100                 105                 110

Thr Leu Val Thr Val Ser Ser
        115


<210> SEQ ID NO 139
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Val Arg Gln Pro Pro Gly Lys Ala Leu Glu Trp Leu
        35                  40                  45

Gly Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser
        115


<210> SEQ ID NO 140
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Val Arg Gln Pro Pro Gly Lys Ala Leu Glu Trp Met
        35                  40                  45

Ala Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser
        115


<210> SEQ ID NO 141
<211> LENGTH: 119
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

Glu Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Thr Tyr
20 25 30

Asn Val His Trp Val Arg Gln Pro Pro Gly Lys Ala Leu Glu Trp Met
35 40 45

Gly Leu Ile Trp Asn Thr Gly Gly Thr Arg Tyr Asn Ser Ala Leu Lys
50 55 60

Ser Arg Leu Thr Ile Ser Lys Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg Asp Pro Val Pro Asn Lys Trp His Phe Asp Phe Trp Gly Arg Gly
100 105 110

Thr Leu Val Thr Val Ser Ser
115

<210> SEQ ID NO 142
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 142

Glu Val Gln Leu Gln Glu Ser Gly Pro Gly Leu Val Lys Pro Ser Glu
1 5 10 15

Thr Leu Ser Leu Thr Cys Thr Val Ser Gly Phe Ser Leu Thr Thr Tyr
20 25 30

Asn Val His Trp Val Arg Gln Pro Pro Gly Lys Gly Leu Glu Trp Met
35 40 45

Gly Leu Ile Trp Asn Thr Gly Gly Thr Arg Tyr Asn Ser Ala Leu Lys
50 55 60

Ser Arg Leu Thr Ile Ser Lys Asp Thr Ser Lys Ser Gln Val Ser Leu
65 70 75 80

Lys Leu Ser Ser Val Thr Ala Ala Asp Thr Ala Val Tyr Tyr Cys Ala
85 90 95

Arg Asp Pro Val Pro Asn Lys Trp His Phe Asp Phe Trp Gly Pro Gly
100 105 110

Thr Leu Val Thr Val Ser Ser
115

<210> SEQ ID NO 143
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 143

Glu Ile Val Met Thr Gln Ser Pro Ala Thr Leu Ser Val Ser Pro Gly

-continued

```
1               5                   10                  15

Glu Arg Ala Thr Leu Ser Cys Leu Ala Ser Glu Asp Ile Tyr Ser Asn
            20                  25                  30

Leu Ala Trp Tyr Gln Gln Lys Pro Gly Gln Ser Pro Arg Leu Leu Ile
        35                  40                  45

Tyr Asp Ala Arg Ser Leu Gln Asp Gly Val Pro Ala Arg Phe Ser Gly
    50                  55                  60

Ser Glu Ser Gly Pro Glu Tyr Thr Leu Thr Ile Ser Ser Leu Gln Ser
65                  70                  75                  80

Glu Asp Phe Ala Val Tyr Phe Cys Gln Gln His His Ala Tyr Pro Phe
                85                  90                  95

Thr Phe Gly Gln Gly Thr Lys Val Glu Ile Lys
            100                 105


<210> SEQ ID NO 144
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Met Thr Gln Ser Pro Ala Thr Leu Ser Val Ser Pro Gly
1               5                   10                  15

Glu Arg Ala Thr Leu Ser Cys Leu Ala Ser Glu Asp Ile Tyr Ser Asn
            20                  25                  30

Leu Ala Trp Tyr Gln Gln Lys Pro Gly Gln Ser Pro Arg Leu Leu Ile
        35                  40                  45

Tyr Asp Ala Arg Ser Leu Gln Asp Gly Val Pro Ala Arg Phe Ser Gly
    50                  55                  60

Ser Glu Ser Gly Pro Glu Tyr Thr Leu Thr Ile Ser Ser Leu Gln Ser
65                  70                  75                  80

Glu Asp Phe Ala Val Tyr Phe Cys Gln Gln His His Ala Tyr Pro Phe
                85                  90                  95

Thr Phe Gly Gln Gly Thr Lys Val Glu Ile Lys
            100                 105


<210> SEQ ID NO 145
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
```

```
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 146
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Val Arg Gln Pro Pro Gly Lys Ala Leu Glu Trp Met
        35                  40                  45

Gly Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 147
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 148
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Gly Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 149
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 149

Asp Ile Gln Met Thr Gln Ser Pro Ser Thr Leu Ser Ala Ser Val Gly
1 5 10 15

Asp Arg Val Thr Ile Thr Cys Leu Ala Ser Glu Asp Ile Tyr Ser Asn
20 25 30

Leu Ala Trp Tyr Gln Gln Lys Pro Gly Lys Ser Pro Lys Leu Leu Ile
35 40 45

Tyr Asp Ala Arg Ser Leu Gln Asp Gly Val Pro Ser Arg Phe Ser Gly
50 55 60

Ser Glu Ser Gly Thr Glu Tyr Thr Leu Thr Ile Ser Ser Leu Gln Pro
65 70 75 80

Asp Asp Phe Ala Thr Tyr Phe Cys Gln Gln His His Ala Tyr Pro Phe
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 150
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 150

Asp Ile Gln Met Thr Gln Ser Pro Ser Thr Leu Ser Ala Ser Val Gly
1 5 10 15

Asp Arg Val Thr Ile Thr Cys Leu Ala Ser Glu Asp Ile Tyr Ser Asn
20 25 30

Leu Ala Trp Tyr Gln Gln Lys Pro Gly Lys Ser Pro Lys Leu Leu Ile
35 40 45

Tyr Asp Ala Arg Ser Leu Gln Asp Gly Val Pro Ser Arg Phe Ser Gly
50 55 60

Ser Glu Ser Gly Pro Glu Phe Thr Leu Thr Ile Ser Ser Leu Gln Pro
65 70 75 80

Asp Asp Phe Ala Thr Tyr Phe Cys Gln Gln His His Ala Tyr Pro Phe
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 151
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Tyr Cys Gln Gln His His Ala Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 152
<211> LENGTH: 449
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 152

Glu Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Thr Thr Tyr
20 25 30

Asn Val His Trp Ile Arg Gln Pro Pro Gly Lys Ala Leu Glu Trp Met
35 40 45

Gly Leu Ile Trp Asn Thr Gly Gly Thr Arg Tyr Asn Ser Ala Leu Lys
50 55 60

Ser Arg Leu Thr Ile Ser Lys Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg Asp Pro Val Pro Asn Lys Trp His Phe Asp Phe Trp Gly Pro Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 153
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Val Arg Gln Pro Pro Gly Lys Ala Leu Glu Trp Leu
        35                  40                  45

Gly Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 154
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Thr Tyr
            20                  25                  30

Asn Val His Trp Val Arg Gln Pro Pro Gly Lys Ala Leu Glu Trp Met
        35                  40                  45

Ala Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

-continued

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 155
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Thr Leu Ser Ala Ser Val Gly
1               5                   10                  15

Asp Arg Val Thr Ile Thr Cys Leu Ala Ser Glu Asp Ile Tyr Ser Asn
            20                  25                  30

Leu Ala Trp Tyr Gln Gln Lys Pro Gly Lys Ser Pro Lys Leu Leu Ile
        35                  40                  45

Tyr Asp Ala Arg Ser Leu Gln Asp Gly Val Pro Ser Arg Phe Ser Gly
    50                  55                  60

Ser Glu Ser Gly Pro Glu Tyr Thr Leu Thr Ile Ser Ser Leu Gln Pro
65                  70                  75                  80

Asp Asp Phe Ala Thr Tyr Phe Cys Gln Gln His His Ala Tyr Pro Phe
                85                  90                  95

Thr Phe Gly Gln Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 156
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Thr Tyr
            20                  25                  30

Asn Val His Trp Val Arg Gln Pro Pro Gly Lys Gly Leu Glu Trp Met
        35                  40                  45

Gly Leu Ile Trp Asn Thr Gly Gly Thr Arg Tyr Asn Ser Ala Leu Lys
    50                  55                  60

Ser Arg Leu Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Asp Pro Val Pro Asn Lys Trp His Phe Asp Phe Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gly Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 157
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Glu Ile Val Met Thr Gln Ser Pro Ala Thr Leu Ser Val Ser Pro Gly
1 5 10 15

Glu Arg Ala Thr Leu Ser Cys Leu Ala Ser Glu Asp Ile Tyr Ser Asn
20 25 30

Leu Ala Trp Tyr Gln Gln Lys Pro Gly Gln Ser Pro Arg Leu Leu Ile
35 40 45

Tyr Asp Ala Arg Ser Leu Gln Asp Gly Val Pro Ala Arg Phe Ser Gly
50 55 60

Ser Glu Ser Gly Pro Glu Tyr Thr Leu Thr Ile Ser Ser Leu Gln Ser
65 70 75 80

Glu Asp Phe Ala Val Tyr Phe Cys Gln Gln His His Ala Tyr Pro Phe
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 158
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Ile Val Met Thr Gln Ser Pro Ala Thr Leu Ser Val Ser Pro Gly
1               5                   10                  15

Glu Arg Ala Thr Leu Ser Cys Leu Ala Ser Glu Asp Ile Tyr Ser Asn
            20                  25                  30

Leu Ala Trp Tyr Gln Gln Lys Pro Gly Gln Ser Pro Arg Leu Leu Ile
        35                  40                  45

Tyr Asp Ala Arg Ser Leu Gln Asp Gly Val Pro Ala Arg Phe Ser Gly
    50                  55                  60

Ser Glu Ser Gly Pro Glu Tyr Thr Leu Thr Ile Ser Ser Leu Gln Ser
65                  70                  75                  80

Glu Asp Phe Ala Val Tyr Phe Cys Gln Gln His His Ala Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 159
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Asp Ile Val Ser Lys Thr Tyr Gln Tyr Thr Thr Tyr Tyr Ser Asp Ser
1               5                   10                  15
```

Val Lys Asp

<210> SEQ ID NO 160
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

Gln Val Gln Leu Gln Gln Ser Gly Pro Glu Leu Val Arg Pro Gly Ala
1 5 10 15

Ser Val Lys Leu Ser Cys Lys Ala Ser Gly Tyr Ile Phe Ile Thr Tyr
20 25 30

Trp Met Asn Trp Val Lys Gln Arg Pro Gly Gln Gly Leu Glu Trp Ile
35 40 45

Gly Gln Ile Phe Pro Ala Ser Gly Ser Thr Asn Tyr Asn Glu Met Phe
50 55 60

Glu Gly Lys Ala Thr Leu Thr Val Asp Thr Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Gly Asp Gly Asn Tyr Ala Leu Asp Ala Met Asp Tyr Trp Gly
100 105 110

Gln Gly Thr Ser Val Thr Val Ser Ser
115 120

<210> SEQ ID NO 161
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Ser Tyr
20 25 30

Gly Asn Ser Phe Met His Trp Tyr Gln Gln Lys Ser Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Arg Thr Asp Phe Thr Leu Thr Ile Asp
65 70 75 80

Pro Val Glu Ala Asp Asp Ala Ala Thr Tyr Tyr Cys Gln Gln Asn Asn
85 90 95

Glu Asp Pro Leu Thr Phe Gly Ala Gly Thr Lys Leu Glu Ile Lys
100 105 110

<210> SEQ ID NO 162
<211> LENGTH: 836
<212> TYPE: PRT
<213> ORGANISM: Homo sapiens

<400> SEQUENCE: 162

Met Ile Pro Phe Leu Pro Met Phe Ser Leu Leu Leu Leu Leu Ile Val

-continued

```
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
            420                 425                 430
```

-continued

```
Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
        675                 680                 685

Leu Gln Pro Ile Ile Lys Thr Glu Gly Pro Thr Leu Thr Lys Val Lys
    690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Glu Thr Leu Lys Lys Leu Leu Gln Glu Glu Val
    770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Arg Leu Arg Glu
            820                 825                 830

Gly Arg Ser Gln
        835
```

<210> SEQ ID NO 163
<211> LENGTH: 757
<212> TYPE: PRT
<213> ORGANISM: Homo sapiens

<400> SEQUENCE: 163

Met Val Pro Asp Thr Ala Cys Val Leu Leu Leu Thr Leu Ala Ala Leu
1 5 10 15

Gly Ala Ser Gly Gln Gly Gln Ser Pro Leu Gly Ser Asp Leu Gly Pro
20 25 30

Gln Met Leu Arg Glu Leu Gln Glu Thr Asn Ala Ala Leu Gln Asp Val
35 40 45

Arg Glu Leu Leu Arg Gln Gln Val Arg Glu Ile Thr Phe Leu Lys Asn
50 55 60

Thr Val Met Glu Cys Asp Ala Cys Gly Met Gln Gln Ser Val Arg Thr
65 70 75 80

Gly Leu Pro Ser Val Arg Pro Leu Leu His Cys Ala Pro Gly Phe Cys
85 90 95

Phe Pro Gly Val Ala Cys Ile Gln Thr Glu Ser Gly Ala Arg Cys Gly
100 105 110

Pro Cys Pro Ala Gly Phe Thr Gly Asn Gly Ser His Cys Thr Asp Val
115 120 125

Asn Glu Cys Asn Ala His Pro Cys Phe Pro Arg Val Arg Cys Ile Asn
130 135 140

Thr Ser Pro Gly Phe Arg Cys Glu Ala Cys Pro Pro Gly Tyr Ser Gly
145 150 155 160

Pro Thr His Gln Gly Val Gly Leu Ala Phe Ala Lys Ala Asn Lys Gln
165 170 175

Val Cys Thr Asp Ile Asn Glu Cys Glu Thr Gly Gln His Asn Cys Val
180 185 190

Pro Asn Ser Val Cys Ile Asn Thr Arg Gly Ser Phe Gln Cys Gly Pro
195 200 205

Cys Gln Pro Gly Phe Val Gly Asp Gln Ala Ser Gly Cys Gln Arg Arg
210 215 220

Ala Gln Arg Phe Cys Pro Asp Gly Ser Pro Ser Glu Cys His Glu His
225 230 235 240

Ala Asp Cys Val Leu Glu Arg Asp Gly Ser Arg Ser Cys Val Cys Ala
245 250 255

Val Gly Trp Ala Gly Asn Gly Ile Leu Cys Gly Arg Asp Thr Asp Leu
260 265 270

Asp Gly Phe Pro Asp Glu Lys Leu Arg Cys Pro Glu Arg Gln Cys Arg
275 280 285

Lys Asp Asn Cys Val Thr Val Pro Asn Ser Gly Gln Glu Asp Val Asp
290 295 300

Arg Asp Gly Ile Gly Asp Ala Cys Asp Pro Asp Ala Asp Gly Asp Gly
305 310 315 320

Val Pro Asn Glu Lys Asp Asn Cys Pro Leu Val Arg Asn Pro Asp Gln
325 330 335

Arg Asn Thr Asp Glu Asp Lys Trp Gly Asp Ala Cys Asp Asn Cys Arg
340 345 350

Ser Gln Lys Asn Asp Asp Gln Lys Asp Thr Asp Gln Asp Gly Arg Gly
355 360 365

Asp Ala Cys Asp Asp Asp Ile Asp Gly Asp Arg Ile Arg Asn Gln Ala
370 375 380

```
Asp Asn Cys Pro Arg Val Pro Asn Ser Asp Gln Lys Asp Ser Asp Gly
385                 390                 395                 400

Asp Gly Ile Gly Asp Ala Cys Asp Asn Cys Pro Gln Lys Ser Asn Pro
                405                 410                 415

Asp Gln Ala Asp Val Asp His Asp Phe Val Gly Asp Ala Cys Asp Ser
            420                 425                 430

Asp Gln Asp Gln Asp Gly Asp Gly His Gln Asp Ser Arg Asp Asn Cys
        435                 440                 445

Pro Thr Val Pro Asn Ser Ala Gln Glu Asp Ser Asp His Asp Gly Gln
    450                 455                 460

Gly Asp Ala Cys Asp Asp Asp Asp Asp Asn Asp Gly Val Pro Asp Ser
465                 470                 475                 480

Arg Asp Asn Cys Arg Leu Val Pro Asn Pro Gly Gln Glu Asp Ala Asp
                485                 490                 495

Arg Asp Gly Val Gly Asp Val Cys Gln Asp Asp Phe Asp Ala Asp Lys
            500                 505                 510

Val Val Asp Lys Ile Asp Val Cys Pro Glu Asn Ala Glu Val Thr Leu
        515                 520                 525

Thr Asp Phe Arg Ala Phe Gln Thr Val Val Leu Asp Pro Glu Gly Asp
    530                 535                 540

Ala Gln Ile Asp Pro Asn Trp Val Val Leu Asn Gln Gly Arg Glu Ile
545                 550                 555                 560

Val Gln Thr Met Asn Ser Asp Pro Gly Leu Ala Val Gly Tyr Thr Ala
                565                 570                 575

Phe Asn Gly Val Asp Phe Glu Gly Thr Phe His Val Asn Thr Val Thr
            580                 585                 590

Asp Asp Asp Tyr Ala Gly Phe Ile Phe Gly Tyr Gln Asp Ser Ser Ser
        595                 600                 605

Phe Tyr Val Val Met Trp Lys Gln Met Glu Gln Thr Tyr Trp Gln Ala
    610                 615                 620

Asn Pro Phe Arg Ala Val Ala Glu Pro Gly Ile Gln Leu Lys Ala Val
625                 630                 635                 640

Lys Ser Ser Thr Gly Pro Gly Glu Gln Leu Arg Asn Ala Leu Trp His
                645                 650                 655

Thr Gly Asp Thr Glu Ser Gln Val Arg Leu Leu Trp Lys Asp Pro Arg
            660                 665                 670

Asn Val Gly Trp Lys Asp Lys Lys Ser Tyr Arg Trp Phe Leu Gln His
        675                 680                 685

Arg Pro Gln Val Gly Tyr Ile Arg Val Arg Phe Tyr Glu Gly Pro Glu
    690                 695                 700

Leu Val Ala Asp Ser Asn Val Val Leu Asp Thr Thr Met Arg Gly Gly
705                 710                 715                 720

Arg Leu Gly Val Phe Cys Phe Ser Gln Glu Asn Ile Ile Trp Ala Asn
                725                 730                 735

Leu Arg Tyr Arg Cys Asn Asp Thr Ile Pro Glu Asp Tyr Glu Thr His
            740                 745                 750

Gln Leu Arg Gln Ala
        755
```

<210> SEQ ID NO 164
<211> LENGTH: 3713
<212> TYPE: DNA
<213> ORGANISM: Homo sapiens

<400> SEQUENCE: 164

```
gcactcggct gtgcggcggg gcaggcatgg gagccgcgcg ctctctcccg gcgcccacac     60
ctgtctgagc ggcgcagcga gccgcggccc gggcgggctg ctcggcgcgg aacagtgctc    120
ggcatggcag ggattccagg gctcctcttc cttctcttct ttctgctctg tgctgttggg    180
caagtgagcc cttacagtgc cccctggaaa cccacttggc ctgcataccg cctccctgtc    240
gtcttgcccc agtctaccct caatttagcc aagccagact ttggagccga agccaaatta    300
gaagtatctt cttcatgtgg accccagtgt cataagggaa ctccactgcc cacttacgaa    360
gaggccaagc aatatctgtc ttatgaaacg ctctatgcca atggcagccg cacagagacg    420
caggtgggca tctacatcct cagcagtagt ggagatgggg cccaacaccg agactcaggg    480
tcttcaggaa agtctcgaag gaagcggcag atttatggct atgacagcag gttcagcatt    540
tttgggaagg acttcctgct caactaccct ttctcaacat cagtgaagtt atccacgggc    600
tgcaccggca ccctggtggc agagaagcat gtcctcacag ctgcccactg catacacgat    660
ggaaaaacct atgtgaaagg aacccagaag cttcgagtgg gcttcctaaa gcccaagttt    720
aaagatggtg gtcgaggggc caacgactcc acttcagcca tgcccgagca gatgaaattt    780
cagtggatcc gggtgaaacg cacccatgtg cccaagggtt ggatcaaggg caatgccaat    840
gacatcggca tggattatga ttatgccctc ctggaactca aaaagcccca caagagaaaa    900
tttatgaaga ttggggtgag ccctcctgct aagcagctgc cagggggcag aattcacttc    960
tctggttatg acaatgaccg accaggcaat ttggtgtatc gcttctgtga cgtcaaagac   1020
gagacctatg acttgctcta ccagcaatgc gatgcccagc caggggccag cgggtctggg   1080
gtctatgtga ggatgtggaa gagacagcag cagaagtggg agcgaaaaat tattggcatt   1140
ttttcagggc accagtgggt ggacatgaat ggttccccac aggatttcaa cgtggctgtc   1200
agaatcactc ctctcaaata tgcccagatt tgctattgga ttaaaggaaa ctacctggat   1260
tgtagggagg ggtgacacag tgttccctcc tggcagcaat taagggtctt catgttctta   1320
ttttaggaga ggccaaattg tttttttgtca ttggcgtgca cacgtgtgtg tgtgtgtgtg   1380
tgtgtgtgta aggtgtctta taatctttta cctatttctt acaattgcaa gatgactggc   1440
tttactattt gaaaactggt ttgtgtatca tatcatatat catttaagca gtttgaaggc   1500
atacttttgc atagaaataa aaaaaatact gatttggggc aatgaggaat atttgacaat   1560
taagttaatc ttcacgtttt tgcaaacttt gatttttatt tcatctgaac ttgtttcaaa   1620
gatttatatt aaatatttgg catacaagag atatgaattc ttatatgtgt gcatgtgtgt   1680
tttcttctga gattcatctt ggtggtgggt ttttttgttt ttttaattca gtgcctgatc   1740
tttaatgctt ccataaggca gtgttcccat ttaggaactt tgacagcatt tgttaggcag   1800
aatattttgg atttggaggc atttgcatgg tagtctttga acagtaaaat gatgtgttga   1860
ctatactgat acacatatta aactatacct tatagtaaac cagtatccca agctgctttt   1920
agttccaaaa atagtttctt ttccaaaggt tgttgctcta ctttgtagga agtctttgca   1980
tatggccctc ccaactttaa agtcatacca gagtggccaa gagtgtttat cccaaccctt   2040
ccatttaaca ggatttcact cacatttctg gaactagcta tttttcagaa gacaataatc   2100
agggcttaat tagaacaggc tgtatttcct cccagcaaac agttgtggcc acactaaaaa   2160
caatcatagc attttacccc tggattatag cacatctcat gttttatcat ttggatggag   2220
taatttaaaa tgaattaaat tccagagaac aatggaagca ttgcctggca gatgtcacaa   2280
cagaataacc acttgtttgg agcctggcac agtcctccag cctgatcaaa aattattctg   2340
```

catagttttc agtgtgcttt ctgggagcta tgtacttctt caatttggaa acttttctct 2400
ctcatttata gtgaaaatac ttggaagtta ctttaagaaa accagtgtgg ccttttttccc 2460 tctagcttta aaagggccgc ttttgctgga atgctctagg ttatagataa acaattaggt 2520
ataatagcaa aaatgaaaat tggaagaatg caaaatggat cagaatcatg ccttccaata 2580
aaggccttta cacatgtttt atcaatatga ttatcaaatc acagcatata cagaaaagac 2640
ttggacttat tgtatgtttt tattttatgg ctctcggcct aagcacttct ttctaaatgt 2700
atcggagaaa aaatcaaatg gactacaagc acgtgtttgc tgtgcttgca ccccaggtaa 2760
acctgcattg tagcaatttg taaggatatt cagatggagc actgtcactt agacattctc 2820
tgggggattt tctgcttgtc tttcttgagc tttttggaag gataattctg ataaggcact 2880
caagaaacgt acaaccacag tgctttcttc aaatcatatg agaaatacta tgcatagcaa 2940
ggagatgcag agccgccagg aaaattctga gttccagcac aattttcttt ggaatctaac 3000
aggaatctag cctgaggaag aagggaggtc tccatttcta tgtctggtat ttgggggttt 3060
tgtttgtttt tgctttagct tggtgaaaaa aagttcactg aacaccaaga ccagaatgga 3120 ttttttttaaa aaaatagatg ttccttttgt gaagcacctt gattccttga ttttgatttt 3180
ttgcaaagtt agacaatggc acaaagtcaa aatgaaatca atgtttagtt cacaagtaga 3240
tgtaatttac taaagaatga tacacccata tgctatatac agcttaactc acagaactgt 3300
aaaagaaaat tataaaataa ttcaacatgt ccatcttttt agtgataata aaagaaagca 3360
tggtattaaa ctatcataga agtagacaga aaaagaaaaa aggactcatg gcattattaa 3420
tataattagt gctttacatg tgttagttat acatattaga agcatatttg cctagtaagg 3480
ctagtagaac cacatttccc aaagtgtgct ccttaaacac tcatgcctta tgattttcta 3540
ccaaaagtaa aaagggttgt attaagtcag aggaagatgc ctctccattt tccctctctt 3600
tatcagaggt tcacatgcct gtctgcacat taaaagctct gggaagacct gttgtaaagg 3660
gacaagttga ggttgtaaaa tctgcattta aataaacatc tttgatcaca aaa 3713

<210> SEQ ID NO 165
<211> LENGTH: 6817
<212> TYPE: DNA
<213> ORGANISM: Homo sapiens

<400> SEQUENCE: 165
gcagtcggga gccggccgtg gtggctccgt gcgtccgagc gtccgtccgc gccgtcggcc 60
atggccaagc gctccagggg ccccgggcgc cgctgcctgt tggcgctcgt gctgttctgc 120 gcctgggggga cgctggccgt ggtggcccag aagccgggcg cagggtgtcc gagccgctgc 180
ctgtgcttcc gcaccaccgt gcgctgcatg catctgctgc tggaggccgt gcccgccgtg 240
gcgccgcaga cctccatcct agatcttcgc tttaacagaa tcagagagat ccaacctggg 300
gcattcaggc ggctgaggaa cttgaacaca ttgcttctca ataataatca gatcaagagg 360
atacctagtg gagcatttga agacttggaa aatttaaaat atctctatct gtacaagaat 420
gagatccagt caattgacag gcaagcattt aagggacttg cctctctaga gcaactatac 480
ctgcacttta atcagataga aactttggac ccagattcgt tccagcatct cccgaagctc 540
gagaggctat ttttgcataa caaccggatt acacatttag ttccagggac atttaatcac 600
ttggaatcta tgaagagatt gcgactggac tcaaacacac ttcactgcga ctgtgaaatc 660
ctgtggttgg cggatttgct gaaaacctac gcggagtcgg ggaacgcgca ggcagcggcc 720

-continued

```
atctgtgaat atcccagacg catccaggga cgctcagtgg caaccatcac cccggaagag    780
ctgaactgtg aaaggccccg gatcacctcc gagccccagg acgcagatgt gacctcgggg    840
aacaccgtgt acttcacctg cagagccgaa ggcaacccca agcctgagat catctggctg    900
cgaaacaata atgagctgag catgaagaca gattcccgcc taaacttgct ggacgatggg    960
accctgatga tccagaacac acaggagaca gaccagggta tctaccagtg catggcaaag   1020
aacgtggccg gagaggtgaa gacgcaagag gtgaccctca ggtacttcgg gtctccagct   1080
cgacccactt ttgtaatcca gccacagaat acagaggtgc tggttgggga gagcgtcacg   1140
ctggagtgca gcgccacagg ccaccccccg ccgcggatct cctggacgag aggtgaccgc   1200
acacccttgc cagttgaccc gcgggtgaac atcacgcctt ctggcgggct ttacatacag   1260
aacgtcgtac agggggacag cggagagtat gcgtgctctg cgaccaacaa cattgacagc   1320
gtccatgcca ccgctttcat catcgtccag gctcttcctc agttcactgt gacgcctcag   1380
gacagagtcg ttattgaggg ccagaccgtg gatttccagt gtgaagccaa gggcaacccg   1440
ccgcccgtca tcgcctggac caagggaggg agccagctct ccgtggaccg gcggcacctg   1500
gtcctgtcat cgggaacact tagaatctct ggtgttgccc tccacgacca gggccagtac   1560
gaatgccagg ctgtcaacat catcggctcc cagaaggtcg tggcccacct gactgtgcag   1620
cccagagtca ccccagtgtt tgccagcatt cccagcgaca caacagtgga ggtgggcgcc   1680
aatgtgcagc tcccgtgcag ctcccagggc gagcccgagc cagccatcac ctggaacaag   1740
gatggggttc aggtgacaga aagtggaaaa tttcacatca gccctgaagg attcttgacc   1800
atcaatgacg ttggccctgc agacgcaggt cgctatgagt gtgtggcccg gaacaccatt   1860
gggtcggcct cggtgagcat ggtgctcagt gtgaatgttc ctgacgtcag tcgaaatgga   1920
gatccgtttg tagctacctc catcgtggaa gcgattgcga ctgttgacag agctataaac   1980
tcaacccgaa cacatttgtt tgacagccgt cctcgttctc caaatgattt gctggccttg   2040
ttccggtatc cgagggatcc ttacacagtt gaacaggcac gggcgggaga aatctttgaa   2100
cggacattgc agctcattca ggagcatgta cagcatggct tgatggtcga cctcaacgga   2160
acaagttacc actacaacga cctggtgtct ccacagtacc tgaacctcat cgcaaacctg   2220
tcgggctgta ccgcccaccg gcgcgtgaac aactgctcgg acatgtgctt ccaccagaag   2280
taccggacgc acgacggcac ctgtaacaac ctgcagcacc ccatgtgggg cgcctcgctg   2340
accgccttcg agcgcctgct gaaatccgtg tacgagaatg gcttcaacac ccctcggggc   2400
atcaaccccc accgactgta caacgggcac gcccttccca tgccgcgcct ggtgtccacc   2460
accctgatcg ggacggagac cgtcacaccc gacgagcagt tcacccacat gctgatgcag   2520
tggggccagt tcctggacca cgacctcgac tccacggtgg tggccctgag ccaggcacgc   2580
ttctccgacg gacagcactg cagcaacgtg tgcagcaacg acccccccctg cttctctgtc   2640
atgatccccc ccaatgactc ccgggccagg agcggggccc gctgcatgtt cttcgtgcgc   2700
tccagccctg tgtgcggcag cggcatgact tcgctgctca tgaactccgt gtacccgcgg   2760
gagcagatca accagctcac ctcctacata gacgcatcca acgtgtacgg gagcacggag   2820
catgaggccc gcagcatccg cgacctggcc agccaccgcg gcctgctgcg gcagggcatc   2880
gtgcagcggt ccgggaagcc gctgctcccc ttcgccaccg ggccgcccac ggagtgcatg   2940
cgggacgaga acgagagccc catcccctgc ttcctggccg gggaccaccg cgccaacgag   3000
cagctgggcc tgaccagcat gcacacgctg tggttccgcg agcacaaccg cattgccacg   3060
gagctgctca agctgaaccc gcactgggac ggcgacacca tctactatga gaccaggaag   3120
```

-continued

```
atcgtgggtg cggagatcca gcacatcacc taccagcact ggctcccgaa gatcctgggg   3180
gaggtgggca tgaggacgct gggagagtac cacggctacg accccggcat caatgctggc   3240
atcttcaacg ccttcgccac cgcggccttc aggtttggcc acacgcttgt caacccactg   3300
ctttaccggc tggacgagaa cttccagccc attgcacaag atcacctccc ccttcacaaa   3360
gctttcttct ctcccttccg gattgtgaat gagggcggca tcgatccgct tctcaggggg   3420
ctgttcgggg tggcggggaa aatgcgtgtg ccctcgcagc tgctgaacac ggagctcacg   3480
gagcggctgt tctccatggc acacacggtg gctctggacc tggcggccat caacatccag   3540
cggggccggg accacgggat cccaccctac cacgactaca gggtctactg caatctatcg   3600
gcggcacaca cgttcgagga cctgaaaaat gagattaaaa accctgagat ccgggagaaa   3660
ctgaaaaggt tgtatggctc gacactcaac atcgacctgt ttccggcgct cgtggtggag   3720
gacctggtgc ctggcagccg gctgggcccc accctgatgt gtcttctcag cacacagttc   3780
aagcgcctgc gagatgggga caggttgtgg tatgagaacc ctggggtgtt ctccccggcc   3840
cagctgactc agatcaagca gacgtcgctg gccaggatcc tatgcgacaa cgcggacaac   3900
atcacccggg tgcagagcga cgtgttcagg gtggcggagt tccctcacgg ctacggcagc   3960
tgtgacgaga tccccagggt agacctccgg gtgtggcagg actgctgtga agactgtagg   4020
accagggggc agttcaatgc cttttcctat catttccgag gcagacggtc tcttgagttc   4080
agctaccagg aggacaagcc gaccaagaaa acaagaccac ggaaaatacc cagtgttggg   4140
agacaggggg aacatctcag caacagcacc tcagccttca gcacacgctc agatgcatct   4200
gggacaaatg acttcagaga gtttgttctg gaaatgcaga agaccatcac agacctcaga   4260
acacagataa agaaacttga atcacggctc agtaccacag agtgcgtgga tgccgggggc   4320
gaatctcacg ccaacaacac caagtggaaa aaagatgcat gcaccatttg tgaatgcaaa   4380
gacgggcagg tcacctgctt cgtggaagct tgcccccctg ccacctgtgc tgtccccgtg   4440
aacatcccag gggcctgctg tccagtctgc ttacagaaga gggcggagga aaagccctag   4500
gctcctggga ggctcctcag agtttgtctg ctgtgccatc gtgagatcgg gtggccgatg   4560
gcagggagct gcggactgca gaccaggaaa cacccagaac tcgtgacatt tcatgacaac   4620
gtccagctgg tgctgttaca gaaggcagtg caggaggctt ccaaccagag catctgcgga   4680
gaaggaggca cagcaggtgc ctgaagggaa gcaggcagga gtcctagctt cacgttagac   4740
ttctcaggtt tttatttaat tcttttaaaa tgaaaaattg gtgctactat taaattgcac   4800
agttgaatca tttaggcgcc taaattgatt ttgcctccca acaccatttc tttttaaata   4860
aagcaggata cctctatatg tcagccttgc cttgttcaga tgccaggagc cggcagacct   4920
gtcacccgca ggtggggtga gtcttggagc tgccagaggg gctcaccgaa atcggggttc   4980
catcacaagc tatgtttaaa aagaaaattg gtgtttggca aacggaacag aacctttgat   5040
gagagcgttc acagggacac tgtctggggg tgcagtgcaa gcccccggcc tcttccctgg   5100
gaacctctga actcctcctt cctctgggct ctctgtaaca tttcaccaca cgtcagcatc   5160
taatcccaag acaaacattc ccgctgctcg aagcagctgt atagcctgtg actctccgtg   5220
tgtcagctcc ttccacacct gattagaaca ttcataagcc acatttagaa acaggtttgc   5280
tttcagctgt cacttgcaca catactgcct agttgtgaac caaatgtgaa aaaacctcct   5340
tcatcccatt gtgtatctga tacctgccga gggccaaggg tgtgtgttga caacgccgct   5400
cccagccggc cctggttgcg tccacgtcct gaacaagagc cgcttccgga tggctcttcc   5460
```

-continued

```
caagggagga ggagctcaag tgtcgggaac tgtctaactt caggttgtgt gagtgcgtta   5520

aaaaaaaaaa aaaaaaagaa tccctatacc tcatttgtat ttttaaaatg cgtgatgttt   5580

tatgaaattg tgtccatttt ttaggtatta gatatggcag aaaaaccatt tccactatgc   5640

aaagttcttt tagacgtcag tgaaaatcaa ctctcatacc tcatggtctc tctttaattg   5700

accaaaacct tccatttttc tctaaataca aagcgatctg tgttctgagc aacctttccc   5760

cgaacacaca gcttcagtgc agcacgctga cctgagtatc caccatgtgc caggcacagt   5820

gctgggcaca cgaggcacca aggtccgggc cacctgcccg cagcaaggcc cagctgaggt   5880

ggtggaggga gcccctgagg tcaggggccg tttcggttca gggtggcagg tgtccagcac   5940

tggggtatgg cgtcgaggct tccatggggt gggggaggcc agcttccttc tgacaggatg   6000

ggcgcataca gtgcctggtg tgatttgtgc acaacccgtg ttccaggtgc acatcctccc   6060

aaggagacac ccagaccctt ccagcacggg ccggccaagt tgctgcggcg gaggcagcat   6120

ttcagctgtg aggaaggtca ttggattcat gtgttttatc tgtaaaaatg gttgtcttaa   6180

cttcttaacc tcatattggt aagtgattga taaaaattgg ttggtgtttc atgacatgtg   6240

gacttctttt gaaatagcaa gtcaaatgta gtgaccaaat tgtggaagag atttctgtca   6300

aataggaaat gtgtaagttc gtctaaaagc tgatggttat gtaagttgct caggcactca   6360

gatgacagca gattctgggt tctgggagtg ttctgtgcct cttacatgcc ctggaggcct   6420

catggtctca gtgctgaggc ggcacacctg tagcacacct gcgtaatgtg cggtctgggc   6480

cagtcacaag gaattgtgtt gtctaagcca aaggggggaag ctgactgtga tttaccaaaa   6540

aaaattctgt aattcaaacc aaaatgtctg cggaatcacc agtttgatac tctctgtaat   6600

cagaacagtg ggcagtgcct gggtgaacgt gtctagcagc cactgtgcgg gatcgctgta   6660

acaggagtgg aatgtacata tttatttact tttctaactg ctccaacagc caaatgcctt   6720

ttttatgacc attgtattca gttcattacc aaagaaatgt ttgcactttg taatgatgcc   6780

tttcagttca aataaatggg tcacattttc aaatgga                            6817
```

<210> SEQ ID NO 166
<211> LENGTH: 5577
<212> TYPE: DNA
<213> ORGANISM: Homo sapiens

<400> SEQUENCE: 166

```
ggatcacagc ccttccccga tcctctccgt gggagccagc gagcctctct ccctgatctt     60

acgtgctcaa gggagctcac acgttcacca actcaccctt gaagtcatct caagaacaaa    120

agacaactga aagaagctgt tgtgaaggca gagcagcatc tgctgaagag acagaaacca    180

gccccagagg tgtcacagga aggcaccagc aaggacattg gtctttgatt tgattcagca    240

gtcctgtcaa gtataaatgt gatggctgtg ctgcctggcc ctctgcagct gctgggagtg    300

ctgcttacca tttccctgag ttccatcagg ctcattcagg ctggtgccta ctatgggatc    360

aagccgctgc cacctcaaat tcctcctcag atgccaccac aaattccaca ataccagccc    420

ctgggtcagc aagtacctca catgcctttg gccaaagatg gccttgccat gggcaaggag    480

atgccccact tgcagtatgg caaagagtat ccacacctac cccaatatat gaaggaaatt    540

caaccggcgc caagaatggg caaggaagcc gtacccaaga aaggcaaaga aataccatta    600

gccagtttac gaggggaaca aggtccccgt ggagagcctg gcccaagagg accacctggg    660

ccccctggtt tgccaggtca tgggatacct ggaattaaag gaaaaccagg gccacaggga    720

tatccaggag ttggaaagcc aggtatgcct ggaatgccag ggaagccagg agccatgggc    780
```

```
atgcctgggg caaaaggaga aattggacag aaaggggaaa ttgggcctat ggggatccca    840
ggaccacaag gacctccagg gcctcatgga cttcctggca ttgggaagcc aggtgggcca    900
gggttaccag ggcaaccagg accaaagggt gatcgaggac ccaaaggact accaggacct    960
caaggccttc ggggtcctaa aggagacaag ggcttcggga tgccaggtgc gccaggtgta   1020
aaggggcctc cagggatgca cggccctccc ggccctgttg gactgccagg agtgggcaaa   1080
ccaggagtga caggcttccc tgggccccag ggccccctgg gaaagccagg ggctccagga   1140
gaacctgggc cacaaggccc tattggggta ccgggggttc aaggacctcc tgggataccc   1200
ggaattggaa agccaggcca ggatgggatc ccaggccagc caggatttcc aggtggcaaa   1260
ggggagcaag gactgccagg gctaccagga cccccaggcc ttccagggat tgggaaacca   1320
ggcttcccag gacccaaagg tgaccggggc atgggaggtg ttcctggggc tcttggacca   1380
agaggggaga aaggaccaat aggtgcccca ggaatagggg gtcctccagg agagccaggc   1440
ctgcctggaa tcccaggtcc tatgggccct ccaggtgcta ttggttttcc tggacccaaa   1500
ggagaaggtg ggattgtagg gccacagggg ccaccaggtc ccaagggtga gccagggctt   1560
caaggcttcc caggaaagcc aggtttcctt ggtgaagtag ggcctcctgg catgaggggt   1620
ttgccaggtc ccatagggcc caagggggaa gctgggcaaa aaggtgtacc aggactccct   1680
ggtgttccag ggcttctcgg acctaaggga gagccaggaa tcccagggga tcagggttta   1740
cagggccccc caggtatccc agggattggg ggccctagtg gccccattgg accacctggg   1800
attccaggcc ccaaagggga gccgggcctc ccagggcccc ctgggttccc tggtataggg   1860
aaacccggag tggcaggact tcatggcccc ccagggaagc ctggtgccct tggtcctcaa   1920
ggccagcctg gccttccagg acccccaggc cctccaggac ctccaggacc cccagctgtg   1980
atgcccccta caccaccacc ccagggagag tatctgccag atatggggct gggaattgat   2040
ggcgtgaaac ccccccatgc ctacggggct aagaaaggca agaatggagg gccagcctat   2100
gagatgcctg catttaccgc cgagctaacc gcacctttcc caccggtggg ggccccagtg   2160
aagtttaaca aactgctgta taacggcaga cagaactaca acccgcagac aggcatcttc   2220
acctgtgagg tccctggtgt ctactacttt gcataccacg ttcactgcaa gggggggcaac   2280
gtgtgggttg ctctattcaa gaacaacgag cccgtgatgt acacgtacga cgagtacaaa   2340
aagggcttcc tggaccaggc atctgggagt gcagtgctgc tgctcaggcc cggagaccgg   2400
gtgttcctcc agatgccctc agaacaggct gcaggactgt atgccgggca gtatgtccac   2460
tcctcctttt caggatattt attgtatccc atgtaaaaac aaaaaaacaa aaaacaaaga   2520
aaagaaagag attttataga agaaaatgac acaccaaaaa atccaaatga aaaacataat   2580
tgcttcaaaa cacttacaca gttggaaagt tatatgtaag tgaaaatttg gaccattgtg   2640
tacaaataaa aactaagatg catgtttaat actccacaca gcagcctgta attgcgaatg   2700
atgggataga gttatgtatc aagtactgac acttggttgt acccactgga atcatattag   2760
ctgttttatg ttatatgctt ccacagtaac ctgcttattc agatcagtca aaatatatca   2820
gtatgaaaga tcatagctaa tgaaaggcac tcactcatat tgtttacttt aaaatattta   2880
taaatatgcc ttaaagaaat acaaatgata acaattacat accgtattta cttgcttaat   2940
ttcctctgta tttgtgtaga tactttgaca tggaatatat ggtggggaga cccgtagtgt   3000
taccgcccca gtgggagggg gccctgggga ccctggtaat gctttagtca aagggatatc   3060
tctcttgtat cagaggctgt gtcttttagt aacaggagtc ctcgtcagaa ttgcgtgtct   3120
```

-continued

```
gttgtctcta aaagaatggg tgaaccaatc ggcctttgtg aatttattca gtgccttctc   3180
tgtaccaagc actgggtaag gcacttttgt ggagcattag acagtaaccc tcaaggagct   3240
agagaaccgg atgggagaca tgagcagtaa ttaactcact tgttccccag agtttctatt   3300
tgttttgatt ttctttttct gtgacttatt ttcctatttt ctttcctcca tgtaattttc   3360
actatggccc aactaatata aacacctgga aattacaagg aaaaaaaatt cttcctctaa   3420
taactttcca aatttgtgga atatttattt gtaatagcag ttatcagtta tgcttatata   3480
gcattaaaaa ttctcctcct ttgactacac acacaaccac agtgtggttc taatcatgga   3540
gatatcagta atttttagta actgaatttt gaggacattt ctctgtttag catgtatgca   3600
aactgatatg taatctgagg ttccaaagtc aatttttttc tttttttttt gagatggagt   3660
cttactctgt cacccaggct ggagtgcagt agcacgatct tggcttactg caacctctac   3720
ctcctaggtt caagcaattg tcctgtctca gcctcccgag tactgggact actgtcttgc   3780
gccaccatgc ctggctaatt tttgtatatt tagtaaagat gggttttcgc catgttggcc   3840
aggctggtct caaactcctg gcctcaagtg atgcacctgc ctcagccttc caaagtgctg   3900
ggattacagg catgagccac cgtgcccggc caaagtcagc tttcaaaatc caagccataa   3960
ttggtgaggg gggagtttca gaattacata gaaaaaattaa tatttgaaaa aataattctg   4020
aaatttcgaa tttaaaaaca gatgtgctgc ttctgggtgt aggtagtaaa agtataggaa   4080
aagaactgtt tccttagaag cggactgtgg aagggctatg tagaatgtca aagggcaaca   4140
agagcctgtg tttttaatgt catcctgtac tcggcacaaa tcaaaggcca atacaagtct   4200
gaaaagcaga aataaatatt tttccaggtt tttgcttggg cacatactaa ctgctttggg   4260
cattctaatc tggtctccaa acaccaaaga cccatttcga gcctgctatt agcctgctgc   4320
tgactctatc acttggagca ataatgtggg gttatggtgg tggaatcttg tatatttttg   4380
tcaaaaataa aaccatgagt taaggggata gatatagatg gaaaaataca caaataaata   4440
cggtatgaaa acacatggaa atgtgtcttt gtcaaatctg aatcattatt accatcacaa   4500
aaattcttct cttggccaat atctcatttc cctatatagt atacaagcac catttcttct   4560
caatttttaa gaagagaaat tagtccatta ccacaggggt tcttgtcact actaattata   4620
caacaatctt ttcccaacaa aaagatgtcc tccacaacct ttgttttcaa agcagacagc   4680
atctatgtgg ccaaatatac tttgggttgt tcttgaggat actggttttg ggctgatgac   4740
tatggtgggc agcatggatc cattgggctc cttctgctaa acagccacat tgaaatggtt   4800
taaaagcaag tcagatcagg tgatttgtaa aattgtattt atctgtacat gtatgggctt   4860
ttaattccca ccaagaaaga gagaaattat ctttttagtt aaaaccaaat ttcacttttc   4920
aaaatatctt ccaacttatt tattggttgt cactcaattg cctatatata tatatatatg   4980
tgtgtgtgtg tgtgtgtgcg cgtgagcgca cgtgtgtgta tgcgtgcgca tgtgtgtgta   5040
tgtgtattat cagacatagg tttctaactt ttagatagaa gaggagcaac atctatgcca   5100
aatactgtgc attctacaat ggtgctaatc tcagacctaa atgatactcc atttaattta   5160
aaaaagagtt ttaaataatt atctatgtgc ctgtatttcc cttttgagtg ctgcacaaca   5220
tgttaacata ttagtgtaaa agcagatgaa acaaccacgt gttctaaagt ctagggattg   5280
tgctataatc cctatttagt tcaaaattaa ccagaattct tccatgtgaa atggaccaaa   5340
ctcatattat tgttatgtaa atacagagtt ttaatgcagt atgacatccc acaggggaaa   5400
agaatgtctg tagtgggtga ctgttatcaa atattttata gaatacaatg aacggtgaac   5460
agactggtaa cttgtttgag ttcccatgac agatttgaga cttgtcaata gcaaatcatt   5520
```

tttgtattta aatttttgta ctgatttgaa aaacatcatt aaatatcttt aaaagta 5577

<210> SEQ ID NO 167
<211> LENGTH: 10532
<212> TYPE: DNA
<213> ORGANISM: Homo sapiens

<400> SEQUENCE: 167
agtcttccac caaaggccgt tcagttctcc tgggctccag cctcctgcaa ggactgcaag 60
agttttcctc cgcagctctg agtctccact tttttggtgg agaaaggctg caaaaagaaa 120
aagagacgca gtgagtggga aaagtatgca tcctattcaa acctaattga atcgaggagc 180
ccagggacac acgccttcag gtttgctcag gggttcatat ttggtgctta gacaaattca 240
aaatgaggaa acatcggcac ttgcccttag tggccgtctt ttgcctcttt ctctcaggct 300
ttcctacaac tcatgcccag cagcagcaag cagatgtcaa aaatggtgcg gctgctgata 360
taatatttct agtggattcc tcttggacca ttggagagga acatttccaa cttgttcgag 420
agtttctata tgatgttgta aaatccttag ctgtgggaga aaatgatttc cattttgctc 480
tggtccagtt caacggaaac ccacataccg agttcctgtt aaatacgtat cgtactaaac 540
aagaagtcct ttctcatatt tccaacatgt cttatattgg gggaaccaat cagactggaa 600
aaggattaga atacataatg caaagccacc tcaccaaggc tgctggaagc cgggccggtg 660
acggagtccc tcaggttatc gtagtgttaa ctgatggaca ctcgaaggat ggccttgctc 720
tgccctcagc ggaacttaag tctgctgatg ttaacgtgtt tgcaattgga gttgaggatg 780
cagatgaagg agcgttaaaa gaaatagcaa gtgaaccgct caatatgcat atgttcaacc 840
tagagaattt tacctcactt catgacatag taggaaactt agtgtcctgt gtgcattcat 900
ccgtgagtcc agaaagggct ggggacacgg aaacccttaa agacatcaca gcacaagact 960
ctgctgacat tattttcctt attgatggat caaacaacac cggaagtgtc aatttcgcag 1020
tcattctcga cttccttgta aatctccttg agaaactccc aattggaact cagcagatcc 1080
gagtgggggt ggtccagttt agcgatgagc ccagaaccat gttctccttg gacacctact 1140
ccaccaaggc ccaggttctg ggtgcagtga aagccctcgg gtttgctggt ggggagttgg 1200
ccaatatcgg cctcgccctt gatttcgtgg tggagaacca cttcacccgg gcagggggca 1260
gccgcgtgga ggaaggggtt ccccaggtgc tggtcctcat aagtgccggg ccttctagtg 1320
acgagattcg ctacggggtg gtagcactga agcaggctag cgtgttctca ttcggccttg 1380
gagcccaggc cgcctccagg gcagagcttc agcacatagc taccgatgac aacttggtgt 1440
ttactgtccc ggaattccgt agctttgggg acctccagga gaaattactg ccgtacattg 1500
ttggcgtggc ccaaaggcac attgtcttga aaccgccaac cattgtcaca caagtcattg 1560
aagtcaacaa gagagacata gtcttcctgg tggatggctc atctgcactg ggactggcca 1620
acttcaatgc catccgagac ttcattgcta aagtcatcca gaggctggaa atcggacagg 1680
atcttatcca ggtggcagtg gcccagtatg cagacactgt gaggcctgaa ttttatttca 1740
atacccatcc aacaaaaagg gaagtcataa ccgctgtgcg gaaaatgaag cccctggacg 1800
gctcggccct gtacacgggc tctgctctag actttgttcg taacaaccta ttcacgagtt 1860
cagccggcta ccgggctgcc gaggggattc ctaagctttt ggtgctgatc acaggtggta 1920
agtccctaga tgaaatcagc cagcctgccc aggagctgaa gagaagcagc ataatggcct 1980
ttgccattgg gaacaagggt gccgatcagg ctgagctgga agagatcgct ttcgactcct 2040
ccctggtgtt catcccagct gagttccgag ccgccccatt gcaaggcatg ctgcctggct 2100
tgctggcacc tctcaggacc ctctctggaa cccctgaagt tcactcaaac aaaagggata 2160
tcatctttct tttggatgga tcagccaacg ttggaaaaac caatttccct tatgtgcgcg 2220
actttgtaat gaacctagtt aacagccttg atattggaaa tgacaatatt cgtgttggtt 2280
tagtgcaatt tagtgacact cctgtaacgg agttctcttt aaacacatac cagaccaagt 2340
cagatatcct tggtcatctg aggcagctgc agctccaggg aggttcgggc ctgaacacag 2400
gctcagccct aagctatgtc tatgccaacc acttcacgga agctggcggc agcaggatcc 2460
gtgaacacgt gccgcagctc ctgcttctgc tcacagctgg gcagtctgag gactcctatt 2520
tgcaagctgc caacgccttg acacgcgcgg gcatcctgac tttttgtgtg ggagctagcc 2580
aggcgaataa ggcagagctt gagcagattg cttttaaccc aagcctggtg tatctcatgg 2640
atgatttcag ctccctgcca gctttgcctc agcagctgat tcagccccta accacatatg 2700
ttagtggagg tgtggaggaa gtaccactcg ctcagccaga gagcaagcga gacattctgt 2760
tcctctttga cggctcagcc aatcttgtgg gccagttccc tgttgtccgt gactttctct 2820
acaagattat cgatgagctc aatgtgaagc cagaggggac ccgaattgcg gtggctcagt 2880
acagcgatga tgtcaaggtg gagtcccgtt ttgatgagca ccagagtaag cctgagatcc 2940
tgaatcttgt gaagagaatg aagatcaaga cgggcaaagc cctcaacctg ggctacgcgc 3000
tggactatgc acagaggtac atttttgtga agtctgctgg cagccggatc gaggatggag 3060
tgcttcagtt cctggtgctg ctggtcgcag gaaggtcatc tgaccgtgtg gatgggccag 3120
caagtaacct gaagcagagt ggggttgtgc ctttcatctt ccaagccaag aacgcagacc 3180
ctgctgagtt agagcagatc gtgctgtctc cagcgtttat cctggctgca gagtcgcttc 3240
ccaagattgg agatcttcat ccacagatag tgaatctctt aaaatcagtg cacaacggag 3300
caccagcacc agtttcaggt gaaaaggacg tggtgtttct gcttgatggc tctgagggcg 3360
tcaggagcgg cttccctctg ttgaaagagt ttgtccagag agtggtggaa agcctggatg 3420
tgggccagga ccgggtccgc gtggccgtgg tgcagtacag cgaccggacc aggcccgagt 3480
tctacctgaa ttcatacatg aacaagcagg acgtcgtcaa cgctgtccgc cagctgaccc 3540
tgctgggagg gccgaccccc aacaccgggg ccgccctgga gtttgtcctg aggaacatcc 3600
tggtcagctc tgcgggaagc aggataacag aaggtgtgcc ccagctgctg atcgtcctca 3660
cggccgacag gtctggggat gatgtgcgga acccctccgt ggtcgtgaag aggggtgggg 3720
ctgtgcccat tggcattggc atcgggaacg ctgacatcac agagatgcag accatctcct 3780
tcatcccgga ctttgccgtg gccattccca cctttcgcca gctggggacc gtccaacagg 3840
tcatctctga gagggtgacc cagctcaccc gcgaggagct gagcaggctg cagccggtgt 3900
tgcagcctct accgagccca ggtgttggtg gcaagaggga cgtggtcttt ctcatcgatg 3960
ggtcccaaag tgccgggcct gagttccagt acgttcgcac cctcatagag aggctggttg 4020
actacctgga cgtgggcttt gacaccaccc gggtggctgt catccagttc agcgatgacc 4080
ccaaggtgga gttcctgctg aacgcccatt ccagcaagga tgaagtgcag aacgcggtgc 4140
agcggctgag gcccaaggga gggcggcaga tcaacgtggg caatgccctg gagtacgtgt 4200
ccaggaacat cttcaagagg cccctgggga gccgcattga agagggcgtc ccgcagttcc 4260
tggtcctcat ctcgtctgga aagtctgacg atgaggtgga cgacccggcg gtggagctca 4320
agcagtttgg cgtggcccct ttcacgatcg ccaggaacgc agaccaggag gagctggtga 4380
agatctcgct gagccccgaa tatgtgttct cggtgagcac cttccgggag ctgcccagcc 4440

```
tggagcagaa actgctgacg cccatcacga ccctgacctc agagcagatc cagaagctct   4500
tagccagcac tcgctatcca cctccagcag ttgagagtga tgctgcagac attgtctttc   4560
tgatcgacag ctctgaggga gttaggccag atggctttgc acatattcga gattttgtta   4620
gcaggattgt tcgaagactc aacatcggcc ccagtaaagt gagagttggg gtcgtgcagt   4680
tcagcaatga tgtcttccca gaattctatc tgaaaaccta cagatcccag gccccggtgc   4740
tggacgccat acggcgcctg aggctcagag gggggtcccc actgaacact ggcaaggctc   4800
tcgaatttgt ggcaagaaac ctctttgtta agtctgcggg gagtcgcata gaagacgggg   4860
tgccccaaca cctggtcctg gtcctgggtg gaaaatccca ggacgatgtg tccaggttcg   4920
cccaggtgat ccgttcctcg ggcattgtga gtttaggggt aggagaccgg aacatcgaca   4980
gaacagagct gcagaccatc accaatgacc ccagactggt cttcacagtg cgagagttca   5040
gagagcttcc caacatagaa gaaagaatca tgaactcgtt tggaccctcc gcagccactc   5100
ctgcacctcc aggggtggac acccctcctc cttcacggcc agagaagaag aaagcagaca   5160
ttgtgttcct gttggatggt tccatcaact tcaggaggga cagtttccag gaagtgcttc   5220
gttttgtgtc tgaaatagtg gacacagttt atgaagatgg cgactccatc caagtggggc   5280
ttgtccagta caactctgac cccactgacg aattcttcct gaaggacttc tctaccaaga   5340
ggcagattat tgacgccatc aacaaagtgg tctacaaagg gggaagacac gccaacacta   5400
aggtgggcct tgagcacctg cgggtaaacc actttgtgcc tgaggcaggc agccgcctgg   5460
accagcgggt ccctcagatt gcctttgtga tcacgggagg aaagtcggtg gaagatgcac   5520
aggatgtgag cctggccctc acccagaggg gggtcaaagt gtttgctgtt ggagtgagga   5580
atatcgactc ggaggaggtt ggaaagatag cgtccaacag cgccacagcg ttccgcgtgg   5640
gcaacgtcca ggagctgtcc gaactgagcg agcaagtttt ggaaactttg catgatgcga   5700
tgcatgaaac cctttgccct ggtgtaactg atgctgccaa agcttgtaat ctggatgtga   5760
ttctggggtt tgatggttct agagaccaga atgtttttgt ggcccagaag ggcttcgagt   5820
ccaaggtgga cgccatcttg aacagaatca gccagatgca cagggtcagc tgcagcggtg   5880
gccgctcgcc caccgtgcgt gtgtcagtgg tggccaacac gccctcgggc ccggtggagg   5940
cctttgactt tgacgagtac cagccagaga tgctcgagaa gttccggaac atgcgcagcc   6000
agcaccccta cgtcctcacg gaggacaccc tgaaggtcta cctgaacaag ttcagacagt   6060
cctcgccgga cagcgtgaag gtggtcattc attttactga tggagcagac ggagatctgg   6120
ctgatttaca cagagcatct gagaacctcc gccaagaagg agtccgtgcc ttgatcctgg   6180
tgggccttga acgagtggtc aacttggagc ggctaatgca tctggagttt gggcgagggt   6240
ttatgtatga caggcccctg aggcttaact tgctggactt ggattatgaa ctagcggagc   6300
agcttgacaa cattgccgag aaagcttgct gtggggttcc ctgcaagtgc tctgggcaga   6360
ggggagaccg cgggcccatc ggcagcatcg ggccaaaggg tattcctgga gaagacggct   6420
accgaggcta tcctggtgat gagggtggac ccggtgagcg tggtccgcct ggtgtgaacg   6480
gcactcaagg tttccagggc tgcccgggcc agagaggagt aaagggctct cggggattcc   6540
caggagagaa gggcgaagta ggagaaattg gactggatgg tctggatggt gaagatggag   6600
acaaaggatt gcctggttct tctggagaga aagggaatcc tggaagaagg ggtgataaag   6660
gacctcgagg agagaaagga gaaagaggag atgttgggat tcgaggggac ccgggtaacc   6720
caggacaaga cagccaggag agaggaccca aaggagaaac cggtgacctc ggccccatgg   6780
```

```
gtgtcccagg gagagatgga gtacctggag gacctggaga aactgggaag aatggtggct   6840
ttggccgaag gggacccccc ggagctaagg gcaacaaggg cggtcctggc cagccgggct   6900
ttgagggaga gcaggggacc agaggtgcac agggcccagc tggtcctgct ggtcctccag   6960
ggctgatagg agaacaaggc atttctggac ctcggggaag cggaggtgcc gctggtgctc   7020
ctggagaacg aggcagaacc ggtccactgg gaagaaaggg tgagcccgga gagccaggac   7080
caaaaggagg aatcgggaac cggggccctc gtggggagac gggagatgac gggagagacg   7140
gagttggcag tgaaggacgc agaggcaaaa aaggagaaag aggattccct ggatacccag   7200
gaccaaaggg taacccaggt gaacctgggc taaatggaac aacaggaccc aaaggcatca   7260
gaggccgaag gggaaattcg ggacctccag ggatagttgg acagaaggga gaccctggct   7320
acccaggacc agctggtccc aagggcaaca ggggcgactc catcgatcaa tgtgccctca   7380
tccaaagcat caaagataaa tgcccttgct gttacgggcc cctggagtgc cccgtcttcc   7440
caacagaact agcctttgct ttagacacct ctgagggagt caaccaagac actttcggcc   7500
ggatgcgaga tgtggtcttg agtattgtga atgacctgac cattgctgag agcaactgcc   7560
cacgggggc ccgggtggct gtggtcacct acaacaacga ggtgaccacg gagatccggt   7620
ttgctgactc caagaggaag tcggtcctcc tggacaagat taagaacctt caggtggctc   7680
tgacatccaa acagcagagt ctggagactg ccatgtcgtt tgtggccagg aacacattta   7740
agcgtgtgag gaacggattc ctaatgagga aagtggctgt tttcttcagc aacacaccca   7800
caagagcatc cccacagctc agagaggctg tgctcaagct ctcagatgcg gggatcaccc   7860
ccttgttcct tacaaggcag gaagaccggc agctcatcaa cgctttgcag atcaataaca   7920
cagcagtggg gcatgcgctt gtcctgcctg cagggagaga cctcacagac ttcctggaga   7980
atgtcctcac gtgtcatgtt tgcttggaca tctgcaacat cgacccatcc tgtggatttg   8040
gcagttggag gccttccttc agggacagga gagcggcagg gagcgatgtg gacatcgaca   8100
tggctttcat cttagacagc gctgagacca ccaccctgtt ccagttcaat gagatgaaga   8160
agtacatagc gtacctggtc agacaactgg acatgagccc agatcccaag gcctcccagc   8220
acttcgccag agtggcagtt gtgcagcacg cgccctctga gtccgtggac aatgccagca   8280
tgccacctgt gaaggtggaa ttctccctga ctgactatgg ctccaaggag aagctggtgg   8340
acttcctcag caggggaatg acacagttgc agggaaccag ggccttaggc agtgccattg   8400
aatacaccat agagaatgtc tttgaaagtg ccccaaaccc acgggacctg aaaattgtgg   8460
tcctgatgct gacgggcgag gtgccggagc agcagctgga ggaggcccag agagtcatcc   8520
tgcaggccaa atgcaagggc tacttcttcg tggtcctggg cattggcagg aaggtgaaca   8580
tcaaggaggt atacaccttc gccagtgagc caaacgacgt cttcttcaaa ttagtggaca   8640
agtccaccga gctcaacgag gagcctttga tgcgcttcgg gaggctgttg ccatccttcg   8700
tcagcagtga aaatgctttt tacttgtccc cagatatcag gaaacagtgt gattggttcc   8760
aaggggacca acccacaaag aaccttgtga agtttggtca caaacaagta aatgttccga   8820
ataacgttac ttcaagtcct acatccaacc cagtgacgac aacgaagccg gtgactacga   8880
cgaagccggt gaccaccaca acaaagcctg taaccaccac aacaaagcct gtgactatta   8940
taaatcagcc atctgtgaag ccagccgctg caaagccggc ccctgcgaaa cctgtggctg   9000
ccaagcctgt ggccacaaag atggccactg ttagaccccc agtggcggtg aagccagcaa   9060
cggcagcgaa gcctgtagca gcaaagccag cagctgtaag accccccgct gctgctgctg   9120
caaaaccagt ggcgaccaag cctgaggtcc ctaggccaca ggcagccaaa ccagctgcca   9180
```

```
ccaagccagc caccactaag cccatggtta agatgtcccg tgaagtccag gtgtttgaga   9240
taacagagaa cagcgccaaa ctccactggg agagggctga gcccccccggt ccttattttt   9300
atgacctcac cgtcacctca gcccatgatc agtccctggt tctgaagcag aacctcacgg   9360
tcacggaccg cgtcattgga ggcctgctcg ctgggcagac ataccatgtg gctgtggtct   9420
gctacctgag gtctcaggtc agagccacct accacggaag tttcagtaca aagaaatctc   9480
agcccccacc tccacagcca gcaaggtcag cttctagttc aaccatcaat ctaatggtga   9540
gcacagaacc attggctctc actgaaacag atatatgcaa gttgccgaaa gacgaaggaa   9600
cttgcaggga tttcatatta aaatggtact atgatccaaa caccaaaagc tgtgcaagat   9660
tctggtatgg aggttgtggt ggaaacgaaa acaaatttgg atcacagaaa gaatgtgaaa   9720
aggtttgcgc tcctgtgctc gccaaacccg gagtcatcag tgtgatggga acctaagcgt   9780
gggtggccaa catcatatac ctcttgaaga agaaggagtc agccatcgcc aacttgtctc   9840
tgtagaagct ccgggtgtag attcccttgc actgtatcat ttcatgcttt gatttacact   9900
cgaactcggg agggaacatc ctgctgcatg acctatcagt atggtgctaa tgtgtctgtg   9960
gaccctcgct ctctgtctcc aggcagttct ctcgaatact ttgaatgttg tgtaacagtt  10020
agccactgct ggtgtttatg tgaacattcc tatcaatcca aattccctct ggagtttcat  10080
gttatgcctg ttgcaggcaa atgtaaagtc tagaaaataa tgcaaatgtc acggctactc  10140
tatatacttt tgcttggttc atttttttttc ccttttagtt aagcatgact ttagatggga  10200
agcctgtgta tcgtggagaa acaagagacc aactttttca ttccctgccc ccaatttccc  10260
agactagatt tcaagctaat tttctttttc tgaagcctct aacaaatgat ctagttcaga  10320
aggaagcaaa atcccttaat ctatgtgcac cgttgggacc aatgccttaa ttaaagaatt  10380
taaaaaagtt gtaatagaga atatttttgg cattcctcta atgttgtgtg tttttttttt  10440
gtgtgtgctg gagggagggg atttaatttt aattttaaaa tgtttaggaa atttatacaa  10500
agaaactttt taataaagta tattgaaagt tt                                10532
```

<210> SEQ ID NO 168
<211> LENGTH: 2259
<212> TYPE: DNA
<213> ORGANISM: Homo sapiens

<400> SEQUENCE: 168

```
cgataaagcc cccgccgccg cggcagccag cttgcgctgt ggggctgccc gggctgcgcg     60
gcgtctgcag gcgccaccgc tgcctctttc cggctgtgac cctcctcgcc gccgccgctt    120
ggctgcgtcc tccgactccc cgcgccgccg agaccaggct cccgctccgg ttgcggccgc    180
accgccctcc gcggccgccc cctggggatc cagcgagcgc ggtcgtcctt ggtggaagga    240
accatgaact ggcatctccc cctcttcctc ttggcctctg tgacgctgcc ttccatctgc    300
tcccacttca atcctctgtc tctcgaggaa ctaggctcca acacggggat ccaggttttc    360
aatcagattg tgaagtcgag gcctcatgac aacatcgtga tctctcccca tgggattgcg    420
tcggtcctgg ggatgcttca gctgggggcg gacggcagga ccaagaagca gctcgccatg    480
gtgatgagat acggcgtaaa tggagttggt aaaatattaa agaagatcaa caaggccatc    540
gtctccaaga agaataaaga cattgtgaca gtggctaacg ccgtgtttgt taagaatgcc    600
tctgaaattg aagtgccttt tgttacaagg aacaaagatg tgttccagtg tgaggtccgg    660
aatgtgaact ttgaggatcc agcctctgcc tgtgattcca tcaatgcatg ggttaaaaat    720
```

-continued gaaaccaggg atatgattga caatctgctg tccccagatc ttattgatgg tgtgctcacc 780
agactggtcc tcgtcaacgc agtgtatttc aagggtctgt ggaaatcacg gttccaaccc 840
gagaacacaa agaaacgcac tttcgtggca gccgacggga aatcctatca agtgccaatg 900
ctggcccagc tctccgtgtt ccggtgtggg tcgacaagtg cccccaatga tttatggtac 960
aacttcattg aactgcccta ccacggggaa agcatcagca tgctgattgc actgccgact 1020
gagagctcca ctccgctgtc tgccatcatc ccacacatca gcaccaagac catagacagc 1080
tggatgagca tcatggtgcc caagagggtg caggtgatcc tgcccaagtt cacagctgta 1140
gcacaaacag atttgaagga gccgctgaaa gttcttggca ttactgacat gtttgattca 1200
tcaaaggcaa attttgcaaa aataacaaca gggtcagaaa acctccatgt ttctcatatc 1260
ttgcaaaaag caaaaattga agtcagtgaa gatggaacca aagcttcagc agcaacaact 1320
gcaattctca ttgcaagatc atcgcctccc tggtttatag tagacagacc ttttctgttt 1380
ttcatccgac ataatcctac aggtgctgtg ttattcatgg ggcagataaa caaaccctga 1440
agagtataca aaagaaacca tgcaaagcaa cgactacttt gctacgaaga aagactcctt 1500
tcctgcatct ttcatagttc tgttaaatat ttttgtacat cgcttctttt tcaaaactag 1560
ttcttaggaa cagactcgat gcaagtgttt ctgttctggg aggtattgga gggaaaaaac 1620
aagcaggatg gctggaacac tgtactgagg aatgaataga aaggcttcca gatgtctaaa 1680
agattcttta aactactgaa ctgttaccta ggttaacaac cctgttgagt atttgctgtt 1740
tgtccagttc aggaattttt gttttgtttt gtctatatgt gcggcttttc agaagaaatt 1800
taatcagtgt gacagaaaaa aaaatgtttt atggtagctt ttacttttta tgaaaaaaaa 1860
attatttgcc ttttaaattc ttttcccccca tccccctcca aagtcttgat agcaagcgtt 1920
attttggggg tagaaacggt gaaatctcta gcctctttgt gtttttgttg ttgttgttgt 1980
tgttgtttta tataatgcat gtattcacta aaataaaatt taaaaaactc ctgtcttgct 2040
agacaaggtt gctgttgtgc agtgtgcctg tcactactgg tctgtactcc ttggatttgc 2100
atttttgtat tttgtacaaa gtaaaaataa actgttatga gtagtaaaaa taaagctatt 2160
tctctgctat ttgaaaatac aatagaagaa actgagcctt ttagacattc gtcagcctct 2220
tctaataaac ctttgtacta tgtaaacatc aggaaattc 2259

<210> SEQ ID NO 169
<211> LENGTH: 8500
<212> TYPE: DNA
<213> ORGANISM: Homo sapiens

<400> SEQUENCE: 169
ggccacagcc tgcctactgt cacccgcctc tcccgcgcgc agatacacgc ccccgcctcc 60
gtgggcacaa aggcagcgct gctggggaac tcgggggaac gcgcacgtgg gaaccgccgc 120
agctccacac tccaggtact tcttccaagg acctaggtct ctcgcccatc ggaaagaaaa 180
taattctttc aagaagatca gggacaactg atttgaagtc tactctgtgc ttctaaatcc 240
ccaattctgc tgaaagtgag ataccctaga gccctagagc cccagcagca cccagccaaa 300
cccacctcca ccatgggggc catgactcag ctgttggcag gtgtctttct tgctttcctt 360
gccctcgcta ccgaaggtgg ggtcctcaag aaagtcatcc ggcacaagcg acagagtggg 420
gtgaacgcca ccctgccaga agagaaccag ccagtggtgt ttaaccacgt ttacaacatc 480
aagctgccag tgggatccca gtgttcggtg gatctggagt cagccagtgg ggagaaagac 540
ctggcaccgc cttcagagcc cagcgaaagc tttcaggagc acacagtgga tggggaaaac 600

-continued

```
cagattgtct tcacacatcg catcaacatc ccccgccggg cctgtggctg tgccgcagcc    660
cctgatgtta aggagctgct gagcagactg gaggagctgg agaacctggt gtcttccctg    720
agggagcaat gtactgcagg agcaggctgc tgtctccagc ctgccacagg ccgcttggac    780
accaggccct tctgtagcgg tcggggcaac ttcagcactg aaggatgtgg ctgtgtctgc    840
gaacctggct ggaaaggccc caactgctct gagcccgaat gtccaggcaa ctgtcacctt    900
cgaggccggt gcattgatgg gcagtgcatc tgtgacgacg gcttcacggg cgaggactgc    960
agccagctgg cttgccccag cgactgcaat gaccagggca agtgcgtaaa tggagtctgc   1020
atctgtttcg aaggctacgc cggggctgac tgcagccgtg aaatctgccc agtgccctgc   1080
agtgaggagc acggcacatg tgtagatggc ttgtgtgtgt gccacgatgg ctttgcaggc   1140
gatgactgca acaagcctct gtgtctcaac aattgctaca accgtggacg atgcgtggag   1200
aatgagtgcg tgtgtgatga gggtttcacg ggcgaagact gcagtgagct catctgcccc   1260
aatgactgct tcgaccgggg ccgctgcatc aatggcacct gctactgcga agaaggcttc   1320
acaggtgaag actgcgggaa acccacctgc ccacatgcct gccacaccca gggccggtgt   1380
gaggaggggc agtgtgtatg tgatgagggc tttgccggtg tggactgcag cgagaagagg   1440
tgtcctgctg actgtcacaa tcgtggccgc tgtgtagacg ggcggtgtga gtgtgatgat   1500
ggtttcactg gagctgactg tggggagctc aagtgtccca atggctgcag tggccatggc   1560
cgctgtgtca atgggcagtg tgtgtgtgat gagggctata ctggggagga ctgcagccag   1620
ctacggtgcc ccaatgactg tcacagtcgg ggccgctgtg tcgagggcaa atgtgtatgt   1680
gagcaaggct tcaagggcta tgactgcagt gacatgagct gccctaatga ctgtcaccag   1740
cacggccgct gtgtgaatgg catgtgtgtt tgtgatgacg gctacacagg ggaagactgc   1800
cgggatcgcc aatgccccag ggactgcagc aacaggggcc tctgtgtgga cggacagtgc   1860
gtctgtgagg acggcttcac cggccctgac tgtgcagaac tctcctgtcc aaatgactgc   1920
catggccagg gtcgctgtgt gaatgggcag tgcgtgtgcc atgaaggatt tatgggcaaa   1980
gactgcaagg agcaaagatg tcccagtgac tgtcatggcc agggccgctg cgtggacggc   2040
cagtgcatct gccacgaggg cttcacaggc ctggactgtg gccagcactc ctgccccagt   2100
gactgcaaca acttaggaca atgcgtctcg ggccgctgca tctgcaacga gggctacagc   2160
ggagaagact gctcagaggt gtctcctccc aaagacctcg ttgtgacaga agtgacggaa   2220
gagacggtca acctggcctg ggacaatgag atgcgggtca cagagtacct tgtcgtgtac   2280
acgcccaccc acgagggtgg tctggaaatg cagttccgtg tgcctgggga ccagacgtcc   2340
accatcatcc aggagctgga gcctggtgtg gagtacttta tccgtgtatt tgccatcctg   2400
gagaacaaga agagcattcc tgtcagcgcc agggtggcca cgtacttacc tgcacctgaa   2460
ggcctgaaat tcaagtccat caaggagaca tctgtggaag tggagtggga tcctctagac   2520
attgcttttg aaacctggga gatcatcttc cggaatatga ataaagaaga tgagggagag   2580
atcaccaaaa gcctgaggag gccagagacc tcttaccggc aaactggtct agctcctggg   2640
caagagtatg agatatctct gcacatagtg aaaaacaata cccggggccc tggcctgaag   2700
agggtgacca ccacacgctt ggatgccccc agccagatcg aggtgaaaga tgtcacagac   2760
accactgcct tgatcacctg gttcaagccc ctggctgaga tcgatggcat tgagctgacc   2820
tacggcatca aagacgtgcc aggagaccgt accaccatcg atctcacaga ggacgagaac   2880
cagtactcca tcgggaacct gaagcctgac actgagtacg aggtgtccct catctcccgc   2940
```

-continued

```
agaggtgaca tgtcaagcaa cccagccaaa gagaccttca caacaggcct cgatgctccc   3000
aggaatcttc gacgtgtttc ccagacagat aacagcatca ccctggaatg gaggaatggc   3060
aaggcagcta ttgacagtta cagaattaag tatgccccca tctctggagg ggaccacgct   3120
gaggttgatg ttccaaagag ccaacaagcc acaaccaaaa ccacactcac aggtctgagg   3180
ccgggaactg aatatgggat tggagtttct gctgtgaagg aagacaagga gagcaatcca   3240
gcgaccatca acgcagccac agagttggac acgcccaagg accttcaggt ttctgaaact   3300
gcagagacca gcctgaccct gctctggaag acaccgttgg ccaaatttga ccgctaccgc   3360
ctcaattaca gtctccccac aggccagtgg gtgggagtgc agcttccaag aaacaccact   3420
tcctatgtcc tgagaggcct ggaaccagga caggagtaca atgtcctcct gacagccgag   3480
aaaggcagac acaagagcaa gcccgcacgt gtgaaggcat ccactgaaca agcccctgag   3540
ctggaaaacc tcaccgtgac tgaggttggc tgggatggcc tcagactcaa ctggaccgca   3600
gctgaccagg cctatgagca ctttatcatt caggtgcagg aggccaacaa ggtggaggca   3660
gctcggaacc tcaccgtgcc tggcagcctt cgggctgtgg acataccggg cctcaaggct   3720
gctacgcctt atacagtctc catctatggg gtgatccagg gctatagaac accagtgctc   3780
tctgctgagg cctccacagg ggaaactccc aatttgggag aggtcgtggt ggccgaggtg   3840
ggctgggatg ccctcaaact caactggact gctccagaag gggcctatga gtactttttc   3900
attcaggtgc aggaggctga cacagtagag gcagcccaga acctcaccgt cccaggagga   3960
ctgaggtcca cagacctgcc tgggctcaaa gcagccactc attataccat caccatccgc   4020
ggggtcactc aggacttcag cacaacccct ctctctgttg aagtcttgac agaggaggtt   4080
ccagatatgg gaaacctcac agtgaccgag gttagctggg atgctctcag actgaactgg   4140
accacgccag atggaaccta tgaccagttt actattcagg tccaggaggc tgaccaggtg   4200
gaagaggctc acaatctcac ggttcctggc agcctgcgtt ccatggaaat cccaggcctc   4260
agggctggca ctccttacac agtcaccctg cacggcgagg tcaggggcca cagcactcga   4320
ccccttgctg tagaggtcgt cacagaggat ctcccacagc tgggagattt agccgtgtct   4380
gaggttggct gggatggcct cagactcaac tggaccgcag ctgacaatgc ctatgagcac   4440
tttgtcattc aggtgcagga ggtcaacaaa gtggaggcag cccagaacct cacgttgcct   4500
ggcagcctca gggctgtgga catcccgggc ctcgaggctg ccacgcctta tagagtctcc   4560
atctatgggg tgatccgggg ctatagaaca ccagtactct ctgctgaggc ctccacagcc   4620
aaagaacctg aaattggaaa cttaaatgtt tctgacataa ctcccgagag cttcaatctc   4680
tcctggatgg ctaccgatgg gatcttcgag acctttacca ttgaaattat tgattccaat   4740
aggttgctgg agactgtgga atataatatc tctggtgctg aacgaactgc ccatatctca   4800
gggctacccc ctagtactga ttttattgtc tacctctctg gacttgctcc cagcatccgg   4860
accaaaacca tcagtgccac agccacgaca gaggccctgc cccttctgga aaacctaacc   4920
atttccgaca ttaatcccta cgggttcaca gtttcctgga tggcatcgga gaatgccttt   4980
gacagctttc tagtaacggt ggtggattct gggaagctgc tggacccccca ggaattcaca   5040
ctttcaggaa cccagaggaa gctggagctt agaggcctca taactggcat tggctatgag   5100
gttatggtct ctggcttcac ccaagggcat caaaccaagc ccttgagggc tgagattgtt   5160
acagaagccg aaccggaagt tgacaacctt ctggtttcag atgccacccc agacggtttc   5220
cgtctgtcct ggacagctga tgaaggggtc ttcgacaatt ttgttctcaa aatcagagat   5280
accaaaaagc agtctgagcc actggaaata accctacttg cccccgaacg taccagggac   5340
```

ataacaggtc tcagagaggc tactgaatac gaaattgaac tctatggaat aagcaaagga 5400
aggcgatccc agacagtcag tgctatagca acaacagcca tgggctcccc aaaggaagtc 5460
attttctcag acatcactga aaattcggct actgtcagct ggagggcacc cacagcccaa 5520
gtggagagct tccggattac ctatgtgccc attacaggag gtacaccctc catggtaact 5580
gtggacggaa ccaagactca gaccaggctg gtgaaactca tacctggcgt ggagtacctt 5640
gtcagcatca tcgccatgaa gggctttgag gaaagtgaac ctgtctcagg gtcattcacc 5700
acagctctgg atggcccatc tggcctggtg acagccaaca tcactgactc agaagccttg 5760
gccaggtggc agccagccat tgccactgtg gacagttatg tcatctccta cacaggcgag 5820
aaagtgccag aaattacacg cacggtgtcc gggaacacag tggagtatgc tctgaccgac 5880
ctcgagcctg ccacggaata cacactgaga atctttgcag agaaagggcc ccagaagagc 5940
tcaaccatca ctgccaagtt cacaacagac ctcgattctc caagagactt gactgctact 6000
gaggttcagt cggaaactgc cctccttacc tggcgacccc cccgggcatc agtcaccggt 6060
tacctgctgg tctatgaatc agtggatggc acagtcaagg aagtcattgt gggtccagat 6120
accacctcct acagcctggc agacctgagc ccatccaccc actacacagc caagatccag 6180
gcactcaatg ggcccctgag gagcaatatg atccagacca tcttcaccac aattggactc 6240
ctgtacccct tccccaagga ctgctcccaa gcaatgctga atggagacac gacctctggc 6300
ctctacacca tttatctgaa tggtgataag gctgaggcgc tggaagtctt ctgtgacatg 6360
acctctgatg gggtggatg gattgtgttc ctgagacgca aaaacggacg cgagaacttc 6420
taccaaaact ggaaggcata tgctgctgga tttggggacc gcagagaaga attctggctt 6480
gggctggaca acctgaacaa aatcacagcc caggggcagt acgagctccg ggtggacctg 6540
cgggaccatg gggagacagc ctttgctgtc tatgacaagt tcagcgtggg agatgccaag 6600
actcgctaca agctgaaggt ggaggggtac agtgggacag caggtgactc catggcctac 6660
cacaatggca gatccttctc cacctttgac aaggacacag attcagccat caccaactgt 6720
gctctgtcct acaaaggggc tttctggtac aggaactgtc accgtgtcaa cctgatgggg 6780
agatatgggg acaataacca cagtcagggc gttaactggt tccactggaa gggccacgaa 6840
cactcaatcc agtttgctga gatgaagctg agaccaagca acttcagaaa tcttgaaggc 6900
aggcgcaaac gggcataaat tccagggacc actgggtgag agaggaataa ggcccagagc 6960
gaggaaagga ttttaccaaa gcatcaatac aaccagccca accatcggtc cacacctggg 7020
catttggtga gagtcaaagc tgaccatgga tccctggggc caacggcaac agcatgggcc 7080
tcacctcctc tgtgatttct ttctttgcac caaagacatc agtctccaac atgtttctgt 7140
tttgttgttt gattcagcaa aaatctccca gtgacaacat cgcaatagtt ttttacttct 7200
cttaggtggc tctgggaatg ggagaggggt aggatgtaca ggggtagttt gttttagaac 7260
cagccgtatt ttacatgaag ctgtataatt aattgtcatt atttttgtta gcaaagatta 7320
aatgtgtcat tggaagccat cccttttttt acatttcata caacagaaac cagaaaagca 7380
atactgtttc cattttaagg atatgattaa tattattaat ataataatga tgatgatgat 7440
gatgaaaact aaggattttt caagagatct ttctttccaa aacatttctg gacagtacct 7500
gattgtattt ttttttaaa taaaagcaca agtacttttg agtttgttat tttgctttga 7560
attgttgagt ctgaatttca ccaaagccaa tcatttgaac aaagcgggga atgttgggat 7620
aggaaaggta agtagggata gtggtcaagt gggaggggtg gaaaggagac taaagactgg 7680

-continued

```
gagagaggga agcacttttt ttaaataaag ttgaacacac ttgggaaaag cttacaggcc   7740
aggcctgtaa tcccaacact ttgggaggcc aaggtgggag gatagcttaa ccccaggagt   7800
ttgagaccag cctgagcaac atagtgagaa cttgtctcta cagaaaaaaa aaaaaaaaaa   7860
aatttaatta ggcaagcgtg gtagtgcgca cctgtcgtcc cagctactca ggaggctgag   7920
gtaggaaaat cactggagcc caggagttag aggttacagt gagctatgat cacactactg   7980
cactccagcc tgggcaacag agggagaccc tgtctctaaa taaaaaaaga aaagaaaaaa   8040
aaagcttaca acttgagatt cagcatcttg ctcagtattt ccaagactaa tagattatgg   8100
tttaaaagat gcttttatac tcattttcta atgcaactcc tagaaactct atgatatagt   8160
tgaggtaagt attgttacca cacatgggct aagatcccca gaggcagact gcctgagttc   8220
aattcttggc tccaccattc ccaagttccc taacctctct atgcctcagt ttcctcttct   8280
gtaaagtagg gacactcata cttctcattt cagaacattt ttgtgaagaa taaattatgt   8340
tatccatttg aggcccttag aatggtaccc ggtgtatatt aagtgctagt acatgttagc   8400
tatcatcatt atcactttat atgagatgga ctggggttca tagaaaccca atgacttgat   8460
tgtggctact actcaataaa taatagaatt tggatttaaa                         8500
```

<210> SEQ ID NO 170
<211> LENGTH: 2452
<212> TYPE: DNA
<213> ORGANISM: Homo sapiens

<400> SEQUENCE: 170

```
agaaagcgag cagccaccca gctccccgcc accgccatgg tccccgacac cgcctgcgtt     60
cttctgctca ccctggctgc cctcggcgcg tccggacagg gccagagccc gttgggctca    120
gacctgggcc cgcagatgct tcgggaactg caggaaacca acgcggcgct gcaggacgtg    180
cgggagctgc tgcggcagca ggtcagggag atcacgttcc tgaaaaacac ggtgatggag    240
tgtgacgcgt gcgggatgca gcagtcagta cgcaccggcc tacccagcgt gcggcccctg    300
ctccactgcg cgcccggctt ctgcttcccc ggcgtggcct gcatccagac ggagagcggc    360
gcgcgctgcg gcccctgccc cgcgggcttc acgggcaacg gctcgcactg caccgacgtc    420
aacgagtgca acgcccaccc ctgcttcccc cgagtccgct gtatcaacac cagcccgggg    480
ttccgctgcg aggcttgccc gccggggtac agcggcccca cccaccaggg cgtggggctg    540
gctttcgcca aggccaacaa gcaggtttgc acggacatca acgagtgtga gaccgggcaa    600
cataactgcg tccccaactc cgtgtgcatc aacacccggg gctccttcca gtgcggcccg    660
tgccagcccg gcttcgtggg cgaccaggcg tccggctgcc agcggcgcgc acagcgcttc    720
tgccccgacg gctcgcccag cgagtgccac gagcatgcag actgcgtcct agagcgcgat    780
ggctcgcggt cgtgcgtgtg tgccgttggc tgggccggca acgggatcct ctgtggtcgc    840
gacactgacc tagacggctt cccggacgag aagctgcgct gcccggagcg ccagtgccgt    900
aaggacaact gcgtgactgt gcccaactca gggcaggagg atgtggaccg cgatggcatc    960
ggagacgcct gcgatccgga tgccgacggg gacggggtcc ccaatgaaaa ggacaactgc   1020
ccgctggtgc ggaacccaga ccagcgcaac acggacgagg acaagtgggg cgatgcgtgc   1080
gacaactgcc ggtcccagaa gaacgacgac caaaaggaca cagaccagga cggccggggc   1140
gatgcgtgcg acgacgacat cgacggcgac cggatccgca accaggccga caactgccct   1200
agggtaccca actcagacca gaaggacagt gatggcgatg gtatagggga tgcctgtgac   1260
aactgtcccc agaagagcaa cccggatcag gcggatgtgg accacgactt tgtgggagat   1320
```

gcttgtgaca gcgatcaaga ccaggatgga gacggacatc aggactctcg ggacaactgt 1380
cccacggtgc ctaacagtgc ccaggaggac tcagaccacg atggccaggg tgatgcctgc 1440
gacgacgacg acgacaatga cggagtccct gacagtcggg acaactgccg cctggtgcct 1500
aaccccggcc aggaggacgc ggacagggac ggcgtgggcg acgtgtgcca ggacgacttt 1560
gatgcagaca aggtggtaga caagatcgac gtgtgtccgg agaacgctga agtcacgctc 1620
accgacttca gggccttcca gacagtcgtg ctggacccgg agggtgacgc gcagattgac 1680
cccaactggg tggtgctcaa ccagggaagg gagatcgtgc agacaatgaa cagcgaccca 1740
ggcctggctg tgggttacac tgccttcaat ggcgtggact tcgagggcac gttccatgtg 1800
aacacggtca cggatgacga ctatgcgggc ttcatctttg gctaccagga cagctccagc 1860
ttctacgtgg tcatgtggaa gcagatggag caaacgtatt ggcaggcgaa ccccttccgt 1920
gctgtggccg agcctggcat ccaactcaag gctgtgaagt cttccacagg ccccggggaa 1980
cagctgcgga acgctctgtg gcatacagga gacacagagt cccaggtgcg gctgctgtgg 2040
aaggacccgc gaaacgtggg ttggaaggac aagaagtcct atcgttggtt cctgcagcac 2100
cggccccaag tgggctacat cagggtgcga ttctatgagg gccctgagct ggtggccgac 2160
agcaacgtgg tcttggacac aaccatgcgg ggtggccgcc tgggggtctt ctgcttctcc 2220
caggagaaca tcatctgggc caacctgcgt taccgctgca atgacaccat cccagaggac 2280
tatgagaccc atcagctgcg gcaagcctag ggaccagggt gaggacccgc cggatgacag 2340
ccaccctcac cgcggctgga tggggggctct gcacccagcc ccaaggggtg gccgtcctga 2400
gggggaagtg agaagggctc agagaggaca aaataaagtg tgtgtgcagg ga 2452

<210> SEQ ID NO 171
<211> LENGTH: 7789
<212> TYPE: DNA
<213> ORGANISM: Homo sapiens

<400> SEQUENCE: 171
agccgctgcg cccgagctgg cctgcgagtt cagggctcct gtcgctctcc aggagcaacc 60
tctactccgg acgcacaggc attccccgcg cccctccagc cctcgccgcc ctcgccaccg 120
ctcccggccg ccgcgctccg gtacacacag gatccctgct gggcaccaac agctccacca 180
tggggctggc ctggggacta ggcgtcctgt tcctgatgca tgtgtgtggc accaaccgca 240
ttccagagtc tggcggagac aacagcgtgt ttgacatctt tgaactcacc ggggccgccc 300
gcaaggggtc tgggcgccga ctggtgaagg gccccgaccc ttccagccca gctttccgca 360
tcgaggatgc caacctgatc ccccctgtgc ctgatgacaa gttccaagac ctggtggatg 420
ctgtgcgggc agaaaagggt ttcctccttc tggcatccct gaggcagatg aagaagaccc 480
ggggcacgct gctggccctg gagcggaaag accactctgg ccaggtcttc agcgtggtgt 540
ccaatggcaa ggcgggcacc ctggacctca gcctgaccgt ccaaggaaag cagcacgtgg 600
tgtctgtgga agaagctctc ctggcaaccg gccagtggaa gagcatcacc ctgtttgtgc 660
aggaagacag ggcccagctg tacatcgact gtgaaaagat ggagaatgct gagttggacg 720
tccccatcca aagcgtcttc accagagacc tggccagcat cgccagactc cgcatcgcaa 780 agggggggcgt caatgacaat ttccaggggg tgctgcagaa tgtgaggttt gtctttggaa 840
ccacaccaga agacatcctc aggaacaaag gctgctccag ctctaccagt gtcctcctca 900
cccttgacaa caacgtggtg aatggttcca gccctgccat ccgcactaac tacattggcc 960

-continued

```
acaagacaaa ggacttgcaa gccatctgcg gcatctcctg tgatgagctg tccagcatgg   1020
tcctggaact caggggcctg cgcaccattg tgaccacgct gcaggacagc atccgcaaag   1080
tgactgaaga gaacaaagag ttggccaatg agctgaggcg gcctccccta tgctatcaca   1140
acggagttca gtacagaaat aacgaggaat ggactgttga tagctgcact gagtgtcact   1200
gtcagaactc agttaccatc tgcaaaaagg tgtcctgccc catcatgccc tgctccaatg   1260
ccacagttcc tgatggagaa tgctgtcctc gctgttggcc cagcgactct gcggacgatg   1320
gctggtctcc atggtccgag tggacctcct gttctacgag ctgtggcaat ggaattcagc   1380
agcgcggccg ctcctgcgat agcctcaaca accgatgtga gggctcctcg gtccagacac   1440
ggacctgcca cattcaggag tgtgacaaga gatttaaaca ggatggtggc tggagccact   1500
ggtccccgtg gtcatcttgt tctgtgacat gtggtgatgg tgtgatcaca aggatccggc   1560
tctgcaactc tcccagcccc cagatgaacg ggaaaccctg tgaaggcgaa gcgcgggaga   1620
ccaaagcctg caagaaagac gcctgcccca tcaatggagg ctggggtcct tggtcaccat   1680
gggacatctg ttctgtcacc tgtggaggag ggtacagaa acgtagtcgt ctctgcaaca    1740
accccacacc ccagtttgga ggcaaggact gcgttggtga tgtaacagaa aaccagatct   1800
gcaacaagca ggactgtcca attgatggat gcctgtccaa tccctgcttt gccggcgtga   1860
agtgtactag ctaccctgat ggcagctgga aatgtggtgc ttgtcccccct ggttacagtg  1920
gaaatggcat ccagtgcaca gatgttgatg agtgcaaaga agtgcctgat gcctgcttca   1980
accacaatgg agagcaccgg tgtgagaaca cggaccccgg ctacaactgc ctgccctgcc   2040
ccccacgctt caccggctca cagcccttcg gccagggtgt cgaacatgcc acggccaaca   2100
aacaggtgtg caagccccgt aacccctgca cggatgggac ccacgactgc aacaagaacg   2160
ccaagtgcaa ctacctgggc cactatagcg accccatgta ccgctgcgag tgcaagcctg   2220
gctacgctgg caatggcatc atctgcgggg aggacacaga cctggatggc tggcccaatg   2280
agaacctggt gtgcgtggcc aatgcgactt accactgcaa aaaggataat tgccccaacc   2340
ttcccaactc agggcaggaa gactatgaca aggatggaat tggtgatgcc tgtgatgatg   2400
acgatgacaa tgataaaatt ccagatgaca gggacaactg tccattccat tacaacccag   2460
ctcagtatga ctatgacaga gatgatgtgg gagaccgctg tgacaactgt ccctacaacc   2520
acaacccaga tcaggcagac acagacaaca atggggaagg agacgcctgt gctgcagaca   2580
ttgatggaga cggtatcctc aatgaacggg acaactgcca gtacgtctac aatgtggacc   2640
agagagacac tgatatggat ggggttggag atcagtgtga caattgcccc ttggaacaca   2700
atccggatca gctggactct gactcagacc gcattggaga tacctgtgac aacaatcagg   2760
atattgatga agatggccac cagaacaatc tggacaactg tccctatgtg cccaatgcca   2820
accaggctga ccatgacaaa gatggcaagg gagatgcctg tgaccacgat gatgacaacg   2880
atggcattcc tgatgacaag gacaactgca gactcgtgcc caatcccgac cagaaggact   2940
ctgacggcga tggtcgaggt gatgcctgca aagatgattt tgaccatgac agtgtgccag   3000
acatcgatga catctgtcct gagaatgttg acatcagtga gaccgatttc cgccgattcc   3060
agatgattcc tctggacccc aaagggacat cccaaaatga ccctaactgg gttgtacgcc   3120
atcagggtaa agaactcgtc cagactgtca actgtgatcc tggactcgct gtaggttatg   3180
atgagtttaa tgctgtggac ttcagtggca ccttcttcat caacaccgaa agggacgatg   3240
actatgctgg atttgtcttt ggctaccagt ccagcagccg cttttatgtt gtgatgtgga   3300
agcaagtcac ccagtcctac tgggacacca accccacgag ggctcaggga tactcgggcc   3360
```

-continued

```
tttctgtgaa agttgtaaac tccaccacag ggcctggcga gcacctgcgg aacgccctgt   3420
ggcacacagg aaacacccct ggccaggtgc gcaccctgtg gcatgaccct cgtcacatag   3480
gctggaaaga tttcaccgcc tacagatggc gtctcagcca caggccaaag acgggtttca   3540
ttagagtggt gatgtatgaa gggaagaaaa tcatggctga ctcaggaccc atctatgata   3600
aaacctatgc tggtggtaga ctagggttgt ttgtcttctc tcaagaaatg gtgttcttct   3660
ctgacctgaa atacgaatgt agagatccct aatcatcaaa ttgttgattg aaagactgat   3720
cataaaccaa tgctggtatt gcaccttctg gaactatggg cttgagaaaa cccccaggat   3780
cacttctcct tggcttcctt cttttctgtg cttgcatcag tgtggactcc tagaacgtgc   3840
gacctgcctc aagaaaatgc agttttcaaa aacagactca gcattcagcc tccaatgaat   3900
aagacatctt ccaagcatat aaacaattgc tttggtttcc ttttgaaaaa gcatctactt   3960
gcttcagttg ggaaggtgcc cattccactc tgcctttgtc acagagcagg gtgctattgt   4020
gaggccatct ctgagcagtg gactcaaaag cattttcagg catgtcagag aagggaggac   4080
tcactagaat tagcaaacaa aaccaccctg acatcctcct tcaggaacac ggggagcaga   4140
ggccaaagca ctaaggggag ggcgcatacc cgagacgatt gtatgaagaa aatatggagg   4200
aactgttaca tgttcggtac taagtcattt tcaggggatt gaaagactat tgctggattt   4260
catgatgctg actggcgtta gctgattaac ccatgtaaat aggcacttaa atagaagcag   4320
gaaagggaga caaagactgg cttctggact tcctccctga tccccaccct tactcatcac   4380
ctgcagtggc cagaattagg gaatcagaat caaaccagtg taaggcagtg ctggctgcca   4440
ttgcctggtc acattgaaat tggtggcttc attctagatg tagcttgtgc agatgtagca   4500
ggaaaatagg aaaacctacc atctcagtga gcaccagctg cctcccaaag gaggggcagc   4560
cgtgcttata tttttatggt tacaatggca caaaattatt atcaacctaa ctaaaacatt   4620
ccttttctct tttttcctga attatcatgg agttttctaa ttctctcttt tggaatgtag   4680
attttttta aatgctttac gatgtaaaat atttattttt tacttattct ggaagatctg   4740
gctgaaggat tattcatgga acaggaagaa gcgtaaagac tatccatgtc atctttgttg   4800
agagtcttcg tgactgtaag attgtaaata cagattattt attaactctg ttctgcctgg   4860
aaatttaggc ttcatacgga aagtgtttga gagcaagtag ttgacattta tcagcaaatc   4920
tcttgcaaga acagcacaag gaaaatcagt ctaataagct gctctgcccc ttgtgctcag   4980
agtggatgtt atgggattct tttttctct gttttatctt ttcaagtgga attagttggt   5040
tatccatttg caaatgtttt aaattgcaaa gaaagccatg aggtcttcaa tactgtttta   5100
ccccatccct tgtgcatatt tccagggaga aggaaagcat atacactttt ttctttcatt   5160
tttccaaaag agaaaaaaat gacaaaaggt gaaacttaca tacaaatatt acctcatttg   5220
ttgtgtgact gagtaaagaa tttttggatc aagcggaaag agtttaagtg tctaacaaac   5280
ttaaagctac tgtagtacct aaaaagtcag tgttgtacat agcataaaaa ctctgcagag   5340
aagtattccc aataaggaaa tagcattgaa atgttaaata caatttctga aagttatgtt   5400
ttttttctat catctggtat accattgctt tatttttata aattattttc tcattgccat   5460
tggaatagat atctcagatt gtgtagatat gctatttaaa taatttatca ggaaatactg   5520
cctgtagagt tagtatttct atttttatat aatgtttgca cactgaattg aagaattgtt   5580
ggtttttct ttttttgtt ttgttttttt tttttttt ttttgctttt gacctcccat   5640
ttttactatt tgccaatacc tttttctagg aatgtgcttt tttttgtaca catttttatc   5700
```

cattttacat tctaaagcag tgtaagttgt atattactgt ttcttatgta caaggaacaa 5760
caataaatca tatggaaatt tatatttata cttactgtat ccatgcttat ttgttctcta 5820
ctggctttat gtcatgaagt atatgcgtaa ataccattca taaatcaata tagcatatac 5880
aaaaataaat tacagtaagt catagcaaca ttcacagttt gtatgtgatt gagaaagact 5940
gagttgctca ggcctaggct tagaatttgc tgcgtttgtg gaataaaaga acaaaatgat 6000
acattagcct gccatatcaa aaacatataa aagagaaatt atccctaagt caagggcccc 6060
cataagaata aaatttctta ttaaggtcat tagatgtcat tgaatccttt tcaaagtgca 6120
gtatgaaaac aaagggaaaa acactgaagc acacgcaact ctcacagcga cattttctga 6180
cccacgaatg atgccttggg tgggcaacac gattgcatgt tgtggagaca cttcggaagt 6240
aaatgtggat gagggaggag ctgtccttgc aatgttgagc caagcattac agatacctcc 6300
tcttgaagaa ggaataataa gtttaatcaa aaaagaagac taaaaaatgt aaaatttgga 6360
aggaatccat aaatgcgtgt gtgtctaaat acaaattatc atgtgaagaa aaggcccaag 6420
tgtaccaata agcagacctt gatttttgga tgggctaatt atgaatgtgg aatactgacc 6480
agttaatttc cagttttaat gaaaacagat caaagaagaa attttatgag taggttaaag 6540
gtctggcttt gaggtctatt aaacactaga aaggactggc tgggtgagat aaaatcttcc 6600
ttgttgattt tcactctcat tctataaata ctcatctttc tgagtagcca tgatcacata 6660
caaatgtaaa ttgccaaatc attttatagt accaaggtga agaagcagga actagaaagt 6720
gttgataata gctgtggagt taggaaaact gatgtgaagg aaataattct ttgaaatggc 6780
aaagaattaa ataccatcat tcattatcag aagagttcaa cgtttgaagt gctgggagat 6840
aattctaatt cattcttgga tagtgaagca aaactgattg aaaataccaa gataagacag 6900
aaaaagtgac tggaaagagg agcttttctt ccaggcatgt tccagtttca ccctaagact 6960
gaccttcaaa taatcaggtt gtactgaaat aaaggacttg ttaaaaatta aaattatgtc 7020
atcgagatga tagctttttt cctcctccaa cagtttattg tcatgtgttg tgggagagct 7080
cgagtgaaga gcaataaact ccaggtctta taagaatgta catacaataa aggtggtgcc 7140
agcagttttt ttttttctaa agagtcacat gtagaaaagc ctccagtatt aagctcctga 7200
attcattcct taaataaatt ggctctctct ctcttctata atttcttttt ctttttattt 7260
ttgagatgaa gtcttgctct gtcgcccagg ctggagtgca gtgacacaat ctcggctcac 7320
tgcaacctct gcctccccgg ttcaagcaat tctccctcct gcctcagcct cccaagtagc 7380
tgggactaca agcgcccgcc accaagcctg gctaattctg tatttttagt aaagacgggg 7440
tttcaccttg ttccggacaa acactaagcc ctaaagggaa atccaaaata aaaacatcta 7500
tttttaataa cactttctat ctaaatcagg gtgacttttt aaaaaaaatc cggaagcttt 7560
ttgttgaatt acgttacaga cttagttacc agtccttgtt agagttacct tcagttgaca 7620
tgctgtgaat ggtcccacct cttttatggc agaattcatt acttaaaata actctatttt 7680
cttccccctt acctaaataa cagaaaggct cactatgtcc caaatatcat tggcagaagc 7740
aaactataaa gtcataagcc ctttgcagtg caagtctaga aataatttt 7789

<210> SEQ ID NO 172
<211> LENGTH: 7311
<212> TYPE: DNA
<213> ORGANISM: Homo sapiens

<400> SEQUENCE: 172
actgacggca tgaagccttt aggggcacac agtactctca gcttgttggt ggaagcccct 60

```
catctgcctt cattctgaag gcagggcccg gcagaggaag gatcagaggg tcgcggccgg    120
agggtcccgg ccggtggggc caactcagag ggagaggaaa gggctagaga cacgaagaac    180
gcaaaccatc aaatttagaa gaaaaagccc tttgactttt tccccctctc cctccccaat    240
ggctgtgtag caaacatccc tggcgatacc ttggaaagga cgaagttggt ctgcagtcgc    300
aatttcgtgg gttgagttca cagttgtgag tgcggggctc ggagatggag ccgtggtcct    360
ctaggtggaa aacgaaacgg tggctctggg atttcaccgt aacaaccctc gcattgacct    420
tcctcttcca agctagagag gtcagaggag ctgctccagt tgatgtacta aaagcactag    480
attttcacaa ttctccagag ggaatatcaa aaacaacggg attttgcaca aacagaaaga    540
attctaaagg ctcagatact gcttacagag tttcaaagca agcacaactc agtgccccaa    600
caaaacagtt atttccaggt ggaactttcc cagaagactt ttcaatacta tttacagtaa    660
aaccaaaaaa aggaattcag tctttccttt tatctatata taatgagcat ggtattcagc    720
aaattggtgt tgaggttggg agatcacctg tttttctgtt tgaagaccac actggaaaac    780
ctgccccaga agactatccc ctcttcagaa ctgttaacat cgctgacggg aagtggcatc    840
gggtagcaat cagcgtggag aagaaaactg tgacaatgat tgttgattgt aagaagaaaa    900
ccacgaaacc acttgataga agtgagagag caattgttga taccaatgga atcacggttt    960
ttggaacaag gattttggat gaagaagttt ttgaggggga cattcagcag tttttgatca   1020
caggtgatcc caaggcagca tatgactact gtgagcatta tagtccagac tgtgactctt   1080
cagcacccaa ggctgctcaa gctcaggaac ctcagataga tgagtatgca ccagaggata   1140
taatcgaata tgactatgag tatggggaag cagagtataa agaggctgaa agtgtaacag   1200
agggacccac tgtaactgag gagacaatag cacagacgga ggcaaacatc gttgatgatt   1260
ttcaagaata caactatgga acaatggaaa gttaccagac agaagctcct aggcatgttt   1320
ctgggacaaa tgagccaaat ccagttgaag aaatatttac tgaagaatat ctaacgggag   1380
aggattatga ttcccagagg aaaaattctg aggatacact atatgaaaac aaagaaatag   1440
acggcaggga ttctgatctt ctggtagatg gagatttagg cgaatatgat ttttatgaat   1500
ataaagaata tgaagataaa ccaacaagcc cccctaatga agaatttggt ccaggtgtac   1560
cagcagaaac tgatattaca gaaacaagca taaatggcca tggtgcatat ggagagaaag   1620
gacagaaagg agaaccagca gtggttgagc ctggtatgct tgtcgaagga ccaccaggac   1680
cagcaggacc tgcaggtatt atgggtcctc caggtctaca aggccccact ggacccccctg   1740
gtgaccctgg cgataggggc cccccaggac gtcctggctt accaggggct gatggtctac   1800
ctggtcctcc tggtactatg ttgatgttac cgttccgtta tggtggtgat ggttccaaag   1860
gaccaaccat ctctgctcag gaagctcagg ctcaagctat tcttcagcag gctcggattg   1920
ctctgagagg cccacctggc ccaatgggtc taactggaag accaggtcct gtgggggggc   1980
ctggttcatc tggggccaaa ggtgagagtg gtgatccagg tcctcagggc cctcgaggcg   2040
tccagggtcc ccctggtcca acgggaaaac ctggaaaaag ggtcgtcca ggtgcagatg   2100
gaggaagagg aatgccagga gaacctgggg caaagggaga tcgagggttt gatggacttc   2160
cgggtctgcc aggtgacaaa ggtcacaggg gtgaacgagg tcctcaaggt cctccaggtc   2220
ctcctggtga tgatggaatg aggggagaag atggagaaat tggaccaaga ggtcttccag   2280
gtgaagctgg cccacgaggt ttgctgggtc caaggggaac tccaggagct ccagggcagc   2340
ctggtatggc aggtgtagat ggcccccccag gaccaaaagg gaacatgggt ccccaagggg   2400
```

```
agcctgggcc tccaggtcaa caagggaatc caggacctca gggtcttcct ggtccacaag   2460
gtccaattgg tcctcctggt gaaaaaggac cacaaggaaa accaggactt gctggacttc   2520
ctggtgctga tgggcctcct ggtcatcctg ggaaagaagg ccagtctgga gaaaaggggg   2580
ctctgggtcc ccctggtcca caaggtccta ttggataccc gggcccccgg ggagtaaagg   2640
gagcagatgg tgtcagaggt ctcaagggat ctaaaggtga aaagggtgaa gatggttttc   2700
caggattcaa aggtgacatg ggtctaaaag gtgacagagg agaagttggt caaattggcc   2760
caagagggga agatggccct gaaggaccca aaggtcgagc aggcccaact ggagacccag   2820
gtccttcagg tcaagcagga gaaaagggaa aacttggagt tccaggatta ccaggatatc   2880
caggaagaca aggtccaaag ggttccactg gattccctgg gtttccaggt gccaatggag   2940
agaaaggtgc acggggagta gctggcaaac caggccctcg ggtcagcgt ggtccaacgg    3000
gtcctcgagg ttcaagaggt gcaagaggtc ccactgggaa acctgggcca aagggcactt   3060
caggtggcga tggccctcct ggccctccag gtgaaagagg tcctcaagga cctcagggtc   3120
cagttggatt ccctggacca aaaggccctc ctggaccacc tgggaaggat gggctgccag   3180
gacaccctgg gcaacgtggg gagactggat ttcaaggcaa gaccggccct cctgggccag   3240
ggggagtggt tggaccacag ggaccaaccg gtgagactgg tccaataggg gaacgtgggc   3300
atcctggccc tcctggccct cctggtgagc aaggtcttcc tggtgctgca ggaaaagaag   3360
gtgcaaaggg tgatccaggt cctcaaggta tctcagggaa agatggacca gcaggattac   3420
gtggtttccc aggggaaaga ggtcttcctg gagctcaggg tgcacctgga ctgaaaggag   3480
gggaaggtcc ccagggccca ccaggtccag ttggctcacc aggagaacgt gggtcagcag   3540
gtacagctgg cccaattggt ttaccagggc gcccgggacc tcagggtcct cctggtccag   3600
ctggagagaa aggtgctcct ggagaaaaag gtccccaagg gcctgcaggg agagatggag   3660
ttcaaggtcc tgttggtctc ccagggccag ctggtcctgc cggctcccct ggggaagacg   3720
gagacaaggg tgaaattggt gagccgggac aaaaaggcag caagggtgac aagggagaaa   3780
atggccctcc cggtccccca ggtcttcaag gaccagttgg tgcccctgga attgctggag   3840
gtgatggtga accaggtcct agaggacagc aggggatgtt tgggcaaaaa ggtgatgagg   3900
gtgccagagg cttccctgga cctcctggtc caataggtct tcagggtctg ccaggcccac   3960
ctggtgaaaa aggtgaaaat ggggatgttg gtcccatggg gccacctggt cctccaggcc   4020
caagaggccc tcaaggtccc aatggagctg atggaccaca aggaccccca gggtctgttg   4080
gttcagttgg tggtgttgga gaaaagggtg aacctggaga agcagggaac ccagggcctc   4140
ctggggaagc aggtgtaggc ggtcccaaag gagaaagagg agagaaaggg gaagctggtc   4200
cacctggagc tgctggacct ccaggtgcca aggggccacc aggtgatgat ggccctaagg   4260
gtaacccggg tcctgttggt tttcctggag atcctggtcc tcctggggaa cctggccctg   4320
caggtcaaga tggtgttggt ggtgacaagg gtgaagatgg agatcctggt caaccgggtc   4380
ctcctggccc atctggtgag gctggcccac caggtcctcc tggaaaacga ggtcctcctg   4440
gagctgcagg tgcagaggga agacaaggtg aaaaaggtgc taagggggaa gcaggtgcag   4500
aaggtcctcc tggaaaaacc ggcccagtcg gtcctcaggg acctgcagga aagcctggtc   4560
cagaaggtct tcggggcatc cctggtcctg tgggagaaca aggtctccct ggagctgcag   4620
gccaagatgg accacctggt cctatgggac ctcctggctt acctggtctc aaaggtgacc   4680
ctggctccaa gggtgaaaag ggacatcctg gtttaattgg cctgattggt cctccaggag   4740
aacaagggga aaaaggtgac cgagggctcc ctggaactca aggatctcca ggagcaaaag   4800
```

-continued

```
gggatggggg aattcctggt cctgctggtc ccttaggtcc acctggtcct ccaggtttac   4860
caggtcctca aggcccaaag ggtaacaaag gctctactgg acccgctggc cagaaaggtg   4920
acagtggtct tccagggcct cctgggtctc caggtccacc tggtgaagtc attcagcctt   4980
taccaatctt gtcctccaaa aaaacgagaa gacatactga aggcatgcaa gcagatgcag   5040
atgataatat tcttgattac tcggatggaa tggaagaaat atttggttcc ctcaattccc   5100
tgaaacaaga cattgagcat atgaaatttc caatgggtac tcagaccaat ccagcccgaa   5160
cttgtaaaga cctgcaactc agccatcctg acttcccaga tggtgaatat tggattgatc   5220
ctaaccaagg ttgctcagga gattccttca aagtttactg taatttcaca tctggtggtg   5280
agacttgcat ttatccagac aaaaaatctg agggagtaag aatttcatca tggccaaagg   5340
agaaaccagg aagttggttt agtgaattta agaggggaaa actgctttca tacttagatg   5400
ttgaaggaaa ttccatcaat atggtgcaaa tgacattcct gaaacttctg actgcctctg   5460
ctcggcaaaa tttcacctac cactgtcatc agtcagcagc ctggtatgat gtgtcatcag   5520
gaagttatga caaagcactt cgcttcctgg gatcaaatga tgaggagatg tcctatgaca   5580
ataatccttt tatcaaaaca ctgtatgatg gttgtgcgtc cagaaaaggc tatgaaaaga   5640
ctgtcattga aatcaataca ccaaaaattg atcaagtacc tattgttgat gtcatgatca   5700
atgactttgg tgatcagaat cagaagttcg gatttgaagt tggtcctgtt tgtttttcttg   5760
gctaagatta agacaaagaa catatcaaat caacagaaaa tataccttgg tgccaccaac   5820
ccattttgtg ccacatgcaa gttttgaata aggatggtat agaaaacaac gctgcatata   5880
caggtaccat ttaggaaata ccgatgcctt tgtgggggca gaatcacatg gcaaaagctt   5940
tgaaaatcat aaagatataa gttggtgtgg ctaagatgga aacagggctg attcttgatt   6000
cccaattctc aactctcctt ttcctatttg aatttctttg gtgctgtaga aaacaaaaaa   6060
agaaaaatat atattcataa aaaatatggt gctcattctc atccatccag gatgtactaa   6120
aacagtgtgt ttaataaatt gtaattattt tgtgtacagt tctatactgt tatctgtgtc   6180
catttccaaa acttgcacgt gtccctgaat tccatctgac tctaatttta tgagaattgc   6240
agaactctga tggcaataaa tatatgtatt atgaaaaaat aaagttgtaa tttctgatga   6300
ctctaagtcc ctttctttgg ttaataataa aatgcctttg tatatattga tgttgaagag   6360
ttcaattatt tgatgtcgcc aacaaaattc tcagagggca aaaatctgga agacttttgg   6420
aagcacactc tgatcaactc ttctctgccg acagtcattt tgctgaattt cagccaaaaa   6480
tattatgcat tttgatgctt tattcaaggc tatacctcaa actttttctt ctcagaatcc   6540
aggatttcac aggatacttg tatatatgga aaacaagcaa gtttatattt ttggacaggg   6600
aaatgtgtgt aagaaagtat attaacaaat caatgcctcc gtcaagcaaa caatcatatg   6660
tatacttttt ttctacgtta tctcatctcc ttgttttcag tgtgcttcaa taatgcaggt   6720
taatattaaa gatggaaatt aagcaattat ttatgaattt gtgcaatgtt agattttctt   6780
atcaatcaag ttcttgaatt tgattctaag ttgcatatta taacagtctc gaaaattatt   6840
ttacttgccc aacaaatatt actttttttcc tttcaagata attttataaa tcatttgacc   6900
tacctaattg ctaaatgaat aacatatggt ggactgttat taagagtatt tgttttaagt   6960
cattcaggaa aatctaaact tttttttcca ctaaggtatt tactttaagg tagcttgaaa   7020
tagcaataca atttaaaaat taaaaactga attttgtatc tattttaagt aatatatgta   7080
agacttgaaa ataaatgttt tatttcttat ataaagtgtt aaattaattg ataccagatt   7140
```

-continued

```
tcactggaac agtttcaact gataatttat gacaaaagaa catacctgta atattgaaat   7200

taaaaagtga aatttgtcat aaagaatttc ttttattttt gaaatcgagt ttgtaaatgt   7260

ccttttaaga agggagatat gaatccaata aataaactca agtcttggct a            7311


<210> SEQ ID NO 173
<211> LENGTH: 5914
<212> TYPE: DNA
<213> ORGANISM: Homo sapiens

<400> SEQUENCE: 173

gcagacggga gtttctcctc ggggtcggag caggaggcac gcggagtgtg aggccacgca     60

tgagcggacg ctaacccccct ccccagccac aaagagtcta catgtctagg gtctagacat    120

gttcagcttt gtggacctcc ggctcctgct cctcttagcg gccaccgccc tcctgacgca    180

cggccaagag gaaggccaag tcgagggcca agacgaagac atcccaccaa tcacctgcgt    240

acagaacggc ctcaggtacc atgaccgaga cgtgtggaaa cccgagccct gccggatctg    300

cgtctgcgac aacggcaagg tgttgtgcga tgacgtgatc tgtgacgaga ccaagaactg    360

ccccggcgcc gaagtccccg agggcgagtg ctgtcccgtc tgccccgacg gctcagagtc    420

acccaccgac caagaaacca ccggcgtcga gggacccaag ggagacactg gcccccgagg    480

cccaaggggga cccgcaggcc cccctggccg agatggcatc cctggacagc ctggacttcc    540

cggacccccc ggacccccccg gacctcccgg acccccctggc ctcggaggaa actttgctcc    600

ccagctgtct tatggctatg atgagaaatc aaccggagga atttccgtgc ctggccccat    660

gggtccctct ggtcctcgtg gtctccctgg ccccccctggt gcacctggtc cccaaggctt    720

ccaaggtccc cctggtgagc ctggcgagcc tggagcttca ggtcccatgg gtccccgagg    780

tcccccaggt cccccctggaa agaatggaga tgatggggaa gctggaaaac ctggtcgtcc    840

tggtgagcgt gggcctcctg ggcctcaggg tgctcgagga ttgcccggaa cagctggcct    900

ccctggaatg aagggacaca gaggtttcag tggtttggat ggtgccaagg gagatgctgg    960

tcctgctggt cctaagggtg agcctggcag ccctggtgaa aatggagctc ctggtcagat   1020

gggcccccgt ggcctgcctg gtgagagagg tcgccctgga gcccctggcc ctgctggtgc   1080

tcgtggaaat gatggtgcta ctggtgctgc cgggcccccct ggtcccaccg gccccgctgg   1140

tcctcctggc ttccctggtg ctgttggtgc taagggtgaa gctggtcccc aagggccccg   1200

aggctctgaa ggtccccagg gtgtgcgtgg tgagcctggc cccccctggcc ctgctggtgc   1260

tgctggccct gctggaaacc ctggtgctga tggacagcct ggtgctaaag gtgccaatgg   1320

tgctcctggt attgctggtg ctcctggctt ccctggtgcc cgaggcccct ctggacccca   1380

gggccccggc ggccctcctg gtcccaaggg taacagcggt gaacctggtg ctcctggcag   1440

caaaggagac actggtgcta agggagagcc tggccctgtt ggtgttcaag gacccccctgg   1500

ccctgctgga gaggaaggaa agcgaggagc tcgaggtgaa cccggaccca ctggcctgcc   1560

cggacccccct ggcgagcgtg gtggacctgg tagccgtggt ttccctggcg cagatggtgt   1620

tgctggtccc aagggtcccg ctggtgaacg tggttctcct ggccctgctg gccccaaagg   1680

atctcctggt gaagctggtc gtcccggtga agctggtctg cctggtgcca agggtctgac   1740

tggaagccct ggcagccctg gtcctgatgg caaaactggc ccccctggtc ccgccggtca   1800

agatggtcgc ccccggaccccc caggcccacc tggtgcccgt ggtcaggctg gtgtgatggg   1860

attccctgga cctaaaggtg ctgctggaga gcccggcaag gctggagagc gaggtgttcc   1920

cggacccccct ggcgctgtcg gtcctgctgg caaagatgga gaggctggag ctcagggacc   1980
```

ccctggccct gctggtcccg ctggcgagag aggtgaacaa ggccctgctg gctcccccgg 2040
attccagggt ctccctggtc ctgctggtcc tccaggtgaa gcaggcaaac ctggtgaaca 2100
gggtgttcct ggagaccttg gcgcccctgg cccctctgga gcaagaggcg agagaggttt 2160
ccctggcgag cgtggtgtgc aaggtccccc tggtcctgct ggtccccgag gggccaacgg 2220
tgctcccggc aacgatggtg ctaagggtga tgctggtgcc cctggagctc ccggtagcca 2280
gggcgcccct ggccttcagg gaatgcctgg tgaacgtggt gcagctggtc ttccagggcc 2340
taagggtgac agaggtgatg ctggtcccaa aggtgctgat ggctctcctg gcaaagatgg 2400
cgtccgtggt ctgactggcc ccattggtcc tcctggccct gctggtgccc ctggtgacaa 2460
gggtgaaagt ggtcccagcg gccctgctgg tcccactgga gctcgtggtg cccccggaga 2520
ccgtggtgag cctggtcccc ccggccctgc tggctttgct ggcccccctg gtgctgacgg 2580
ccaacctggt gctaaaggcg aacctggtga tgctggtgct aaaggcgatg ctggtccccc 2640
tggccctgcc ggacccgctg gacccccctgg ccccattggt aatgttggtg ctcctggagc 2700
caaaggtgct cgcggcagcg ctggtccccc tggtgctact ggtttccctg gtgctgctgg 2760
ccgagtcggt cctcctggcc cctctggaaa tgctggaccc cctggccctc ctggtcctgc 2820
tggcaaagaa ggcggcaaag gtccccgtgg tgagactggc cctgctggac gtcctggtga 2880
agttggtccc cctggtcccc ctggccctgc tggcgagaaa ggatcccctg gtgctgatgg 2940
tcctgctggt gctcctggta ctcccgggcc tcaaggtatt gctggacagc gtggtgtggt 3000
cggcctgcct ggtcagagag gagagagagg cttccctggt cttcctggcc cctctggtga 3060
acctggcaaa caaggtccct ctggagcaag tggtgaacgt ggtcccccctg gtcccatggg 3120
ccccccctgga ttggctggac cccctggtga atctggacgt gagggggctc ctggtgccga 3180
aggttcccct ggacgagacg gttctcctgg cgccaagggt gaccgtggtg agaccggccc 3240
cgctggaccc cctggtgctc ctggtgctcc tggtgcccct ggccccgttg gccctgctgg 3300
caagagtggt gatcgtggtg agactggtcc tgctggtccc gccggtcctg tcggccctgt 3360
tggcgcccgt ggccccgccg gaccccaagg cccccgtggt gacaagggtg agacaggcga 3420
acagggcgac agaggcataa agggtcaccg tggcttctct ggcctccagg gtccccctgg 3480
ccctcctggc tctcctggtg aacaaggtcc ctctggagcc tctggtcctg ctggtccccg 3540
aggtcccccct ggctctgctg gtgctcctgg caaagatgga ctcaacggtc tccctggccc 3600
cattgggccc cctggtcctc gcggtcgcac tggtgatgct ggtcctgttg gtcccccccgg 3660
ccctcctgga cctcctggtc cccctggtcc tcccagcgct ggtttcgact tcagcttcct 3720
gccccagcca cctcaagaga aggctcacga tggtggccgc tactaccggg ctgatgatgc 3780
caatgtggtt cgtgaccgtg acctcgaggt ggacaccacc ctcaagagcc tgagccagca 3840
gatcgagaac atccggagcc cagagggcag ccgcaagaac cccgcccgca cctgccgtga 3900
cctcaagatg tgccactctg actggaagag tggagagtac tggattgacc ccaaccaagg 3960
ctgcaacctg gatgccatca aagtcttctg caacatggag actggtgaga cctgcgtgta 4020
ccccactcag cccagtgtgg cccagaagaa ctggtacatc agcaagaacc ccaaggacaa 4080
gaggcatgtc tggttcggcg agagcatgac cgatggattc cagttcgagt atggcggcca 4140
gggctccgac cctgccgatg tggccatcca gctgaccttc ctgcgcctga tgtccaccga 4200
ggcctcccag aacatcacct accactgcaa gaacagcgtg gcctacatgg accagcagac 4260
tggcaacctc aagaaggccc tgctcctcca gggctccaac gagatcgaga tccgcgccga 4320

```
gggcaacagc cgcttcacct acagcgtcac tgtcgatggc tgcacgagtc acaccggagc   4380
ctggggcaag acagtgattg aatacaaaac caccaagacc tcccgcctgc ccatcatcga   4440
tgtggccccc ttggacgttg gtgccccaga ccaggaattc ggcttcgacg ttggccctgt   4500
ctgcttcctg taaactccct ccatcccaac ctggctccct cccacccaac caactttccc   4560
cccaacccgg aaacagacaa gcaacccaaa ctgaaccccc tcaaaagcca aaaaatggga   4620
gacaatttca catggacttt ggaaaatatt tttttccttt gcattcatct ctcaaactta   4680
gtttttatct ttgaccaacc gaacatgacc aaaaaccaaa agtgcattca accttaccaa   4740
aaaaaaaaaa aaaaaaagaa taaataaata actttttaaa aaaggaagct tggtccactt   4800
gcttgaagac ccatgcgggg gtaagtccct ttctgcccgt tgggcttatg aaaccccaat   4860
gctgcccttt ctgctccttt ctccacaccc cccttggggc ctcccctcca ctccttccca   4920
aatctgtctc cccagaagac acaggaaaca atgtattgtc tgcccagcaa tcaaaggcaa   4980
tgctcaaaca cccaagtggc ccccaccctc agcccgctcc tgcccgccca gcacccccag   5040
gccctggggg acctggggtt ctcagactgc caaagaagcc ttgccatctg gcgctcccat   5100
ggctcttgca acatctcccc ttcgtttttg agggggtcat gccgggggag ccaccagccc   5160
ctcactgggt tcggaggaga gtcaggaagg gccacgacaa agcagaaaca tcggatttgg   5220
ggaacgcgtg tcaatccctt gtgccgcagg gctgggcggg agagactgtt ctgttccttg   5280
tgtaactgtg ttgctgaaag actacctcgt tcttgtcttg atgtgtcacc ggggcaactg   5340
cctgggggcg gggatggggg cagggtggaa gcggctcccc attttatacc aaaggtgcta   5400
catctatgtg atgggtgggg tggggaggga atcactggtg ctatagaaat tgagatgccc   5460
ccccaggcca gcaaatgttc ctttttgttc aaagtctatt tttattcctt gatatttttc   5520
ttttttttt tttttttttg tggatgggga cttgtgaatt tttctaaagg tgctatttaa   5580
catgggagga gagcgtgtgc ggctccagcc cagcccgctg ctcactttcc accctctctc   5640
cacctgcctc tggcttctca ggcctctgct ctccgacctc tctcctctga aaccctcctc   5700
cacagctgca gcccatcctc ccggctccct cctagtctgt cctgcgtcct ctgtccccgg   5760
gtttcagaga caacttccca aagcacaaag cagtttttcc ccctaggggt gggaggaagc   5820
aaaagactct gtacctattt tgtatgtgta taataatttg agatgttttt aattattttg   5880
attgctggaa taaagcatgt ggaaatgacc caaa                                5914
```

```
<210> SEQ ID NO 174
<211> LENGTH: 6829
<212> TYPE: DNA
<213> ORGANISM: Homo sapiens

<400> SEQUENCE: 174

gcagactgtg ctggagctgg tgctgaaaaa gggggtttgc agaggctgcc ctggggctgg     60
tgctgaaaga agagcccaca gctgacttca tggtgctaca ataacctcag aatctacttt    120
tcactctcag gagaacccac atgtctaata tttagacatg atggcaaact gggcggaagc    180
aagacctctc ctcattctta ttgttttatt agggcaattt gtctcaataa aagcccagga    240
agaagacgag gatgaaggat atggtgaaga aatagcctgc actcagaatg gccagatgta    300
cttaaacagg gacatttgga aacctgcccc ttgtcagatc tgtgtctgtg acaatggagc    360
cattctctgt gacaagatag aatgccagga tgtgctggac tgtgccgacc ctgtaacgcc    420
ccctggggaa tgctgtcctg tctgttcaca aacacctgga ggtggcaata ccaattttgg    480
tagaggaaga aagggacaaa agggagaacc aggattagtg cctgttgtaa caggcatacg    540
```

tggtcgtcca ggaccggcag gacctccagg atcacaggga ccaagaggag agcgagggcc 600
aaaaggaaga cctggccctc gtggacctca gggaattgat ggagaaccag gtgttcctgg 660
tcaacctggt gctccaggac ctcctggaca tccgtcccac ccaggacccg atggcttgag 720
caggccgttt tcagctcaaa tggctgggtt ggatgaaaaa tctggacttg ggagtcaagt 780
aggactaatg cctggctctg tgggtcctgt tggcccaagg ggaccacagg gtttacaagg 840
acagcaaggt ggtgcaggac ctacaggacc tcctggtgaa cctggtgatc ctggaccaat 900
gggtccgatt ggttcacgtg gaccagaggg ccctcctggt aaacctgggg aagatggtga 960
acctggcaga aatggaaatc ctggtgaagt gggatttgca ggatctccgg gagctcgtgg 1020
atttcctggg gctcctggtc ttccaggtct gaagggtcac cgaggacaca aaggtcttga 1080
aggccctaaa ggtgaagttg gagcacctgg ttccaagggt gaagctggcc ccactggtcc 1140
aatgggtgcc atgggtcctc tgggtccgag gggaatgcca ggagagagag ggagacttgg 1200
gccacagggt gctcctggac aacgaggtgc acatggtatg cctggaaaac ctggaccaat 1260
gggtcctctt gggataccag gctcttctgg ttttccagga aatcctggaa tgaagggaga 1320
agcaggtcct acaggggcgc gaggccctga aggtcctcag gggcagagag gtgaaactgg 1380
gcccccaggt ccagttggct ctccaggtct tcctggtgca ataggaactg atggtactcc 1440
tggtgccaaa ggcccaacgg gctctccagg tacctctggt cctcctggct cagcagggcc 1500
tcctggatct ccaggacctc agggtagcac tggtcctcag ggaattcgag gccaaccggg 1560
tgatccagga gttccaggtt tcaaaggaga agctggccca aaaggggaac cagggccaca 1620
tggtattcag ggtccgatag gcccacccgg tgaagaaggc aaaagaggtc ccagaggtga 1680
cccaggaaca gttggtcctc cagggccagt gggagaaagg ggtgctcctg gcaatcgtgg 1740
ttttccaggc tctgatggtt tacctgggcc aaagggtgct caaggagaac ggggtcctgt 1800
aggttcttca ggacccaaag gaagccaggg ggatccagga cgtccagggg aacctgggct 1860
tccaggtgct cggggtttga caggaaatcc tggtgttcaa ggtcctgaag gaaaacttgg 1920
acctttgggt gcgccagggg aagatggccg tccaggtcct ccaggctcca taggaatcag 1980
agggcagccc gggagcatgg gccttccagg ccccaaaggt agcagtggtg accctgggaa 2040
acctggagaa gcaggaaatg ctggagttcc tgggcagagg ggagctcctg gaaaagatgg 2100
tgaagttggt ccttctggtc ctgtgggccc gccgggtcta gctggtgaaa gaggagaaca 2160
aggacctcca ggccccacag gttttcaggg gcttcctggt cctccagggc ctcctggaga 2220
aggtggaaaa ccaggtgatc aaggtgttcc tggagatccc ggagcagttg gcccgttagg 2280
acctagagga gaacgaggaa atcctgggga aagaggagaa cctgggataa ctggactccc 2340
tggtgagaag ggaatggctg gaggacatgg tcctgatggc ccaaaaggca gtccaggtcc 2400
atctgggacc cctggagata caggcccacc aggtcttcaa ggtatgccgg gagaaagagg 2460
aattgcagga actcctggcc ccaagggtga cagaggtggc ataggagaaa aaggtgctga 2520
aggcacagct ggaaatgatg gtgcaagagg tcttccaggt cctttgggcc ctccaggtcc 2580
ggcaggtcct actggagaaa agggtgaacc tggtcctcga ggtttagttg gccctcctgg 2640
ctcccggggc aatcctggtt ctcgaggtga aaatgggcca actggagctg ttggttttgc 2700
cggaccccag ggtcctgacg gacagcctgg agtaaaaggt gaacctggag agccaggaca 2760
gaagggagat gctggttctc ctggaccaca aggtttagca ggatcccctg gccctcatgg 2820
tcctaatggt gttcctggac taaaaggtgg tcgaggaacc caaggtccgc ctggtgctac 2880

```
aggatttcct ggttctgcgg gcagagttgg acctccaggc cctgctggag ctccaggacc   2940
tgcgggaccc ctaggggaac ccgggaagga gggacctcca ggtcttcgtg gggaccctgg   3000
ctctcatggg cgtgtgggag atcgaggacc agctggcccc cctggtggcc caggagacaa   3060
aggggaccca ggagaagatg ggcaacctgg tccagatggc ccccctggtc cagctggaac   3120
gaccgggcag agaggaattg ttggcatgcc tgggcaacgt ggagagagag gcatgcccgg   3180
cctaccaggc ccagcgggaa caccaggaaa agtaggacca actggtgcaa caggagataa   3240
aggtccacct ggacctgtgg ggcccccagg ctccaatggt cctgtagggg aacctggacc   3300
agaaggtcca gctggcaatg atggtacccc aggacgggat ggtgctgttg gagaacgtgg   3360
tgatcgtgga gaccctgggc ctgcaggtct gccaggctct cagggtgccc ctggaactcc   3420
tggccctgtg ggtgctccag gagatgcagg acaaagagga gatccgggtt ctcggggtcc   3480
tataggacca cctggtcgag ctgggaaacg tggattacct ggaccccaag gacctcgtgg   3540
tgacaaaggt gatcatggag accgaggtga cagaggtcag aagggccaca gaggctttac   3600
tggtcttcag ggtcttcctg gccctcctgg tccaaatggt gaacaaggaa gtgctggaat   3660
ccctggacca tttggcccaa gaggtcctcc aggcccagtt ggtccttcag gtaaagaagg   3720
aaaccctggg ccacttgggc caattggacc tccaggtgta cgaggcagtg taggagaagc   3780
aggacctgag ggccctcctg gtgagcctgg cccacctggc cctccgggtc cccctggcca   3840
ccttacagct gctcttgggg atatcatggg gcactatgat gaaagcatgc cagatccact   3900
tcctgagttt actgaagatc aggcggctcc tgatgacaaa aacaaaacgg acccaggggt   3960
tcatgctacc ctgaagtcac tcagtagtca gattgaaacc atgcgcagcc ccgatggctc   4020
gaaaaagcac ccagcccgca cgtgtgatga cctaaagctt tgccattccg caaagcagag   4080
tggtgaatac tggattgatc ctaaccaagg atctgttgaa gatgcaatca aagtttactg   4140
caacatggaa acaggagaaa catgtatttc agcaaaccca tccagtgtac cacgtaaaac   4200
ctggtgggcc agtaaatctc ctgacaataa acctgtttgg tatggtcttg atatgaacag   4260
agggtctcag ttcgcttatg gagaccacca atcacctaat acagccatta ctcagatgac   4320
ttttttgcgc cttttatcaa aagaagcctc ccagaacatc acttacatct gtaaaaacag   4380
tgtaggatac atggacgatc aagctaagaa cctcaaaaaa gctgtggttc tcaaaggggc   4440
aaatgactta gatatcaaag cagagggaaa tattagattc cggtatatcg ttcttcaaga   4500
cacttgctct aagcggaatg gaaatgtggg caagactgtc tttgaatata gaacacagaa   4560
tgtggcacgc ttgcccatca tagatcttgc tcctgtggat gttggcggca cagaccagga   4620
attcggcgtt gaaattgggc cagtttgttt tgtgtaaagt aagccaagac acatcgacaa   4680
tgagcaccac catcaatgac caccgccatt cacaagaact ttgactgttt gaagttgatc   4740
ctgagactct tgaagtaatg gctgatcctg catcagcatt gtatatatgg tcttaagtgc   4800
ctggcctcct tatccttcag aatatttatt ttacttacaa tcctcaagtt ttaattgatt   4860
ttaaatattt ttcaatacaa cagtttaggt ttaagatgac caatgacaat gaccaccttt   4920
gcagaaagta aactgattga ataaataaat ctccgttttc ttcaatttat ttcagtgtaa   4980
tgaaaaagtt gcttagtatt tatgaggaaa ttcttcttcc tggcaggtag cttaaagagt   5040
ggggtatata gagccacaac acatgtttat tttgcttggc tgcagttgaa aaatagaaat   5100
tagtgccctt ttgtgacctc tcattccaag attgtcaatt aaaaatgagt ttaaaatgtt   5160
taacttgtga tcgagaccta catgcatgtc ttgatattgt gtaactataa tagagactct   5220
ttaaggagaa tcttaaaaaa aaaaaaacgt ttctcactgt cttaaataga atttttaaat   5280
```

agtatatatt cagtggcatt ttggagaaca aagtgaattt acttcgactt cttaaatttt 5340
tgtaaaagac tataagttta gacatctttc tcattcaaat ttaaagatat ctttctcctc 5400
ttgatcaatc tatcaatatt gatagaagtc acactagtat ataccattta atacatttac 5460
actttcttat ttaagaagat attgaatgca aaataattga catatagaac tttacaaaca 5520
tatgtccaag gactctaaat tgagactctt ccacatgtac aatctcatca tcctgaagcc 5580
tataatgaag aaaaagatct agaaactgag ttgtggagct gactctaatc aaatgtgatg 5640
attggaatta gaccatttgg cctttgaact ttcataggaa aaatgaccca acatttctta 5700
gcatgagcta cctcatctct agaagctggg atggacttac tattcttgtt tatattttag 5760
atactgaaag gtgctatgct tctgttatta ttccaagact ggagataggc agggctaaaa 5820
aggtattatt atttttcctt taatgatggt gctaaaattc ttcctataaa attccttaaa 5880
aataaagatg gtttaatcac taccattgtg aaaacataac tgttagactt cccgtttctg 5940
aaagaaagag catcgttcca atgcttgttc actgttcctc tgtcatactg tatctggaat 6000
gctttgtaat acttgcatgc ttcttagacc agaacatgta ggtccccttg tgtctcaata 6060
cttttttttt cttaattgca tttgttggct ctattttaat ttttttcttt taaaataaac 6120
agctgggacc atcccaaaag acaagccatg catacaactt tggtcatgta tctctgcaaa 6180
gcatcaaatt aaatgcacgc ttttgtcatg tcagtggttt ttgttttgtg aaattccttt 6240
gaccatatta gatctatttc atttccaata gtgaaaagga gatgtggtgg tatactttgt 6300
ttgccatttg tttaaaagat acaacggata ccttctatca tgtatgtact ggcttataaa 6360
tgaaaatcta tctacaacat tacccacaaa ggcaacatga caccaattat cactgcctct 6420
gcccttaaaa atgtcagagt agtattattg ataaaaaggg caagcaatag atttttcatg 6480
actgaataaa ctgtaataat aaaacatatg tctcaaagtg tatcacatat gaatttagcc 6540
taattgtttt cagtttcatt ctcaatattt agtttacaac atcattttcc cctaaactgg 6600
ttatattttg acctgtatat cttaaatttg agtatttata tgcctaaata catgtgtgag 6660
ttttgtttga cttccaagtc caaactataa gattatataa gttcatatag atgaatcaga 6720
aatatgtggt aatactatta agtcacaaac actaacaatt tccaactata gaaataacag 6780
ttcttatttg gattttggga atgctaccaa taaaagcctg cccagacca 6829

<210> SEQ ID NO 175
<211> LENGTH: 5072
<212> TYPE: DNA
<213> ORGANISM: Homo sapiens

<400> SEQUENCE: 175
agcaccacgg cagcaggagg tttcggctaa gttggaggta ctggccacga ctgcatgccc 60
gcgcccgcca ggtgatacct ccgccggtga cccaggggct ctgcgacaca aggagtctgc 120
atgtctaagt gctagacatg ctcagctttg tggatacgcg gactttgttg ctgcttgcag 180
taaccttatg cctagcaaca tgccaatctt tacaagagga aactgtaaga aagggcccag 240
ccggagatag aggaccacgt ggagaaaggg gtccaccagg ccccccaggc agagatggtg 300
aagatggtcc cacaggccct cctggtccac ctggtcctcc tggcccccct ggtctcggtg 360
ggaactttgc tgctcagtat gatggaaaag gagttggact tggccctgga ccaatgggct 420
taatgggacc tagaggccca cctggtgcag ctggagcccc aggccctcaa ggtttccaag 480
gacctgctgg tgagcctggt gaacctggtc aaactggtcc tgcaggtgct cgtggtccag 540

-continued

```
ctggccctcc tggcaaggct ggtgaagatg gtcaccctgg aaaacccgga cgacctggtg    600
agagaggagt tgttggacca cagggtgctc gtggtttccc tggaactcct ggacttcctg    660
gcttcaaagg cattagggga cacaatggtc tggatggatt gaagggacag cccggtgctc    720
ctggtgtgaa gggtgaacct ggtgcccctg gtgaaaatgg aactccaggt caaacaggag    780
cccgtgggct tcctggtgag agaggacgtg ttggtgcccc tggcccagct ggtgcccgtg    840
gcagtgatgg aagtgtgggt cccgtgggtc ctgctggtcc cattgggtct gctggccctc    900
caggcttccc aggtgcccct ggccccaagg gtgaaattgg agctgttggt aacgctggtc    960
ctgctggtcc cgccggtccc cgtggtgaag tgggtcttcc aggcctctcc ggccccgttg   1020
gacctcctgg taatcctgga gcaaacggcc ttactggtgc caagggtgct gctggccttc   1080
ccggcgttgc tggggctccc ggcctccctg gaccccgcgg tattcctggc cctgttggtg   1140
ctgccggtgc tactggtgcc agaggacttg ttggtgagcc tggtccagct ggctccaaag   1200
gagagagcgg taacaagggt gagcccggct ctgctgggcc ccaaggtcct cctggtccca   1260
gtggtgaaga aggaaagaga ggccctaatg gggaagctgg atctgccggc cctccaggac   1320
ctcctgggct gagaggtagt cctggttctc gtggtcttcc tggagctgat ggcagagctg   1380
gcgtcatggg ccctcctggt agtcgtggtg caagtggccc tgctggagtc cgaggaccta   1440
atggagatgc tggtcgccct ggggagcctg gtctcatggg acccagaggt cttcctggtt   1500
cccctggaaa tatcggcccc gctggaaaag aaggtcctgt cggcctccct ggcatcgacg   1560
gcaggcctgg cccaattggc ccagctggag caagaggaga gcctggcaac attggattcc   1620
ctggacccaa aggccccact ggtgatcctg gcaaaaacgg tgataaaggt catgctggtc   1680
ttgctggtgc tcggggtgct ccaggtcctg atggaaacaa tggtgctcag ggacctcctg   1740
gaccacaggg tgttcaaggt ggaaaaggtg aacagggtcc ccctggtcct ccaggcttcc   1800
agggtctgcc tggcccctca ggtcccgctg gtgaagttgg caaaccagga gaaaggggtc   1860
tccatggtga gtttggtctc cctggtcctg ctggtccaag aggggaacgc ggtcccccag   1920
gtgagagtgg tgctgccggt cctactggtc ctattggaag ccgaggtcct tctggacccc   1980
cagggcctga tggaaacaag ggtgaacctg gtgtggttgg tgctgtgggc actgctggtc   2040
catctggtcc tagtggactc ccaggagaga ggggtgctgc tggcatacct ggaggcaagg   2100
gagaaaaggg tgaacctggt ctcagaggtg aaattggtaa ccctggcaga gatggtgctc   2160
gtggtgctcc tggtgctgta ggtgcccctg gtcctgctgg agccacaggt gaccggggcg   2220
aagctggggc tgctggtcct gctggtcctg ctggtcctcg gggaagccct ggtgaacgtg   2280
gtgaggtcgg tcctgctggc cccaatggat ttgctggtcc tgctggtgct gctggtcaac   2340
ctggtgctaa aggagaaaga ggagccaaag ggcctaaggg tgaaaacggt gttgttggtc   2400
ccacaggccc cgttggagct gctggcccag ctggtccaaa tggtcccccc ggtcctgctg   2460
gaagtcgtgg tgatggaggc ccccctggta tgactggttt ccctggtgct gctggacgga   2520
ctggtccccc aggaccctct ggtatttctg gccctcctgg tccccctggt cctgctggga   2580
aagaagggct tcgtggtcct cgtggtgacc aaggtccagt tggccgaact ggagaagtag   2640
gtgcagttgg tccccctggc ttcgctggtg agaagggtcc ctctggagag gctggtactg   2700
ctggacctcc tggcactcca ggtcctcagg gtcttcttgg tgctcctggt attctgggtc   2760
tccctggctc gagaggtgaa cgtggtctac caggtgttgc tggtgctgtg ggtgaacctg   2820
gtcctcttgg cattgccggc cctcctgggg cccgtggtcc tcctggtgct gtgggtagtc   2880
ctggagtcaa cggtgctcct ggtgaagctg gtcgtgatgg caaccctggg aacgatggtc   2940
```

```
ccccaggtcg cgatggtcaa cccggacaca agggagagcg cggttaccct ggcaatattg   3000
gtcccgttgg tgctgcaggt gcacctggtc ctcatggccc cgtgggtcct gctggcaaac   3060
atggaaaccg tggtgaaact ggtccttctg gtcctgttgg tcctgctggt gctgttggcc   3120
caagaggtcc tagtggccca caaggcattc gtggcgataa gggagagccc ggtgaaaagg   3180
ggcccagagg tcttcctggc ttaaagggac acaatggatt gcaaggtctg cctggtatcg   3240
ctggtcacca tggtgatcaa ggtgctcctg gctccgtggg tcctgctggt cctaggggcc   3300
ctgctggtcc ttctggccct gctggaaaag atggtcgcac tggacatcct ggtacagttg   3360
gacctgctgg cattcgaggc cctcagggtc accaaggccc tgctggcccc cctggtcccc   3420
ctggccctcc tggacctcca ggtgtaagcg gtggtggtta tgactttggt tacgatggag   3480
acttctacag ggctgaccag cctcgctcag caccttctct cagacccaag gactatgaag   3540
ttgatgctac tctgaagtct ctcaacaacc agattgagac ccttcttact cctgaaggct   3600
ctagaaagaa cccagctcgc acatgccgtg acttgagact cagccaccca gagtggagca   3660
gtggttacta ctggattgac cctaaccaag gatgcactat ggatgctatc aaagtatact   3720
gtgatttctc tactggcgaa acctgtatcc gggcccaacc tgaaaacatc ccagccaaga   3780
actggtatag gagctccaag gacaagaaac acgtctggct aggagaaact atcaatgctg   3840
gcagccagtt tgaatataat gtagaaggag tgacttccaa ggaaatggct acccaacttg   3900
ccttcatgcg cctgctggcc aactatgcct ctcagaacat cacctaccac tgcaagaaca   3960
gcattgcata catggatgag gagactggca acctgaaaaa ggctgtcatt ctacagggct   4020
ctaatgatgt tgaacttgtt gctgagggca acagcaggtt cacttacact gttcttgtag   4080
atggctgctc taaaaagaca aatgaatggg gaaagacaat cattgaatac aaaacaaata   4140
agccatcacg cctgcccttc cttgatattg cacctttgga catcggtggt gctgaccagg   4200
aattctttgt ggacattggc ccagtctgtt tcaaataaat gaactcaatc taaattaaaa   4260
aagaaagaaa tttgaaaaaa ctttctcttt gccatttctt cttcttcttt tttaactgaa   4320
agctgaatcc ttccatttct tctgcacatc tacttgctta aattgtgggc aaaagagaaa   4380
aagaaggatt gatcagagca ttgtgcaata cagtttcatt aactccttcc cccgctcccc   4440
caaaaatttg aatttttttt tcaacactct tacacctgtt atggaaaatg tcaacctttg   4500
taagaaaacc aaaataaaaa ttgaaaaata aaaaccataa acatttgcac cacttgtggc   4560
ttttgaatat cttccacaga gggaagttta aaacccaaac ttccaaaggt ttaaactacc   4620
tcaaaacact ttcccatgag tgtgatccac attgttaggt gctgacctag acagagatga   4680
actgaggtcc ttgttttgtt ttgttcataa tacaaaggtg ctaattaata gtatttcaga   4740
tacttgaaga atgttgatgg tgctagaaga atttgagaag aaatactcct gtattgagtt   4800
gtatcgtgtg gtgtattttt taaaaaattt gatttagcat tcatattttc catcttattc   4860
ccaattaaaa gtatgcagat tatttgccca aatcttcttc agattcagca tttgttcttt   4920
gccagtctca ttttcatctt cttccatggt tccacagaag ctttgtttct tgggcaagca   4980
gaaaaattaa attgtaccta ttttgtatat gtgagatgtt taaataaatt gtgaaaaaaa   5040
tgaaataaag catgtttggt tttccaaaag aa                                 5072
```

<210> SEQ ID NO 176
<211> LENGTH: 6540
<212> TYPE: DNA
<213> ORGANISM: Homo sapiens

<400> SEQUENCE: 176
aggtctccgc ttggagccgc cgcacccggg acggtgcgta gcgctggaag tccggccttc 60
cgagagctag ctgtccgccg cggcccccgc acgccgggca gccgtccctc gccgcctcgg 120
gcgcgccacc atggggcccc ggctcagcgt ctggctgctg ctgctgcccg ccgcccttct 180
gctccacgag gagcacagcc gggccgctgc gaagggtggc tgtgctggct ctggctgtgg 240
caaatgtgac tgccatggag tgaagggaca aaagggtgaa agaggcctcc cggggttaca 300
aggtgtcatt gggtttcctg gaatgcaagg acctgagggg ccacagggac caccaggaca 360
aaagggtgat actggagaac caggactacc tggaacaaaa gggacaagag gacctccggg 420
agcatctggc taccctggaa acccaggact tcccggaatt cctggccaag acggcccgcc 480
aggcccccca ggtattccag gatgcaatgg cacaaagggg gagagagggc cgctcgggcc 540
tcctggcttg cctggtttcg ctggaaatcc cggaccacca ggcttaccag ggatgaaggg 600
tgatccaggt gagatacttg gccatgtgcc cgggatgctg ttgaaaggtg aaagaggatt 660
tcccggaatc ccagggactc caggcccacc aggactgcca gggcttcaag gtcctgttgg 720
gcctccagga tttaccggac caccaggtcc cccaggccct cccggccctc caggtgaaaa 780
gggacaaatg ggcttaagtt ttcaaggacc aaaaggtgac aagggtgacc aaggggtcag 840
tgggcctcca ggagtaccag gacaagctca agttcaagaa aaaggagact tcgccaccaa 900
gggagaaaag ggccaaaaag gtgaacctgg atttcagggg atgccagggg tcggagagaa 960
aggtgaaccc ggaaaaccag gacccagagg caaacccgga aaagatggtg acaaagggga 1020
aaaagggagt cccggttttc ctggtgaacc cgggtaccca ggactcatag gccgccaggg 1080
cccgcaggga gaaaagggtg aagcaggtcc tcctggccca cctggaattg ttataggcac 1140
aggacctttg ggagaaaaag gagagagggg ctaccctgga actccggggc caagaggaga 1200
gccaggccca aaaggtttcc caggactacc aggccaaccc ggacctccag gcctccctgt 1260
acctgggcag gctggtgccc ctggcttccc tggtgaaaga ggagaaaaag gtgaccgagg 1320
atttcctggt acatctctgc caggaccaag tggaagagat gggctcccgg gtcctcctgg 1380
ttcccctggg ccccctgggc agcctggcta cacaaatgga attgtggaat gtcagcccgg 1440
acctccaggt gaccagggtc ctcctggaat tccagggcag ccaggattta taggcgaaat 1500
tggagagaaa ggtcaaaaag gagagagttg cctcatctgt gatatagacg gatatcgggg 1560
gcctcccggg ccacagggac ccccgggaga aataggtttc ccagggcagc caggggccaa 1620
gggcgacaga ggtttgcctg gcagagatgg tgttgcagga gtgccaggcc ctcaaggtac 1680
accagggctg ataggccagc caggagccaa gggggagcct ggtgagtttt atttcgactt 1740
gcggctcaaa ggtgacaaag gagacccagg ctttccagga cagcccggca tgccagggag 1800
agcgggttct cctggaagag atggccatcc gggtcttcct ggccccaagg gctcgccggg 1860
ttctgtagga ttgaaaggag agcgtggccc ccctggagga gttggattcc caggcagtcg 1920
tggtgacacc ggcccccctg ggcctccagg atatggtcct gctggtccca ttggtgacaa 1980
aggacaagca ggctttcctg gaggccctgg atccccaggc ctgccaggtc caaagggtga 2040
accaggaaaa attgttcctt taccaggccc ccctggagca gaaggactgc cggggtcccc 2100
aggcttccca ggtccccaag gagaccgagg ctttcccgga accccaggaa ggccaggcct 2160
gccaggagag aagggcgctg tgggccagcc aggcattgga tttccagggc cccccggccc 2220
caaaggtgtt gacggcttac ctggagacat ggggccaccg gggactccag gtcgcccggg 2280
atttaatggc ttacctggga acccaggtgt gcagggccag aagggagagc ctggagttgg 2340

-continued

```
tctaccggga ctcaaaggtt tgccaggtct tcccggcatt cctggcacac ccggggagaa   2400
ggggagcatt ggggtaccag gcgttcctgg agaacatgga gcgatcggac cccctgggct   2460
tcaggggatc agaggtgaac cgggacctcc tggattgcca ggctccgtgg ggtctccagg   2520
agttccagga ataggccccc ctggagctag ggtccccct ggaggacagg gaccaccggg   2580
gttgtcaggc cctcctggaa taaaaggaga gaagggtttc cccggattcc ctggactgga   2640
catgccgggc cctaaaggag ataaaggggc tcaaggactc cctggcataa cgggacagtc   2700
ggggctccct ggccttcctg gacagcaggg ggctcctggg attcctgggt ttccaggttc   2760
caagggagaa atgggcgtca tggggacccc cgggcagccg ggctcaccag gaccagtggg   2820
tgctcctgga ttaccgggtg aaaaagggga ccatggcttt ccgggctcct caggacccag   2880
gggagaccct ggcttgaaag gtgataaggg ggatgtcggt ctccctggca agcctggctc   2940
catggataag gtggacatgg gcagcatgaa gggccagaaa ggagaccaag gagagaaagg   3000
acaaattgga ccaattggtg agaagggatc ccgaggagac cctgggaccc caggagtgcc   3060
tggaaaggac gggcaggcag gacagcctgg gcagccagga cctaaaggtg atccaggtat   3120
aagtggaacc ccaggtgctc caggacttcc gggaccaaaa ggatctgttg gtggaatggg   3180
cttgccagga acacctggag agaaaggtgt gcctggcatc cctggcccac aaggttcacc   3240
tggcttacct ggagacaaag gtgcaaaagg agagaaaggg caggcaggcc cacctggcat   3300
aggcatccca gggctgcgag gtgaaaaggg agatcaaggg atagcgggtt tcccaggaag   3360
ccctggagag aagggagaaa aaggaagcat tgggatccca ggaatgccag ggtccccagg   3420
ccttaaaggg tctcccggga gtgttggcta tccaggaagt cctgggctac ctggagaaaa   3480
aggtgacaaa ggcctcccag gattggatgg catccctggt gtcaaaggag aagcaggtct   3540
tcctgggact cctggcccca caggcccagc tggccagaaa ggggagccag gcagtgatgg   3600
aatcccgggg tcagcaggag agaagggtga accaggtcta ccaggaagag gattcccagg   3660
gtttccaggg gccaaaggag acaaaggttc aaagggtgag gtgggtttcc caggattagc   3720
cgggagccca ggaattcctg gatccaaagg agagcaagga ttcatgggtc ctccggggcc   3780
ccagggacag ccggggttac cgggatcccc aggccatgcc acggaggggc ccaaaggaga   3840
ccgcggacct cagggccagc ctggcctgcc aggacttccg ggacccatgg ggcctccagg   3900
gcttcctggg attgatggag ttaaaggtga caaaggaaat ccaggctggc caggagcacc   3960
cggtgtccca gggcccaagg gagaccctgg attccagggc atgcctggta ttggtggctc   4020
tccaggaatc acaggctcta agggtgatat ggggcctcca ggagttccag gatttcaagg   4080
tccaaaaggt cttcctggcc tccagggaat taaaggtgat caaggcgatc aaggcgtccc   4140
gggagctaaa ggtctcccgg gtcctcctgg ccccccaggt ccttacgaca tcatcaaagg   4200
ggagcccggg ctccctggtc ctgagggccc cccagggctg aaagggcttc agggactgcc   4260
aggcccgaaa ggccagcaag gtgttacagg attggtgggt atacctggac ctccaggtat   4320
tcctgggttt gacggtgccc ctggccagaa aggagagatg ggacctgccg ggcctactgg   4380
tccaagagga tttccaggtc caccaggccc cgatgggttg ccaggatcca tggggccccc   4440
aggcacccca tctgttgatc acggcttcct tgtgaccagg catagtcaaa caatagatga   4500
cccacagtgt ccttctggga ccaaaattct ttaccacggg tactctttgc tctacgtgca   4560
aggcaatgaa cgggcccatg gccaggactt gggcacggcc ggcagctgcc tgcgcaagtt   4620
cagcacaatg cccttcctgt tctgcaatat taacaacgtg tgcaactttg catcacgaaa   4680
```

-continued

```
tgactactcg tactggctgt ccacccctga gcccatgccc atgtcaatgg cacccatcac   4740
gggggaaaac ataagaccat ttattagtag gtgtgctgtg tgtgaggcgc ctgccatggt   4800
gatggccgtg cacagccaga ccattcagat cccaccgtgc cccagcgggt ggtcctcgct   4860
gtggatcggc tactcttttg tgatgcacac cagcgctggt gcagaaggct ctggccaagc   4920
cctggcgtcc cccggctcct gcctggagga gtttagaagt gcgccattca tcgagtgtca   4980
cggccgtggg acctgcaatt actacgcaaa cgcttacagc ttttggctcg ccaccataga   5040
gaggagcgag atgttcaaga agcctacgcc gtccaccttg aaggcagggg agctgcgcac   5100
gcacgtcagc cgctgccaag tctgtatgag aagaacataa tgaagcctga ctcagctaat   5160
gtcacaacat ggtgctactt cttcttcttt ttgttaacag caacgaaccc tagaaatata   5220
tcctgtgtac ctcactgtcc aatatgaaaa ccgtaaagtg ccttatagga atttgcgtaa   5280
ctaacacacc ctgcttcatt gacctctact tgctgaagga gaaaaagaca gcgataagct   5340
ttcaatagtg gcataccaaa tggcactttt gatgaaataa aatatcaata ttttctgcaa   5400
tccaatgcac tgatgtgtga agtgagaact ccatcagaaa accaaagggt gctaggaggt   5460
gtgggtgcct tccatactgt ttgcccattt tcattcttgt attataatta attttctacc   5520
cccagagata aatgtttgtt tatatcactg tctagctgtt tcaaaattta ggtcccttgg   5580
tctgtacaaa taatagcaat gtaaaaatgg ttttttgaac ctccaaatgg aattacagac   5640
tcagtagcca tatcttccaa ccccccagta taaatttctg tctttctgct atgtgtggta   5700
ctttgcagct gcttttgcag aaatcacaat tttcctgtgg aataaagatg gtccaaaaat   5760
agtcaaaaat taaatatata tatatattag taatttatat agatgtcagc aattaggcag   5820
atcaaggttt agtttaactt ccactgttaa aataaagctt acatagtttt cttcctttga   5880
aagactgtgc tgtcctttaa cataggtttt taaagactag gatattgaat gtgaaacatc   5940
cgttttcatt gttcacttct aaaccaaaaa ttatgtgttg ccaaaaccaa acccaggttc   6000
atgaatatgg tgtctattat agtgaaacat gtactttgag cttattgttt ttattctgta   6060
ttaaatattt tcagggtttt aaacactaat cacaaactga atgacttgac ttcaaaagca   6120
acaaccttaa aggccgtcat ttcattagta ttcctcattc tgcatcctgg cttgaaaaac   6180
agctctgttg aatcacagta tcagtatttt cacacgtaag cacattcggg ccatttccgt   6240
ggtttctcat gagctgtgtt cacagacctc agcagggcat cgcatggacc gcaggagggc   6300
agattcggac cactaggcct gaaatgacat ttcactaaaa gtctccaaaa catttctaag   6360
actactaagg ccttttatgt aatttcttta aatgtgtatt tcttaagaat tcaaatttgt   6420
aataaaacta tttgtataaa aattaagctt ttattaattt gttgctagta ttgccacaga   6480
cgcattaaaa gaaacttact gcacaagctg ctaataaatt tgtaagcttt gcatacctta   6540
```

<210> SEQ ID NO 177
<211> LENGTH: 6446
<212> TYPE: DNA
<213> ORGANISM: Homo sapiens

<400> SEQUENCE: 177

```
gagtgtggct gcagtgcgcc gggacaccag ggctccgcgc tccgcactca agaggctccc     60
gcgtcccaac ccctcgcgcc cgcgcgttcg cggatccagg ccgaggaccg aaaggggccg    120
cccgagcccc cggggccggc gcccagagag cccagcaagg ccggccgccc tgccggtgtg    180
ccgccggcgg gtgcttctgg aagggccaat gcgttcgggc agcagcccct gaagccgagc    240
ccgaggctaa gtgggactga ccggggccca gagtggacga accgccagca tggggagaga    300
```

-continued

```
ccagcgcgcg gtggccggcc ctgccctacg gcggtggctg ctgctgggga cagtgaccgt    360
ggggttcctc gcccagagcg tcttggcggg tgtgaagaag tttgatgtgc cgtgtggagg    420
aagagattgc agtgggggct gccagtgcta ccctgagaaa ggtggacgtg gtcagcctgg    480
gccagtgggc cccccagggt acaatgggcc accaggatta caaggattcc cgggactgca    540
gggacgtaaa ggagacaagg gtgaaagggg agcccccgga gtaacgggac ccaagggcga    600
cgtgggagca agaggcgttt ctggattccc tggtgccgat ggaattcctg gacacccggg    660
gcaaggtggg cccaggggaa ggccgggcta cgatggctgc aacggaaccc agggagactc    720
aggtccacag ggccccccg gctctgaggg gttcaccggg cctcccgggc cccaaggacc    780
aaaagggcag aaaggtgagc cttatgcact gcctaaagag gagcgcgaca gatatcgggg    840
tgaacctgga gagcctggat tggtcggttt ccagggacct cccggccgcc ctgggcatgt    900
gggacagatg ggtccagttg gagctccagg gagaccagga ccacctggac cccctggacc    960
aaaaggacag caaggcaaca gaggacttgg tttctacgga gttaagggtg aaaagggtga   1020
cgtagggcag ccgggaccca acgggattcc atcagacacc ctccacccca tcatcgcgcc   1080
cacaggagtc accttccacc cagatcagta caagggtgaa aaaggcagtg agggggaacc   1140
aggaataaga ggcatttcct tgaagggaga agaaggaatc atgggctttc ctggactgag   1200
gggttaccct ggcttgagtg gtgaaaaagg atcaccagga cagaagggaa gccgaggcct   1260
ggatggctat caagggcctg atggaccccg gggacccaag ggagaagccg gagacccagg   1320
gcccccctgga ctacctgcct actcccctca cccttcccta gcaaaaggtg ccagaggtga   1380
cccgggattc ccaggggccc aaggggagcc aggaagccag ggtgagccag gagacccggg   1440
cctcccaggt ccccctggcc tctccatcgg agatggagat cagaggagag gcctgccggg   1500
tgagatggga cccaagggct tcatcggaga ccccggcatc cctgcgctct acgggggccc   1560
acctggacct gatggaaagc gagggcctcc aggaccccc gggctccctg gaccacctgg    1620
acctgatggc ttcctgtttg ggctgaaagg agcaaaagga agagcaggct tccctgggct   1680
tcccggctcc cctggagccc gcggaccaaa ggggtggaaa ggtgacgctg ggaatgcag    1740
atgtacagaa ggcgacgaag ctatcaaagg tcttccggga ctgccaggac ccaagggctt   1800
cgcaggcatc aacggggagc cggggaggaa aggggacaga ggagaccccg gccaacacgg   1860
cctccctggg ttcccagggc tcaagggagt gcctggcaac attggtgctc ccggacccaa   1920
aggagcaaaa ggagattcca gaacaatcac aaccaaaggt gagcggggac agcccggcgt   1980
cccaggtgtg cccgggatga aaggtgacga tggcagccca ggccgcgatg ggctcgatgg   2040
attccccggc ctcccaggcc ctcccggtga tggcatcaag ggccctccag gggacccagg   2100
ctatccagga atacctggaa cgaagggtac tccaggagaa atgggccccc caggactggg   2160
ccttcccggc ctcaaaggcc aacgtggttt ccctggagac gccggcttac ctggaccacc   2220
aggcttcctg ggccctcctg gccccgcagg gaccccagga caaatagatt gtgacacaga   2280
tgtgaaaagg gccgttggag gtgacagaca ggaggccatc cagccaggtt gcataggagg   2340
gcccaaggga ttgccaggcc tgccaggacc cccaggcccc acaggtgcca aaggcctccg   2400
aggaatccca ggcttcgcag gagctgatgg aggaccaggg cccaggggct tgccaggaga   2460
cgcaggtcgt gaagggttcc caggaccccc agggttcata ggaccccgag gatccaaagg   2520
tgcagtgggc ctccctggcc cagatggatc cccaggtccc atcggcctgc cagggccaga   2580
tgggcccccct ggggaaaggg gcctccctgg agaagtcctg ggagctcagc ccgggccacg   2640
```

-continued

```
gggagatgct ggtgtgcctg gacagcctgg gcttaaaggc cttcccggag acagaggccc   2700
ccctggattc agaggaagcc aagggatgcc tgggatgcca gggctgaagg gccagccagg   2760
cctcccagga ccttccggcc agccaggcct gtatgggcct ccaggactgc atggattccc   2820
aggagctcct ggccaagagg ggcccttggg gctgccagga atcccaggcc gtgaaggtct   2880
gcctggtgat agaggggacc ctggggacac aggcgctcct ggccctgtgg gcatgaaagg   2940
tctctctggt gacagaggag atgctggctt cacaggggag caaggccatc caggaagccc   3000
tggatttaaa ggaattgatg gaatgcctgg gacccccggg ctaaaaggag atagaggctc   3060
acctgggatg gatggtttcc aaggcatgcc tggactcaaa gggagacccg ggtttccagg   3120
gagcaaaggc gaggctggat tttcggaat acccggtctg aagggtctgg ctggtgagcc   3180
aggttttaaa ggcagccgag ggaccctgg gcccccagga ccacctcctg tcatcctgcc   3240
aggaatgaaa gacattaaag gagagaaagg agatgaaggg cctatggggc tgaaaggata   3300
cctgggcgca aaaggtatcc aaggaatgcc aggcatccca gggctgtcag gaatccctgg   3360
gctgcctggg aggcccggcc acatcaaagg agtcaaggga gacatcggag tccccggcat   3420
ccccggtttg ccaggattcc ctggggtggc tggccccct ggaattacgg gattcccagg   3480
attcatagga agccggggtg acaaaggtgc cccagggaga gcaggcctgt atggcgagat   3540
tggcgcgact ggtgatttcg gtgacatcgg ggacactata aatttaccag gaagaccagg   3600
cctgaagggg gagcggggca ccactggaat accaggtctg aagggattct ttggagagaa   3660
gggaacagaa ggtgacatcg gcttccctgg gataacaggc gtgactggag tccaaggccc   3720
tcctggactt aaaggacaaa caggctttcc agggctgact gggcctccag ggtcgcaggg   3780
agagctgggg cggattggac tgcctggtgg caaaggagat gatggctggc cgggagctcc   3840
gggcttacca ggttttccgg gactccgtgg gatccgcggc ttacacggct tgccaggcac   3900
caagggcttt ccaggatccc caggttctga catccacgga gacccaggct tcccaggccc   3960
tcctggggaa agaggtgacc caggagaggc caacaccctt ccaggccctg tgggagtccc   4020
aggacagaaa ggagaccaag gagctccagg ggaacgaggc ccacctggga gcccaggact   4080
tcaggggttc cctggtatca caccccttc caacatctct ggggcacctg gtgacaaagg   4140
ggcgccaggg atatttggcc tgaaaggtta tcggggccca ccagggccac caggttctgc   4200
tgctcttcct ggaagcaaag gtgacacagg gaacccagga gctccaggaa ccccagggac   4260
caaaggatgg gccggggact ccgggcccca gggcaggcct ggtgtgtttg gtctcccagg   4320
agaaaaaggg cccaggggtg aacaaggctt catggggaac actggaccca ctggggcggt   4380
gggcgacaga ggccccaagg gacccaaggg agacccagga ttccctggtg cccccgggac   4440
tgtgggagcc cccgggattg caggaatccc ccagaagatt gccgtccaac cagggacagt   4500
gggtccccag gggaggcgag gcccccctgg ggcaccgggg gagatggggc cccagggccc   4560
ccccggagaa ccaggtttcc gtggggctcc agggaaagct gggccccaag gaagaggtgg   4620
tgtgtctgct gttcccggct tccggggaga tgaaggaccc ataggccacc aggggccgat   4680
tggccaagaa ggtgcaccag gccgtccagg gagcccgggc ctgccgggta tgccaggccg   4740
cagcgtcagc atcggctacc tcctggtgaa gcacagccag acggaccagg agcccatgtg   4800
cccagtgggc atgaacaaac tctggagtgg atacagcctg ctgtacttcg agggccagga   4860
gaaggcgcac aaccaggacc tggggctggc gggctcctgc ctggcgcggt tcagcaccat   4920
gcccttcctg tactgcaacc ctggtgatgt ctgctactat gccagccgga acgacaagtc   4980
ctactggctc tctaccactg cgccgctgcc catgatgccc gtggccgagg acgagatcaa   5040
```

```
gccctacatc agccgctgtt ctgtgtgtga ggccccggcc atcgccatcg cggtccacag   5100

tcaggatgtc tccatcccac actgcccagc tgggtggcgg agtttgtgga tcggatattc   5160

cttcctcatg cacacggcgg cgggagacga aggcggtggc caatcactgg tgtcaccggg   5220

cagctgtcta gaggacttcc gcgccacacc attcatcgaa tgcaatggag gccgcggcac   5280

ctgccactac tacgccaaca agtacagctt ctggctgacc accattcccg agcagagctt   5340

ccagggctcg ccctccgccg acacgctcaa ggccggcctc atccgcacac acatcagccg   5400

ctgccaggtg tgcatgaaga acctgtgagc cggcgcgtgc caggaagggc cattttggtg   5460

cttattctta acttattacc tcaggtgcca acccaaaaat tggttttatt tttttcttaa   5520

aaaaaaaaaa gtctaccaaa ggaatttgca tccagcagca gcacttagac ctgccagcca   5580

ctgtcaccga gcgggtgcaa gcactcgggg tccctggagg gcaagccctg cccacagaaa   5640

gccaggagca gccctggccc ccatcagccc tgctagacgc accgcctgaa ggcacagcta   5700

accacttcgc acacacccat gtaaccactg cactttccaa tgccacagac aactcacatt   5760

gttcaactcc cttctcgggg tgggacagac gagacaacag cacacaggca gccagccgtg   5820

gccagaggct cgaggggctc agggcctcag gcacccgtcc ccacacgagg gccccgtggg   5880

tgggcctggc cctgctttct acgccaatgt tatgccagct ccatgttctc ccaaataccg   5940

ttgatgtgaa ttattttaaa ggcaaaaccg tgctctttat tttaaaaaac actgataatc   6000

acactgcggt aggtcattct tttgccacat ccctatagac cactgggttt ggcaaaactc   6060

aggcagaagt ggagaccttt ctagacatca ttgtcagcct tgctacttga aggtacaccc   6120

catagggtcg gaggtgctgt ccccactgcc ccacgttgtc cctgagattt aacccctcca   6180

ctgctggggg tgagctgtac tcttctgact gccccctcct gtgtaacgac tacaaaataa   6240

aacttggttc tgaatatttt taaaccccga gttgttgacc gccttaatct cgtgtccata   6300

gagcaaaacg tctgctcaga tggatgcgag gcacagcgtc cgcccacgct gctgttttta   6360

atccatctca gtagagttga acccattcgt ggtattacag ccatttctcg gggaatgtgt   6420

ttgtttataa ctcactaatg cttaca                                        6446
```

<210> SEQ ID NO 178
<211> LENGTH: 2868
<212> TYPE: DNA
<213> ORGANISM: Homo sapiens

<400> SEQUENCE: 178

```
ggctgcgctc cgagctgcgg agtccgggac tggagctgcc cgggcgggtt cgcgccccga     60

aggctgagag ctggcgctgc tcgtgccctg tgtgccagac ggcggagctc cgcggccgga    120

ccccgcggcc ccgctttgct gccgactgga gtttgggggga agaaactctc ctgcgcccca    180

gaggatttct tcctcggcga agggacagcg aaagatgagg gtggcaggaa gagaagggcg    240

ctttctgtct gccggggtcg cagcgcgaga gggcagtgcc atgttcctct ccatcctagt    300

ggcgctgtgc ctgtggctgc acctggcgct gggcgtgcgc ggcgcgccct gcgaggcggt    360

gcgcatccct atgtgccggc acatgccctg gaacatcacg cggatgccca accacctgca    420

ccacagcacg caggagaacg ccatcctggc catcgagcag tacgaggagc tggtggacgt    480

gaactgcagc gccgtgctgc gcttcttcct ctgtgccatg tacgcgccca tttgcaccct    540

ggagttcctg cacgacccta tcaagccgtg caagtcggtg tgccaacgcg cgcgcgacga    600

ctgcgagccc ctcatgaaga tgtacaacca cagctggccc gaaagcctgg cctgcgacga    660
```

-continued

```
gctgcctgtc tatgaccgtg gcgtgtgcat ctcgcctgaa gccatcgtca cggacctccc     720
ggaggatgtt aagtggatag acatcacacc agacatgatg gtacaggaaa ggcctcttga     780
tgttgactgt aaacgcctaa gccccgatcg gtgcaagtgt aaaaaggtga agccaacttt     840
ggcaacgtat ctcagcaaaa actacagcta tgttattcat gccaaaataa aagctgtgca     900
gaggagtggc tgcaatgagg tcacaacggt ggtggatgta aaagagatct tcaagtcctc     960
atcacccatc cctcgaactc aagtcccgct cattacaaat tcttcttgcc agtgtccaca    1020
catcctgccc catcaagatg ttctcatcat gtgttacgag tggcgctcaa ggatgatgct    1080
tcttgaaaat tgcttagttg aaaaatggag agatcagctt agtaaaagat ccatacagtg    1140
ggaagagagg ctgcaggaac agcggagaac agttcaggac aagaagaaaa cagccgggcg    1200
caccagtcgt agtaatcccc ccaaaccaaa gggaaagcct cctgctccca aaccagccag    1260
tcccaagaag aacattaaaa ctaggagtgc ccagaagaga acaaacccga aaagagtgtg    1320
agctaactag tttccaaagc ggagacttcc gacttcctta caggatgagg ctgggcattg    1380
cctgggacag cctatgtaag gccatgtgcc ccttgcccta acaactcact gcagtgctct    1440
tcatagacac atcttgcagc atttttctta aggctatgct tcagtttttc tttgtaagcc    1500
atcacaagcc atagtggtag gtttgccctt tggtacagaa ggtgagttaa agctggtgga    1560
aaaggcttat tgcattgcat tcagagtaac ctgtgtgcat actctagaag agtagggaaa    1620
ataatgcttg ttacaattcg acctaatatg tgcattgtaa aataaatgcc atatttcaaa    1680
caaaacacgt aattttttta cagtatgttt tattaccttt tgatatctgt tgttgcaatg    1740
ttagtgatgt tttaaaatgt gatcgaaaat ataatgcttc taagaaggaa cagtagtgga    1800
atgaatgtct aaaagatctt tatgtgttta tggtctgcag aaggattttt gtgatgaaag    1860
gggatttttt gaaaaatcta gagaagtagc atatggaaaa ctataatgtg tcttttttac    1920
aatgacttca gctctgtttt tagctagaaa ctctaaaaac aaaaataata ataaagaaaa    1980
ataaataaaa aggagaggca gacaatgtct ggattcctgt tttttggtta cctgatttca    2040
tgatcatgat gcttcttgtc aacaccctct taagcagcac cagaaacagt gagtttgtct    2100
gtaccattag gagttaggta ctaattagtt ggctaatgct caagtatttt atacccacaa    2160
gagaggtatg tcactcatct tacttcccag gacatccacc ctgagaataa tttgacaagc    2220
ttaaaaatgg ccttcatgtg agtgccaaat tttgttttct tcatttaaat attttctttg    2280
cctaaataca tgtgagagga gttaaatata aatgtacaga gaggaaagtt gaggttccac    2340
ctctgaaatg agaattactt gacagttggg atactttaat cagaaaaaaa gaacttatct    2400
tgcagcattt tatcaacaaa tttcataatt gtggacaatt ggaggcattt attttaaaaa    2460
acaattttat tggcctttg ctaacacagt aagcatgtat tctctataag gcattcaata    2520
aatgcacaac gcccaaagga aataaaatcc tatctaatcc tactctccac tacacagagg    2580
taatcactat tagtattttg gcatattatt ctccaggtgt ttcttatgca cttataaaat    2640
gatttgaaca aataaaacta ggaacctgct atacatgtgt ttcataacct gcctcctttg    2700
cttggccctt tattgagata agttttcctg tcaagaaagc agaaaccatc tcatttctaa    2760
cagctgtgtt atattccata gtatgcatta ctcaacaaac tgttgtgcta ttggatactt    2820
aggtggtttc ttcactgaca atactgaata aacatctcaa tagtcaaa                 2868
```

<210> SEQ ID NO 179
<211> LENGTH: 7437
<212> TYPE: DNA
<213> ORGANISM: Homo sapiens

<400> SEQUENCE: 179

```
agaaacagcc ctcaagtttc atcacaggga tgctaaaata tattctccag cttcagcaat     60
gacctagttc actgaagggc ggggaaaaaa tgctcttctt ccagaacttc cccgggcatg    120
gaatttcccc tcttaggaag agatgaactt tctggaagca gacccatcta tgctttgacc    180
tgatcatgga agaccctgag ccctataaac tcctttgaat ccctgtcccg ggaacaggga    240
cacccaatca atgcctcaca cacagcctgg ggaatccaca gctgagccag ccctcctaca    300
acatttcttg gacaaagagt actgaaaaat ttggtgcggc atgaaaggat gaaagactcc    360
gaagggcccc agaggccccc gctgtgtttt ttatctacat tgctttccca gaaggttcct    420
gagaagtcag acgctgtgct tcgctgcata atatctggtc agcccaagcc agaggtaact    480
tggtataaga atggtcaggc catcgatggg agtggcatta tttccaacta tgaattcttt    540
gagaatcagt atattcatgt gttacatctc tcttgctgta ccaaaaatga tgctgctgtc    600
tatcaaatct cggctaaaaa ctcttttgga atgatctgtt gttctgcttc cgttgaggtt    660
gagtgctcat cagagaaccc acaattgtct cctaacctgg aagatgacag ggacaggggt    720
tggaaacatg aaacagggac acatgaagaa gaaagggcaa atcagattga tgagaaggaa    780
catccttata aggaagaaga aagcatctcc ccgggcactc ccaggtcagc tgactcctcc    840
ccctccaaat ccaaccattc actctccctc cagtcattgg gcaatcttga cattagtgtg    900
tccagttctg aaaatccttt gggtgttaaa ggaacaaggc acactggaga ggcttatgat    960
ccaagtaaca cagaagaaat tgcaaatggg ttgctttttc ttaattcaag tcatatttat   1020
gaaaaacaag acagatgttg ccacaagaca gtgcattcca tggcatcaaa gttcacggat   1080
ggtgacctga acaatgatgg tcctcatgat gaaggcttac gctctagtca gcaaaatccc   1140
aaagtacaga aatacattag cttcagcctc ccgctatctg aggcaactgc acacatttac   1200
ccaggtgaca gtgccgtggc caacaaacaa cccagcccac agctttccag tgaagactct   1260
gacagtgact atgaactttg cccagagata accctaacct acaccgagga gttttcagat   1320
gatgacctgg agtatctgga atgttctgat gttatgacgg attactctaa tgcagtttgg   1380
caaaggaacc tgctggggac tgagcatgtt tttttattag aaagcgatga cgaagagatg   1440
gaattcggtg agcattgcct gggtgggtgt gagcatttcc tcagtggaat gggttgtggg   1500
tctcgggtgt cgggtgacgc tgggcctatg gttgccactg ctggcttctg tggtcatcac   1560
tcacaacccc aagaagttgg ggtgaggagc agcagagtct ccaagcacgg tccctcatcc   1620
ccacaaacag ggatgactct cattttggga cctcaccagg atggaacgtc ttcagtgaca   1680
gaacagggga gatataaact ccccactgct cccgaggctg ctgaaaatga ttatccagga   1740
attcaaggag aaaccagaga cagccaccaa gcaagagagg aatttgccag tgacaatctg   1800
ctcaacatgg atgaatcagt aagagagaca gagatgaagc tcttgtctgg tgagtcagaa   1860
aactcaggga tgagccagtg ttgggagacg gcagctgaca agagagtggg gggaaaggac   1920
ttatggagca agaggggttc aaggaaatct gccagggtga ggcagccggg aatgaaggga   1980
aatcccaaga agccgaatgc caacctgaga gaaagtacaa cagaaggtac ccttcatctc   2040
tgctctgcca aagaatctgc tgagccccca ctaacccaga gtgataaaag agagacttct   2100
cacaccacag cagcagcgac tggtcggagt tcccatgctg atgcaagaga atgtgctatt   2160
tcaacccagg cagagcaaga agcaaaaacc cttcaaactt caacagactc agtctccaaa   2220
gaaggcaaca caaattgcaa gggagaaggc atgcaagtta atactctatt tgaaacaagc   2280
```

-continued

```
caggttccag actggagtga tcctcctcag gtacaagttc aggaaacagt cagagagaca   2340
atctcttgca gccagatgcc agctttctca gagcctgctg gggaggagtc cccattcact   2400
gggaccacaa caatttcctt ctcaaactta ggaggggtcc acaaggaaaa tgcatcatta   2460
gctcaacact cggaggtcaa accctgtacc tgtggtccac agcatgaaga aaaacaagac   2520
agagatggca acatacctga caatttcagg gaagacctaa aatatgagca gagcatctca   2580
gaagccaatg atgagactat gtccccaggt gtgttctcaa ggcatctccc caaggatgct   2640
cgtgctgact tcagggagcc tgtggctgtc tctgttgctt cccctgaacc cacagatact   2700
gccctcaccc tggaaaatgt gtgtgatgag ccaagggaca gagaagcagt gtgtgcaatg   2760
gagtgttttg aggctggtga ccaaggaacg tgttttgata ccatagattc tcttgttggg   2820
agaccagttg ataaatattc gcctcaagaa atttgctctg tagatacgga actggcagaa   2880
ggtcaaaaca aagtatctga tttatgttct tctaatgaca agacactgga agtctttttt   2940
cagacacaag tgtctgagac ttcagtgtct acgtgcaaaa gcagcaagga cggcaactca   3000
gtcatgtccc ctctttttac cagtactttc accttgaaca tttcacacac agctagtgaa   3060
ggtgccacag gagaaaatct agccaaggtg gagaattcca cctacccact ggcctccaca   3120
gtacatgctg gccaggagca gccaagcccc agcaactcag gagggcttga tgaaacacag   3180
ctcctttctt ctgagaacaa tcctttagtg caatttaaag aaggaggtga caagagcccc   3240
agtcctagtg ccgcagacac cacagccaca ccagccagtt atagttcaat tgtgagtttt   3300
ccttgggaga agccaacaac attaactgct aataatgagt gctttcaagc gaccagggag   3360
actgaggaca catcaactgt taccattgcc accgaagtcc acccagccaa ataccttgct   3420
gtgtcaattc ctgaggacaa gcatgcaggt ggcactgagg agaggttccc tcgtgcatcc   3480
catgaaaagg tttcccaatt tccttcccaa gtgcagttgg atcatatttt aagtggtgct   3540
accatcaaat ctacaaaaga gctactttgc agggcaccca gtgtgccagg agtcccacac   3600
catgtcctgc agctcccaga gggagagggt ttctgcagta attcccctct tcaggttgat   3660
aacctgtctg gagataagag ccagactgtg gacagagcag actttaggag ctatgaagag   3720
aatttccaag aaagaggaag tgaaacaaag caggggggtcc agcagcagag cctgtcccag   3780
cagggttctc tttctgcacc tgatttccaa caaagtttgc ctacgacatc tgctgcacaa   3840
gaggaaagaa acttggtgcc cacggcccac tcacccgcaa gctctaggga aggagcaggg   3900
cagcgctcag gttgggggac gagggtctcc gtggtggctg aaactgctgg ggaagaagac   3960
agtcaggctc tgagcaacgt tccatctctc tctgatatcc ttttggaaga gtctaaagaa   4020
tatagacctg gaaattggga ggcaggcaac aagctgaaga ttataactct agaggcttcc   4080
gcttctgaaa tctggccacc acgacaactg acaaattctg agagcaaggc atcagacggt   4140
ggtctcataa ttcctgacaa ggtctgggct gtacctgata gtctaaaggc agatgctgtt   4200
gtgcctgaat tggccccctc tgaaatagca gcattggctc acagtccaga ggatgctgag   4260
tcagcccttg ctgatagcag agaaagccat aaaggcgaag agcccaccat cagtgtacat   4320
tggagaagtc tttcttcccg ggtttcagc caacccagac tcctggagtc atccgtggac   4380
cctgtagatg aaaaggagtt atctgtcaca gattcactgt cagcggcttc tgaaactgga   4440
gggaaggaaa atgttaacaa tgtgagtcaa gaccaggagg aaaaacaact caagatggat   4500
cacactgcct tctttaaaaa gtttctgacc tgccctaaaa tcctagagtc ctctgtagat   4560
cccattgatg agataagtgt gatagagtac accagggctg gaaaaccaga gccctctgaa   4620
accacaccac agggcgccag agaagggggt caatcaaatg acggaaacat gggccacgaa   4680
```

-continued

```
gcggaaatcc agccggccat tttgcaagtt ccatgtctcc agggaaccat tctgagtgaa   4740
aatagaatca gcagaagcca agaaggcagt atgaagcagg aggctgaaca aattcaacct   4800
gaggaggcaa aaactgccat ttggcaagtc ctgcaaccca gcgaaggcgg tgaaagaatt   4860
ccaagtggat gtagcatagg ccaaatacaa gaaagcagtg atgggagctt aggggaggct   4920
gagcaaagca aaaaggacaa agcagaattg atttccccca cttcacctct ttctagttgt   4980
cttccaataa tgactcacgc ttctcttggg gttgacacgc acaactccac aggccaaatt   5040
catgacgtcc ctgaaaatga catagttgag cccagaaagc gtcagtatgt gtttcctgtt   5100
tcacagaaaa ggggaactat tgagaatgag cgtgggaaac ctttgccctc ttctcctgat   5160
cttaccaggt tcccttgtac ttcatctcct gaaggaaatg tcacagactt tttgataagc   5220
cacaaaatgg aggaacctaa aatagaggtg cttcaaattg ggaaaaccaa acccccaagc   5280
tcatctagct cctcagcgaa gaccttggca tttatttcag gagaacgtga gttagagaaa   5340
gcccctaaat tactgcagga tccatgtcaa aagggcaccc tgggctgtgc gaaaaagtcc   5400
agggagagag agaagtccct ggaagcccga gcaggcaaat cgccagggac cctcacagca   5460
gtgacggggt cagaggaggt caagaggaag ccagaagccc caggcagtgg acatttagct   5520
gagggagtaa agaagaaaat tttgtccagg gtggcagcac tgaggctgaa actggaagaa   5580
aaggaaaata tcagaaagaa ctcagccttt cttaaaaaga tgcccaaact cgaaacatca   5640
ttatcacaca cagaagagaa acaagaccca aaaaagccat cttgcaaaag agaaggaaga   5700
gctccagtat tactgaaaaa gatccaagct gagatgttcc ctgaacactc tggaaatgta   5760
aaattaagct gccaatttgc agaaattcat gaagattcta ctatctgctg gacaaaagat   5820
tcaaagtcca tagcccaagt gcagagaagt gcaggggaca actccactgt ttcctttgcc   5880
atcgtgcaag ccagtccgaa ggaccaggga ctctattact gctgcatcaa gaacagctac   5940
ggaaaagtga ctgctgaatt taacctcaca gctgaagttc tcaaacagct gtcaagtcgc   6000
caggatacta aaggatgtga agagattgaa ttcagccaac tcatcttcaa agaagacttc   6060
ctccatgaca gctactttgg gggccgcctg cgtggtcaga tcgccacgga ggagctgcac   6120
tttggagaag gggttcaccg caaagccttc cgcagcacag tgatgcacgg cctcatgcct   6180
gtcttcaaac ctggccatgc ctgtgtgctt aaggtgcaca atgccattgc ctatgggacc   6240
agaaataatg atgagctcat ccaaaggaac tacaaactcg ctgcccagga atgctatgtt   6300
caaaatactg ccaggtatta tgccaagatc tacgctgctg aagcacagcc tctggaaggc   6360
tttggagaag tacctgagat cattcctatt tttcttatcc atcggcctga gaacaatatc   6420
ccgtatgcta cagtggagga ggagctgatt ggagaatttg tgaagtattc catcagggat   6480
gggaaagaaa taaacttctt gagaagagaa tcagaagctg gtcagaaatg ttgcaccttc   6540
cagcactggg tgtaccagaa aacaagtggc tgcctcctgg tgacggacat gcaaggtgta   6600
ggaatgaagc taactgacgt tggcatagca acgctggcta aagggtacaa gggatttaaa   6660
ggcaactgtt ccatgacctt cattgatcag tttaaagcac tacaccagtg taacaagtat   6720
tgcaaaatgc tgggactgaa atcccttcaa aacaacaacc agaaacagaa gcagccgagc   6780
attgggaaaa gcaaagttca aacaaactct atgacaataa agaaggcagg gcctgagacc   6840
ccaggcgaaa agaaaaccta acgtccctgg gtaacctaat ggccactggc tagcagcaca   6900
caatctcgcc agggaaaatc tgaggccaca caggagagaa tatacagcct gcagagagtg   6960
cgtggcaatc cttactccca gccgactgtg cgccaagatg cttctaaacc catcacctgc   7020
```

tgtcttcact caaatgattt cagaacagga tttgcgacca ggtttatggg gagattgaat 7080
caacgattgg tctcaaagac agtccattct ttatatacat gtttagcatt tttaccaacc 7140
tcacatcatg tgtatatttg tgtatttgca catggttgtg ctgtcgagga cctggtgctg 7200
agaagagtct gttcacagcc aaaattcttc ccactgtcat tcctaacctg ggatttctag 7260
acacatcctg ctgtgatgta aacagaaatc acgaattcgc tcactggatc aagttgttcc 7320
actggtgtct aatacgctat tgttgccgga ggtgggttct gtgacgtgaa gccatttccc 7380
atcattcaac agccagttac aattttctgt ttaattaaat tcatatttaa acaaaaa 7437

<210> SEQ ID NO 180
<211> LENGTH: 8442
<212> TYPE: DNA
<213> ORGANISM: Homo sapiens

<400> SEQUENCE: 180
gtccgcactc tccgtccccg cggctggcgc aggacctcac tcgagcggag cgcccacggg 60
gagcgggtcg cggggcggcg gcggcgagga ggaggcgaga aggagttgga ggaggaggag 120
gaggaggcga gggcgagcta gcccagcggg gtcccggccg ccccgcgggc caaagtcgag 180
ccctcccgcc cgtgggcgag cgcgccagcc gcccccttcca gaacagccgc cgccacaaag 240
aagaacgggg ggtgccgagg tccccatgac ctcctaaagt ggtgcggtcc ctgctgagtg 300
cgctgcccgg gccgtgaccc gcgcccctgt gcgtccccgc gcgcctccga gcgcccctgt 360
gcgccccggc ccgcgccccg ccggcatgga cgtccatacc cgctggaaag cgcgcagcgc 420
gctccgcccg ggcgccccgc tgctgccccc gctgctgctg ctgctgctgt gggcgccgcc 480
tccgagccgc gcagctcagc cagcagatct cctgaaggtt ctagattttc acaacttgcc 540
tgatggaata acaaagacaa caggcttttg cgccacgcgg cgatcttcca aaggcccgga 600
tgtcgcttac agagtcacca aagacgcgca gctcagcgca cccaccaagc agctgtaccc 660
tgcgtctgca tttcccgagg acttctccat cctaacaact gtgaaagcca agaaaggcag 720
ccaggccttc ctggtctcca tctacaacga gcagggtatc cagcagattg ggctggagct 780
gggccgctct cccgtcttcc tctacgagga ccacacgggg aagcctggcc cggaagacta 840
ccccctcttc cggggcatca acctgtcaga tggcaagtgg cacagaattg ctctcagcgt 900
ccacaagaaa aatgtcacct tgatcctcga ctgtaaaaag aagaccacca aattcctcga 960
ccgcagcgac caccccatga tcgacatcaa tggcatcatc gtgtttggca cccggatcct 1020
ggatgaggag gtgtttgagg gtgacatcca gcagctgctc tttgtctcgg accaccgggc 1080
agcttatgat tactgtgagc actacagccc tgactgtgac accgcagtac ctgacacccc 1140
acagtcgcag gaccccaatc cagatgaata ttacacggaa ggagacggcg agggtgagac 1200
ctattactac gaatacccct actacgaaga ccccgaagac ctagggaagg agcccacccc 1260
cagcaagaag cccgtggaag ctgccaaaga aaccacagag gtccccgagg agctgacccc 1320
gacccccacg gaagctgctc ccatgcctga aaccagtgaa ggggctggga aggaagagga 1380
cgtcggcatc ggggactatg actacgtgcc cagtgaggac tactacacgc cctcaccgta 1440
tgatgacctc acctatggcg agggggagga gaaccccgac cagcccacag acccaggcgc 1500
tggggccgaa attcccacca gcaccgccga cacctccaac tcctccaatc cagctccgcc 1560
tccaggggaa ggtgcggatg acttggaggg ggagttcact gaggaaacga tccggaacct 1620
tgacgagaac tactacgacc cctactacga ccccaccagc tccccgtcgg agatcgggcc 1680
gggaatgccg gcgaaccagg ataccatcta tgaagggatt ggaggacctc ggggcgagaa 1740

```
aggccaaaag ggagaaccag cgattatcga gccgggcatg ctcatcgagg gcccgcctgg   1800
cccagaaggc cccgcgggtc ttcccggacc tccaggaacc atgggtccca ctggccaagt   1860
cggggaccct ggagaaaggg gcccccctgg acgcccaggc cttcctgggg ccgatggcct   1920
gcccggtcct ccaggaacca tgctcatgct gcccttccgg tttggaggtg gcggcgatgc   1980
gggctccaaa ggccccatgg tctcagccca ggagtcccag gcgcaagcca ttctccagca   2040
ggccaggttg gcactgaggg gaccagctgg cccgatgggt ctcacaggga gacctggccc   2100
tgtgggtccc cctgggagcg gaggtttgaa gggcgagccg ggagacgtgg ggcctcaggg   2160
tcctcgaggt gtgcaaggcc cgcctggtcc ggccgggaag cccggaagac ggggtcgggc   2220
tgggagtgat ggagccagag gaatgcctgg acaaactggc cccaagggtg accggggttt   2280
cgacggcctg gctgggttgc caggcgagaa gggccacagg ggtgaccctg gtccttccgg   2340
cccaccagga cctccgggag acgatggaga aaggggtgac gacggagaag ttgggcccag   2400
ggggctgcct ggggagcccg ggccacgtgg tctgcttggg ccgaaggggc ccccaggtcc   2460
tcccggacct cccggtgtca cgggtatgga cggccagccg gggccaaaag gaaatgtggg   2520
tccccaggga gagcctggcc ccccaggaca gcagggtaat ccaggcgccc agggtcttcc   2580
aggcccccag ggtgcaattg gtcctccagg agaaaagggt cccttgggga aaccaggcct   2640
tccaggaatg cccggtgctg acggaccccc gggacaccct ggcaaagaag gccctccagg   2700
agagaaagga ggtcagggtc cacctggccc ccagggtccg attggctacc caggtcctcg   2760
aggagtcaag gggggccgatg gcatccgtgg tctgaagggc acaaagggcg agaagggtga   2820
agacggcttt cctgggttta aaggagacat gggcatcaag ggtgatcggg gggagatcgg   2880
cccacccggt cccaggggag aagatggccc tgaaggccca aagggtcgcg gaggtcccaa   2940
tggtgacccc ggtcctctgg gacccccctgg ggagaaggga aaactcggag tcccagggtt   3000
accagggtat ccaggaagac aaggaccaaa gggctctatt ggattccctg gatttcctgg   3060
cgccaatgga gagaagggcg gcagggggac ccctggaaag ccaggaccgc gggggcagcg   3120
aggcccaacg ggtccgaggg gtgaaagagg cccccggggc atcactggga agcctggccc   3180
caagggcaac tccggaggtg acggcccagc tggccctcct ggtgaacggg gacccaatgg   3240
accccaagga cccacaggat ttcctggacc aaagggcccc cctggccctc caggcaagga   3300
tggactccca ggacaccctg gacagagagg cgagactggt ttccaaggca agaccggccc   3360
tccaggcccc cccggcgtgg tcggccctca gggtcccacg ggagaaacgg gcccaatggg   3420
tgagcgtggc caccctgggc cccctggacc ccccggtgaa caggggcttc cgggccttgc   3480
tggaaaagaa gggacgaagg gtgacccagg ccctgcaggc ctccctggga aagatggccc   3540
tccaggatta cgtggtttcc ctggggaccg agggcttcct ggtccagtgg gagctcttgg   3600
actgaaaggc aatgaagggc cccctggccc accaggccct gcgggatctc caggggagag   3660
aggtccagct ggagccgctg ggcccatcgg aattccaggg agacctgggc cccagggacc   3720
cccagggccg gcaggagaga aaggggctcc tggcgagaaa ggcccacaag gcccagctgg   3780
ccgagacggt ctccaggggc ctgtggggct cccgggtcca gctggccctg tgggtccccc   3840
tggagaagac ggagataagg gagagatcgg ggagccgggg cagaaaggaa gcaaggggga   3900
caaaggagaa cagggtcctc ctgggcctac aggtcctcaa ggccccatcg gacagccagg   3960
cccctctgga gctgacggcg agccggggcc tcggggccag cagggccttt tcgggcagaa   4020
aggtgatgaa ggtcccagag gctttcctgg acccccctggg ccagtggggc tgcagggttt   4080
```

-continued

```
gccaggacct ccaggcgaga agggtgagac aggagacgtg ggccagatgg gccccccggg   4140
tccccctggc ccccgaggac cctccggagc tccaggtgct gatggcccac aaggtccccc   4200
aggtggaata ggaaaccctg gtgcagtggg agagaagggc gagcctggcg aagcaggtga   4260
gcctggcctt ccgggagaag gcggcccccc gggacccaaa ggagaaaggg gagagaaggg   4320
cgagtcaggc ccttcaggtg ctgccggacc ccctggaccc aaaggccctc ccggagatga   4380
tggtcccaaa ggcagccctg gcccagtggg ttttcctgga gatcctggcc cccccggaga   4440
gcctggcccc gcgggtcaag atggtccccc tggtgacaaa ggagatgatg gtgaacccgg   4500
gcagacggga tcccccggcc ctactggtga accaggtcca tcggggcctc caggaaaaag   4560
gggtccccca ggccccgcag gccccgaagg cagacaggga gagaaagggg ccaagggaga   4620
agccggcttg gaaggccctc ctgggaagac tggccccatc ggcccccagg gggcccctgg   4680
gaagcccgga ccggatggcc ttcgagggat ccctggccct gtgggagaac aaggtctccc   4740
aggatcccca ggcccggacg gtccccccgg ccccatgggt cccccaggac ttcccggcct   4800
caaaggagat tctggtccca aaggtgaaaa gggtcatcca ggcctgatcg ggctcatcgg   4860
tcctccgggt gaacagggtg agaagggcga ccgtggtctc cctggccccc agggctcctc   4920
cggtcctaag ggagaacagg gtatcactgg tccttctggc ccgattgggc ctcctgggcc   4980
ccctggcctg ccgggtccgc ctggtccaaa aggtgctaag ggctcctcgg gtccaactgg   5040
cccgaagggt gaggcaggcc acccaggacc cccaggcccc ccgggccccc cgggagaggt   5100
catccagccc ctgccaatcc aggcatccag gacgcggcgg aacatcgacg ccagccagct   5160
gctggacgac gggaatggcg agaactacgt ggactacgcg gacggcatgg aagagatctt   5220
cggctctctc aactctctga agctggagat tgagcagatg aaacggcccc tgggcacgca   5280
gcagaacccc gcccgcacct gcaaggacct gcagctctgc caccccgact tcccagatgg   5340
tgaatactgg gtcgatccta accaaggatg ctccagggat tccttcaagg tttactgcaa   5400
cttcacagcc ggggggtcga catgcgtctt ccctgacaag aagtccgaag ggggccagaat   5460
cacttcttgg cccaaagaaa acccgggctc ctggttcagt gaattcaagc gtgggaaact   5520
gctctcctat gtggacgccg agggcaaccc tgtgggtgtg gtacagatga ccttcctgcg   5580
gctgctgagc gcctctgccc accagaacgt cacctaccac tgctaccagt cagtggcctg   5640
gcaggacgca gccacgggca gctacgacaa ggccctccgc ttcctgggct ccaacgacga   5700
ggagatgtcc tatgacaaca acccctacat ccgcgccctg gtggacggct gtgctaccaa   5760
gaaaggctac cagaagacgg ttctggagat cgacaccccc aaagtggagc aggtgcccat   5820
cgtggacatc atgttcaatg acttcggtga agcgtcacag aaatttggat ttgaagtggg   5880
gccggcttgc ttcatgggct aggagccgcc gagcccgggc tcccgagagc aacctcgtga   5940
cctcagcatg ccattcgttc gtgagtgtcc cgtgcacgtc ctgaccctgg acagtgaagg   6000
cttctccctc ccctcccacc tgacttcatc tacgcctcgg caccacgggg tgtgggaccc   6060
cagcccggag agaacagagg gaaggagccg cgcccccacc tggagctgaa tcacatgacc   6120
tagctgcacc ccagcgcctg ggcccgcccc acgctctgtc cacacccacg cgccccggga   6180
gcggggccat gcctccagcc ccccagctcg cccgacccat cctgttcgtg aataggtctc   6240
aggggttggg ggagggactg ccagatttgg acactatatt tttttctaaa ttcaacttga   6300
agatgtgtat ttcccctgac cttcaaaaaa tgttccaagg taagcctcgt aaaggtcatc   6360
ccaccatcac caaagcctcc gtttttaaca acctccaaca cgatccattt agaggccaaa   6420
tgtcattctg caggtgcctt cccgatggat taaaggtgct tatgtttttg tgagttttaa   6480
```

gtaaatattt gtattgtatt gttataaatg ttaagtgtgc ctggctttca atcatgcacg 6540
gaaacccagt ctcagtccca cggacagaat gggcgaggca tggattctgg gttgcagtac 6600
cgttctgatt agaaatagga agtctcccca cccccgccct ggccaagaac gtgcaataaa 6660
ttggaagttt gccccggggc agcaagaatt tatgctgcca ttgaaaagca ggtaccagtg 6720 cccctttca gacagttttt gattcgctct agactttttt tttttttaat agggaaaaaa 6780
tttgataatt ttcttttttc tacatgcact taagactaaa acacaggttt ggattaattt 6840
tatttgcttc ctttttccgc ttttcttccc gcagagcctg atgggagaat gtccagggca 6900
gggaaaccac attttttgta ggtgataact caatgaaaat tggtgcttat tttttacact 6960
tctctcttgt ggctctcttg tggtgctatc tatctgtttt aaggtctcct tgaaggcgca 7020
ctggggaccc tggccatgcc tcgttctccc tgctttcttt atcctgttat tgcctccaca 7080
gtctgttgcc aaggactcta agatcaatgc acgtcacttt cctttccact gggcaggata 7140
gccaagcaca ctccctcctg cgctctcccg ccccggtgcg tccactcccg agggctgtta 7200
tgaggactgg gttgtgccta cttgatttga aaacacacac aagcaataaa aagcctcttc 7260
ctgcattgtc tgtggtgtga ccatagcaga ttatatttgg ttcctgaatg tttgtggtgc 7320
taatttctgt gtttgttcca agccgttcag tcatgccatg cgctgcctcg gtagatggag 7380
taatgtacaa tgaactccat gagtctctcc agggctgcct gcagcacgtc ttttccaagt 7440
agcctatttg gattcccatc tcaaatgtcc tggatgcgag cgtcagcggc tccagagctc 7500
ggggcgggtg aggtcccctt tggggaaccc tttcctggcc atcgaggtcg gggggctgcc 7560
gtctgtgggc aggaggaccc gaggggcagc caggaaaggc gatctcttca ctgtgaaaag 7620
ttgcccgggt gcagcgcctt ttccttctac catgggaaat gcaggctggg cccttggggt 7680
gagcctgcgg ggctctggtg ctgtccccga cccccaccac caccagaatg cagttccagc 7740
ttaggaagcc acaaacaagc cacccaggag gaacaaaaca ccgccagcgt ggattttcca 7800
aatttccctg gaaagtaagt ctcgctcttg ccaaagaaaa gtctggcttg gagagtctct 7860
ggagcccagg atgccagcat gtgccaatga ctgtcacctt catctcttca aaagaaaagc 7920
catagccgag gactgtcccg cgaccccgt ggactgcgtc taggtcatgt gattctgttt 7980
tcatttctca tcccatccaa tttgtccttt tctcctgtca ttttcttcct ctgtggtccc 8040
ttcaaagttg ttataatttg tactgaactt caaaatgtgt cccgttctcc ccagaccact 8100
ctagccacag tatattgcaa taaaattact tcttatattt gcagaaattc ttttggtgta 8160
attttatttt ttcctctcaa tatatataat tggacaaacg ctggcaaaaa gaaaaaaatg 8220
gtaagcaaaa aacccaagat aaagtttcga ggacatcagg ccttttgaaa tacaatgtca 8280
aatgacacat tgtacggttt caaaaaatcc gctagacatg tcataagttt taactgtaat 8340
gcccaggaaa ggatatctta aaatattcta aacttgtgta acaaaggaat aattaactgt 8400
aatagttttt caataaatcg agttgggtgt ttccaccgta aa 8442

<210> SEQ ID NO 181
<211> LENGTH: 4260
<212> TYPE: DNA
<213> ORGANISM: Homo sapiens

<400> SEQUENCE: 181
cgaggagcga gccagtgggg gaggctgaca tcaccacggc ggcagccctt taaacccctc 60
acccagccag cgccccatcc tgtctgtccg aacccagaca caagtcttca ctccttcctg 120

-continued

```
cgagccctga ggaagccttg tgagtgcatt ggctggggct tggagggaag ttgggctgga    180
gctggacagg agcagtgggt gcatttcagg caggctctcc tgaggtccca ggcgccagct    240
ccagctccct ggctagggaa acccaccctc tcagtcagca tgggggccca agctccaggc    300
agggtgggct ggatcactag cgtcctggat ctctctcaga ctgggcagcc ccgggctcat    360
tgaaatgccc cggatgactt ggctagtgca gaggaattga tggaaaccac cggggtgaga    420
gggaggctcc ccatctcagc cagccacatc cacaaggtgt gtgtaagggt gcaggcgccg    480
gccggttagg ccaaggctct actgtctgtt gcccctccag gagaacttcc aaggagcttt    540
ccccagacat ggccaacaag ggtccttcct atggcatgag ccgcgaagtg cagtccaaaa    600
tcgagaagaa gtatgacgag gagctggagg agcggctggt ggagtggatc atagtgcagt    660
gtggccctga tgtgggccgc ccagaccgtg ggcgcttggg cttccaggtc tggctgaaga    720
atggcgtgat tctgagcaag ctggtgaaca gcctgtaccc tgatggctcc aagccggtga    780
aggtgcccga gaacccaccc tccatggtct tcaagcagat ggagcaggtg gctcagttcc    840
tgaaggcggc tgaggactat ggggtcatca agactgacat gttccagact gttgacctct    900
ttgaaggcaa agacatggca gcagtgcaga ggaccctgat ggctttgggc agcttggcag    960
tgaccaagaa tgatgggcac taccgtggag atcccaactg gtttatgaag aaagcgcagg   1020
agcataagag ggaattcaca gagagccagc tgcaggaggg aaagcatgtc attggccttc   1080
agatgggcag caacagaggg gcctcccagg ccggcatgac aggctacgga cgacctcggc   1140
agatcatcag ttagagcgga gagggctagc cctgagcccg gccctccccc agctccttgg   1200
ctgcagccat cccgcttagc ctgcctcacc cacacccgtg tggtaccttc agccctggcc   1260
aagctttgag gctctgtcac tgagcaatgg taactgcacc tgggcagctc ctccctgtgc   1320
ccccagcctc agcccaactt cttacccgaa agcatcactg ccttggcccc tccctcccgg   1380
ctgcccccat cacctctact gtctcctccc tgggctaagc aggggagaag cgggctgggg   1440
gtagcctgga tgtgggccaa gtccactgtc ctccttggcg gcaaaagccc attgaagaag   1500
aaccagccca gcctgccccc tatcttgtcc tggaatattt ttggggttgg aactcaaaaa   1560
aaaaaaaaaa aaatcaatct tttctcaggc ctggctggca gagtttgatt tgccctggtc   1620
acttttgtta tggtttcaga tctgcgcagg ggacaggcag gcatctcggg cttgtatgtg   1680
ttcctggctg ccgtcctctg aaggaccctt catgtgccaa gattccagga cagtcagatt   1740
ctttcagagg aaacaggcca tagaacagga gagtgaatct tggggaccga agggaaaaag   1800
gagccactca gcagcatgca gtggctttgg ggagacagag gaaaggagag attgcgagtg   1860
gcagaattgt ttggaaggtt tttattttgg aaaagctgtg cagaaaaaaa ttcaagaaaa   1920
tgttgctgtg aaaagagaaa aacaaatctt aagcattaaa aaaaattcaa ccaactagct   1980
cagaagaggg gagaaggcca aggttgagag aagagtcaca gcctgtcagg cagatagctg   2040
gcctccggcg ggaaggccat ttccctgagc acttgcagag gaagacaggg tggtggcagg   2100
actggagtgg cagtggctcc caaggctctc tcctccaaca tgtgcatctg ccatctgctc   2160
tgcagtcctg ccgcaggatt ccctagtgaa gcagctcagg cctgggggag ccgtgtgtat   2220
cccagctgtg ccggcagcat cataccaatc gtgggggtgg tgaaggagcc aggggttcat   2280
tcatggttgg tttctgatca ggcatcttgg gaatggataa tggaggcagc cgctttcagg   2340
acaggcatgt ccaggggctc ctcccagcct ctaccccgaa gtcctcttcc caagtgaccc   2400
cagtgatgtt tccattgaga tgcgctcctg gctatggcag gcaccttctc aacttatatg   2460
tgggaagggg tcccccatgc ttgggggacc taggcagctg gcttggccca agagagatga   2520
```

ggatggaggc caaaccaaag gggggcgcca atcccctgtc caacaccttc tcaccaaaag 2580
ctcccgtttg gctggaggca gaccctgtgg ctctgaccag acttctctgg cagcaatcct 2640
ccaccatttg tatcttaaga aggccctcac cctctttgag tggagtcaga ggatgcctca 2700
gattccagat gtaagcatca gaactgcttt ctgtcaagag ctccctaatt ttgggaaaga 2760
agagcctgtc ccacactgtc aggccctgag gtcagcagat ctgctcctcc ttcccgtgcg 2820
gtacgtctag gtgctgatga gggcagtcca gggcgctctt gttctgggac aggctccagt 2880
ccccttgctc cagcaggtct ggggcaagga ggtcagaggt ggtgggaggg cccctgctct 2940
ctgtttccac ttcgtctgga tccttgctgc tgcaaagtgg cactgattct agctctgtcc 3000
cttcctcctt ggctttccgg ctccgatggg gccagtggca gggtccactc ctacaaactt 3060
gattggaagc cacattcctc tggctcaaat atacttccag catgtagtaa acagtccaga 3120
agacggtgaa acagcctacc agcaccaggg tctggggccg aggcaagcac ctacgtgagg 3180
cactgtttcc cgaagcctac agcctttctc agcccaggac aatgagctca gaaagtcttt 3240
ttccttctag ggactgcctt tttcacccaa actgttccct ctgccccctc ccccgacaag 3300
gcctgtcctg taagagttag gctagcaggg taggagcaat gctatgaaac cactgctggg 3360
acccaggtct tcccagtcct tcaccccgca ggtcaccctg agaaacacac taagaactcc 3420
atcccccaga caggacagtc ccatctaccc gcagcttgag tcttggccct agtaccttga 3480
gggtgttggg ggtgatggtg taaccatctt cctcaggaat tttcagcccc ggtgggcagg 3540
gcagggcgaa gtcatcgtgc aggtattttc cactcatggc actctctaac agcctgtgga 3600
gaagaaaaga ggtgaggatg ccccactgac tatggttcct ataccatctg ccctcaccca 3660
ttttcctgcc ttacaggtga agacagggaa gccccacagc aaaaaggaga ggcccagact 3720
gtgagttccc agcccggggc tccatctacc ggcttgacgc tggaactggg aagcacagct 3780
ggggttcaga gggcgatggg ctccctaggc ggcccttccc ctgtgactgg ccttccctct 3840
gacacatgcg gctttaccca cctttgtctg tccctgatgt ctactgcact ccacacagag 3900
ccatataggg tcagctgcca ttgccggagg atgccgacct ggaatgactc atcccctagg 3960
gcagcaaggg gcagctcgtg agccacgccc ctctgtcagc catgccagac agcagaggcc 4020
ctgcccgccc tgccacccaa aggggctcag gccacatggt ctgctccagg agctgcctca 4080
ctgtgtccca ctgaccccag gttctgcaga agggcctcac tgggtgccct tagggatgga 4140
aagggttgaa aggctgtact ccaaagcaga gtcttgcttt tctctcccgt attttggggg 4200
ttcagctggg attagaaaaa aatgtctttc caccaaatta aagaaagctt tgaaaaccac 4260

<210> SEQ ID NO 182
<211> LENGTH: 3156
<212> TYPE: DNA
<213> ORGANISM: Homo sapiens

<400> SEQUENCE: 182
acagctgtgt ttggctgcag ggccaagagc gctgtcaaga agacccacac gccccccctcc 60 agcagctgaa ttcctgcagc tcagcagccg ccgccagagc aggacgaacc gccaatcgca 120
aggcacctct gagaacttca ggatgcagat gtctccagcc ctcacctgcc tagtcctggg 180
cctggccctt gtctttggtg aagggtctgc tgtgcaccat cccccatcct acgtggccca 240
cctggcctca gacttcgggg tgagggtgtt tcagcaggtg gcgcaggcct ccaaggaccg 300
caacgtggtt ttctcaccct atggggtggc ctcggtgttg gccatgctcc agctgacaac 360

-continued

```
aggaggagaa acccagcagc agattcaagc agctatggga ttcaagattg atgacaaggg    420
catggccccc gccctccggc atctgtacaa ggagctcatg ggccatggga acaaggatga    480
gatcagcacc acagacgcga tcttcgtcca gcgggatctg aagctggtcc agggcttcat    540
gccccacttc ttcaggctgt tccggagcac ggtcaagcaa gtggactttt cagaggtgga    600
gagagccaga ttcatcatca atgactgggt gaagacacac acaaaaggta tgatcagcaa    660
cttgcttggg aaaggagccg tggaccagct gacacggctg gtgctggtga atgccctcta    720
cttcaacggc cagtggaaga ctcccttccc cgactccagc acccaccgcc gcctcttcca    780
caaatcagac ggcagcactg tctctgtgcc catgatggct cagaccaaca agttcaacta    840
tactgagttc accacgcccg atggccatta ctacgacatc ctggaactgc cctaccacgg    900
ggacaccctc agcatgttca ttgctgcccc ttatgaaaaa gaggtgcctc tctctgccct    960
caccaacatt ctgagtgccc agctcatcag ccactggaaa ggcaacatga ccaggctgcc   1020
ccgcctcctg gttctgccca agttctccct ggagactgaa gtcgacctca ggaagcccct   1080
agagaacctg ggaatgaccg acatgttcag acagtttcag gctgacttca cgagtctttc   1140
agaccaagag cctctccacg tcgcgcaggc gctgcagaaa gtgaagatcg aggtgaacga   1200
gagtggcacg gtggcctcct catccacagc tgtcatagtc tcagcccgca tggcccccga   1260
ggagatcatc atggacagac ccttcctctt tgtggtccgg cacaacccca caggaacagt   1320
ccttttcatg ggccaagtga tggaaccctg accctgggga aagacgcctt catctgggac   1380
aaaactggag atgcatcggg aaagaagaaa ctccgaagaa aagaatttta gtgttaatga   1440
ctctttctga aggaagagaa gacatttgcc ttttgttaaa agatggtaaa ccagatctgt   1500
ctccaagacc ttggcctctc cttggaggac ctttaggtca aactccctag tctccacctg   1560
agaccctggg agagaagttt gaagcacaac tcccttaagg tctccaaacc agacggtgac   1620
gcctgcggga ccatctgggg cacctgcttc cacccgtctc tctgcccact cgggtctgca   1680
gacctggttc ccactgaggc cctttgcagg atggaactac ggggcttaca ggagcttttg   1740
tgtgcctggt agaaactatt tctgttccag tcacattgcc atcactcttg tactgcctgc   1800
caccgcggag gaggctggtg acaggccaaa ggccagtgga agaaacaccc tttcatctca   1860
gagtccactg tggcactggc cacccctccc cagtacaggg gtgctgcagg tggcagagtg   1920
aatgtccccc atcatgtggc ccaactctcc tggcctggcc atctccctcc ccagaaacag   1980
tgtgcatggg ttattttgga gtgtaggtga cttgtttact cattgaagca gatttctgct   2040
tccttttatt tttataggaa tagaggaaga aatgtcagat gcgtgcccag ctcttcaccc   2100
cccaatctct tggtggggag gggtgtacct aaatatttat catatccttg cccttgagtg   2160
cttgttagag agaaagagaa ctactaagga aaataatatt atttaaactc gctcctagtg   2220
tttctttgtg gtctgtgtca ccgtatctca ggaagtccag ccacttgact ggcacacacc   2280
cctccggaca tccagcgtga cggagcccac actgccacct tgtggccgcc tgagaccctc   2340
gcgccccccg cgcccctctt tttccccttg atggaaattg accatacaat ttcatcctcc   2400
ttcaggggat caaaaggacg gagtgggggg acagagactc agatgaggac agagtggttt   2460
ccaatgtgtt caatagattt aggagcagaa atgcaagggg ctgcatgacc taccaggaca   2520
gaactttccc caattacagg gtgactcaca gccgcattgg tgactcactt caatgtgtca   2580
tttccggctg ctgtgtgtga gcagtggaca cgtgaggggg gggtgggtga gagagacagg   2640
cagctcggat tcaactacct tagataatat ttctgaaaac ctaccagcca gagggtaggg   2700
cacaaagatg gatgtaatgc actttgggag gccaaggcgg gaggattgct tgagcccagg   2760
```

agttcaagac cagcctgggc aacataccaa gacccccgtc tctttaaaaa tatatatatt 2820
ttaaatatac ttaaatatat atttctaata tctttaaata tatatatata ttttaaagac 2880
caatttatgg gagaattgca cacagatgtg aaatgaatgt aatctaatag aagcctaatc 2940
agcccaccat gttctccact gaaaaatcct ctttctttgg ggtttttctt tctttctttt 3000
ttgattttgc actggacggt gacgtcagcc atgtacagga tccacagggg tggtgtcaaa 3060
tgctattgaa attgtgttga attgtatgct ttttcacttt tgataaataa acatgtaaaa 3120
atgtttcaaa aaaataataa aataaataaa tacgaa 3156

<210> SEQ ID NO 183
<211> LENGTH: 5490
<212> TYPE: DNA
<213> ORGANISM: Homo sapiens

<400> SEQUENCE: 183
ggctgagttt tatgacgggc ccggtgctga agggcaggga acaacttgat ggtgctactt 60
tgaactgctt ttcttttctc ctttttgcac aaagagtctc atgtctgata tttagacatg 120
atgagctttg tgcaaaaggg gagctggcta cttctcgctc tgcttcatcc cactattatt 180
ttggcacaac aggaagctgt tgaaggagga tgttcccatc ttggtcagtc ctatgcggat 240
agagatgtct ggaagccaga accatgccaa atatgtgtct gtgactcagg atccgttctc 300
tgcgatgaca taatatgtga cgatcaagaa ttagactgcc ccaacccaga aattccattt 360
ggagaatgtt gtgcagtttg cccacagcct ccaactgctc ctactcgccc tcctaatggt 420
caaggacctc aaggccccaa gggagatcca ggccctcctg gtattcctgg gagaaatggt 480
gaccctggta ttccaggaca accagggtcc cctggttctc ctggcccccc tggaatctgt 540
gaatcatgcc ctactggtcc tcagaactat tctccccagt atgattcata tgatgtcaag 600
tctggagtag cagtaggagg actcgcaggc tatcctggac cagctggccc cccaggccct 660
cccggtcccc ctggtacatc tggtcatcct ggttcccctg gatctccagg ataccaagga 720
ccccctggtg aacctgggca agctggtcct tcaggccctc caggacctcc tggtgctata 780
ggtccatctg gtcctgctgg aaaagatgga gaatcaggta gacccggacg acctggagag 840
cgaggattgc ctggacctcc aggtatcaaa ggtccagctg ggatacctgg attccctggt 900
atgaaaggac acagaggctt cgatggacga aatggagaaa agggtgaaac aggtgctcct 960
ggattaaagg gtgaaaatgg tcttccaggc gaaaatggag ctcctggacc catgggtcca 1020
agaggggctc ctggtgagcg aggacggcca ggacttcctg gggctgcagg tgctcggggt 1080
aatgacggtg ctcgaggcag tgatggtcaa ccaggccctc ctggtcctcc tggaactgcc 1140
ggattccctg gatcccctgg tgctaagggt gaagttggac ctgcagggtc tcctggttca 1200
aatggtgccc ctggacaaag aggagaacct ggacctcagg gacacgctgg tgctcaaggt 1260
cctcctggcc ctcctgggat taatggtagt cctggtggta aaggcgaaat gggtcccgct 1320
ggcattcctg gagctcctgg actgatggga gcccggggtc ctccaggacc agccggtgct 1380
aatggtgctc ctggactgcg aggtggtgca ggtgagcctg gtaagaatgg tgccaaagga 1440
gagcccggac cacgtggtga acgcggtgag gctggtattc caggtgttcc aggagctaaa 1500
ggcgaagatg gcaaggatgg atcacctgga gaacctggtg caaatgggct tccaggagct 1560
gcaggagaaa ggggtgcccc tgggttccga ggacctgctg gaccaaatgg catcccagga 1620
gaaaagggtc ctgctggaga gcgtggtgct ccaggccctg cagggcccag aggagctgct 1680

-continued

```
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaggg acccccaggg   1980
cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcaggggcc ccaggactta gaggtggagc tggtcccccct   2220
ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg tccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
gaaactggcc ctccaggacc tgctggtttc cctggtgctc ctggacagaa tggtgaacct   2580
ggtggtaaag gagaaagagg ggctccgggt gagaaaggtg aaggaggccc tcctggagtt   2640
gcaggacccc ctggaggttc tggacctgct ggtcctcctg gtccccaagg tgtcaaaggt   2700
gaacgtggca gtcctggtgg acctggtgct gctggcttcc ctggtgctcg tggtcttcct   2760
ggtcctcctg gtagtaatgg taacccagga cccccaggtc ccagcggttc tccaggcaag   2820
gatgggcccc caggtcctgc gggtaacact ggtgctcctg gcagccctgg agtgtctgga   2880
ccaaaaggtg atgctggcca accaggagag aagggatcgc ctggtgccca gggcccacca   2940
ggagctccag gcccacttgg gattgctggg atcactggag cacggggtct tgcaggacca   3000
ccaggcatgc caggtcctag gggaagccct ggccctcagg gtgtcaaggg tgaaagtggg   3060
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240
gcccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc cagaggacct   3540
gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
gccgctgcca ttgctgggat tggaggtgaa aaagctggcg gttttgcccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tggggaaaca   4020
tgcataagtg ccaatccttt gaatgttcca cggaaacact ggtggacaga ttctagtgct   4080
```

```
gagaagaaac acgtttggtt tggagagtcc atggatggtg gttttcagtt tagctacggc   4140

aatcctgaac ttcctgaaga tgtccttgat gtgcatctgg cattccttcg acttctctcc   4200

agccgagctt cccagaacat cacatatcac tgcaaaaata gcattgcata catggatcag   4260

gccagtggaa atgtaaagaa ggccctgaag ctgatggggt caaatgaagg tgaattcaag   4320

gctgaaggaa atagcaaatt cacctacaca gttctggagg atggttgcac gaaacacact   4380

ggggaatgga gcaaaacagt ctttgaatat cgaacacgca aggctgtgag actacctatt   4440

gtagatattg caccctatga cattggtggt cctgatcaag aatttggtgt ggacgttggc   4500

cctgtttgct ttttataaac caaactctat ctgaaatccc aacaaaaaaa atttaactcc   4560

atatgtgttc ctcttgttct aatcttgtca accagtgcaa gtgaccgaca aaattccagt   4620

tatttatttc caaaatgttt ggaaacagta taatttgaca aagaaaaatg atacttctct   4680

tttttgctg ttccaccaaa tacaattcaa atgctttttg ttttattttt ttaccaattc   4740

caatttcaaa atgtctcaat ggtgctataa taaataaact tcaacactct ttatgataac   4800

aacactgtgt tatattcttt gaatcctagc ccatctgcag agcaatgact gtgctcacca   4860

gtaaaagata acctttcttt ctgaaatagt caaatacgaa attagaaaag ccctccctat   4920

tttaactacc tcaactggtc agaaacacag attgtattct atgagtccca gaagatgaaa   4980

aaaattttat acgttgataa aacttataaa tttcattgat taatctcctg gaagattggt   5040

ttaaaaagaa aagtgtaatg caagaattta aagaaatatt tttaaagcca caattatttt   5100

aatattggat atcaactgct tgtaaaggtg ctcctctttt ttcttgtcat tgctggtcaa   5160

gattactaat atttgggaag gctttaaaga cgcatgttat ggtgctaatg tactttcact   5220

tttaaactct agatcagaat tgttgacttg cattcagaac ataaatgcac aaaatctgta   5280

catgtctccc atcagaaaga ttcattggca tgccacaggg gattctcctc cttcatcctg   5340

taaaggtcaa caataaaaac caaattatgg ggctgctttt gtcacactag catagagaat   5400

gtgttgaaat ttaactttgt aagcttgtat gtggttgttg atcttttttt tccttacaga   5460

cacccataat aaaatatcat attaaaattc                                    5490
```

<210> SEQ ID NO 184
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
```

-continued

```
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Pro Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 185
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185
```

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
            20                  25                  30

Leu Gly Trp Tyr Gln Gln Lys Pro Gly Lys Ala Pro Ile Leu Leu Ile
        35                  40                  45

Tyr Gly Thr Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Pro Val Thr Lys Ser Phe
        195                 200                 205

Asn Arg Gly Glu Cys
    210


<210> SEQ ID NO 186
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Ile Val Leu Thr Gln Ser Pro Gly Thr Leu Ser Leu Ser Pro Gly
1               5                   10                  15

Glu Arg Ala Thr Leu Ser Cys Gln Ser Ser Gln Ser Val Tyr Asn Asn
            20                  25                  30

Asn Tyr Leu Ser Trp Phe Gln Gln Lys Pro Gly Gln Ala Pro Arg Leu
        35                  40                  45

Leu Ile Tyr Gly Ala Ser Thr Leu Thr Ser Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Ala Gly Gly Tyr Ser Gly
                85                  90                  95

Ser Ser Asp Lys Tyr Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 187
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Ser Tyr
20 25 30

Leu Asn Trp Tyr Gln Gln Lys Pro Gly Lys Ala Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Gly Asn Thr Leu Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 188
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES -continued
<222> LOCATION: (1)..(1)
<223> OTHER INFORMATION: Predominantly pyroglutamic acid (pE)

<400> SEQUENCE: 188

```
Glu Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

-continued

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

ISOFORM-SELECTIVE ANTI-TGFβ ANTIBODIES AND METHODS OF USE

CROSS-REFERENCE TO RELATED APPLICATIONS

This application claims the benefit of priority to U.S. Provisional Application No. 63/044,478 filed Jun. 26, 2020, and U.S. Provisional Application No. 62/991,806 filed Mar. 19, 2020, the disclosure of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Mar. 12, 2021, is named "P35791-US-2_Sequence_Listing.txt", and is 492,347 bytes in size.

FIELD OF THE INVENTION

The present invention relates to isoform-selective anti-TGFβ antibodies (e.g., monospecific anti-TGFβ2 and anti-TGFβ3 antibodies, and dual-specific, anti-TGFβ2/3 antibodies) and methods of using the same, e.g., for the treatment of TGFβ-related disorders.

BACKGROUND

TGFβ comprises a pleiotropic set of three cytokines—TGFβ1, TGFβ2, and TGFβ3—that play critical roles in cell differentiation, tissue development, wound repair, immunoregulation, and, when dysregulated, tissue fibrosis. In the case of interstitial lung diseases (ILD) such as idiopathic pulmonary fibrosis (IPF), TGFβ activity is implicated in multiple aspects of disease pathogenesis. Genetic risk for IPF is conferred by mutations in genes expressed in lung epithelial cells that increase their susceptibility to injury and/or compromise their regenerative capacity. This epithelial stress or damage can activate innate immune cells such as alveolar macrophages to produce cytokines that activate mesenchymal cells to initiate a wound-healing response by proliferating, migrating, differentiating into myofibroblasts, and secreting extracellular matrix (ECM). TGFβ can contribute to many of these processes; in particular, it has been shown to promote apoptosis of lung epithelial cells while promoting activation, differentiation, and survival of myofibroblasts. Systemic sclerosis (SSc)/scleroderma is an autoimmune disease that begins with microvascular inflammation progressing to multi-organ connective tissue dysfunction involving tissues in skin, lung, heart, kidney, and intestine. TGFβ is involved in the dysregulation of vascular, connective tissue, and immune components in SSc (Lafyatis R. *Nat Rev Rheumatol.* 2014 December; 10(12): 706-19).

TGFβ signaling also plays roles in cancer pathogenesis, particularly in peritumoral stroma and immune compartments, where it can inhibit productive anti-tumor immune responses both by promoting excessive ECM production that prevents T cell infiltration into tumor tissue and by promoting T regulatory cell differentiation and activation, which can suppress anti-tumor immunity. Taken together, these findings implicate TGFβ as a potential therapeutic target for fibrotic diseases and cancer. However, the multifarious homeostatic functions of TGFβ and complexity in context-dependent mechanisms of TGFβ activation have contributed to limitations in terms of both safety and efficacy to establish a favorable therapeutic index in interventional studies of TGFβ inhibitors in human fibrotic disorders. For example, pan-TGFβ inhibitors have been associated with undesirable safety signals. In particular, the small molecule ALK5 inhibitors AZ12601011 and AZ12799734 (Anderton et al. (2011) Toxicologic Pathology, 39: 916-924) caused microscopic heart valve lesions in rats, and the pan-TGFβ 1D11 antibody (Lonning et al. (2011) Current Pharmaceutical Biotechnology, 12, 2176-2189) caused mice treated with 1D11 to develop histologic lesions, weight loss, non-neoplastic cystic epithelial hyperplasia and inflammation of the tongue and dental dysplasia and epithelial hyperplasia of the gingiva and esophagus. Further, CAT-192 (metelimumab), an antibody predominantly selective for TGFβ1, had a high serious adverse event rate with multiple gastric hemorrhages observed in a phase 1-2 study in SSc (Denton *A&R* 56:323 (2007)).

Thus, there remains a need in the art for safe and efficacious molecules that target TGFβ. The present invention provides such molecules and related uses.

SUMMARY

The invention provides isoform-selective anti-TGFβ antibodies and methods of using the same.

In one aspect, an isolated anti-TGFβ3 antibody is provided, wherein the antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9. In some aspects, the antibody selectively neutralizes TGFβ3.

In another aspect, an isolated anti-TGFβ3 antibody is provided, wherein the antibody selectively neutralizes TGFβ3, and wherein the antibody comprises one or more of the following features: (a) the anti-TGFβ3 antibody specifically binds to the beta6/beta7 hairpin region of TGFβ3; (b) binding of the anti-TGFβ3 antibody sterically blocks the ability of TGFBR2, but not TGFBR1, to bind TGFβ3; (c) binding of the anti-TGFβ3 antibody to TGFβ3 blocks TGFBR2 binding and inhibits the TGFBR1/TGFBR2 signaling receptors from binding to TGFβ3; (d) the anti-TGFβ3 antibody directly contacts amino acid residue R394 in the beta6/beta7 hairpin region of human TGFβ3; (e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2; (f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering); (g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering); (h) the anti-TGFβ3 antibody has reduced toxicity relative to the pan-TGFβ antibody 1D11; (i) the anti-TGFβ3 antibody has reduced toxicity in rodents or cynomolgus monkeys relative to the pan-TGFβ antibody 1D11; (j) the anti-TGFβ3 antibody has reduced toxicity relative to the pan-TGFβ small molecule inhibitor galunisertib; (k) the anti-TGFβ3 antibody has reduced toxicity in rodents relative to the pan-TGFβ small molecule inhibitor galunisertib; (1) the anti-TGFβ3 antibody has reduced toxicity relative to the anti-TGFβ1 antibody CAT-192; (m) the anti-TGFβ3 antibody has reduced toxicity relative to an isoform selective anti-TGFβ2 antibody and/or anti-TGFβ2/3 antibody; (n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

In another aspect, an isolated anti-TGFβ3 antibody is provided, wherein the antibody selectively neutralizes TGFβ3, and wherein the antibody comprises one or more of the following features: (a) the anti-TGFβ3 antibody specifically binds to the beta6/beta7 hairpin region of TGFβ3; (b) binding of the anti-TGFβ3 antibody sterically blocks the ability of TGFBR2, but not TGFBR1, to bind TGFβ3; (c) binding of the anti-TGFβ3 antibody to TGFβ3 blocks TGFBR2 binding and inhibits the TGFBR1/TGFBR2 signaling receptors from binding to TGFβ3; (d) the anti-TGFβ3 antibody directly contacts amino acid residue R394 in the beta6/beta7 hairpin region of human TGFβ3; (e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2; (f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering); (g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering); (h) the anti-TGFβ3 antibody has reduced toxicity relative to the pan-TGFβ antibody 1D11; (i) the anti-TGFβ3 antibody has reduced toxicity in rodents or cynomolgus monkeys relative to the pan-TGFβ antibody 1D11; (j) the anti-TGFβ3 antibody has reduced toxicity relative to the pan-TGFβ small molecule inhibitor galunisertib; (k) the anti-TGFβ3 antibody has reduced toxicity in rodents relative to the pan-TGFβ small molecule inhibitor galunisertib; (1) the anti-TGFβ3 antibody has reduced toxicity relative to the anti-TGFβ1 antibody CAT-192; (m) the anti-TGFβ3 antibody has reduced toxicity relative to an isoform selective anti-TGFβ2 antibody and/or anti-TGFβ2/3 antibody; (n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues. In some aspects, the anti-TGFβ3 antibody comprises a heavy chain variable region (VH) amino acid sequence having at least 95%, at least 96%, at least 97%, at least 98%, at least 99%, or 100% sequence identity to an amino acid sequence selected from the group consisting of SEQ ID NOs: 23, 37, and 42-50. In some aspects, the anti-TGFβ3 antibody comprises a VH amino acid sequence selected from the group consisting of SEQ ID NOs: 23, 37, and 42-50. In some aspects, the anti-TGFβ3 antibody comprises a complete heavy (H) chain amino acid sequence having at least 95%, at least 96%, at least 97%, at least 98%, at least 99%, or 100% sequence identity to an amino acid sequence selected from the group consisting of SEQ ID NOs: 29, 59, 64, and 65-72. In some aspects, the anti-TGFβ3 antibody comprises a complete heavy (H) chain amino acid sequence selected from the group consisting of SEQ ID NOs: 29, 59, 64, and 65-72. In further aspects, the anti-TGFβ3 antibody comprises a light chain variable region (VL) amino acid sequence having at least 95%, at least 96%, at least 97%, at least 98%, at least 99%, or 100% sequence identity an amino acid sequence selected from the group consisting of SEQ ID NOs: 22, 36, and 38-41. In yet other aspects, the anti-TGFβ3 antibody comprises a complete light (L) chain amino acid sequence having at least 95%, at least 96%, at least 97%, at least 98%, at least 99%, or 100% sequence identity to an amino acid sequence selected from the group consisting of SEQ ID NOs: 28, 58, and 60-63. In some aspects, the anti-TGFβ3 antibody comprises a complete L chain amino acid sequence selected from the group consisting of SEQ ID NOs: 28, 58, and 60-63. In some aspects, the anti-TGFβ3 antibody comprises a VH/VL pair, the VH/VL pair comprising amino acid sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9). In some aspects, the anti-TGFβ3 antibody comprises a complete H/L chain pair, the complete H/L chain pair comprising amino acid sequences (respectively) selected from the group consisting of SEQ ID NOs: 29/28 (rat 2A10), SEQ ID NOs: 59/58 (vi), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9). In some aspects, the anti-TGFβ3 antibody comprises a VL of SEQ ID NO: 22 comprising one or more framework modifications selected from the group consisting of: 4L or 4M, 38H or 38Q, 43A or 43Q, and 58V. In some aspects, the anti-TGFβ3 antibody VL comprises a set of framework modifications selected from the group consisting of (i) 4L in FR1, 38H and 43Q in FR2, 58I in FR3 (h2A10.v1 and h2A10.v2); (ii) 4M in FR1 (h2A10.v1.1 and h2A10.v2.1); (iii) 38Q in FR2 (h2A10.v1.2 and h2A10.v2.2); (iv) 43A in FR2 (h2A10.v1.3 and h2A10.v2.3); (v) 58V in FR3 (h2A10.v1.4 and h2A10.v2.4); (vi) 38Q, 43A in FR2, 58V in FR3 (h2A10.v3 and h2A10.v4); (vii) 58V in FR3 (h2A10.v1.4 and h2A10.v2.4); and (vi) 38Q, 43A in FR2, 58V in FR3 (h2A10.v3 and h2A10.v4), wherein the mutations are relative to the rat 2A10 VL having SEQ ID NO: 22. In other aspects, the anti-TGFβ3 antibody comprises a VH of SEQ ID NO: 23 comprising one or more framework modifications selected from the group consisting of: 47L or 47W; 49A, 49S, or 49G; 73D or 73N; and 76N, 78D or 78L, 78A, or 78V. In some aspects, the anti-TGFβ3 antibody VH comprises a set of framework modifications selected from the group consisting of: (i) 47L, 49A in FR2, 78V in FR3 (h2A10.v1); (ii) 47L, 49A in FR2, 73D, 76S, 78V in FR3 (h2A10.v2); (iii) 47W in FR2 (h2A10.v1.5); (iv): 49G in FR2 (h2A10.v1.6); (v) 78A in FR3 (h2A10.v1.7); (vi) 47W in FR2 (h2A10.v2.5); (vii) 49S in FR2 (h2A10.v2.6); (viii) 73N in FR3 (h2A10.v2.7); (ix) 76N in FR3 (h2A10.v2.8); (x) 78L in FR3 (h2A10.v2.9); and (xi) 49S in FR2, 76N, 78L in FR3 (h2A10.v3 and h2A10.v4), wherein the mutations are relative to the rat 2A10 VH having SEQ ID NO: 23.

In certain embodiments of the above anti-TGFβ3 antibodies, the VL of the anti-TGFβ3 antibody retains leucine (L) at position 4 in framework I and leucine (L) at position 47 in framework II (relative to the rat 2A10 VL having SEQ ID NO: 22). In some embodiments, the VH retains D at position 73 in framework III of VH from rat 2A10 (relative to the rat 2A10 VH having SEQ ID NO: 23).

In another aspect, an isolated anti-TGFβ3 antibody is provided, wherein the antibody selectively neutralizes TGFβ3, and wherein the antibody comprises one or more of the following features: (a) the anti-TGFβ3 antibody specifically binds to the beta6/beta7 hairpin region of TGFβ3; (b) binding of the anti-TGFβ3 antibody sterically blocks the ability of TGFBR2, but not TGFBR1, to bind TGFβ3; (c) binding of the anti-TGFβ3 antibody to TGFβ3 blocks TGFBR2 binding and inhibits the TGFBR1/TGFBR2 signaling receptors from binding to TGFβ3; (d) the anti-TGFβ3 antibody directly contacts amino acid residue R394 in the beta6/beta7 hairpin region of human TGFβ3; (e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2; (f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering); (g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering); (h) the anti-TGFβ3 antibody has reduced toxicity relative to the pan-TGFβ antibody 1D11; (i) the anti-TGFβ3 antibody has reduced toxicity in rodents or cynomolgus monkeys relative to the pan-TGFβ antibody 1D11; (j) the anti-TGFβ3 antibody has reduced toxicity relative to the pan-TGFβ small molecule inhibitor galunisertib; (k) the anti-TGFβ3 antibody has reduced toxicity in rodents relative to the pan-TGFβ small molecule inhibitor galunisertib; (1) the anti-TGFβ3 antibody has reduced toxicity relative to the anti-TGFβ1 antibody CAT-192; (m) the anti-TGFβ3 antibody has reduced toxicity relative to an isoform selective anti-TGFβ2 antibody and/or anti-TGFβ2/3 antibody; (n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues. In some aspects of this embodiment, the anti-TGFβ3 antibody comprises a VH amino acid sequence having at least 95%, at least 96%, at least 97%, at least 98%, at least 99%, or 100% sequence identity to the amino acid sequence of SEQ ID NO: 52. In some aspects, the anti-TGFβ3 antibody comprises the VH amino acid sequence of SEQ ID NO: 52. In some aspects, the anti-TGFβ3 antibody comprises a complete H chain amino acid sequence having at least 95%, at least 96%, at least 97%, at least 98%, at least 99%, or 100% sequence identity to the amino acid sequence of SEQ ID NO: 74. In some aspects, the anti-TGFβ3 antibody comprises the complete H chain amino acid sequence of SEQ ID NO: 74. In some aspects, the anti-TGFβ3 comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41. In some aspects, the anti-TGFβ3 antibody comprises a VL amino acid sequence selected from the group consisting of SEQ ID NOs: 22, 36, and 38-41. In some aspects, the anti-TGFβ3 antibody comprises a complete L chain amino acid sequence having at least 95%, at least 96%, at least 97%, at least 98%, at least 99%, or 100% sequence identity to an amino acid sequence selected from the group consisting of SEQ ID NOs: 28, 58, and 60-63. In some aspects, the anti-TGFβ3 comprises a complete L chain amino acid sequence selected from the group consisting of SEQ ID NOs: 28, 58, and 60-63. In further aspects, the anti-TGFβ3 antibody comprises a VH/VL pair comprising the amino acid sequences (respectively) of SEQ ID NOs: 52/36. In some aspects, the anti-TGFβ3 antibody comprises a complete H/L chain pair, the H/L chain pair comprising the amino acid sequences (respectively) of SEQ ID NOs: 74/58.

In another aspect, an isolated anti-TGFβ3 antibody is provided, wherein the antibody selectively neutralizes TGFβ3, and wherein the antibody comprises one or more of the following features: (a) the anti-TGFβ3 antibody specifically binds to the beta6/beta7 hairpin region of TGFβ3; (b) binding of the anti-TGFβ3 antibody sterically blocks the ability of TGFBR2, but not TGFBR1, to bind TGFβ3; (c) binding of the anti-TGFβ3 antibody to TGFβ3 blocks TGFBR2 binding and inhibits the TGFBR1/TGFBR2 signaling receptors from binding to TGFβ3; (d) the anti-TGFβ3 antibody directly contacts amino acid residue R394 in the beta6/beta7 hairpin region of human TGFβ3; (e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2; (f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering); (g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering); (h) the anti-TGFβ3 antibody has reduced toxicity relative to the pan-TGFβ antibody 1D11; (i) the anti-TGFβ3 antibody has reduced toxicity in rodents or cynomolgus monkeys relative to the pan-TGFβ antibody 1D11; (j) the anti-TGFβ3 antibody has reduced toxicity relative to the pan-TGFβ small molecule inhibitor galunisertib; (k) the anti-TGFβ3 antibody has reduced toxicity in rodents relative to the pan-TGFβ small molecule inhibitor galunisertib; (1) the anti-TGFβ3 antibody has reduced toxicity relative to the anti-TGFβ1 antibody CAT-192; (m) the anti-TGFβ3 antibody has reduced toxicity relative to an isoform selective anti-TGFβ2 antibody and/or anti-TGFβ2/3 antibody; (n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues. In some aspects, the anti-TGFβ3 antibody comprises a VH amino acid sequence having at least 95%, at least 96%, at least 97%, at least 98%, at least 99%, or 100% sequence identity to the amino acid sequence of SEQ ID NO: 51 or 55. In some aspects, the anti-TGFβ3 antibody comprises the VH amino acid sequence of SEQ ID NO: 51 or 55. In some aspects, the anti-TGFβ3 antibody comprises a complete H chain amino acid sequence having at least 95%, at least 96%, at least 97%, at least 98%, at least 99%, or 100% sequence identity to the amino acid sequence of SEQ ID NO: 73 or 77. In some aspects, the anti-TGFβ3 antibody comprises the complete H chain amino acid sequence of SEQ ID NO: 73. In some aspects, the anti-TGFβ3 antibody comprises the complete H chain amino acid sequence of SEQ ID NO: 77. In some aspects, the anti-TGFβ3 antibody comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41. In some aspects, the anti-TGFβ3 antibody comprises a VL amino acid sequence selected from the group consisting of SEQ ID NOs: 22, 36, and 38-41. In some aspects, the anti-TGFβ3 antibody comprises a complete L chain amino acid sequence having at least 95%, at least 96%, at least 97%, at least 98%, at least 99%, or 100% sequence identity to an amino acid sequence selected from the group consisting of SEQ ID NOs: 28, 58, and 60-63. In some aspects, the anti-TGFβ3 antibody comprises a complete L chain amino acid sequence selected from the group consisting of SEQ ID NOs: 28, 58, and 60-63. In some aspects, the anti-TGFβ3 antibody comprises a VH/VL pair, the VH/VL pair comprising the amino acid sequences (respectively) of SEQ ID NOs: 51/36 or SEQ ID NOs: 55/54. In some aspects, the anti-TGFβ3 antibody comprises a complete H/L chain pair, the H/L chain pair comprising the amino acid sequences (respectively) of SEQ ID NOs: 73/58 or SEQ ID NOs: 77/76.

In another aspect, an isolated anti-TGFβ3 antibody is provided, wherein the antibody selectively neutralizes TGFβ3, and wherein the antibody comprises one or more of the following features: (a) the anti-TGFβ3 antibody specifically binds to the beta6/beta7 hairpin region of TGFβ3; (b) binding of the anti-TGFβ3 antibody sterically blocks the ability of TGFBR2, but not TGFBR1, to bind TGFβ3; (c) binding of the anti-TGFβ3 antibody to TGFβ3 blocks TGFBR2 binding and inhibits the TGFBR1/TGFBR2 signaling receptors from binding to TGFβ3; (d) the anti-TGFβ3 antibody directly contacts amino acid residue R394 in the beta6/beta7 hairpin region of human TGFβ3; (e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2; (f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering); (g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering); (h) the anti-TGFβ3 antibody has reduced toxicity relative to the pan-TGFβ antibody 1D11; (i) the anti-TGFβ3 antibody has reduced toxicity in rodents or cynomolgus monkeys relative to the pan-TGFβ antibody 1D11; (j) the anti-TGFβ3 antibody has reduced toxicity relative to the pan-TGFβ small molecule inhibitor galunisertib; (k) the anti-TGFβ3 antibody has reduced toxicity in rodents relative to the pan-TGFβ small molecule inhibitor galunisertib; (1) the anti-TGFβ3 antibody has reduced toxicity relative to the anti-TGFβ1 antibody CAT-192; (m) the anti-TGFβ3 antibody has reduced toxicity relative to an isoform selective anti-TGFβ2 antibody and/or anti-TGFβ2/3 antibody; (n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues. In some aspects, the anti-TGFβ3 antibody comprises a VH amino acid sequence having at least 95%, at least 96%, at least 97%, at least 98%, at least 99%, or 100% sequence identity to the amino acid sequence of SEQ ID NO: 53 or 57. In some aspects, the anti-TGFβ3 antibody comprises the VH amino acid sequence of SEQ ID NO: 53. In some aspects, the anti-TGFβ3 antibody comprises the VH amino acid sequence of SEQ ID NO: 57. In some aspects, the anti-TGFβ3 antibody comprises a complete H chain amino acid sequence having at least 95%, at least 96%, at least 97%, at least 98%, at least 99%, or 100% sequence identity to the amino acid sequence of SEQ ID NO: 75 or 79. In some aspects, the anti-TGFβ3 antibody comprises the complete H chain amino acid sequence of SEQ ID NO: 75. In some aspects, the anti-TGFβ3 antibody comprises a complete H chain amino acid sequence of SEQ ID NO: 79. In some aspects, the anti-TGFβ3 antibody comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41. In some aspects, the anti-TGFβ3 antibody comprises a VL amino acid sequence selected from the group consisting of SEQ ID NOs: 22, 36, and 38-41. In some aspects, the anti-TGFβ3 antibody comprises a complete L chain amino acid sequence having at least 95%, at least 96%, at least 97%, at least 98%, at least 99%, or 100% sequence identity to the amino acid sequence selected from the group consisting of SEQ ID NOs: 28, 58, and 60-63. In some aspects, the anti-TGFβ3 antibody comprises a complete L chain amino acid sequence selected from the group consisting of SEQ ID NOs: 28, 58, and 60-63. In some aspects, the anti-TGFβ3 antibody comprises a VH/VL pair comprising the amino acid sequences (respectively) of SEQ ID NOs: 53/36 or SEQ ID NOs: 57/56. In some aspects, the anti-TGFβ3 antibody comprises a complete H/L chain pair, the H/L chain pair comprising the amino acid sequences (respectively) of SEQ ID NOs: 75/58 or SEQ ID NOs: 79/78.

In another aspect, an anti-TGFβ3 antibody is provided, the antibody comprising: (a) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78.

In another aspect, an isolated anti-TGFβ2/3 antibody is provided, wherein the antibody selectively neutralizes TGFβ2 and TGFβ3, and wherein the antibody comprises one or more of the following features: (a) selectivity of the anti-TGFβ2/3 antibody for TGFβ2 and TGFβ3 over human TGFβ1, with respect to selective neutralization, is achieved by direct contact of the antibody's antigen binding domain with amino acid residue E373 TGFβ2 or TGFβ3 (human TGFβ2 numbering); (b) the anti-TGFβ2/3 antibody neutralizes TGFβ2 and/or TGFβ3 via an allosteric mechanism; (c) the anti-TGFβ2/3 antibody induces a conformational change in TGFβ2 and/or TGFβ3 homodimer; (d) the anti-TGFβ2/3 antibody induces a conformational change in TGFβ2 and/or TGFβ3 homodimer, wherein the conformational change comprises the two monomers pinching together by several degrees; (e) the anti-TGFβ2/3 antibody is a divalent antibody or a monovalent antibody; (f) the anti-TGFβ2/3 antibody comprises (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15; (g) the anti-TGFβ2/3 antibody specifically binds to TGFβ2 homodimer, the TGFβ2 homodimer having a first and a second TGFβ2 monomer, and wherein the anti-TGFβ2/3 antibody comprises an antigen binding domain that directly contacts (i) amino acid residues V313, Q314, D315, R320, L322, Y323, R328, D329, F345, and A347 of the first TGFβ2 monomer, and (ii) amino acid residues N368, T369, I370, N371, P372, E373, A374, S375, A376, and S377 of the second TGFβ2 monomer (human TGFβ2 numbering); (h) the anti-TGFβ2/3 antibody as in (g), wherein the antigen binding domain is within 5 angstroms of the TGFβ2 and/or TGFβ3 amino acid residues; (i) wherein the anti-TGFβ2/3 antibody specifically binds to the same epitope on TGFβ3 as in (g); and (j) the anti-TGFβ2/3 antibody does not neutralize TGFβ2 and/or TGFβ3 in monovalent form. In one aspect, the anti-TGFβ2/3 antibody comprises a VH amino acid sequence having at least 95%, at least 96%, at least 97%, at least 98%, at least 99%, or 100% sequence identity to an amino acid sequence selected from the group consisting of SEQ ID NOs: 27, 81, 83, 86-88, 93-100, and 102-105. In one aspect, the anti-TGFβ2/3 antibody comprises a VH amino acid sequence selected from the group consisting of SEQ ID NOs: 27, 81, 83, 86-88, 93-100, and 102-105. In one aspect, the anti-TGFβ2/3 antibody comprises a complete H chain amino acid sequence having at least 95%, at least 96%, at least 97%, at least 98%, at least 99%, or 100% sequence identity to the amino acid sequence selected from the group consisting of SEQ ID NOs: 33, 107, 109, 112-114, and 119-130. In one aspect, the anti-TGFβ2/3 comprises a VL amino acid sequence having at least 95%, at least 96%, at least 97%, at least 98%, at least 99%, or 100% sequence identity to the amino acid sequence selected from the group consisting of SEQ ID NOs: 26, 80, 82, 84, 85, 89-92, and 101. In one aspect, the anti-TGFβ2/3 antibody comprises a VL amino acid sequence selected from the group consisting of SEQ ID NOs: 26, 80, 82, 84, 85, 89-92, and 101. In one aspect, the anti-TGFβ2/3 antibody comprises a complete L chain amino acid sequence having at least 95%, at least 96%, at least 97%, at least 98%, at least 99%, or 100% sequence identity to an amino acid sequence selected from the group consisting of SEQ ID NOs: 32, 106, 108, 110, 111, 115-118, and 186. In one aspect, the anti-TGFβ2/3 antibody comprises a complete L chain amino acid sequence selected from the group consisting of SEQ ID NOs: 32, 106, 108, 110, 111, 115-118, and 186. In one aspect, the anti-TGFβ2/3 antibody comprises a VH/VL pair, the VH/VL pair comprising amino acid sequences (respectively) selected from the group consisting of SEQ ID NOs: 27/26 (rabbit 4A11), SEQ ID NOs: 81/80 (v1), SEQ ID NOs: 81/82 (v2), SEQ ID NOs: 83/80 (v3), SEQ ID NOs: 83/82 (v4), SEQ ID NOs: 81/84 (v5), SEQ ID NOs: 81/85 (v6), SEQ ID NOs: 83/84 (v7), SEQ ID NOs: 86/84 (v7/1), SEQ ID NOs: 87/84 (v7.2), SEQ ID NOs: 88/84 (v7.3), SEQ ID NOs: 83/89 (v7.4), SEQ ID NOs: 83/90 (v7.5), SEQ ID NOs: 83/91 (v7.6), SEQ ID NOs: 83/92 (v7.7), SEQ ID NOs: 93/84 (v7.8), SEQ ID NOs: 94/84 (v7.9), SEQ ID NOs: 95/84 (v7.10), SEQ ID NOs: 96/84 (v7.11), SEQ ID NOs: 97/84 (v7.12), SEQ ID NOs: 98/84 (v7.13), SEQ ID NOs: 99/84 (v7.14), SEQ ID NOs: 100/84 (v7.15), SEQ ID NOs: 102/101 (v7.16), SEQ ID NOs: 103/101 (v7.17), SEQ ID NOs: 104/101 (v7.18), SEQ ID NOs: 105/101 (v7.19), and SEQ ID NOs: 83/85 (v8). In one aspect, the anti-TGFβ2/3 antibody comprises a complete H/L chain pair, the complete H/L chain pair comprising amino acid sequences (respectively) selected from the group consisting of SEQ ID NOs: 32/33 (rabbit 4A11), SEQ ID NOs: 107/106 (v1), SEQ ID NOs: 107/108 (v2), SEQ ID NOs: 109/106 (v3), SEQ ID NOs: 109/108 (v4), SEQ ID NOs: 107/110 (v5), SEQ ID NOs: 107/111 (v6), SEQ ID NOs: 109/110 (v7), SEQ ID NOs: 112/110 (v7.1), SEQ ID NOs: 113/110 (v7.2), SEQ ID NOs: 114/110 (v7.3), SEQ ID NOs: 114/115 (v7.4), SEQ ID NOs: 114/116 (v7.5), SEQ ID NOs: 114/117 (v7.6), SEQ ID NOs: 114/118 (v7.7), SEQ ID NOs: 119/110 (v7.8), SEQ ID NOs:120/110 (v7.9), SEQ ID NOs: 121/110 (v7.10), SEQ ID NOs: 122/110 (v7.11), SEQ ID NOs: 123/110 (v7.12), SEQ ID NOs: 124/110 (v7.13), SEQ ID NOs: 125/110 (v7.14), SEQ ID NOs: 126/110 (v7.15), SEQ ID NOs: 127/186 (v7.16), SEQ ID NOs: 128/186 (v7.17), SEQ ID NOs: 129/186 (v7.18), SEQ ID NOs: 130/186 (v7.19), and SEQ ID NOs: 114/111 (v8). In one aspect, the anti-TGFβ2/3 antibody comprises a VL comprising the amino acid sequence of SEQ ID NO: 26 comprising one or more framework modifications selected from the group consisting of: 2A or 2I, 4L, 36F or 36Y, 43P or 43A, and 58V or 581. In one aspect, the anti-TGFβ2/3 antibody VL comprises a set of framework modifications selected from the group consisting of: (i) 2A and 4L in FR1 and 36F in FR2 (h4A11.v1 and h4A11.v3); (ii) 2A and 4L in FR1 and 36F and 43P in FR2 (h4A11.v2 and h4A11.v4); (iii) 2A in FR1, 36F and 43P in FR2 and 58V in FR3 (h4A11.v5 and h4A11.v7); (iv) 2A and 4L in FR1 and 36F in FR2 (h4A11.v6 and h4A11.v8); (v) 2I in FR1 (h4A11.v7.4); (vi) 36Y in FR2 (h4A11.v7.5); (vii) 43A in FR2 (h4A11.v7.6); (viii) 581 in FR3 (h4A11.v7.7); and (ix) 2I in FR1, 43A in FR2, 581 in FR3 (h4A11.v7.16-19), wherein the mutations are relative to the VL comprising the amino acid sequence of SEQ ID NO: 26. In one aspect, the anti-TGFβ2/3 antibody comprises a VH comprising the amino acid sequence of SEQ ID NO: 27 comprising one or more framework modifications selected from the group consisting of: deletion of 1E, 2Q or 2V, 24V, 37V or 37I, 48I, 49G, 67F or 67V, 71K or 71V, 73S or 73T, deletion of 75K and 76N, 78V or 78F, 91F or 91Y, 105P or 105Q. In one aspect, the anti-TGFβ2/3 antibody VL comprises a set of framework modifications selected from the group consisting of: (i) 2Q and 24V in FR1, 48I and 49G in FR2, 71K, 73S, 78V and 91F in FR3 and 105P in FR4 (h4A 1.v1, h4A11.v2, h4A11.v5, h4A11.v6); (ii) 2Q in FR1, 37V in FR2, 67F, 71K, 73S, 78V and 91F in FR3 and 105P in FR4 (h4A11.v3, h4A11.v4, h4A11.v7, h4A11.v8); (iii) delete 1E in FR1 (h4A11.v7.1); (iv) delete 75K and 76N in FR3 (h4A11.v7.2); (v) delete 1E in FR1 and 75K76N in FR3 (h4A11.v7.3); (vi) 2V in FR1 (h4A11.v7.8); (vi) 37I in FR2 (h4A11.v7.9); (vii) 67V in FR3 (h4A11.v7.10); (viii) 71V in FR3 (h4A11.v7.11); (ix) 73T in FR3 (h4A11.v7.12); (x) 78F in FR3 (h4A11.v7.13); (xi) 91Y in FR3 (h4A11.v7.14); (xii) 105Q in FR4 (h4A11.v7.15); (xiii) 2V in FR1, 37I in FR2, 67V, 73T, 78F in FR3, 105Q in FR4 ((h4A11.v7.16); (xiv) 2V in FR1, 37I in FR2, 67V, 73T, 91Y in FR3, 105Q in FR4 (h4A11.v7.17); (xv) 2V in FR1, 37I in FR2, 67V, 73T in FR3, 105Q in FR4 (h4A11.v7.18); and (xvi) 2V in FR1, 37I in FR2, 67V, 73T, deletion of 75K and 76N in FR3, 105Q in FR4 (h4A11.v7.19), wherein the mutations are relative to the VH comprising the amino acid sequence of SEQ ID NO: 27.

In another aspect, an isolated anti-TGFβ2 antibody is provided, wherein the antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142. In one aspect, the anti-TGFβ2 antibody comprises a complete H chain amino acid sequence having at least 95%, at least 96%, at least 97%, at least 98%, at least 99%, or 100% sequence identity to the amino acid sequence selected from the group consisting of SEQ ID NOs: 31, 146, and 152-156. In one aspect, the anti-TGFβ2 antibody comprises a complete H chain amino acid sequence selected from the group consisting of SEQ ID NOs: 31, 146, and 152-156. In one aspect, the anti-TGFβ2 antibody comprises a VL amino acid sequence having at least 95%, at least 96%, at least 97%, at least 98%, at least 99%, or 100% sequence identity to the amino acid sequence selected from the group consisting of SEQ ID NOs: 24, 131, 133-137, 143, and 144. In another aspect, the anti-TGFβ2 antibody comprises a VL amino acid sequence selected from the group consisting of SEQ ID NOs: 24, 131, 133-137, 143, and 144. In one aspect, the anti-TGFβ2 antibody comprises a complete L chain amino acid sequence having at least 95%, at least 96%, at least 97%, at least 98%, at least 99%, or 100% sequence identity to an amino acid sequence selected from the group consisting of SEQ ID NOs: 30, 145, 147-151, 157, and 158. In one aspect, the anti-TGFβ2 antibody comprises a complete L chain amino acid sequence selected from the group consisting of SEQ ID NOs: 30, 145, 147-151, 157, and 158. In one aspect, the anti-TGFβ2 antibody comprises a VH/VL pair, the VH/VL pair comprising amino acid sequences selected from the group consisting of SEQ ID NOs: 25/24 (rabbit 6F12), SEQ ID NOs: 132/131 (v1), SEQ ID NOs: 132/133 (v1.1), SEQ ID NOs: 132/134 (v1.2), SEQ ID NOs: 132/135 (v1.3), SEQ ID NOs: 132/136 (v1.4), SEQ ID NOs: 132/137 (v1.5), SEQ ID NOs: 138/131 (v1.6), SEQ ID NOs: 139/131 (v1.7), SEQ ID NOs: 140/131 (v1.8), SEQ ID NOs: 141/131 (v1.9), SEQ ID NOs: 142/131 (v2), SEQ ID NOs: 132/143 (v3), and SEQ ID NOs: 142/144 (v4). In one aspect, the anti-TGFβ2 comprises a complete H/L chain pair, the complete H/L chain pair comprising amino acid sequences selected from the group consisting of SEQ ID NOs: 31/30 (rabbit 6F12), SEQ ID NOs: 146/145 (v1), SEQ ID NOs: 146/147 (v1.1), SEQ ID NOs: 146/148 (v1.2), SEQ ID NOs: 146/149 (v1.3), SEQ ID NOs: 146/150 (v1.4), SEQ ID NOs: 146/151 (v1.5), SEQ ID NOs: 152/145 (v1.6), SEQ ID NOs: 153/145 (v1.7), SEQ ID NOs: 154/145 (v1.8), SEQ ID NOs: 155/145 (v1.9), SEQ ID NOs: 156/145 (v2), SEQ ID NOs: 146/157 (v3), and SEQ ID NOs: 156/158 (v4). In one aspect, the anti-TGFβ2 antibody comprises a VL comprising the amino acid sequence of SEQ ID NO: 24 comprising one or more framework mutations selected from the group consisting of 43S or 43A, 66G, 69T, 71F, and 87Y. In one aspect, the anti-TGFβ2 antibody VL comprises a set of framework mutations selected from the group consisting of: (i) 43S in FR2 and 66E, 69P, 71Y and 87F in FR3 (h6F12.v1 and h6F12.v2); (ii) 43S in FR2 and 58V, 66E, 69P, 71Y and 87F in FR3 (h6F12.v3 and h6F12.v4); (iii) 43A in FR2 (h6F12.v1.1); (iv) 66G in FR3 (h6F12.v1.2); (v) 69T in FR3 (h6F12.v1.3); (vi) 71F in FR3 (h6F12.v1.4); and (vii) 87Y in FR3 (h6F12.v1.5), wherein the mutations are relative to the VL comprising the amino acid sequence of SEQ ID NO: 24. In one aspect, the anti-TGFβ2 antibody comprises a VH comprising the amino acid sequence of SEQ ID NO: 25 comprising one or more framework mutations selected from the group consisting of 37V or 37I, 48M or 48L, 49G or 49A, 67L, 71K and 78V, and 105P or 105R. In one aspect, the anti-TGFβ2 antibody VH comprises a set of framework mutations selected from the group consisting of: (i) 37V, 48M and 49G in FR2 and 105P in FR4 (h6F12.v1 and h6F12.v3); (ii) 37V and 48M in FR2, 67L, 71K and 78V in FR3 and 105P in FR4 (h6F12.v2 and h6F12.v4); (iii) 37I in FR2 (h6F12.v1.6); (iv) 48L in FR2 (h6F12.v1.7); (v) 49A in FR2 (h6F12.v1.8); (vi) 105R in FR4 (h6F12.v1.9); (vii) 37V, 48M and 49G in FR2 and 105P in FR4 (h6F12.v1 and h6F12.v3); (viii) 37V and 48M in FR2, 67L, 71K and 78V in FR3 and 105P in FR4 (6F12.v2 and h6F12.v4); (ix) 37I in FR2 (h6F12.v1.6); (x) 48L in FR2 (h6F12.v1.7); (xi): 49A in FR2 (h6F12.v1.8); and (xii) 105R in FR4 (h6F12.v1.9), wherein the mutations are relative to the VH comprising the amino acid sequence of SEQ ID NO: 25.

In certain embodiments of any of the above aspects, the anti-TGFβ3 antibody and/or the anti-TGFβ2/3 antibody specifically binds to human TGFβ3. In some embodiments of any of the above aspects, the anti-TGFβ3 antibody specifically binds to both the immature and mature forms of TGFβ3. In some embodiments of any of the above aspects, the anti-TGFβ2/3 antibody and/or the anti-TGFβ2 specifically binds to human TGFβ2. In some embodiments of any of the above aspects, the antibody is a monoclonal antibody. In some embodiments of any of the above aspects, the antibody is a human, humanized, or chimeric antibody. In some embodiments of any of the above aspects, the antibody is an antibody fragment. In some embodiments of any of the above aspects, the antibody comprises a human Fc region that is an IgG1 or IgG4 isotype. In some embodiments of any of the above aspects, the antibody comprises a human Fc region that is an IgG1 isotype. In some embodiments of any of the above aspects, the Fc region of the antibody is modified to remove effector function. In some aspects, the Fc region comprises a modification to remove the glycosylation site at amino acid residue position N297 (EU numbering as in Kabat). In some aspects, the modification is a mutation selected from N297G or N297A. In some aspects, the modification is the mutation N297G. In some embodiments of any of the above aspects, the antibody has a Cmax of about 230-260 μg/ml and/or a half life ($t_{1/2}$) of about 15 to 16 days.

Also provided are isolated nucleic acids encoding the antibody according to any of the above aspects and embodiments, and host cells comprising the nucleic acids. In some aspects, a method of producing an antibody is provided. The method can include culturing the host cell provided herein so that the antibody is produced. In some aspects, the method further comprises recovering the antibody from the host cell. Also provided is an antibody produced by the method of producing the antibody.

In another aspect, an immunoconjugate comprising an antibody, such as any of the antibodies as described above, and a cytotoxic agent is provided. In some embodiments, the antibody is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In some embodiments, the antibody is an anti-TGFβ2 antibody, wherein the antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In some embodiments, the antibody is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

In another aspect, a pharmaceutical formulation or immunoconjugate comprising the antibody of any one of the above aspects and embodiments and a pharmaceutically acceptable carrier is provided. In some embodiments, the antibody is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-LT, -L2 and -L3, wherein CDR-LT has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In some embodiments, the antibody is an anti-TGFβ2 antibody, wherein the antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In some embodiments of the pharmaceutical formulation or conjugate, the antibody is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

In some aspects, the pharmaceutical formulation further comprises an additional therapeutic agent. In some aspects, the additional therapeutic agent is selected from the group consisting of pirfenidone, nintedanib, mycophenylate mofetil, an IL-6 inhibitor (e.g., tocilizumab), an anti-CTFG antibody (e.g., FG-3019), an autotaxin inhibitor, a JAK inhibitor, an IL-11 inhibitor, and PTX2.

Also provided is an antibody according to any of the above aspects and embodiments for use as a medicament. In some embodiments, the antibody for use as a medicament is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In some embodiments, the antibody for use as a medicament is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

Also provided is an antibody according to any of the above aspects and embodiments for use in treating a TGFβ-related disorder. In some embodiments, the antibody for use in treating a TGFβ-related disorder is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In some embodiments, the antibody for use in treating a TGFβ-related disorder is an anti-TGFβ2 antibody, wherein the antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In some embodiments, the antibody for use in treating a TGFβ-related disorder is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

In one aspect, an anti-TGFβ3 antibody according to any of the above aspects and embodiments is provided and an anti-TGFβ2 antibody according to any of the above aspects and embodiments is provided for use in combination to treat a TGFβ-related disorder. In one embodiment, the anti-TGFβ3 antibody for use in such combination comprises: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In another embodiment, the anti-TGFβ2 antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142.

Also provided is an antibody according to any of the above aspects and embodiments for use in the manufacture of a medicament for treating a TGFβ-related disorder, for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin, and/or for inhibiting new collagen synthesis. In one embodiment, the antibody for such medicament is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In another embodiment, the antibody for such medicament is an anti-TGFβ2 antibody comprising: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142. In another aspect, the antibody is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

In some embodiments of the above uses and medicaments for treating TGFβ-related disorders, the TGFβ-related disorder is fibrosis. In some embodiments, the fibrosis is a fibrotic condition of the lung, liver, heart, kidney, pancreas, eye, and/or skin. In some aspects, the fibrosis is a lung fibrosis selected from the group consisting of idiopathic pulmonary fibrosis (IPF), idiopathic pulmonary upper lobe fibrosis (Amitani disease), familial pulmonary fibrosis, pulmonary fibrosis (e.g., pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma), cystic fibrosis, non-specific interstitial pneumonia (NSIP), cryptogenic organizing pneumonia (COP), progressive massive fibrosis, scleroderma/systemic sclerosis (SSc, including limited cutaneous (lcSSc) and diffuse cutaneous (dcSSc) forms and SSc-associated interstitial lung disease (SSc-ILD)), bronchiolitis obliterans-organizing pneumonia, connective tissue disease-associated ILD (CT-ILD), hypersensitivity pneumonitis, pulmonary hypertension, pulmonary tuberculosis, silicosis, asbestosis, acute lung injury, and acute respiratory distress (ARD, including bacterial pneumonia induced, trauma-induced, and viral pneumonia-induced, ventilator-induced, non-pulmonary sepsis induced). In some aspects, the fibrosis is a fibrotic condition of the liver selected from the group consisting of liver cirrhosis, congenital hepatic fibrosis, obesity, fatty liver, alcohol induced liver fibrosis, non-alcoholic steatohepatitis (NASH), biliary duct injury, primary biliary cirrhosis (PBC), primary sclerosing cholangitis (PSC), infection- or viral-induced liver fibrosis (e.g., chronic hepatitis B and C virus infections), cystic fibrosis, autoimmune hepatitis, necrotizing hepatitis, primary sclerosing cholangitis, hemochromatosis, disorders of the biliary tree, and hepatic dysfunction attributable to infections. In some aspects, the fibrosis is a fibrotic condition of the heart and/or pericardium selected from the group consisting of endomyocardial fibrosis, cardiac allograft vasculopathy (CAV), myocardial infarction, atrial fibrosis, congestive heart failure, arteriosclerosis, atherosclerosis, vascular stenosis, myocarditis, congestive cardiomyopathy, coronary infarcts, varicose veins, coronary artery stenosis and other post-ischemic conditions, and idiopathic retroperitoneal fibrosis. In some aspects, the fibrosis is a fibrotic condition of the kidney selected from the group consisting of glomerulonephritis (including membranoproliferative, diffuse proliferative, rapidly progressive or sclerosing, post-infectious and chronic forms), diabetic glomerulosclerosis, focal segmental glomerulosclerosis, IgA nephropathy, diabetic nephropathy, ischemic nephropathy, tubulointerstitial kidney fibrosis, HIV-associated nephropathy, membrane nephropathy, glomerulonephritis secondary to systemic inflammatory diseases such as lupus, scleroderma and diabetes glomerulonephritis, idiopathic membranoproliferative glomerular nephritis, mesangial proliferative glomerulonephritis, crescentic glomerulonephritis, amyloidosis (which affects the kidney among other tissues), autoimmune nephritis, renal tubuloinsterstitial fibrosis, renal arteriosclerosis, Alport's syndrome, nephrotic syndrome, chronic renal failure, chronic kidney disease, periglomerular fibrosis/atubular glomeruli, combined apical emphysema and basal fibrosis syndrome (emphysema/fibrosis syndrome), glomerular hypertension, nephrogenic fibrosing dermatopathy, polycystic kidney disease, Fabry's disease, and renal hypertension. In some aspects, the fibrosis is a fibrotic condition of the pancreas selected from the group consisting of stromal remodeling pancreatitis and stromal fibrosis. In some aspects, the fibrosis is a fibrotic condition of the gastrointestinal tract selected from the group consisting of Crohn's disease, ulcerative colitis, collagenous colitis, colorectal fibrosis, villous atrophy, crypt hyperplasia, polyp formation, healing gastric ulcer, and microscopic colitis. In some aspects, the fibrosis is a fibrotic condition of the eye selected from the group consisting of ocular fibrosis, ophthalmic fibrosis, proliferative vitreoretinopathy, vitreoretinopathy of any etiology, fibrosis associated with retinal dysfunction, fibrosis associated with wet or dry macular degeneration, scarring in the cornea and conjunctiva, fibrosis in the corneal endothelium, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), tractional retinal detachment in association with contraction of the tissue in diabetic retinopathy, congenital orbital fibrosis, lacrimal gland fibrosis, corneal subepithelial fibrosis, and Grave's ophthalmopathy. In some aspects, the fibrosis is selected from fibrosis resulting from spinal cord injury/fibrosis or central nervous system fibrosis such as fibrosis after a stroke, Duchenne muscular dystrophy, fibrosis associated with neurodegenerative disorder such as Alzheimer's disease or multiple sclerosis, vascular restenosis, uterine fibrosis, endometriosis, ovarian fibroids, Peyronie's disease, polycystic ovarian syndrome, disease related pulmonary apical fibrosis in ankylosing spondylitis, scarring, and fibrosis incident to microbial infections (e.g., bacterial, viral, parasitic, fungal). In a specific embodiment, the fibrosis is SSc. In a specific embodiment, the fibrosis is IPF. In a specific embodiment, the fibrosis is chronic obstructive pulmonary disease (COPD). In a specific embodiment, the fibrosis is progressive-fibrosing interstitial lung disease (PF-ILD). In a specific embodiment, the PF-ILD is a disease or condition selected from the group consisting of non-specific interstitial pneumonia (NSIP), cryptogenic organizing pneumonia (COP), progressive massive fibrosis, a complication of coal worker's pneumoconiosis, scleroderma/systemic sclerosis, bronchiolitis obliterans-organizing pneumonia; connective tissue disease-associated ILD (CT-ILD), and hypersensitivity pneumonitis. In a specific embodiment, the fibrosis is liver cirrhosis or chronic hepatic fibrosis. In a specific embodiment, the fibrosis is GI tract fibrosis. In a specific embodiment, the fibrosis is a fibrotic condition of the eye, fibrosis resulting from spinal cord injury, fibrosis or central nervous system fibrosis, or fibrosis associated with a neurodegenerative disorder.

In another aspect, a method of treating a subject having a TGFβ-related disorder is provided. In some embodiments, the method comprises administering an effective amount of an antibody or pharmaceutical formulation according to any of the above aspects and embodiments to a subject in need thereof. In another aspect a method for inhibiting TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin, and/or for inhibiting new collagen synthesis in a subject is provided. In some aspects, the method includes administering to a subject in need thereof an effective amount of the antibody according to any of the above aspects and embodiments to inhibit TGFBR-dependent SMAD signaling, to inhibit the assembly of TGFβ-TGFBR signaling complexes, to inhibit TGFβ signaling through the TGFBR1/R2 complex, to inhibit TGFβ signaling through the TGFBR2/ALK1 complex facilitated by endoglin and/or to inhibit new collagen synthesis in the subject. In some aspects, the method includes administering an additional therapeutic agent to the subject. In some aspects, the additional therapeutic agent is selected from the group consisting of pirfenidone, nintedanib, mycophenylate mofetil, an IL-6 inhibitor (e.g., tocilizumab, sarilumab), an anti-CTFG antibody (e.g., FG-3019), an autotaxin inhibitor, and PTX2. In one embodiment of such methods, the antibody is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In another embodiment of such methods, the antibody is an anti-TGFβ2 antibody comprising: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142. In another embodiment of such methods, the antibody is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

In a further aspect of the above methods, the method can include administering to the subject an effective amount of an anti-TGFβ3 antibody and an effective amount of an anti-TGFβ2 antibody. In one embodiment, the anti-TGFβ3 antibody for use in such combination comprises: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In another embodiment, the anti-TGFβ2 antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142.

In further embodiments of the above methods for treating TGFβ-related disorders, the TGFβ-related disorder can be fibrosis. In some embodiments, the fibrosis is a fibrotic condition of the lung, liver, heart, kidney, pancreas, eye, and/or skin. In some aspects, the fibrosis is a lung fibrosis selected from the group consisting of idiopathic pulmonary fibrosis (IPF), idiopathic pulmonary upper lobe fibrosis (Amitani disease), familial pulmonary fibrosis, pulmonary fibrosis (e.g., pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma), cystic fibrosis, non-specific interstitial pneumonia (NSIP), cryptogenic organizing pneumonia (COP), progressive massive fibrosis, scleroderma/systemic sclerosis (SSc, including limited cutaneous (lcSSc) and diffuse cutaneous (dcSSc) forms and SSc-associated interstitial lung disease (SSc-ILD)), bronchiolitis obliterans-organizing pneumonia, connective tissue disease-associated ILD (CT-ILD), hypersensitivity pneumonitis, pulmonary hypertension, pulmonary tuberculosis, silicosis, asbestosis, acute lung injury, and acute respiratory distress (ARD, including bacterial pneumonia induced, trauma-induced, and viral pneumonia-induced, ventilator-induced, non-pulmonary sepsis induced). In some aspects, the fibrosis is a fibrotic condition of the liver selected from the group consisting of liver cirrhosis, congenital hepatic fibrosis, obesity, fatty liver, alcohol induced liver fibrosis, non-alcoholic steatohepatitis (NASH), biliary duct injury, primary biliary cirrhosis (PBC), primary sclerosing cholangitis (PSC), infection- or viral-induced liver fibrosis (e.g., chronic hepatitis B and C virus infections), cystic fibrosis, autoimmune hepatitis, necrotizing hepatitis, primary sclerosing cholangitis, hemochromatosis, disorders of the biliary tree, and hepatic dysfunction attributable to infections. In some aspects, the fibrosis is a fibrotic condition of the heart and/or pericardium selected from the group consisting of endomyocardial fibrosis, cardiac allograft vasculopathy (CAV), myocardial infarction, atrial fibrosis, congestive heart failure, arterioclerosis, atherosclerosis, vascular stenosis, myocarditis, congestive cardiomyopathy, coronary infarcts, varicose veins, coronary artery stenosis and other post-ischemic conditions, and idiopathic retroperitoneal fibrosis. In some aspects, the fibrosis is a fibrotic condition of the kidney selected from the group consisting of glomerulonephritis (including membranoproliferative, diffuse proliferative, rapidly progressive or sclerosing, post-infectious and chronic forms), diabetic glomerulosclerosis, focal segmental glomerulosclerosis, IgA nephropathy, diabetic nephropathy, ischemic nephropathy, tubulointerstitial kidney fibrosis, HIV-associated nephropathy, membrane nephropathy, glomerulonephritis secondary to systemic inflammatory diseases such as lupus, scleroderma and diabetes glomerulonephritis, idiopathic membranoproliferative glomerular nephritis, mesangial proliferative glomerulonephritis, crescentic glomerulonephritis, amyloidosis (which affects the kidney among other tissues), autoimmune nephritis, renal tubuloinsterstitial fibrosis, renal arteriosclerosis, Alport's syndrome, nephrotic syndrome, chronic renal failure, chronic kidney disease, periglomerular fibrosis/atubular glomeruli, combined apical emphysema and basal fibrosis syndrome (emphysema/fibrosis syndrome), glomerular hypertension, nephrogenic fibrosing dermatopathy, polycystic kidney disease, Fabry's disease, and renal hypertension. In some aspects, the fibrosis is a fibrotic condition of the pancreas selected from the group consisting of stromal remodeling pancreatitis and stromal fibrosis. In some aspects, the fibrosis is a fibrotic condition of the gastrointestinal tract selected from the group consisting of Crohn's disease, ulcerative colitis, collagenous colitis, colorectal fibrosis, villous atrophy, crypt hyperplasia, polyp formation, healing gastric ulcer, and microscopic colitis. In some aspects, the fibrosis is a fibrotic condition of the eye selected from the group consisting of ocular fibrosis, ophthalmic fibrosis, proliferative vitreoretinopathy, vitreoretinopathy of any etiology, fibrosis associated with retinal dysfunction, fibrosis associated with wet or dry macular degeneration, scarring in the cornea and conjunctiva, fibrosis in the corneal endothelium, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), tractional retinal detachment in association with contraction of the tissue in diabetic retinopathy, congenital orbital fibrosis, lacrimal gland fibrosis, corneal subepithelial fibrosis, and Grave's ophthalmopathy. In some aspects, the fibrosis is selected from fibrosis resulting from spinal cord injury/fibrosis or central nervous system fibrosis such as fibrosis after a stroke, Duchenne muscular dystrophy, fibrosis associated with neurodegenerative disorder such as Alzheimer's disease or multiple sclerosis, vascular restenosis, uterine fibrosis, endometriosis, ovarian fibroids, Peyronie's disease, polycystic ovarian syndrome, disease related pulmonary apical fibrosis in ankylosing spondylitis, scarring, and fibrosis incident to microbial infections (e.g., bacterial, viral, parasitic, fungal). In a specific embodiment, the fibrosis is SSc. In a specific embodiment, the fibrosis is IPF. In a specific embodiment, the fibrosis is chronic obstructive pulmonary disease (COPD). In a specific embodiment, the fibrosis is progressive-fibrosing interstitial lung disease (PF-ILD). In a specific embodiment, the PF-ILD is a disease or condition selected from the group consisting of non-specific interstitial pneumonia (NSIP), cryptogenic organizing pneumonia (COP), progressive massive fibrosis, a complication of coal worker's pneumoconiosis, scleroderma/systemic sclerosis, bronchiolitis obliterans-organizing pneumonia; connective tissue disease-associated ILD (CT-ILD), and hypersensitivity pneumonitis. In a specific embodiment, the fibrosis is liver cirrhosis or chronic hepatic fibrosis. In a specific embodiment, the fibrosis is GI tract fibrosis, e.g., intestinal fibrosis, optionally, selected from the group consisting of fibrosis associated with Crohn's disease, ulcerative colitis, collagenous colitis, colorectal fibrosis, villous atrophy, crypt hyperplasia, polyp formation, healing gastric ulcer, and microscopic colitis. In a specific embodiment, the fibrosis is a fibrotic condition of the eye, fibrosis resulting from spinal cord injury, fibrosis or central nervous system fibrosis, or fibrosis associated with a neurodegenerative disorder.

In another aspect, a method of diagnosing a subject as having SSc is provided. In some embodiments, the method includes detecting the expression levels of the genes in an 18-gene signature set consisting of PRSS23, PXDN, COL8A1, COL6A3, SERPINE2, TNC, COMP, THBS1, COL11A1, COL1A1, COL5A2, COL1A2, COL4A1, COL4A2, SFRP4, ALPK2, COL5A1, and TAGLN, and diagnosing the subject with SSc if the levels of the genes are determined to be elevated relative to the gene levels in a healthy control set or reference gene signature. In some aspects, a gene level is elevated if the expression increase relative to the healthy control set or reference gene signature is statistically significant, optionally, at least two-fold increased, or at least three-fold increased, or at least four-fold increased, relative to the healthy control set or reference gene signature. In some aspects, the gene expression level is detected using qPCR or microarray or RNAseq.

In another aspect, a method of monitoring response to treatment of a subject with an anti-TGFβ2 antibody and/or an anti-TGFβ3 antibody is provided. In some aspects, the method includes determining the expression level of one or more of the TGFβ-inducible genes selected from the group consisting of serpine1, col1a1, col1a2, and col3a1 in a sample from the subject, wherein the subject has received one or more administrations of the anti-TGFβ2 antibody and/or the anti-TGFβ3 antibody. In some aspects, the subject is determined to be responding to treatment with the anti-TGFβ2 antibody and/or anti-TGFβ3 antibody, if the expression level of the one or more TGFβ-inducible genes is significantly reduced compared to pre-treatment levels of the one or more TGFβ-inducible genes, wherein optionally the method further comprises administering one or more additional administrations of the anti-TGFβ2 antibody and/or the anti-TGFβ3 antibody if the expression level of the one or more TGFβ-inducible genes is determined to be significantly reduced. In some aspects, the subject is administered the anti-TGFβ2 antibody as a monotherapy. In some aspects, the subject is administered the anti-TGFβ3 antibody as a monotherapy. In some aspects, the expression level of the one or more TGFβ-inducible genes is determined by qPCR or microarray analysis. In one embodiment of the method, the antibody is an anti-TGFβ3 antibody comprising: (a1) (i)

heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In another embodiment of the method, the antibody is an anti-TGFβ2 antibody comprising: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142.

In any of the above aspects and embodiments for uses, medicaments, and methods of treatment and diagnosis and monitoring response to treatment, the subject can be a human, e.g., a human patient.

In another aspect, a kit comprising an antibody of any of the above aspects and embodiments is provided. In one embodiment of the kit, the antibody is an anti-TGFβ3 antibody comprising: (a1) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 5, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a2) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 34, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (a3) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (a4) (i) heavy chain CDRs comprising CDR-H1, -H2 and -H3, wherein CDR-H1 has the amino acid sequence of SEQ ID NO: 4, CDR-H2 has the amino acid sequence of SEQ ID NO: 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; or (b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78. In another embodiment of the kit, the antibody is an anti-TGFβ2 antibody comprising: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In one aspect, the anti-TGFβ2 antibody selectively neutralizes TGFβ2. In some aspects, the anti-TGFβ2 antibody: (a) has reduced toxicity relative to the pan-TGFβ antibody 1D11; (b) has reduced toxicity in rodents relative to the pan-TGFβ antibody 1D11; (c) has reduced toxicity relative to the pan-TGFβ small molecule inhibitor galunisertib; and/or (d) has reduced toxicity in rodents relative to the pan-TGFβ small molecule inhibitor galunisertib. In one aspect, the anti-TGFβ2 antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142. In one aspect, the anti-TGFβ2 antibody comprises a VH amino acid sequence selected from the group consisting of SEQ ID NOs: 25, 132, and 138-142. In another embodiment of the kit, the antibody is an anti-TGFβ2/3 antibody comprising (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15.

BRIEF DESCRIPTION OF THE FIGURES

FIG. 7 contains plots showing distribution of change in MRSS from baseline to 48 weeks of patients in the FaSScinate study stratified by baseline TGFβ skin gene signature cluster. PBO: placebo; TCZ: tocilizumab treatment; Cum Prob: cumulative probability of MRSS change.

FIG. 11 is a table showing loss of expression and stability for most of the h2A10v1 variants during framework and CDR polishing.

FIG. 12 contains amino acid sequence alignments of the light chain (upper panel) and heavy chain (lower panel) variable region sequences of the rat 2A10 antibody and its humanized variants v1-v4; the amino acid sequences shown in the figure are SEQ ID NOs: 22, 36, 36, 54, and 56 (upper panel, from top sequence to bottom sequence in the alignment) and SEQ ID NOs: 23, 37, 45, 55, and 57 (lower panel, from top sequence to bottom sequence in the alignment). Residue numbering is according to Kabat; "*" indicates Vernier zone. CDR regions according to Chothia or Kabat (as indicated) are boxed; mutated residues are highlighted.

FIG. 15 contains amino acid sequence alignments of the light chain (upper panel) and heavy chain (lower panel) variable region sequences of the rat 2A10 antibody and humanized v2 variants; the amino acid sequences shown in the figure are SEQ ID NOs: 22, 36, 36, 36, and 36 (upper panel, from top sequence to bottom sequence in the alignment) and SEQ ID NOs: 23, 45, and 51-53 (lower panel, from top sequence to bottom sequence in the alignment). Residue numbering is according to Kabat; "*" indicates Vernier zone. CDR regions according to Chothia or Kabat (as indicated) are boxed; mutated residues are highlighted.

FIG. 16 contains amino acid sequence alignments of the light chain (upper panel) and heavy chain (lower panel) variable region sequences of the rat 2A10 antibody its humanized v4 variant; the amino acid sequences shown in the figure are SEQ ID NOs: 22 and 56 (upper panel, from top sequence to bottom sequence in the alignment) and SEQ ID NOs: 23 and 57 (lower panel, from top sequence to bottom sequence in the alignment). Residue numbering is according to Kabat; "*" indicates Vernier zone. CDR regions according to Chothia or Kabat (as indicated) are boxed; mutated residues are highlighted.

FIG. 19 contains an amino acid sequence alignment of the heavy chain variable region of the rabbit 4A11 and humanized variants, v1-v8; the sequences shown correspond to SEQ ID NOs: 27, 81, 81, 83, 83, 81, 81, 83, and 83 (from top sequence to bottom sequence in the alignment). Residue numbering is according to Kabat; "*" indicates Vernier zone. CDR regions according to Chothia or Kabat (as indicated) are boxed; mutated residues are highlighted.

FIG. 20 contains an amino acid sequence alignment of the light chain variable regions of the humanized 4A11 variants v7-v7.19; the sequences shown correspond to SEQ ID NOs: 84, 84, 84, 84, 89-92, 101, 101, 101, and 101 (from top sequence to bottom sequence in the alignment). Residue numbering is according to Kabat; "*" indicates Vernier zone. CDR regions according to Chothia or Kabat (as indicated) are boxed; mutated residues are highlighted.

FIG. 21 contains an amino acid sequence alignment of the heavy chain variable region of the humanized 4A11 variants v7-v7.19; the sequences shown correspond to SEQ ID NOs: 83, 86, 87, 88, 83, 83, 83, 83, 93-100, and 102-105 (from top sequence to bottom sequence in the alignment). Residue numbering is according to Kabat; "*" indicates Vernier zone. CDR regions according to Chothia or Kabat (as indicated) are boxed; mutated residues are highlighted.

FIG. 23 contains an amino acid sequence alignment of the light chain variable regions of the humanized 6F12 v1 variants v1-v1.9; the sequences shown correspond to SEQ ID NOs: 131, 133-137, 131, 131, 131, and 131 (from top sequence to bottom sequence in the alignment). Residue numbering is according to Kabat; "*" indicates Vernier zone. CDR regions according to Chothia or Kabat (as indicated) are boxed; mutated residues are highlighted.

FIG. 24 contains an amino acid sequence alignment of the heavy chain variable regions of the humanized 6F12 v1 variants v1-v1.9; the sequences shown correspond to SEQ ID NOs: 132, 132, 132, 132, 132, 132, and 138-141 (from top sequence to bottom sequence in the alignment). Residue numbering is according to Kabat; "*" indicates Vernier zone. CDR regions according to Chothia or Kabat (as indicated) are boxed; mutated residues are highlighted.

In FIG. 43A, supernatants (SN) were collected from 293T cells transfected with a plasmid encoding FL-TGFβ1, FL-TGFβ2, FL-TGFβ3 or an empty vector (control). In FIG. 43B, SN were collected from COS-7 cells transfected with a plasmid encoding FL-TGFβ1, FL-TGFβ3 or an empty vector (control). , $P<0.01$; *, $P<0.001$; ****, $P<10^{-4}$; NS, $P>0.05$ by unpaired two-tailed Student's t-test. Data are averages±SEM from experiments run in triplicate. Error bars are not shown when they are shorter than sizes of their corresponding symbols.

FIG. 51 is a table showing the IC50s based on the titration curves shown in FIG. 50.

FIG. 52A and FIG. 52B are graphs showing percentages (%) of new hydroxyproline (mean±SEM) measured as an indicator of newly synthesized collagen in WT or TGFβ isoform CKO mice. In FIG. 52A, n=5 (each saline group), n=20 (WT, bleomycin treated ("BLM")), n=24 mice (β2.cKO, BLM); in FIG. 52B, n=7 (WT, saline), n=14 (WT, BLM), n=13 (β3.cKO, BLM) and n=13 (β2/3.cDKO, BLM); *P<0.05, ***P<0.001 by One-way ANOVA with Dunnett's test.

In FIG. 53A, n=5 (Saline), n=15 (control, bleomcyin ("BLM")) and n=14 (6F12, BLM); In FIG. 53B, n=5 (Saline), n=19 (control, BLM) and n=20 mice (2A10, BLM). *P<0.05, P<0.01, * P<0.001, **** P<0.0001, NS, P>0.05 by One-way ANOVA with Dunnett's test.

DETAILED DESCRIPTION OF EMBODIMENTS OF THE INVENTION

I. Definitions

Figure 1:
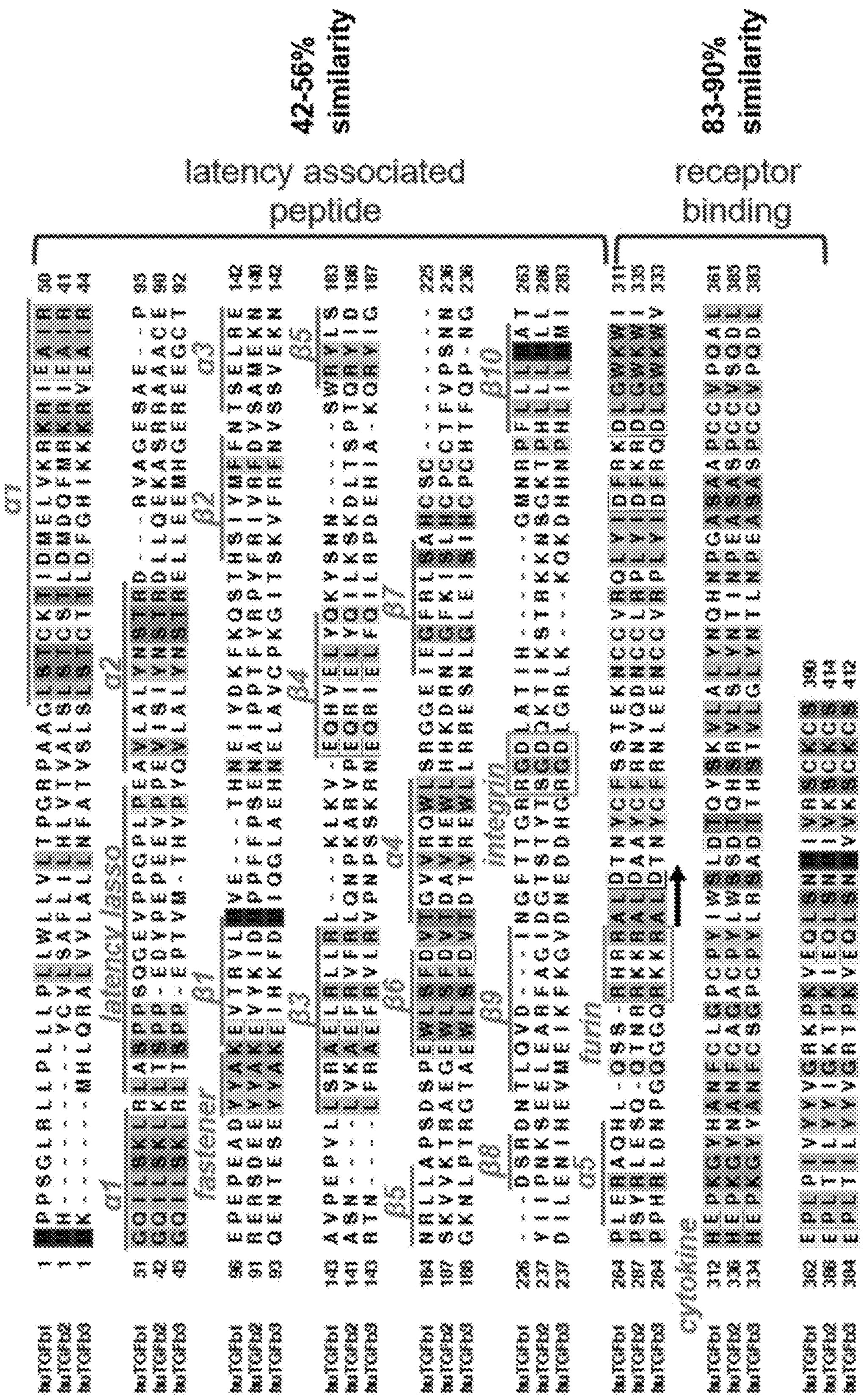
FIG. 1 shows the primary amino acid sequence alignment of human TGFβ1, 2, and 3 having accession numbers as follows: huTGFβ1: XP_011525544.1, huTGFβ2: NP_003229.1, huTGFβ3: ABQ59024.1, with domains of TGFβ1 (α-sheets and β-strands, latency lasso, fastener, integrin-binding, furin cleavage, and cytokine) indicated as per Shi et al., Nature 474:343 (2011). Residues are numbered from the predicted ATG (methionine) start site; Shi et al. numbering starts from L30 at the start of the α1 helix. The black arrow underneath the sequences indicates the start of the receptor-binding domain. Frameshift, premature stop, and splice site mutations reported for TGFβ2 and TGFβ3 are omitted for clarity. The sequences shown in the figure correspond to SEQ ID NOs: 1-3, respectively.

As used herein, the terms "tumor necrosis factor β" and "TGFβ" are used interchangeably and refer to any native TGFβ isoform from any vertebrate source, including mammals such as primates (e.g. humans) and rodents (e.g., mice and rats), unless otherwise indicated. The term encompasses "full-length," unprocessed TGFβ as well as any form of TGFβ that results from processing in the cell. The term also encompasses naturally occurring variants of TGFβ, e.g., splice variants or allelic variants. TGFβ isoforms have precursor forms (immature) and mature forms. The latency-associated peptide, as shown in FIG. 1, is cleaved by furin proteases intracellularly and forms a non-covalent interaction with the receptor-binding domain. This complex is secreted from the cell, alone or covalently bound via the latency-associated peptide to 'milieu' molecules such as GARP, LRRC33, or latent TGFβ-binding proteins (LTBP) 1-4. The complex of LAP and the receptor-binding domain is termed the small latent complex (SLC) and the complex of the LAP, the receptor-binding domain, and a milieu molecule is termed the large latent complex (LLC).

Amino acid sequences for TGFβ1, TGFβ2, and TGFβ3 are as follows:

Human TGFβ1

(SEQ ID NO: 1)

MPPSGLRLLPLLLPLLWLLVLTPGRPAAGLSTCKTIDMELVKRKRIEAI

RGQILSKLRLASPPSQGEVPPGPLPEAVLALYNSTRDRVAGESAEPEPE

PEADYYAKEVTRVLMVETHNEIYDKFKQSTHSIYMFFNTSELREAVPEP

VLLSRAELRLLRLKLKVEQHVELYQKYSNNSWRYLSNRLLAPSDSPEWL

SFDVTGVVRQWLSRGGEIEGFRLSAHCSCDSRDNTLQVDINGFTTGRRG

DLATIHGMNRPFLLLMATPLERAQHLQSSRHRRALDTNYCFSSTEKNCC

VRQLYIDFRKDLGWKWIHEPKGYHANFCLGPCPYIWSLDTQYSKVLALY

NQHNPGASAAPCCVPQALEPLPIVYYVGRKPKVEQLSNMIVRSCKCS.

Human TGFβ2

(SEQ ID NO: 2)

MHYCVLSAFLILHLVTVALSLSTCSTLDMDQFMRKRIEAIRGQILSKLK

LTSPPEDYPEPEEVPPEVISIYNSTRDLLQEKASRRAAACERERSDEEY

YAKEVYKIDMPPFFPSENAIPPTFYRPYFRIVRFDVSAMEKNASNLVKA

EFRVFRLQNPKARVPEQRIELYQILKSKDLTSPTQRYIDSKVVKTRAEG

EWLSFDVTDAVHEWLHHKDRNLGFKISLHCPCCTFVPSNNYIIPNKSEE

LEARFAGIDGTSTYTSGDQKTIKSTRKKNSGKTPHLLLMLLPSYRLESQ

QTNRRKKRALDAAYCFRNVQDNCCLRPLYIDFKRDLGWKWIHEPKGYNA

NFCAGACPYLWSSDTQHSRVLSLYNTINPEASASPCCVSQDLEPLTILY

YIGKTPKIEQLSNMIVKSCKCS.

Human TGFβ3

(SEQ ID NO: 3)

MKMHLQRALVVLALLNFATVSLSLSTCTTLDFGHIKKKRVEAIRGQILS

KLRLTSPPEPTVMTHVPYQVLALYNSTRELLEEMHGEREEGCTQENTES

EYYAKEIHKFDMIQGLAEHNELAVCPKGITSKVFRFNVSSVEKNRTNLF

RAEFRVLRVPNPSSKRNEQRIELFQILRPDEHIAKQRYIGGKNLPTRGT

AEWLSFDVTDTVREWLLRRESNLGLEISIHCPCHTFQPNGDILENIHEV

MEIKFKGVDNEDDHGRGDLGRLKKQKDHHNPHLILMMIPPHRLDNPGQG

GQRKKRALDTNYCFRNLEENCCVRPLYIDFRQDLGWKWVHEPKGYYANF

CSGPCPYLRSADTTHSTVLGLYNTLNPEASASPCCVPQDLEPLTILYYV

GRTPKVEQLSNMVVKSCKCS.

The term "TGFβ1" as used herein, refers to any native TGFβ1 from any vertebrate source, including mammals such as primates (e.g., humans) and rodents (e.g., mice and rats), unless otherwise indicated. The term encompasses "full-length," unprocessed TGFβ1 as well as any form of TGFβ1 that results from processing in the cell. The term also encompasses naturally occurring variants of TGFβ1, e.g., splice variants or allelic variants. The amino acid sequence of an exemplary human TGFβ1 is shown in FIG. 1 (SEQ ID NO: 1).

The term "TGFβ2" as used herein, refers to any native TGFβ2 from any vertebrate source, including mammals such as primates (e.g., humans) and rodents (e.g., mice and rats), unless otherwise indicated. The term encompasses "full-length," unprocessed TGFβ2 as well as any form of TGFβ2 that results from processing in the cell. The term also encompasses naturally occurring variants of TGFβ2, e.g., splice variants or allelic variants. The amino acid sequence of an exemplary human TGFβ2 is shown in in FIG. 1 (SEQ ID NO: 2).

The term "TGFβ3" as used herein, refers to any native TGFβ3 from any vertebrate source, including mammals such as primates (e.g., humans) and rodents (e.g., mice and rats), unless otherwise indicated. The term encompasses "full-length," unprocessed TGFβ3 as well as any form of TGFβ3 that results from processing in the cell. The term also encompasses naturally occurring variants of TGFβ3, e.g., splice variants or allelic variants. The amino acid sequence of an exemplary human TGFβ3 is shown in in FIG. 1 (SEQ ID NO: 3).

As used herein, the term "TGFβ" means any one, two or all three of the TGFβ isoforms TGFβ1, TGFβ2 and TGFβ3, as described above.

As used herein, the terms "specifically binds" and "binds specifically to" refer to an antibody selectively or preferentially binding to its target antigen. Preferably the binding affinity for antigen is of $K_D$ value of $10^{-9}$ mol/l or lower (e.g. $10^{-10}$ mol/l), preferably with a $K_D$ value of $10^{-10}$ mol/l or lower (e.g., $10^{-12}$ mol/l). The binding affinity is determined with a standard binding assay, such as surface plasmon resonance technique (BIACORE®).

As used herein, the term "anti-TGFβ antibody" means an antibody that specifically binds to one or more TGFβ isoform(s). Thus, as used herein, the term "anti-TGFβ3 antibody" refers to a monospecific antibody that specifically binds to TGFβ3; the term "anti-TGFβ2 antibody" refers to a monospecific antibody that specifically binds to TGFβ2 (e.g., human TGFβ2); the term "anti-TGFβ2/3 antibody" refers to a dual-specific antibody that specifically binds to TGFβ2 (e.g., human TGFβ2) and TGFβ3 (e.g., human TGFβ3); the term "anti-TGFβ1 antibody" refers to a monospecific antibody that specifically binds to TGFβ1 (e.g., human TGFβ1); and the term "pan-specific TGFβ antibody" refers to an antibody that binds to all three TGFβ isoforms (TGFβ1, TGFβ2, and TGFβ3, e.g., human TGFβ1, TGFβ2 and TGFβ3)). An anti-TGFβ antibody described herein that is mono- or dual-specific for certain TGFβ isoform(s) is also referred to herein as an "isoform-selective anti-TGFβ antibody." In one embodiment, the extent of binding of an isoform-selective anti-TGFβ antibody (e.g., an anti-TGFβ1 antibody, an anti-TGFβ2 antibody, an anti-TGFβ2/3 antibody, or an anti-TGFβ3 antibody) to the TGFβ isoform(s) for which the antibody is not specific is less than about 10% of the binding of the antibody to its target TGFβ isoform(s), as measured, e.g., by a radioimmunoassay (RIA) or surface plasmon resonance (SPR). In another embodiment, the extent of binding of an isoform-selective anti-TGFβ antibody to the TGFβ isoform(s) for which the antibody is not specific is less than about 9%, 8%, 7%, 6%, 5%, 4%, 3%, 2%, or preferably less than about 1% of the binding of the antibody to its target TGFβ isoform(s), as measured, e.g., by RIA or SPR. In one embodiment, an isoform-selective anti-TGFβ antibody refers to an antibody that is capable of binding the TGFβ isoform(s) for which the antibody is specific with sufficient affinity such that the antibody is useful as a diagnostic and/or therapeutic agent in targeting the TGFβ isoform(s). In one embodiment, the extent of binding of an isoform-selective anti-TGFβ antibody to an unrelated protein is less than about 10%, or less than about 9%, 8%, 7%, 6%, 5%, 4%, 3%, 2%, or preferably less than about 1% of the binding of the isoform-selective anti-TGFβ antibody as measured, e.g., by a radioimmunoassay (RIA). In certain embodiments, an anti-TGFβ antibody has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$ M to $10^{-13}$ M, e.g., from $10^{-9}$ M to $10^{-13}$ M) to its target TGFβ isoform(s). In a preferred embodiment, an isoform-selective anti-TGFβ antibody has a $K_D$ of ≤250 μM.

As used herein, the term "selectively neutralize" and its grammatical variations, with respect to an isoform-selective anti-TGFβ antibody described herein, means that the antibody specifically binds to and neutralizes the isoform(s) for which the antibody is selective but does not neutralize the other isoform(s). Thus, for example, an anti-TGFβ1 antibody that selectively neutralizes TGFβ1 does not neutralize TGFβ2 or TGFβ3; an anti-TGFβ2 antibody that selectively neutralizes TGFβ2 does not neutralize TGFβ1 or TGFβ3; an anti-TGFβ3 antibody that selectively neutralizes TGFβ3 does not neutralize TGFβ1 or TGFβ2; an anti-TGFβ2/3 antibody that selectively neutralizes TGFβ2 and TGFβ3 does not neutralize TGFβ1. In certain embodiments, an isoform-selective anti-TGFβ antibody as described herein specifically binds to an epitope of a TGFβ isoform that is conserved across different species. In some embodiments, the ability of an antibody (e.g., an isoform-selective anti-TGFβ antibody described herein) to selectively neutralize one or more TGFβ isoforms may be determined in an in vitro inhibition assay, e.g., the cell-based inhibition TGFβ assay described herein below.

As used herein, a "TGFBR" means a TGFβ receptor. Dimeric receptor-binding domains of all three TGFβ isoforms bind to pairs of heterodimeric receptor complexes of TGFBR1 and TGFBR2; the tetrameric receptor complex then activates intracellular signaling via receptor tyrosine kinase (RTK) activity of TGFBR1, also known as ALK5 (Weiss et al., *Wiley Interdiscip. Rev. Dev. Biol.* 2:47-63 (2013)). In canonical TGFBR signaling, ALK5 phosphorylates SMAD2 and SMAD3, which then associate with SMAD4, translocate to the nucleus, and direct gene transcription. The Smad complex activates transcription of myofibroblast genes including αSMA, calponin and collagen (Usuki et al., *J. Nippon Med. Sch.* 79:46-59 (2012); Carthy et al., *PloS one* 6:e19809 (2011); and Gu et al., *Acta Pharmacol. Sin.* 28:382-391 (2007)). There are additional non-SMAD dependent signaling pathways that may be activated by TGFβ under certain contexts including MAP kinases, AKT, JAK-STAT, and NFκB. Biochemical and structural studies have shown that the assembly of TGFβ-TGFβR signaling complexes may have subtle isoform-specific differences: TGFβ1 and TGFβ3 bind more strongly to TGFβR2 and only form strong interactions with TGFβR1 when in complex with TGFβR2, whereas TGFβ2 binds weakly to both TGFBR1 and TGFBR2 alone, and avidity may drive full complex formation (Radaev JBC 2009; 285, 14806-14814). TGFβ1 and TGFβ2 crystallize in "closed" structures that facilitate binding to TGFBR1 and TGFBR2, while TGFβ3 can adopt a similar "closed" or less ordered "open" structure in crystal form, which may lead to differences in the avidity of ligand-receptor complex assembly (Hinck, A. P. et al. 2016; Cold Spring Harb Perspect Biol doi: 10.1101/cshperspect.a02210). In addition, TGFBR3 (betaglycan), a non-signaling receptor, can facilitate TGFβ2 binding to TGFβR1/2 complexes, but does not appear to play a similar role in TGFβ1 or TGFβ3 receptor binding (del Re, JBC 2004; 279, 22765-22772). While in most cells (including endothelial cells) TGFβ signals through TGFBR1/2 complexes, in endothelial cells TGFβ1 and TGFβ3 can also signal through a TGFBR2/ALK1 complex facilitated by endoglin, which contributes to SMAD1/5 dependent vascular endothelial proliferation and angiogenesis (EMBO J. 2004 Oct. 13; 23(20):4018-28). Ultimately, despite these differences in signaling complex assembly, recombinant receptor-binding domains of TGFβ1, 2, and 3 are all able to induce TGFBR-dependent SMAD signaling to a similar degree in cell-based in vitro assays. Hence, any biological differences in the activity of endogenous TGFβ isoforms are more likely due to differences in their patterns of expression and mechanisms of release from SLC or LLC than to differences in their receptor-binding domains.

As used herein, the term "neutralize" and its grammatical variations, with respect to an isoform-selective anti-TGFβ antibody described herein, means that the antibody inhibits to a measurable extent its target TGFβ isoform(s) from inducing signaling through a TGFBR complex.

As used herein, the term "directly contacts" and its grammatical variations, with respect to an antigen-binding domain of an anti-TGFβ antibody, means that the antigen-binding domain is within 15-8, 8, 8-5, or preferably within 5 angstroms of the residue of an amino acid in its corresponding epitope.

"TGFβ disorders" or "TGFβ-related disorders" refers to any disorder, disease, or condition that would benefit from treatment with an isoform-selective anti-TGFβ antibody provided herein. This includes chronic and acute disorders or diseases including those pathological conditions that predispose the mammal to the disorder in question. Disorders to be treated herein include diseases characterized by accumulation of extracellular matrix, diseases caused by circulating TGFβ or TGFβ activated at a local site, including one or more TGFβ isoforms, conditions caused by suppression of the immune system due to endogenous TGFβ production, acute immune deficiencies resulting from severe injuries, burns, and illnesses such as viral or bacterial infections, multi-organ systemic illnesses due to TGFβ production or overproduction, and TGFβ-producing tumors.

As used herein, the terms "fibrosis," "fibrosis conditions," and "fibrotic conditions" are intended to have the same meaning. In certain embodiments, the fibrotic conditions are those mediated by a fibrotic stimulator. Exemplary fibrotic stimulators include, without limitation, TGFβ, endothelin, lactic acid (via lactate dehydrogenase), IL-1, Thy-1 (CD90), connective tissue growth factor ("CTGF"), as well as combinations thereof. In certain embodiments, the fibrotic condition is one that is mediated by TGFβ. In certain embodiments, the fibrotic condition is one that is mediated by one or more of TGFβ1, TGFβ2, and TGFβ3. In certain embodiments, the fibrotic condition is one that is mediated by one or both of TGFβ2 and TGFβ3. In certain embodiments, the fibrotic condition is one that is mediated by TGFβ2. In certain embodiments, the fibrotic condition is one that is mediated by TGFβ3. Exemplary fibrotic conditions are described in more detail herein, below.

"Systemic sclerosis" (SSc) or "scleroderma" is a complex and heterogeneous disease with skin and tissue fibrosis, vascular alterations, and autoantibodies against various cellular antigens being amongst its principal features. The clinical manifestations of systemic sclerosis can range from limited skin involvement to severe internal organ dysfunction. Internal visceral organ pathology is a major factor contributing to the morbidity of this disease, with the kidneys, esophagus, heart, and lungs being the most frequently involved. There are two major subgroups in the commonly accepted classification of SSc: limited cutaneous SSc (lcSSc) and diffuse cutaneous SSc (dcSSc). Gabrielli et al. Mechanisms of disease. Scleroderma. *N Engl J Med*

360:1989-2003 (2009). In one embodiment, the patient with systemic sclerosis has been classified according to the American College of Rheumatology (formerly, the American Rheumatism Association) criteria for the classification of systemic scleroderma based on: major criterion: diffuse (truncal) sclerosis (skin tightness, thickening, and non-pitting induration); and minor criteria: (1) sclerodactyly (only fingers and/or toes), (2) digital pitting scars or loss of substance of the digital finger pads (pulp loss), and (3) bilateral basilar pulmonary fibrosis, wherein a patient with systemic sclerosis should fulfill the major criterion or two of the three minor criteria. See Subcommittee for Scleroderma Criteria of the American Rheumatism Association, Diagnostic and Therapeutic Criteria Committee. Preliminary criteria for the classification of systemic sclerosis (scleroderma). *Arthritis Rheum* 23:581-90 (1980).

As used herein, Chronic Obstructive Pulmonary Disease ("COPD") is an umbrella term used to describe a group of respiratory tract diseases generally characterized by airflow obstruction or limitation. This condition may also be known under the terms chronic obstructive respiratory disease (CORD), chronic obstructive airways disease (COAD), chronic obstructive lung disease (COLD), or chronic airway limitation (CAL). As used herein, the term COPD is intended to encompass all such references. The clinical course of COPD is characterized by chronic disability, with intermittent, acute exacerbations that occur more often during the winter months. An acute exacerbation of COPD can be defined as a sustained worsening of the patient's symptoms from his or her usual stable state that is beyond normal day-to-day variations, and is acute in onset. When acute exacerbations occur, they typically manifest as increased sputum production, more purulent sputum, change in sputum color, increased coughing, upper airway symptoms (e.g., colds and sore throats), increased wheezing, chest tightness, reduced exercise tolerance, increased fatigue, fluid retention, acute confusion, and worsening of dyspnea. Although infectious etiologies account for most exacerbations, exposure to allergens, pollutants, or inhaled irritants may also play a role. Infectious agents known to cause acute exacerbations of COPD include: rhinoviruses, influenza, parainfluenza, coronavirus, adenovirus, respiratory syncytial virus, *Chlamydia pneumoniae, Haemophilus influenzae, Streptococcus pneumoniae, Moraxella catarrhalis, Staphylococcus aureus, Mycloplasma pneumoniae*, and *Pseudomonas aeruginosa*. Pollutants known to cause acute exacerbations include nitrogen dioxide, particulates, sulfur dioxide, and ozone. Despite these known causes, the exact cause of exacerbations may be unidentifiable in up to 30% of diagnosed cases of exacerbation of COPD. The Global Initiative for Chronic Obstructive Lung Disease (GOLD) defines COPD as a disease state characterized by airflow limitation that is not fully reversible. The airflow limitation is usually progressive and associated with abnormal inflammatory response of the lungs to noxious particles or gases. The American Thoracic Society (ATS) defines COPD as a disease process involving progressive chronic airflow obstruction because of chronic bronchitis, emphysema, or both. Chronic bronchitis is defined clinically as excessive cough and sputum production on most days for at least three months during at least two consecutive years. Emphysema is characterized by chronic dyspnea (shortness of breath) resulting from the destruction of lung tissue and the enlargement of air spaces. A further condition typically encompassed by the term COPD is bronchiectasis, which is an abnormal stretching and enlarging of the respiratory passages caused by mucus accumulation and blockage. Under such conditions, the weakened passages can become scarred and deformed, allowing more mucus and bacteria to accumulate, resulting in a cycle of infection and blocked airways.

As used herein, the term "ILD" refers to interstitial lung disease. Interstitial lung diseases include a large and diverse group of more than 200 lung diseases and respiratory conditions characterized by inflammation and fibrosis of the interstitium, the tissue and space between the air sacs of the lung (see, for instance, du Bois, Nat. Rev. Drug Discov. 2010, 9, 129-140). In "Progressive Fibrosing Interstitial Lung Diseases (PF-ILD)" the response to lung injury in fibrosing ILDs includes the development of fibrosis which becomes progressive, self-sustaining and independent of the original clinical association or trigger.

As used herein, the terms "idiopathic pulmonary fibrosis" and "IPF" refer to a restrictive lung disease characterized by progressive interstitial fibrosis of lung parenchyma, affecting approximately 100,000 patients in the United States (Raghu et al., Am J Respir Crit Care Med 174:810-816 (2006)). This interstitial fibrosis associated with IPF leads to progressive loss of lung function, resulting in death due to respiratory failure in most patients. The median survival from the time of diagnosis is 2-3 years (Raghu et al., Am J Respir Crit Care Med 183:788-824 (2011)). The etiology and key molecular and pathophysiological drivers of IPF are unknown. In some embodiments, a diagnosis of IPF is confirmed by the finding of usual interstitial pneumonia (UIP) on histopathological evaluation of lung tissue obtained by surgical biopsy. The criteria for a diagnosis of IPF are known. Ryu et al. (1998) Mayo Clin. Proc. 73:1085-1101.

As used herein, "GI tract fibrosis" refers to fibrosis of the gastrointestinal tract, including, e.g., the mouth, esophagus, stomach, small intestine, large intestine, and anus. "GI tract fibrosis" thus includes intestinal fibrosis. "Intestinal fibrosis" is a common complication of inflammatory bowel disease (IBD), and is usually defined as an excessive accumulation of scar tissue in the intestinal wall. Intestinal fibrosis can occur in both forms of IBD: ulcerative colitis and Crohn's disease. "GI tract fibrosis" includes, but is not limited to, fibrosis associated with Crohn's disease, ulcerative colitis, collagenous colitis, colorectal fibrosis, villous atrophy, crypt hyperplasia, polyp formation, healing gastric ulcer, and microscopic colitis.

As used herein "monitoring disease progression" refers to assessing a subject (e.g., a subject suffering from a TGFβ-related disorder, e.g. a subject undergoing treatment with an anti-TGFβ antibody as described elsewhere herein) at successive time intervals to determine whether disease symptoms have worsened, stabilized, or improved (i.e., become less severe). For example, monitoring the progression of fibrosis (e.g., SSc or IPF, or other fibrosis) in a subject can, in certain instances, include monitoring changes in the 18-gene TGFβ signature set described in Table 2, below, overall response rate, duration of response, quality of life, expression and/or activity of disease markers (e.g., expression of certain other genes and/or proteins), or other criteria known in the art. Additional approaches to monitoring disease progression in a patient with a TGFβ-related disorder can be employed, including for example, measurement of response to treatment via imaging techniques, which are described in further detail elsewhere herein.

As used herein, the terms "monitoring treatment progress" or "monitoring response to treatment" are used interchangeably and refer to assessing a subject (e.g., a subject suffering from a TGFβ-related disorder, e.g., a subject undergoing treatment with an anti-TGFβ antibody as described elsewhere herein) at successive time intervals during or following treatment to determine whether disease symptoms have worsened, stabilized, or improved (i.e., become less severe) as a result of the treatment. For example, treatment progress in a subject (e.g., a subject who has or is receiving treatment with an immunotherapeutic agent, such as but not limited to an anti-TGFβ antibody described herein) can be monitored using the same criteria as those used to monitor disease progression.

As used herein, the term "detection" includes any means of detecting, including direct and indirect detection.

As used herein, the term "diagnosis" is used herein to refer to the identification or classification of a molecular or pathological state, disease or condition. For example, "diagnosis" may refer to identification of a particular type of fibrosis (e.g., SSc, IPF, etc.) or other TGFβ-mediated disorder. "Diagnosis" may also refer to the classification of a particular subtype of a fibrotic condition, e.g., by histopathological or radiographic criteria or by molecular features (e.g., a subtype characterized by expression of one or a combination of particular genes or proteins encoded by said genes).

The term "prognosis" is used herein to refer to the prediction of the likelihood of survival over time as well as one or more TGFβ-attributable disease symptoms worsening over time.

As used herein, a "control subject" refers to a healthy subject who has not been diagnosed as having the disease or condition of interest, e.g., fibrosis, e.g., IPF, SSc, etc., and who does not suffer from any sign or symptom associated with the disease or condition.

The term "sample," as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue" or "cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. A "reference sample", "reference cell", "reference tissue", "control sample", "control cell", or "control tissue", as used herein, refers to a sample, cell or tissue obtained from a source known, or believed, not to be afflicted with the disease or condition for which a method or composition of the invention is being used to identify. In one embodiment, a reference sample, reference cell, reference tissue, control sample, control cell, or control tissue is obtained from a healthy part of the body of the same subject or patient in whom a disease or condition is being identified using a composition or method of the invention. In one embodiment, a reference sample, reference cell, reference tissue, control sample, control cell, or control tissue is obtained from a healthy part of the body of an individual who is not the subject or patient in whom a disease or condition is being identified using a composition or method of the invention.

As used herein, the term "gene signature" is used interchangeably with "gene expression signature" and refers to one or a combination of genes whose expression is indicative of a subject or tissue or other sample isolated from a subject having high TGFβ activity and/or indicative of a subject being likely to benefit from treatment with an inhibitor of a TGFβ isoform characterized by certain molecular, pathological, histological, radiographic and/or clinical features. In certain embodiments, the expression of one or more genes comprising the gene signature is elevated compared to that in control subjects.

As used herein, the term "elevated expression level" or "elevated levels" refers to an increased expression of a mRNA or a protein in a subject (e.g., a subject, e.g., a patient, suspected of having or diagnosed as having a TGFβ-related disorder, e.g., fibrosis, e.g., IPF, COPD, PF-ILD (e.g., SSc), hepatic fibrosis (e.g., liver cirrhosis or chronic hepatic fibrosis)) relative to a control, such as an individual or individuals who are not suffering from the TGFβ-related disorder.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof, and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "therapeutically effective amount" refers to an amount of, e.g., an immunotherapeutic agent (such as an immunotherapeutic agent described elsewhere herein) effective to "treat" a disease or disorder in a subject (e.g., a mammal, such as a human).

As used herein, "tocilizumab" is a recombinant humanized monoclonal antibody that binds to human interleukin-6 receptor (IL-6R). It is an IgG1κ (gamma 1, kappa) antibody with a two heavy chains and two light chains forming two antigen-binding sites. In a preferred embodiment, the light chain and heavy chain amino acid sequences of tocilizumab comprise SEQ ID NOs. 187 and 188, respectively.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs (e.g., CDRs): three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified in FIGS. 12-16 and 18-24 or elsewhere in the specification.

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an isoform-selective anti-TGFβ antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (x) and lambda (k), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Where used herein, "and/or" is to be taken as specific disclosure of each of the two specified features or components with or without the other. For example "A and/or B" is to be taken as specific disclosure of each of (i) A, (ii) B and (iii) A and B, just as if each is set out individually herein.

II. Compositions and Methods

In one aspect, the invention is based, in part, on the provision of isoform-selective anti-TGFβ antibodies (e.g., monospecific anti-TGFβ2 and anti-TGFβ3 antibodies, and dual-specific, anti-TGFβ2/3 antibodies) and methods of using the same. TGFβ is involved in the control of several key cellular functions including cell proliferation, differentiation, migration, apoptosis and extracellular matrix production. As a consequence, the growth factor influences many biologic processes including embryonic development, wound repair, immune function, malignant transformation and aging. Isoform-selective anti-TGFβ antibodies of the invention are thus useful, e.g., for the diagnosis or treatment of TGFβ-related disorders, such as but not limited to fibrotic disease and cancer.

In some aspects, the epitopes bound by the isoform-selective anti-TGFβ antibodies are provided. The antigen binding domains of the isoform-selective anti-TGFβ antibodies were determined based on their crystal structures. By way of example, the binding epitope of the 2A10 and 4A11 antibodies were mapped by solving their antibody/TGFβ complex crystal structures. See, Example 10, below. As will be appreciated by one of skill in the art, the results from Example 10 demonstrate where anti-TGFβ2/3 antibody 4A11 interacts with TGFβ2 (and, by inference, where it also binds in the same highly conserved region in TGFβ3), and where anti-TGFβ3 antibody 2A10 interacts with TGFβ3. Thus, antibodies that interact with or block any of these residues in TGFβ2 or TGFβ3 can be useful as antibodies that neutralize TGFβ2 or TGFβ3, respectively. In some embodiments, antibodies that, when bound to their target TGFβ isoform(s), interact with or block residues on the TGFβ isoform, or are within 15-8, 8, 8-7, 8-6, 8-5, or 5 angstroms of the residues, are contemplated to provide useful neutralization of the TGFβ isoform(s). By way of non-limiting example, the anti-TGFβ3 antibody 2A10 was determined to bind to an epitope on TGFβ3 containing amino acid residues R325, K331, W332, H334, E335, T387, I388, L389, Y391, V392, G393, R394, P396, K397, and V398 on human TGFβ3 (i.e., the antigen-binding domain directly contacted those residues on TGFβ3), and this binding resulted in neutralization of TGFβ3. Thus, in some embodiments, antibodies that, when bound to TGFβ3, interact with or block those residues on TGFβ3 or are within 15-8, 8, 8-5, or preferably within 5 angstroms of those residues, are contemplated to provide useful neutralization of TGFβ3. By way of further, non-limiting example, the anti-TGFβ2/3 antibody 4A11 was determined to bind to TGFβ2 homodimer, and to directly contact amino acid residues V313, Q314, D315, R320, L322, Y323, R328, D329, F345, and A347 in the first TGFβ2 monomer of the homodimer, and amino acid residues N368, T369, I370, N371, P372, E373, A374, 5375, A376, and S377 in the second TGFβ2 monomer. Thus, in some embodiments, antibodies that, when bound to TGFβ2, interact with or block those residues on TGFβ2 or are within 15-8, 8, 8-5, or preferably within 5 angstroms of those residues, are contemplated to provide useful neutralization of TGFβ2. In some embodiments, the antigen binding domain binds within 30, 30-25, 25-20, 20-15, 15-8, 8, 8-5, 5, 5-4, 4 or less angstroms from one or more of the above residues. In some embodiments, the antigen binding domain, when bound to a TGFβ isoform, is within at least one of the above distances, for more than one of the above noted residues. For example, in some embodiments, the antigen binding domain is within one of the recited distances (e.g., 30, 30-25, 25-20, 20-15, 15-8, 8, 8-5, 5, 5-4, 4 or less) for at least 2, 3, 4, 5, 6, 7, 8, 9, 10, 11, 12, 13, 14, 15, 16, 17, 18, 19, 20, 20-25, 25-30, 30-35, 35-40, 40-45, 45-50, 50-55, 55-60, 60-65, 65-70, 70-75 or more of the above residues. In some embodiments, the antigen binding domain is within one of the recited distances for at least 1-10, 10-20, 20-30, 30-40, 40-50, 50-60, 60-70, 70-80, 80-90, 90-95, 95-99, 99-100% of the residues identified in each group of subgroup thereof (such as only those surface residues in the group). Unless specifically stated otherwise, the distance between the antigen binding domain and a TGFβ isoform is the shortest distance between the covalently bonded atom on the TGFβ isoform and the covalently bonded atom of the antigen binding domain that are the closest atoms of the TGFβ isoform and the antigen binding domain. Similarly, unless specifically stated otherwise, the distance between a residue on the antigen-binding domain and the TGFβ isoform for which it is specific is the distance from the closest point on the identified residue to the closest covalently bonded part of the TGFβ isoform, or vice versa. In some embodiments, the distance can be measured from the backbone of the amino acid chains. In some embodiments, the distance can be measured between an edge of the paratope and an edge (closest to one another) of the epitope. In some embodiments, the distance can be measured between the center of the surface of the paratope and the center of the surface of the epitope. As will be appreciated by one of skill in the art, the present description is applicable for each of the individual sets of residues listed herein. For example, the above ranges are contemplated generally and specifically for the epitope and paratope residues listed in Example 10.

A. Exemplary Isoform-Selective Anti-TGFβ Antibodies

Anti-TGFβ2 Antibodies

In one aspect, the invention provides isolated antibodies that bind to TGFβ2. In certain embodiments, an anti-TGFβ2 antibody selectively neutralizes TGFβ2. In certain embodiments, an anti-TGFβ2 antibody has one or more of the properties: (a) selectively neutralizes TGFβ2; (b) has reduced toxicity relative to the pan-TGFβ antibody 1D11; (c) has reduced toxicity relative to the pan-TGFβ antibody 1D11; (d) has reduced toxicity in rodents relative to the pan-TGFβ antibody 1D11; (e) has reduced toxicity relative to the pan-TGFβ small molecule inhibitor galunisertib; and/or (f) has reduced toxicity in rodents relative to the pan-TGFβ small molecule inhibitor galunisertib.

In certain aspects, an anti-TGFβ2 antibody provided herein binds to TGFβ2 with a $K_D$ of less than 10 pM and/or a cell-based $IC_{50}$ less than 250 pM. In one aspect, an anti-TGFβ2 antibody provided herein binds to TGFβ2 with a $K_D$ of less than or equal to about 5 pM, about 4 pM, about 3 pM, about 2 pM, or about 1 pM. In one aspect, an anti-TGFβ2 antibody provided herein binds to TGFβ2 with a $K_D$ of less than 1 pM. In one aspect, an anti-TGFβ2 antibody provided herein has a cell-based $IC_{50}$ less than or equal to about 250 pM, about 200 pM, about 150 pM, about 100 pM, about 75 pM, or about 50 pM. In one aspect, an anti-TGFβ2 antibody provided herein has a cell-based $IC_{50}$ for inhibition (neutralization) of TGFβ2 of 40 pM.

In one aspect, the invention provides an anti-TGFβ2 antibody comprising at least one, two, three, four, five, or six HVRs selected from (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In one aspect, the invention provides an anti-TGFβ2 antibody comprising at least one, at least two, or all three VH HVR sequences selected from (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18. In another aspect, the invention provides an antibody comprising (a) HVR-H1 comprising the amino acid sequence of SEQ ID NO: 16; (b) HVR-H2 comprising the amino acid sequence of SEQ ID NO:17; ad (c) HVR-H3 comprising the amino acid sequence of SEQ ID NO: 18.

In another aspect, the invention provides an anti-TGFβ2 antibody comprising at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another embodiment, the anti-TGFβ2 antibody comprises HVR-H3 comprising the amino acid sequence of SEQ ID NO: 18 and HVR-L3 comprising the amino acid sequence of SEQ ID NO: 21. In a further embodiment, the anti-TGFβ2 antibody comprises HVR-H3 comprising the amino acid sequence of SEQ ID NO: 18, HVR-L3 comprising the amino acid sequence of SEQ ID NO: 21, and HVR-H2 comprising the amino acid sequence of SEQ ID NO: 17.

In another aspect, an anti-TGFβ2 antibody of the invention comprises (a) a VH domain comprising at least one, at least two, or all three VH HVR sequences selected from (i) HVR-H1 comprising the amino acid sequence of SEQ ID NO: 16; (ii) HVR-H2 comprising the amino acid sequence of SEQ ID NO:17; (iii) HVR-H3 comprising the amino acid sequence of SEQ ID NO: 18; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21.

In another aspect, the invention provides an anti-TGFβ2 antibody comprising a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments, an anti-TGFβ2 antibody is humanized. In one embodiment, an anti-TGFβ2 antibody comprises HVRs as in any of the above embodiments, and further comprises an acceptor human framework, e.g. a human immunoglobulin framework or a human consensus framework. In any of the above embodiments, a humanized anti-TGFβ2 antibody comprises one or more mutations in the VH framework selected from the group consisting of 37V or 37I, 48M or 48L, 49G or 49A, 67L, 71K and 78V, and 105P or 105R. In some embodiments, the anti-TGFβ2 antibody comprises a VH, wherein the VH comprises the amino acid sequence of SEQ ID NO: 25, wherein the VH comprises a set of framework mutations selected from the group consisting of (i) 37V, 48M and 49G in FR2 and 105P in FR4 (h6F12.v1 and h6F12.v3); (ii) 37V and 48M in FR2, 67L, 71K and 78V in FR3 and 105P in FR4 (h6F12.v2 and h6F12.v4); (iii) 37I in FR2 (h6F12.v1.6); (iv) 48L in FR2 (h6F12.v1.7); (v) 49A in FR2 (h6F12.v1.8); (vi) 105R in FR4 (h6F12.v1.9); (vii) 37V, 48M and 49G in FR2 and 105P in FR4 (h6F12.v1 and h6F12.v3); (viii) 37V and 48M in FR2, 67L, 71K and 78V in FR3 and 105P in FR4 (6F12.v2 and h6F12.v4); (ix) 37I in FR2 (h6F12.v1.6); (x) 48L in FR2 (h6F12.v1.7); (xi): 49A in FR2 (h6F12.v1.8); and (xii) 105R in FR4 (h6F12.v1.9). In any of the above embodiments, a humanized anti-TGFβ2 antibody comprises one or more mutations in the VL framework selected from the group consisting of 43S or 43A, 66G, 69T, 71F, and 87Y. In some embodiments, the anti-TGFβ2 antibody comprises a VL, wherein the VL comprises the amino acid sequence of SEQ ID NO: 24, wherein the VL comprises a set of framework mutations selected from the group consisting of: (i) 43S in FR2 and 66E, 69P, 71Y and 87F in FR3 (h6F12.v1 and h6F12.v2); (ii) 43S in FR2 and 58V, 66E, 69P, 71Y and 87F in FR3 (h6F12.v3 and h6F12.v4); (iii) 43A in FR2 (h6F12.v1.1); (iv) 66G in FR3 (h6F12.v1.2); (v) 69T in FR3 (h6F12.v1.3); (vi) 71F in FR3 (h6F12.v1.4); and (vii) 87Y in FR3 (h6F12.v1.5).

In another aspect, an anti-TGFβ2 antibody comprises a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NO: 25, 132, and 138-142. In certain embodiments, a VH sequence having at least 90%, 91%, 92%, 93%, 94%, 95%, 96%, 97%, 98%, or 99% sequence identity contains substitutions (e.g., conservative substitutions), insertions, or deletions relative to the reference sequence, but an isoform-selective anti-TGFβ antibody comprising that sequence retains the ability to bind to and selectively neutralize TGFβ2. In certain embodiments, a total of 1 to 10 amino acids have been substituted, inserted and/or deleted in SEQ ID NO: 25. In certain embodiments, substitutions, insertions, or deletions occur in regions outside the HVRs (i.e., in the FRs). Optionally, the anti-TGFβ2 antibody comprises the VH sequence selected from the group consisting of SEQ ID NOs: 25, 132, and 138-142, including post-translational modifications of that sequence. In a particular embodiment, the VH comprises one, two or three HVRs selected from: (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18.

In another aspect, an anti-TGFβ2 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence selected from the group consisting of SEQ ID NO: 24, 131, 133-137, 143, and 144. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TGFβ2 antibody comprising that sequence retains the ability to bind to PRO. In certain embodiments, a total of 1 to 10 amino acids have been substituted, inserted and/or deleted in SEQ ID NO: 24. In certain embodiments, the substitutions, insertions, or deletions occur in regions outside the HVRs (i.e., in the FRs). Optionally, the anti-TGFβ2 antibody comprises the VL sequence selected from the group consisting of SEQ ID NO: 24, 131, 133-137, 143, and 144, including post-translational modifications of that sequence. In a particular embodiment, the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, an anti-TGFβ2 antibody is provided, wherein the antibody comprises a VH as in any of the embodiments provided above, and a VL as in any of the embodiments provided above. In one embodiment, the antibody comprises the VH/VL sequences (respectively) selected from the group consisting of SEQ ID NOs: 25/24 (rabbit 6F12), SEQ ID NOs: 132/131 (v1), SEQ ID NOs: 132/133 (v1.1), SEQ ID NOs: 132/134 (v1.2), SEQ ID NOs: 132/135 (v1.3), SEQ ID NOs: 132/136 (v1.4), SEQ ID NOs: 132/137 (v1.5), SEQ ID NOs: 138/131 (v1.6), SEQ ID NOs: 139/131 (v1.7), SEQ ID NOs: 140/131 (v1.8), SEQ ID NOs: 141/131 (v1.9), SEQ ID NOs: 142/131 (v2), SEQ ID NOs: 132/143 (v3), and SEQ ID NOs: 142/144 (v4), including post-translational modifications of those sequences.

In another aspect, an anti-TGFβ2 antibody is provided, wherein the antibody comprises a complete H chain amino acid sequence having at least 95% sequence identity to the amino acid sequence selected from the group consisting of SEQ ID NOs: 31, 146, and 152-156 and/or a complete L chain amino acid sequence having an amino acid sequence selected from the group consisting of SEQ ID NOs: 30, 145, 147-151, 157, and 158. In some embodiments, the anti-TGFβ2 antibody comprises a complete H/L chain pair, the complete H/L chain pair (respectively) comprising amino acid sequences selected from the group consisting of SEQ ID NOs: 31/30 (rabbit 6F12), SEQ ID NOs: 146/145 (vi), SEQ ID NOs: 146/147 (v1.1), SEQ ID NOs: 146/148 (v1.2), SEQ ID NOs: 146/149 (v1.3), SEQ ID NOs: 146/150 (v1.4), SEQ ID NOs: 146/151 (v1.5), SEQ ID NOs: 152/145 (v1.6), SEQ ID NOs: 153/145 (v1.7), SEQ ID NOs: 154/145 (v1.8), SEQ ID NOs: 155/145 (v1.9), SEQ ID NOs: 156/145 (v2), SEQ ID NOs: 146/157 (v3), and SEQ ID NOs: 156/158 (v4).

In a further aspect, the invention provides an antibody that binds to the same epitope as an anti-TGFβ2 antibody provided herein. For example, in certain embodiments, an antibody is provided that binds to the same epitope as an anti-TGFβ2 antibody comprising a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

Anti-TGFβ2/3 Antibodies

In another aspect, the invention provides isolated antibodies that bind to both TGFβ2 and TGFβ3 (anti-TGFβ2/3 antibodies). In certain aspects, the antibody selectively neutralizes TGFβ2 and TGFβ3, and comprises one or more of the following features:

(a) selectivity of the anti-TGFβ2/3 antibody for TGFβ2 and TGFβ3 over human TGFβ1, with respect to selective neutralization, is achieved by direct contact of the antibody's antigen binding domain with amino acid residue E373 of TGFβ2 or TGFβ3 (human TGFβ2 numbering);

(b) the anti-TGFβ2/3 antibody neutralizes TGFβ2 and/or TGFβ3 via an allosteric mechanism;

(c) the anti-TGFβ2/3 antibody induces a conformational change in TGFβ2 homodimer;

(d) the anti-TGFβ2/3 antibody induces a conformational change in TGFβ2 homodimer, wherein the conformational change comprises the two monomers pinching together by several degrees;

(e) the anti-TGFβ2/3 antibody is a divalent antibody or a monovalent antibody;

(f) the anti-TGFβ2/3 antibody comprises (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15;

(g) the anti-TGFβ2/3 antibody binds to TGFβ2 homodimer, the TGFβ2 homodimer having a first and a second TGFβ2 monomer, and wherein the anti-TGFβ2/3 antibody comprises an antigen binding domain that directly contacts (i) amino acid residues V313, Q314, D315, R320, L322, Y323, R328, D329, F345, and A347 of the first TGFβ2 monomer, and (ii) amino acid residues N368, T369, I370, N371, P372, E373, A374, S375, A376, and S377 of the second TGFβ2 monomer (human TGFβ2 numbering);

(h) the anti-TGFβ2/3 antibody as in (g), wherein the antigen binding domain is within 5 angstroms of the TGFβ2 and/or TGFβ3 amino acid residues;

(i) wherein the anti-TGFβ2/3 antibody binds to a substantially similar epitope as in (g) in TGFβ3; and (j) the anti-TGFβ2/3 antibody does not neutralize TGFβ2 and/or TGFβ3 in single arm form.

In certain embodiments, an anti-TGFβ2/3 antibody selectively neutralizes TGFβ2 and TGFβ3. In certain aspects, an anti-TGFβ2/3 antibody provided herein binds to TGFβ2/3 with a $K_D$ of less than 10 pM and/or a cell-based $IC_{50}$ less than 250 pM. In one aspect, an anti-TGFβ2/3 antibody provided herein binds to TGFβ2 and/or TGFβ3 with a $K_D$ of less than about 10 pM, about 9 pM, about 8 pM, about 7 pM, about 6 pM, about 5 pM, about 4 pM, about 3 pM, about 2 pM, or about 1 pM. In one aspect, an anti-TGFβ2/3 antibody provided herein binds to TGFβ2 with a $K_D$ of about 5 pM. In one aspect, an anti-TGFβ2/3 antibody provided herein has a cell-based $IC_{50}$ for inhibition of TGFβ2 of about 250 pM, about 200 pM, about 150 pM, about 100 pM, about 75 pM, or about 50 pM. In one aspect, an anti-TGFβ2/3 antibody provided herein has a cell-based $IC_{50}$ for inhibition of TGFβ3 of about 250 pM, about 200 pM, about 150 pM, about 100 pM, about 75 pM, about 50 pM, about 40 pM, about 30 pM or less than about 30 pM. In one aspect, an anti-TGFβ2/3 antibody provided herein has a cell-based $IC_{50}$ for inhibition of TGFβ2 of about 250 pM and/or a cell-based $IC_{50}$ for inhibition (neutralization) of TGFβ3 of about 30 pM.

In one aspect, the invention provides an comprising at least one, two, three, four, five, or six HVRs selected from (a) HVR-H1 comprising the amino acid sequence of SEQ ID NO: 10; (b) HVR-H2 comprising the amino acid anti-TGFβ2/3 antibody sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15.

In one aspect, the invention provides an anti-TGFβ2/3 antibody comprising at least one, at least two, or all three VH HVR sequences selected from (a) HVR-H1 comprising the amino acid sequence of SEQ ID NO: 10; (b) HVR-H2 comprising the amino acid anti-TGFβ2/3 antibody sequence of SEQ ID NO: 11; (c) HVR-H3 comprising the amino acid sequence of SEQ ID NO: 12. In one embodiment, the antibody comprises HVR-H3 comprising the amino acid sequence of SEQ ID NO: 12. In another embodiment, the antibody comprises HVR-H3 comprising the amino acid sequence of SEQ ID NO: 12 and HVR-L3 comprising the amino acid sequence of SEQ ID NO: 15. In a further embodiment, the antibody comprises HVR-H3 comprising the amino acid sequence of SEQ ID NO: 12, HVR-L3 comprising the amino acid sequence of SEQ ID NO: 15, and HVR-H2 comprising the amino acid sequence of SEQ ID NO: 11. In a further embodiment, the antibody comprises (a) HVR-H1 comprising the amino acid sequence of SEQ ID NO: 10; (b) HVR-H2 comprising the amino acid sequence of SEQ ID NO: 11; and (c) HVR-H3 comprising the amino acid sequence of SEQ ID NO:12.

In another aspect, the invention provides an anti-TGFβ2/3 antibody comprising at least one, at least two, or all three VL HVR sequences selected from (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15. In one embodiment, the anti-TGFβ2/3 antibody comprises (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15.

In another aspect, an anti-TGFβ2/3 antibody of the invention comprises (a) a VH domain comprising at least one, at least two, or all three VH HVR sequences selected from (i) HVR-H1 comprising the amino acid sequence of SEQ ID NO: 10, (ii) HVR-H2 comprising the amino acid sequence of SEQ ID NO: 11, and (iii) HVR-H3 comprising an amino acid sequence selected from SEQ ID NO: 12; and (b) a VL domain comprising at least one, at least two, or all three VL HVR sequences selected from (i) HVR-L1 comprising the amino acid sequence of SEQ ID NO: 13, (ii) HVR-L2 comprising the amino acid sequence of SEQ ID NO: 14, and (c) HVR-L3 comprising the amino acid sequence of SEQ ID NO: 15.

In another aspect, the invention provides an anti-TGFβ2/3 antibody comprising (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15.

In any of the above embodiments, an anti-TGFβ2/3 antibody is humanized. In one embodiment, an anti-TGFβ2/3 antibody comprises HVRs as in any of the above embodiments, and further comprises an acceptor human framework, e.g. a human immunoglobulin framework or a human consensus framework. In another embodiment, an anti-TGFβ2/3 antibody comprises HVRs as in any of the above embodiments, and further comprises a VH comprising FR modifications selected from the group consisting of 1E, 2Q or 2V, 24V, 37V or 37I, 48I, 49G, 67F or 67V, 71K or 71V, 73S or 73T, deletion of 75K and 76N, 78V or 78F, 91F or 91Y, 105P or 105Q. In some embodiments, the anti-TGFβ2/3 antibody comprises a VH, wherein the VH comprises the amino acid sequence of SEQ ID NO: 27, wherein the VH comprises a set of framework modifications selected from the group consisting of: (i) 2Q and 24V in FR1, 481 and 49G in FR2, 71K, 73S, 78V and 91F in FR3 and 105P in FR4 (h4A 1.v1, h4A11.v2, h4A11.v5, h4A11.v6); (ii) 2Q in FR1, 37V in FR2, 67F, 71K, 73S, 78V and 91F in FR3 and 105P in FR4 (h4A11.v3, h4A11.v4, 4A11.v7, h4A11.v8); (iii) delete 1E in FR1 (h4A11.v7.1); (iv) delete 75K and 76N in FR3 (h4A11.v7.2); (v) delete 1E in FR1 and 75K76N in FR3 (h4A11.v7.3); (vi) 2V in FR1 (h4A11.v7.8); (vi) 37I in FR2 (h4A11.v7.9); (vii) 67V in FR3 (h4A11.v7.10); (viii) 71V in FR3 (h4A11.v7.11); (ix) 73T in FR3 (h4A11.v7.12); (x) 78F in FR3 (h4A11.v7.13); (xi) 91Y in FR3 (h4A11.v7.14); (xii) 105Q in FR4 (h4A11.v7.15); (xiii) 2V in FR1, 37I in FR2, 67V, 73T, 78F in FR3, 105Q in FR4 ((h4A11.v7.16); (xiv) 2V in FR1, 37I in FR2, 67V, 73T, 91Y in FR3, 105Q in FR4 (h4A11.v7.17); (xv) 2V in FR1, 37I in FR2, 67V, 73T in FR3, 105Q in FR4 (h4A11.v7.18); and (xvi) 2V in FR1, 37I in FR2, 67V, 73T, deletion of 75K and 76N in FR3, 105Q in FR4 (h4A11.v7.19. In another embodiment, an anti-TGFβ2/3 antibody comprises HVRs as in any of the above embodiments, and further comprises a VL comprising FR modifications selected from the group consisting of: 2A or 2I, 4L, 36F or 36Y, 43P or 43A, and 58V or 581. In some embodiments, the anti-TGFβ2/3 antibody comprises a VL, wherein the VL comprises the amino acid sequence of SEQ ID NO: 26, wherein the VL comprises a set of framework modifications selected from the group consisting of (i) 2A and 4L in FR1 and 36F in FR2 (h4A11.v1 and h4A11.v3); (ii) 2A and 4L in FR1 and 36F and 43P in FR2 (h4A11.v2 and h4A11.v4); (iii) 2A in FR1, 36F and 43P in FR2 and 58V in FR3 (h4A11.v5 and h4A11.v7); (iv) 2A and 4L in FR1 and 36F in FR2 (h4A11.v6 and h4A11.v8); (v) 2I in FR1 (h4A11.v7.4); (vi) 36Y in FR2 (h4A11.v7.5); (vii) 43A in FR2 (h4A11.v7.6); (viii) 581 in FR3 (h4A11.v7.7); and (ix) 2I in FR1, 43A in FR2, 58I in FR3 (h4A11.v7.16-19).

In another aspect, an anti-TGFβ2/3 antibody comprises a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 27, 81, 83, 86-88, 93-100, and 102-105. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TGFβ2/3 antibody comprising that sequence retains the ability to bind to TGFβ2 and to TGFβ3. In certain embodiments, a total of 1 to 10 amino acids have been substituted, inserted and/or deleted in SEQ ID NO: 27. In certain embodiments, substitutions, insertions, or deletions occur in regions outside the HVRs (i.e., in the FRs). Optionally, the anti-TGFβ2/3 antibody comprises the VH sequence selected from the group consisting of SEQ ID NO: SEQ ID NOs: 27, 81, 83, 86-88, 93-100, and 102-105, including post-translational modifications of that sequence. In a particular embodiment, the VH comprises one, two or three HVRs selected from: (a) HVR-H1 comprising the amino acid sequence of SEQ ID NO: 10, (b) HVR-H2 comprising the amino acid sequence of SEQ ID NO: 11, and (c) HVR-H3 comprising the amino acid sequence of SEQ ID NO: 12.

In another aspect, an anti-TGFβ2/3 antibody is provided, wherein the anti-TGFβ2/3 antibody comprises a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 26, 80, 82, 84, 85, 89-92, and 101. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TGFβ2/3 antibody comprising that sequence retains the ability to bind to TGFβ2 and TGFβ3. In certain embodiments, a total of 1 to 10 amino acids have been substituted, inserted and/or deleted in SEQ ID NO: 26. In certain embodiments, the substitutions, insertions, or deletions occur in regions outside the HVRs (i.e., in the FRs). Optionally, the anti-TGFβ2/3 antibody comprises the VL sequence selected from the group consisting of SEQ ID NOs: 26, 80, 82, 84, 85, 89-92, and 101, including post-translational modifications of that sequence. In a particular embodiment, the VL comprises one, two or three HVRs selected from (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15.

In another aspect, an anti-TGFβ2/3 antibody is provided, wherein the antibody comprises a VH as in any of the embodiments provided above, and a VL as in any of the embodiments provided above. In one embodiment, the anti-TGFβ2/3 antibody comprises the VH and VL sequences (respectively) selected from the group consisting of SEQ ID NOs: 27/26 (rabbit 4A11), SEQ ID NOs: 81/80 (v1), SEQ ID NOs: 81/82 (v2), SEQ ID NOs: 83/80 (v3), SEQ ID NOs: 83/82 (v4), SEQ ID NOs: 81/84 (v5), SEQ ID NOs: 81/85 (v6), SEQ ID NOs: 83/84 (v7), SEQ ID NOs: 86/84 (v7/1), SEQ ID NOs: 87/84 (v7.2), SEQ ID NOs: 88/84 (v7.3), SEQ ID NOs: 83/89 (v7.4), SEQ ID NOs: 83/90 (v7.5), SEQ ID NOs: 83/91 (v7.6), SEQ ID NOs: 83/92 (v7.7), SEQ ID NOs: 93/84 (v7.8), SEQ ID NOs: 94/84 (v7.9), SEQ ID NOs: 95/84 (v7.10), SEQ ID NOs: 96/84 (v7.11), SEQ ID NOs: 97/84 (v7.12), SEQ ID NOs: 98/84 (v7.13), SEQ ID NOs: 99/84 (v7.14), SEQ ID NOs: 100/84 (v7.15), SEQ ID NOs: 102/101 (v7.16), SEQ ID NOs: 103/101 (v7.17), SEQ ID NOs: 104/101 (v7.18), SEQ ID NOs: 105/101 (v7.19), SEQ ID NOs: 83/85 (v8), including post-translational modifications of those sequences.

In another aspect, an anti-TGFβ2/3 antibody is provided, wherein the antibody comprises a complete H chain amino acid sequence having at least 95% sequence identity to the amino acid sequence selected from the group consisting of SEQ ID NOs: 33, 107, 109, 112-114, and 119-130 and/or a complete L chain amino acid sequence having an amino acid sequence selected from the group consisting of SEQ ID NOs: 32, 106, 108, 110, 111, 115-118, and 186. In some embodiments, the anti-TGFβ2/3 antibody comprises a complete H/L chain pair, the complete H/L chain pair (respectively) comprising amino acid sequences selected from the group consisting of SEQ ID NOs: 32/33 (rabbit 4A11), SEQ ID NOs: 107/106 (v1), SEQ ID NOs: 107/108 (v2), SEQ ID NOs: 109/106 (v3), SEQ ID NOs: 109/108 (v4), SEQ ID NOs: 107/110 (v5), SEQ ID NOs: 107/111 (v6), SEQ ID NOs: 109/110 (v7), SEQ ID NOs: 112/110 (v7.1), SEQ ID NOs: 113/110 (v7.2), SEQ ID NOs: 114/110 (v7.3), SEQ ID NOs: 114/115 (v7.4), SEQ ID NOs: 114/116 (v7.5), SEQ ID NOs: 114/117 (v7.6), SEQ ID NOs: 114/118 (v7.7), SEQ ID NOs: 119/110 (v7.8), SEQ ID NOs:120/110 (v7.9), SEQ ID NOs: 121/110 (v7.10), SEQ ID NOs: 122/110 (v7.11), SEQ ID NOs: 123/110 (v7.12), SEQ ID NOs: 124/110 (v7.13), SEQ ID NOs: 125/110 (v7.14), SEQ ID NOs: 126/110 (v7.15), SEQ ID NOs: 127/186 (v7.16), SEQ ID NOs: 128/186 (v7.17), SEQ ID NOs: 129/186 (v7.18), SEQ ID NOs: 130/186 (v7.19), and SEQ ID NOs: 114/111 (v8).

In a further aspect, the invention provides an anti-TGFβ2/3 antibody that binds to the same epitope as an anti-TGFβ2/3 antibody provided herein. For example, in certain embodiments, an antibody is provided that binds to the same epitope as an anti-TGFβ2/3 antibody comprising (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15. In certain embodiments, an anti-TGFβ2/3 antibody is provided that binds to an epitope spanning a TGFβ2 homodimer, the TGFβ2 homodimer having a first and a second TGFβ2 monomer, wherein the anti-TGFβ2/3 antibody comprises an antigen-binding domain that directly contacts amino acid residues V313, Q314, D315, R320, L322, Y323, R328, D329, F345, and A347 of the first TGFβ2 monomer, and amino acid residues N368, T369, I370, N371, P372, E373, A374, S375, A376, and S377 of the second TGFβ2 monomer, and wherein, in some embodiments, the anti-TGFβ2/3 antibody binds to the same epitope in TGFβ3. TGFβ2 and TGFβ3 are highly conserved at the region comprising amino acid positions 368-377 (TGFβ2 numbering), thus the anti-TGFβ2/3 antibody binds to same region in both TGFβ2 and TGFβ3.

Anti-TGFβ3 Antibodies

In one aspect, the invention provides isolated antibodies that bind to TGFβ3. In certain embodiments, an anti-TGFβ3 antibody selectively neutralizes TGFβ3. Further, it is presently discovered that the anti-TGFβ3 antibodies described herein have improved safety profiles (e.g., reduced toxicity) compared to pan-TGFβ inhibitors as well as compared to isoform-selective antibodies specific for TGFβ2 (Example 2) and anti-TGFβ1 selective antibodies. Several inhibitors of TGFβ signaling have been investigated in preclinical toxicology studies, including both small molecule inhibitors of the kinase activity of TGFBR1 (ALK5), e.g., galunisertib, and antibody-based inhibitors of TGFβ-TGFBR interactions, e.g., fresolimumab, a pan-TGFβ antibody. Rat toxicology studies of ALK5 small molecule inhibitors from different chemical series consistently showed hemorrhagic, inflammatory, and degenerative heart valve lesions and physeal dysplasia (Frazier Toxicol Pathol 35, 284-95. 2007; Anderton Toxicol Pathol 39: 916, 2011). In early clinical studies, galunisertib has been dosed at levels that do not completely inhibit ALK5 activity for relatively short periods of time and cardiac findings have not yet emerged in the clinic. Mice treated with pan-TGFβ antibody 1D11 (Lonning et al. (2011) Current Pharmaceutical Biotechnology, 12, 2176-2189) developed histologic lesions, weight loss, nonneoplastic cystic epithelial hyperplasia and inflammation of the tongue and dental dysplasia and epithelial hyperplasia of the gingiva and esophagus. Fresolimumab, a humanized form of GC1008 antibody that binds to and inhibits the activity of all three TGFβ isoforms with comparable affinities for the TGFβ isoforms as 1D11 antibody, was investigated in cynomolgus monkeys and led to dose-dependent bleeding, anemia, and hyperplasia in urinary, nasal, and bladder epithelia. In humans, fresolimumab treatment resulted in anemia and bleeding (gingival, nasal, and subconjunctival), and an increased rate of keratoacanthomas (pre-cancerous squamous skin lesions) that reversed with treatment cessation (Rice, *JCI* 125:2795 (2015); Lacouture, *Cancer Immunol Immunother* 64:437 (2015)). CAT-192, an antibody predominantly selective for TGFβ1, had a high serious adverse event rate with multiple gastric hemorrhages observed in a phase 1-2 study in SSc (Denton *A&R* 56:323 (2007); see, also, the World Wide Web at tripod.nih.gov/ginas/app/substance/4AR6718OL0). Taken together, these observations suggest that bleeding, cardiac lesions, and epithelial hyperplasia are significant concerns with long-term chronic pharmacologic TGFβ inhibition.

In contrast to the concerning safety issues that have been observed with past attempts to neutralize TGFβ in vivo, in certain aspects, the present invention provides anti-TGFβ3 antibodies having improved safety profiles (e.g., reduced toxicity). For example, in Example 2, below, mice treated with an anti-TGFβ3 antibody at doses up to 50 mg/kg administered thrice weekly for a total of 4-weeks had no or very minor side effects (physeal dysplasia at the highest dose), and none of the serious side effects caused by small molecule inhibitors, anti-TGFβ1 or pan-TGFβ antibodies, as discussed above, were observed. The anti-TGFβ3 antibodies described herein were also discovered to have improved safety profiles relative to isoform-selective anti-TGFβ2/3 and anti-TGFβ2 antibodies (Example 2, see Table 8).

In certain aspects, an isolated anti-TGFβ3 antibody is provided, wherein the antibody selectively neutralizes TGFβ3, and wherein the antibody comprises one or more of the following features:

(a) the anti-TGFβ3 antibody binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody binds amino acid residue R394 in the beta6/beta7 hairpin region of human TGFβ3;

(e) the anti-TGFβ3 antibody binds amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

(j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody.

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

In certain aspects, an anti-TGFβ3 antibody provided herein binds to TGFβ3 with a $K_D$ of less than 10 pM and/or a cell-based $IC_{50}$ less than 250 pM. In one aspect, an anti-TGFβ3 antibody provided herein binds to TGFβ3 with a $K_D$ of less than about 5 pM, about 4 pM, about 3 pM. In one aspect, an anti-TGFβ3 antibody provided herein binds to TGFβ3 with a $K_D$ of less than about 2 pM. In one aspect, an anti-TGFβ3 antibody provided herein has a cell-based $IC_{50}$ less than about 200 pM, about 150 pM, about 100 pM, about 75 pM, or about 50 pM. In one aspect, an anti-TGFβ3 antibody provided herein has a cell-based $IC_{50}$ for inhibition (neutralization) of TGFβ3 of less than about 20 pM.

In another aspect, an anti-TGFβ3 antibody provided herein selectively neutralizes TGFβ3 and has reduced toxicity in mice relative to the pan-TGFβ antibody 1D11 (see, Lonning et al. (2011)). In another aspect, an anti-TGFβ3 antibody provided herein selectively neutralizes TGFβ3 and has an improved safety profile, e.g., relative to the pan-TGFβ inhibitors such as the ALK5 inhibitors described in Anderton et al. and/or 1D11 antibody described in Lonning et al. (2011). In another aspect, an anti-TGFβ3 antibody provided herein selectively neutralizes TGFβ3 and has reduced toxicity in mice relative to the anti-TGFβ1 antibody CAT-192/metelimumab.

In certain aspects, the CAT-192 antibody has the following heavy and light chain variable amino acid sequences:

```
VH
                                        (SEQ ID NO: 184)
EVQLVESGGGVVQPGRSLRLSCAASGFTFSSYGMHWVRQAPGKELEWVA

VISYDGSIKYYADSVKGRFTISRDNSKNTLYLQMNSLRAEDTAVYYCAR

TGEYSGYDTDPQYSWGQGTTVTVSSASTKGPSVFPLAPCSRSTSESTAA

LGCLVKDYFPEPVTVSWNSGALTSGVHTFPAVLQSSGLYSLSSVVTVPS

SSLGTKTYTCNVDHKPSNTKVDKRVESKYGPPCPSCPAPEFLGGPSVFL

FPPKPKPTLMISRTPEVTCVVVDVSQEDPEVQFNWYVDGVEVHNAKTKP
```

-continued

```
REEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPEN

NYKTTPPVLDSDGSFFLYSRLTVDKSRWQEGNVFSCSVMHEALHNHYTQ

KSLSLSLGK.

VL
                                        (SEQ ID NO: 185)
EIVLTQSPSSLSASVGDRVTITCRASQGIGDDLGWYQQKPGKAPILLIY

GTSTLQSGVPSRFSGSGSGTDFTLTINSLQPEDFATYYCLQDSNYPLTF

GGGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSPVTKSFNRGEC.
```

In any of the above aspects, the anti-TGFβ3 antibody comprising at least one, two, three, four, five, or six HVRs selected from (a) HVR-H1 comprising the amino acid sequence of SEQ ID NO: 4; (b) HVR-H2 comprising the amino acid sequence selected from SEQ ID NOs: 5, 34, 35, and 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9.

In one aspect, the invention provides an anti-TGFβ3 antibody comprising at least one, at least two, or all three VH HVR sequences selected from (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO: 6. In another aspect, the invention provides an anti-TGFβ3 antibody comprising at least one, at least two, or all three VH HVR sequences selected from (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO: 6. In another aspect, the invention provides an anti-TGFβ3 antibody comprising at least one, at least two, or all three VH HVR sequences selected from (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO: 6. In another aspect, the invention provides an anti-TGFβ3 antibody comprising at least one, at least two, or all three VH HVR sequences selected from (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO: 6.

In one embodiment, the antibody comprises HVR-H3 comprising the amino acid sequence of SEQ ID NO: 6. In another embodiment, the antibody comprises HVR-H3 comprising the amino acid sequence of SEQ ID NO: 6 and HVR-L3 comprising the amino acid sequence of SEQ ID NO: 9. In a further embodiment, the antibody comprises HVR-H3 comprising the amino acid sequence of SEQ ID NO: 6, HVR-L3 comprising the amino acid sequence of SEQ ID NO: 9, and HVR-H2 comprising the amino acid sequence of SEQ ID NO: 5. In a further embodiment, the anti-TGFβ3 antibody comprises HVR-H3 comprising the amino acid sequence of SEQ ID NO: 6, HVR-L3 comprising the amino acid sequence of SEQ ID NO: 9, and HVR-H2 comprising the amino acid sequence of SEQ ID NO: 34. In a further embodiment, the anti-TGFβ3 antibody comprises HVR-H3 comprising the amino acid sequence of SEQ ID NO: 6, HVR-L3 comprising the amino acid sequence of SEQ ID NO: 9, and HVR-H2 comprising the amino acid sequence of SEQ ID NO: 35. In a further embodiment, the anti-TGFβ3 antibody comprises HVR-H3 comprising the amino acid sequence of SEQ ID NO: 6, HVR-L3 comprising the amino acid sequence of SEQ ID NO: 9, and HVR-H2 comprising the amino acid sequence of SEQ ID NO: 159. In a further embodiment, the anti-TGFβ3 antibody comprises (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO:6. In a further embodiment, the anti-TGFβ3 antibody comprises (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO:6. In a further embodiment, the anti-TGFβ3 antibody comprises (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO:6. In a further embodiment, the anti-TGFβ3 antibody comprises (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO:6.

In another aspect, the invention provides an anti-TGFβ3 antibody comprising at least one, at least two, or all three VL HVR sequences selected from (a) HVR-L1 comprising the amino acid sequence of SEQ ID NO: 7; (b) HVR-L2 comprising the amino acid sequence of SEQ ID NO: 8; and (c) HVR-L3 comprising the amino acid sequence of SEQ ID NO: 9. In one embodiment, the antibody comprises (a) HVR-L1 comprising the amino acid sequence of SEQ ID NO: 7; (b) HVR-L2 comprising the amino acid sequence of SEQ ID NO: 8; and (c) HVR-L3 comprising the amino acid sequence of SEQ ID NO: 9.

In another aspect, an anti-TGFβ3 antibody of the invention comprises (a) a VH domain comprising at least one, at least two, or all three VH HVR sequences selected from (i) HVR-H1 comprising the amino acid sequence of SEQ ID NO: 4, (ii) HVR-H2 comprising the amino acid sequence of SEQ ID NO: 5, and (iii) HVR-H3 comprising an amino acid sequence selected from SEQ ID NO: 6; and (b) a VL domain comprising at least one, at least two, or all three VL HVR sequences selected from (i) HVR-L1 comprising the amino acid sequence of SEQ ID NO: 7, (ii) HVR-L2 comprising the amino acid sequence of SEQ ID NO: 8, and (c) HVR-L3 comprising the amino acid sequence of SEQ ID NO: 9. In another aspect, an anti-TGFβ3 antibody of the invention comprises (a) a VH domain comprising at least one, at least two, or all three VH HVR sequences selected from (i) HVR-H1 comprising the amino acid sequence of SEQ ID NO: 4, (ii) HVR-H2 comprising the amino acid sequence of SEQ ID NO: 34, and (iii) HVR-H3 comprising an amino acid sequence selected from SEQ ID NO: 6; and (b) a VL domain comprising at least one, at least two, or all three VL HVR sequences selected from (i) HVR-L1 comprising the amino acid sequence of SEQ ID NO: 7, (ii) HVR-L2 comprising the amino acid sequence of SEQ ID NO: 8, and (c) HVR-L3 comprising the amino acid sequence of SEQ ID NO: 9. In another aspect, an anti-TGFβ3 antibody of the invention comprises (a) a VH domain comprising at least one, at least two, or all three VH HVR sequences selected from (i) HVR-H1 comprising the amino acid sequence of SEQ ID NO: 4, (ii) HVR-H2 comprising the amino acid sequence of SEQ ID NO: 35, and (iii) HVR-H3 comprising an amino acid sequence selected from SEQ ID NO: 6; and (b) a VL domain comprising at least one, at least two, or all three VL HVR sequences selected from (i) HVR-L1 comprising the amino acid sequence of SEQ ID NO: 7, (ii) HVR-L2 comprising the amino acid sequence of SEQ ID NO: 8, and (c) HVR-L3 comprising the amino acid sequence of SEQ ID NO: 9. In another aspect, an anti-TGFβ3 antibody of the invention comprises (a) a VH domain comprising at least one, at least two, or all three VH HVR sequences selected from (i) HVR-H1 comprising the amino acid sequence of SEQ ID NO: 4, (ii) HVR-H2 comprising the amino acid sequence of SEQ ID NO: 159, and (iii) HVR-H3 comprising an amino acid sequence selected from SEQ ID NO: 6; and (b) a VL domain comprising at least one, at least two, or all three VL HVR sequences selected from (i) HVR-L1 comprising the amino acid sequence of SEQ ID NO: 7, (ii) HVR-L2 comprising the amino acid sequence of SEQ ID NO: 8, and (c) HVR-L3 comprising the amino acid sequence of SEQ ID NO: 9.

In another aspect, the invention provides an anti-TGFβ3 antibody comprising (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9. In another aspect, the invention provides an anti-TGFβ3 antibody comprising (a) HVR-H1 comprising the amino acid sequence of SEQ ID NO: 4; (b) HVR-H2 comprising the amino acid sequence of SEQ ID NO: 34; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9. In another aspect, the invention provides an anti-TGFβ3 antibody comprising (a) HVR-H1 comprising the amino acid sequence of SEQ ID NO: 4; (b) HVR-H2 comprising the amino acid sequence of SEQ ID NO: 35; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9. In another aspect, the invention provides an anti-TGFβ3 antibody comprising (a) HVR-H1 comprising the amino acid sequence of SEQ ID NO: 4; (b) HVR-H2 comprising the amino acid sequence of SEQ ID NO: 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9.

In certain embodiments, any one or more amino acids of an anti-TGFβ3 antibody as provided above are substituted at the following HVR positions:

in HVR-H2 (SEQ ID NO: 5): at position N54 (e.g., N54S, N54Q) or T56 (e.g., T56A).

In certain embodiments, the substitutions are conservative substitutions, as provided herein.

Figure 10:
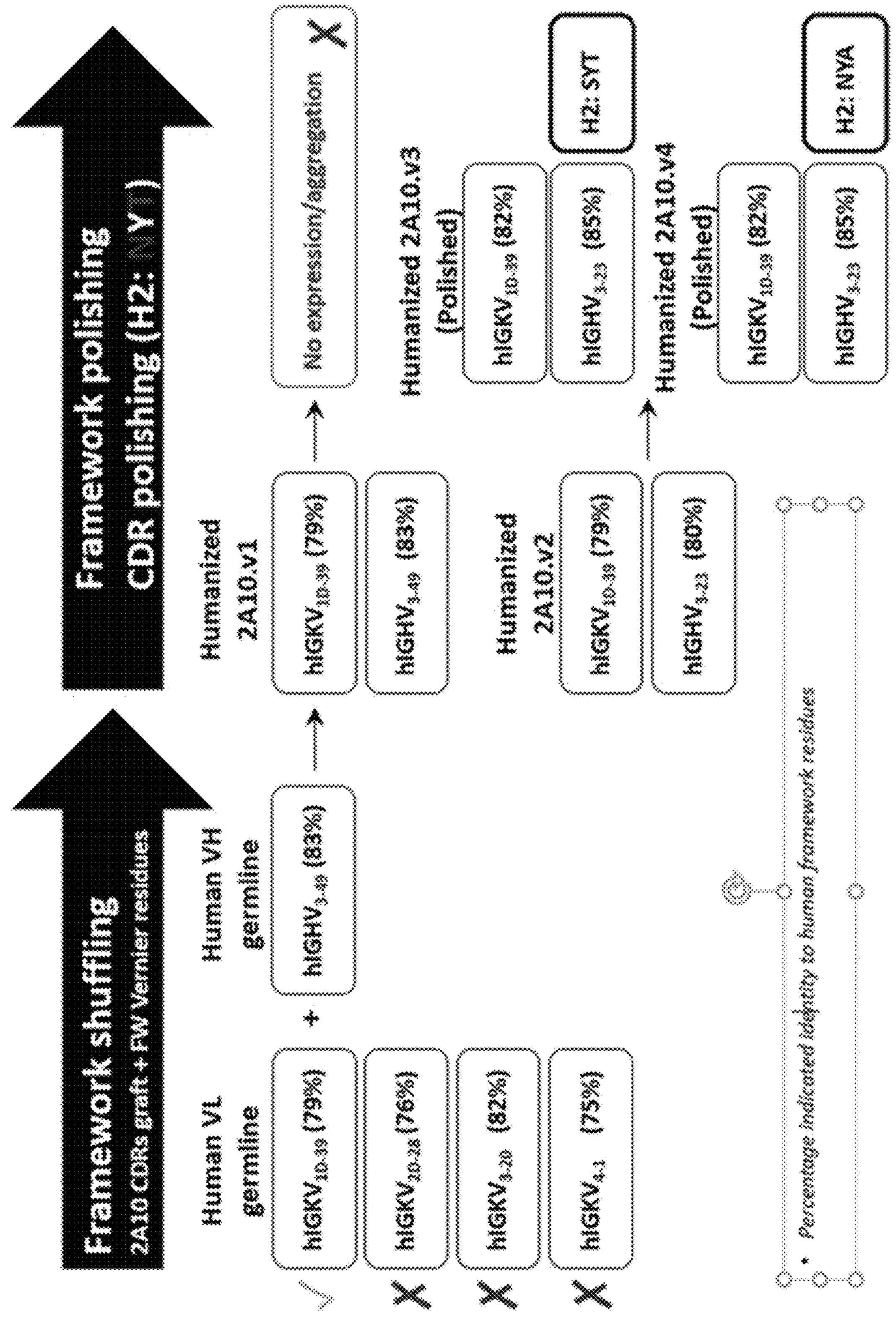
FIG. 10 is a schematic showing the attempts to express various humanized variants of 2A10 mAb.
Figure 13:
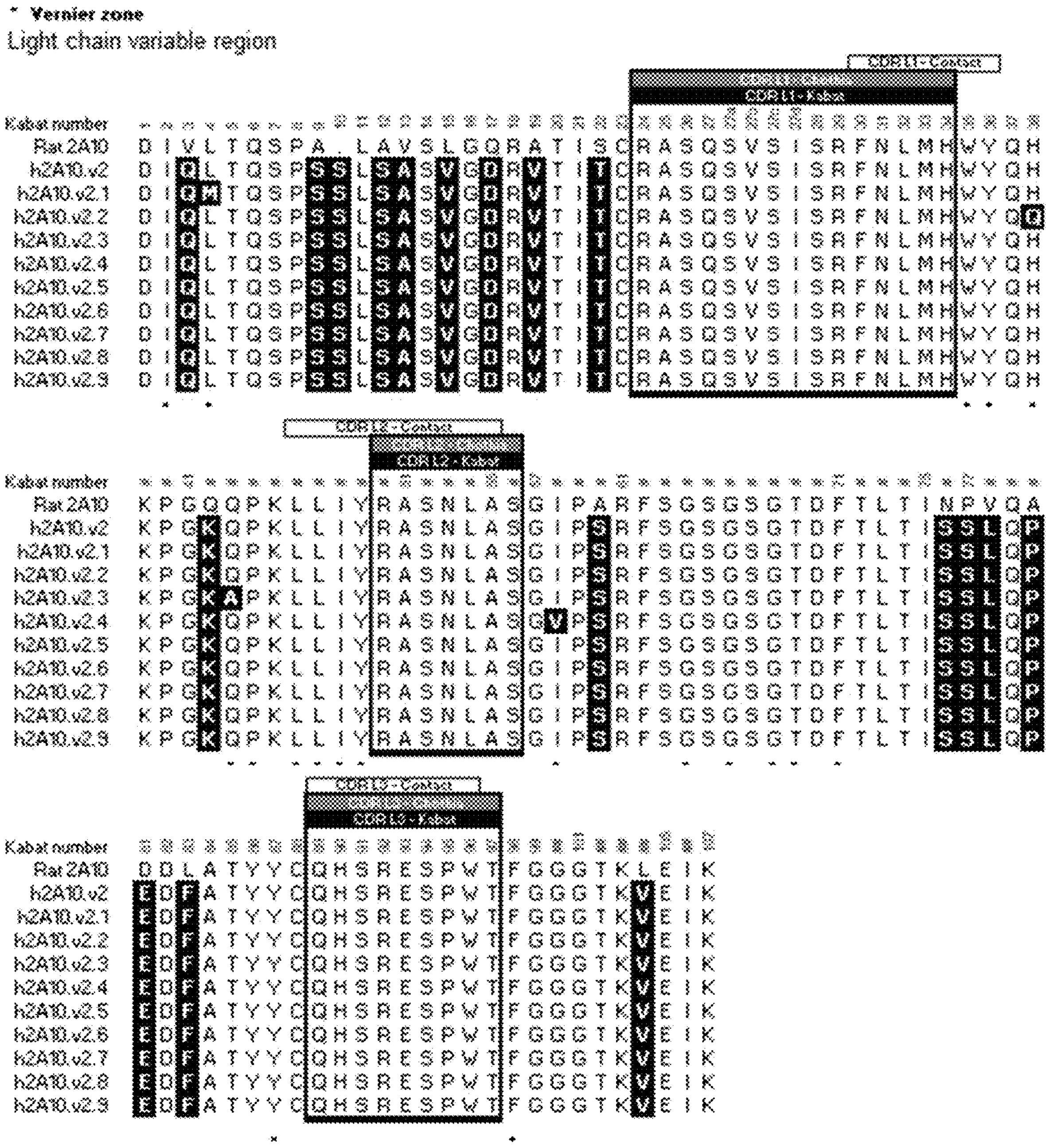
FIG. 13 contains an amino acid sequence alignment of the light chain variable region of the rat 2A10 and humanized h2A10 v2 variants, v2-v2.9; the sequences shown correspond to SEQ ID NOs: 22, 36, 38, 39, 40, 41, 36, 36, 36, 36, and 36 (from top sequence to bottom sequence in the alignment). Residue numbering is according to Kabat; "*" indicates Vernier zone. CDR regions according to Chothia or Kabat (as indicated) are boxed; mutated residues are highlighted.
Figure 14:
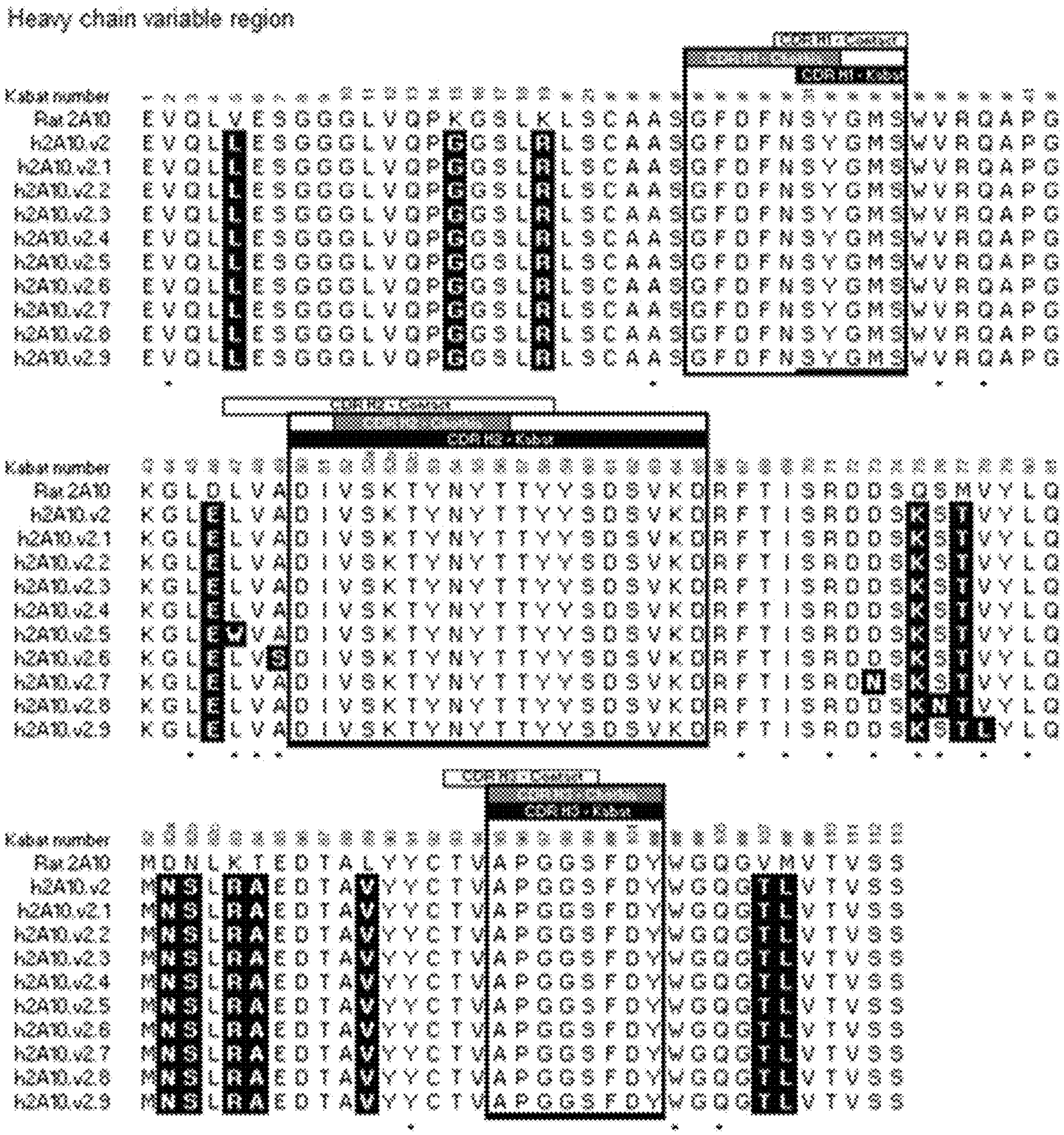
FIG. 14 contains an amino acid sequence alignment of the heavy chain variable region of the rat 2A10 and humanized h2A10 v2 variants, v2-v2.9; the sequences shown correspond to SEQ ID NOs: 23, 45, 45, 45, 45, 45, and 46-50 (from top sequence to bottom sequence in the alignment). Residue numbering is according to Kabat; "*" indicates Vernier zone. CDR regions according to Chothia or Kabat (as indicated) are boxed; mutated residues are highlighted.

In any of the above embodiments, an anti-TGFβ3 antibody is humanized. In some aspects, an anti-TGFβ3 antibody provided herein that has undergone one or more humanization steps has TGFβ blocking ability similar to the parent antibody, and/or human TGFβ binding similar to the parent antibody, and/or maintains solubility, and/or is able to be expressed, whereas such capabilities may be unknown or not observed in variants potentially or actually derived from other TGFβ3 antibodies (Example 6, Tables 9 and 10; FIGS. 10, 11). In one embodiment, an anti-TGFβ3 antibody comprises HVRs as in any of the above embodiments, and further comprises an acceptor human framework, e.g. a human immunoglobulin framework or a human consensus framework. In another embodiment, an anti-TGFβ3 antibody comprises HVRs as in any of the above embodiments, and further comprises a VH comprising FR modifications selected from the group consisting of 47L or 47W; 49A, 49S, or 49G; 73D or 73N; and 76N, 78D or 78L, 78A, or 78V. In some embodiments, the anti-TGFβ3 antibody comprises a VH, wherein the VH comprises the amino acid sequence of SEQ ID NO: 23, wherein the VH comprises a set of framework modifications selected from the group consisting of (i) 47L, 49A in FR2, 78V in FR3 (h2A10.v1); (ii) 47L, 49A in FR2, 73D, 76S, 78V in FR3 (h2A10.v2); (iii) 47W in FR2 (h2A10.v1.5); (iv): 49G in FR2 (h2A10.v1.6); (v) 78A in FR3 (h2A10.v1.7); (vi) 47W in FR2 (h2A10.v2.5); (vii) 49S in FR2 (h2A10.v2.6); (viii) 73N in FR3 (h2A10.v2.7); (ix) 76N in FR3 (h2A10.v2.8); (x) 78L in FR3 (h2A10.v2.9); and (xi) 49S in FR2, 76N, 78L in FR3 (h2A10.v3 and h2A10.v4). In another embodiment, an anti-TGFβ3 antibody comprises HVRs as in any of the above embodiments, and further comprises a VL comprising FR modifications selected from the group consisting of: 4L or 4M, 38H or 38Q, 43A or 43Q, and 58V (relative to the VL amino acid sequence of SEQ ID NO: 22). In another embodiment, the antibody comprises the VL of SEQ ID NO: 22, wherein the VL comprises a set of framework modifications selected from the group consisting of: (i) 4L in FR1, 38H and 43Q in FR2, 581 in FR3 (h2A10.v1 and h2A10.v2); (ii) 4M in FR1 (h2A10.v1.1 and h2A10.v2.1); (iii) 38Q in FR2 (h2A10.v1.2 and h2A10.v2.2); (iv) 43A in FR2 (h2A10.v1.3 and h2A10.v2.3); (v) 58V in FR3 (h2A10.v1.4 and h2A10.v2.4); (vi) 38Q, 43A in FR2, 58V in FR3 (h2A10.v3 and h2A10.v4); (vii) 58V in FR3 (h2A10.v1.4 and h2A10.v2.4); and (vi) 38Q, 43A in FR2, 58V in FR3 (h2A10.v3 and h2A10.v4).

In another aspect, an anti-TGFβ3 antibody comprises a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, 42-50, 55, and 57. In another aspect, an anti-TGFβ3 antibody comprises a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, and 42-50. In some aspects, an anti-TGFβ3 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 57. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TGFβ3 antibody comprising that sequence retains the ability to bind to TGFβ3. In certain embodiments, a total of 1 to 10 amino acids have been substituted, inserted and/or deleted in SEQ ID NO: 23. In certain embodiments, substitutions, insertions, or deletions occur in regions outside the HVRs (i.e., in the FRs). Optionally, the anti-TGFβ3 antibody comprises the VH sequence selected from the group consisting of SEQ ID NOs: 23, 37, 42-50, 55, and 57, including post-translational modifications of that sequence. Optionally, the anti-TGFβ3 antibody comprises the VH sequence selected from the group consisting of SEQ ID NOs: 23, 37, and 42-50, including post-translational modifications of that sequence. In a particular embodiment, the VH comprises one, two or three HVRs selected from: (a) HVR-H1 comprising the amino acid sequence of SEQ ID NO: 4, (b) HVR-H2 comprising the amino acid sequence of SEQ ID NO: 5, and (c) HVR-H3 comprising the amino acid sequence of SEQ ID NO: 6. In a particular embodiment, the VH comprises one, two or three HVRs selected from: (a) HVR-H1 comprising the amino acid sequence of SEQ ID NO: 4, (b) HVR-H2 comprising the amino acid sequence of SEQ ID NO: 34, and (c) HVR-H3 comprising the amino acid sequence of SEQ ID NO: 6. In a particular embodiment, the VH comprises one, two or three HVRs selected from: (a) HVR-H1 comprising the amino acid sequence of SEQ ID NO: 4, (b) HVR-H2 comprising the amino acid sequence of SEQ ID NO: 35, and (c) HVR-H3 comprising the amino acid sequence of SEQ ID NO: 6. In a particular embodiment, the VH comprises one, two or three HVRs selected from: (a) HVR-H1 comprising the amino acid sequence of SEQ ID NO: 4, (b) HVR-H2 comprising the amino acid sequence of SEQ ID NO: 159, and (c) HVR-H3 comprising the amino acid sequence of SEQ ID NO: 6.

In another aspect, an anti-TGFβ3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, 38-41, 54, and 56. In another aspect, an anti-TGFβ3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, and 38-41. In some aspects, an anti-TGFβ3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence SEQ ID NO: 56. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-TGFβ3 antibody comprising that sequence retains the ability to bind to TGFβ3. In certain embodiments, a total of 1 to 10 amino acids have been substituted, inserted and/or deleted in SEQ ID NO: 22. In certain embodiments, the substitutions, insertions, or deletions occur in regions outside the HVRs (i.e., in the FRs). Optionally, the anti-TGFβ3 antibody comprises the VL sequence selected from the group consisting of SEQ ID NOs: 22, 36, 38-41, 54, and 56, including post-translational modifications of that sequence. Optionally, the anti-TGFβ3 antibody comprises the VL sequence selected from the group consisting of SEQ ID NOs: 22, 36, and 38-41, including post-translational modifications of that sequence. In a particular embodiment, the VL comprises one, two or three HVRs selected from (a) HVR-L1 comprising the amino acid sequence of SEQ ID NO: 7; (b) HVR-L2 comprising the amino acid sequence of SEQ ID NO: 8; and (c) HVR-L3 comprising the amino acid sequence of SEQ ID NO: 9.

In another aspect, an anti-TGFβ3 antibody is provided, wherein the antibody comprises a VH as in any of the embodiments provided above, and a VL as in any of the embodiments provided above. In one embodiment, the anti-TGFβ3 antibody comprises VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4), including post-translational modifications of those sequences. In one embodiment, the anti-TGFβ3 antibody comprises VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9), including post-translational modifications of those sequences. In some embodiments, the anti-TGFβ3 antibody comprises VH/VL sequences (respectively) of SEQ ID NOs: 57/56.

In another aspect, an anti-TGFβ3 antibody is provided, wherein the antibody comprises a complete H chain amino acid sequence having at least 95% sequence identity to the amino acid sequence selected from the group consisting of SEQ ID NOs: 29, 59, 64, 65-72, 77, and 79 and/or a complete L chain amino acid sequence having an amino acid sequence selected from the group consisting of SEQ ID NOs: 28, 58, 60-63, 76, and 78. In another aspect, an anti-TGFβ3 antibody is provided, wherein the antibody comprises a complete H chain amino acid sequence having at least 95% sequence identity to the amino acid sequence selected from the group consisting of SEQ ID NOs: 29, 59, 64, and 65-72 and/or a complete L chain amino acid sequence having an amino acid sequence selected from the group consisting of SEQ ID NOs: 28, 58, and 60-63. In some embodiments, the antibody comprises a complete H chain amino acid sequence having at least 95% sequence identity to SEQ ID NO: 79, and/or a complete L chain amino acid sequence of SEQ ID NO: 78. In some embodiments, the anti-TGFβ3 antibody comprises a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 77/76 (v3), and SEQ ID NOs: 79/78 (v4). In some embodiments, the anti-TGFβ3 antibody comprises a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9).

In another embodiment, an anti-TGFβ3 antibody is provided, wherein the antibody comprises a VH having at least 90%, 91%, 92%, 93%, 94%, 95%, 96%, 97%, 98%, 99%, or 100% sequence identity to the amino acid sequence of SEQ ID NO: 52. In some aspects, the anti-TGFβ3 antibody comprises a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41. In some aspects, the antibody comprises VH/VL sequences (respectively) comprising the amino acid sequences of SEQ ID NOs: 52/36 (h2A10.v2.N54Q). In some aspects, the antibody comprises a complete H chain having at least 90%, 91%, 92%, 93%, 94%, 95%, 96%, 97%, 98%, 99%, or 100% sequence identity to the amino acid sequence of SEQ ID NO: 74. In some aspects, the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63. In some aspects, the anti-TGFβ3 antibody comprises a complete H chain having at least 90%, 91%, 92%, 93%, 94%, 95%, 96%, 97%, 98%, 99%, or 100% sequence identity to the amino acid sequence of SEQ ID NO: 74 and a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63. In some aspects, the antibody comprises complete H/L chain sequences (respectively) comprising the amino acid sequences of SEQ ID NOs: 74/58.

In another embodiment, an anti-TGFβ3 antibody is provided, wherein the antibody comprises a VH having at least 90%, 91%, 92%, 93%, 94%, 95%, 96%, 97%, 98%, 99%, or 100% sequence identity to the amino acid sequence of SEQ ID NO: 51 or 55. In some aspects, the anti-TGFβ3 antibody comprises a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 54. In some aspects, the anti-TGFβ3 antibody comprises VH/VL sequences (respectively) comprising the amino acid sequences of SEQ ID NO: 51/36 or SEQ ID NO: 55/54 (h2A10.v3). In some aspects, the antibody comprises a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 76. In some aspects, the antibody comprises complete H/L chain sequences (respectively) comprising the amino acid sequences of SEQ ID NOs: 73/58 or SEQ ID NOs: 77/76.

In another embodiment, an anti-TGFβ3 antibody is provided, wherein the antibody comprises a VH having at least 90%, 91%, 92%, 93%, 94%, 95%, 96%, 97%, 98%, 99%, or 100% sequence identity to the amino acid sequence of SEQ ID NO: 53 or 57. In some aspects, the anti-TGFβ3 antibody comprises a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 56. In some aspects, the anti-TGFβ3 antibody comprises a VH having at least 90%, 91%, 92%, 93%, 94%, 95%, 96%, 97%, 98%, 99%, or 100% sequence identity to the amino acid sequence of SEQ ID NO: 57. In other aspects, the anti-TGFβ3 antibody comprises a VL having at least 90%, 91%, 92%, 93%, 94%, 95%, 96%, 97%, 98%, 99%, or 100% sequence identity to the amino acid sequence of SEQ ID NO: 56. In some aspects, the anti-TGFβ3 antibody comprises a VH having at least 90%, 91%, 92%, 93%, 94%, 95%, 96%, 97%, 98%, 99%, or 100% sequence identity to the amino acid sequence of SEQ ID NO: 57, and a VL amino acid sequence having at least 90%, 91%, 92%, 93%, 94%, 95%, 96%, 97%, 98%, 99%, or 100% sequence identity to the amino acid sequence of SEQ ID NOs: 56. In some aspects, the anti-TGFβ3 antibody comprises VH/VL sequences (respectively) comprising the amino acid sequences of SEQ ID NOs: 53/36 or SEQ ID NOs: 57/56 (h2A10.v4). In some aspects, the anti-TGFβ3 antibody comprises VH/VL sequences (respectively) comprising the amino acid sequences of SEQ ID NOs: 57/56 (h2A10.v4). In some aspects, the antibody comprises a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, 76, and 78. In some aspects, the anti-TGFβ3 antibody comprises a complete H chain having at least 90%, 91%, 92%, 93%, 94%, 95%, 96%, 97%, 98%, 99%, or 100% sequence identity to an amino acid sequence of SEQ ID NO: 79. In other aspects, the anti-TGFβ3 antibody comprises a complete L chain having at least 90%, 91%, 92%, 93%, 94%, 95%, 96%, 97%, 98%, 99%, or 100% sequence identity to an amino acid sequence of SEQ ID NO: 78. In still further aspects, the anti-TGFβ3 antibody comprises a complete H chain having at least 90%, 91%, 92%, 93%, 94%, 95%, 96%, 97%, 98%, 99%, or 100% sequence identity to an amino acid sequence of SEQ ID NO: 79; and comprises a complete L chain having at least 90%, 91%, 92%, 93%, 94%, 95%, 96%, 97%, 98%, 99%, or 100% sequence identity to an amino acid sequence of SEQ ID NO: 78. In some aspects, the antibody comprises a complete H chain having at least 95% sequence identity to the amino acid sequence of SEQ ID NO: 79 and/or a complete L chain amino acid sequence having at least 90%, 91%, 92%, 93%, 94%, 95%, 96%, 97%, 98%, 99%, or 100% sequence identity to an amino acid sequence of SEQ ID NO: 78. In some aspects, the anti-TGFβ3 antibody comprises complete H/L chain sequences (respectively) comprising the amino acid sequences of SEQ ID NOs: 75/58 or SEQ ID NOs: 79/78. In certain aspects, the anti-TGFβ3 antibody comprises complete H/L chain sequences (respectively) comprising the amino acid sequences of SEQ ID NOs: 79/78.

In a further aspect, the invention provides an anti-TGFβ3 antibody that binds to the same epitope as an anti-TGFβ3 antibody provided herein. For example, in certain embodiments, an antibody is provided that binds to the same epitope as the anti-TGFβ3 antibody comprising (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO:6. In one embodiment, an antibody is provided that binds to the same epitope as the anti-TGFβ3 antibody comprising (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO:6. In another embodiment, an antibody is provided that binds to the same epitope as the anti-TGFβ3 antibody comprising (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO:6. In another embodiment, an antibody is provided that binds to the same epitope as the anti-TGFβ3 antibody comprising (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO:6.

In another aspect, an anti-TGFβ3 antibody is provided that binds to the same epitope as the anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4). In another aspect, an anti-TGFβ3 antibody is provided that binds to the same epitope as the anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9).

In one embodiment, an anti-TGFβ3 antibody is provided that binds to the same epitope as the anti-TGFβ3 antibody comprising VH/VL sequences (respectively) of SEQ ID NOs: 57/56 (h2A10.v4).

In certain embodiments, an isolated anti-TGFβ3 antibody is provided that comprises an antigen binding domain that directly contacts amino acid residues R325, K331, W332, H334, E335, T387, I388, L389, Y391, V392, G393, R394, P396, K397, and V398 on human TGFβ3, wherein the anti-TGFβ3 antibody selectively neutralizes TGFβ3.

In some aspects, provided herein is an isolated anti-TGFβ3 antibody that comprises: heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9. In some embodiments, the CDR-H2 has the amino acid sequence of SEQ ID NO: 35. In certain embodiments, the isolated anti-TGFβ3 antibody further comprises a VH having at least 90%, 91%, 92%, 93%, 94%, 95%, 96%, 97%, 98%, 99%, or 100% sequence identity to the amino acid sequence of SEQ ID NO: 57. In some embodiments, the anti-TGFβ3 antibody further comprises a VL having at least 90%, 91%, 92%, 93%, 94%, 95%, 96%, 97%, 98%, 99%, or 100% sequence identity to the amino acid sequence of SEQ ID NO: 56. In certain embodiments, the anti-TGFβ3 antibody further comprises a complete H chain having at least 90%, 91%, 92%, 93%, 94%, 95%, 96%, 97%, 98%, 99%, or 100% sequence identity to an amino acid sequence of SEQ ID NO: 79. In other embodiments, the anti-TGFβ3 antibody further comprises a complete L chain having at least 90%, 91%, 92%, 93%, 94%, 95%, 96%, 97%, 98%, 99%, or 100% sequence identity to an amino acid sequence of SEQ ID NO: 78.

In another embodiment, an isolated anti-TGFβ3 antibody is provided that selectively neutralizes TGFβ3 and has reduced toxicity in mice relative to the pan-TGFβ antibody 1D11. In some embodiments, the anti-TGFβ3 antibody provided herein has reduced toxicity in mice relative to the pan-TGFβ antibody 1D11 at a dose of 50 mg/kg. The 1D11 antibody is described in Lonning et al. (Current Pharmaceutical Biotechnology, 2011, 12, 2176-2189) and has the following amino acid sequences:

```
VH:
                                  (SEQ ID NO: 160)
QVQLQQSGPELVRPGASVKLSCKASGYIFITYWMNWVKQRPGQGLEWIG
QIFPASGSTNYNEMFEGKATLTVDTSSSTAYMQLSSLTSEDSAVYYCAR
GDGNYALDAMDYWGQGTSVTVSS

VL:
                                  (SEQ ID NO: 161)
DIVLTQSPASLAVSLGQRATISCRASESVDSYGNSFMHWYQQKSGQPPK
LLIYLASNLESGVPARFSGSGSRTDFTLTIDPVEADDAATYYCQQNNED
PLTFGAGTKLEIK
```

In a further aspect of the invention, an isoform-selective anti-TGFβ antibody according to any of the above embodiments (e.g., monospecific anti-TGFβ2 and anti-TGFβ3 antibodies, and dual-specific, anti-TGFβ2/3 antibodies described herein) is a monoclonal antibody, including a chimeric, humanized or human antibody. In one embodiment, an isoform-selective anti-TGFβ antibody is an antibody fragment, e.g., a Fv, Fab, Fab', scFv, diabody, or F(ab')2 fragment. In another embodiment, the antibody is a full-length antibody, e.g., an intact IgG1 or IgG4 antibody, preferably a human IgG1, and still more preferably a human IgG1 comprising an N297 mutation (EU numbering as in Kabat), e.g., N297A or N297G, preferably N297G, or other antibody class or isotype as defined herein.

In a further aspect, an isoform-selective anti-TGFβ antibody according to any of the above embodiments may incorporate any of the features, singly or in combination, as described in Sections 1-7 below:

1. Antibody Affinity

In certain embodiments, an antibody provided herein has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, $K_D$ is measured by a radiolabeled antigen-binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER© multi-well plates (Thermo Scientific) are coated overnight with 5 pg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™ Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE©-2000 or a BIACORE®-3000 (BIAcore, Inc., Piscataway, N.J.) is performed at 25° C. with immobilized antigen CM5 chips at -10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 pg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., Proc. Nat'l *Acad. Sci.* USA 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J Immunol.,* 133: 3001 (1984); Brodeur et al., *Monoclonal Antibody Production Techniques and Applications*, pp. 51-63 (Marcel Dekker, Inc., New York, 1987); and Boerner et al., *J Immunol.,* 147: 86 (1991).) Human antibodies generated via human B-cell hybridoma technology are also described in Li et al., *Proc. Natl. Acad Sci USA,* 103:3557-3562 (2006) Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937

(2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol.* Biol. 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J.* Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for a TGFβ isoform (e.g., TGFβ1, TGFβ2, TGFβ3, or TGFβ2/3) and the other is for any other antigen. In certain embodiments, one of the binding specificities is for one TGFβ isoform (e.g., TGFβ1, TGFβ2, or TGFβ3) and the other is for a different TGFβ isoform. In certain embodiments, bispecific antibodies may bind to two different epitopes within a single TGFβ isoform. Bispecific antibodies may also be used to localize cytotoxic agents to cells that express one or more TGFβ isoform(s). Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J Immunol.,* 152:5368 (1994)); and preparing trispecific antibodies as described, e.g., in Tutt et al. *J Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to one or more TGFβ isoform(s) (e.g., TGFβ1, TGFβ2, and/or TGFβ3) as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |

TABLE 1-continued

| Original Residue | Exemplary Substitutions | Preferred Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

In certain embodiments, the N-glycosylation site in the CH2 domain of an isoform-selective anti-TGFβ antibody of the invention is mutated to prevent glycosylation. For example, an isoform-selective anti-TGFβ antibody with an aglycosylated Fc region can be made by mutagenizing the amino acid residue at position 297 as in the EU index in the CH2 domain of the Fc region (e.g., N297). In certain embodiments, the glycosylation in the CH2 domain of the Fc region can be eliminated by altering the glycosylation consensus site, i.e., Asn at position 297 followed by any amino acid residue (in the case of human IgG, Ser) and Thr. The glycosylation site can be altered by amino acid insertions, deletions, and/or substitutions. For example, one or more amino acid residues can be inserted between Asn and Ser or between Ser and Thr to alter the original glycosylation site, wherein the insertions do not regenerate an N-glycosylation site. In certain particular embodiments, the amino acid residue at position 297 as in the EU index (e.g., the N-glycosylated site in Fc) within the CH2 domain of human IgG Fc is mutated to abolish the glycosylation site. In certain particular embodiments, the amino acid residue at position 297 as in the EU index (e.g., N297) is changed to Gly, Ala, Gln, Asp, or Glu. In some particular embodiments, the amino acid residue at position 297 as in the EU index (e.g., N297) is changed to Gly or Ala. In other particular embodiments, the amino acid residue at position 297 as in the EU index (e.g., N297) is changed to Gly. In certain other embodiments, the amino acid residue at position 299 as in the EU index can be substituted with another amino acid, for example, Ala, Val, or Gly. In certain particular embodiments, the mutations that result in an aglycosylated Fc do not affect the structure and/or stability of the isoform-selective anti-TGFβ antibody.

In certain embodiments, an isoform-selective anti-TGFβ antibody of the invention comprises an Fc region in which the amino acid residue at position 297 as in the EU index in the CH2 domain is mutated. In certain embodiments, the amino acid residue at position 297 as in the EU index is changed to Gly or Ala, preferably to Gly. In certain other embodiments, the amino acid residue at position 297 as in the EU index is deleted. In other embodiments, the N-glycan attached to the wild type amino acid residue at position 297 as in the EU index (e.g., N297) can be removed enzymatically, e.g., by deglycosylation. Suitable glycolytic enzymes include without limitation, peptide-N-glycosidase (PNGase).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci.* USA 83:7059-7063 (1986)) and Hellstrom, I et al., *Proc. Nat'l Acad. Sci.* USA 82:1499-1502 (1985); U.S. Pat. No. 5,821,337 (see Bruggemann, M. et al., *J Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an isoform-selective anti-TGFβ antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an isoform-selective anti-TGFβ antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an isoform-selective anti-TGFβ antibody, nucleic acid encoding an antibody, e.g., as described above, is isolated and inserted into one or more vectors for further cloning and/or expression in a host cell.

Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES' technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J Gen Virol.* 36:59 (1977); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Isoform-selective anti-TGFβ antibodies provided herein may be identified, screened for, or characterized for their physical/chemical properties and/or biological activities by various assays known in the art, and their crystal structures may be solved.

1. Binding Assays and Other Assays

In one aspect, an antibody of the invention is tested for its antigen binding activity, e.g., by known methods such as ELISA, Western blot, etc.

In one aspect, antibody binding is detected using enzyme immunoassay. This technique is well-known in the art. See, Schuurs and VanWeemen, *Clinica Chimica Acta,* 81:1-40 (1977). In this technique, enzymes are applied as labels on antigen or antibodies for identification and localization of the immunoreactants. Any method in which the extent of binding of enzyme-labeled antigen, or enzyme labeled-antibody to its immunoreactant is measured, is included in this invention. The variety of enzymes used, methods of linking enzymes to the immunological components, purification of the conjugates, as well as various assay principles and methods are well described Schuurs and VanWeemen, supra.

In one aspect, antibody binding affinity is determined using Surface Plasmon Resonance (SPR) measurement with a BIAcore™-T200 instrument. In this method, a series S CM5 biosensor chip with protein A is applied to capture the antibody to achieve approximately 100 response units (RU) on each flow cell, followed by injection of 3-fold serial dilutions of the target antigen in appropriate buffer (e.g., HBS-EP buffer) at 25° C. with a flow rate of 50 μl/min for kinetics measurement. Association rates ($k_{on}$) and dissociation rates ($k_{off}$) may be calculated using a simple one-to-one Langmuir binding model (BIAcore T200 evaluation software version 2.0) to determine the equilibrium dissociation constant ($K_D$), calculated as the ratio $k_{off}/k_{on}$.

In another aspect, competition assays may be used to identify an antibody that competes with an isoform-specific anti-TGFβ antibody described herein. In certain embodiments, such a competing antibody binds to the same epitope (e.g., a linear or a conformational epitope) that is bound by the 4A11, 6F12, or 2A10 antibodies and humanized variants thereof as described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, an immobilized TGFβ isoform (e.g., TGFβ1, TGFβ2, or TGFβ3) is incubated in a solution comprising a first labeled antibody that binds to the TGFβ isoform (e.g., the 4A11, 6F12, or 2A10 antibody or a humanized variant thereof, e.g., as shown in Tables 5, 6, 7, 12, 13, 14, 19, 20, 23 and 24) and a second unlabeled antibody that is being tested for its ability to compete with the first antibody for binding to the TGFβ isoform. The second antibody may be present in a hybridoma supernatant. As a control, immobilized TGFβ isoform is incubated in a solution comprising the first labeled antibody but not the second unlabeled antibody. After incubation under conditions permissive for binding of the first antibody to the TGFβ isoform, excess unbound antibody is removed, and the amount of label associated with the immobilized TGFβ isoform is measured. If the amount of label associated with the immobilized TGFβ isoform is substantially reduced in the test sample relative to the control sample, then that indicates that the second antibody is competing with the first antibody for binding to the TGFβ isoform. See Harlow and Lane (1988) *Antibodies: A Laboratory Manual* ch. 14 (Cold Spring Harbor Laboratory, Cold Spring Harbor, N.Y.).

In another example, antibody binding and/or binding competition is assayed using a radioimmunoassay (RIA). RIA is a well-known technique. See, e.g., Chard, "An Introduction to Radioimmunoassy and Related Techniques", North-Holland Publishing Company, 1978. Any of the many variations of RIA can be used, such as homogeneous phase RIA, or heterogeneous or solid phase RIA, single antibody methods or "double" antibody methods, and direct (forward) or reverse sandwich assays. Particularly preferred are solid phase systems wherein the is covalently coupled to an insoluble support so that both the antibody and the bound complex after incubation can be readily separated from the soluble free fraction. A wide variety of solid phase supports have been described, which include particles of dextran, cellulose, continuous surfaces such as polystyrene or polypropylene discs, walls of plastic tubes, glass discs, glass particles, and the like. Particulate solid phases are widely used for a variety of different assays and are included in the present invention. Antibodies are attached to the particles by any of a number of techniques designed to yield a non-reversible covalent or non-covalent link between protein and particle, for example directly or by cyanogen bromide activation. Other alternatives are the use of antibodies entrapped in the interstices of a polyacrylamide gel, or bound to magnetic particles. The assay tube is set up with sample or standard, tracer and the appropriate amount of solid phase bound antibody, plus a detergent to prevent aggregation of the particles and non-specific absorption of the tracer. After an incubation period during which the tubes are continuously mixed, the solid phase is sedimented by centrifugation; the supernatant is removed and the solid phase subject to two or more washes with buffer in order to remove free tracer trapped within and between the particles. The counts on the solid phase (bound fraction) are then measured. Immunoradiometric assays, Chards, supra at 423, can also be used.

2. Activity Assays

In one aspect, assays are provided for identifying isoform-selective anti-TGFβ antibodies thereof having biological activity. Biological activity may include, e.g., the ability to bind to and neutralize one or more TGFβ isoforms in vitro and/or in vivo.

In certain embodiments, an antibody of the invention is tested for such biological activity in an in vitro assay. In one embodiment, HEK-Blue™ TGFβ cells (InvivoGen, San Diego, Calif.) stably expressing human TGFβRI, Smad3, Smad4 proteins and secreted alkaline phosphatase (SEAP) reporter gene under the control of the β-globin minimal promoter fused to three Smad3/4-binding elements (SBE) may be used to evaluate the blocking potency of anti-TGFβ antibodies.

In another embodiment, the biological activity of anti-TGFβ antibodies of the invention may be assessed using the assay described in Abe et al. *Analytical Biochemistry* (1994); 216 (2): 276-284. Briefly, this assay uses a mink lung epithelial (MLE) cell-based TGFβ blocking assay in which the MLE cells are transfected with a plasmid containing the luciferase gene downstream of plasminogen activator inhibitor 1 promoter. The antibodies are incubated with each TGFβ isoform (PeproTech, Rocky Hill, N.J.) at 25° C. for 1 h prior to the addition into $4\times10^4$ MLE reporter cells seeded in 96-well plate in 75 μL of assay buffer (DMEM high glucose with 0.5% heat inactivated FBS, 2 mM L-glutamine and 0.5% Penicillin Streptomycin). The final concentration of antibody and TGFβ is in the range of 0.001-200 nM and 20 pM respectively. The plate is incubated at 37° C. and 5% C02 for 20 h. The luciferase activity in cells is determined by adding Firefly Luciferase substrate according to the manufacturer's recommendations (Dual-Luciferase Reporter Assay System, Promega).

D. Immunoconjugates

The invention also provides immunoconjugates comprising an isoform-selective anti-TGFβ antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$ $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

E. Methods and Compositions for Diagnostics and Detection

In certain embodiments, any of the isoform-selective anti-TGFβ antibodies provided herein is useful for detecting the presence of one or more TGFβ isoforms (e.g., TGFβ1, TGFβ2, or TGFβ3) in a biological sample. The term "detecting" as used herein encompasses quantitative or qualitative detection. In certain embodiments, a biological sample comprises a cell or tissue, such as a cell or tissue from the lung, kidney, heart, pancreas, liver, or skin.

In one embodiment, an isoform-selective anti-TGFβ antibody for use in a method of diagnosis or detection is provided. In a further aspect, a method of detecting the presence of one or more TGFβ isoforms (e.g., TGFβ1, TGFβ2, or TGFβ3) in a biological sample is provided. In certain embodiments, the method comprises contacting the biological sample with an isoform-selective anti-TGFβ antibody as described herein under conditions permissive for binding of the isoform-selective anti-TGFβ antibody to one or more TGFβ isoforms (e.g., TGFβ1, TGFβ2, and/or TGFβ3), and detecting whether a complex is formed between the isoform-selective anti-TGFβ antibody and the TGFβ isoform(s). Such method may be an in vitro or in vivo method. In one embodiment, an anti-TGFβ antibody is used to select subjects eligible for therapy with an isoform-selective anti-TGFβ antibody, e.g., where the TGFβ isoform is a biomarker for selection of patients.

For example, it is demonstrated in Example 4, below, that TGFβ3 expression is markedly upregulated in SSc patients as compared to healthy controls, and further, that in qPCR analysis of bulk lung biopsy samples from patients with idiopathic pulmonary fibrosis (IPF), TGFβ3, and to a lesser extent, TGFβ2, were expressed at significantly higher levels compared to control lungs, whereas TGFβ1 expression was slightly lower on average in IPF compared to control. Thus in some embodiments, the expression levels of TGFβ isoforms, e.g., in a particular tissue, can be used to diagnose a patient with a condition of that tissue.

In some embodiments, the expression level of TGFβ2 and/or TGFβ3 can be used to identify patients that are likely to respond to treatment with an isoform-selective anti-TGFβ antibody of the invention, e.g., an anti-TGFβ2, anti-TGFβ2/3, or anti-TGFβ3 antibody as described herein. In some embodiments, a patient is determined to be more likely to respond to treatment with an isoform-selective anti-TGFβ antibody of the invention if the patient has elevated baseline level (prior to treatment with an isoform-selective anti-TGFβ antibody) relative to a reference level (e.g., healthy or control subject) of one or more or all of the biomarkers selected from TGFβ2, TGFβ3, periostin (POSTN) and cartilage oligomeric matrix protein (COMP). In some embodiments, such a patient has previously been administered an IL-6 inhibitor therapy, and has insufficient, minimal, or no response to said therapy. In some such embodiments, the IL-6 inhibitor is tocilizumab.

In some embodiments, the serum levels of the biomarkers (e.g., TGFβ2, TGFβ3, COMP and/or POSTN) are quantified in order to determine whether the patient is likely to respond to treatment with an isoform-selective anti-TGFβ antibody. In some embodiments, the patient is selected for treatment if the serum level of the one or more biomarkers (e.g., TGFβ2, TGFβ3, COMP and/or POSTN) is/are elevated at baseline relative to the reference level (e.g., in a healthy subject). In further embodiments, the patient that is identified as likely to respond to treatment with an isoform-selective anti-TGFβ antibody of the invention and/or that is selected for treatment is administered the isoform-selective anti-TGFβ antibody, e.g., in a therapeutically effective amount.

In certain embodiments, the serum levels of the biomarkers (e.g., TGFβ2, TGFβ3, COMP and/or POSTN) are quantified in order to determine that a patient is less likely to improve if the patient is administered a treatment comprising a therapeutic agent other than an isoform-selective anti-TGFβ antibody of the invention.

It is well within the skill in the art to measure levels of serum biomarkers, such as, e.g., TGFβ2, TGFβ3, POSTN and COMP. TGFβ isoform sequences have been provided, above. The nucleic and amino acid sequences of COMP and POSTN are known in the art and for reference, exemplary amino acid sequences are provided below:

The canonical amino acid sequence of human POSTN is:

```
                                     (SEQ ID NO: 162)
MIPFLPMFSLLLLLIVNPINANNHYDKILAHSRIRGRDQGPNVCALQQI

LGTKKKYFSTCKNWYKKSICGQKTTVLYECCPGYMRMEGMKGCPAVLPI

DHVYGTLGIVGATTTQRYSDASKLREEIEGKGSFTYFAPSNEAWDNLDS

DIRRGLESNVNVELLNALHSHMINKRMLTKDLKNGMIIPSMYNNLGLFI

NHYPNGVVTVNCARIIHGNQIATNGVVHVIDRVLTQIGTSIQDFIEAED

DLSSFRAAAITSDILEALGRDGHFTLFAPTNEAFEKLPRGVLERIMGDK

VASEALMKYHILNTLQCSESIMGGAVFETLEGNTIEIGCDGDSITVNGI

KMVNKKDIVTNNGVIHLIDQVLIPDSAKQVIELAGKQQTTFTDLVAQLG

LASALRPDGEYTLLAPVNNAFSDDTLSMDQRLLKLILQNHILKVKVGLN

ELYNGQILETIGGKQLRVFVYRTAVCIENSCMEKGSKQGRNGAIHIFRE

IIKPAEKSLHEKLKystQDKRFSTFLSLLEAADLKELLTQPGDWTLFVP

TNDAFKGMTSEEKEILIRDKNALQNIILYHLTPGVFIGKGFEPGVTNIL

KTTQGSKIFLKEVNDTLLVNELKSKESDIMTTNGVIHVVDKLLYPADTP

VGNDQLLEILNKLIKYIQIKFVRGSTFKEIPVTVYTTKIITKVVEPKIK

VIEGSLQPIIKTEGPTLTKVKIEGEPEFRLIKEGETITEVIHGEPIIKK

YTKIIDGVPVEITEKETREERIITGPEIKYTRISTGGGETEETLKKLLQ

EEVTKVTKFIEGGDGHLFEDEEIKRLLQGDTPVRKLQANKKVQGSRRRL

REGRSQ.
```

The nucleic acid sequences and other variant amino acid sequences encoding human POSTN are known in the art and may be found in the Uniprot database accessible on the World Wide Web at uniprot.org/uniprot/Q15063 for Uniprot ID Q15063.

The canonical amino acid sequence of human COMP is:

(SEQ ID NO: 163)

```
MVPDTACVLLLTLAALGASGQGQSPLGSDLGPQMLRELQETNAALQDVR

ELLRQQVREITFLKNTVMECDACGMQQSVRTGLPSVRPLLHCAPGFCFP

GVACIQTESGARCGPCPAGFTGNGSHCTDVNECNAHPCFPRVRCINTSP

GFRCEACPPGYSGPTHQGVGLAFAKANKQVCTDINECETGQHNCVPNSV

CINTRGSFQCGPCQPGFVGDQASGCQRRAQRFCPDGSPSECHEHADCVL

ERDGSRSCVCAVGWAGNGILCGRDTDLDGFPDEKLRCPERQCRKDNCVT

VPNSGQEDVDRDGIGDACDPDADGDGVPNEKDNCPLVRNPDQRNTDEDK

WGDACDNCRSQKNDDQKDTDQDGRGDACDDDIDGDRIRNQADNCPRVPN

SDQKDSDGDGIGDACDNCPQKSNPDQADVDHDFVGDACDSDQDQDGDGH

QDSRDNCPTVPNSAQEDSDHDGQGDACDDDDDNDGVPDSRDNCRLVPNP

GQEDADRDGVGDVCQDDFDADKVVDKIDVCPENAEVTLTDFRAFQTVVL

DPEGDAQIDPNWVVLNQGREIVQTMNSDPGLAVGYTAFNGVDFEGTFHV

NTVTDDDYAGFIFGYQDSSSFYVVMWKQMEQTYWQANPFRAVAEPGIQL

KAVKSSTGPGEQLRNALWHTGDTESQVRLLWKDPRNVGWKDKKSYRWFL

QHRPQVGYIRVRFYEGPELVADSNVVLDTTMRGGRLGVFCFSQENIIWA

NLRYRCNDTIPEDYETHQLRQA.
```

The nucleic acid sequences and other variant amino acid sequences encoding human COMP are known in the art and may be found in the Uniprot database, accessible on the World Wide Web uniprot.org/uniprot/P49747 for Uniprot ID P49747.

Serum levels of POSTN and COMP may be determined by any suitable method known in the art, e.g., ELISA, microarray, or PCR. In another embodiment, protein levels of POSTN and COMP may be detected using IMPACT-based specific immunoassays, e.g., as described below, in Example 4. For example, whole blood may be collected from a subject or patient according to suitable methods in the art, allowed to clot, and then spun down. Serum biomarker levels are determined using IMPACT-based specific immunoassays (Roche Diagnostics, Penzberg, Germany). In brief, samples may be incubated with an IMPACT chip coated with biotinylated F(ab')2 antibody fragments specific for a target protein of interest (e.g., a biomarker, such as, e.g., TGFβ2, TGFβ3, COMP or POSTN). After wash steps, biomarker-specific detection antibodies labelled with digoxigenin are added and incubated. After washing, fluorescence anti-digoxigenin-latex conjugate was added, and the specifically-bound fluorescence label may be detected with a charge-coupled detector camera. Emitted fluorescence is transformed into signal intensities using a standard curve composed of recombinant protein standards (R&D Systems, Minneapolis, Minn., USA) and dedicated software (Roche Diagnostics).

Nucleic acid, according to any of the methods described herein may be RNA transcribed from genomic DNA or cDNA generated from RNA. Nucleic acid may be derived from a vertebrate, e.g., a mammal. A nucleic acid is said to be "derived from" a particular source if it is obtained directly from that source or if it is a copy of a nucleic acid found in that source.

Nucleic acid includes copies of the nucleic acid, e.g., copies that result from amplification. Amplification may be desirable in certain instances, e.g., in order to obtain a desired amount of material for detecting variations. The amplicons may then be subjected to a variation detection method, such as those described below, to determine expression of certain genes.

A microarray is a multiplex technology that typically uses an arrayed series of thousands of nucleic acid probes to hybridize with, e.g., a cDNA or cRNA sample under high-stringency conditions. Probe-target hybridization is typically detected and quantified by detection of fluorophore-, silver-, or chemiluminescence-labeled targets to determine relative abundance of nucleic acid sequences in the target. In typical microarrays, the probes are attached to a solid surface by a covalent bond to a chemical matrix (via epoxy-silane, amino-silane, lysine, polyacrylamide or others). The solid surface is for example, glass, a silicon chip, or microscopic beads. Various microarrays are commercially available, including those manufactured, for example, by Affymetrix, Inc. and Illumina, Inc.

In another embodiment, serum biomarker levels may be measured using the clinical trial version of the Elecsys (Roche Diagnostics) POSTN immunoassay intended for use on the cobas e601 (Roche Diagnostics).

In some embodiments, a method of determining disease burden and/or prognosis in a subject having a fibrotic condition is provided. In some non-limiting embodiments, the fibrotic condition is SSc or IPF. The method can include detecting the peripheral blood serum levels of POSTN and/or COMP in the subject.

Methods for detecting levels of proteins are known in the art. Expression levels of proteins may be detected in samples of whole blood, plasma, or serum. Various methods are known in the art for detecting protein expression levels in such biological samples, including various immunoassay methods. A wide range of immunoassay techniques have been previously described, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used assays. A number of variations of the sandwich assay technique exist, and all are intended to be encompassed by the present invention. Briefly, in a typical forward assay, an unlabeled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

In other embodiments, the presence of elevated levels of one or more TGFβ isoforms can be used diagnostically to determine the presence or incipient presence of pathologies deriving from a TGFβ-related disorder (e.g., fibrosis or cancer). For example, immunoassays utilizing anti-TGFβ antibodies provide such a diagnostic test. Various formats of such assays are available and well known to those skilled in the art, including RIA, ELISA and immunofluorescence. See generally, Ruoslahti et al., M. Enz., 82:803-831 (1982). Alternatively, nucleic acid probes can be used to detect and quantitate TGFβ mRNA for the same purpose. Such methods are also well known in the art.

In some embodiments, the subject is monitored over time, and starting serum levels of the biomarkers are compared to the levels at later timepoints during treatment, to assess whether the subject's disease burden is changing and/or whether the subject's prognosis is improving or worsening. In some embodiments, a subject's condition and/or prognosis is less likely to improve if the expression level of one or both of POSTN and COMP is increased relative to a healthy control or reference standard, or relative to the subject's POSTN or COMP levels at the start of or prior to starting a treatment regimen for the TGFβ-related disorder, e.g., IPF or SSc.

In some aspects, a method of identifying a subject as one who has high TGFβ activity and/or as likely to benefit from treatment with an inhibitor of a TGFβ isoform, e.g., with an isoform-selective anti-TGFβ antibody of the invention (e.g., an anti-TGFβ2, anti-TGFβ2/3, or anti-TGFβ3 antibody as described herein), is provided. In some aspects the subject has SSc. In some aspects, the subject has IPF. In some aspects, the method comprises detecting the expression levels of one or more of the genes in an 18-gene signature set with the following genes: PRSS23, PXDN, COL8A1, COL6A3, SERPINE2, TNC, COMP, THBS1, COL11A1, COL1A1, COL5A2, COL1A2, COL4A1, COL4A2, SFRP4, ALPK2, COL5A1, TAGLN. The genes of the 18-gene signature set are described in Table 2, below. In some aspects, the method comprises identifying the subject as one who has high TGFβ activity and/or as likely to benefit from treatment with an inhibitor of a TGFβ isoform if the levels of 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, or all 18 of the genes in the 18-gene signature set are elevated relative to the levels of the gene in a healthy control set (e.g., a reference value). In one aspect, the method comprises identifying the subject as one having high TGFβ activity and/or as likely to benefit from treatment with an inhibitor of a TGFβ isoform if the level of each and all of the 18 genes in the 18-gene signature set is elevated relative to the levels of the respective gene in a healthy control set.

TABLE 2

18-gene signature set

| | Gene Name | GenBank ® Accession No. (nucleotide) | SEQ ID NOs: |
|---|---|---|---|
| 1 | PRSS23 | NM_007173.6 | 164 |
| 2 | PXDN | NM_012293.3 | 165 |
| 3 | COL8A1 | NM_001850.5 | 166 |
| 4 | COL6A3 | NM_004369.4 | 167 |
| 5 | SERPINE2 | NM_006216.3 | 168 |
| 6 | TNC | NM_002160.4 | 169 |
| 7 | COMP | NM_000095.3 | 170 |
| 8 | THBSI | NM_003246.4 | 171 |
| 9 | COL11A1 | NM_001854.4 | 172 |
| 10 | COL1A1 | NM_000088.4 | 173 |
| 11 | COL5A2 | NM_000393.5 | 174 |
| 12 | COL1A2 | NM_000089.4 | 175 |
| 13 | COL4A1 | NM_001845.6 | 176 |
| 14 | COL4A2 | NM_001846.4 | 177 |
| 15 | SFRP4 | NM_003014.4 | 178 |
| 16 | ALPK2 | NM_052947.4 | 179 |
| 17 | COL5A1 | NM_000093.5 | 180 |
| 18 | TAGLN | NM_001001522.2 | 181 |

In a specific embodiment, a subject is identified as one who has high TGFβ 3 activity and/or as likely to benefit from treatment with an inhibitor of a TGFβ 3 isoform if the levels of one or more of the genes selected from SERPINE1, COL1A1, COL1A2, and COL1A1 are elevated relative to the level of the respective gene in a healthy control set (e.g., a reference value). The genes of this gene set are described in more detail in Table 3, below. In some aspects, the method comprises identifying the subject as one who has high TGFβ activity and/or as likely to benefit from treatment with an inhibitor of a TGFβ isoform if the levels of 1 or more, 2 or more, 3 or more, or all 4 of the genes SERPINE1, COL1A1, COL1A2, and COL3A1 are elevated relative to the level of the respective gene in a healthy control set (e.g., a reference value).

TABLE 3

TGFβ Gene Signature

| | Gene Name | GenBank ® Accession No. (nucleotide) | SEQ ID NO: |
|---|---|---|---|
| 1 | SERPINE1 | NM_000602.5 | 182 |
| 2 | COL1A1 | NM_000088.4 | 173 |
| 3 | COL1A2 | NM_000089.4 | 175 |
| 4 | COL3A1 | NM_000090.4 | 183 |

In some embodiments of the above methods, the gene expression level is considered to be elevated if its increase in expression relative to the control or reference level of the gene is statistically significant. Methods for determining statistical significance are well-known in the art. By way of non-limiting example, statistical significance may be determined using, e.g., the unpaired two-tailed Student's t-test. In other embodiments, the gene expression level is considered to be elevated if its increase in expression relative to the control or reference level of the gene is at least 2-fold, at least 3-fold, or at least 4-fold.

In other aspects, methods of monitoring response to treatment of a subject with a TGFβ inhibitor, such as, e.g., an anti-TGFβ2 antibody and/or an anti-TGFβ3 antibody as described herein, are provided. The method includes determining the expression level of one or more of the TGFβ-inducible genes selected from PRSS23, PXDN, COL8A1, COL6A3, SERPINE2, TNC, COMP, THBS1, COL11A1, COL1A1, COL5A2, COL1A2, COL4A1, COL4A2, SFRP4, ALPK2, COL5A1, TAGLN and/or one or more of the genes selected from SERPINE1, COL1A1, COL1A2, and COL3A1. In some embodiments, the method further comprises stopping treatment with the TGFβ inhibitor if the expression levels of one or more of the genes selected from PRSS23, PXDN, COL8A1, COL6A3, SERPINE2, TNC, COMP, THBS1, COL11A1, COL1A1, COL5A2, COL1A2, COL4A1, COL4A2, SFRP4, ALPK2, COL5A1, TAGLN and/or one or more of the genes selected from SERPINE1, COL1A1, COL1A2, and COL3A1 are not decreased relative to the respective level at an earlier timepoint, e.g., prior to or at the beginning of treatment with the TGFβ inhibitor.

In another embodiment, a method of selecting a subject for treatment with a TGFβ inhibitor, such as, e.g., an anti-TGFβ2 antibody and/or an anti-TGFβ3 antibody as described herein is provided. The method can include detecting the level of one or both of serum POSTN and COMP in the subject, and administering the subject the TGFβ inhibitor if the levels of one or both of serum POSTN and COMP are elevated compared to a healthy control level. In some embodiments, the TGFβ inhibitor is an anti-TGFβ3 antibody, e.g., the antibody 2A10 or a humanized variant thereof, e.g., as shown in FIGS. 12-16 or Tables 5-7 in Example 1, below.

In some embodiments, the method of identifying the subject as one who has high TGFβ activity and/or as likely to benefit from treatment with an inhibitor of a TGFβ isoform, and/or for selecting a subject for treatment with a TGFβ inhibitor, comprises administering a therapy to the subject. In some embodiments, the therapy is for treating a TGFβ-related disorder, e.g., as described herein. In some embodiments, the therapy is for treating a fibrotic condition, e.g., as described herein. In some embodiments, the therapy comprises administering an anti-TGFβ2, anti-TGFβ2/3, or anti-TGFβ3 antibody as described herein. In a preferred embodiment, the therapy comprises administering an anti-TGFβ3 antibody as described herein, e.g., an isolated anti-TGFβ3 antibody, wherein the antibody selectively neutralizes TGFβ3, and wherein the antibody comprises one or more of the following features: (a) the anti-TGFβ3 antibody binds to the beta6/beta7 hairpin region of TGFβ3; (b) binding of the anti-TGFβ3 antibody sterically blocks the ability of TGFBR2, but not TGFBR1, to bind TGFβ3; (c) binding of the anti-TGFβ3 antibody to TGFβ3 blocks TGFBR2 binding and inhibits the TGFBR1/TGFBR2 signaling receptors from binding to TGFβ3; (d) the anti-TGFβ3 antibody binds amino acid residue R394 in the beta6/beta7 hairpin region of human TGFβ3; (e) the anti-TGFβ3 antibody binds amino acid residue R394 in the beta6/beta7 hairpin region of human TGFβ3 and residue R394 of TGFβ3 makes an ionic salt bridge with the anti-TGFβ3 antibody in the heavy chain CDR2; (f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering); (g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering); (h) the anti-TGFβ3 antibody has reduced toxicity relative to the pan-TGFβ antibody 1D11; (i) the anti-TGFβ3 antibody has reduced toxicity in rodents or cynomolgus monkeys relative to the pan-TGFβ antibody 1D11; (j) the anti-TGFβ3 antibody has reduced toxicity relative to the pan-TGFβ small molecule inhibitor galunisertib; (k) the anti-TGFβ3 antibody has reduced toxicity in rodents relative to the pan-TGFβ small molecule inhibitor galunisertib; (1) the anti-TGFβ3 antibody has reduced toxicity relative to the anti-TGFβ1 antibody CAT-192; (m) the anti-TGFβ3 antibody has reduced toxicity relative to an isoform selective anti-TGFβ2 antibody and/or anti-TGFβ2/3 antibody; (n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9; (o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

In some aspects of the above embodiments, the anti-TGFβ3 antibody comprises a VH/VL pair, the VH/VL pair comprising amino acid sequences (respectively) selected from SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9). In some embodiments, the anti-TGFβ3 antibody comprises a VH/VL pair comprising the amino acid sequences (respectively) of SEQ ID NOs: 52/36, or the amino acid sequences (respectively) of SEQ ID NOs: 51/36 or SEQ ID NOs: 55/54, or the amino acid sequences (respectively) of SEQ ID NOs: 53/36 or SEQ ID NOs: 57/56. In some embodiments, the anti-TGFβ3 antibody comprises a VH/VL pair comprising the amino acid sequences (respectively) of SEQ ID NOs: 57/56.

In some aspects of the above embodiments, the anti-TGFβ3 antibody comprises a complete H/L chain pair, the complete H/L chain pair comprising amino acid sequences (respectively) selected from SEQ ID NOs: 29/28 (rat 2A10), SEQ ID NOs: 59/58 (vi), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), or the amino acid sequences (respectively) of SEQ ID NOs: 74/58, or the amino acid sequences (respectively) of SEQ ID NOs: 73/58 or SEQ ID NOs: 77/76, or the amino acid sequences (respectively) of SEQ ID NOs: 75/58 or SEQ ID NOs: 79/78. In some aspects, the anti-TGFβ3 antibody comprises a complete H/L chain pair comprising the amino acid sequences (respectively) of SEQ ID NOs: 79/78.

In some aspects of the above embodiments, the therapy comprises administering an anti-TGFβ2/3 antibody as described herein, e.g., an isolated anti-TGFβ2/3 antibody, wherein the antibody selectively neutralizes TGFβ2 and TGFβ3, wherein the antibody comprises one or more of the following features: (a) selectivity of the anti-TGFβ2/3 antibody for TGFβ2 and TGFβ3 over human TGFβ1, with respect to selective neutralization, is achieved by direct contact of the antibody's antigen binding domain with amino acid residue E373 of TGFβ2 or TGFβ3 (human TGFβ2 numbering); (b) the anti-TGFβ2/3 antibody neutralizes TGFβ2 and/or TGFβ3 via an allosteric mechanism; (c) the anti-TGFβ2/3 antibody induces a conformational change in TGFβ2 homodimer; (d) the anti-TGFβ2/3 antibody induces a conformational change in TGFβ2 homodimer, wherein the conformational change comprises the two monomers pinching together by several degrees; (e) the anti-TGFβ2/3 antibody is a divalent antibody or a monovalent antibody; (f) the anti-TGFβ2/3 antibody comprises (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15; (g) the anti-TGFβ2/3 antibody binds to TGFβ2 homodimer, the TGFβ2 homodimer having a first and a second TGFβ2 monomer, and wherein the anti-TGFβ2/3 antibody comprises an antigen binding domain that directly contacts (i) amino acid residues V313, Q314, D315, R320, L322, Y323, R328, D329, F345, and A347 of the first TGFβ2 monomer, and (ii) amino acid residues N368, T369, I370, N371, P372, E373, A374, S375, A376, and S377 of the second TGFβ2 monomer (human TGFβ2 numbering); (h) the anti-TGFβ2/3 antibody as in (g), wherein the antigen-binding domain is within 5 angstroms of the TGFβ2 and/or TGFβ3 amino acid residues; (i) wherein the anti-TGFβ2/3 antibody binds to the same epitope on TGFβ3 as in (g); and (j) the anti-TGFβ2/3 antibody does not neutralize TGFβ2 and/or TGFβ3 in single arm form.

In some aspects of the above embodiments, the anti-TGFβ2/3 antibody comprises a VH/VL pair, the VH/VL pair comprising amino acid sequences (respectively) selected from SEQ ID NOs: 27/26 (rabbit 4A11), SEQ ID NOs: 81/80 (v1), SEQ ID NOs: 81/82 (v2), SEQ ID NOs: 83/80 (v3), SEQ ID NOs: 83/82 (v4), SEQ ID NOs: 81/84 (v5), SEQ ID NOs: 81/85 (v6), SEQ ID NOs: 83/84 (v7), SEQ ID NOs: 86/84 (v7/1), SEQ ID NOs: 87/84 (v7.2), SEQ ID NOs: 88/84 (v7.3), SEQ ID NOs: 83/89 (v7.4), SEQ ID NOs: 83/90 (v7.5), SEQ ID NOs: 83/91 (v7.6), SEQ ID NOs: 83/92 (v7.7), SEQ ID NOs: 93/84 (v7.8), SEQ ID NOs: 94/84 (v7.9), SEQ ID NOs: 95/84 (v7.10), SEQ ID NOs: 96/84 (v7.11), SEQ ID NOs: 97/84 (v7.12), SEQ ID NOs: 98/84 (v7.13), SEQ ID NOs: 99/84 (v7.14), SEQ ID NOs: 100/84 (v7.15), SEQ ID NOs: 102/101 (v7.16), SEQ ID NOs: 103/101 (v7.17), SEQ ID NOs: 104/101 (v7.18), SEQ ID NOs: 105/101 (v7.19), and SEQ ID NOs: 83/85 (v8).

In some aspects of the above embodiments, the anti-TGFβ2/3 antibody comprises a complete H/L chain pair, the complete H/L chain pair comprising amino acid sequences (respectively) selected from SEQ ID NOs: 32/33 (rabbit 4A11), SEQ ID NOs: 107/106 (v1), SEQ ID NOs: 107/108 (v2), SEQ ID NOs: 109/106 (v3), SEQ ID NOs: 109/108 (v4), SEQ ID NOs: 107/110 (v5), SEQ ID NOs: 107/111 (v6), SEQ ID NOs: 109/110 (v7), SEQ ID NOs: 112/110 (v7.1), SEQ ID NOs: 113/110 (v7.2), SEQ ID NOs: 114/110 (v7.3), SEQ ID NOs: 114/115 (v7.4), SEQ ID NOs: 114/116 (v7.5), SEQ ID NOs: 114/117 (v7.6), SEQ ID NOs: 114/118 (v7.7), SEQ ID NOs: 119/110 (v7.8), SEQ ID NOs:120/110 (v7.9), SEQ ID NOs: 121/110 (v7.10), SEQ ID NOs: 122/110 (v7.11), SEQ ID NOs: 123/110 (v7.12), SEQ ID NOs: 124/110 (v7.13), SEQ ID NOs: 125/110 (v7.14), SEQ ID NOs: 126/110 (v7.15), SEQ ID NOs: 127/186 (v7.16), SEQ ID NOs: 128/186 (v7.17), SEQ ID NOs: 129/186 (v7.18), SEQ ID NOs: 130/186 (v7.19), and SEQ ID NOs: 114/111 (v8).

In some aspects of the above embodiments, the therapy comprises administering an anti-TGFβ2 antibody as described herein, e.g., an isolated anti-TGFβ2 antibody, wherein the antibody comprises: (a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21. In some aspects, the antibody selectively neutralizes TGFβ2. In some aspects, the anti-TGFβ2 antibody has one or more of the following properties: (a) selectively neutralizes TGFβ2; (b) has reduced toxicity relative to the pan-TGFβ antibody 1D11; (c) has reduced toxicity relative to the pan-TGFβ antibody 1D11; (d) has reduced toxicity in rodents relative to the pan-TGFβ antibody 1D11; (e) has reduced toxicity relative to the pan-TGFβ small molecule inhibitor galunisertib; and/or (f) has reduced toxicity in rodents relative to the pan-TGFβ small molecule inhibitor galunisertib.

In some aspects of the above embodiments, the anti-TGFβ2 antibody comprises a VH/VL pair, the VH/VL pair comprising amino acid sequences (respectively) selected from SEQ ID NOs: 25/24 (rabbit 6F12), SEQ ID NOs: 132/131 (v1), SEQ ID NOs: 132/133 (v1.1), SEQ ID NOs: 132/134 (v1.2), SEQ ID NOs: 132/135 (v1.3), SEQ ID NOs: 132/136 (v1.4), SEQ ID NOs: 132/137 (v1.5), SEQ ID NOs: 138/131 (v1.6), SEQ ID NOs: 139/131 (v1.7), SEQ ID NOs: 140/131 (v1.8), SEQ ID NOs: 141/131 (v1.9), SEQ ID NOs: 142/131 (v2), SEQ ID NOs: 132/143 (v3), and SEQ ID NOs: 142/144 (v4).

In some aspects of the above embodiments, the anti-TGFβ2 antibody comprises complete H/L chain pair, the complete H/L chain pair comprising amino acid sequences (respectively) selected from SEQ ID NOs: 31/30 (rabbit 6F12), SEQ ID NOs: 146/145 (v1), SEQ ID NOs: 146/147 (v1.1), SEQ ID NOs: 146/148 (v1.2), SEQ ID NOs: 146/149 (v1.3), SEQ ID NOs: 146/150 (v1.4), SEQ ID NOs: 146/151 (v1.5), SEQ ID NOs: 152/145 (v1.6), SEQ ID NOs: 153/145 (v1.7), SEQ ID NOs: 154/145 (v1.8), SEQ ID NOs: 155/145 (v1.9), SEQ ID NOs: 156/145 (v2), SEQ ID NOs: 146/157 (v3), and SEQ ID NOs: 156/158 (v4).

Exemplary conditions and disorders that may be diagnosed and/or treated according to the present invention, e.g., as described above, include TGFβ-related disorders, e.g., diseases characterized by accumulation of extracellular matrix, diseases caused by circulating TGFβ or TGFβ activated at a local site, including one or more TGFβ isoforms, conditions caused by suppression of the immune system due to endogenous TGFβ production, acute immune deficiencies resulting from severe injuries, burns, and illnesses such as viral or bacterial infections, multi-organ systemic illnesses due to TGFβ production or overproduction, and TGFβ-producing tumors. In some embodiments, disorders that may be diagnosed using an isoform-selective anti-TGFβ antibody of the invention includes fibrotic disease, e.g., as described herein. In some embodiments, the fibrotic disease is a fibrotic disorder of the lung, liver, heart, kidney, pancreas, eye, and/or skin. In some embodiments, the fibrosis is a fibrotic condition or disorder as described in Section G, below.

In some embodiments, a TGFβ-related disorder that may be diagnosed using an antibody of the invention is diagnosed using one or more of the antibodies 4A11, 6F12, and 2A10, or a humanized variant thereof, e.g., as described herein, e.g., in FIGS. 12-16 and 18-24. In certain embodiments, labeled isoform-selective anti-TGFβ antibodies e.g., the antibodies described above, are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an isoform-selective anti-TGFβ antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a therapeutic agent selected from pirfenidone, nintedanib, mycophenylate mofetil, an IL-6 inhibitor (e.g., tocilizumab, see, e.g., U.S. Pat. No. 9,539,263, sarilumab), an anti-CTFG antibody (e.g., FG-3019), an autotaxin inhibitor, a JAK inhibitor, an IL-11 inhibitor, and serum amyloid P (PTX2). (See, Raghu et al. European Respiratory Journal 2012 40: 2819) (FG-309, Ninou et al. (2018) *Front Med* (*Lausanne*); 5: 180 (autotaxin inhibitors).) Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

It is presently discovered that the isoform-selective anti-TGFβ antibodies described herein are useful in therapeutic methods. TGFβ has long been implicated as a key mediator of pathological fibrosis but its multifarious homeostatic functions have presented challenges to developing therapeutic TGFβ inhibitors with an acceptable therapeutic index. While the three TGFβ isoforms are capable of mediating similar signaling activities on target cells, their divergent LAP domains and expression patterns implicate unique roles for each isoform, supported by genetic loss-of-function evidence in mice and humans. While not intending to bound by any one particular theory or mechanism of action, it is discovered herein that the thresholds for and mechanisms of activation of latent TGFβ2 and TGFβ3 are distinct from those of TGFβ1 (see, e.g., Example 14); TGFβ2 and TGFβ3, unlike TGFβ1, are expressed at elevated levels in human fibrotic tissue and in mouse models of lung and liver; and isoform-selective therapeutic inhibition of TGFβ2 and TGFβ3 with a potent allosteric antibody can ameliorate experimental fibrosis in vivo. These findings support isoform-selective TGFβ2 and/or TGFβ3 inhibition as a therapeutic strategy for patients with chronic fibrotic disorders. For example, in Example 4, below, it is demonstrated that TGFβ2 and/or TGFβ3 expression levels are elevated in human fibrotic tissue and TGFβ3 expression is highly correlated with TGFβR signaling in IPF and SSc, two different fibrotic disorders, and in Example 5, describing a mouse model of bleomycin-induced lung fibrosis, in which neutralization of TGFβ2 with 6F12, neutralization of TGFβ3 with 2A10, and neutralization of both TGFβ2 and TGFβ3 with either the combination of 6F12+2A10 antibodies or monotherapy with dual-specific (anti-TGFβ2/3) 4A11 antibody reduced new collagen synthesis. Further, in skin biopsies taken at baseline in the FaSScinate trial (SSc of the skin, see, Khanna et al. (2016) *The Lancet*; vol. 387:10038, p. 2630-2640), it is presently demonstrated that TGFβ3 expression, as well as expression of a specific set of genes in a TGFβ signature, are markedly upregulated in SSc patients as compared to healthy controls, and that TGFβ3 expression correlated strongly and positively with the TGFβ signature, supporting inhibition of TGβ3 for the treatment of SSc using an anti-TGFβ3 antibody as described herein. Further, the data in Example 16 show that treatment with neutralizing antibodies to TGFβ2 and TGFβ3 can reduce lung fibrosis in vivo, and the data in Example 17 show that TGFβ2 and TGFβ3 inhibition can reduce hepatic fibrosis in vivo. Thus, these data support the inhibition of TGFβ2 and/or TGFβ3 for the treatment of TGFβ-related disorders, such as but not limited to fibrotic conditions.

Thus, in certain aspects, the isoform-selective anti-TGFβ antibodies are useful for the treatment of TGFβ-related disorders. Non-limiting specific examples of TGFβ-related disorders include neuronal, glial, astrocytal, hypothalamic and other glandular, macrophagal, epithelial, stromal and blastocoelic disorders, fibrosis, scarring, tissue damage such as caused by radiation, and adhesion during wound healing, fibrotic skin disorders such as scleroderma, CNS pathology scar tissue, dermal scarring, keloid scarring, and neural scarring, fibrotic diseases of the peritoneal cavity, lungs, liver, and kidneys such as chronic hepatic fibrosis, acute liver injury, interstitial lung and renal fibrosis, and liver cirrhosis, cystic fibrosis, vascular disorders, e.g., cardiac fibrosis, arterial injury such as atherosclerosis and arteriosclerosis, benign and malignant tumors, certain leukemias not inhibited by TGFβ, and malignancies (e.g., sarcomas, carcinomas, and melanomas), including prostate, fibrotic, ovarian, malignant melanoma, breast, lung, colon, rectal, colorectal, or cervical cancer and metastatic cancer, as well as neuroendocrine tumors of the digestive system and glioblastomas, angiopathy, vasculopathy, nephropathy, systemic sclerosis, infections such as macrophage pathogen infections and viral infections such as hepatitis C and HIV, immunological, angiogenic, and inflammatory disorders and deficiencies such as rheumatoid arthritis, an ocular disorder, especially those involving ocular fibrosis, including proliferative retinopathy, retinal detachment and post-glaucoma drainage surgery such as neural retina, retinal pigment epithelium-choroid and vitreous of the human eye, and cataracts, osteoporosis, adult respiratory distress syndrome, post-myocardial infarction, post-angioplasty restenosis, glomerulonephritis, a diabetes-related condition such as hyperglycemia, diabetes, diabetic kidney disease, diabetic nephropathy, diabetic neuropathy or retinopathy, and macrophage-deficiency diseases.

Preferably, the TGFβ-related disorder is fibrosis, an arterial injury, an infection, rheumatoid arthritis, diabetes or a diabetic condition, or a malignancy, such as cancer that expresses TGFβ, more preferably wherein the cancer is characterized by excessive activation of TGFβ. Such cancer may overexpress TGFβ, or alternatively not be characterized by overexpression of TGFβ.

In further aspects, the isoform-selective anti-TGFβ antibodies are useful for the treatment of fibrotic diseases, e.g., fibrotic diseases of the lung, liver, kidney, skin, heart, pancreas, gastrointestinal organs, and genitourinary organs; vascular tissue; and ocular tissue such as corneal tissue, retinal tissue, and lacrimal gland tissues. In some embodiments, the isoform-selective anti-TGFβ antibodies are useful for the treatment of diseases and disorders associated with aberrant TGFβ regulation and function, for example, and without limitation, pulmonary fibrosis, glomerulonephritis and diabetic kidney disease, congestive heart failure, liver cirrhosis, Marfan syndrome hypertrophic scars and SSc. In certain embodiments, the fibrotic condition is related to an autoimmune condition. In other embodiments, the fibrotic condition is subsequent to injury, including radiation, alkali burn, physical burn, surgery, physical trauma, or a combination thereof. See, Niessen et al., "On the nature of hypertrophic scars and keloids: a review," *Plast. Reconstr. Surg.* 104:1435-1458 (1999); Friedlander M., "Fibrosis and diseases of the eye," *J. Clin. Invest.* 117:576-586 (2007); Noble et al., "Pulmonary fibrosis: patterns and perpetrators," *J. Clin. Invest.* 122:2756-2762 (2012); Bahn R. S., "Graves' ophthalmopathy," *N. Engl. J. Med.* 362:726-738 (2010); Hinz B., "Formation and function of the myofibroblast during tissue repair," *J. Invest. Dermatol.* 127:526-537 (2007); Gauglitz et al., "Hypertrophic scarring and keloids: pathomechanisms and current and emerging treatment strategies," *Mol. Med.* 17:113-125 (2011); Lehmann et al., "Immune mechanisms in thyroid eye disease," *Thyroid: official journal of the American Thyroid Association* 18:959-965 (2008); Phan S. H., "The myofibroblast in pulmonary fibrosis," *Chest* 122:286S-289S (2002); Kuriyan et al., "The eye and thyroid disease," *Curr. Opin. Ophthalmol.* 19:499-506 (2008).

Exemplary fibrotic conditions that may be treated with the isoform-selective anti-TGFβ antibodies described herein are described in more detail below.

1. Fibrosis of the Lung

Exemplary fibrotic conditions of the lung (i.e., pulmonary fibrosis) include, but are not limited to, idiopathic pulmonary fibrosis (IPF); idiopathic pulmonary upper lobe fibrosis (Amitani disease); familial pulmonary fibrosis; pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma; cystic fibrosis; non-specific interstitial pneumonia (NSIP); cryptogenic organizing pneumonia (COP); progressive massive fibrosis, a complication of coal worker's pneumoconiosis; scleroderma/systemic sclerosis (SSc, including limited cutaneous (lcSSc) and diffuse cutaneous (dcSSc) forms and SSc-associated interstitial lung disease (SSc-ILD)); bronchiolitis obliterans-organizing pneumonia; connective tissue disease-associated ILD (CT-ILD), progressive fibrosing ILD, hypersensitivity pneumonitis, pulmonary hypertension; pulmonary tuberculosis; silicosis; asbestosis; acute lung injury; and acute respiratory distress (ARD; including bacterial pneumonia induced, trauma-induced, and viral pneumonia-induced, ventilator-induced, non-pulmonary sepsis induced).

2. Fibrosis of the Liver

Exemplary fibrotic conditions of the liver (i.e., liver fibrosis) include, but are not limited to, liver cirrhosis due to all etiologies; congenital hepatic fibrosis; obesity; fatty liver; alcohol induced liver fibrosis; non-alcoholic steatohepatitis (NASH); biliary duct injury; primary biliary cirrhosis (PBC), primary sclerosing cholangitis (PSC); infection- or viral-induced liver fibrosis (e.g., chronic hepatitis B and C virus infections); cystic fibrosis; autoimmune hepatitis; necrotizing hepatitis; primary sclerosing cholangitis; hemochromatosis; disorders of the biliary tree; hepatic dysfunction attributable to infections.

3. Fibrosis of the Heart

Exemplary fibrotic conditions of the heart and/or pericardium (i.e., heart or pericardial fibrosis, or fibrosis of the associate vasculature) include, but are not limited to, endomyocardial fibrosis; cardiac allograft vasculopathy (CAV); myocardial infarction; atrial fibrosis; congestive heart failure; arterioclerosis; atherosclerosis; vascular stenosis; myocarditis; congestive cardiomyopathy; coronary infarcts; varicose veins; coronary artery stenosis and other post-ischemic conditions; and idiopathic retroperitoneal fibrosis.

4. Fibrosis of the Kidney

Exemplary fibrotic conditions of the kidney (i.e., kidney fibrosis) include, but are not limited to, glomerulonephritis (including membranoproliferative, diffuse proliferative, rapidly progressive or sclerosing, post-infectious and chronic forms); diabetic glomerulosclerosis; focal segmental glomerulosclerosis; IgA nephropathy; diabetic nephropathy; ischemic nephropathy, tubulointerstitial kidney fibrosis, HIV-associated nephropathy; membrane nephropathy; glomerulonephritis secondary to systemic inflammatory diseases such as lupus, scleroderma and diabetes glomerulonephritis; idiopathic membranoproliferative glomerular nephritis; mesangial proliferative glomerulonephritis; crescentic glomerulonephritis; amyloidosis (which affects the kidney among other tissues); autoimmune nephritis; renal tubuloinsterstitial fibrosis; renal arteriosclerosis; Alport's syndrome; nephrotic syndrome; chronic renal failure; chronic kidney disease, periglomerular fibrosis/atubular glomeruli; combined apical emphysema and basal fibrosis syndrome (emphysema/fibrosis syndrome); glomerular hypertension; nephrogenic fibrosing dermatopathy; polycystic kidney disease; Fabry's disease and renal hypertension.

5. Fibrosis of the Pancreas

Exemplary fibrotic conditions of the pancreas (i.e., pancreatic fibrosis) include, but are not limited to, stromal remodeling pancreatitis and stromal fibrosis.

Exemplary fibrotic conditions of the gastrointestinal tract (i.e., GI tract fibrosis) include, but are not limited to, Crohn's disease; ulcerative colitis; collagenous colitis; colorectal fibrosis; villous atrophy; crypt hyperplasia; polyp formation; healing gastric ulcer; and microscopic colitis.

6. Fibrosis of the Eye

Exemplary fibrotic conditions of the eye include, but are not limited to, ocular fibrosis, ophthalmic fibrosis, proliferative vitreoretinopathy; vitreoretinopathy of any etiology; fibrosis associated with retinal dysfunction; fibrosis associated with wet or dry macular degeneration; scarring in the cornea and conjunctiva; fibrosis in the corneal endothelium; anterior subcapsular cataract and posterior capsule opacification; anterior segment fibrotic diseases of the eye; fibrosis of the corneal stroma (e.g., associated with corneal opacification); fibrosis of the trabecular network (e.g., associated with glaucoma); posterior segment fibrotic diseases of the eye; fibrovascular scarring (e.g., in retinal or choroidal vasculature of the eye); retinal fibrosis; epiretinal fibrosis; retinal gliosis; subretinal fibrosis (e.g., associated with age related macular degeneration); tractional retinal detachment in association with contraction of the tissue in diabetic retinopathy; congenital orbital fibrosis; lacrimal gland fibrosis; corneal subepithelial fibrosis; and Grave's ophthalmopathy.

7. Additional Fibrotic Disorders

Additional fibrotic disorders or fibrosis resulting from any one of the aforementioned conditions include, but are not limited to, spinal cord injury/fibrosis or central nervous system fibrosis such as fibrosis after a stroke, Duchenne muscular dystrophy, dupuytren's contracture, fibrosis associated with neurodegenerative disorder such as Alzheimer's disease or multiple sclerosis; vascular restenosis; uterine fibrosis; endometriosis; ovarian fibroids; Peyronie's disease; polycystic ovarian syndrome; disease related pulmonary apical fibrosis in ankylosing spondylitis; post-surgical adhesions, scarring, and fibrosis incident to microbial infections (e.g., bacterial, viral, parasitic, fungal etc.). Fibroses of the skin can include, for example, and without limitation, scleroderma, keloids, and morphea.

Methods of Treatment

As used herein, treatment of fibrosis or fibrotic conditions, e.g., those described above, is meant to include disruption of the fibrotic processes so as to halt progression of the fibrotic condition, slow progression of the fibrotic condition, or cause regression of the fibrotic condition (i.e., improve the patient's state of health with respect to the degree of fibrosis in the affected tissue or organ). In certain embodiments, where treatment precedes onset of the fibrotic condition, i.e., treatment is performed prior to a known or an otherwise expected onset of fibrosis, then such treatment may include preventing development or onset of the fibrotic condition. Administration of the various active agents can therefore be carried out for a suitable duration to either control or halt progression of the fibrotic condition, or prevent onset thereof.

Thus, in some aspects, the invention provides a method for treating fibrosis, wherein the fibrosis is a fibrotic condition of the lung, liver, heart, kidney, pancreas, eye and/or skin. In one aspect, the fibrosis is a lung fibrosis selected from idiopathic pulmonary fibrosis (IPF); idiopathic pulmonary upper lobe fibrosis (Amitani disease); familial pulmonary fibrosis; pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma; cystic fibrosis; non-specific interstitial pneumonia (NSIP); cryptogenic organizing pneumonia (COP); progressive massive fibrosis, a complication of coal worker's pneumoconiosis; scleroderma/systemic sclerosis (SSc, including limited cutaneous (lcSSc) and diffuse cutaneous (dcSSc) forms and SSc-associated interstitial lung disease (SSc-ILD)); bronchiolitis obliterans-organizing pneumonia; connective tissue disease-associated ILD (CT-ILD), progressive fibrosing ILD, hypersensitivity pneumonitis, pulmonary hypertension; pulmonary tuberculosis; silicosis; asbestosis; acute lung injury; and acute respiratory distress (ARD; including bacterial pneumonia induced, trauma-induced, and viral pneumonia-induced, ventilator-induced, non-pulmonary sepsis induced). In another aspect, the fibrosis is a fibrotic condition of the liver selected from liver cirrhosis due to all etiologies; congenital hepatic fibrosis; obesity; fatty liver; alcohol induced liver fibrosis; non-alcoholic steatohepatitis (NASH); biliary duct injury; primary biliary cirrhosis (PBC), primary sclerosing cholangitis (PSC); infection- or viral-induced liver fibrosis (e.g., chronic hepatitis B and C virus infections); cystic fibrosis; autoimmune hepatitis; necrotizing hepatitis; primary sclerosing cholangitis; hemochromatosis; disorders of the biliary tree; hepatic dysfunction attributable to infections. In another aspect, the fibrosis is a fibrotic condition of the heart and/or pericardium (i.e., heart or pericardial fibrosis, or fibrosis of the associate vasculature) selected from endomyocardial fibrosis; cardiac allograft vasculopathy (CAV); myocardial infarction; atrial fibrosis; congestive heart failure; arterioclerosis; atherosclerosis; vascular stenosis; myocarditis; congestive cardiomyopathy; coronary infarcts; varicose veins; coronary artery stenosis and other post-ischemic conditions; and idiopathic retroperitoneal fibrosis. In another aspect, the fibrosis is a fibrotic condition of the kidney selected from glomerulonephritis (including membranoproliferative, diffuse proliferative, rapidly progressive or sclerosing, post-infectious and chronic forms); diabetic glomerulosclerosis; focal segmental glomerulosclerosis; IgA nephropathy; diabetic nephropathy; ischemic nephropathy, tubulointerstitial kidney fibrosis, HIV-associated nephropathy; membrane nephropathy; glomerulonephritis secondary to systemic inflammatory diseases such as lupus, scleroderma and diabetes glomerulonephritis; idiopathic membranoproliferative glomerular nephritis; mesangial proliferative glomerulonephritis; crescentic glomerulonephritis; amyloidosis (which affects the kidney among other tissues); autoimmune nephritis; renal tubuloinsterstitial fibrosis; renal arteriosclerosis; Alport's syndrome; nephrotic syndrome; chronic renal failure; chronic kidney disease, periglomerular fibrosis/atubular glomeruli; combined apical emphysema and basal fibrosis syndrome (emphysema/fibrosis syndrome); glomerular hypertension; nephrogenic fibrosing dermatopathy; polycystic kidney disease; Fabry's disease and renal hypertension. In another aspect, the fibrosis is a fibrotic condition of the pancreas selected from stromal remodeling pancreatitis and stromal fibrosis. In another aspect, the fibrosis is a fibrotic condition of the gastrointestinal tract (i.e., GI tract fibrosis) selected from Crohn's disease; ulcerative colitis; collagenous colitis; colorectal fibrosis; villous atrophy; crypt hyperplasia; polyp formation; healing gastric ulcer; and microscopic colitis. In another aspect, the fibrosis is a fibrotic condition of the eye selected from ocular fibrosis, ophthalmic fibrosis, proliferative vitreoretinopathy; vitreoretinopathy of any etiology; fibrosis associated with retinal dysfunction; fibrosis associated with wet or dry macular degeneration; scarring in the cornea and conjunctiva; fibrosis in the corneal endothelium; anterior subcapsular cataract and posterior capsule opacification; anterior segment fibrotic diseases of the eye; fibrosis of the corneal stroma (e.g., associated with corneal opacification); fibrosis of the trabecular network (e.g., associated with glaucoma); posterior segment fibrotic diseases of the eye; fibrovascular scarring (e.g., in retinal or choroidal vasculature of the eye); retinal fibrosis; epiretinal fibrosis; retinal gliosis; subretinal fibrosis (e.g., associated with age related macular degeneration); tractional retinal detachment in association with contraction of the tissue in diabetic retinopathy; congenital orbital fibrosis; lacrimal gland fibrosis; corneal subepithelial fibrosis; and Grave's ophthalmopathy. In another aspect, the fibrosis is a selected from fibrosis resulting from spinal cord injury/fibrosis or central nervous system fibrosis such as fibrosis after a stroke, Duchenne muscular dystrophy, dupuytren's contracture, fibrosis associated with neurodegenerative disorder such as Alzheimer's disease or multiple sclerosis; vascular restenosis; uterine fibrosis; endometriosis; ovarian fibroids; Peyronie's disease; polycystic ovarian syndrome; disease related pulmonary apical fibrosis in ankylosing spondylitis; scarring; multi-organ connective tissue dysfunction involving tissues in skin, lung, heart, kidney, and/or intestine, e.g., systemic sclerosis (SSc), SSc of the skin, and fibrosis incident to microbial infections (e.g., bacterial, viral, parasitic, fungal etc.).

In one embodiment, the invention provides a method for treating a TGFβ-related disorder, wherein the method includes administering to a subject having such TGFβ-related disorder an effective amount of an isoform-selective anti-TGFβ antibody (e.g., anti-TGFβ2, anti-TGFβ2/3, or anti-TGFβ3 antibody). In one such embodiment, the method further comprises administering to the subject an effective amount of at least one additional therapeutic agent, as described below. In another embodiment, the invention provides a method for treating fibrosis (e.g., a fibrotic condition as described above), wherein the method includes administering to a subject having such fibrosis an effective amount of an isoform-selective anti-TGFβ antibody (e.g., anti-TGFβ2, anti-TGFβ2/3, or anti-TGFβ3 antibody). In one such embodiment, the method further comprises administering to the subject an effective amount of at least one additional therapeutic agent, as described below. In a further embodiment, the invention provides a method for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin, and/or for inhibiting new collagen synthesis in a subject. In another embodiment, the method comprises administering to the subject an effective amount of an isoform-selective anti-TGFβ antibody (e.g., anti-TGFβ2, anti-TGFβ2/3, or anti-TGFβ3 antibody) to inhibit TGFBR-dependent SMAD signaling, to inhibit the assembly of TGFβ-TGFBR signaling complexes, to inhibit TGFβ signaling through the TGFBR1/R2 complex, to inhibit TGFβ signaling through the TGFBR2/ALK1 complex facilitated by endoglin and/or for inhibiting new collagen synthesis. Exemplary embodiments using the isoform-selective anti-TGFβ antibodies of the invention are provided, below.

Methods of Treating Idiopathic Pulmonary Fibrosis

The present invention provides methods of treating idiopathic pulmonary fibrosis (IPF). The methods generally involve administering to an individual having IPF an effective amount of an isoform-selective anti-TGFβ antibody described herein (e.g., anti-TGFβ2, anti-TGFβ2/3, or anti-TGFβ3 antibody). In some embodiments, the dosing and efficacy of the treatment can be monitored by reversal or slowing of progressing of usual interstitial pneumonia (UIP) on histopathological evaluation of lung tissue obtained by surgical biopsy. The criteria for a diagnosis of IPF are known. Ryu et al. (1998) Mayo Clin. Proc. 73:1085-1101. In other embodiments, a diagnosis of IPF is a definite or probable IPF made by high resolution computer tomography (HRCT). In a diagnosis by HRCT, the presence of the following characteristics is noted: (1) presence of reticular abnormality and/or traction bronchiectasis with basal and peripheral predominance; (2) presence of honeycombing with basal and peripheral predominance; and (3) absence of atypical features such as micronodules, peribronchovascular nodules, consolidation, isolated (non-honeycomb) cysts, ground glass attenuation (or, if present, is less extensive than reticular opacity), and mediastinal adenopathy (or, if present, is not extensive enough to be visible on chest x-ray). A diagnosis of definite IPF is made if characteristics (1), (2), and (3) are met. A diagnosis of probable IPF is made if characteristics (1) and (3) are met. In certain preferred embodiments, the treatment results in an increase, such as a statistically significant increase, in pulmonary function. Pulmonary function values are well known in the art. The following is an example of pulmonary function values that may be used. Other pulmonary function values, or combinations thereof, are intended to be within the scope of this invention. The values include, but are not limited to, FEV (forced expiratory volume), FVC (forced vital capacity), FEF (forced expiratory flow), Vmax (maximum flow), PEFR (peak expiratory flow rate), FRC (functional residual capacity), RV (residual volume), TLC (total lung capacity). FEV measures the volume of air exhaled over a predetermined period of time by a forced expiration immediately after a full inspiration. FVC measures the total volume of air exhaled immediately after a full inspiration. Forced expiratory flow measures the volume of air exhaled during a FVC divided by the time in seconds. Vmax is the maximum flow measured during FVC. PEFR measures the maximum flow rate during a forced exhale starting from full inspiration. RV is the volume of air remaining in the lungs after a full expiration.

Methods of Treating Liver Fibrosis

The present invention provides methods of treating liver fibrosis, including reducing clinical liver fibrosis, reducing the likelihood that liver fibrosis will occur, and reducing a parameter associated with liver fibrosis. Of particular interest in many embodiments is treatment of humans. Liver fibrosis is a precursor to the complications associated with liver cirrhosis, such as portal hypertension, progressive liver insufficiency, and hepatocellular carcinoma. A reduction in liver fibrosis thus reduces the incidence of such complications. Accordingly, the present invention further provides methods of reducing the likelihood that an individual will develop complications associated with cirrhosis of the liver by conjoint therapy involving the administration of an effective amount of an isoform-selective anti-TGFβ antibody described herein (e.g., anti-TGFβ2, anti-TGFβ2/3, or anti-TGFβ3 antibody). Whether treatment with an effective amount of an isoform-selective anti-TGFβ antibody described herein (e.g., anti-TGFβ2, anti-TGFβ2/3, or anti-TGFβ3 antibody) is effective in reducing liver fibrosis is determined by any of a number of well-established techniques for measuring liver fibrosis and liver function. Whether liver fibrosis is reduced is determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems. The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis. Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431. In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372. The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P- and/or P-C) with occasional nodules (incomplete cirrhosis); stage 6, Cirrhosis, probable or definite. The benefit of anti-fibrotic therapy can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

Methods of Treating Renal Fibrosis

Renal fibrosis is characterized by the excessive accumulation of extracellular matrix (ECM) components. Overproduction of TGFβ is believed to underly tissue fibrosis caused by excess deposition of ECM, resulting in disease. The fibrogenic action of TGFβ results from simultaneous stimulation of matrix protein synthesis, inhibition of matrix degradation and enhanced integrin expression that facilitates ECM assembly. The present invention provides methods of treating renal fibrosis. The methods generally involve administering to an individual having renal fibrosis an isoform-selective anti-TGFβ antibody described herein (e.g., anti-TGFβ2, anti-TGFβ2/3, or anti-TGFβ3 antibody). As used herein, an "effective amount" of an isoform-selective anti-TGFβ antibody described herein (e.g., anti-TGFβ2, anti-TGFβ2/3, or anti-TGFβ3 antibody) is a dosage that is effective in reducing renal fibrosis; and/or that is effective in reducing the likelihood that an individual will develop renal fibrosis; and/or that is effective in reducing a parameter associated with renal fibrosis; and/or that is effective in reducing a disorder associated with fibrosis of the kidney. In one embodiment, an effective amount of an isoform-selective anti-TGFβ antibody described herein (e.g., anti-TGFβ2, anti-TGFβ2/3, or anti-TGFβ3 antibody) is an amount that is sufficient to reduce renal fibrosis by at least about 10%, at least about 15%, at least about 20%, at least about 25%, at least about 30%, at least 20 about 35%, at least about 40%, at least about 45%, at least about 50%, compared to the degree of renal fibrosis in the individual prior to treatment with the isoform-selective anti-TGFβ antibody. Whether fibrosis is reduced in the kidney is determined using any known method. For example, histochemical analysis of kidney biopsy samples for the extent of ECM deposition and/or fibrosis is performed. Other methods are known in the art. See, e.g., Masseroli et al. (1998) Lab. Invest. 78:511-522; U.S. Pat. No. 6,214,542. In some embodiments, an effective amount of an isoform-selective anti-TGFβ antibody described herein (e.g., anti-TGFβ2, anti-TGFβ2/3, or anti-TGFβ3 antibody) is an amount that is effective to increase kidney function by at least about 10%, at least about 15%, at least about 20%, at least about 25%, at 30 least about 30%, at least about 35%, at least about 40%, at least about 45%, at least about 50%, compared to the basal level of kidney function in the individual prior to treatment with the isoform-selective anti-TGFβ antibody (e.g., anti-TGFβ2, anti-TGFβ2/3, or anti-TGFβ3 antibody) of the present invention. In some embodiments, an effective amount of the isoform-selective anti-TGFβ antibody is the amount that is effective to slow the decline in kidney function by at least about 10%, at least about 15%, at least about 20%, at least about 25%, at least about 30%, at least about 35%, at least about 40%, at least about 45%, at least about 50%, compared to the decline in kidney function that would occur in the absence of treatment with the isoform-selective anti-TGFβ antibody of the present invention. Kidney function can be measured using any known assay, including, but not limited to, plasma creatinine level (where normal levels are generally in a range of from about 0.6 to about 1.2 mg/dL); creatinine clearance (where the normal range for creatinine clearance is from about 97 to about 137 mL/minute in men, and from about 88 to about 128 mL/minute in women); the glomerular filtration rate (either calculated or obtained from inulin clearance or other methods), blood urea nitrogen (where the normal range is from about 7 to about 20 mg/dL); and urine protein levels. The invention also provides a method for treatment of renal fibrosis in an individual comprising administering to the individual an isoform-selective anti-TGFβ antibody in an amount that is effective for prophylaxis or therapy of renal fibrosis in the individual, e.g., increasing the time to doubling of serum creatinine levels, increasing the time to end-stage renal disease requiring renal replacement therapy (e.g., dialysis or transplant), increasing the probability of survival, reducing the risk of death, ameliorating the disease burden or slowing the progression of disease in the individual, while reducing the incidence or severity of one or more side effects that would ordinarily arise without such treatment.

Anti-TGFβ2 Antibodies

In some aspects of the above methods for treating a TGFβ-related disorder, such as but not limited to fibrosis (e.g., fibrosis of the lung, liver, pancreas, heart, kidney, eye, and/or skin) are provided, the method comprises administering to a subject having such TGFβ-related disorder an effective amount of an anti-TGFβ2 antibody of the invention having one or more of the following properties:

the anti-TGFβ2 antibody:

(a) selectively neutralizes TGFβ2;

(b) has reduced toxicity relative to the pan-TGFβ antibody 1D11;

(c) has reduced toxicity relative to the pan-TGFβ antibody 1D11;

(d) has reduced toxicity in rodents relative to the pan-TGFβ antibody 1D11;

(e) has reduced toxicity relative to the pan-TGFβ small molecule inhibitor galunisertib; and/or (f) has reduced toxicity in rodents relative to the pan-TGFβ small molecule inhibitor galunisertib.

In another aspect, the invention provides a method for treating a fibrosis condition, e.g., such as a fibrotic condition described above, the method comprising administering to a subject having such fibrosis an effective amount of an isoform-selective anti-TGFβ antibody having one or more of the following properties:

the anti-TGFβ2 antibody selectively neutralizes TGFβ2; the anti-TGFβ2 binds to TGFβ2 with a $K_D$ of less than 10 pM and/or has a cell-based $IC_{50}$ of less than 250 pM; binds to TGFβ2 with a $K_D$ of less than or equal to about 5 pM, about 4 pM, about 3 pM, about 2 pM, or about 1 pM; the anti-TGFβ2 antibody provided herein has a cell-based $IC_{50}$ less than or equal to about 250 pM, about 200 pM, about 150 pM, about 100 pM, about 75 pM, about 50 pM, or about 40 pM.

In one aspect, the invention provides a method for treating fibrosis, the method comprising administering to a subject having such fibrosis an effective amount of an isoform-selective anti-TGFβ antibody selected from the following:

(i) an anti-TGFβ2 antibody comprising at least one, two, three, four, five, or six HVRs selected from (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21;

(ii) an anti-TGFβ2 antibody comprising at least one, at least two, or all three VH HVR sequences selected from (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18. In another aspect, the invention provides an antibody comprising (a) HVR-H1 comprising the amino acid sequence of SEQ ID NO: 16; (b) HVR-H2 comprising the amino acid sequence of SEQ ID NO:17; ad (c) HVR-H3 comprising the amino acid sequence of SEQ ID NO: 18;

(iii) an anti-TGFβ2 antibody comprising at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21;

(iv) an anti-TGFβ2 antibody comprising HVR-H3 comprising the amino acid sequence of SEQ ID NO: 18 and HVR-L3 comprising the amino acid sequence of SEQ ID NO: 21. In a further embodiment, the anti-TGFβ2 antibody comprises HVR-H3 comprising the amino acid sequence of SEQ ID NO: 18, HVR-L3 comprising the amino acid sequence of SEQ ID NO: 21, and HVR-H2 comprising the amino acid sequence of SEQ ID NO: 17;

(v) an anti-TGFβ2 antibody comprising (a) a VH domain comprising at least one, at least two, or all three VH HVR sequences selected from (i) HVR-H1 comprising the amino acid sequence of SEQ ID NO: 16; (ii) HVR-H2 comprising the amino acid sequence of SEQ ID NO:17; (iii) HVR-H3 comprising the amino acid sequence of SEQ ID NO: 18; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21; and (vi) an anti-TGFβ2 antibody comprising a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments for the methods of treating fibrosis, the anti-TGFβ2 antibody may be humanized. In one embodiment, the isoform-selective anti-TGFβ antibody comprises HVRs as in any of the above embodiments, and further comprises an acceptor human framework, e.g. a human immunoglobulin framework or a human consensus framework. In any of the above embodiments, a humanized anti-TGFβ2 antibody comprises one or more mutations in the VH framework selected from the group consisting of 37V or 37I, 48M or 48L, 49G or 49A, 67L, 71K and 78V, and 105P or 105R. In some embodiments, the anti-TGFβ2 antibody comprises a VH, wherein the VH comprises the amino acid sequence of SEQ ID NO: 25, wherein the VH comprises a set of framework mutations selected from the group consisting of: (i) 37V, 48M and 49G in FR2 and 105P in FR4 (h6F12.v1 and h6F12.v3); (ii) 37V and 48M in FR2, 67L, 71K and 78V in FR3 and 105P in FR4 (h6F12.v2 and h6F12.v4); (iii) 37I in FR2 (h6F12.v1.6); (iv) 48L in FR2 (h6F12.v1.7); (v) 49A in FR2 (h6F12.v1.8); (vi) 105R in FR4 (h6F12.v1.9); (vii) 37V, 48M and 49G in FR2 and 105P in FR4 (h6F12.v1 and h6F12.v3); (viii) 37V and 48M in FR2, 67L, 71K and 78V in FR3 and 105P in FR4 (6F12.v2 and h6F12.v4); (ix) 37I in FR2 (h6F12.v1.6); (x) 48L in FR2 (h6F12.v1.7); (xi): 49A in FR2 (h6F12.v1.8); and (xii) 105R in FR4 (h6F12.v1.9). In any of the above embodiments, a humanized anti-TGFβ2 antibody comprises one or more mutations in the VL framework selected from the group consisting of 43S or 43A, 66G, 69T, 71F, and 87Y. In some embodiments, the anti-TGFβ2 antibody comprises a VL, wherein the VL comprises the amino acid sequence of SEQ ID NO: 24, wherein the VL comprises a set of framework mutations selected from the group consisting of (i) 43S in FR2 and 66E, 69P, 71Y and 87F in FR3 (h6F12.v1 and h6F12.v2); (ii) 43S in FR2 and 58V, 66E, 69P, 71Y and 87F in FR3 (h6F12.v3 and h6F12.v4); (iii) 43A in FR2 (h6F12.v1.1); (iv) 66G in FR3 (h6F12.v1.2); (v) 69T in FR3 (h6F12.v1.3); (vi) 71F in FR3 (h6F12.v1.4); and (vii) 87Y in FR3 (h6F12.v1.5).

In a further aspect, the invention provides a method for treating fibrosis, the method comprising administering to a subject having such fibrosis an effective amount of an isoform-selective anti-TGFβ antibody selected from the following:

an anti-TGFβ2 antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NO: 25, 132, and 138-142; or the VH comprises one, two or three HVRs selected from: (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; and the antibody comprises a light chain variable domain (VL) having at least 90%, 91%, 92%, 93%, 94%, 95%, 96%, 97%, 98%, 99%, or 100% sequence identity to the amino acid sequence selected from the group consisting of SEQ ID NO: 24, 131, 133-137, 143, and 144, or the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21;

an anti-TGFβ2 antibody comprising the VH/VL sequences (respectively) selected from the group consisting of SEQ ID NOs: 25/24 (rabbit 6F12), SEQ ID NOs: 132/131 (v1), SEQ ID NOs: 132/133 (v1.1), SEQ ID NOs: 132/134 (v1.2), SEQ ID NOs: 132/135 (v1.3), SEQ ID NOs: 132/136 (v1.4), SEQ ID NOs: 132/137 (v1.5), SEQ ID NOs: 138/131 (v1.6), SEQ ID NOs: 139/131 (v1.7), SEQ ID NOs: 140/131 (v1.8), SEQ ID NOs: 141/131 (v1.9), SEQ ID NOs: 142/131 (v2), SEQ ID NOs: 132/143 (v3), and SEQ ID NOs: 142/144 (v4); or an anti-TGFβ2 antibody comprising a complete H chain amino acid sequence having at least 95% sequence identity to the amino acid sequence selected from the group consisting of SEQ ID NOs: 31, 146, and 152-156 and/or a complete L chain amino acid sequence having an amino acid sequence selected from the group consisting of SEQ ID NOs: 30, 145, 147-151, 157, and 158;

an anti-TGFβ2 antibody comprising a complete H/L chain pair, the complete H/L chain pair (respectively) comprising amino acid sequences selected from the group consisting of SEQ ID NOs: 31/30 (rabbit 6F12), SEQ ID NOs: 146/145 (v1), SEQ ID NOs: 146/147 (v1.1), SEQ ID NOs: 146/148 (v1.2), SEQ ID NOs: 146/149 (v1.3), SEQ ID NOs: 146/150 (v1.4), SEQ ID NOs: 146/151 (v1.5), SEQ ID NOs: 152/145 (v1.6), SEQ ID NOs: 153/145 (v1.7), SEQ ID NOs: 154/145 (v1.8), SEQ ID NOs: 155/145 (v1.9), SEQ ID NOs: 156/145 (v2), SEQ ID NOs: 146/157 (v3), and SEQ ID NOs: 156/158 (v4); or an antibody that binds to the same epitope as an anti-TGFβ2 antibody comprising a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

Anti-TGFβ2/3 Antibodies

In some aspects of the above methods for treating a TGFβ-related disorder, such as but not limited to fibrosis (e.g., fibrosis of the lung, liver, pancreas, heart, kidney, eye, and/or skin) are provided, the method comprises administering to a subject having such TGFβ-related disorder (e.g.) fibrosis an effective amount of an isoform-selective anti-TGFβ2/3 antibody of the invention that selectively neutralizes TGFβ2 and TGFβ3 and has one or more of the following properties:

(a) selectivity of the anti-TGFβ2/3 antibody for TGFβ2 and TGFβ3 over human TGFβ1, with respect to selective neutralization, is achieved by direct contact of the antibody's antigen binding domain with amino acid residue E373 of TGFβ2 or TGFβ3 (human TGFβ2 numbering);

(b) the anti-TGFβ2/3 antibody neutralizes TGFβ2 and/or TGFβ3 via an allosteric mechanism;

(c) the anti-TGFβ2/3 antibody induces a conformational change in TGFβ2 homodimer;

(d) the anti-TGFβ2/3 antibody induces a conformational change in TGFβ2 homodimer, wherein the conformational change comprises the two monomers pinching together by several degrees;

(e) the anti-TGFβ2/3 antibody is a divalent antibody or a monovalent antibody;

(f) the anti-TGFβ2/3 antibody comprises (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15;

(g) the anti-TGFβ2/3 antibody binds to TGFβ2 homodimer, the TGFβ2 homodimer having a first and a second TGFβ2 monomer, and wherein the anti-TGFβ2/3 antibody comprises an antigen binding domain that directly contacts (i) amino acid residues V313, Q314, D315, R320, L322, Y323, R328, D329, F345, and A347 of the first TGFβ2 monomer, and (ii) amino acid residues N368, T369, I370, N371, P372, E373, A374, S375, A376, and S377 of the second TGFβ2 monomer (human TGFβ2 numbering);

(h) the anti-TGFβ2/3 antibody as in (g), wherein the antigen binding domain is within 5 angstroms of the TGFβ2 and/or TGFβ3 amino acid residues;

(i) wherein the anti-TGFβ2/3 antibody binds to a substantially similar epitope as in (g) in TGFβ3; and j) the anti-TGFβ2/3 antibody does not neutralize TGFβ2 and/or TGFβ3 in single arm form.

In a further aspect, the invention provides a method for treating fibrosis, the method comprising administering to a subject having such fibrosis an effective amount of an anti-TGFβ2/3 antibody that has one or more of the following properties:

selectively neutralizes TGFβ2 and TGFβ3; binds to TGFβ2 and/or TGFβ3 with a $K_D$ of less than 10 pM and/or has a cell-based $IC_{50}$ less than 250 pM;

binds to TGFβ2 and/or TGFβ3 with a $K_D$ of less than about 10 pM, about 9 pM, about 8 pM, about 7 pM, about 6 pM, about 5 pM, about 4 pM, about 3 pM, about 2 pM, or about 1 pM;

has a cell-based $IC_{50}$ for inhibition of TGFβ2 of about 250 pM, about 200 pM, about 150 pM, about 100 pM, about 75 pM, or about 50 pM;

has a cell-based $IC_{50}$ for inhibition of TGFβ3 of about 250 pM, about 200 pM, about 150 pM, about 100 pM, about 75 pM, about 50 pM, about 40 pM, about 30 pM or less than about 30 pM; or has a cell-based $IC_{50}$ for inhibition of TGFβ2 of about 250 pM and a cell-based $IC_{50}$ for inhibition (neutralization) of TGFβ3 of about 30 pM.

In a further aspect, the invention provides a method for treating fibrosis, the method comprising administering to a subject having such fibrosis an effective amount of an anti-TGFβ2/3 antibody selected from the following:

an antibody comprising at least one, two, three, four, five, or six HVRs selected from (a) HVR-H1 comprising the amino acid sequence of SEQ ID NO: 10; (b) HVR-H2 comprising the amino acid anti-TGFβ2/3 antibody sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15;

an antibody comprising at least one, at least two, or all three VH HVR sequences selected from (a) HVR-H1 comprising the amino acid sequence of SEQ ID NO: 10; (b) HVR-H2 comprising the amino acid anti-TGFβ2/3 antibody sequence of SEQ ID NO: 11; (c) HVR-H3 comprising the amino acid sequence of SEQ ID NO: 12, and at least one, at least two, or all three VL HVR sequences selected from (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15;

an antibody comprising (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15.

In any of the above embodiments for treating fibrosis, the anti-TGFβ2/3 antibody may be humanized. In one embodiment, an anti-TGFβ2/3 antibody comprises HVRs as in any of the above embodiments, and further comprises an acceptor human framework, e.g. a human immunoglobulin framework or a human consensus framework. In some embodiments, the anti-TGFβ2/3 antibody comprises a VH, wherein the VH comprises the amino acid sequence of SEQ ID NO: 27, wherein the VH comprises a set of framework modifications selected from the group consisting of: (i) 2Q and 24V in FR1, 481 and 49G in FR2, 71K, 73S, 78V and 91F in FR3 and 105P in FR4 (h4A 1.v1, h4A11.v2, h4A11.v5, h4A11.v6); (ii) 2Q in FR1, 37V in FR2, 67F, 71K, 73S, 78V and 91F in FR3 and 105P in FR4 (h4A11.v3, h4A11.v4, 4A11.v7, h4A11.v8); (iii) delete 1E in FR1 (h4A11.v7.1); (iv) delete 75K and 76N in FR3 (h4A11.v7.2); (v) delete 1E in FR1 and 75K76N in FR3 (h4A11.v7.3); (vi) 2V in FR1 (h4A11.v7.8); (vi) 37I in FR2 (h4A11.v7.9); (vii) 67V in FR3 (h4A11.v7.10); (viii) 71V in FR3 (h4A11.v7.11); (ix) 73T in FR3 (h4A11.v7.12); (x) 78F in FR3 (h4A11.v7.13); (xi) 91Y in FR3 (h4A11.v7.14); (xii) 105Q in FR4 (h4A11.v7.15); (xiii) 2V in FR1, 37I in FR2, 67V, 73T, 78F in FR3, 105Q in FR4 ((h4A11.v7.16); (xiv) 2V in FR1, 37I in FR2, 67V, 73T, 91Y in FR3, 105Q in FR4 (h4A11.v7.17); (xv) 2V in FR1, 37I in FR2, 67V, 73T in FR3, 105Q in FR4 (h4A11.v7.18); and (xvi) 2V in FR1, 37I in FR2, 67V, 73T, deletion of 75K and 76N in FR3, 105Q in FR4 (h4A11.v7.19). In another embodiment, an anti-TGFβ2/3 antibody comprises HVRs as in any of the above embodiments, and further comprises a VL comprising FR modifications selected from the group consisting of: 2A or 2I, 4L, 36F or 36Y, 43P or 43A, and 58V or 581, relative to the VL amino acid sequence of SEQ ID NO: 26. In some embodiments, the anti-TGFβ2/3 antibody comprises a VL, wherein the VL comprises the amino acid sequence of SEQ ID NO: 26, wherein the VL comprises a set of framework modifications selected from the group consisting of: (i) 2A and 4L in FR1 and 36F in FR2 (h4A11.v1 and h4A11.v3); (ii) 2A and 4L in FR1 and 36F and 43P in FR2 (h4A11.v2 and h4A11.v4); (iii) 2A in FR1, 36F and 43P in FR2 and 58V in FR3 (h4A11.v5 and h4A11.v7); (iv) 2A and 4L in FR1 and 36F in FR2 (h4A11.v6 and h4A11.v8); (v) 2I in FR1 (h4A11.v7.4); (vi) 36Y in FR2 (h4A11.v7.5); (vii) 43A in FR2 (h4A11.v7.6); (viii) 58I in FR3 (h4A11.v7.7); and (ix) 2I in FR1, 43A in FR2, 581 in FR3 (h4A11.v7.16-19).

In a further aspect, the invention provides a method for treating fibrosis, the method comprising administering to a subject having such fibrosis an effective amount of an anti-TGFβ2/3 antibody selected from the following:

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 27, 81, 83, 86-88, 93-100, and 102-105, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 26, 80, 82, 84, 85, 89-92, and 101;

an antibody comprising the VH and VL sequences (respectively) selected from the group consisting of SEQ ID NOs: 27/26 (rabbit 4A11), SEQ ID NOs: 81/80 (v1), SEQ ID NOs: 81/82 (v2), SEQ ID NOs: 83/80 (v3), SEQ ID NOs: 83/82 (v4), SEQ ID NOs: 81/84 (v5), SEQ ID NOs: 81/85 (v6), SEQ ID NOs: 83/84 (v7), SEQ ID NOs: 86/84 (v7/1), SEQ ID NOs: 87/84 (v7.2), SEQ ID NOs: 88/84 (v7.3), SEQ ID NOs: 83/89 (v7.4), SEQ ID NOs: 83/90 (v7.5), SEQ ID NOs: 83/91 (v7.6), SEQ ID NOs: 83/92 (v7.7), SEQ ID NOs: 93/84 (v7.8), SEQ ID NOs: 94/84 (v7.9), SEQ ID NOs: 95/84 (v7.10), SEQ ID NOs: 96/84 (v7.11), SEQ ID NOs: 97/84 (v7.12), SEQ ID NOs: 98/84 (v7.13), SEQ ID NOs: 99/84 (v7.14), SEQ ID NOs: 100/84 (v7.15), SEQ ID NOs: 102/101 (v7.16), SEQ ID NOs: 103/101 (v7.17), SEQ ID NOs: 104/101 (v7.18), SEQ ID NOs: 105/101 (v7.19), SEQ ID NOs: 83/85 (v8);

an antibody comprising a complete H chain amino acid sequence having at least 95% sequence identity to the amino acid sequence selected from the group consisting of SEQ ID NOs: 33, 107, 109, 112-114, and 119-130 and/or a complete L chain amino acid sequence having an amino acid sequence selected from the group consisting of SEQ ID NOs: 32, 106, 108, 110, 111, 115-118, and 186;

an antibody comprising a complete H/L chain pair, the complete H/L chain pair (respectively) comprising amino acid sequences selected from the group consisting of SEQ ID NOs: 32/33 (rabbit 4A11), SEQ ID NOs: 107/106 (v1), SEQ ID NOs: 107/108 (v2), SEQ ID NOs: 109/106 (v3), SEQ ID NOs: 109/108 (v4), SEQ ID NOs: 107/110 (v5), SEQ ID NOs: 107/111 (v6), SEQ ID NOs: 109/110 (v7), SEQ ID NOs: 112/110 (v7.1), SEQ ID NOs: 113/110 (v7.2), SEQ ID NOs: 114/110 (v7.3), SEQ ID NOs: 114/115 (v7.4), SEQ ID NOs: 114/116 (v7.5), SEQ ID NOs: 114/117 (v7.6), SEQ ID NOs: 114/118 (v7.7), SEQ ID NOs: 119/110 (v7.8), SEQ ID NOs:120/110 (v7.9), SEQ ID NOs: 121/110 (v7.10), SEQ ID NOs: 122/110 (v7.11), SEQ ID NOs: 123/110 (v7.12), SEQ ID NOs: 124/110 (v7.13), SEQ ID NOs: 125/110 (v7.14), SEQ ID NOs: 126/110 (v7.15), SEQ ID NOs: 127/186 (v7.16), SEQ ID NOs: 128/186 (v7.17), SEQ ID NOs: 129/186 (v7.18), SEQ ID NOs: 130/186 (v7.19), and SEQ ID NOs: 114/111 (v8);

an antibody that binds to the same epitope as an anti-TGFβ2/3 antibody comprising (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15;

an antibody that binds to an epitope spanning a TGFβ2 homodimer, the TGFβ2 homodimer having a first and a second TGFβ2 monomer, wherein the anti-TGFβ2/3 antibody comprises an antigen-binding domain that directly contacts amino acid residues V313, Q314, D315, R320, L322, Y323, R328, D329, F345, and A347 of the first TGFβ2 monomer, and amino acid residues N368, T369, I370, N371, P372, E373, A374, S375, A376, and S377 of the second TGFβ2 monomer, and wherein, in some embodiments, the anti-TGFβ2/3 antibody binds to the same epitope in TGFβ3.

Anti-TGFβ3 Antibodies

In some aspects of the above methods for treating a TGFβ-related disorder, such as but not limited to fibrosis (e.g., fibrosis of the lung, liver, pancreas, heart, kidney, eye, and/or skin), are provided, the method comprises administering to a subject having such TGFβ-related disorder an effective amount of an anti-TGFβ3 antibody that selectively neutralizes TGFβ3 having one or more of the following properties:

(a) the anti-TGFβ3 antibody binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody binds amino acid residue R394 in the beta6/beta7 hairpin region of human TGFβ3;

(e) the anti-TGFβ3 antibody binds amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

(j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody;

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

In a further aspect, the invention provides a method for treating fibrosis, the method comprising administering to a subject having such fibrosis an effective amount of an isoform-selective anti-TGFβ antibody having one or more of the following properties:

an antibody that selectively neutralizes TGFβ3;

an antibody that binds to TGFβ3 with a $K_D$ of less than 10 pM and/or has a cell-based $IC_{50}$ less than 250 pM;

an antibody that binds to TGFβ3 with a $K_D$ of less than about 5 pM, about 4 pM, about 3 pM, or less than about 2 pM;

an antibody that has a cell-based $IC_{50}$ less of than about 200 pM, about 150 pM, about 100 pM, about 75 pM, or about 50 pM;

an antibody provided herein that has a cell-based $IC_{50}$ for inhibition (neutralization) of TGFβ3 of less than about 20 pM;

an antibody that selectively neutralizes TGFβ3 and has reduced toxicity in mice relative to the pan-TGFβ antibody 1D11;

an antibody that selectively neutralizes TGFβ3 and has an improved safety profile.

In a further aspect, the invention provides a method for treating fibrosis, the method comprising administering to a subject having such fibrosis an effective amount of an anti-TGFβ3 antibody selected from the following:

an antibody comprising at least one, two, three, four, five, or six HVRs selected from (a) HVR-H1 comprising the amino acid sequence of SEQ ID NO: 4; (b) HVR-H2 comprising the amino acid sequence selected from SEQ ID NOs: 5, 34, 35, and 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9;

an antibody comprising (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an antibody comprising (a) HVR-H1 comprising the amino acid sequence of SEQ ID NO: 4; (b) HVR-H2 comprising the amino acid sequence of SEQ ID NO: 34; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an antibody comprising (a) HVR-H1 comprising the amino acid sequence of SEQ ID NO: 4; (b) HVR-H2 comprising the amino acid sequence of SEQ ID NO: 35; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9; and an antibody comprising (a) HVR-H1 comprising the amino acid sequence of SEQ ID NO: 4; (b) HVR-H2 comprising the amino acid sequence of SEQ ID NO: 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9.

In certain embodiments, any one or more amino acids of an anti-TGFβ3 antibody as provided above are substituted at the following HVR positions:

in HVR-H2 (SEQ ID NO: 5): at position N54 (e.g., N54S, N54Q) or T56 (e.g., T56A).

In certain embodiments, the substitutions are conservative substitutions, as provided herein.

In any of the above embodiments of methods for treating fibrosis, an anti-TGFβ3 antibody may be humanized. In one embodiment, an anti-TGFβ3 antibody comprises HVRs as in any of the above embodiments, and further comprises an acceptor human framework, e.g. a human immunoglobulin framework or a human consensus framework. In another embodiment, an anti-TGFβ3 antibody comprises HVRs as in any of the above embodiments, and further comprises a VH comprising FR modifications selected from the group consisting of 47L or 47W; 49A, 49S, or 49G; 73D or 73N; and 76N, 78D or 78L, 78A, or 78V, relative to the VH having amino acid sequence of SEQ ID NO: 23. In some embodiments, the anti-TGFβ3 antibody comprises a VH, wherein the VH comprises the amino acid sequence of SEQ ID NO: 23, wherein the VH comprises a set of framework modifications selected from the group consisting of: (i) 47L, 49A in FR2, 78V in FR3 (h2A10.v1); (ii) 47L, 49A in FR2, 73D, 76S, 78V in FR3 (h2A10.v2); (iii) 47W in FR2 (h2A10.v1.5); (iv): 49G in FR2 (h2A10.v1.6); (v) 78A in FR3 (h2A10.v1.7); (vi) 47W in FR2 (h2A10.v2.5); (vii) 49S in FR2 (h2A10.v2.6); (viii) 73N in FR3 (h2A10.v2.7); (ix) 76N in FR3 (h2A10.v2.8); (x) 78L in FR3 (h2A10.v2.9); and (xi) 49S in FR2, 76N, 78L in FR3 (h2A10.v3 and h2A10.v4). In another embodiment, an anti-TGFβ3 antibody comprises HVRs as in any of the above embodiments, and further comprises a VL comprising FR modifications selected from the group consisting of: 4L or 4M, 38H or 38Q, 43A or 43Q, and 58V, relative to the VL having amino acid sequence of SEQ ID NO; 22. In another embodiment, the antibody comprises the VL of SEQ ID NO: 22, wherein the VL comprises a set of framework modifications selected from the group consisting of (i) 4L in FR1, 38H and 43Q in FR2, 581 in FR3 (h2A10.v1 and h2A10.v2); (ii) 4M in FR1 (h2A10.v1.1 and h2A10.v2.1); (iii) 38Q in FR2 (h2A10.v1.2 and h2A10.v2.2); (iv) 43A in FR2 (h2A10.v1.3 and h2A10.v2.3); (v) 58V in FR3 (h2A10.v1.4 and h2A10.v2.4); (vi) 38Q, 43A in FR2, 58V in FR3 (h2A10.v3 and h2A10.v4); (vii) 58V in FR3 (h2A10.v1.4 and h2A10.v2.4); and (vi) 38Q, 43A in FR2, 58V in FR3 (h2A10.v3 and h2A10.v4).

In a further aspect, the invention provides a method for treating fibrosis, the method comprising administering to a subject having such fibrosis an effective amount of an anti-TGFβ3 antibody selected from the following:

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, and 42-50, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, and 38-41;

an antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, 42-50, 55, and 57, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, 38-41, 54, and 56;

an antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4);

an antibody comprises a complete H chain amino acid sequence having at least 95% sequence identity to the amino acid sequence selected from the group consisting of SEQ ID NOs: 29, 59, 64, and 65-72 and/or a complete L chain amino acid sequence having an amino acid sequence selected from the group consisting of SEQ ID NOs: 28, 58, and 60-63;

an antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (vi), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9);

an antibody comprises a complete H chain amino acid sequence having at least 95% sequence identity to the amino acid sequence selected from the group consisting of SEQ ID NOs: 29, 59, 64, 65-72, 77, and 79 and/or a complete L chain amino acid sequence having an amino acid sequence selected from the group consisting of SEQ ID NOs: 28, 58, 60-63, 76, and 78;

an antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 77/76 (v3), and SEQ ID NOs: 79/78;

an antibody comprising a VH having at least 90%, 91%, 92%, 93%, 94%, 95%, 96%, 97%, 98%, 99%, or 100% sequence identity to the amino acid sequence of SEQ ID NO: 52 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising VH/VL sequences (respectively) comprising the amino acid sequences of SEQ ID NOs: 52/36 (h2A10.v2.N54Q);

an antibody comprising a complete H chain having at least 90%, 91%, 92%, 93%, 94%, 95%, 96%, 97%, 98%, 99%, or 100% sequence identity to the amino acid sequence of SEQ ID NO: 74 and a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising complete H/L chain sequences (respectively) comprising the amino acid sequences of SEQ ID NOs: 74/58 (h2A10.v2.N54Q);

an antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 54;

an antibody comprising VH/VL sequences (respectively) comprising the amino acid sequences of SEQ ID NO: 51/36 (h2A10.v2.N54S) or SEQ ID NO: 55/54 (h2A10.v3);

an antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 76;

an antibody comprising complete H/L chain sequences (respectively) comprising the amino acid sequences of SEQ ID NOs: 73/58 (h2A10.v2.N54S) or SEQ ID NOs: 77/76 (h2A10.v3);

an antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 56;

an antibody comprising VH/VL sequences (respectively) comprising the amino acid sequences of SEQ ID NOs: 53/36 (h2A10.v2.T56A) or SEQ ID NOs: 57/56 (h2A10.v4);

an antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 78;

an antibody comprising complete H/L chain sequences (respectively) comprising the amino acid sequences of SEQ ID NOs: 75/58 (h2A10.v2.T56A) or SEQ ID NOs: 79/78 (h2A10.v4);

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO:6;

an antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4);

an antibody that binds to the same epitope as an anti-TGFβ3 antibody comprising VH/VL sequences (respectively) of SEQ ID NOs: 57/56 (h2A10.v4);

an antibody that comprises an antigen binding domain that directly contacts amino acid residues R325, K331, W332, H334, E335, T387, I388, L389, Y391, V392, G393, R394, P396, K397, and V398 on human TGFβ3, wherein the anti-TGFβ3 antibody selectively neutralizes TGFβ3;

an antibody that selectively neutralizes TGFβ3 and has reduced toxicity in mice relative to the pan-TGFβ antibody 1D11;

an antibody that has reduced toxicity in mice relative to the pan-TGFβ antibody 1D11 at a dose of 50 mg/kg.

In some aspects of the above methods for treating a TGFβ-related disorder, the method comprises administering to a subject having systemic sclerosis (SSc) an effective amount of an anti-TGFβ3 antibody that selectively neutralizes TGFβ3 having one or more of the following properties:

(a) the anti-TGFβ3 antibody binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody binds amino acid residue R394 in the beta6/beta7 hairpin region of human TGFβ3;

(e) the anti-TGFβ3 antibody binds amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

(j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody;

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

In a further aspect, the invention provides a method for treating SSc, the method comprising administering to a subject having SSc an effective amount of an isoform-selective anti-TGFβ antibody having one or more of the following properties:

an antibody that selectively neutralizes TGFβ3;

an antibody that binds to TGFβ3 with a $K_D$ of less than 10 pM and/or has a cell-based $IC_{50}$ less than 250 pM;

an antibody that binds to TGFβ3 with a $K_D$ of less than about 5 pM, about 4 pM, about 3 pM, or less than about 2 pM;

an antibody that has a cell-based $IC_{50}$ less of than about 200 pM, about 150 pM, about 100 pM, about 75 pM, or about 50 pM;

an antibody provided herein that has a cell-based $IC_{50}$ for inhibition (neutralization) of TGFβ3 of less than about 20 pM;

an antibody that selectively neutralizes TGFβ3 and has reduced toxicity in mice relative to the pan-TGFβ antibody 1D11;

an antibody that selectively neutralizes TGFβ3 and has an improved safety profile.

In a further aspect, the invention provides a method for treating SSc, the method comprising administering to a subject having SSc an effective amount of an anti-TGFβ3 antibody selected from the following:

an antibody comprising at least one, two, three, four, five, or six HVRs selected from (a) HVR-H1 comprising the amino acid sequence of SEQ ID NO: 4; (b) HVR-H2 comprising the amino acid sequence selected from SEQ ID NOs: 5, 34, 35, and 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9;

an antibody comprising (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an antibody comprising (a) HVR-H1 comprising the amino acid sequence of SEQ ID NO: 4; (b) HVR-H2 comprising the amino acid sequence of SEQ ID NO: 34; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an antibody comprising (a) HVR-H1 comprising the amino acid sequence of SEQ ID NO: 4; (b) HVR-H2 comprising the amino acid sequence of SEQ ID NO: 35; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9; and an antibody comprising (a) HVR-H1 comprising the amino acid sequence of SEQ ID NO: 4; (b) HVR-H2 comprising the amino acid sequence of SEQ ID NO: 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9.

In certain embodiments, any one or more amino acids of an anti-TGFβ3 antibody as provided above are substituted at the following HVR positions:

in HVR-H2 (SEQ ID NO: 5): at position N54 (e.g., N54S, N54Q) or T56 (e.g., T56A).

In certain embodiments, the substitutions are conservative substitutions, as provided herein.

In any of the above embodiments of methods for treating SSc, an anti-TGFβ3 antibody may be humanized. In one embodiment, an anti-TGFβ3 antibody comprises HVRs as in any of the above embodiments, and further comprises an acceptor human framework, e.g. a human immunoglobulin framework or a human consensus framework. In another embodiment, an anti-TGFβ3 antibody comprises HVRs as in any of the above embodiments, and further comprises a VH comprising FR modifications selected from the group consisting of 47L or 47W; 49A, 49S, or 49G; 73D or 73N; and 76N, 78D or 78L, 78A, or 78V. In some embodiments, the anti-TGFβ3 antibody comprises a VH, wherein the VH comprises the amino acid sequence of SEQ ID NO: 23, wherein the VH comprises a set of framework modifications selected from the group consisting of (i) 47L, 49A in FR2, 78V in FR3 (h2A10.v1); (ii) 47L, 49A in FR2, 73D, 76S, 78V in FR3 (h2A10.v2); (iii) 47W in FR2 (h2A10.v1.5); (iv): 49G in FR2 (h2A10.v1.6); (v) 78A in FR3 (h2A10.v1.7); (vi) 47W in FR2 (h2A10.v2.5); (vii) 49S in FR2 (h2A10.v2.6); (viii) 73N in FR3 (h2A10.v2.7); (ix) 76N in FR3 (h2A10.v2.8); (x) 78L in FR3 (h2A10.v2.9); and (xi) 49S in FR2, 76N, 78L in FR3 (h2A10.v3 and h2A10.v4). In another embodiment, an anti-TGFβ3 antibody comprises HVRs as in any of the above embodiments, and further comprises a VL comprising FR modifications selected from the group consisting of: 4L or 4M, 38H or 38Q, 43A or 43Q, and 58V. In another embodiment, the antibody comprises the VL of SEQ ID NO: 22, wherein the VL comprises a set of framework modifications selected from the group consisting of: (i) 4L in FR1, 38H and 43Q in FR2, 581 in FR3 (h2A10.v1 and h2A10.v2); (ii) 4M in FR1 (h2A10.v1.1 and h2A10.v2.1); (iii) 38Q in FR2 (h2A10.v1.2 and h2A10.v2.2); (iv) 43A in FR2 (h2A10.v1.3 and h2A10.v2.3); (v) 58V in FR3 (h2A10.v1.4 and h2A10.v2.4); (vi) 38Q, 43A in FR2, 58V in FR3 (h2A10.v3 and h2A10.v4); (vii) 58V in FR3 (h2A10.v1.4 and h2A10.v2.4); and (vi) 38Q, 43A in FR2, 58V in FR3 (h2A10.v3 and h2A10.v4).

In a further aspect, the invention provides a method for treating SSc, the method comprising administering to a subject having SSc an effective amount of an anti-TGFβ3 antibody selected from the following:

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, and 42-50, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, and 38-41;

an antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, 42-50, 55, and 57, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, 38-41, 54 and 56;

an antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4);

an antibody comprises a complete H chain amino acid sequence having at least 95% sequence identity to the amino acid sequence selected from the group consisting of SEQ ID NOs: 29, 59, 64, and 65-72 and/or a complete L chain amino acid sequence having an amino acid sequence selected from the group consisting of SEQ ID NOs: 28, 58, and 60-63;

an antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9);

an antibody comprises a complete H chain amino acid sequence having at least 95% sequence identity to the amino acid sequence selected from the group consisting of SEQ ID NOs: 29, 59, 64, 65-72, 77 and 79, and/or a complete L chain amino acid sequence having an amino acid sequence selected from the group consisting of SEQ ID NOs: 28, 58, 60-63, 76 and 78;

an antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 77/76 (v3), and SEQ ID NOs: 79/78 (v4);

an antibody comprising a VH having at least 90%, 91%, 92%, 93%, 94%, 95%, 96%, 97%, 98%, 99%, or 100% sequence identity to the amino acid sequence of SEQ ID NO: 52 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising VH/VL sequences (respectively) comprising the amino acid sequences of SEQ ID NOs: 52/36 (h2A10.v2.N54Q);

an antibody comprising a complete H chain having at least 90%, 91%, 92%, 93%, 94%, 95%, 96%, 97%, 98%, 99%, or 100% sequence identity to the amino acid sequence of SEQ ID NO: 74 and a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising complete H/L chain sequences (respectively) comprising the amino acid sequences of SEQ ID NOs: 74/58 (h2A10.v2.N54Q);

an antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 54;

an antibody comprising VH/VL sequences (respectively) comprising the amino acid sequences of SEQ ID NO: 51/36 (h2A10.v2.N54S) or SEQ ID NO: 55/54 (h2A10.v3);

an antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 76;

an antibody comprising complete H/L chain sequences (respectively) comprising the amino acid sequences of SEQ ID NOs: 73/58 (h2A10.v2.N54S) or SEQ ID NOs: 77/76 (h2A10.v3);

an antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 56;

an antibody comprising VH/VL sequences (respectively) comprising the amino acid sequences of SEQ ID NOs: 53/36 (h2A10.v2.T56A) or SEQ ID NOs: 57/56 (h2A10.v4);

an antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 78;

an antibody comprising complete H/L chain sequences (respectively) comprising the amino acid sequences of SEQ ID NOs: 75/58 (h2A10.v2.T56A) or SEQ ID NOs: 79/78 (h2A10.v4);

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO:6;

an antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3) and SEQ ID NOs: 57/56 (v4);

an antibody that binds to the same epitope as an anti-TGFβ3 antibody comprising VH/VL sequences (respectively) of SEQ ID NOs: 57/56 (h2A10.v4);

an antibody that comprises an antigen binding domain that directly contacts amino acid residues R325, K331, W332, H334, E335, T387, I388, L389, Y391, V392, G393, R394, P396, K397, and V398 on human TGFβ3, wherein the anti-TGFβ3 antibody selectively neutralizes TGFβ3;

an antibody that selectively neutralizes TGFβ3 and has reduced toxicity in mice relative to the pan-TGFβ antibody 1D11;

an antibody that has reduced toxicity in mice relative to the pan-TGFβ antibody 1D11 at a dose of 50 mg/kg.

In some aspects of the above methods for treating a TGFβ-related disorder, the method comprises administering to a subject having idiopathic pulmonary fibrosis (IPF) an effective amount of an anti-TGFβ3 antibody that selectively neutralizes TGFβ3 having one or more of the following properties:

(a) the anti-TGFβ3 antibody binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody binds amino acid residue R394 in the beta6/beta7 hairpin region of human TGFβ3;

(e) the anti-TGFβ3 antibody binds amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

(j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody;

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

In a further aspect, the invention provides a method for treating IPF, the method comprising administering to a subject having IPF an effective amount of an isoform-selective anti-TGFβ antibody having one or more of the following properties:

an antibody that selectively neutralizes TGFβ3;

an antibody that binds to TGFβ3 with a $K_D$ of less than 10 pM and/or has a cell-based $IC_{50}$ less than 250 pM;

an antibody that binds to TGFβ3 with a $K_D$ of less than about 5 pM, about 4 pM, about 3 pM, or less than about 2 pM;

an antibody that has a cell-based $IC_{50}$ less of than about 200 pM, about 150 pM, about 100 pM, about 75 pM, or about 50 pM;

an antibody provided herein that has a cell-based $IC_{50}$ for inhibition (neutralization) of TGFβ3 of less than about 20 pM;

an antibody that selectively neutralizes TGFβ3 and has reduced toxicity in mice relative to the pan-TGFβ antibody 1D11;

an antibody that selectively neutralizes TGFβ3 and has an improved safety profile.

In a further aspect, the invention provides a method for treating IPF, the method comprising administering to a subject having IPF an effective amount of an anti-TGFβ3 antibody selected from the following:

an antibody comprising at least one, two, three, four, five, or six HVRs selected from (a) HVR-H1 comprising the amino acid sequence of SEQ ID NO: 4; (b) HVR-H2 comprising the amino acid sequence selected from SEQ ID NOs: 5, 34, 35, and 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9;

an antibody comprising (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an antibody comprising (a) HVR-H1 comprising the amino acid sequence of SEQ ID NO: 4; (b) HVR-H2 comprising the amino acid sequence of SEQ ID NO: 34; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an antibody comprising (a) HVR-H1 comprising the amino acid sequence of SEQ ID NO: 4; (b) HVR-H2 comprising the amino acid sequence of SEQ ID NO: 35; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9; and an antibody comprising (a) HVR-H1 comprising the amino acid sequence of SEQ ID NO: 4; (b) HVR-H2 comprising the amino acid sequence of SEQ ID NO: 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9.

In certain embodiments, any one or more amino acids of an anti-TGFβ3 antibody as provided above are substituted at the following HVR positions:

in HVR-H2 (SEQ ID NO: 5): at position N54 (e.g., N54S, N54Q) or T56 (e.g., T56A).

In certain embodiments, the substitutions are conservative substitutions, as provided herein.

In any of the above embodiments of methods for treating IPF, an anti-TGFβ3 antibody may be humanized. In one embodiment, an anti-TGFβ3 antibody comprises HVRs as in any of the above embodiments, and further comprises an acceptor human framework, e.g. a human immunoglobulin framework or a human consensus framework. In another embodiment, an anti-TGFβ3 antibody comprises HVRs as in any of the above embodiments, and further comprises a VH comprising FR modifications selected from the group consisting of 47L or 47W; 49A, 49S, or 49G; 73D or 73N; and 76N, 78D or 78L, 78A, or 78V. In some embodiments, the anti-TGFβ3 antibody comprises a VH, wherein the VH comprises the amino acid sequence of SEQ ID NO: 23, wherein the VH comprises a set of framework modifications selected from the group consisting of (i) 47L, 49A in FR2, 78V in FR3 (h2A10.v1); (ii) 47L, 49A in FR2, 73D, 76S, 78V in FR3 (h2A10.v2); (iii) 47W in FR2 (h2A10.v1.5); (iv): 49G in FR2 (h2A10.v1.6); (v) 78A in FR3

(h2A10.v1.7); (vi) 47W in FR2 (h2A10.v2.5); (vii) 49S in FR2 (h2A10.v2.6); (viii) 73N in FR3 (h2A10.v2.7); (ix) 76N in FR3 (h2A10.v2.8); (x) 78L in FR3 (h2A10.v2.9); and (xi) 49S in FR2, 76N, 78L in FR3 (h2A10.v3 and h2A10.v4). In another embodiment, an anti-TGFβ3 antibody comprises HVRs as in any of the above embodiments, and further comprises a VL comprising FR modifications selected from the group consisting of: 4L or 4M, 38H or 38Q, 43A or 43Q, and 58V. In another embodiment, the antibody comprises the VL of SEQ ID NO: 22, wherein the VL comprises a set of framework modifications selected from the group consisting of: (i) 4L in FR1, 38H and 43Q in FR2, 581 in FR3 (h2A10.v1 and h2A10.v2); (ii) 4M in FR1 (h2A10.v1.1 and h2A10.v2.1); (iii) 38Q in FR2 (h2A10.v1.2 and h2A10.v2.2); (iv) 43A in FR2 (h2A10.v1.3 and h2A10.v2.3); (v) 58V in FR3 (h2A10.v1.4 and h2A10.v2.4); (vi) 38Q, 43A in FR2, 58V in FR3 (h2A10.v3 and h2A10.v4); (vii) 58V in FR3 (h2A10.v1.4 and h2A10.v2.4); and (vi) 38Q, 43A in FR2, 58V in FR3 (h2A10.v3 and h2A10.v4).

In a further aspect, the invention provides a method for treating IPF, the method comprising administering to a subject having IPF an effective amount of an anti-TGFβ3 antibody selected from the following:

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, and 42-50, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, and 38-41;

an antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, 42-50, 55, and 57, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, 38-41, 54, and 56;

an antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4);

an antibody comprises a complete H chain amino acid sequence having at least 95% sequence identity to the amino acid sequence selected from the group consisting of SEQ ID NOs: 29, 59, 64, and 65-72 and/or a complete L chain amino acid sequence having an amino acid sequence selected from the group consisting of SEQ ID NOs: 28, 58, and 60-63;

an antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (vi), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9);

an antibody comprises a complete H chain amino acid sequence having at least 95% sequence identity to the amino acid sequence selected from the group consisting of SEQ ID NOs: 29, 59, 64, 65-72, 77 and 79, and/or a complete L chain amino acid sequence having an amino acid sequence selected from the group consisting of SEQ ID NOs: 28, 58, 60-63, 76, and 78;

an antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 77/76 (v3), and SEQ ID NOs: 79/78;

an antibody comprising a VH having at least 90%, 91%, 92%, 93%, 94%, 95%, 96%, 97%, 98%, 99%, or 100% sequence identity to the amino acid sequence of SEQ ID NO: 52 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising VH/VL sequences (respectively) comprising the amino acid sequences of SEQ ID NOs: 52/36 (h2A10.v2.N54Q);

an antibody comprising a complete H chain having at least 90%, 91%, 92%, 93%, 94%, 95%, 96%, 97%, 98%, 99%, or 100% sequence identity to the amino acid sequence of SEQ ID NO: 74 and a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising complete H/L chain sequences (respectively) comprising the amino acid sequences of SEQ ID NOs: 74/58 (h2A10.v2.N54Q);

an antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 54;

an antibody comprising VH/VL sequences (respectively) comprising the amino acid sequences of SEQ ID NO: 51/36 (h2A10.v2.N54S) or SEQ ID NO: 55/54 (h2A10.v3);

an antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 76;

an antibody comprising complete H/L chain sequences (respectively) comprising the amino acid sequences of SEQ ID NOs: 73/58 (h2A10.v2.N54S) or SEQ ID NOs: 77/76 (h2A10.v3);

an antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 56;

an antibody comprising VH/VL sequences (respectively) comprising the amino acid sequences of SEQ ID NOs: 53/36 (h2A10.v2.T56A) or SEQ ID NOs: 57/56 (h2A10.v4);

an antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 78;

an antibody comprising complete H/L chain sequences (respectively) comprising the amino acid sequences of SEQ ID NOs: 75/58 (h2A10.v2.T56A) or SEQ ID NOs: 79/78 (h2A10.v4);

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO:6;

an antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO:6;

an antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4);

an antibody that binds to the same epitope as an anti-TGFβ3 antibody comprising VH/VL sequences (respectively) of SEQ ID NOs: 57/56 (h2A10.v4);

an antibody that comprises an antigen binding domain that directly contacts amino acid residues R325, K331, W332, H334, E335, T387, I388, L389, Y391, V392, G393, R394, P396, K397, and V398 on human TGFβ3, wherein the anti-TGFβ3 antibody selectively neutralizes TGFβ3;

an antibody that selectively neutralizes TGFβ3 and has reduced toxicity in mice relative to the pan-TGFβ antibody 1D11;

an antibody that has reduced toxicity in mice relative to the pan-TGFβ antibody 1D11 at a dose of 50 mg/kg.

An isoform-selective anti-TGFβ antibody according to any of the above aspects of the methods of treating fibrosis may be a monoclonal antibody, including a chimeric, humanized or human antibody. In one embodiment, an isoform-selective anti-TGFβ antibody is an antibody fragment, e.g., a Fv, Fab, Fab', scFv, diabody, or $F(ab')_2$ fragment. In another embodiment, the antibody is a full length antibody, e.g., an intact IgG1 or IgG4 antibody, preferably an IgG1, or other antibody class or isotype as defined herein.

In some aspects of the provided methods for treating a TGFβ-related disorder, the method comprises administering to a subject having a TGFβ-related disorder an effective amount of an anti-TGFβ3 antibody comprising: heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9. In some embodiments, the CDR-H2 has the amino acid sequence of SEQ ID NO: 35. In certain embodiments, the isolated anti-TGFβ3 antibody further comprises a VH having at least 90%, 91%, 92%, 93%, 94%, 95%, 96%, 97%, 98%, 99%, or 100% sequence identity to the amino acid sequence of SEQ ID NO: 57. In some embodiments, the anti-TGFβ3 antibody further comprises a VL having at least 90%, 91%, 92%, 93%, 94%, 95%, 96%, 97%, 98%, 99%, or 100% sequence identity to the amino acid sequence of SEQ ID NO: 56. In certain embodiments, the anti-TGFβ3 antibody further comprises a complete H chain having at least 90%, 91%, 92%, 93%, 94%, 95%, 96%, 97%, 98%, 99%, or 100% sequence identity to an amino acid sequence of SEQ ID NO: 79. In other embodiments, the anti-TGFβ3 antibody further comprises a complete L chain having at least 90%, 91%, 92%, 93%, 94%, 95%, 96%, 97%, 98%, 99%, or 100% sequence identity to an amino acid sequence of SEQ ID NO: 78. In some embodiments, the disorder is fibrosis. In certain embodiments, the disorder is SSc. In some embodiments, the disorder is IPF. In certain embodiments, the anti-TGFβ3 antibody is a monoclonal antibody, such as a chimeric, humanized or human antibody. In some embodiments, the anti-TGFβ3 antibody is an antibody fragment, e.g., a Fv, Fab, Fab', scFv, diabody, or $F(ab')_2$ fragment. In other embodiments, the anti-TGFβ3 antibody is a full length antibody, e.g., an intact IgG1 or IgG4 antibody, such as an IgG1, or other antibody class or isotype as defined herein.

Medicaments and Uses of the Antibodies

As used herein, medicaments comprising an isoform-selective anti-TGFβ-antibody of the invention, manufacture of such medicaments, and uses of the medicaments and isoform-selective anti-TGFβ-antibodies of the invention for the treatment of a TGFβ-related disorder can include disruption of TGFβ-driven processes so as to halt progression of the TGFβ-related disorder, slow progression of the TGFβ-related disorder, or cause regression of the TGFβ-related disorder (i.e., improve the subject's (patient's) state of health with respect to the degree of the TGFβ-related disorder in the affected tissue or organ). In certain embodiments, where such uses and treatments precede onset of the TGFβ-related disorder, i.e., use or treatment is performed prior to a known or an otherwise expected onset of TGFβ-related disorder, then such use or treatment may include preventing development or onset of the TGFβ-related disorder. Administration of the various active agents can therefore be carried out for a suitable duration to either control or halt progression of the TGFβ-related disorder, or prevent onset thereof.

As used herein, medicaments comprising an isoform-selective anti-TGFβ-antibody of the invention, manufacture of such medicaments, and uses of the medicaments and isoform-selective anti-TGFβ-antibodies of the invention for the treatment of fibrosis or fibrotic conditions, includes disruption of the fibrotic processes so as to halt progression of the fibrotic condition, slow progression of the fibrotic condition, or cause regression of the fibrotic condition (i.e., improve the subject's (patient's) state of health with respect to the degree of fibrosis in the affected tissue or organ). In certain embodiments, where such uses and treatments precede onset of the fibrotic condition, i.e., the use or treatment is performed prior to a known or an otherwise expected onset of fibrosis, then such use or treatment may include preventing development or onset of the fibrotic condition. Administration of the various active agents can therefore be carried out for a suitable duration to either control or halt progression of the fibrotic condition, or prevent onset thereof.

Thus, in some aspects, the invention provides a medicament comprising an isoform-selective anti-TGFβ-antibody of the invention and/or uses of such medicament or antibody for treating fibrosis, wherein the fibrosis is a fibrotic condition of the lung, liver, heart, kidney, pancreas, eye and/or skin. In one aspect, the fibrosis is a lung fibrosis selected from idiopathic pulmonary fibrosis (IPF); idiopathic pulmonary upper lobe fibrosis (Amitani disease); familial pulmonary fibrosis; pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma; cystic fibrosis; non-specific interstitial pneumonia (NSIP); cryptogenic organizing pneumonia (COP); progressive massive fibrosis, a complication of coal worker's pneumoconiosis; scleroderma/systemic sclerosis (SSc, including limited cutaneous (lcSSc) and diffuse cutaneous (dcSSc) forms and SSc-associated interstitial lung disease (SSc-ILD)); bronchiolitis obliterans-organizing pneumonia; connective tissue disease-associated ILD (CT-ILD), progressive fibrosing ILD, hypersensitivity pneumonitis, pulmonary hypertension; pulmonary tuberculosis; silicosis; asbestosis; acute lung injury; and acute respiratory distress (ARD; including bacterial pneumonia induced, trauma-induced, and viral pneumonia-induced, ventilator-induced, non-pulmonary sepsis induced). In another aspect, the fibrosis is a fibrotic condition of the liver selected from liver cirrhosis due to all etiologies; congenital hepatic fibrosis; obesity; fatty liver; alcohol induced liver fibrosis; non-alcoholic steatohepatitis (NASH); biliary duct injury; primary biliary cirrhosis (PBC), primary sclerosing cholangitis (PSC); infection- or viral-induced liver fibrosis (e.g., chronic hepatitis B and C virus infections); cystic fibrosis; autoimmune hepatitis; necrotizing hepatitis; primary sclerosing cholangitis; hemochromatosis; disorders of the biliary tree; hepatic dysfunction attributable to infections. In another aspect, the fibrosis is a fibrotic condition of the heart and/or pericardium (i.e., heart or pericardial fibrosis, or fibrosis of the associate vasculature) selected from endomyocardial fibrosis; cardiac allograft vasculopathy (CAV); myocardial infarction; atrial fibrosis; congestive heart failure; arterioclerosis; atherosclerosis; vascular stenosis; myocarditis; congestive cardiomyopathy; coronary infarcts; varicose veins; coronary artery stenosis and other post-ischemic conditions; and idiopathic retroperitoneal fibrosis. In another aspect, the fibrosis is a fibrotic condition of the kidney selected from glomerulonephritis (including membranoproliferative, diffuse proliferative, rapidly progressive or sclerosing, post-infectious and chronic forms); diabetic glomerulosclerosis; focal segmental glomerulosclerosis; IgA nephropathy; diabetic nephropathy; ischemic nephropathy, tubulointerstitial kidney fibrosis, HIV-associated nephropathy; membrane nephropathy; glomerulonephritis secondary to systemic inflammatory diseases such as lupus, scleroderma and diabetes glomerulonephritis; idiopathic membranoproliferative glomerular nephritis; mesangial proliferative glomerulonephritis; crescentic glomerulonephritis; amyloidosis (which affects the kidney among other tissues); autoimmune nephritis; renal tubuloinsterstitial fibrosis; renal arteriosclerosis; Alport's syndrome; nephrotic syndrome; chronic renal failure; chronic kidney disease, periglomerular fibrosis/atubular glomeruli; combined apical emphysema and basal fibrosis syndrome (emphysema/fibrosis syndrome); glomerular hypertension; nephrogenic fibrosing dermatopathy; polycystic kidney disease; Fabry's disease and renal hypertension. In another aspect, the fibrosis is a fibrotic condition of the pancreas selected from stromal remodeling pancreatitis and stromal fibrosis. In another aspect, the fibrosis is a fibrotic condition of the gastrointestinal tract (i.e., GI tract fibrosis) selected from Crohn's disease; ulcerative colitis; collagenous colitis; colorectal fibrosis; villous atrophy; crypt hyperplasia; polyp formation; healing gastric ulcer; and microscopic colitis. In another aspect, the fibrosis is a fibrotic condition of the eye selected from ocular fibrosis, ophthalmic fibrosis, proliferative vitreoretinopathy; vitreoretinopathy of any etiology; fibrosis associated with retinal dysfunction; fibrosis associated with wet or dry macular degeneration; scarring in the cornea and conjunctiva; fibrosis in the corneal endothelium; anterior subcapsular cataract and posterior capsule opacification; anterior segment fibrotic diseases of the eye; fibrosis of the corneal stroma (e.g., associated with corneal opacification); fibrosis of the trabecular network (e.g., associated with glaucoma); posterior segment fibrotic diseases of the eye; fibrovascular scarring (e.g., in retinal or choroidal vasculature of the eye); retinal fibrosis; epiretinal fibrosis; retinal gliosis; subretinal fibrosis (e.g., associated with age related macular degeneration); tractional retinal detachment in association with contraction of the tissue in diabetic retinopathy; congenital orbital fibrosis; lacrimal gland fibrosis; corneal subepithelial fibrosis; and Grave's ophthalmopathy. In another aspect, the fibrosis is a selected from fibrosis resulting from spinal cord injury/fibrosis or central nervous system fibrosis such as fibrosis after a stroke, Duchenne muscular dystrophy, dupuytren's contracture, fibrosis associated with neurodegenerative disorder such as Alzheimer's disease or multiple sclerosis; vascular restenosis; uterine fibrosis; endometriosis; ovarian fibroids; Peyronie's disease; polycystic ovarian syndrome; disease related pulmonary apical fibrosis in ankylosing spondylitis; scarring; and fibrosis incident to microbial infections (e.g., bacterial, viral, parasitic, fungal etc.).

In one embodiment, the invention provides a medicament comprising an isoform-selective anti-TGFβ-antibody of the invention and/or uses of such medicament or antibody for treating a TGFβ-related disorder, wherein the use includes administering to a subject having such TGFβ-related disorder an effective amount of an isoform-selective anti-TGFβ antibody (e.g., anti-TGFβ2, anti-TGFβ2/3, or anti-TGFβ3 antibody). In one such embodiment, the use further comprises administering to the subject an effective amount of at least one additional therapeutic agent, as described below.

In one embodiment, the invention provides a medicament comprising an isoform-selective anti-TGFβ-antibody of the invention and/or uses of such medicament or antibody for treating fibrosis (e.g., a fibrotic condition as described above), wherein the use includes administering to a subject having such fibrosis an effective amount of an isoform-selective anti-TGFβ antibody (e.g., anti-TGFβ2, anti-TGFβ2/3, or anti-TGFβ3 antibody). In one such embodiment, the use further comprises administering to the subject an effective amount of at least one additional therapeutic agent, as described below.

In a further aspect, an isoform-selective anti-TGFβ antibody as described herein (e.g., anti-TGFβ2, anti-TGFβ2/3, or anti-TGFβ3 antibody) for use as a medicament is provided. In further aspects, an isoform-selective anti-TGFβ antibody (e.g., anti-TGFβ2, anti-TGFβ2/3, or anti-TGFβ3 antibody) for use in treating a TGFβ-related disorder (e.g., fibrosis, e.g., fibrosis of the lung, e.g., IPF, liver, pancreas, heart, kidney, eye, and/or skin, e.g., SSc) is provided. In certain embodiments, an isoform-selective anti-TGFβ antibody (e.g., anti-TGFβ2, anti-TGFβ2/3, or anti-TGFβ3 antibody) for use in a method of treatment is provided. In certain embodiments, the invention provides an isoform-selective anti-TGFβ antibody (e.g., anti-TGFβ2, anti-TGFβ2/3, or anti-TGFβ3 antibody) for use in a method of treating a subject having fibrosis comprising administering to the individual an effective amount of the isoform-selective anti-TGFβ antibody (e.g., anti-TGFβ2, anti-TGFβ2/3, or anti-TGFβ3 antibody). In one such embodiment, the use further comprises administering to the individual an effective amount of at least one additional therapeutic agent, e.g., as described below. In further embodiments, the invention provides an isoform-selective anti-TGFβ antibody (e.g., anti-TGFβ2, anti-TGFβ2/3, or anti-TGFβ3 antibody) for use in inhibiting TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin and/or for inhibiting new collagen synthesis in a subject. In certain embodiments, the invention provides an isoform-selective anti-TGFβ antibody (e.g., anti-TGFβ2, anti-TGFβ2/3, or anti-TGFβ3 antibody) for use in a method of inhibiting TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin and/or for inhibiting new collagen synthesis in a subject comprising administering to the subject an effective amount of the isoform-selective anti-TGFβ antibody (e.g., anti-TGFβ2, anti-TGFβ2/3, or anti-TGFβ3 antibody) to inhibit TGFBR-dependent SMAD signaling, to inhibit the assembly of TGFβ-TGFBR signaling complexes, to inhibit TGFβ signaling through the TGFBR1/R2 complex, to inhibit TGFβ signaling through the TGFBR2/ALK1 complex facilitated by endoglin, and/or for inhibiting new collagen synthesis in the subject. A subject according to any of the above embodiments is preferably a human.

In a further aspect, the invention provides for the use of an isoform-selective anti-TGFβ antibody (e.g., anti-TGFβ2, anti-TGFβ2/3, or anti-TGFβ3 antibody) in the manufacture or preparation of a medicament. In one embodiment, the medicament is for treatment of a TGFβ-related disorder, e.g., fibrosis, such as but not limited to fibrosis, e.g., fibrosis of the lung, e.g., IPF, liver, pancreas, heart, kidney, eye, and/or skin, e.g., SSc. In a further embodiment, the medicament is for use in a method of treating fibrosis comprising administering to a subject having fibrosis an effective amount of the medicament. In one such embodiment, the use further comprises administering to the subject an effective amount of at least one additional therapeutic agent, e.g., as described below. In a further embodiment, the medicament is for inhibiting TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin, and/or for inhibiting new collagen synthesis in a subject. In a further embodiment, the medicament is for use in a method of inhibiting TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin, and/or for inhibiting new collagen synthesis in a subject, comprising administering to the individual an effective amount of the medicament to inhibit TGFBR-dependent SMAD signaling, to inhibit the assembly of TGFβ-TGFBR signaling complexes, to inhibit TGFβ signaling through the TGFBR1/R2 complex, to inhibit TGFβ signaling through the TGFBR2/ALK1 complex facilitated by endoglin, and/or to inhibit new collagen synthesis in the subject.

Anti-TGFβ2 Antibodies

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin, and/or for inhibiting new collagen synthesis in a subject, e.g., for treating fibrosis (e.g., fibrosis of the lung, e.g., IPF, liver, pancreas, heart, kidney, eye, and/or skin, e.g., SSc), an anti-TGFβ2 antibody of the invention can have one or more of the following properties:

the anti-TGFβ2 antibody:

(a) selectively neutralizes TGFβ2;

(b) has reduced toxicity relative to the pan-TGFβ antibody 1D11;

(c) has reduced toxicity relative to the pan-TGFβ antibody 1D11;

(d) has reduced toxicity in rodents relative to the pan-TGFβ antibody 1D11;

(e) has reduced toxicity relative to the pan-TGFβ small molecule inhibitor galunisertib; and/or (f) has reduced toxicity in rodents relative to the pan-TGFβ small molecule inhibitor galunisertib; and wherein in some embodiments, the use, medicament, or method is for treating fibrosis and wherein the fibrosis is SSc or IPF.

In further aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβ2 antibody of the invention can have one or more of the following properties:

the anti-TGFβ2 antibody selectively neutralizes TGFβ2; the anti-TGFβ2 binds to TGFβ2 with a $K_D$ of less than 10 pM and/or has a cell-based $IC_{50}$ of less than 250 pM; binds to TGFβ2 with a $K_D$ of less than or equal to about 5 pM, about 4 pM, about 3 pM, about 2 pM, or about 1 pM; the anti-TGFβ2 antibody provided herein has a cell-based $IC_{50}$ less than or equal to about 250 pM, about 200 pM, about 150 pM, about 100 pM, about 75 pM, about 50 pM, or about 40 pM.

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβs antibody of the invention can have one or more of the following properties:

an anti-TGFβ2 antibody comprising at least one, two, three, four, five, or six HVRs selected from (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21;

an anti-TGFβ2 antibody comprising at least one, at least two, or all three VH HVR sequences selected from (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18. In another aspect, the invention provides an antibody comprising (a) HVR-H1 comprising the amino acid sequence of SEQ ID NO: 16; (b) HVR-H2 comprising the amino acid sequence of SEQ ID NO:17; ad (c) HVR-H3 comprising the amino acid sequence of SEQ ID NO: 18;

an anti-TGFβ2 antibody comprising at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21;

an anti-TGFβ2 antibody comprising HVR-H3 comprising the amino acid sequence of SEQ ID NO: 18 and HVR-L3 comprising the amino acid sequence of SEQ ID NO: 21. In a further embodiment, the anti-TGFβ2 antibody comprises HVR-H3 comprising the amino acid sequence of SEQ ID NO: 18, HVR-L3 comprising the amino acid sequence of SEQ ID NO: 21, and HVR-H2 comprising the amino acid sequence of SEQ ID NO: 17;

an anti-TGFβ2 antibody comprising (a) a VH domain comprising at least one, at least two, or all three VH HVR sequences selected from (i) HVR-H1 comprising the amino acid sequence of SEQ ID NO: 16; (ii) HVR-H2 comprising the amino acid sequence of SEQ ID NO:17; (iii) HVR-H3 comprising the amino acid sequence of SEQ ID NO: 18; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21; and an anti-TGFβ2 antibody comprising a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above aspects, the isoform-selective anti-TGFβ may be humanized. In one embodiment, the isoform-selective anti-TGFβ antibody comprises HVRs as in any of the above embodiments, and further comprises an acceptor human framework, e.g. a human immunoglobulin framework or a human consensus framework. In any of the above embodiments, a humanized anti-TGFβ2 antibody comprises one or more mutations in the VH framework selected from the group consisting of 37V or 37I, 48M or 48L, 49G or 49A, 67L, 71K and 78V, and 105P or 105R. In some embodiments, the anti-TGFβ2 antibody comprises a VH, wherein the VH comprises the amino acid sequence of SEQ ID NO: 25, wherein the VH comprises a set of framework mutations selected from the group consisting of: (i) 37V, 48M and 49G in FR2 and 105P in FR4 (h6F12.v1 and h6F12.v3); (ii) 37V and 48M in FR2, 67L, 71K and 78V in FR3 and 105P in FR4 (h6F12.v2 and h6F12.v4); (iii) 37I in FR2 (h6F12.v1.6); (iv) 48L in FR2 (h6F12.v1.7); (v) 49A in FR2 (h6F12.v1.8); (vi) 105R in FR4 (h6F12.v1.9); (vii) 37V, 48M and 49G in FR2 and 105P in FR4 (h6F12.v1 and h6F12.v3); (viii) 37V and 48M in FR2, 67L, 71K and 78V in FR3 and 105P in FR4 (6F12.v2 and h6F12.v4); (ix) 37I in FR2 (h6F12.v1.6); (x) 48L in FR2 (h6F12.v1.7); (xi): 49A in FR2 (h6F12.v1.8); and (xii) 105R in FR4 (h6F12.v1.9). In any of the above embodiments, a humanized anti-TGFβ2 antibody comprises one or more mutations in the VL framework selected from the group consisting of 43S or 43A, 66G, 69T, 71F, and 87Y relative to the VL having the amino acid sequence of SEQ ID NO: 24. In some embodiments, the anti-TGFβ2 antibody comprises a VL, wherein the VL comprises the amino acid sequence of SEQ ID NO: 24, wherein the VL comprises a set of framework mutations selected from the group consisting of: (i) 43S in FR2 and 66E, 69P, 71Y and 87F in FR3 (h6F12.v1 and h6F12.v2); (ii) 43S in FR2 and 58V, 66E, 69P, 71Y and 87F in FR3 (h6F12.v3 and h6F12.v4); (iii) 43A in FR2 (h6F12.v1.1); (iv) 66G in FR3 (h6F12.v1.2); (v) 69T in FR3 (h6F12.v1.3); (vi) 71F in FR3 (h6F12.v1.4); and (vii) 87Y in FR3 (h6F12.v1.5).

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an isoform-selective anti-TGFβ antibody of the invention can have one or more of the following properties:

an anti-TGFβ2 antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NO: 25, 132, and 138-142; or the VH comprises one, two or three HVRs selected from: (a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; and the antibody comprises a light chain variable domain (VL) having at least 90%, 91%, 92%, 93%, 94%, 95%, 96%, 97%, 98%, 99%, or 100% sequence identity to the amino acid sequence selected from the group consisting of SEQ ID NO: 24, 131, 133-137, 143, and 144, or the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21;

an anti-TGFβ2 antibody comprising the VH/VL sequences (respectively) selected from the group consisting of SEQ ID NOs: 25/24 (rabbit 6F12), SEQ ID NOs: 132/131 (v1), SEQ ID NOs: 132/133 (v1.1), SEQ ID NOs: 132/134 (v1.2), SEQ ID NOs: 132/135 (v1.3), SEQ ID NOs: 132/136 (v1.4), SEQ ID NOs: 132/137 (v1.5), SEQ ID NOs: 138/131 (v1.6), SEQ ID NOs: 139/131 (v1.7), SEQ ID NOs: 140/131 (v1.8), SEQ ID NOs: 141/131 (v1.9), SEQ ID NOs: 142/131 (v2), SEQ ID NOs: 132/143 (v3), and SEQ ID NOs: 142/144 (v4); or an anti-TGFβ2 antibody comprising a complete H chain amino acid sequence having at least 95% sequence identity to the amino acid sequence selected from the group consisting of SEQ ID NOs: 31, 146, and 152-156 and/or a complete L chain amino acid sequence having an amino acid sequence selected from the group consisting of SEQ ID NOs: 30, 145, 147-151, 157, and 158;

an anti-TGFβ2 antibody comprising a complete H/L chain pair, the complete H/L chain pair (respectively) comprising amino acid sequences selected from the group consisting of SEQ ID NOs: 31/30 (rabbit 6F12), SEQ ID NOs: 146/145 (v1), SEQ ID NOs: 146/147 (v1.1), SEQ ID NOs: 146/148 (v1.2), SEQ ID NOs: 146/149 (v1.3), SEQ ID NOs: 146/150 (v1.4), SEQ ID NOs: 146/151 (v1.5), SEQ ID NOs: 152/145 (v1.6), SEQ ID NOs: 153/145 (v1.7), SEQ ID NOs: 154/145 (v1.8), SEQ ID NOs: 155/145 (v1.9), SEQ ID NOs: 156/145 (v2), SEQ ID NOs: 146/157 (v3), and SEQ ID NOs: 156/158 (v4);

an antibody that binds to the same epitope as an anti-TGFβ2 antibody comprising a) HVR-H1 comprising the amino acid sequence of SEQ ID NO: 16; (b) HVR-H2 comprising the amino acid sequence of SEQ ID NO:17; (c) HVR-H3 comprising the amino acid sequence of SEQ ID NO: 18; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

Anti-TGFβ2/3 Antibodies

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβ2/3 antibody that selectively neutralizes TGFβ2 and TGFβ3 as described herein can have one or more of the following properties:

(a) selectivity of the anti-TGFβ2/3 antibody for TGFβ2 and TGFβ3 over human TGFβ1, with respect to selective neutralization, is achieved by direct contact of the antibody's antigen binding domain with amino acid residue E373 of TGFβ2 or TGFβ3 (human TGFβ2 numbering);

(b) the anti-TGFβ2/3 antibody neutralizes TGFβ2 and/or TGFβ3 via an allosteric mechanism;

(c) the anti-TGFβ2/3 antibody induces a conformational change in TGFβ2 homodimer;

(d) the anti-TGFβ2/3 antibody induces a conformational change in TGFβ2 homodimer, wherein the conformational change comprises the two monomers pinching together by several degrees;

(e) the anti-TGFβ2/3 antibody is a divalent antibody or a monovalent antibody;

(f) the anti-TGFβ2/3 antibody comprises (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15;

(g) the anti-TGFβ2/3 antibody binds to TGFβ2 homodimer, the TGFβ2 homodimer having a first and a second TGFβ2 monomer, and wherein the anti-TGFβ2/3 antibody comprises an antigen binding domain that directly contacts (i) amino acid residues V313, Q314, D315, R320, L322, Y323, R328, D329, F345, and A347 of the first TGFβ2 monomer, and (ii) amino acid residues N368, T369, I370, N371, P372, E373, A374, S375, A376, and S377 of the second TGFβ2 monomer (human TGFβ2 numbering);

(h) the anti-TGFβ2/3 antibody as in (g), wherein the antigen binding domain is within 5 angstroms of the TGFβ2 and/or TGFβ3 amino acid residues;

(i) wherein the anti-TGFβ2/3 antibody binds to a substantially similar epitope as in (g) in TGFβ3; and j) the anti-TGFβ2/3 antibody does not neutralize TGFβ2 and/or TGFβ3 in single arm form; and wherein in some embodiments, the use, medicament, or method is for treating fibrosis and wherein the fibrosis is SSc or IPF.

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβ2/3 antibody of the invention can have one or more of the following properties:

selectively neutralizes TGFβ2 and TGFβ3; binds to TGFβ2 and/or TGFβ3 with a $K_D$ of less than 10 pM and/or has a cell-based $IC_{50}$ less than 250 pM;

binds to TGFβ2 and/or TGFβ3 with a $K_D$ of less than about 10 pM, about 9 pM, about 8 pM, about 7 pM, about 6 pM, about 5 pM, about 4 pM, about 3 pM, about 2 pM, or about 1 pM;

has a cell-based $IC_{50}$ for inhibition of TGFβ2 of about 250 pM, about 200 pM, about 150 pM, about 100 pM, about 75 pM, or about 50 pM;

has a cell-based $IC_{50}$ for inhibition of TGFβ3 of about 250 pM, about 200 pM, about 150 pM, about 100 pM, about 75 pM, about 50 pM, about 40 pM, about 30 pM or less than about 30 pM; or has a cell-based $IC_{50}$ for inhibition of TGFβ2 of about 250 pM and a cell-based $IC_{50}$ for inhibition (neutralization) of TGFβ3 of about 30 pM.

In any of the above aspects, with respect to the use of an isoform-selective anti-TGFβ antibody as described herein (e.g., anti-TGFβ2, anti-TGFβ2/3, or anti-TGFβ3 antibody) as a medicament (and manufacture or preparation thereof) and/or for use in a method of treatment, e.g., for treating fibrosis (e.g., fibrosis of the lung, liver, pancreas, heart, kidney, eye, and/or skin), the isoform-selective anti-TGFβ antibody can be selected from:

an anti-TGFβ2/3 antibody comprising at least one, two, three, four, five, or six HVRs selected from (a) HVR-H1 comprising the amino acid sequence of SEQ ID NO: 10; (b) HVR-H2 comprising the amino acid anti-TGFβ2/3 antibody sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15;

an anti-TGFβ2/3 antibody comprising at least one, at least two, or all three VH HVR sequences selected from (a) HVR-H1 comprising the amino acid sequence of SEQ ID NO: 10; (b) HVR-H2 comprising the amino acid anti-TGFβ2/3 antibody sequence of SEQ ID NO: 11; (c) HVR-H3 comprising the amino acid sequence of SEQ ID NO: 12, and at least one, at least two, or all three VL HVR sequences selected from (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15; an anti-TGFβ2/3 antibody comprising (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15.

In any of the above uses, the anti-TGFβ2/3 antibody may be humanized. In one embodiment, an anti-TGFβ2/3 antibody comprises HVRs as in any of the above embodiments, and further comprises an acceptor human framework, e.g. a human immunoglobulin framework or a human consensus framework. In some embodiments, the anti-TGFβ2/3 antibody comprises a VH, wherein the VH comprises the amino acid sequence of SEQ ID NO: 27, wherein the VH comprises a set of framework modifications selected from the group consisting of: (i) 2Q and 24V in FR1, 481 and 49G in FR2, 71K, 73S, 78V and 91F in FR3 and 105P in FR4 (h4A11.v1, h4A11.v2, h4A11.v5, h4A11.v6); (ii) 2Q in FR1, 37V in FR2, 67F, 71K, 73S, 78V and 91F in FR3 and 105P in FR4 (h4A11.v3, h4A11.v4, 4A11.v7, h4A11.v8); (iii) delete 1E in FR1 (h4A11.v7.1); (iv) delete 75K and 76N in FR3 (h4A11.v7.2); (v) delete 1E in FR1 and 75K76N in FR3 (h4A11.v7.3); (vi) 2V in FR1 (h4A11.v7.8); (vi) 37I in FR2 (h4A11.v7.9); (vii) 67V in FR3 (h4A11.v7.10); (viii) 71V in FR3 (h4A11.v7.11); (ix) 73T in FR3 (h4A11.v7.12); (x) 78F in FR3 (h4A11.v7.13); (xi) 91Y in FR3 (h4A11.v7.14); (xii) 105Q in FR4 (h4A11.v7.15); (xiii) 2V in FR1, 37I in FR2, 67V, 73T, 78F in FR3, 105Q in FR4 ((h4A11.v7.16); (xiv) 2V in FR1, 37I in FR2, 67V, 73T, 91Y in FR3, 105Q in FR4 (h4A11.v7.17); (xv) 2V in FR1, 37I in FR2, 67V, 73T in FR3, 105Q in FR4 (h4A11.v7.18); and (xvi) 2V in FR1, 37I in FR2, 67V, 73T, deletion of 75K and 76N in FR3, 105Q in FR4 (h4A11.v7.19. In another embodiment, an anti-TGFβ2/3 antibody comprises HVRs as in any of the above embodiments, and further comprises a VL comprising FR modifications selected from the group consisting of: 2A or 2I, 4L, 36F or 36Y, 43P or 43A, and 58V or 581, relative to the VL having the amino acid sequence of SEQ ID NO: 26. In some embodiments, the anti-TGFβ2/3 antibody comprises a VL, wherein the VL comprises the amino acid sequence of SEQ ID NO: 26, wherein the VL comprises a set of framework modifications selected from the group consisting of: (i) 2A and 4L in FR1 and 36F in FR2 (h4A11.v1 and h4A11.v3); (ii) 2A and 4L in FR1 and 36F and 43P in FR2 (h4A11.v2 and h4A11.v4); (iii) 2A in FR1, 36F and 43P in FR2 and 58V in FR3 (h4A11.v5 and h4A11.v7); (iv) 2A and 4L in FR1 and 36F in FR2 (h4A11.v6 and h4A11.v8); (v) 2I in FR1 (h4A11.v7.4); (vi) 36Y in FR2 (h4A11.v7.5); (vii) 43A in FR2 (h4A11.v7.6); (viii) 58I in FR3 (h4A11.v7.7); and (ix) 2I in FR1, 43A in FR2, 581 in FR3 (h4A11.v7.16-19).

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβ2/3 antibody of the invention can have one or more of the following properties:

an anti-TGFβ2/3 antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 27, 81, 83, 86-88, 93-100, and 102-105, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 26, 80, 82, 84, 85, 89-92, and 101;

an anti-TGFβ2/3 antibody comprising the VH and VL sequences (respectively) selected from the group consisting of SEQ ID NOs: 27/26 (rabbit 4A11), SEQ ID NOs: 81/80 (v1), SEQ ID NOs: 81/82 (v2), SEQ ID NOs: 83/80 (v3), SEQ ID NOs: 83/82 (v4), SEQ ID NOs: 81/84 (v5), SEQ ID NOs: 81/85 (v6), SEQ ID NOs: 83/84 (v7), SEQ ID NOs: 86/84 (v7/1), SEQ ID NOs: 87/84 (v7.2), SEQ ID NOs: 88/84 (v7.3), SEQ ID NOs: 83/89 (v7.4), SEQ ID NOs: 83/90 (v7.5), SEQ ID NOs: 83/91 (v7.6), SEQ ID NOs: 83/92 (v7.7), SEQ ID NOs: 93/84 (v7.8), SEQ ID NOs: 94/84 (v7.9), SEQ ID NOs: 95/84 (v7.10), SEQ ID NOs: 96/84 (v7.11), SEQ ID NOs: 97/84 (v7.12), SEQ ID NOs: 98/84 (v7.13), SEQ ID NOs: 99/84 (v7.14), SEQ ID NOs: 100/84 (v7.15), SEQ ID NOs: 102/101 (v7.16), SEQ ID NOs: 103/101 (v7.17), SEQ ID NOs: 104/101 (v7.18), SEQ ID NOs: 105/101 (v7.19), SEQ ID NOs: 83/85 (v8);

an anti-TGFβ2/3 antibody comprising a complete H chain amino acid sequence having at least 95% sequence identity to the amino acid sequence selected from the group consisting of SEQ ID NOs: 33, 107, 109, 112-114, and 119-130 and/or a complete L chain amino acid sequence having an amino acid sequence selected from the group consisting of SEQ ID NOs: 32, 106, 108, 110, 111, 115-118, and 186;

an anti-TGFβ2/3 antibody comprising a complete H/L chain pair, the complete H/L chain pair (respectively) comprising amino acid sequences selected from the group consisting of SEQ ID NOs: 32/33 (rabbit 4A11), SEQ ID NOs: 107/106 (v1), SEQ ID NOs: 107/108 (v2), SEQ ID NOs: 109/106 (v3), SEQ ID NOs: 109/108 (v4), SEQ ID NOs: 107/110 (v5), SEQ ID NOs: 107/111 (v6), SEQ ID NOs: 109/110 (v7), SEQ ID NOs: 112/110 (v7.1), SEQ ID NOs: 113/110 (v7.2), SEQ ID NOs: 114/110 (v7.3), SEQ ID NOs: 114/115 (v7.4), SEQ ID NOs: 114/116 (v7.5), SEQ ID NOs: 114/117 (v7.6), SEQ ID NOs: 114/118 (v7.7), SEQ ID NOs: 119/110 (v7.8), SEQ ID NOs:120/110 (v7.9), SEQ ID NOs: 121/110 (v7.10), SEQ ID NOs: 122/110 (v7.11), SEQ ID NOs: 123/110 (v7.12), SEQ ID NOs: 124/110 (v7.13), SEQ ID NOs: 125/110 (v7.14), SEQ ID NOs: 126/110 (v7.15), SEQ ID NOs: 127/186 (v7.16), SEQ ID NOs: 128/186 (v7.17), SEQ ID NOs: 129/186 (v7.18), SEQ ID NOs: 130/186 (v7.19), and SEQ ID NOs: 114/111 (v8);

an antibody that binds to the same epitope as an anti-TGFβ2/3 antibody comprising (a) HVR-H1 comprising the amino acid sequence of SEQ ID NO: 10; (b) HVR-H2 comprising the amino acid sequence of SEQ ID NO: 11; (c) HVR-H3 comprising the amino acid sequence of SEQ ID NO: 12; (d) HVR-L1 comprising the amino acid sequence of SEQ ID NO: 13; (e) HVR-L2 comprising the amino acid sequence of SEQ ID NO: 14; and (f) HVR-L3 comprising an amino acid sequence selected from SEQ ID NO: 15;

an anti-TGFβ2/3 antibody that binds to an epitope within a fragment of TGFβ2 homodimer, the TGFβ2 homodimer having a first and a second TGFβ2 monomer, wherein the anti-TGFβ2/3 antibody comprises an antigen binding domain that directly contacts amino acid residues V313, Q314, D315, R320, L322, Y323, R328, D329, F345, and A347 of the first TGFβ2 monomer, and amino acid residues N368, T369, I370, N371, P372, E373, A374, S375, A376, and S377 of the second TGFβ2 monomer, and wherein, in some embodiments, the anti-TGFβ2/3 antibody binds to the same region and/or epitope in TGFβ3.

Anti-TGFβ3 Antibodies

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβ3 antibody that selectively neutralizes TGFβ3 as described herein can have one or more of the following properties:

(a) the anti-TGFβ3 antibody binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody binds amino acid residue R394 in the beta6/beta7 hairpin region of human TGFβ3;

(e) the anti-TGFβ3 antibody binds amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

(j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody;

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues; and wherein in some embodiments, the use, medicament, or method is for treating fibrosis and wherein the fibrosis is SSc or IPF.

In further aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an isoform-selective anti-TGFβ antibody of the invention can have one or more of the following properties:

an anti-TGFβ3 antibody that selectively neutralizes TGFβ3;

an anti-TGFβ3 antibody that binds to TGFβ3 with a $K_D$ of less than 10 pM and/or has a cell-based $IC_{50}$ less than 250 pM;

an anti-TGFβ3 antibody that binds to TGFβ3 with a $K_D$ of less than about 5 pM, about 4 pM, about 3 pM, or less than about 2 pM;

an anti-TGFβ3 antibody that has a cell-based $IC_{50}$ less of than about 200 pM, about 150 pM, about 100 pM, about 75 pM, or about 50 pM;

an anti-TGFβ3 antibody provided herein that has a cell-based $IC_{50}$ for inhibition (neutralization) of TGFβ3 of less than about 20 pM;

an anti-TGFβ3 antibody that selectively neutralizes TGFβ3 and has reduced toxicity in mice relative to the pan-TGFβ antibody 1D11; and an anti-TGFβ3 antibody that selectively neutralizes TGFβ3 and has an improved safety profile; and wherein in some embodiments, the use, medicament, or method is for treating fibrosis and wherein the fibrosis is SSc or IPF.

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an anti-TGFβ3 antibody of the invention can have one or more of the following properties:

an anti-TGFβ3 antibody comprising at least one, two, three, four, five, or six HVRs selected from (a) HVR-H1 comprising the amino acid sequence of SEQ ID NO: 4; (b) HVR-H2 comprising the amino acid sequence selected from SEQ ID NOs: 5, 34, 35, and 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9;

an anti-TGFβ3 antibody comprising (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an anti-TGFβ3 antibody comprising (a) HVR-H1 comprising the amino acid sequence of SEQ ID NO: 4; (b) HVR-H2 comprising the amino acid sequence of SEQ ID NO: 34; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an anti-TGFβ3 antibody comprising (a) HVR-H1 comprising the amino acid sequence of SEQ ID NO: 4; (b) HVR-H2 comprising the amino acid sequence of SEQ ID NO: 35; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9;

an anti-TGFβ3 antibody comprising (a) HVR-H1 comprising the amino acid sequence of SEQ ID NO: 4; (b) HVR-H2 comprising the amino acid sequence of SEQ ID NO: 159; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising an amino acid sequence selected from SEQ ID NO: 9.

In certain embodiments, any one or more amino acids of an anti-TGFβ3 antibody as provided above are substituted at the following HVR positions:

in HVR-H2 (SEQ ID NO: 5): at position N54 (e.g., N54S, N54Q) or T56 (e.g., T56A).

In certain embodiments, the substitutions are conservative substitutions, as provided herein.

In any of the above embodiments, an anti-TGFβ3 antibody may be humanized. In one embodiment, an anti-TGFβ3 antibody comprises HVRs as in any of the above embodiments, and further comprises an acceptor human framework, e.g. a human immunoglobulin framework or a human consensus framework. In another embodiment, an anti-TGFβ3 antibody comprises HVRs as in any of the above embodiments, and further comprises a VH comprising FR modifications selected from the group consisting of 47L or 47W; 49A, 49S, or 49G; 73D or 73N; and 76N, 78D or 78L, 78A, or 78V. In some embodiments, the anti-TGFβ3 antibody comprises a VH, wherein the VH comprises the amino acid sequence of SEQ ID NO: 23, wherein the VH comprises a set of framework modifications selected from the group consisting of: (i) 47L, 49A in FR2, 78V in FR3 (h2A10.v1); (ii) 47L, 49A in FR2, 73D, 76S, 78V in FR3 (h2A10.v2); (iii) 47W in FR2 (h2A10.v1.5); (iv): 49G in FR2 (h2A10.v1.6); (v) 78A in FR3 (h2A10.v1.7); (vi) 47W in FR2 (h2A10.v2.5); (vii) 49S in FR2 (h2A10.v2.6); (viii) 73N in FR3 (h2A10.v2.7); (ix) 76N in FR3 (h2A10.v2.8); (x) 78L in FR3 (h2A10.v2.9); and (xi) 49S in FR2, 76N, 78L in FR3 (h2A10.v3 and h2A10.v4). In another embodiment, an anti-TGFβ3 antibody comprises HVRs as in any of the above embodiments, and further comprises a VL comprising FR modifications selected from the group consisting of: 4L or 4M, 38H or 38Q, 43A or 43Q, and 58V, relative to the VL having the amino acid sequence of SEQ ID NO: 22. In another embodiment, the antibody comprises the VL of SEQ ID NO: 22, wherein the VL comprises a set of framework modifications selected from the group consisting of (i) 4L in FR1, 38H and 43Q in FR2, 58I in FR3 (h2A10.v1 and h2A10.v2); (ii) 4M in FR1 (h2A10.v1.1 and h2A10.v2.1); (iii) 38Q in FR2 (h2A10.v1.2 and h2A10.v2.2); (iv) 43A in FR2 (h2A10.v1.3 and h2A10.v2.3); (v) 58V in FR3 (h2A10.v1.4 and h2A10.v2.4); (vi) 38Q, 43A in FR2, 58V in FR3 (h2A10.v3 and h2A10.v4); (vii) 58V in FR3 (h2A10.v1.4 and h2A10.v2.4); and (vi) 38Q, 43A in FR2, 58V in FR3 (h2A10.v3 and h2A10.v4).

In any of the above aspects, with respect to the isoform-selective anti-TGFβ antibodies as described herein (e.g., anti-TGFβ2, anti-TGFβ2/3, or anti-TGFβ3 antibody) as a medicament (and manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), an isoform-selective anti-TGFβ antibody of the invention can have one or more of the following properties:

an anti-TGFβ3 antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, and 42-50, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, and 38-41;

an anti-TGFβ3 antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an anti-TGFβ3 antibody comprising a heavy chain variable domain (VH) sequence having at least 90%, 91%, 92%, 93%, 94%, 95%, 96%, 97%, 98%, 99%, or 100% sequence identity to the amino acid sequence selected from the group consisting of SEQ ID NOs: 23, 37, 42-50 55, and 57, and a light chain variable domain (VL) having at least 90%, 91%, 92%, 93%, 94%, 95%, 96%, 97%, 98%, 99%, or 100% sequence identity to the amino acid sequence selected from the group consisting of SEQ ID NOs: 22, 36, 38-41, 54, and 56;

an anti-TGFβ3 antibody comprising VH/VL sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 55/54 (v3), and SEQ ID NOs: 57/56 (v4);

an anti-TGFβ3 antibody comprises a complete H chain amino acid sequence having at least 95% sequence identity to the amino acid sequence selected from the group consisting of SEQ ID NOs: 29, 59, 64, and 65-72 and/or a complete L chain amino acid sequence having an amino acid sequence selected from the group consisting of SEQ ID NOs: 28, 58, and 60-63;

an anti-TGFβ3 antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9);

an anti-TGFβ3 antibody comprising a complete H chain amino acid sequence having at least 95% sequence identity to the amino acid sequence selected from the group consisting of SEQ ID NOs: 29, 59, 64, 65-72, 77 and 79 and/or a complete L chain amino acid sequence having an amino acid sequence selected from the group consisting of SEQ ID NOs: 28, 58, 60-63, 76, and 78;

an anti-TGFβ3 antibody comprising a complete H/L chain pair, the complete H/L chain pair (respectively) comprising amino acid sequences selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 77/76 (v3), and SEQ ID NOs: 79/78;

an anti-TGFβ3 antibody comprising a VH having at least 90%, 91%, 92%, 93%, 94%, 95%, 96%, 97%, 98%, 99%, or 100% sequence identity to the amino acid sequence of SEQ ID NO: 52 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an anti-TGFβ3 antibody comprising VH/VL sequences (respectively) comprising the amino acid sequences of SEQ ID NOs: 52/36 (h2A10.v2.N54Q);

an anti-TGFβ3 antibody comprising a complete H chain having at least 90%, 91%, 92%, 93%, 94%, 95%, 96%, 97%, 98%, 99%, or 100% sequence identity to the amino acid sequence of SEQ ID NO: 74 and a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an anti-TGFβ3 antibody comprising complete H/L chain sequences (respectively) comprising the amino acid sequences of SEQ ID NOs: 74/58 (h2A10.v2.N54Q);

an anti-TGFβ3 antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an anti-TGFβ3 antibody comprising a VH having at least 90%, 91%, 92%, 93%, 94%, 95%, 96%, 97%, 98%, 99%, or 100% sequence identity to the amino acid sequence of SEQ ID NO: 51 or 55 and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 54;

an anti-TGFβ3 antibody comprising VH/VL sequences (respectively) comprising the amino acid sequences of SEQ ID NO: 51/36 (h2A10.v2.N54S) or SEQ ID NO: 55/54 (h2A10.v3);

an anti-TGFβ3 antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an anti-TGFβ3 antibody comprising a complete H chain having at least 95% sequence identity to the amino acid sequence of SEQ ID NO: 73 or 77 and/or the anti-TGFβ3 antibody comprises a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 76;

an anti-TGFβ3 antibody comprising complete H/L chain sequences (respectively) comprising the amino acid sequences of SEQ ID NOs: 73/58 (h2A10.v2.N54S) or SEQ ID NOs: 77/76 (h2A10.v3);

an anti-TGFβ3 antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, and 38-41;

an anti-TGFβ3 antibody comprising a VH having at least 90%, 91%, 92%, 93%, 94%, 95%, 96%, 97%, 98%, 99%, or 100% sequence identity to the amino acid sequence of SEQ ID NO: 53 or 57, and a VL amino acid sequence having at least 90%, 91%, 92%, 93%, 94%, 95%, 96%, 97%, 98%, 99%, or 100% sequence identity to an amino acid sequence selected from the group consisting of SEQ ID NOs: 22, 36, 38-41, and 56;

an anti-TGFβ3 antibody comprising VH/VL sequences (respectively) comprising the amino acid sequences of SEQ ID NOs: 53/36 (h2A10.v2.T56A) or SEQ ID NOs: 57/56 (h2A10.v4);

an anti-TGFβ3 antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, and 60-63;

an anti-TGFβ3 antibody comprising a complete H chain having at least 95% sequence identity to the amino acid sequence of SEQ ID NO: 74 or 79 and/or a complete L chain amino acid sequence having at least 90%, 91%, 92%, 93%, 94%, 95%, 96%, 97%, 98%, 99%, or 100% sequence identity to an amino acid sequence selected from the group consisting of SEQ ID NOs: 28, 58, 60-63, and 78;

an anti-TGFβ3 antibody comprising complete H/L chain sequences (respectively) comprising the amino acid sequences of SEQ ID NOs: 75/58 (h2A10.v2.T56A) or SEQ ID NOs: 79/78 (h2A10.v4);

an anti-TGFβ3 antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO:6;

an anti-TGFβ3 antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 34; and (c) HVR-H3 comprising the amino acid sequence of SEQ ID NO:6;

an anti-TGFβ3 antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 35; and (c) HVR-H3 comprising the amino acid sequence of SEQ ID NO: 6;

an anti-TGFβ3 antibody that binds to the same epitope as an anti-TGFβ3 antibody comprising (a) HVR-H1 comprising the amino acid sequence of SEQ ID NO: 4; (b) HVR-H2 comprising the amino acid sequence of SEQ ID NO: 159; and (c) HVR-H3 comprising the amino acid sequence of SEQ ID NO:6;

an anti-TGFβ3 antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9);

an anti-TGFβ3 antibody that binds to the same epitope as an anti-TGFβ3 antibody comprising VH/VL sequences (respectively) selected from the group consisting of SEQ ID NOs: 53/36 (h2A10.v2.t56A), SEQ ID NOs: 57/56 (h2A10.v4), SEQ ID NOs: 51/36 (h2A10.v2.N54S), SEQ ID NOs: 55/54 (h2A10.v3), SEQ ID NOs: 52/36 (h2A10.v2.N54Q), SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9), SEQ ID NOs: 55/54 (v3), and SEQ ID NOs: 57/56 (v4);

an anti-TGFβ3 antibody that binds to the same epitope as an anti-TGFβ3 antibody comprising VH/VL sequences (respectively) of SEQ ID NOs: 57/56 (h2A10.v4);

an anti-TGFβ3 antibody that comprises an antigen binding domain that directly contacts amino acid residues R325, K331, W332, H334, E335, T387, I388, L389, Y391, V392, G393, R394, P396, K397, and V398 on human TGFβ3, wherein the anti-TGFβ3 antibody selectively neutralizes TGFβ3;

an anti-TGFβ3 antibody that selectively neutralizes TGFβ3 and has reduced toxicity in mice relative to the pan-TGFβ antibody 1D11;

an anti-TGFβ3 antibody that has reduced toxicity in mice relative to the pan-TGFβ antibody 1D11 at a dose of 50 mg/kg.

An isoform-selective anti-TGFβ antibody according to any of the above uses (e.g. as a medicament for treating fibrosis) may be a monoclonal antibody, including a chimeric, humanized or human antibody. In one embodiment, an isoform-selective anti-TGFβ antibody is an antibody fragment, e.g., a Fv, Fab, Fab', scFv, diabody, or $F(ab')_2$ fragment. In another embodiment, the antibody is a full length antibody, e.g., an intact IgG1 or IgG4, preferably an IgG1, antibody or other antibody class or isotype as defined herein.

In any of the aspects provided herein, for use of an anti-TGFβ3 antibody as a medicament (and the manufacture or preparation or use thereof) and/or for use in a method of treatment, and/or for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin in a subject, and/or for inhibiting new collagen synthesis e.g., for treating fibrosis (e.g., fibrosis of the lung, liver, pancreas, heart, kidney, eye, and/or skin), the anti-TGFβ3 antibody is one that selectively neutralizes TGFβ3 as described herein and comprises: heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9. In some embodiments, the CDR-H2 has the amino acid sequence of SEQ ID NO: 35. In certain embodiments, the anti-TGFβ3 antibody further comprises a VH having at least 90%, 91%, 92%, 93%, 94%, 95%, 96%, 97%, 98%, 99%, or 100% sequence identity to the amino acid sequence of SEQ ID NO: 57. In some embodiments, the anti-TGFβ3 antibody further comprises a VL having at least 90%, 91%, 92%, 93%, 94%, 95%, 96%, 97%, 98%, 99%, or 100% sequence identity to the amino acid sequence of SEQ ID NO: 56. In certain embodiments, the anti-TGFβ3 antibody further comprises a complete H chain having at least 90%, 91%, 92%, 93%, 94%, 95%, 96%, 97%, 98%, 99%, or 100% sequence identity to an amino acid sequence of SEQ ID NO: 79. In other embodiments, the anti-TGFβ3 antibody further comprises a complete L chain having at least 90%, 91%, 92%, 93%, 94%, 95%, 96%, 97%, 98%, 99%, or 100% sequence identity to an amino acid sequence of SEQ ID NO: 78. In some embodiments, the disorder is fibrosis. In certain embodiments, the disorder is SSc. In some embodiments, the disorder is IPF. In certain embodiments, the anti-TGFβ3 antibody is a monoclonal antibody, such as a chimeric, humanized or human antibody. In some embodiments, the anti-TGFβ3 antibody is an antibody fragment, e.g., a Fv, Fab, Fab', scFv, diabody, or $F(ab')_2$ fragment. In other embodiments, the anti-TGFβ3 antibody is a full length antibody, e.g., an intact IgG1 or IgG4 antibody, such as an IgG1, or other antibody class or isotype as defined herein.

Uses of Pharmaceutical Formulations

In a further aspect, the invention provides pharmaceutical formulations comprising any of the isoform-selective anti-TGFβ antibodies (e.g., anti-TGFβ2, anti-TGFβ2/3, or anti-TGFβ3 antibodies) provided herein, e.g., for use in any of the above therapeutic methods, uses and medicaments. In one embodiment, a pharmaceutical formulation comprises any of the isoform-selective anti-TGFβ antibodies (e.g., anti-TGFβ2, anti-TGFβ2/3, or anti-TGFβ3 antibodies) provided herein and a pharmaceutically acceptable carrier. In another embodiment, a pharmaceutical formulation comprises any of the isoform-selective anti-TGFβ antibodies (e.g., anti-TGFβ2, anti-TGFβ2/3, or anti-TGFβ3 antibodies, e.g., an antibody having VL and VH amino acid sequence as shown in any of FIGS. 12-16 and 18-24 or Tables 5, 6, 7, 12, 13, 14, 19, 20, 23 and 24) provided herein and at least one additional therapeutic agent, e.g., as described below.

Combination Therapies

Antibodies of the invention can be used either alone or in combination with other agents in a therapy. For instance, an antibody of the invention may be co-administered with at least one additional therapeutic agent. In some embodiments, the therapeutic agent is selected from pirfenidone, nintedanib, mycophenylate mofetil, an IL-6 inhibitor (e.g., tocilizumab, sarilumab), an anti-CTFG antibody (e.g., FG-3019), an autotaxin inhibitor, a JAK inhibitor, an IL-11 inhibitor, and serum amyloid P (PTX2). See, Raghu et al. European Respiratory Journal 2012 40: 2819) (FG-309, Ninou et al. (2018) *Front Med* (*Lausanne*); 5: 180 (autotaxin inhibitors). In a preferred embodiment, an anti-TGFβ antibody (e.g., anti-TGFβ2, anti-TGFβ2/3, or anti-TGFβ3 antibody) is administered to a subject in need thereof in combination with tocilizumab. In a preferred embodiment, the subject in need thereof is a patient suffering from SSc. In some embodiments, the anti-TGFβ antibody is an anti-TGFβ3 antibody that selectively neutralizes TGFβ3. Therapeutic dosages of tocilizumab which may be administered to a subject, e.g., in combination with an anti-TGFβ3 antibody (or anti-TGFβ2 or anti-TGFβ2/3 antibody) according to the present invention are described in U.S. Pat. No. 9,539,263, and includes, e.g., a dose of about 162 mg per dose, administered, e.g., every week or ever two weeks, wherein the preferred route of administration is subcutaneous.

In certain embodiments, a subject is administered an anti-TGFβ antibody of the invention in combination with a therapeutic agent for the treatment of IPF. Certain therapeutic agents have been previously described as candidates or agents for the treatment of IPF. These have been described in the published literature and are reviewed, for example, in Rafli et al., J. Thorac. Dis (2013) 5(1):48-73. Such agents include agents that have antioxidant, immunosuppressant and/or anti-inflammatory activities such as N-acetylcysteine; agents that have antifibrotic, anti-inflammatory and/or antioxidant activities such as pirfenidone, an orally administered pyridine which has been approved for clinical use in the treatment of IPF; or an antibody against αvβ6 integrin (e.g., STX-100); agents that inhibit connective tissue growth factor (CTGF), such as an anti-CTGF antibody (e.g., FG-3019); agents that inhibit somatostatin receptors, such as somatostatin analogs (e.g., SOM230, octreotide); agents that inhibit IL-13, IL-4 and CCL2, such as an anti-IL13 antibody (e.g., QAX576, tralokinumab, lebrikizumab), an anti-IL4 antibody, a combination anti-IL13/anti-IL4 agent (e.g., a bispecific anti-IL13/anti-IL4 antibody such as SAR156597), an anti-IL-6 inhibitor (e.g., tocilizumab, sarilumab), an anti-CCL2 antibody (e.g., CNTO888); agents that have anti-angiogenic, immunomodulatory, and/or anti-inflammatory activities such as thalidomide or minocycline; agents that inhibit the enzyme lysyl oxidase-like 2 (LOXL2), such as an anti-LOXL2 antibody (e.g., GS-6624 [simtuzumab]); agents that inhibit angiogenesis such as the tyrosine kinase inhibitor, BIBF 1120, tetrathiomolybdate; agents that inhibit deposition of extracellular matrix and/or disrupt collagen deposition, such as doxycycline; agents that target the renin-angiotensin system such as losartan; and other agents having anti-proliferative and/or anti-fibrotic activities such as carbon monoxide.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the isoform-selective anti-TGFβ antibody (e.g., anti-TGFβ2, anti-TGFβ2/3, or anti-TGFβ3 antibody) and administration of an additional therapeutic agent (e.g., an anti-IL-6 inhibitor (e.g., tozilumab, sarilumab) occur within about one month, or within about one, two or three weeks, or within about one, two, three, four, five, or six days, of each other.

In a specific embodiment, a combination therapy comprises administering to a subject in need of such combination therapy, e.g., a patient diagnosed as having a TGFβ-related disorder, e.g., fibrosis, e.g., IPF, COPD, PF-ILD (e.g., SSc), hepatic fibrosis (e.g., liver cirrhosis or chronic hepatic fibrosis, or other fibrotic condition or cancer described herein), a therapeutically effective amount of an anti-TGFβ antibody of the present invention (e.g., an anti-TGFβ2, an anti-TGFβ2/3, or an anti-TGFβ3 antibody) in combination with an agent selected from the group consisting of N-acetylcysteine; agents that have antifibrotic, anti-inflammatory and/or antioxidant activities such as pirfenidone, an orally administered pyridine which has been approved for clinical use in the treatment of IPF; or an antibody against αvβ6 integrin (e.g., STX-100); agents that inhibit connective tissue growth factor (CTGF), such as an anti-CTGF antibody (e.g., FG-3019); agents that inhibit somatostatin receptors, such as somatostatin analogs (e.g., SOM230, octreotide); agents that inhibit IL-13, IL-4 and CCL2, such as an anti-IL13 antibody (e.g., QAX576, tralokinumab, lebrikizumab), an anti-IL4 antibody, a combination anti-IL13/anti-IL4 agent (e.g., a bispecific anti-IL13/anti-IL4 antibody such as SAR156597), an anti-IL-6 inhibitor (e.g., tozilumab, sarilumab), an anti-CCL2 antibody (e.g., CNTO888); agents that have anti-angiogenic, immunomodulatory, and/or anti-inflammatory activities such as thalidomide or minocycline; agents that inhibit the enzyme lysyl oxidase-like 2 (LOXL2), such as an anti-LOXL2 antibody (e.g., GS-6624 [simtuzumab]); agents that inhibit angiogenesis such as the tyrosine kinase inhibitor, BIBF 1120, tetrathiomolybdate; agents that inhibit deposition of extracellular matrix and/or disrupt collagen deposition, such as doxycycline; agents that target the renin-angiotensin system such as losartan; and other agents having anti-proliferative and/or anti-fibrotic activities such as carbon monoxide.

Administration and Formulation

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. In preferred embodiments, the administration of an anti-TGFβ antibody described herein is subcutaneous or intravenous. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the use of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 pg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 pg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

A "subject" or "individual" according to any of the above embodiments may be a human. It is understood that any of the above formulations or therapeutic methods may be carried out using an immunoconjugate of the invention in place of or in addition to an isoform-selective anti-TGFβ antibody (e.g., anti-TGFβ2, anti-TGFβ2/3, or anti-TGFβ3 antibody).

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an isoform-selective anti-TGFβ antibody (e.g., anti-TGFβ2, anti-TGFβ2/3, or anti-TGFβ3 antibody).

III. Enumerated Embodiments

Embodiment 1. An isolated anti-tumor necrosis factor beta 3 (TGFβ3) antibody, wherein the antibody selectively neutralizes TGFβ3, and wherein the antibody comprises one or more of the following features:

(a) the anti-TGFβ3 antibody specifically binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody directly contacts amino acid residue R394 in the beta6/beta7 hairpin region of human TGFβ3;

(e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody;

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

Embodiment 2. An isolated anti-TGFβ3 antibody, wherein the antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9.

Embodiment 3. The anti-TGFβ3 antibody of Embodiment 1 or Embodiment 2, wherein the antibody comprises a CDR-H2 having the amino acid sequence of SEQ ID NO: 5.

Embodiment 4. The anti-TGFβ3 antibody of any of Embodiments 1 to 3, wherein the antibody comprises a heavy chain variable region (VH) amino acid sequence having at least 95%, at least 96%, at least 97%, at least 98%, at least 99%, or 100% sequence identity to an amino acid sequence selected from the group consisting of SEQ ID NOs: 23, 37, and 42-50.

Embodiment 5. The anti-TGFβ3 antibody of any of Embodiments 1 to 4, wherein the antibody comprises a VH amino acid sequence selected from the group consisting of SEQ ID NOs: 23, 37, and 42-50.

Embodiment 6. The anti-TGFβ3 antibody of any of Embodiments 1 to 5, wherein the antibody comprises complete heavy (H) chain amino acid sequence having at least 95%, at least 96%, at least 97%, at least 98%, at least 99%, or 100% sequence identity to an amino acid sequence selected from the group consisting of SEQ ID NOs: 29, 59, 64, and 65-72.

Embodiment 7. The anti-TGFβ3 antibody of any of Embodiments 1 to 6, wherein the antibody comprises complete heavy (H) chain amino acid sequence selected from the group consisting of SEQ ID NOs: 29, 59, 64, and 65-72.

Embodiment 8. The anti-TGFβ3 antibody of any of Embodiments 1 to 7, wherein the antibody comprises a light chain variable region (VL) amino acid sequence having at least 95%, at least 96%, at least 97%, at least 98%, at least 99%, or 100% sequence identity an amino acid sequence selected from the group consisting of SEQ ID NOs: 22, 36, and 38-41.

Embodiment 9. The anti-TGFβ3 antibody of any of Embodiments 1 to 8, wherein the antibody comprises a complete light (L) chain amino acid sequence having at least 95%, at least 96%, at least 97%, at least 98%, at least 99%, or 100% sequence identity to an amino acid sequence selected from the group consisting of SEQ ID NOs: 28, 58, and 60-63.

Embodiment 10. The anti-TGFβ3 antibody of any of Embodiments 1 to 9, wherein the antibody comprises a complete L chain amino acid sequence selected from the group consisting of SEQ ID NOs: 28, 58, and 60-63.

Embodiment 11. The anti-TGFβ3 antibody of any of Embodiments 1 to 10, wherein the antibody comprises a VH/VL pair, the VH/VL pair comprising amino acid sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), and SEQ ID NOs: 50/36 (v2.9).

Embodiment 12. The anti-TGFβ3 antibody of any of Embodiments 1 to 11, wherein the antibody comprises a complete H/L chain pair, the complete H/L chain pair comprising amino acid sequences (respectively) selected from the group consisting of SEQ ID NOs: 29/28 (rat 2A10), SEQ ID NOs: 59/58 (vi), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9).

Embodiment 13. The anti-TGFβ3 antibody of any of Embodiments 1 to 10, wherein the antibody comprises a VL of SEQ ID NO: 22 comprising one or more framework modifications selected from the group consisting of: 4L or 4M, 38H or 38Q, 43A or 43Q, and 58V.

Embodiment 14. The anti-TGFβ3 antibody of any of Embodiments 1 to 10, wherein the VL comprises a set of framework modifications selected from the group consisting of:

(i) 4L in FR1, 38H and 43Q in FR2, 58I in FR3 (h2A10.v1 and h2A10.v2);

(ii) 4M in FR1 (h2A10.v1.1 and h2A10.v2.1);

(iii) 38Q in FR2 (h2A10.v1.2 and h2A10.v2.2);

(iv) 43A in FR2 (h2A10.v1.3 and h2A10.v2.3);

(v) 58V in FR3 (h2A10.v1.4 and h2A10.v2.4);

(vi) 38Q, 43A in FR2, 58V in FR3 (h2A10.v3 and h2A10.v4);

(vii) 58V in FR3 (h2A10.v1.4 and h2A10.v2.4); and (vi) 38Q, 43A in FR2, 58V in FR3 (h2A10.v3 and h2A10.v4).

Embodiment 15. The anti-TGFβ3 antibody of any of Embodiments 1 to 10, 13 and 14, wherein the antibody comprises a VH of SEQ ID NO: 23 comprising one or more framework modifications selected from the group consisting of: 47L or 47W; 49A, 49S, or 49G; 73D or 73N; and 76N, 78D or 78L, 78A, or 78V.

Embodiment 16. The anti-TGFβ3 antibody of Embodiment 15, wherein the VH comprises a set of framework modifications selected from the group consisting of:

(i) 47L, 49A in FR2, 78V in FR3 (h2A10.v1);

(ii) 47L, 49A in FR2, 73D, 76S, 78V in FR3 (h2A10.v2);

(iii) 47W in FR2 (h2A10.v1.5);

(iv): 49G in FR2 (h2A10.v1.6);

(v) 78A in FR3 (h2A10.v1.7);

(vi) 47W in FR2 (h2A10.v2.5);

(vii) 49S in FR2 (h2A10.v2.6);

(viii) 73N in FR3 (h2A10.v2.7);

(ix) 76N in FR3 (h2A10.v2.8);

(x) 78L in FR3 (h2A10.v2.9); and (xi) 49S in FR2, 76N, 78L in FR3 (h2A10.v3 and h2A10.v4).

Embodiment 17. The antibody of Embodiment 13 or 15 comprising a VL, wherein the VL retains leucine (L) at position 4 in framework I and leucine (L) at position 47 in framework II.

Embodiment 18. The antibody of Embodiment 15 or 17, wherein the VH retains D at position 73 in framework III of VH from r2A10.

Embodiment 19. The anti-TGFβ3 antibody of Embodiment 1 or 2, wherein the anti-TGFβ3 antibody comprises a CDR-H2 having the amino acid sequence of SEQ ID NO: 159.

Embodiment 20. The anti-TGFβ3 antibody of Embodiment 19, wherein the antibody comprises a VH amino acid sequence having at least 95%, at least 96%, at least 97%, at least 98%, at least 99%, or 100% sequence identity to the amino acid sequence of SEQ ID NO: 52.

Embodiment 21. The anti-TGFβ3 antibody of Embodiment 19 or 20, wherein the antibody comprises the VH amino acid sequence of SEQ ID NO: 52.

Embodiment 22. The anti-TGFβ3 antibody of any of Embodiments 19 to 21, wherein the antibody comprises a complete H chain amino acid sequence having at least 95%, at least 96%, at least 97%, at least 98%, at least 99%, or 100% sequence identity to the amino acid sequence of SEQ ID NO: 74.

Embodiment 23. The anti-TGFβ3 antibody of any of Embodiments 19 to 22, wherein the antibody comprises the complete H chain amino acid sequence of SEQ ID NO: 74.

Embodiment 24. The anti-TGFβ3 antibody of any of Embodiments 19 to 23, wherein the antibody comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41.

Embodiment 25. The anti-TGFβ3 antibody of any of Embodiments 19 to 24, wherein the antibody comprises a VL amino acid sequence selected from the group consisting of SEQ ID NOs: 22, 36, and 38-41.

Embodiment 26. The anti-TGFβ3 antibody of any of Embodiments 19 to 25, wherein the antibody comprises a complete L chain amino acid sequence having at least 95%, at least 96%, at least 97%, at least 98%, at least 99%, or 100% sequence identity to an amino acid sequence selected from the group consisting of SEQ ID NOs: 28, 58, and 60-63.

Embodiment 27. The anti-TGFβ3 antibody of any of Embodiments 19 to 26, wherein the antibody comprises a complete L chain amino acid sequence selected from the group consisting of SEQ ID NOs: 28, 58, and 60-63.

Embodiment 28. The anti-TGFβ3 antibody of Embodiment 19, wherein the antibody comprises a VH/VL pair comprising the amino acid sequences (respectively) of SEQ ID NOs: 52/36.

Embodiment 29. The anti-TGFβ3 antibody of Embodiment 19, wherein the antibody comprises a complete H/L chain pair, the H/L chain pair comprising the amino acid sequences (respectively) of SEQ ID NOs: 74/58.

Embodiment 30. The anti-TGFβ3 antibody of Embodiment 1 or 2, wherein the antibody comprises a CDR-H2 having the amino acid sequence of SEQ ID NO: 34.

Embodiment 31. The anti-TGFβ3 antibody of Embodiment 30, wherein the antibody comprises a VH amino acid sequence having at least 95%, at least 96%, at least 97%, at least 98%, at least 99%, or 100% sequence identity to the amino acid sequence of SEQ ID NO: 51 or 55.

Embodiment 32. The anti-TGFβ3 antibody of Embodiment 30 or 31, wherein the antibody comprises the VH amino acid sequence of SEQ ID NO: 51 or 55.

Embodiment 33. The anti-TGFβ3 antibody of any of Embodiments 30 to 32, wherein the antibody comprises a complete H chain amino acid sequence having at least 95%, at least 96%, at least 97%, at least 98%, at least 99%, or 100% sequence identity to the amino acid sequence of SEQ ID NO: 73 or 77.

Embodiment 34. The anti-TGFβ3 antibody of any of Embodiments 30 to 33, wherein the antibody comprises the complete H chain amino acid sequence of SEQ ID NO: 73.

Embodiment 35. The anti-TGFβ3 antibody of any of Embodiments 30 to 33, wherein the antibody comprises the complete H chain amino acid sequence of SEQ ID NO: 77.

Embodiment 36. The anti-TGFβ3 antibody of any of Embodiments 30 to 35 wherein the antibody comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41.

Embodiment 37. The anti-TGFβ3 antibody of any of Embodiments 30 to 36, wherein the antibody comprises a VL amino acid sequence selected from the group consisting of SEQ ID NOs: 22, 36, and 38-41.

Embodiment 38. The anti-TGFβ3 antibody of any of Embodiments 30 to 37, wherein the antibody comprises a complete L chain amino acid sequence having at least 95%, at least 96%, at least 97%, at least 98%, at least 99%, or 100% sequence identity to an amino acid sequence selected from the group consisting of SEQ ID NOs: 28, 58, and 60-63.

Embodiment 39. The anti-TGFβ3 antibody of any one of Embodiments 30 to 38, wherein the antibody comprises a complete L chain amino acid sequence selected from the group consisting of SEQ ID NOs: 28, 58, and 60-63.

Embodiment 40. The anti-TGFβ3 antibody of Embodiment 30, wherein the antibody comprises a VH/VL pair, the VH/VL pair comprising the amino acid sequences (respectively) of SEQ ID NOs: 51/36 or SEQ ID NOs: 55/54.

Embodiment 41. The anti-TGFβ3 antibody of Embodiment 30, wherein the antibody comprises a complete H/L chain pair, the H/L chain pair comprising the amino acid sequences (respectively) of SEQ ID NOs: 73/58 or SEQ ID NOs: 77/76.

Embodiment 42. The anti-TGFβ3 antibody of Embodiment 1 or 2, wherein the antibody comprises a CDR-H2 having the amino acid sequence of SEQ ID NO: 35.

Embodiment 43. The anti-TGFβ3 antibody of Embodiment 42, wherein the antibody comprises a VH amino acid sequence having at least 95%, at least 96%, at least 97%, at least 98%, at least 99%, or 100% sequence identity to the amino acid sequence of SEQ ID NO: 53 or 57.

Embodiment 44. The anti-TGFβ3 antibody of Embodiment 42 or 43, wherein the antibody comprises the VH amino acid sequence of SEQ ID NO: 53.

Embodiment 45. The anti-TGFβ3 antibody of Embodiment 42 or 43, wherein the antibody comprises the VH amino acid sequence of SEQ ID NO: 57.

Embodiment 46. The anti-TGFβ3 antibody of any of Embodiments 42 to 45, wherein the antibody comprises a complete H chain amino acid sequence having at least 95%, at least 96%, at least 97%, at least 98%, at least 99%, or 100% sequence identity to the amino acid sequence of SEQ ID NO: 75 or 79.

Embodiment 47. The anti-TGFβ3 antibody of any of Embodiments 42 to 46, wherein the antibody comprises the complete H chain amino acid sequence of SEQ ID NO: 75.

Embodiment 48. The anti-TGFβ3 antibody of any of Embodiments 42 to 46, wherein the antibody comprises a complete H chain amino acid sequence of SEQ ID NO: 79.

Embodiment 49. The anti-TGFβ3 antibody of any of Embodiments 42 to 48, wherein the antibody comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41.

Embodiment 50. The anti-TGFβ3 antibody of any one of Embodiments 42 to 49, wherein the antibody comprises a VL amino acid sequence selected from the group consisting of SEQ ID NOs: 22, 36, and 38-41.

Embodiment 51. The anti-TGFβ3 antibody of any of Embodiments 42 to 50, wherein the antibody comprises a complete L chain amino acid sequence having at least 95%, at least 96%, at least 97%, at least 98%, at least 99%, or 100% sequence identity to the amino acid sequence selected from the group consisting of SEQ ID NOs: 28, 58, and 60-63.

Embodiment 52. The anti-TGFβ3 antibody of any of Embodiments 42 to 51, wherein the antibody comprises a complete L chain amino acid sequence selected from the group consisting of SEQ ID NOs: 28, 58, and 60-63.

Embodiment 53. The anti-TGFβ3 antibody of Embodiment 42, wherein the antibody comprises a VH/VL pair comprising the amino acid sequences (respectively) of SEQ ID NOs: 53/36 or SEQ ID NOs: 57/56.

Embodiment 54. The anti-TGFβ3 antibody of Embodiment 42, wherein the antibody comprises a complete H/L chain pair, the H/L chain pair comprising the amino acid sequences (respectively) of SEQ ID NOs: 75/58 or SEQ ID NOs: 79/78.

Embodiment 55. An anti-TGFβ3 antibody comprising:

(a) (i) heavy chain CDRs comprising CDR-H1, -H2 and -H3, wherein CDR-H1 has the amino acid sequence of SEQ ID NO: 4, CDR-H2 has the amino acid sequence of one of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78.

Embodiment 56. An isolated anti-TGFβ2/3 antibody, wherein the antibody selectively neutralizes TGFβ2 and TGFβ3, and wherein the antibody comprises one or more of the following features:

(a) selectivity of the anti-TGFβ2/3 antibody for TGFβ2 and TGFβ3 over human TGFβ1, with respect to selective neutralization, is achieved by direct contact of the antibody's antigen binding domain with amino acid residue E373 TGFβ2 or TGFβ3 (human TGFβ2 numbering);

(b) the anti-TGFβ2/3 antibody neutralizes TGFβ2 and/or TGFβ3 via an allosteric mechanism;

(c) the anti-TGFβ2/3 antibody induces a conformational change in TGFβ2 and/or TGFβ3 homodimer;

(d) the anti-TGFβ2/3 antibody induces a conformational change in TGFβ2 and/or TGFβ3 homodimer, wherein the conformational change comprises the two monomers pinching together by several degrees;

(e) the anti-TGFβ2/3 antibody is a divalent antibody or a monovalent antibody;

(f) the anti-TGFβ2/3 antibody comprises (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15;

(g) the anti-TGFβ2/3 antibody specifically binds to TGFβ2 homodimer, the TGFβ2 homodimer having a first and a second TGFβ2 monomer, and wherein the anti-TGFβ2/3 antibody comprises an antigen binding domain that directly contacts (i) amino acid residues V313, Q314, D315, R320, L322, Y323, R328, D329, F345, and A347 of the first TGFβ2 monomer, and (ii) amino acid residues N368, T369, I370, N371, P372, E373, A374, S375, A376, and S377 of the second TGFβ2 monomer (human TGFβ2 numbering);

(h) the anti-TGFβ2/3 antibody as in (g), wherein the antigen binding domain is within 5 angstroms of the TGFβ2 and/or TGFβ3 amino acid residues;

(i) wherein the anti-TGFβ2/3 antibody specifically binds to the same epitope on TGFβ3 as in (g); and (j) the anti-TGFβ2/3 antibody does not neutralize TGFβ2 and/or TGFβ3 in monovalent form.

Embodiment 57. The anti-TGFβ2/3 antibody of Embodiment 56, wherein the antibody comprises a VH amino acid sequence having at least 95%, at least 96%, at least 97%, at least 98%, at least 99%, or 100% sequence identity to an amino acid sequence selected from the group consisting of SEQ ID NOs: 27, 81, 83, 86-88, 93-100, and 102-105.

Embodiment 58. The anti-TGFβ2/3 antibody of Embodiment 56 or 57, wherein the antibody comprises a VH amino acid sequence selected from the group consisting of SEQ ID NOs: 27, 81, 83, 86-88, 93-100, and 102-105.

Embodiment 59. The anti-TGFβ2/3 antibody of any of Embodiments 56 to 58, wherein the antibody comprises a complete H chain amino acid sequence having at least 95%, at least 96%, at least 97%, at least 98%, at least 99%, or 100% sequence identity to the amino acid sequence selected from the group consisting of SEQ ID NOs: 33, 107, 109, 112-114, and 119-130.

Embodiment 60. The anti-TGFβ2/3 antibody of any of Embodiments 56 to 59, wherein the antibody comprises a VL amino acid sequence having at least 95%, at least 96%, at least 97%, at least 98%, at least 99%, or 100% sequence identity to the amino acid sequence selected from the group consisting of SEQ ID NOs: 26, 80, 82, 84, 85, 89-92, and 101.

Embodiment 61. The anti-TGFβ2/3 antibody of any of Embodiments 56 to 60, wherein the antibody comprises a VL amino acid sequence selected from the group consisting of SEQ ID NOs: 26, 80, 82, 84, 85, 89-92, and 101.

Embodiment 62. The anti-TGFβ2/3 antibody of any of Embodiments 56 to 61, wherein the antibody comprises a complete L chain amino acid sequence having at least 95%, at least 96%, at least 97%, at least 98%, at least 99%, or 100% sequence identity to an amino acid sequence selected from the group consisting of SEQ ID NOs: 32, 106, 108, 110, 111, 115-118, and 186.

Embodiment 63. The anti-TGFβ2/3 antibody of any of Embodiments 56 to 62, wherein the antibody comprises a complete L chain amino acid sequence selected from the group consisting of SEQ ID NOs: 32, 106, 108, 110, 111, 115-118, and 186.

Embodiment 64. The anti-TGFβ2/3 antibody of Embodiment 56, wherein the antibody comprises a VH/VL pair, the VH/VL pair comprising amino acid sequences (respectively) selected from the group consisting of SEQ ID NOs: 27/26 (rabbit 4A11), SEQ ID NOs: 81/80 (v1), SEQ ID NOs: 81/82 (v2), SEQ ID NOs: 83/80 (v3), SEQ ID NOs: 83/82 (v4), SEQ ID NOs: 81/84 (v5), SEQ ID NOs: 81/85 (v6), SEQ ID NOs: 83/84 (v7), SEQ ID NOs: 86/84 (v7.1), SEQ ID NOs: 87/84 (v7.2), SEQ ID NOs: 88/84 (v7.3), SEQ ID NOs: 83/89 (v7.4), SEQ ID NOs: 83/90 (v7.5), SEQ ID NOs: 83/91 (v7.6), SEQ ID NOs: 83/92 (v7.7), SEQ ID NOs: 93/84 (v7.8), SEQ ID NOs: 94/84 (v7.9), SEQ ID NOs: 95/84 (v7.10), SEQ ID NOs: 96/84 (v7.11), SEQ ID NOs: 97/84 (v7.12), SEQ ID NOs: 98/84 (v7.13), SEQ ID NOs: 99/84 (v7.14), SEQ ID NOs: 100/84 (v7.15), SEQ ID NOs: 102/101 (v7.16), SEQ ID NOs: 103/101 (v7.17), SEQ ID NOs: 104/101 (v7.18), SEQ ID NOs: 105/101 (v7.19), and SEQ ID NOs: 83/85 (v8).

Embodiment 65. The anti-TGFβ2/3 antibody of Embodiment 56, wherein the antibody comprises a complete H/L chain pair, the complete H/L chain pair comprising amino acid sequences (respectively) selected from the group consisting of SEQ ID NOs: 32/33 (rabbit 4A11), SEQ ID NOs: 107/106 (v1), SEQ ID NOs: 107/108 (v2), SEQ ID NOs: 109/106 (v3), SEQ ID NOs: 109/108 (v4), SEQ ID NOs: 107/110 (v5), SEQ ID NOs: 107/111 (v6), SEQ ID NOs: 109/110 (v7), SEQ ID NOs: 112/110 (v7.1), SEQ ID NOs: 113/110 (v7.2), SEQ ID NOs: 114/110 (v7.3), SEQ ID NOs: 114/115 (v7.4), SEQ ID NOs: 114/116 (v7.5), SEQ ID NOs: 114/117 (v7.6), SEQ ID NOs: 114/118 (v7.7), SEQ ID NOs: 119/110 (v7.8), SEQ ID NOs:120/110 (v7.9), SEQ ID NOs: 121/110 (v7.10), SEQ ID NOs: 122/110 (v7.11), SEQ ID NOs: 123/110 (v7.12), SEQ ID NOs: 124/110 (v7.13), SEQ ID NOs: 125/110 (v7.14), SEQ ID NOs: 126/110 (v7.15), SEQ ID NOs: 127/186 (v7.16), SEQ ID NOs: 128/186 (v7.17), SEQ ID NOs: 129/186 (v7.18), SEQ ID NOs: 130/186 (v7.19), and SEQ ID NOs: 114/111 (v8).

Embodiment 66. The anti-TGFβ2/3 antibody of Embodiment 56, wherein the antibody comprises a VL comprising the amino acid sequence of SEQ ID NO: 26 comprising one or more framework modifications selected from the group consisting of: 2A or 2I, 4L, 36F or 36Y, 43P or 43A, and 58V or 581.

Embodiment 67. The anti-TGFβ2/3 antibody of Embodiment 56, wherein the VL comprises a set of framework modifications selected from the group consisting of:

(i) 2A and 4L in FR1 and 36F in FR2 (h4A11.v1 and h4A11.v3);

(ii) 2A and 4L in FR1 and 36F and 43P in FR2 (h4A11.v2 and h4A11.v4);

(iii) 2A in FR1, 36F and 43P in FR2 and 58V in FR3 (h4A11.v5 and h4A11.v7); (iv) 2A and 4L in FR1 and 36F in FR2 (h4A11.v6 and h4A11.v8);

(v) 2I in FR1 (h4A11.v7.4);

(vi) 36Y in FR2 (h4A11.v7.5);

(vii) 43A in FR2 (h4A11.v7.6);

(viii) 581 in FR3 (h4A11.v7.7); and (ix) 2I in FR1, 43A in FR2, 581 in FR3 (h4A11.v7.16-19).

Embodiment 68. The anti-TGFβ2/3 antibody of Embodiment 56, wherein the antibody comprises a VH comprising the amino acid sequence of SEQ ID NO: 27 comprising one or more framework modifications selected from the group consisting of: deletion of 1E, 2Q or 2V, 24V, 37V or 37I, 481, 49G, 67F or 67V, 71K or 71V, 73S or 73T, deletion of 75K and 76N, 78V or 78F, 91F or 91Y, 105P or 105Q.

Embodiment 69. The anti-TGFβ2/3 antibody of Embodiment 56 or 68, wherein the VL comprises a set of framework modifications selected from the group consisting of:

(i) 2Q and 24V in FR1, 481 and 49G in FR2, 71K, 73S, 78V and 91F in FR3 and 105P in FR4 (h4A11.v1, h4A11.v2, h4A11.v5, h4A11.v6);

(ii) 2Q in FR1, 37V in FR2, 67F, 71K, 73S, 78V and 91F in FR3 and 105P in FR4 (h4A11.v3, h4A11.v4, h4A11.v7, h4A11.v8);

(iii) delete 1E in FR1 (h4A11.v7.1);

(iv) delete 75K and 76N in FR3 (h4A11.v7.2);

(v) delete 1E in FR1 and 75K76N in FR3 (h4A11.v7.3);

(vi) 2V in FR1 (h4A11.v7.8);

(vi) 37I in FR2 (h4A11.v7.9);

(vii) 67V in FR3 (h4A11.v7.10);

(viii) 71V in FR3 (h4A11.v7.11);

(ix) 73T in FR3 (h4A11.v7.12);

(x) 78F in FR3 (h4A11.v7.13);

(xi) 91Y in FR3 (h4A11.v7.14);

(xii) 105Q in FR4 (h4A11.v7.15);

(xiii) 2V in FR1, 37I in FR2, 67V, 73T, 78F in FR3, 105Q in FR4 ((h4A11.v7.16);

(xiv) 2V in FR1, 37I in FR2, 67V, 73T, 91Y in FR3, 105Q in FR4 (h4A11.v7.17);

(xv) 2V in FR1, 37I in FR2, 67V, 73T in FR3, 105Q in FR4 (h4A11.v7.18); and (xvi) 2V in FR1, 37I in FR2, 67V, 73T, deletion of 75K and 76N in FR3, 105Q in FR4 (h4A11.v7.19).

Embodiment 70. An isolated anti-TGFβ2 antibody, wherein the antibody comprises:

(a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21.

Embodiment 71. The anti-TGFβ2 antibody of Embodiment 70, wherein the antibody selectively neutralizes TGFβ2.

Embodiment 72. The anti-TGFβ2 antibody of Embodiment 71, wherein the antibody:

(a) has reduced toxicity relative to the pan-TGFβ antibody 1D11;

(b) has reduced toxicity in rodents relative to the pan-TGFβ antibody 1D11;

(c) has reduced toxicity relative to the pan-TGFβ small molecule inhibitor galunisertib; and/or (d) has reduced toxicity in rodents relative to the pan-TGFβ small molecule inhibitor galunisertib.

Embodiment 73. The anti-TGFβ2 antibody of Embodiment 70 or 71, wherein the antibody comprises a VH amino acid sequence having at least 95%, at least 96%, at least 97%, at least 98%, at least 99%, or 100% sequence identity to an amino acid sequence selected from the group consisting of SEQ ID NOs: 25, 132, and 138-142.

Embodiment 74. The anti-TGFβ2 antibody of Embodiment 73, wherein the antibody comprises a VH amino acid sequence selected from the group consisting of SEQ ID NOs: 25, 132, and 138-142.

Embodiment 75. The anti-TGFβ2 antibody of Embodiment 70 or 71, wherein the antibody comprises a complete H chain amino acid sequence having at least 95%, at least 96%, at least 97%, at least 98%, at least 99%, or 100% sequence identity to the amino acid sequence selected from the group consisting of SEQ ID NOs: 31, 146, and 152-156.

Embodiment 76. The anti-TGFβ2 antibody of Embodiment 75, wherein the antibody comprises a complete H chain amino acid sequence selected from the group consisting of SEQ ID NOs: 31, 146, and 152-156.

Embodiment 77. The anti-TGFβ2 antibody of Embodiment 70 or 71, wherein the antibody comprises a VL amino acid sequence having at least 95%, at least 96%, at least 97%, at least 98%, at least 99%, or 100% sequence identity to the amino acid sequence selected from the group consisting of SEQ ID NOs: 24, 131, 133-137, 143, and 144.

Embodiment 78. The anti-TGFβ2 antibody of Embodiment 77, wherein the antibody comprises a VL amino acid sequence selected from the group consisting of SEQ ID NOs: 24, 131, 133-137, 143, and 144.

Embodiment 79. The anti-TGFβ2 antibody of Embodiment 70 or 71, wherein the antibody comprises a complete L chain amino acid sequence having at least 95%, at least 96%, at least 97%, at least 98%, at least 99%, or 100% sequence identity to an amino acid sequence selected from the group consisting of SEQ ID NOs: 30, 145, 147-151, 157, and 158.

Embodiment 80. The anti-TGFβ2 antibody of Embodiment 79, wherein the antibody comprises a complete L chain amino acid sequence selected from the group consisting of SEQ ID NOs: 30, 145, 147-151, 157, and 158.

Embodiment 81. The anti-TGFβ2 antibody of Embodiment 70 or 71, wherein the antibody comprises a VH/VL pair, the VH/VL pair comprising amino acid sequences selected from the group consisting of SEQ ID NOs: 25/24 (rabbit 6F12), SEQ ID NOs: 132/131 (v1), SEQ ID NOs: 132/133 (v1.1), SEQ ID NOs: 132/134 (v1.2), SEQ ID NOs: 132/135 (v1.3), SEQ ID NOs: 132/136 (v1.4), SEQ ID NOs: 132/137 (v1.5), SEQ ID NOs: 138/131 (v1.6), SEQ ID NOs: 139/131 (v1.7), SEQ ID NOs: 140/131 (v1.8), SEQ ID NOs: 141/131 (v1.9), SEQ ID NOs: 142/131 (v2), SEQ ID NOs: 132/143 (v3), and SEQ ID NOs: 142/144 (v4).

Embodiment 82. The anti-TGFβ2 antibody of Embodiment 70 or 71, wherein the antibody comprises a complete H/L chain pair, the complete H/L chain pair comprising amino acid sequences selected from the group consisting of SEQ ID NOs: 31/30 (rabbit 6F12), SEQ ID NOs: 146/145 (v1), SEQ ID NOs: 146/147 (v1.1), SEQ ID NOs: 146/148 (v1.2), SEQ ID NOs: 146/149 (v1.3), SEQ ID NOs: 146/150 (v1.4), SEQ ID NOs: 146/151 (v1.5), SEQ ID NOs: 152/145 (v1.6), SEQ ID NOs: 153/145 (v1.7), SEQ ID NOs: 154/145 (v1.8), SEQ ID NOs: 155/145 (v1.9), SEQ ID NOs: 156/145 (v2), SEQ ID NOs: 146/157 (v3), and SEQ ID NOs: 156/158 (v4).

Embodiment 83. The anti-TGFβ2 antibody of Embodiment 70 or 71, wherein the antibody comprises a VL comprising the amino acid sequence of SEQ ID NO: 24 comprising one or more framework mutations selected from the group consisting of 43S or 43A, 66G, 69T, 71F, and 87Y.

Embodiment 84. The anti-TGFβ2 antibody of Embodiment 83, wherein the VL comprises a set of framework mutations selected from the group consisting of:

(i) 43S in FR2 and 66E, 69P, 71Y and 87F in FR3 (h6F12.v1 and h6F12.v2);

(ii) 43S in FR2 and 58V, 66E, 69P, 71Y and 87F in FR3 (h6F12.v3 and h6F12.v4);

(iii) 43A in FR2 (h6F12.v1.1);

(iv) 66G in FR3 (h6F12.v1.2);

(v) 69T in FR3 (h6F12.v1.3);

(vi) 71F in FR3 (h6F12.v1.4); and (vii) 87Y in FR3 (h6F12.v1.5).

Embodiment 85. The anti-TGFβ2 antibody of Embodiment 70 or 71, wherein the antibody comprises a VH comprising the amino acid sequence of SEQ ID NO: 25 comprising one or more framework mutations selected from the group consisting of 37V or 37I, 48M or 48L, 49G or 49A, 67L, 71K and 78V, and 105P or 105R.

Embodiment 86. The anti-TGFβ2 antibody of Embodiment 85, wherein the VH comprises a set of framework mutations selected from the group consisting of:

(i) 37V, 48M and 49G in FR2 and 105P in FR4 (h6F12.v1 and h6F12.v3);

(ii) 37V and 48M in FR2, 67L, 71K and 78V in FR3 and 105P in FR4 (h6F12.v2 and h6F12.v4);

(iii) 37I in FR2 (h6F12.v1.6);

(iv) 48L in FR2 (h6F12.v1.7);

(v) 49A in FR2 (h6F12.v1.8);

(vi) 105R in FR4 (h6F12.v1.9);

(vii) 37V, 48M and 49G in FR2 and 105P in FR4 (h6F12.v1 and h6F12.v3);

(viii) 37V and 48M in FR2, 67L, 71K and 78V in FR3 and 105P in FR4 (6F12.v2 and h6F12.v4);

(ix) 37I in FR2 (h6F12.v1.6);

(x) 48L in FR2 (h6F12.v1.7);

(xi) 49A in FR2 (h6F12.v1.8); and (xii) 105R in FR4 (h6F12.v1.9).

Embodiment 87. The anti-TGFβ3 antibody of any one of Embodiments 1 to 55, or the anti-TGFβ2/3 antibody of any one of Embodiments 56 to 68, wherein the antibody specifically binds to human TGFβ3.

Embodiment 88. The anti-TGFβ3 antibody of any one of Embodiments 1 to 55, wherein the antibody specifically binds to both the immature and mature forms of TGFβ3.

Embodiment 89. The anti-TGFβ2/3 antibody of any one of Embodiments 56 to 68, or the anti-TGFβ2 antibody of any one of Embodiments 70 to 83, wherein the antibody specifically binds to human TGFβ2.

Embodiment I-1. An isolated anti-tumor necrosis factor beta 3 (TGFβ3) antibody, wherein the antibody selectively neutralizes TGFβ3, and wherein the antibody comprises one or more of the following features:

(n) the anti-TGFβ3 antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(a) the anti-TGFβ3 antibody specifically binds to the beta6/beta7 hairpin region of TGFβ3;

(b) binding of the anti-TGFβ3 antibody sterically blocks the ability of TGFBR2, but not TGFBR1, to bind TGFβ3;

(c) binding of the anti-TGFβ3 antibody to TGFβ3 blocks TGFBR2 binding and inhibits the TGFBR1/TGFBR2 signaling receptors from binding to TGFβ3;

(d) the anti-TGFβ3 antibody directly contacts amino acid residue R394 in the beta6/beta7 hairpin region of human TGFβ3;

(e) the anti-TGFβ3 antibody directly contacts amino acid residue R394 in the beta6/beta7 hairpin region of human TGFβ3 and residue R394 of TGFβ3 makes an ionic salt bridge with the anti-TGFβ3 antibody in the heavy chain CDR2;

(f) isoform selectivity of the anti-TGFβ3 antibody for TGFβ3 over TGFβ1 is achieved by direct contact by the antigen binding domain of the anti-TGFβ3 antibody with amino acid residues T387, L389, and T395 of TGFβ3 (human TGFβ3 numbering);

(g) the isoform selectivity of the anti-TGFβ3 antibody for TGFβ3 over TGFβ2 is achieved by direct contact by the antigen binding domain of the anti-TGFβ3 antibody with amino acid residues R325, R394, and V398 of TGFβ3 (human TGFβ3 numbering);

(h) the anti-TGFβ3 antibody has reduced toxicity relative to the pan-TGFβ antibody 1D11;

(i) the anti-TGFβ3 antibody has reduced toxicity in rodents or cynomolgus monkeys relative to the pan-TGFβ antibody 1D11;

(j) the anti-TGFβ3 antibody has reduced toxicity relative to the pan-TGFβ small molecule inhibitor galunisertib;

(k) the anti-TGFβ3 antibody has reduced toxicity in rodents relative to the pan-TGFβ small molecule inhibitor galunisertib;

(l) the anti-TGFβ3 antibody has reduced toxicity relative to the anti-TGFβ1 antibody CAT-192;

(m) the anti-TGFβ3 antibody has reduced toxicity relative to an isoform selective anti-TGFβ2 antibody and/or anti-TGFβ2/3 antibody;

(o) the anti-TGFβ3 antibody comprises an antigen binding domain that directly contacts amino acid residues R325, K331, W332, H334, E335, T387, I388, L389, Y391, V392, G393, R394, P396, K397, and V398 on human TGFβ3; and (p) the anti-TGFβ3 antibody as in (o), wherein the antigen binding domain is within 15-8, 8, 8-5, 7-5, 6-5, or 5 angstroms of the TGFβ3 amino acid residues.

Embodiment I-2. An isolated anti-TGFβ3 antibody, wherein the antibody comprises: (i) heavy chain CDRs comprising CDR-H1, -H2 and -H3, wherein CDR-H1 has the amino acid sequence of SEQ ID NO: 4, CDR-H2 has the amino acid sequence of one of SEQ ID NOs: 5, 34, 35, and 159, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9.

Embodiment I-3. The anti-TGFβ3 antibody of Embodiment I-1 or Embodiment 1-2, wherein the antibody comprises a heavy chain variable region (VH) amino acid sequence having at least 95%, at least 96%, at least 97%, at least 98%, at least 99%, or 100% sequence identity to an amino acid sequence selected from the group consisting of SEQ ID NOs: 23, 37, 42-53, 55 and 57.

Embodiment I-4. The anti-TGFβ3 antibody of any of Embodiment I-1 to Embodiment 1-3, wherein the antibody comprises a VH amino acid sequence selected from the group consisting of SEQ ID NOs: 23, 37, 42-53, 55 and 57.

Embodiment I-5. The anti-TGFβ3 antibody of any of Embodiment I-1 to Embodiment 1-4, wherein the antibody comprises complete heavy (H) chain amino acid sequence having at least 95%, at least 96%, at least 97%, at least 98%, at least 99%, or 100% sequence identity to an amino acid sequence selected from the group consisting of SEQ ID NOs: 29, 59, 64, 65-75, 77, and 79.

Embodiment I-6. The anti-TGFβ3 antibody of any of Embodiment I-1 to Embodiment I-5, wherein the antibody comprises complete heavy (H) chain amino acid sequence selected from the group consisting of SEQ ID NOs: 29, 59, 64, 65-75, 77 and 79.

Embodiment I-7. The anti-TGFβ3 antibody of any of Embodiment I-1 to Embodiment I-6, wherein the antibody comprises a light chain variable region (VL) amino acid sequence having at least 95%, at least 96%, at least 97%, at least 98%, at least 99%, or 100% sequence identity an amino acid sequence selected from the group consisting of SEQ ID NOs: 22, 36, 38-41, 54, and 56.

Embodiment I-8. The anti-TGFβ3 antibody of any of Embodiment I-1 to Embodiment I-7, wherein the antibody comprises a VL amino acid sequence selected from the group consisting of SEQ ID NOs: 22, 36, 38-41, 54, and 56.

Embodiment I-9. The anti-TGFβ3 antibody of any of Embodiment I-1 to Embodiment I-8, wherein the antibody comprises a complete light (L) chain amino acid sequence having at least 95%, at least 96%, at least 97%, at least 98%, at least 99%, or 100% sequence identity to an amino acid sequence selected from the group consisting of SEQ ID NOs: 28, 58, 60-63, 76, and 78.

Embodiment I-10. The anti-TGFβ3 antibody of any of Embodiment I-1 to Embodiment I-9, wherein the antibody comprises a complete L chain amino acid sequence selected from the group consisting of SEQ ID NOs: 28, 58, and 60-63, 76, and 78.

Embodiment I-11. The anti-TGFβ3 antibody of any of Embodiment I-1 to Embodiment I-10, wherein the antibody comprises a VH/VL pair, the VH/VL pair comprising amino acid sequences (respectively) selected from the group consisting of SEQ ID NOs: 23/22 (rat 2A10), SEQ ID NOs: 37/36 (v1), SEQ ID NOs: 37/38 (v1.1), SEQ ID NOs: 37/39 (v1.2), SEQ ID NOs: 37/40 (v1.3), SEQ ID NOs: 37/41 (v1.4), SEQ ID NOs: 42/36 (v1.5), SEQ ID NOs: 43/36 (v1.6), SEQ ID NOs:44/36 (v1.7), SEQ ID NOs: 45/36 (v2), SEQ ID NOs: 45/38 (v2.1), SEQ ID NOs: 45/39 (v2.2), SEQ ID NOs: 45/40 (v2.3), SEQ ID NOs: 45/41 (v2.4), SEQ ID NOs: 46/36 (v2.5), SEQ ID NOs: 47/36 (v2.6), SEQ ID NOs: 48/36 (v2.7), SEQ ID NOs: 49/36 (v2.8), SEQ ID NOs: 50/36 (v2.9), SEQ ID NOs: 51/36 (h2A10.v2.N54S), SEQ ID NOs: 52/36 (h2A10.v2.N54Q), SEQ ID NOs: 53/36 (h2A10.v2.T56A), SEQ ID NOs: 55/54 (v3), and SEQ ID NOs: 57/56 (v4).

Embodiment I-12. The anti-TGFβ3 antibody of any of Embodiment I-1 to Embodiment I-11, wherein the antibody comprises a complete H/L chain pair, the complete H/L chain pair comprising amino acid sequences (respectively) selected from the group consisting of SEQ ID NOs: 29/28 (rat 2A10), SEQ ID NOs: 59/58 (v1), SEQ ID NOs: 59/60 (v1.I), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 73/58 (h2A10.v2.N54S), SEQ ID NOs: 74/58 (h2A10.v2.N54Q), SEQ ID NOs: 75/58 (h2A10.v2.T56A), SEQ ID NOs: 77/76 (v3), and SEQ ID NOs: 79/78 (v4).

Embodiment I-13. The anti-TGFβ3 antibody of any of Embodiment I-1 to Embodiment I-10, wherein the antibody comprises a VL of SEQ ID NO: 22 comprising one or more framework modifications selected from the group consisting of: 4L or 4M, 38H or 38Q, 43A or 43Q, and 58V.

Embodiment I-14. The anti-TGFβ3 antibody of any of Embodiment I-1 to Embodiment I-10, wherein the VL comprises a set of framework modifications selected from the group consisting of:

(i) 4L in FR1, 38H and 43Q in FR2, 58I in FR3 (h2A10.v1 and h2A10.v2);

(ii) 4M in FR1 (h2A10.v1.1 and h2A10.v2.1);

(iii) 38Q in FR2 (h2A10.v1.2 and h2A10.v2.2);

(iv) 43A in FR2 (h2A10.v1.3 and h2A10.v2.3);

(v) 58V in FR3 (h2A10.v1.4 and h2A10.v2.4);

(vi) 38Q, 43A in FR2, 58V in FR3 (h2A10.v3 and h2A10.v4);

(vii) 58V in FR3 (h2A10.v1.4 and h2A10.v2.4); and (vi) 38Q, 43A in FR2, 58V in FR3 (h2A10.v3 and h2A10.v4).

Embodiment I-15. The anti-TGFβ3 antibody of any of Embodiment I-1 to Embodiment I-10, Embodiment 1-13, and Embodiment 1-14, wherein the antibody comprises a VH of SEQ ID NO: 23 comprising one or more framework modifications selected from the group consisting of: 47L or 47W; 49A, 49S, or 49G; 73D or 73N; and 76N, 78D or 78L, 78A, or 78V.

Embodiment I-16. The anti-TGFβ3 antibody of Embodiment I-15, wherein the VH comprises a set of framework modifications selected from the group consisting of:

(i) 47L, 49A in FR2, 78V in FR3 (h2A10.v1);

(ii) 47L, 49A in FR2, 73D, 76S, 78V in FR3 (h2A10.v2);

(iii) 47W in FR2 (h2A10.v1.5);

(iv): 49G in FR2 (h2A10.v1.6);

(v) 78A in FR3 (h2A10.v1.7);

(vi) 47W in FR2 (h2A10.v2.5);

(vii) 49S in FR2 (h2A10.v2.6);

(viii) 73N in FR3 (h2A10.v2.7);

(ix) 76N in FR3 (h2A10.v2.8);

(x) 78L in FR3 (h2A10.v2.9); and (xi) 49S in FR2, 76N, 78L in FR3 (h2A10.v3 and h2A10.v4).

Embodiment I-17. The antibody of Embodiment I-13 or Embodiment I-15 comprising a VL, wherein the VL retains leucine (L) at position 4 in framework I and leucine (L) at position 47 in framework II.

Embodiment I-18. The antibody of Embodiment I-15 or Embodiment I-17, wherein the VH retains D at position 73 in framework III of VH from r2A10.

Embodiment I-19. The anti-TGFβ3 antibody of any one of Embodiment I-1 to Embodiment I-12, wherein the antibody comprises a CDR-H2 having the amino acid sequence of SEQ ID NO: 5.

Embodiment I-20. The anti-TGFβ3 antibody of any one of Embodiment I-1 to Embodiment I-12, wherein the anti-TGFβ3 antibody comprises a CDR-H2 having the amino acid sequence of SEQ ID NO: 159.

Embodiment I-21. The anti-TGFβ3 antibody of Embodiment I-20, wherein the antibody comprises a VH amino acid sequence having at least 95%, at least 96%, at least 97%, at least 98%, at least 99%, or 100% sequence identity to the amino acid sequence of SEQ ID NO: 52.

Embodiment I-22. The anti-TGFβ3 antibody of Embodiment I-20 or Embodiment I-21, wherein the antibody comprises the VH amino acid sequence of SEQ ID NO: 52.

Embodiment I-23. The anti-TGFβ3 antibody of any of Embodiment I-20 to Embodiment I-22, wherein the antibody comprises a complete H chain amino acid sequence having at least 95%, at least 96%, at least 97%, at least 98%, at least 99%, or 100% sequence identity to the amino acid sequence of SEQ ID NO: 74.

Embodiment I-24. The anti-TGFβ3 antibody of any of Embodiment I-20 to Embodiment I-23, wherein the antibody comprises the complete H chain amino acid sequence of SEQ ID NO: 74.

Embodiment I-25. The anti-TGFβ3 antibody of any of Embodiment I-20 to Embodiment I-24, wherein the antibody comprises a VL amino acid sequence having at least 95%, at least 96%, at least 97%, at least 98%, at least 99%, or 100% sequence identity to an amino acid sequence selected from the group consisting of SEQ ID NOs: 22, 36, and 38-41.

Embodiment I-26. The anti-TGFβ3 antibody of any of Embodiment I-20 to Embodiment I-25, wherein the antibody comprises a VL amino acid sequence selected from the group consisting of SEQ ID NOs: 22, 36, and 38-41.

Embodiment I-27. The anti-TGFβ3 antibody of any of Embodiment I-20 to Embodiment I-26, wherein the antibody comprises a complete L chain amino acid sequence having at least 95%, at least 96%, at least 97%, at least 98%, at least 99%, or 100% sequence identity to an amino acid sequence selected from the group consisting of SEQ ID NOs: 28, 58, and 60-63.

Embodiment I-28. The anti-TGFβ3 antibody of any of Embodiment I-20 to Embodiment I-27, wherein the antibody comprises a complete L chain amino acid sequence selected from the group consisting of SEQ ID NOs: 28, 58, and 60-63.

Embodiment I-29. The anti-TGFβ3 antibody of Embodiment I-20, wherein the antibody comprises a VH/VL pair comprising the amino acid sequences (respectively) of SEQ ID NOs: 52/36.

Embodiment I-30. The anti-TGFβ3 antibody of Embodiment I-20, wherein the antibody comprises a complete H/L chain pair, the H/L chain pair comprising the amino acid sequences (respectively) of SEQ ID NOs: 74/58.

Embodiment I-31. The anti-TGFβ3 antibody of any one of Embodiment I-1 to Embodiment I-12, wherein the antibody comprises a CDR-H2 having the amino acid sequence of SEQ ID NO: 34.

Embodiment I-32. The anti-TGFβ3 antibody of Embodiment I-31, wherein the antibody comprises a VH amino acid sequence having at least 95%, at least 96%, at least 97%, at least 98%, at least 99%, or 100% sequence identity to the amino acid sequence of SEQ ID NO: 55.

Embodiment I-33. The anti-TGFβ3 antibody of Embodiment 1-31 or Embodiment 1-32, wherein the antibody comprises the VH amino acid sequence of SEQ ID NO: 55.

Embodiment I-34. The anti-TGFβ3 antibody of any of Embodiment I-31 to Embodiment I-33, wherein the antibody comprises a complete H chain amino acid sequence having at least 95%, at least 96%, at least 97%, at least 98%, at least 99%, or 100% sequence identity to the amino acid sequence of SEQ ID NO: 77.

Embodiment I-35. The anti-TGFβ3 antibody of any of Embodiment I-31 to Embodiment I-34, wherein the antibody comprises the complete H chain amino acid sequence of SEQ ID NO: 77.

Embodiment I-36. The anti-TGFβ3 antibody of any of Embodiment I-31 to Embodiment I-35 wherein the antibody comprises a VL amino acid sequence having at least 95%, at least 96%, at least 97%, at least 98%, at least 99%, or 100% sequence identity to the amino acid sequence of SEQ ID NO: 54.

Embodiment I-37. The anti-TGFβ3 antibody of any of Embodiment I-31 to Embodiment I-37, wherein the antibody comprises the VL amino acid sequence of SEQ ID NO: 54.

Embodiment I-38. The anti-TGFβ3 antibody of any of Embodiment I-31 to Embodiment I-37, wherein the antibody comprises a complete L chain amino acid sequence having at least 95%, at least 96%, at least 97%, at least 98%, at least 99%, or 100% sequence identity to the amino acid sequence of SEQ ID NO: 76.

Embodiment I-39. The anti-TGFβ3 antibody of any one of Embodiment I-31 to Embodiment I-38, wherein the antibody comprises the complete L chain amino acid sequence of SEQ ID NO: 76.

Embodiment I-40. The anti-TGFβ3 antibody of Embodiment I-31, wherein the antibody comprises a VH/VL pair, the VH/VL pair comprising the amino acid sequences (respectively) of SEQ ID NOs: 55/54.

Embodiment I-41. The anti-TGFβ3 antibody of Embodiment I-31, wherein the antibody comprises a complete H/L chain pair, the H/L chain pair comprising the amino acid sequences (respectively) of SEQ ID NOs: 77/76.

Embodiment I-42. The anti-TGFβ3 antibody of any one of Embodiment I-1 to Embodiment I-12, wherein the antibody comprises a CDR-H2 having the amino acid sequence of SEQ ID NO: 35.

Embodiment I-43. The anti-TGFβ3 antibody of Embodiment I-42, wherein the antibody comprises a VH amino acid sequence having at least 95%, at least 96%, at least 97%, at least 98%, at least 99%, or 100% sequence identity to the amino acid sequence of SEQ ID NO: 57.

Embodiment I-44. The anti-TGFβ3 antibody of Embodiment I-42 or Embodiment I-43, wherein the antibody comprises the VH amino acid sequence of SEQ ID NO: 57.

Embodiment I-45. The anti-TGFβ3 antibody of any of Embodiment I-42 to Embodiment I-44, wherein the antibody comprises a complete H chain amino acid sequence having at least 95%, at least 96%, at least 97%, at least 98%, at least 99%, or 100% sequence identity to the amino acid sequence of SEQ ID NO: 79.

Embodiment I-46. The anti-TGFβ3 antibody of any of Embodiment I-42 to Embodiment I-45, wherein the antibody comprises a complete H chain amino acid sequence of SEQ ID NO: 79.

Embodiment I-47. The anti-TGFβ3 antibody of any of Embodiment I-42 to Embodiment I-46, wherein the antibody comprises a VL amino acid sequence having at least 95%, at least 96%, at least 97%, at least 98%, at least 99%, or 100% sequence identity to the amino acid sequence of SEQ ID NO: 56.

Embodiment I-48. The anti-TGFβ3 antibody of any one of Embodiment I-42 to Embodiment I-47, wherein the antibody comprises the VL amino acid sequence of SEQ ID NO: 56.

Embodiment I-49. The anti-TGFβ3 antibody of any of Embodiment I-42 to Embodiment I-48, wherein the antibody comprises a complete L chain amino acid sequence having at least 95%, at least 96%, at least 97%, at least 98%, at least 99%, or 100% sequence identity to the amino acid sequence of SEQ ID NO: 76 Embodiment I-50. The anti-TGFβ3 antibody of any of Embodiment I-42 to Embodiment I-49, wherein the antibody comprises the complete L chain amino acid sequence of SEQ ID NOs: 76.

Embodiment I-51. The anti-TGFβ3 antibody of Embodiment I-42, wherein the antibody comprises a VH/VL pair comprising the amino acid sequences (respectively) of SEQ ID NOs: 57/56.

Embodiment I-52. The anti-TGFβ3 antibody of Embodiment I-42, wherein the antibody comprises a complete H/L chain pair, the H/L chain pair comprising the amino acid sequences (respectively) of SEQ ID NOs: 79/78.

Embodiment I-53. An anti-TGFβ3 antibody comprising:

(a) (i) heavy chain CDRs comprising CDR-H1, -H2 and -H3, wherein CDR-H1 has the amino acid sequence of SEQ ID NO: 4, CDR-H2 has the amino acid sequence of one of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78.

Embodiment 90. An antibody of any one of Embodiments 1 to 89, or Embodiments I-1 to 1-53, which is a monoclonal antibody.

Embodiment 91. An antibody of any one of Embodiments 1 to 89, or Embodiments I-1 to I-53, which is a human, humanized, or chimeric antibody.

Embodiment 92. An antibody of any one of Embodiments 1 to 89, or Embodiments I-1 to I-53, which is an antibody fragment.

Embodiment 93. An antibody of any one of Embodiments 1 to 89, or Embodiments I-1 to I-53, comprising a human Fc region that is an IgG1 or IgG4 isotype.

Embodiment 94. The antibody of Embodiment 93, comprising a human Fc region that is an IgG1 isotype.

Embodiment 95. The antibody of Embodiment 93 or 94, wherein the Fc region comprises a modification to remove the glycosylation site at amino acid residue position N297 (EU numbering as in Kabat).

Embodiment 96. The antibody of Embodiment 95, wherein the modification is a mutation selected from N297G or N297A.

Embodiment 97. The antibody of Embodiment 96, wherein the modification is the mutation N297G.

Embodiment 98. The antibody of any one of Embodiments 93 to 97, wherein the Fc region is modified to remove effector function.

Embodiment 99. An antibody of any one of Embodiments 1 to 98, or Embodiments I-1 to I-53, wherein the antibody has a Cmax of about 230-260 μg/ml and/or a half life ($t_{1/2}$) of about 15 to 16 days.

Embodiment 100. Isolated nucleic acid encoding the antibody of any one of Embodiments 1 to 99, or Embodiments I-1 to I-53.

Embodiment 101. A host cell comprising the nucleic acid of Embodiment 100.

Embodiment 102. A method of producing an antibody comprising culturing the host cell of Embodiment 101 so that the antibody is produced.

Embodiment 103. The method of Embodiment 102, further comprising recovering the antibody from the host cell.

Embodiment 104. An antibody produced by the method of Embodiment 102 or Embodiment 103.

Embodiment 105. An immunoconjugate comprising the antibody of Embodiment 1 and a cytotoxic agent.

Embodiment I-105. An immunoconjugate comprising the antibody of any one of Embodiments 1 to 89, or Embodiments I-1 to I-53, and a cytotoxic agent.

Embodiment 106. A pharmaceutical formulation comprising the antibody of any one of Embodiments 1 to 99, or Embodiments I-1 to I-53, or the immunoconjugate of Embodiment 105, or the immunoconjugate of Embodiment I-105, and a pharmaceutically acceptable carrier.

Embodiment 107. A pharmaceutical formulation comprising the antibody of Embodiment 106, further comprising an additional therapeutic agent.

Embodiment 108. The pharmaceutical formulation of Embodiment 107, wherein the additional therapeutic agent is selected from the group consisting of pirfenidone, nintedanib, mycophenylate mofetil, an IL-6 inhibitor (e.g., tocilizumab), an anti-CTFG antibody (e.g., FG-3019), an autotaxin inhibitor, a JAK inhibitor, an IL-11 inhibitor, and PTX2.

Embodiment 109. The antibody of any one of Embodiments 1 to 99, or Embodiments I-1 to I-53, for use as a medicament.

Embodiment 110. The antibody of any one of Embodiments 1 to 99, or Embodiments I-1 to I-53, for use in treating a TGFβ-related disorder.

Embodiment 111. The antibody of Embodiment 1 and the antibody of Embodiment 70, for use in combination to treat a TGFβ-related disorder.

Embodiment 112. The antibodies of Embodiment 110 or 111, wherein the TGFβ-related disorder is fibrosis.

Embodiment 113. The antibodies of Embodiment 112, wherein the fibrosis is a fibrotic condition of the lung, liver, heart, kidney, pancreas, eye, and/or skin.

Embodiment 114. The antibody of any one of Embodiments 1 to 99, or Embodiments I-1 to I-53, for use in the manufacture of a medicament for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin, and/or for inhibiting new collagen synthesis.

Embodiment 115. Use of an antibody according to any one of Embodiments 1 to 99, or Embodiments I-1 to I-53, in the manufacture of a medicament for treating a TGFβ-related disorder in a subject.

Embodiment 116. The use of Embodiment 115, wherein the TGFβ-related disorder is fibrosis, wherein, optionally, the fibrosis is a fibrotic condition of the lung, liver, heart, kidney, pancreas, eye, and/or skin.

Embodiment 117. Use of an antibody of any one of Embodiments 1 to 99, or Embodiments I-1 to I-53, in the manufacture of a medicament for inhibiting TGFBR-dependent SMAD signaling, for inhibiting the assembly of TGFβ-TGFBR signaling complexes, for inhibiting TGFβ signaling through the TGFBR1/R2 complex, for inhibiting TGFβ signaling through the TGFBR2/ALK1 complex facilitated by endoglin, and/or for inhibiting new collagen synthesis.

Embodiment 118. A method of treating a subject having a TGFβ-related disorder, the method comprising administering to a subject in need thereof an effective amount of the antibody of any one of Embodiments 1 to 99, or Embodiments I-1 to I-53, or administering to the subject the pharmaceutical formulation of Embodiment 106.

Embodiment 119. A method for inhibiting TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin, and/or for inhibiting new collagen synthesis in a subject, comprising administering to a subject in need thereof an effective amount of the antibody of any one of Embodiments 1 to 99, or Embodiments I-1 to I-53, to inhibit TGFBR-dependent SMAD signaling, inhibiting the assembly of TGFβ-TGFBR signaling complexes, inhibiting TGFβ signaling through the TGFBR1/R2 complex, inhibiting TGFβ signaling through the TGFBR2/ALK1 complex facilitated by endoglin and/or for inhibiting new collagen synthesis in the subject.

Embodiment 120. The method of Embodiment 118 or 119, further comprising administering an additional therapeutic agent to the subject.

Embodiment 121. The method of Embodiment 120, wherein the additional therapeutic agent is selected from the group consisting of pirfenidone, nintedanib, mycophenylate mofetil, an IL-6 inhibitor (e.g., tocilizumab, sarilumab), an anti-CTFG antibody (e.g., FG-3019), an autotaxin inhibitor, and PTX2.

Embodiment 122. The method of any one of Embodiments 118 to 121, comprising administering the subject an effective amount of an anti-TGFβ3 antibody according to claim 1 and an effective amount of an anti-TGFβ2 antibody according to Embodiment 70.

Embodiment 123. The method of any one of Embodiments 118 to 122, wherein the subject has a TGFβ-related disorder that is fibrosis.

Embodiment 124. The method of Embodiment 123, wherein the fibrosis is a lung fibrosis selected from the group consisting of idiopathic pulmonary fibrosis (IPF), idiopathic pulmonary upper lobe fibrosis (Amitani disease), familial pulmonary fibrosis, pulmonary fibrosis (e.g., pulmonary fibrosis secondary to systemic inflammatory diseases such as, rheumatoid arthritis, scleroderma, lupus, cryptogenic fibrosing alveolitis, chronic obstructive pulmonary disease (COPD) or chronic asthma), cystic fibrosis, non-specific interstitial pneumonia (NSIP), cryptogenic organizing pneumonia (COP), progressive massive fibrosis, scleroderma/systemic sclerosis (SSc, including limited cutaneous (lcSSc) and diffuse cutaneous (dcSSc) forms and SSc-associated interstitial lung disease (SSc-ILD)), bronchiolitis obliterans-organizing pneumonia, connective tissue disease-associated ILD (CT-ILD), hypersensitivity pneumonitis, pulmonary hypertension, pulmonary tuberculosis, silicosis, asbestosis, acute lung injury, and acute respiratory distress (ARD, including bacterial pneumonia induced, trauma-induced, and viral pneumonia-induced, ventilator-induced, non-pulmonary sepsis induced).

Embodiment 125. The method of Embodiment 123, wherein the fibrosis is a fibrotic condition of the liver selected from the group consisting of liver cirrhosis, congenital hepatic fibrosis, obesity, fatty liver, alcohol induced liver fibrosis, non-alcoholic steatohepatitis (NASH), biliary duct injury, primary biliary cirrhosis (PBC), primary sclerosing cholangitis (PSC), infection- or viral-induced liver fibrosis (e.g., chronic hepatitis B and C virus infections), cystic fibrosis, autoimmune hepatitis, necrotizing hepatitis, primary sclerosing cholangitis, hemochromatosis, disorders of the biliary tree, and hepatic dysfunction attributable to infections.

Embodiment 126. The method of Embodiment 123, wherein the fibrosis is a fibrotic condition of the heart and/or pericardium selected from the group consisting of endomyocardial fibrosis, cardiac allograft vasculopathy (CAV), myocardial infarction, atrial fibrosis, congestive heart failure, arterioclerosis, atherosclerosis, vascular stenosis, myocarditis, congestive cardiomyopathy, coronary infarcts, varicose veins, coronary artery stenosis and other post-ischemic conditions, and idiopathic retroperitoneal fibrosis.

Embodiment 127. The method of Embodiment 123, wherein the fibrosis is a fibrotic condition of the kidney selected from the group consisting of glomerulonephritis (including membranoproliferative, diffuse proliferative, rapidly progressive or sclerosing, post-infectious and chronic forms), diabetic glomerulosclerosis, focal segmental glomerulosclerosis, IgA nephropathy, diabetic nephropathy, ischemic nephropathy, tubulointerstitial kidney fibrosis, HIV-associated nephropathy, membrane nephropathy, glomerulonephritis secondary to systemic inflammatory diseases such as lupus, scleroderma and diabetes glomerulonephritis, idiopathic membranoproliferative glomerular nephritis, mesangial proliferative glomerulonephritis, crescentic glomerulonephritis, amyloidosis (which affects the kidney among other tissues), autoimmune nephritis, renal tubuloinsterstitial fibrosis, renal arteriosclerosis, Alport's syndrome, nephrotic syndrome, chronic renal failure, chronic kidney disease, periglomerular fibrosis/atubular glomeruli, combined apical emphysema and basal fibrosis syndrome (emphysema/fibrosis syndrome), glomerular hypertension, nephrogenic fibrosing dermatopathy, polycystic kidney disease, Fabry's disease, and renal hypertension.

Embodiment 128. The method of Embodiment 123, wherein the fibrosis is a fibrotic condition of the pancreas selected from the group consisting of stromal remodeling pancreatitis and stromal fibrosis.

Embodiment 129. The method of Embodiment 123, wherein the fibrosis is a fibrotic condition of the gastrointestinal tract selected from the group consisting of Crohn's disease, ulcerative colitis, collagenous colitis, colorectal fibrosis, villous atrophy, crypt hyperplasia, polyp formation, healing gastric ulcer, and microscopic colitis.

Embodiment 130. The method of Embodiment 123, wherein the fibrosis is a fibrotic condition of the eye selected from the group consisting of ocular fibrosis, ophthalmic fibrosis, proliferative vitreoretinopathy, vitreoretinopathy of any etiology, fibrosis associated with retinal dysfunction, fibrosis associated with wet or dry macular degeneration, scarring in the cornea and conjunctiva, fibrosis in the corneal endothelium, anterior subcapsular cataract and posterior capsule opacification, anterior segment fibrotic diseases of the eye, fibrosis of the corneal stroma (e.g., associated with corneal opacification), fibrosis of the trabecular network (e.g., associated with glaucoma), posterior segment fibrotic diseases of the eye, fibrovascular scarring (e.g., in retinal or choroidal vasculature of the eye), retinal fibrosis, epiretinal fibrosis, retinal gliosis, subretinal fibrosis (e.g., associated with age related macular degeneration), tractional retinal detachment in association with contraction of the tissue in diabetic retinopathy, congenital orbital fibrosis, lacrimal gland fibrosis, corneal subepithelial fibrosis, and Grave's ophthalmopathy.

Embodiment 131. The method of Embodiment 123, wherein the fibrosis is selected from fibrosis resulting from spinal cord injury/fibrosis or central nervous system fibrosis such as fibrosis after a stroke, Duchenne muscular dystrophy, fibrosis associated with neurodegenerative disorder such as Alzheimer's disease or multiple sclerosis, vascular restenosis, uterine fibrosis, endometriosis, ovarian fibroids, Peyronie's disease, polycystic ovarian syndrome, disease related pulmonary apical fibrosis in ankylosing spondylitis, scarring, and fibrosis incident to microbial infections (e.g., bacterial, viral, parasitic, fungal).

Embodiment 132. The method of Embodiment 123, wherein the fibrosis is SSc.

Embodiment 133. The method of Embodiment 123, wherein the fibrosis is IPF.

Embodiment 134. The method of Embodiment 123, wherein the fibrosis is chronic obstructive pulmonary disease (COPD).

Embodiment 135. The method of Embodiment 123, wherein the fibrosis is progressive-fibrosing interstitial lung disease (PF-ILD).

Embodiment 136. The method of Embodiment 135, wherein the PF-ILD is a disease or condition selected from the group consisting of non-specific interstitial pneumonia (NSIP), cryptogenic organizing pneumonia (COP), progressive massive fibrosis, a complication of coal worker's pneumoconiosis, scleroderma/systemic sclerosis, bronchiolitis obliterans-organizing pneumonia; connective tissue disease-associated ILD (CT-ILD), and hypersensitivity pneumonitis.

Embodiment 137. The method of Embodiment 123, wherein the fibrosis is liver cirrhosis or chronic hepatic fibrosis.

Embodiment 138. The method of Embodiment 123, wherein the fibrosis is GI tract fibrosis, e.g., intestinal fibrosis, optionally, selected from the group consisting of fibrosis associated with Crohn's disease, ulcerative colitis, collagenous colitis, colorectal fibrosis, villous atrophy, crypt hyperplasia, polyp formation, healing gastric ulcer, and microscopic colitis.

Embodiment 139. The method of Embodiment 123, wherein the fibrosis is a fibrotic condition of the eye, fibrosis resulting from spinal cord injury, fibrosis or central nervous system fibrosis, or fibrosis associated with a neurodegenerative disorder.

Embodiment 140. The method of any one of Embodiments 118 to 139, wherein the antibody is an anti-TGFβ2 antibody.

Embodiment 141. The method of Embodiment 140, wherein the anti-TGFβ2 antibody comprises:

(a) heavy chain CDRs comprising CDR-H1, -H2 and -H3, wherein CDR-H1 has the amino acid sequence of SEQ ID NO: 16, CDR-H2 has the amino acid sequence of SEQ ID NO: 17, and CDR-H3 has the amino acid sequence of SEQ ID NO: 18; and (b) light chain CDRs comprising CDR-L1, -L2 and -L3, wherein CDR-L1 has the amino acid sequence of SEQ ID NO: 19; CDR-L2 has the amino acid sequence of SEQ ID NO: 20, and CDR-L3 has the amino acid sequence of SEQ ID NO: 21.

Embodiment 142. The method of any one of Embodiments 118 to 139, wherein the antibody is an anti-TGFβ3 antibody.

Embodiment 143. The method of Embodiment 142, wherein the anti-TGFβ3 antibody comprises:

(a) (i) heavy chain CDRs comprising CDR-H1, -H2 and -H3, wherein CDR-H1 has the amino acid sequence of SEQ ID NO: 4, CDR-H2 has the amino acid sequence of one of SEQ ID NO: 35, and CDR-H3 has the amino acid sequence of SEQ ID NO: 6; and (ii) light chain CDRs comprising CDR-L1, -L2 and -L3, wherein CDR-L1 has the amino acid sequence of SEQ ID NO: 7; CDR-L2 has the amino acid sequence of SEQ ID NO: 8, and CDR-L3 has the amino acid sequence of SEQ ID NO: 9;

(b) a VH/VL pair, the VH of the VH/VL pair comprising the amino acid sequence of SEQ ID NO: 57, and the VL of the VH/VL pair comprising the amino acid sequence of SEQ ID NO: 56; or (c) a complete H/L chain pair, the H chain of the H/L chain pair comprising the amino acid sequence of SEQ ID NO: 79 and the L chain of the H/L chain pair comprising the amino acid sequence of SEQ ID NO: 78.

Embodiment 144. The method of any one of Embodiments 118 to 139, wherein the antibody is an anti-TGFβ2/3 antibody.

Embodiment 145. The method of Embodiment 144, wherein the anti-TGFβ2/3 antibody comprises: (i) heavy chain CDRs comprising CDR-H1, -H2 and -H3, wherein CDR-H1 has the amino acid sequence of SEQ ID NO: 10, CDR-H2 has the amino acid sequence of SEQ ID NO: 11, and CDR-H3 has the amino acid sequence of SEQ ID NO: 12; and (ii) light chain CDRs comprising CDR-L1, -L2 and -L3, wherein CDR-L1 has the amino acid sequence of SEQ ID NO: 13; CDR-L2 has the amino acid sequence of SEQ ID NO: 14, and CDR-L3 has the amino acid sequence of SEQ ID NO: 15; Embodiment 146. A method of diagnosing a subject as having SSc, the method comprising detecting the expression levels of the genes in an 18-gene signature set consisting of PRSS23, PXDN, COL8A1, COL6A3, SERPINE2, TNC, COMP, THBS1, COL11A1, COL1A1, COL5A2, COL1A2, COL4A1, COL4A2, SFRP4, ALPK2, COL5A1, and TAGLN, and diagnosing the subject with SSc if the levels of the genes are determined to be elevated relative to the gene levels in a healthy control set or reference gene signature.

Embodiment 147. The method of Embodiment 146, wherein a gene level is elevated if the expression increase relative to the healthy control set or reference gene signature is statistically significant, optionally, at least two-fold increased, or at least three-fold increased, or at least four-fold increased, relative to the healthy control set or reference gene signature.

Embodiment 148. A method of monitoring response to treatment of a subject with an anti-TGFβ2 antibody and/or an anti-TGFβ3 antibody, the method comprising determining the expression level of one or more of the TGFβ-inducible genes selected from the group consisting of serpine1, col1a1, col1a2, and col3a1 in a sample from the subject, wherein the subject has received one or more administrations of the anti-TGFβ2 antibody and/or the anti-TGFβ3 antibody.

Embodiment 149. The method of Embodiment 148, wherein the subject is determined to be responding to treatment with the anti-TGFβ2 antibody and/or anti-TGFβ3 antibody, if the expression level of the one or more TGFβ-inducible genes is significantly reduced compared to pre-treatment levels of the one or more TGFβ-inducible genes, wherein optionally the method further comprises administering an additional administration of the anti-TGFβ2 antibody and/or the anti-TGFβ3 antibody if the expression level of the one or more TGFβ-inducible genes is determined to be significantly reduced.

Embodiment 150. The method of Embodiment 148 or 149, wherein the subject is administered the anti-TGFβ2 antibody as a monotherapy.

Embodiment 151. The method of Embodiment 148 or 149, wherein the subject is administered the anti-TGFβ3 antibody as a monotherapy.

Embodiment 152. The method of Embodiment 148, wherein the expression level of the one or more TGFβ-inducible genes is determined by qPCR or microarray analysis.

Embodiment 153. The method or use of any one of Embodiments 100 to 152, wherein the subject is a human.

Embodiment 154. A kit comprising an antibody of any one of Embodiments 1 to 99, or Embodiments I-1 to I-53.

Embodiment I-155. A method for treating a TGFβ-related disorder in a subject in need thereof, the method comprising:

determining that a sample from the subject comprises an elevated level of one or more biomarkers; and administering to the subject an effective amount of an isoform-selective anti-TGFβ antibody.

Embodiment I-156. A method for selecting a therapy for a subject with an autoimmune or inflammatory disease, comprising:

determining the level of one or more biomarkers of the subject; and selecting a medicament based on the level of the one or more biomarkers, wherein the medicament selected is an isoform-selective anti-TGFβ antibody if the level of one or more of the biomarkers is elevated.

Embodiment I-157. A method for treating a TGFβ-related disorder in a subject in need thereof, comprising administering to the subject an effective amount of an isoform-selective anti-TGFβ antibody, wherein prior to beginning administration, the subject has an elevated level of one or more biomarkers.

Embodiment I-158. The method of any one of Embodiments I-155 to I-157, wherein the one or more biomarkers are selected from the group consisting of TGFβ2, TGFβ3, periostin (POSTN), and cartilage oligomeric matrix protein (COMP).

Embodiment I-159. The method of any one of Embodiments I-155 to I-157, wherein the one or more biomarkers are selected from the group consisting of PRSS23, PXDN, COL8A1, COL6A3, SERPINE2, TNC, COMP, THBS1, COL11A1, COL1A1, COL5A2, COL1A2, COL4A1, COL4A2, SFRP4, ALPK2, COL5A1, and TAGLN.

Embodiment I-160. The method of any one of Embodiments I-155 to I-157, wherein the one or more biomarkers are selected from the group consisting of SERPINE1, COL1A1, COL1A2, and COL3A1.

Embodiment I-161. The method of any one of Embodiments I-155 to I-160, wherein the level of one or more biomarkers are elevated in a sample from the subject, wherein the sample is a skin, lung, or blood sample.

Embodiment I-162. The method of Embodiments I-158, wherein the sample is a serum sample.

Embodiment I-160. The method of any one of Embodiments I-155 to I-159, wherein the isoform-selective anti-TGFβ antibody is an anti-TGFβ2, anti-TGFβ2/3, or anti-TGFβ3 antibody.

Embodiment I-161. The method of any one of Embodiments I-155 to I-160, wherein the elevated biomarkers are one or both of periostin and COMP.

Embodiment I-162. The method of any one of Embodiments I-155 to I-161, wherein the disorder is a fibrotic disorder.

Embodiment I-163. The method of Embodiment I-162, wherein the fibrotic disorder is lung fibrosis, a fibrotic condition of the liver, a fibrotic condition of the heart and/or pericardium, a fibrotic condition of the kidney, a fibrotic condition of the pancreas, a fibrotic condition of the gastrointestinal tract, a fibrotic condition of the eye, or a fibrosis resulting from spinal cord injury/fibrosis or central nervous system fibrosis.

Embodiment I-164. The method of Embodiment I-162, wherein the fibrotic disorder is selected from the group consisting of IPF, SSc, COPD, and. PF-ILD.

Embodiment I-165. The method of any one of Embodiments I-155 to I-164, wherein the elevated level is relative to a healthy individual or control group, and wherein the elevation is statistically significant, optionally, at least two-fold increased, or at least three-fold increased, or at least four-fold increased, relative to the healthy individual or control group.

Embodiment I-166. The method of any one of Embodiments I-155 to I-164, wherein the subject was not responsive to anti-IL-6 inhibitor therapy.

Embodiment I-167. The method of Embodiment I-166, wherein the anti-IL-6 therapy was tocilizumab.

Embodiment I-168. The method of any one of Embodiments I-155 to I-167, wherein the isoform-selective anti-TGFβ is an antibody of any one Embodiments 1 to 99, or Embodiments I-1 to 1-53.

IV. Examples

The following are examples of methods and compositions of the invention. It is understood that various other embodiments may be practiced, given the general description provided above.

Example 1: Generation and Screening of Isoform-Selective TGFβ Antibodies

Materials and Methods:

Generation of Rabbit Anti-Human TGFβ Monoclonal Antibodies

New Zealand white rabbits were immunized with human TGFβ2 and TGFβ3 isoforms (Peprotech) and single B-cell was isolated using a modified protocol related to published literature (Offner et al. *PLoS ONE* 9(2), 2014). Briefly, rabbit peripheral blood mononuclear cells (PBMCs) were isolated by density centrifugation of blood (1:1 dilution with PBS) collected from ear artery using Lympholyte®-M (Cedarlane Labs). After washing with PBS, PBMCs were resuspended in culture medium RPMI with supplement and transferred to 6-well plate to remove macrophages and monocytes through non-specific adhesion onto the plate. The non-adhesion cells were then collected for B cell enrichment by immunofluorescence staining with biotinylated anti-rabbit CD11b antibody, anti-rabbit T-lymphocyte antibody (AbD Serotec, Bio-Rad) and anti-rabbit IgM (BD Bioscience) to further deplete rabbit myeloid cells, T cells and IgM B cells through MACS Column (Miltenyl Biotec) according to the manufacturer's instructions. The following workflow included using FITC-labeled goat anti-rabbit IgG antibody (Serotec, BioRad), APC-labeled human TGFβ I (Innova Biosciences) and RPE-labeled human TGFβ2/3 (Innova Biosciences) to sort out rabbit IgG+ and human TGFβ2/3+-reactive B cells into single wells. The B-cell culture supernatants were subject to primary ELISA screening for human TGFβ2/3 isoforms binding, and B-cells were lysed and stored at −80° C. In the molecular cloning, the light chain and heavy chain variable region of human TGFβ2/3 specific B cells were amplified by PCR and cloned into expression vectors as described in the published literature (Offner et al. *PLoS ONE* 9(2), 2014). Each recombinant rabbit monoclonal antibody was expressed in Expi293 cells (Thermo Fisher Scientific, Waltham, Mass.) and subsequently purified with protein A. Purified anti-human TGFβ2/3 antibodies were then subjected to functional characterization in blocking, affinity determination.

Development of Rat Anti-Human TGFβ Hybridoma Antibodies

Sprague Dawley rats (Charles River, Hollister, Calif.) were immunized every two weeks with 100 μg of human TGFβ2 or TGFβ3 proteins (Peprotech) mixed with RIBI adjuvant (Sigmal, St. Louis, Mo.) and injected at base of tail, or mixed with Incomplete Freund's Adjuvant (BD) and divided among multiple sites: I.P., S.C. at base of tail, s.c. at nape of neck, and s.c. in both hocks. Multiple lymph nodes were harvested three days after the last immunization. IgM negative B-cells from these rats were purified from lymphocytes using magnetic separation (Miltenyi Biotec, San Diego, Calif.) and were fused with Sp2ab mouse myeloma cells (Enzo Life Sciences, Farmingdale, N.Y.) via electrofusion (Harvard Apparatus, Holliston, Mass.). Fused cells were incubated at 37° C., 7% C02, overnight in Medium C (StemCell Technologies, Vancouver, BC, Canada), before plating into 6-well plates containing Medium E (StemCell Technologies, Vancouver, BC, Canada) supplemented with HAT (Sigma-Aldrich, St. Louis, Mo.) and incubated at 37° C., 7% C02 for three days. TGFβ2 hybridomas were collected and sorted with anti-rat IgG (Sigma-Aldrich) and TGFβ3 hybridomas were sorted with anti-rat IgG (Sigma-Aldrich) and labeled human TGFβ3-PE by Lightning-Link R-PE Antibody Labeling kit (Novus, Centennial, Colo.).

HEKBlue Cell-Based TGFβ Blocking Assay

HEK-Blue™ TGFβ cells (InvivoGen, San Diego, Calif.) stably expressing human TGFβRI, Smad3, Smad4 proteins and secreted alkaline phosphatase (SEAP) reporter gene under the control of the P-globin minimal promoter fused to three Smad3/4-binding elements (SBE) were used to evaluate the blocking potency of monoclonal antibodies generated from rats and rabbits immunized with the mature receptor-binding domains of human TGFβ1, TGFβ2 and TGFβ3. The antibodies were incubated with each TGFβ isoforms (PeproTech, Rocky Hill, N.J.) at 25° C. for 1 h prior to the addition into 4.5×104 HEK-Blue™ TGF-β cells seeded in 96-well plate in 100 μL of assay buffer (DMEM high glucose with 10% heat inactivated FBS, 2 mM L-glutamine and 0.5% Penicillin Streptomycin). The final concentration of antibody and TGFβ was 0.001-200 nM and 20 pM respectively. The plate was incubated at 37° C. and 5% $CO_2$ for 18-22 h. The SEAP level in the cell supernatant was determined by QUANTI-Blue™ assay according to the manufacturer's instructions (InvivoGen). Pan-TGFβ mAb neutralizes TGFβ1, 2, and 3 at low cellular potencies (IC50) of 0.72, 2.2, and 0.026 nM, respectively ELISA Screening An enzyme-linked immunosorbent assay (ELISA) was used to screen the binding of candidate clones to TGFβ1, TGFβ2, and TGFβ3. First, each TGFβ isoform (Peprotech) was immobilized to the wells of Grenier Bio-One 384-well ELISA plates with coating buffer (50 mM carbonate, pH 9.6), at 1 pg/ml; 50 μL/well for overnight incubation at 4° C. Then the coated ELISA plates were washed 3 times with ELISA diluent buffer 100 μl per well (PBS/0.5% Tween20). Next the ELISA plates were blocked with ELISA diluent buffer 100 μl/well for one hour. After blocking, the buffer was discarded and samples and controls were added from 96-well plates to 384-well plates (50 μl/well). Then the ELISA plates with sample in were incubated for 30 minutes at room temperature while the plates were shaking on the shaker. Next the plates were washed three times with wash buffer (PBS/0.05% TWEEN 20, 20× Stock Hyclone SH3A649-01) 100 ul/wee. Then diluted HRP conjugate (Peroxidase AffiniPure Goat Anti-Rat IgG (H+L) Jackson ImmunoResearch Laboratories, INC. 112-035-003 diluted 1:10000, 50 μl/well) was added to each well and the ELISA plates were incubated for 30 minutes at room temperature. After the incubation, the plates were washed 3 times with wash buffer (100 μl/well) and then added substrate (BIOFX TMB Substrate TMBW-1000-01, 50 ul/well). After 5 minutes incubation at room temperature for 5 minutes, the stop solution (BIOFX Stop reagent LBSP-1000-01, 50 μl/well) was added. Finally, the plates were read at 659 nm for absorbance.

Results:

Monoclonal antibodies generated from rats and rabbits immunized with the mature receptor-binding domains of human TGFβ1, TGFβ2 and TGFβ3 were screened for binding via direct ELISA and surface plasmon resonance (SPR), and for their ability to inhibit mature receptor-binding domain induced TGFβR-dependent signaling in a reporter cell line (HEKBlue SMAD2/3 SEAP reporter), as described above. Out of 96 initial rabbit clones that exhibited binding to TGFβ2 and 85 clones that bound to TGFβ3, 48 clones were selected for further screening. For the rabbit antibodies, 1,995 IgG+ TGFβ2 hybridomas and 2,660 IgG+ TGFβ3+ hybridomas were single-cell sorted using a FACSAria Fusion sorter (BD Biosciences, Franklin Lakes, N.J.) into 96-well plates. Seven days after plating, supernatants were screened by ELISA against human TGFβ2 or TGFβ3 proteins. Supernatants from 28 TGFβ2 and 48 TGFβ3 hybridomas demonstrating binding to their respective antigens by ELISA were harvested and purified by protein G (GammaBind Plus, GE Healthcare, Pittsburgh, Pa.). Among the 28 TGFβ2+ clones, 4 showed functional blocking against TGFβ2, including 6F12. Among the 48 TGFβ3+ clones, 28 clones showed functional blocking against human TGFβ3, including 2A10.

Potent inhibitory antibodies ($K_D$<10 pM and cell-based $IC_{50}$<250 pM) were identified with selectivity for TGFβ2 (mAb 6F12 (rat)), TGFβ3 (mAbs 16C10 (rabbit) and 2A10 (rat)), and a dual-specificity antibody that bound to and inhibited the activity of both TGFβ2 and TGFβ3 (mAb 4A11 (rabbit)), but none of these antibodies bound to or inhibited TGFβ1 (see Table 4, below).

The relative potencies of these antibodies for selected TGFβ isoforms were comparable or superior to the activity of a "pan-TGFβ" antibody, 1D11 (Dasch, J R et al. J. Immunol. 142: 1536-41 (1989)) (see Table 4, below). Notably, the TGFβ2-specific antibody 6F12 was nearly 100-fold more potent than 1D11 in blocking TGFβ2-dependent reporter activity in cells ($IC_{50}$ of 40 pM vs. 3.6 nM).

Figures 55A, 55B:
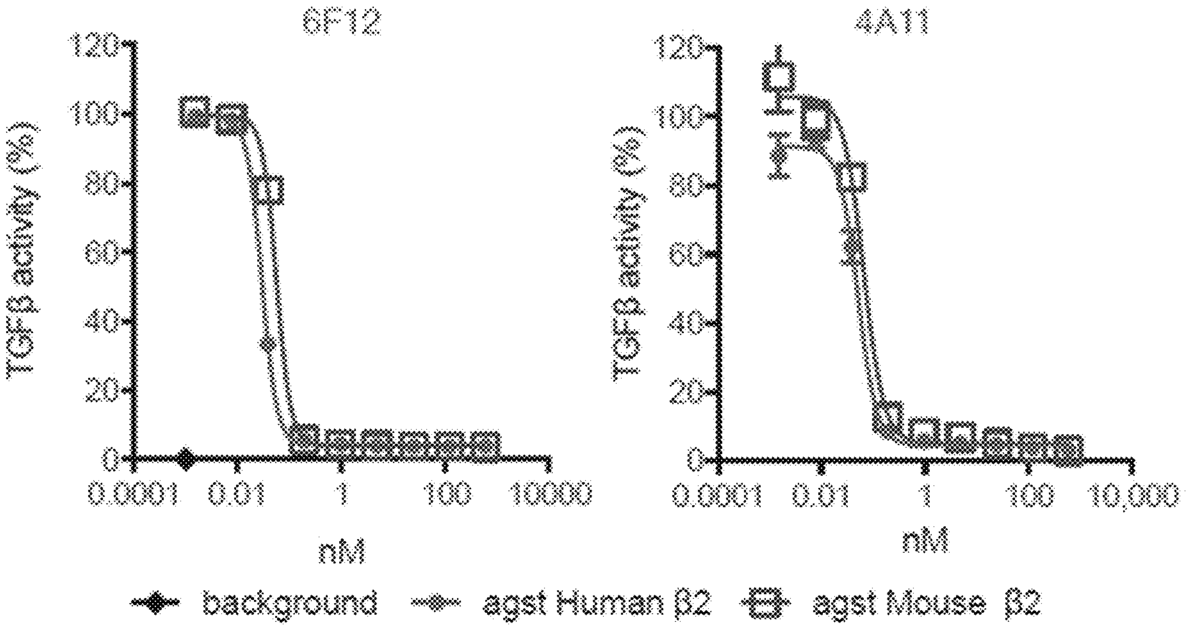
FIG. 55A is a table showing the binding affinity ($K_D$) of antibodies 6F12 and 4A11 for human and mouse TGFβ2 determined by Biacore SPR.
FIG. 55B contains line graphs plotting TGFβ activities as measured with MLEC reporter cells. Mature peptide (1 ng/ml) of human or mouse TGFβ2 was incubated with a series of concentrations of 6F12 or 4A11 antibodies. Curves are best fit to dose-response inhibition model. BKGD (background), no mature peptide added.

Further, there are three amino acid differences between human and mouse mature TGFβ2, and 6F12 and 4A11 bind to both peptides with similar affinities (FIG. 55A) and have similar inhibitory potencies against both (FIG. 55B).

TABLE 4

Potencies of Isoform-selective TGFβ Antibodies

| | | Affinity @ 25° C. (nM) | | | Blocking @ 37° C. (nM) | | |
|---|---|---|---|---|---|---|---|
| Function | Clone | TGFb1 | TGFb2 | TGFb3 | TGFb1 | TGFb2 | TGFb3 |
| TGFb1 blocker | 21D1 | 0.008 | >5 | >5 | 0.013 | >200 | >200 |
| | 20C8 | 0.001 | >25 | >25 | 0.13 | >70 | >70 |
| | 39A3 | 0.085 | 0.7 | >25 | 0.03 | >70 | >70 |
| | 40F8 | 0.003 | >25 | >25 | 0.02 | >70 | >70 |
| TGFβ1 IHC reagent | Rb3.22.C6 | 0.022 | >5 | >5 | 0.5 | 69.3 | >70 |
| | Rb3.23.B6 | 0.021 | >5 | >5 | 20.4 | 29.5 | >70 |
| | Rb3.32.F8 | >5 | >5 | >5 | 3.58 | >70 | >70 |
| TGFb2 blocker | 6F12 | >15 | <0.001 | >15 | >600 | 0.04 | >600 |
| | 36C5 | >25 | 0.003 | 4.9 | >200 | 0.002 | >200 |
| | 1C3 | 0.25 | <0.004 | >25 | >200 | 0.002 | >200 |
| | 9B10 | >25 | 0.003 | 0.21 | >200 | 0.018 | >200 |
| | 31E12 | >25 | 0.003 | 29 | >200 | 0.015 | >200 |
| | 19D3 | >25 | 0.005 | >25 | >200 | 0.015 | >200 |
| | 1G10 | 3.9 | 0.007 | >25 | >200 | 0.011 | >200 |
| TGFβ2 IHC reagent | R62.14.F11 | >5 | 0.004 | 0.521 | >67 | 0.05 | >67 |
| | Rb2.20.F10 | >5 | 0.007 | >5 | | NA | |
| TGFb3 IHC reagent | Rb1.9A8 | >15 | >15 | 0.014 | >200 | >200 | 3.0 |
| & TGFb3 blocker | Rb2.15A7 | >15 | >15 | 0.006 | >200 | >200 | 0.4 |
| | Rb2.16C10 | >15 | 0.19 | <0.003 | >200 | >200 | 0.1 |
| TGFb3 blocker | 2A10 | 1.6 | 0.046 | <0.002 | >600 | 193 | 0.02 |
| | Rb1.9A10 | 0.025 | 0.723 | 0.026 | >200 | >200 | 0.4 |
| | Rb1.25D11 | >15 | >15 | 0.012 | >200 | >200 | 50 |
| TGFb1&2 blocker | Rb1.22C7 | 0.036 | 0.006 | 6.1 | 3.64 | 0.04 | >200 |
| TGFb2&3 blocker | R61.34E4 | >15 | 0.002 | 0.004 | >200 | 0.37 | 1.8 |
| | Rb2.14D7 | >15 | 0.006 | >15 | >200 | 0.02 | 14 |
| | Rb2.13G11 | >15 | 0.143 | >15 | >200 | 0.42 | 28.3 |
| | Rb1.7H10 | >15 | <0.001 | 0.004 | >200 | 1.1 | 2.1 |
| | Rb2.15C2 | 1.9 | 0.23 | 0.41 | >200 | 2.83 | 4.2 |
| | Rb1.4A11 | >15 | 0.008 | 0.005 | >600 | 0.25 | 0.03 |
| | Rb2.11E6 | >15 | 0.11 | 0.019 | >200 | 5.5 | 0.3 |
| | 32F10 | 0.05 | 0.04 | 0.1 | >200 | 0.04 | 0.96 |
| PanTGFb blocker | 1D11 | 0.038 | 0.009 | 0.007 | 0.5 | 3.6 | 0.04 |
| | Rb1.16D9 | <0.001 | <0.001 | 0.084 | 0.01 | 0.01 | 4.86 |
| | Rb1.14E9 | 0.002 | <0.001 | 0.009 | 1.44 | 0.02 | 1.77 |
| | Rb2.19H8 | 0.005 | 0.003 | 0.007 | 11 | 0.02 | 0.12 |
| | 11A8 | 0.015 | 0.004 | 0.003 | 0.36 | 0.015 | 0.017 |

The sequences of the monoclonal antibodies are provided in Tables 5-7 below.

TABLE 5

CDR Sequences of anti-TGFβ isoform-selective monoclonal antibodies

| | CDR H1 | CDR H2 | CDR H3 | CDR L1 | CDR L2 | CDR L3 |
|---|---|---|---|---|---|---|
| 2A10 (anti-TGFβ3) | SYGMS (SEQ ID NO: 4) | DIVSKTYNYTTYYSDSVKD (SEQ ID NO: 5) | APGGSFDY (SEQ ID NO: 6) | RASQSVSISRFNLMH (SEQ ID NO: 7) | RASNLAS (SEQ ID NO: 8) | QHSRESPWT (SEQ ID NO: 9) |
| 4A11 (anti-TGFβ2/3) | SYTVN (SEQ ID NO: 10) | YISYGGSAYYASWANG (SEQ ID NO: 11) | HMQVGGAPTGSMAAFDP (SEQ ID NO: 12) | QSSQSVYNNNYLS (SEQ ID NO: 13) | GASTLTS (SEQ ID NO: 14) | AGGYSGSSDKYA (SEQ ID NO: 15) |
| 6F12 (anti-TGFβ2) | TYNVH (SEQ ID NO: 16) | LIWNTGGTRYNSALKS (SEQ ID NO: 17) | DPVPNKWHFDF (SEQ ID NO: 18) | LASEDIYSNLA (SEQ ID NO: 19) | DARSLQD (SEQ ID NO: 20) | QQHHAYPFT (SEQ ID NO: 21) |

TABLE 6

Heavy and Light Chain Variable Region Sequences of Isoform-selective anti-TGFβ Monoclonal Antibodies

| mAb | VH | VL |
|---|---|---|
| 2A10 | EVQLVESGGGLVQPKGSLKLSCAASGFDFNSYGMSWVRQAPGKGLDLVADIVSKTYNYTTYYSDSVKDRFTISRDDSQSMVYLQMDNLKTEDTALYYCTVAPGGSFDYWGQGVMVTVSS (SEQ ID NO: 23) | DIVLTQSPALAVSLGQRATISCRASQSVSISRFNLMHWYQHKPGQQPKLLIYRASNLASGIPARFSGSGSGTDFTLTINPVQADDLATYYCQHSRESPWTFGGGTKLEIK (SEQ ID NO: 22) |
| 6F12 | QVQLKESGPGLVQPSQTLSLTCTVSGFSLTTYNVHWVRQPPGKGLEWMGLIWNTGGTRYNSALKSRLSISKDTSKSQVFLRMNSLQTEDTATYYCARDPVPNKWHFDFWGPGTMVTVSS (SEQ ID NO: 25) | DIQMTQSPASLSASLGETVTIECLASEDIYSNLAWYQQKPGKSPQLLIYDARSLQDGVPSRFSGSESGPQYSLEINSLQSEDAVTYFCQQHHAYPFTFGSGTKLEIK (SEQ ID NO: 24) |
| 4A11 | QSLEESGGRLVTPGTPLTLTCTVSGFSLSSYTVNWVRQAPGKGLEWIGYISYGGSAYYASWANGRFTISKTSATVDLKITSPTTEDTATYFCARHMQVGGAPTGSMAAFDPWGPGTLVTVSS (SEQ ID NO: 27) | AAVLTQTPSPVSAAVGGTVSISCQSSQSVYNNNYLSWFQQKPGQPPKLLIYGASTLTSGVPSRFKGSGSGTQFTLTISDVQCDDAATYYCAGGYSGSSDKYAFGGGTEVWK (SEQ ID NO: 26) |

TABLE 7

Complete Heavy and Light Chain Sequences of Isoform-selective anti-TGFβ monoclonal antibodies

| mAb | Complete H Chain | Complete L Chain |
|---|---|---|
| 2A10 | EVQLVESGGGLVQPKGSLKLSCAASGFDFNSYGMSWVRQAPGKGLDLVADIVSKTYNYTTYYSDSVKDRFTISRDDSQSMVYLQMDNLKTEDTALYYCTVAPGGSFDYWGQGVMVTVSSAKTTAPSVYPLAPVCGDTTGSSVTLGCLVKGYFPEPVTLTWNSGSLSSGVHTFPAVLQSDLYTLSSSVTVTSSTWPSQSITCNVAHPASSTKVDKKIEPRGPTIKPCPPCKCPAPNAAGGPSVFIFPPKIKDVLMISLSPIVTCVVVDVSEDDPDVQISWFVNNVEVHTAQTQTHREDYNSTLRVVSALPIQHQDWMSGKEFKCKVNNKDLGAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTT | DIVLTQSPALAVSLGQRATISCRASQSVSISRFNLMHWYQHKPGQQPKLLIYRASNLASGIPARFSGSGSGTDFTLTINPVQADDLATYYCQHSRESPWTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC (SEQ ID NO: 28) |

TABLE 7-continued

Complete Heavy and Light Chain Sequences of Isoform-selective anti-TGFβ monoclonal antibodies

| mAb | Complete H Chain | Complete L Chain |
|---|---|---|
| | KSFSRTPGK (SEQ ID NO: 29) | |
| 6F12 | QVQLKESGPGLVQPSQTLSLTCTVSGFSLT TYNVHWVRQPPGKGLEWMGLIWNTGGTR YNSALKSRLSISKDTSKSQVFLRMNSLQTE DTATYYCARDPVPNKWHFDFWGPGTMVT VSSAKTTAPSVYPLAPVCGDTTGSSVTLGC LVKGYFPEPVTLTWNSGSLSSGVHTFPAVL QSDLYTLSSSVTVTSSTWPSQSITCNVAHP ASSTKVDKKIEPRGPTIKPCPPCKCPAPNAA GGPSVFIFPPKIKDVLMISLSPIVTCVVVDV SEDDPDVQISWFVNNVEVHTAQTQTHRED YNSTLRVVSALPIQHQDWMSGKEFKCKVN NKDLGAPIERTISKPKGSVRAPQVYVLPPPE EEMTKKQVTLTCMVTDFMPEDIYVEWTN NGKTELNYKNTEPVLDSDGSYFMYSKLRV EKKNWVERNSYSCSVVHEGLHNHHTTKSF SRTPGK (SEQ ID NO: 31) | DIQMTQSPASLSASLGETVT IECLASEDIYSNLAWYQQKP GKSPQLLIYDARSLQDGVPS RFSGSESGPQYSLEINSLQSE DAVTYFCQQHHAYPFTFGS GTKLEIKRADAAPTVSIFPPS SEQLTSGGASVVCFLNNFYP KDINVKWKIDGSERQNGVL NSWTDQDSKDSTYSMSSTL TLTKDEYERHNSYTCEATH KTSTSPIVKSFNRNEC (SEQ ID NO: 30) |
| 4A11 | QSLEESGGRLVTPGTPLTLTCTVSGFSLSSY TVNWVRQAPGKGLEWIGYISYGGSAYYAS WANGRFTISKTSATVDLKITSPTTEDTATY FCARHMQVGGAPTGSMAAFDPWGPGTLV TVSSGQPKAPSVFPLAPCCGDTPSSTVTLG CLVKGYLPEPVTVTWNSGTLTNGVRTFPS VRQSSGLYSLSSVVSVTSSSQPVTCNVAHP ATNTKVDKTVAPSTCSKPTCPPPELLGGPS VFIFPPKPKDTLMISRTPEVTCVVVDVSQD DPEVQFTWYINNEQVRTARPPLREQQFNST IRVVSTLPIAHQDWLRGKEFKCKVHNKAL PAPIEKTISKARGQPLEPKVYTMGPPREELS SRSVSLTCMINGFYPSDISVEWEKNGKAED NYKTTPAVLDSDGSYFLYNKLSVPTSEWQ RGDVFTCSVMHEALHNHYTQKSISRSPGK (SEQ ID NO: 33) | AAVLTQTPSPVSAAVGGTV SISCQSSQSVYNNNYLSWFQ QKPGQPPKLLIYGASTLTSG VPSRFKGSGSGTQFTLTISD VQCDDAATYYCAGGYSGS SDKYAFGGGTEVVVKGDP VAPTVLIFPPAADQVATGTV TIVCVANKYFPDVTVTWEV DGTTQTTGIENSKTPQNSAD CTYNLSSTLTLTSTQYNSHK EYTCKVTQGTTSVVQSFNR GDC (SEQ ID NO: 32) |

Example 2: Distinct Toxicity Profiles for Inhibition of TGFβ2 and TGFβ3 with Isoform-Selective Anti-TGFβ Monoclonal Antibodies Constitutive germline knockouts of TGFβ2 and TGFβ3 do not survive the perinatal period due to developmental defects including cleft palate in both and cardiovascular defects in TGFβ2 knockouts, and pan-TGFβ inhibitors have substantial toxicities as detailed above. To assess the potential toxicity of inhibiting TGFβ2, TGFβ3, or both, 4-week toxicology studies were conducted with 6F12, 2A10, and 4A11, as follows:

TGFb3 (2A10):

In the pilot toxicology study, 2A10 mAb was administered thrice weekly (TIW) for 4 weeks (12 total doses) to CD-1 mice at doses of 0 (control), 10 and 50 mg/kg I.P. TIW, and 50 mg/kg I.V. TIW in a vehicle consisting of phosphate buffered saline. Males and females (n=5/sex/group) were assigned to the toxicity groups at all dose levels and were scheduled for necropsy at the end of the dosing period (Day 29). Blood for toxicokinetic evaluation was collected from additional mice in the control (n=6 males/group) and 2A10 mAb treated groups (n=9 males/group). Criteria for evaluations included the following parameters: clinical observations, body weight, clinical pathology (hematology and clinical chemistry), anatomic pathology, and toxicokinetics.

The 2A10 AUC exposures increased approximately dose-proportionally with an increase in dose from 10 to 50 mg/kg.

All animals survived to scheduled necropsy, and there were no 2A10-related clinical observations, effects on body weight, or clinical pathology changes. Findings attributed to 2A10 were limited to physeal dysplasia seen in a subset of mice at the high dose (6 mice at 50 mg/kg). In conclusion, administration of 2A10 mAb to CD-1 mice at 10 and 50 mg/kg TIW for 4-weeks was well tolerated and 2A10-related finding were limited physeal dysplasia at the high dose.

TGFb2 (6F12):

In the pilot toxicology study, 6F12 mAb was administered thrice weekly (TIW) for 4 weeks (12 total doses) to CD-1 mice at doses of 0 (control), 10, and 50 mg/kg I.P. in a vehicle consisting of phosphate buffered saline. Males and females (n=5/sex/group) were assigned to the toxicity groups at all dose levels and were scheduled for necropsy at the end of the dosing period (Day 29). Blood for toxicokinetic evaluation was collected from additional mice in the 6F12 mAb treated groups (n=9 males/group). Criteria for evaluations included the following parameters: clinical observations, body weight, clinical pathology (hematology and clinical chemistry), anatomic pathology, and toxicokinetics.

The 6F12 AUC exposures increased approximately dose-proportionally with an increase in dose from 10 to 50 mg/kg.

All animals survived to scheduled necropsy at 10 mg/kg and there were no 6F12-related clinical observations at 10 and 50 mg/kg.

6F12-related findings at 10 and 50 mg/kg included minimal to mild increase in neutrophils and lymphocytes in females with histopathology correlate of peritoneal inflammation indicative of chronic inflammation, and increase in ALT and AST with no histopathology correlate. Additional 6F12-related findings at 50 mg/kg included early euthanasia of 3 mice in the toxicokinetic group due to more than 20% decrease in body weights (observed on Day 8), as well as minimal to mild increases in globulin with corresponding decrease in albumin to globulin ratio in both sexes. All mice in the toxicity groups survived to scheduled necropsy on Day 29, and no changes in body weight were observed.

In conclusion, administration of 6F12 mAb to CD-1 mice at 10 and 50 mg/kg TIW for 4-weeks findings consistent with chronic inflammation were observed at 10 and 50 mg/kg.

TGFb2/3 (4A11):

In the pilot toxicology study, 4A11 mAb was administered thrice weekly (TIW) for 4 weeks (12 total doses) to CD-1 mice at doses of 0 (control), 10 and 50 mg/kg I.P., and 50 mg/kg I.V. in a vehicle consisting of phosphate buffered saline. Males and females (n=5/sex/group) were assigned to the toxicity groups at all dose levels and were scheduled for necropsy at the end of the dosing period (Day 29). Blood for toxicokinetic evaluation was collected from additional mice in the control (n=6 males/group) and 4A11 mAb treated groups (n=9 males/group). Criteria for evaluations included the following parameters: clinical observations, body weight, clinical pathology (hematology and clinical chemistry), anatomic pathology, and toxicokinetics.

Key toxicology findings at 10 and 50 mg/kg included mortality in 3 mice (1 at 10 mg/kg and 2 at 50 mg/kg) and inguinal/scrotal hernias. Additional key findings at 50 mg/kg included clinical observation of hind limb loss of function pathology findings of perirectal serosal hemorrhage and hemoabdomen, periarteritis/arteritis and mural and interstitial hemorrhages in the cardiovascular (ascending aorta and myocardium) system, and degeneration and necrosis of the skeletal muscle.

In conclusion, administration of 4A11 mAb to CD-1 mice at 10 and 50 mg/kg TIW for 4-weeks led to mortality at 10 and 50 mg/kg and adverse pathology findings of hernias at all doses and in the cardiovascular system at 50 mg/kg.

The tox study findings are summarized in Table 8, below.

TABLE 8

Results of Toxicology Study

| Isoform Target (Clone) | Key Toxicology Findings |
|---|---|
| TGFβ2 (6F12) | 10 mg/kg<br>Peritoneal inflammation with corresponding clinical pathology changes (increased neutrophils and lymphocytes, increased globulin)<br>50 mg/kg<br>Peritoneal inflammation with corresponding clinical pathology changes (increased neutrophils and lymphocytes, increased globulin) |
| TGFβ3 (2A10) | 10 mg/kg<br>No tox findings<br>50 mg/kg<br>Physeal dysplasia (minor) |
| TGFβ2/3 (4A11) | 10 mg/kg<br>Mortality<br>Hernias - inguinal/scrotal<br>Physeal dysplasia (minor)<br>Hair follicle hyperplasia and dysplasia (minor)<br>50 mg/kg<br>Mortality<br>Hernias - inguinal/scrotal<br>Bleeding - perirectal serosal hemorrhage, hemoabdomen<br>Cardiovascular (ascending aorta and myocardium) - periarteritis/arteritis, mural and interstitial hemorrhages<br>Skeletal muscle - degeneration and necrosis<br>Hind limb loss of function |

Example 3: Murine PK Study with Anti-TGFβ Monoclonal Antibodies

Materials and Methods:

Fab regions of the anti-TGFβ antibodies were fused to the Fc region of mouse IgG2a with a LALA-PG mutation to attenuate effector function for in vivo mouse studies (see Lo, M. et al. Journal of Biological Chemistry 292, 3900-3908 (2017); Schlothauer, T. et al. Protein Engineering Design and Selection 29, 457-466 (2016)).

Figure 2A:
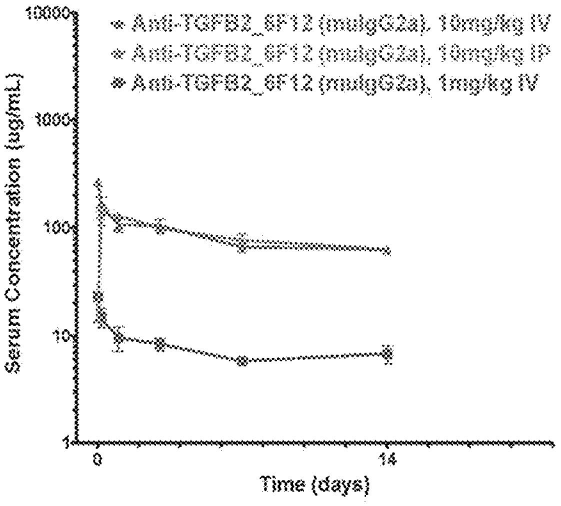
FIG. 2A shows the pharmacokinetic profile of 6F12 muIgG2a antibody given as a single 1 or 10 mg/kg I.V. and 10 mg/kg I.P. dose in C57BL6 mice (n=3 per timepoint).
Figure 2B:
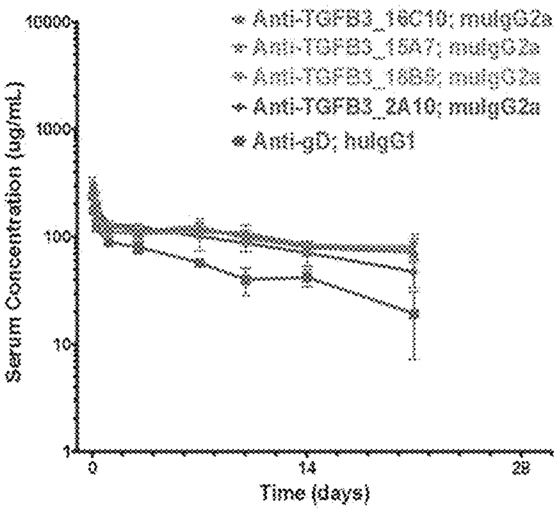
FIG. 2B shows the pharmacokinetic profile of 16C10 muIgG2a, 15A7 muIgG2a, 18B5 muIgG2a, 2A10 muIgG2a and non-binding anti-gD huIgG1 control antibody given as a single 10 mg/kg I.V. dose in C57BL6 mice (n=3 per timepoint).
Figure 2C:
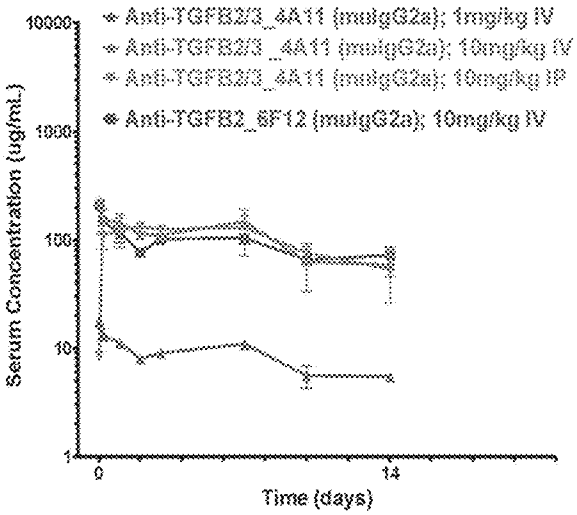
FIG. 2C shows the pharmacokinetic profile of 4A11 muIgG2a given as a single 1 or 10 mg/kg I.V. and 10 mg/kg I.P. dose, and 6F12 muIgG2a antibody given as a single 10 mg/kg I.V. dose in C57BL6 mice (n=3 per timepoint).

Results:

The Fab regions of the anti-TGFβ antibodies were fused to the Fc region of mouse IgG2a with a LALA-PG mutation to attenuate effector function for in vivo mouse studies. In C57/B6 mouse single-dose pharmacokinetic studies, these chimeric antibodies exhibited linear pharmacokinetics with dose dependent accumulation and no evidence of anti-drug antibody formation. The antibodies with the greatest in vitro potency (6F12 (anti-TGFβ2); 2A10 (anti-TGFβ3); and 4A11 (dual-specificity anti-TGFβ2/3) all exhibited in vivo bioavailability of ~95% and clearance of approximately 4 mL/day/kg, whereas 16C10, a slightly less potent anti-TGFβ3 antibody, exhibited clearance of approximately 2 mL/day/kg (FIG. 2).

Example 4: TGFβ2 and TGFβ3 Expression Levels are Elevated in Human Fibrotic Tissue and TGFβ3 Expression is Highly Correlated with TGFβR Signaling in IPF and SSc Materials and Methods:

Tissue Isolation (IPF) and RNA Analyses

RNA analyses of human tissues were described previously (Depianto, D J, et. al. *Thorax.* 2015 January; 70(1): 48-56; Chandriani, S, et. al. *J Immunol.* 2014 Jul. 1; 193 (1):111-9). Briefly, human tissues were obtained in the University of California, San Francisco Lung Center from patients with IPF at the time of biopsy or lung transplantation. Non-diseased normal lung tissues were procured from lungs not used by the Northern California Transplant Donor Network. RNA was isolated from the snap-frozen lung samples. Microarray analysis was done by following manufacturer's recommendations (Agilent, Santa Clara, Calif.).

Derivation of a SSc Skin-Relevant TGFβ-Gene Set and Signature Score:

TGFβ-responsive genes were identified by performing RNA Sequencing on primary human lung fibroblasts stimulated with 5 ng/ml of human TGFβ1 (RnD systems) or control media for 24 hours. Sequencing data was processed using the R programming language and packages from the Bioconductor project (see World Wide Web at bioconductor.org) to express it at gene level as normalized reads per kilobase per million reads (nRPKM). A pilot SSc and normal control skin biopsy microarray dataset (GSE58095) was downloaded from NCBI Gene Expression Omnibus. To identify the set of genes that is upregulated in SSc skin and potentially attributable to TGFβ activity in fibroblasts, a 4-way comparison was made, contrasting the genes significantly dysregulated in vitro (≥4 fold increase by TGFβ) and in SSc vs HC (≥50% increase in disease). This candidate gene set is shown in FIG. 5B. The gene set was evaluated in the microarray data set from FaSScinate skin biopsies (see, Khanna et al. (2016) *The Lancet*; vol. 387:10038, p. 2630-2640 for description of the FaSSCinate study), and pruned to a core signature set of 18 genes as shown in Table 2, above, such that all genes contributed homogeneously to the first principal component (>0.7 for PC1 loading). A composite gene expression score was defined for this gene set, using the first principal component loading, to reduce the aggregate expression of the 18-gene signature to a single continuous variable for each subject.

ScRNAseq

Preparation of Human Lung Tissue:

Explanted lung tissues were obtained from patients with a pathologic diagnosis of usual interstitial pneumonia and a consensus clinical diagnosis of IPF assigned by multidisciplinary discussion and review of clinical materials. After bronchoalveolar lavage, fresh lung explant tissue was stored in complete media on wet ice overnight. The tissue was washed in HBSS and then thoroughly minced in digestion buffer (HBSS, 2.5 mg/mL Collagenase D, 100 μg/mL DNase). Minced tissue was rocked 45 minutes at 37° C. Residual tissue material was transferred into fresh digestion buffer and rocked another 45 minutes at 37° C. Single cells from both rounds of digest were combined and utilized for downstream analyses. Remaining tissue was processed using a gentleMACS Dissociator (Miltenyi Biotec) to liberate additional cells into a single cell suspension. This preparation was then filtered and added to the previously isolated cells.

FACS Isolation of Cell Populations:

Total number of cells were determined and resuspended in appropriate volume of 1×PBS supplemented with 2 mM EDTA and 2% fetal bovine serum (FBS). FcR blocking was performed using the Miltenyi Biotec FcR blocking reagent according to manufacturer's protocol. Cells were then stained with a cocktail of antibodies including CD45-BUV395, EPCAM-PE, CD31-BV605, and Live/Dead-Efluor 780 on ice for 30 minutes and then washed with supplemented PBS buffer 3 times. 5 populations of cells were collected for downstream scRNA-seq: Unsorted live cells, $CD45^+$, $CD45^-/EPCAM^+$, $CD45^-/CD31^+$, and $CD45^-/CD31^-/EPCAM^-$ (triple negative).

Single-Cell RNA-seg:

Single-cell RNA-seq was performed on the 10× Genomics platform using Chromium Single Cell 3' Library and Gel bead kit v2 following manufacturer's user guide (10× Genomics). The cell density was used to impute the volume of single cell suspension needed in the reverse transcription (RT) master mix, aiming to achieve ~6,000 cells per sample. cDNAs and libraries were prepared following manufacturer's user guide (10× Genomics). Libraries were profiled by Bioanalyzer High Sensitivity DNA kit (Agilent Technologies) and quantified using Kapa Library Quantification Kit (Kapa Biosystems). Each library was sequenced in one lane of HiSeq4000 (Illumina) following manufacturer's sequencing specification (10× Genomics).

Processing of Sequencing Data:

Cell Ranger v2.1.0 (10× Genomics, Pleasanton Calif.) was used to align raw sequencing reads against the GRCh38 human reference, count gene features, filter empty droplets, cluster cells, and identify cluster marker genes. Visualization of the tSNE results from Cell Ranger was performed using the Loupe Cell Browser v3.1 (10× Genomics, Pleasanton Calif.).

Immunohistochemistry for pSMAD3 and In Situ Hybridization for TGFβt3

Immunohistochemistry for phoshpho-SMAD3 was performed on formalin-fixed, paraffin-embedded sections using a rabbit monoclonal antibody (EP823Y, 0.76 pg/ml; Abcam). Briefly, sections were depariffinized and used for immunohistochemistry on an automated staining platform (Bond RX; Leica Biosystems) using proprietary reagents for antigen retrieval (ER2; Leica Biosystems), detection of bound primary antibody (anti-rabbit PowerVision polymer-HR; Leica Biosystems). Signal was visualized using DAB.

Quantification of Serum Periostin and COMP Levels

Whole blood was collected from the patients and from 25 age- and gender-matched healthy controls through standard venipuncture technique in serum separator tubes, was allowed to clot for 30 minutes, and was spun down at 4° C. for 10 minutes. Serum was collected and stored at −70° C. until analyzed. Cartilage oligomeric matrix protein (COMP) levels were determined using IMPACT-based specific immunoassays (Roche Diagnostics, Penzberg, Germany). In brief, samples were incubated with an IMPACT chip coated with biotinylated COMP F(ab')2 antibody fragments. After wash steps, biomarker-specific detection antibodies labelled with digoxigenin were added and incubated. After washing, fluorescence anti-digoxigenin-latex conjugate was added, and the specifically bound fluorescence label was detected with a charge-coupled detector camera. Emitted fluorescence was transformed into signal intensities using a standard curve composed of recombinant protein standards (R&D Systems, Minneapolis, Minn., USA) and dedicated software (Roche Diagnostics). Sensitivity was 0.25 ng/mL for COMP. Periostin serum levels were determined using the clinical trial version of the Elecsys (Roche Diagnostics) periostin immunoassay intended for use on the cobas e601 (Roche Diagnostics).

Figure 3A:
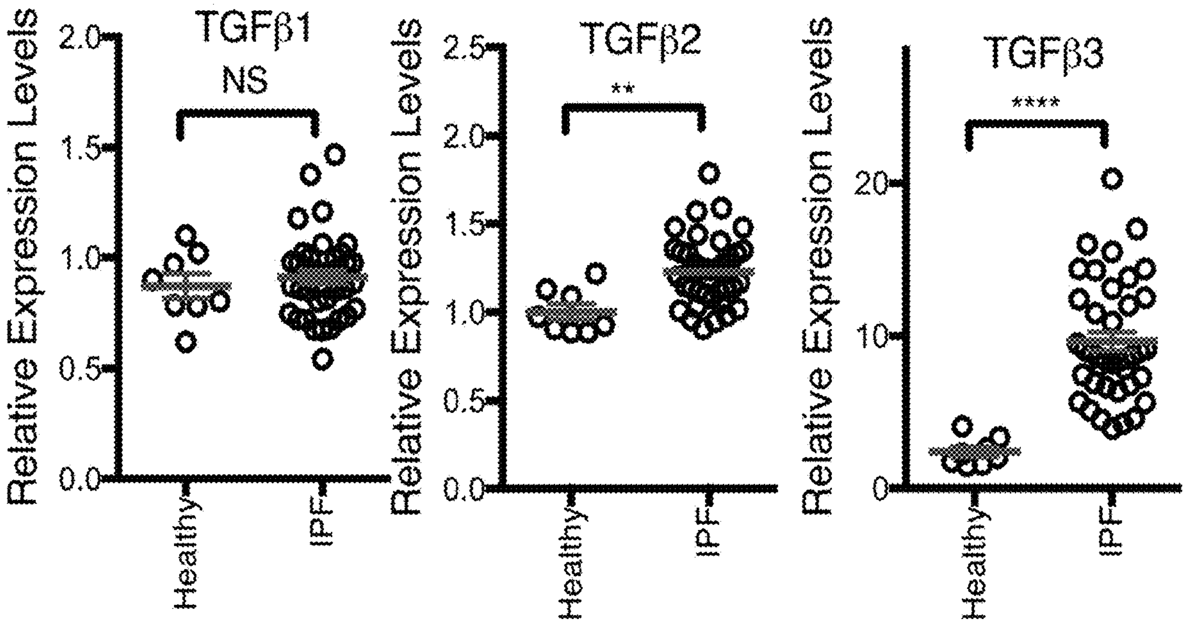
FIG. 3A is a graph showing expression levels determined from microarray analysis of TGFβ isoforms in bulk lung biopsy tissue from control (n=8) and IPF (n=40) lungs. The data show elevated expression of TGFβ2 and TGFβ3 but not TGFβ1 in IPF. P<0.01; ** P<0.0001 (unpaired two-tailed Student's t-tests).
Figure 3B:
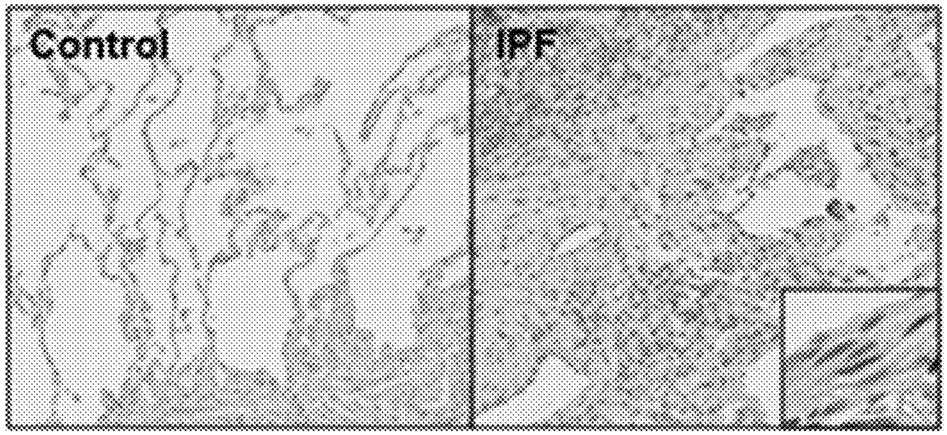
FIG. 3B is an image of pSMAD2/3 immunohistochemistry (IHC) of control and IPF lung tissue showing increased nuclear pSMAD staining in fibroblastic foci of IPF lung tissue.

Results:

In qPCR analysis of bulk lung biopsy samples from patients with idiopathic pulmonary fibrosis (IPF), TGFβ3, and to a lesser extent, TGFβ2, were expressed at significantly higher levels compared to control lungs, whereas TGFβ1 expression was slightly lower on average in IPF compared to control (FIG. 3A). Immunohistochemistry analysis revealed abundant increases in nuclear phospho-SMAD2/3 staining in IPF tissue as compared to control, particularly in fibroblastic foci, regions of activated fibroblasts and myofibroblasts that are pathognomonic for a histological diagnosis of Usual Interstitial Pneumonia (UIP), the hallmark of IPF (FIG. 3B). As differences in gene expression in bulk IPF lung tissue may reflect cytological composition of the sample, it was next sought to characterize the cellular provenance of TGFβ isoforms on a single cell basis using single cell RNA sequencing (scRNAseq). Global gene expression patterns of scRNAseq data from IPF lungs distinguished multiple cell lineages including hematopoietic (macrophages, lymphocytes, plasmablasts, mast cells), epithelial (AEC2 and basal, ciliated, and secretory bronchial epithelial cells), mesenchymal (fibroblasts, myofibroblasts, smooth muscle), and vascular (endothelial) cell types.

Figure 4A:
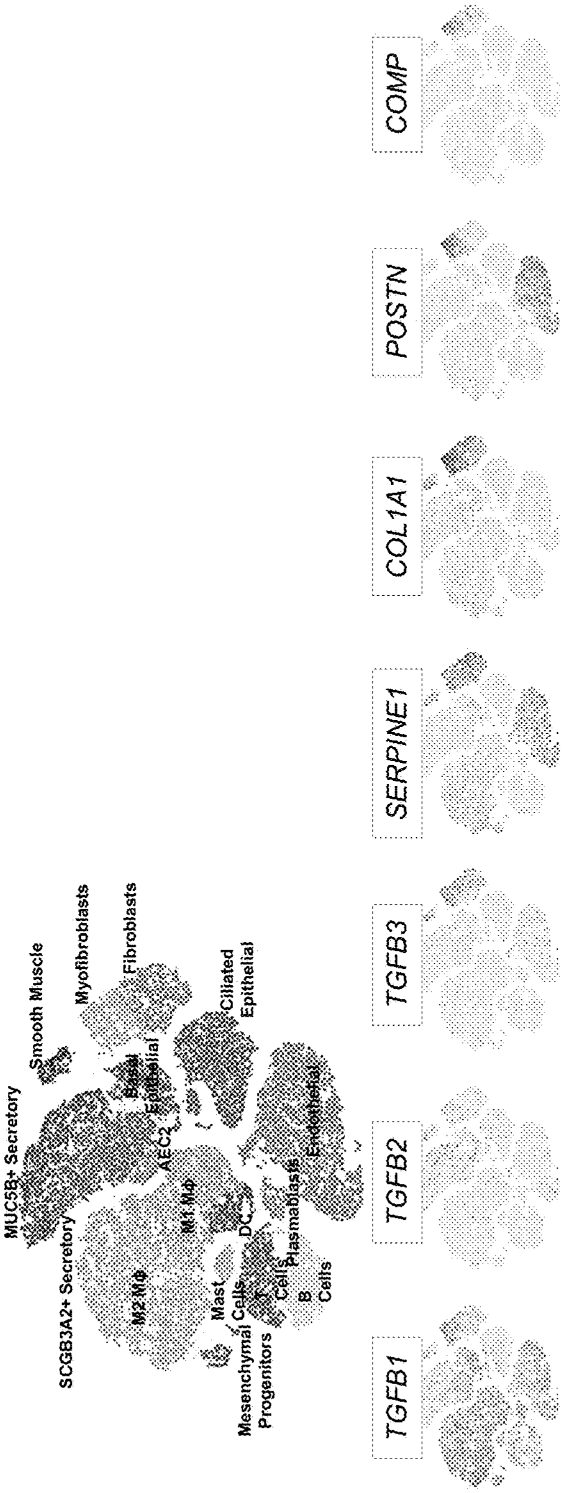
FIG. 4A is a t-SNE plot representing single cell RNAseq of IPF lungs (n=3, combined), showing representation of multiple epithelial, mesenchymal, and hematopoietic cell lineages as labeled. Expression of individual TGFβ isoforms showed broad expression of TGFβ1, predominantly in hematopoietic and endothelial cells; TGFβ2 expression predominantly in epithelial cells; and TGFβ3 predominantly in mesenchymal cells. Expression of TGFβ target genes showed strong overlap of SERPINE1, COL1A1, POSTN, and COMP with TGFβ3 expression in fibroblasts and myofibroblasts. SERPINE1 also overlaps with TGFβ1 expression in endothelial cells and macrophages, and POSTN in endothelial cells.
Figure 4B:
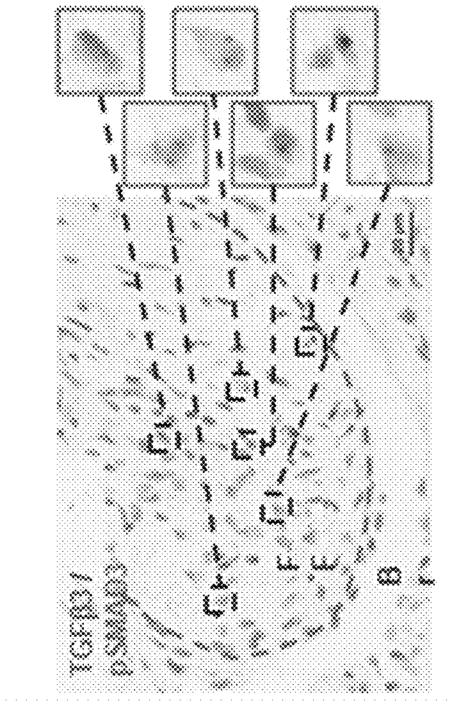
FIG. 4B is an image of dual IHC for pSMAD3 and in situ hybridization (ISH) for TGFβ3 showing colocalization of TGFβ3 mRNA and nuclear pSMAD3 in multiple cells in a fibroblastic focus in IPF lung tissue.

TGFβ1 was broadly expressed, with highest levels in hematopoietic cells, endothelial cells, and myofibroblasts. TGFβ2 was more restricted and primarily detected in epithelial derived cells. TGFβ3 expression was highly restricted to mesenchymal cells (fibroblasts, myofibroblasts, and smooth muscle cells). Expression of TGFβR-dependent target genes revealed distinct patterns, with SERPINE1 expressed in fibroblasts, macrophages, and endothelial cells, periostin (POSTN) in myofibroblasts and endothelial cells, and COL1A1 and COMP in myofibroblasts, largely overlapping with TGFβ3 (FIG. 4A). Dual immunohistochemistry for pSMAD3 and in situ hybridization for TGFβ3 revealed numerous myofibroblasts in fibroblastic foci co-expressing TGFβ3 and nuclear pSMAD3 (FIG. 4B), suggesting that in UIP lesions, TGFβ3 may be driving TGFβR-dependent signaling in an autocrine or paracrine fashion.

Figure 5A:
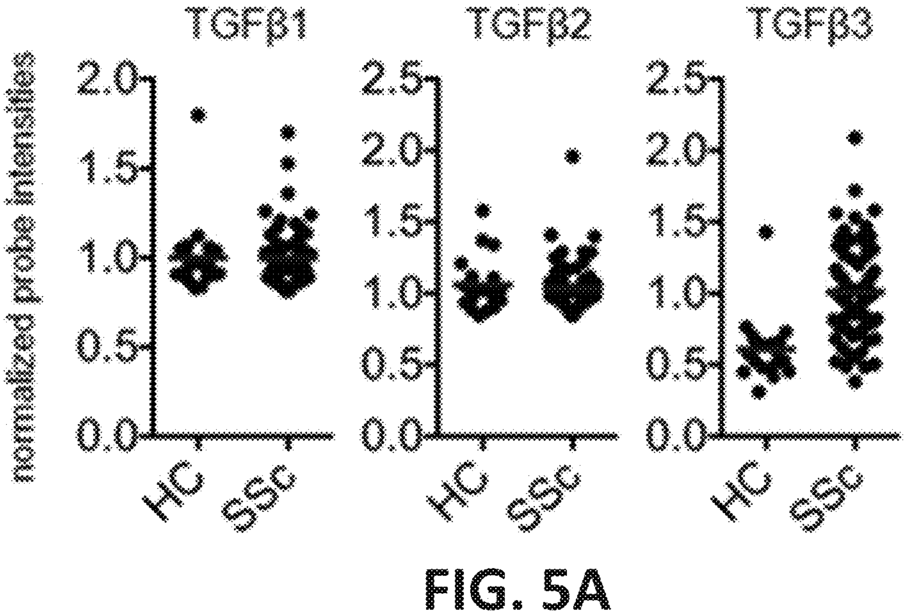
FIG. 5A contains plots showing expression of TGFβ isoforms as determined from microarray analysis of skin biopsies taken from healthy controls (HC) and patients with systemic sclerosis (SSc) at baseline enrolled in the FaSScinate trial.
Figure 5B:
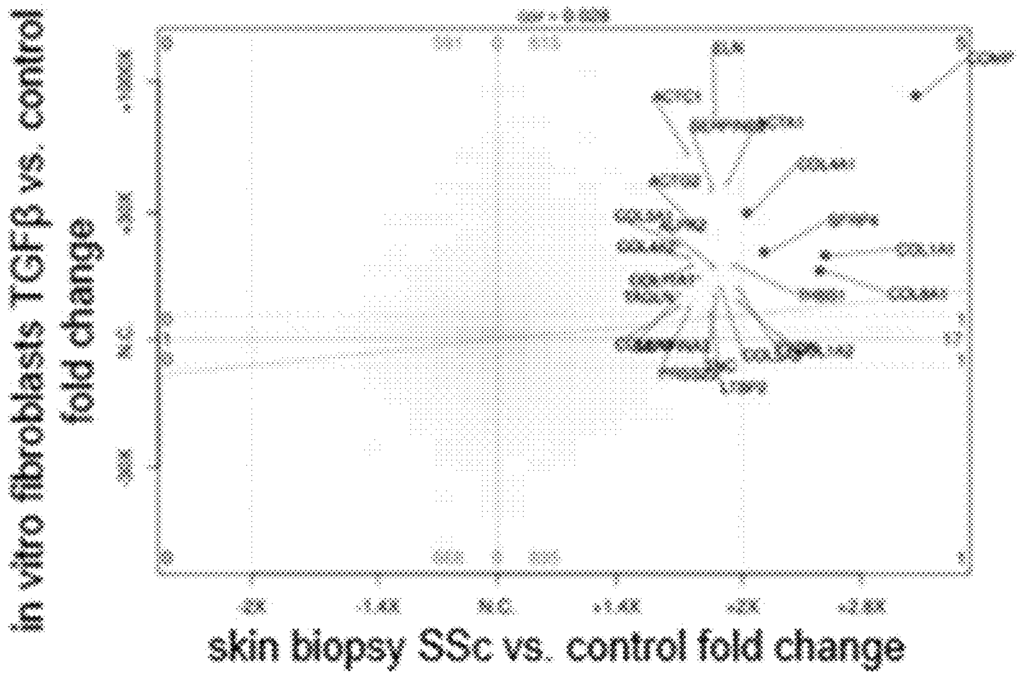
FIG. 5B shows the TGFβR signal dependent skin gene expression signature derived by comparing genes induced in fibroblasts treated in vitro with recombinant TGFβ1 receptor-binding domain and genes significantly upregulated in SSc vs. control skin biopsy. Genes that were significantly elevated in both conditions were selected as a candidate TGFβ signature in SSc skin.

In skin biopsies taken at baseline in the FaSScinate trial, TGFβ3 expression is markedly upregulated in SSc patients as compared to healthy controls, whereas TGFβ1 and TGFβ2 levels are comparable (FIG. 5A). To assess the potential contribution of TGFβ signaling to differentially expressed genes in SSc skin, a gene set was derived that is both attributable to fibroblasts responding to TGFβ signaling and dysregulated in SSc skin. Given the striking heterogeneity in gene expression profiles known to exist in skin biopsies from SSc patients, it was hypothesized that at any given time, only a subset of the SSc cohort would manifest a high TGFβ activity profile.

Using the 18-gene TGFβ signature, a k-means clustering of SSc patients was performed and two clusters were identified—a "TGFβ-high" cluster that displays higher expression levels for many of the members of the gene set a "TGFβ-low" cluster, in which most of the members of the gene set registered a lower expression value.

Figures 6A, 6B, 6C:
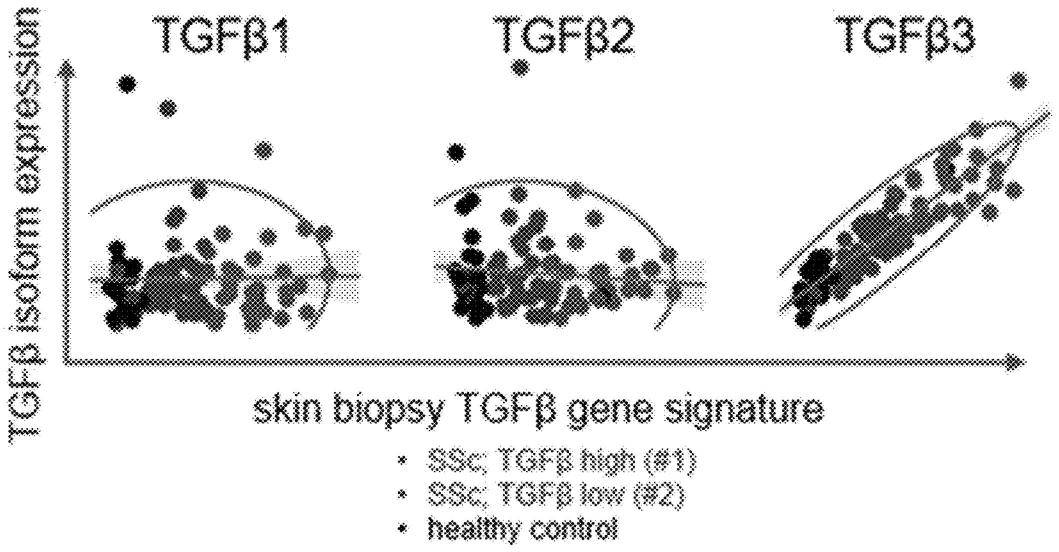
FIG. 6A is a plot showing principal component 1 of the signature defined in FIG. 5B, derived as a continuous variable for magnitude of TGFβR-dependent gene expression across all signature genes in the SSc skin biopsies and compared to TGFβ isoform expression levels in those biopsies. Both "TGFβ-high" and "TGFβ-low" SSc patients had higher levels of this gene signature than healthy controls, and the skin biopsy TGFβ gene signature was highly correlated with TGFβ3, but not TGFβ1 or TGFβ2 expression.
FIG. 6B is a table showing intercorrelations between TGFβ-inducible skin gene signature metric as determined in FIG. 4C and skin gene expression levels of TGFβ isoforms, POSTN, and COMP; and intercorrelations with serum levels of POSTN and COMP proteins in the FaSScinate study.
FIG. 6C is a table summarizing correlation of serum periostin and COMP levels with the Modified Rodnan Skin Score (MRSS), a clinical index of systemic skin fibrosis used in the FaSScinate study.

TGFβ3 expression correlated strongly and positively with the TGFβ-inducible signature (Spearman rho=0.92, $p<0.0001$), while the other two TGFβ isoforms did not correlate with the score (FIG. 6A and FIG. 6B).

The TGFβ-inducible skin gene signature was also highly correlated with the expression levels of two genes encoding soluble secreted ECM components, POSTN and COMP. POSTN and COMP, the proteins encoded by these genes, are detectable in peripheral blood serum as soluble biomarkers and their levels correlated remarkably well with the skin biopsy TGFβ gene signature in contemporaneously collected blood samples (FIG. 6B). Furthermore, serum periostin and COMP levels were significantly correlated with the Modified Rodnan Skin Score (MRSS), a clinical index of systemic skin fibrosis used in SSc trials (FIG. 6C). To assess the relationship between skin TGFβ activity and disease progression, the change in MRSS over the 48-week course of the study was evaluated and it was found that TGFβ signature "high" patients were less likely to improve compared to TGFβ signature "low" patients regardless of treatment assignment (there was no significant benefit of tocilizumab vs. placebo on the MRSS outcome measure in the study; FIG. 7). Taken together, these data suggest that TGFβ3 expression and signaling activity in an isolated skin biopsy reflect overall disease burden and prognosis in SSc. Thus, these data support TGFβ3 inhibition as a target for the treatment of IPF and SSc, as well as the use of serum periostin and COMP protein levels or tissue TGFβ signature gene expression levels as biomarkers of TGFβ3 activity.

Example 5: In Vivo Activity of Isoform-Selective Anti-TGFβ2 and TGFβ3 Antibodies in a Lung Fibrosis Model Materials and Methods:

Bleomycin Instillation

For the bleomycin study, adult mice (>12 weeks) were randomized based on their weights before the study to minimize variance between experimental and control groups. For intratracheal (I.T.) dosing, all mice were lightly anesthetized with isoflurane in an induction chamber. Once anesthetized, the animals were removed from the chamber, manually restrained, the mouth of the animal was opened and the tongue set aside. A 1 ml syringe with 50 microliters of sterile injectable isotonic saline or bleomycin (0.70 U/kg (DNC #0703-3155-01; TEVA) in 50 μl sterile isotonic saline) was connected to a 24 gauge gavage needle. The gavage needle was inserted into the trachea and a dose of either vehicle or bleomycin was delivered intratracheally. After delivery, animals were monitored continuously until fully awake and ambulatory.

For profibrotic gene expression analysis, animals were taken down 14 days post bleomycin delivery. RNA was harvested from whole mouse lungs and the gene expression was determined by RT-qPCR.

To measure the collagen deposition in the lung, mice were taken down 24 days after bleomycin administration. Deuterated water labeling was used to assess the new collagen synthesis in studies (Blaauboer M E, et. al. *Matrix Biol.* 2013; 32(7-8):424-31.). In our studies, the labeling was started at 9th day after bleomycin delivery, by I.P. injecting deuterated water (Cat #DLM-4-99.8-1000; Cambridge Isotope Laboratories) 35 ml/kg in 2 divided doses 4 hours apart. Afterward, 8% deuterated water in drinking water was provided ad lib in a water bottle until the end of the study.

Deuterated water incorporation into hydroxyproline was analyzed as described previously (Gardner J L, et. al. *Am J Physiol Gastrointest Liver Physiol.* 2007; 292(6):G1695-705). Mass spectrometry and analysis were performed by Metabolic Solutions. New hydroxyproline content was expressed as "g per lung".

Gene Expression

Gene expression analyses in the bleomycin induced mouse lung fibrosis model were done by analyzing a published data set, which can be accessed through GEO Series accession number GSE37635 (see World Wide Web @ncbi.nlm.nih.gov/geo/query/acc.cgi?acc=GSE37635) (see, also, Blaauboer, 2013, *Matrix Biol* 32, 424-431).

RNA Sequencing

To perform the RNAseq study on different lung cell populations in a mouse bleomycin model, mouse whole lungs were harvested at day 14 after bleomycin administration. There were 5 mice in the saline control group, and 8 mice in the bleomycin group. Single cells were isolated after the protease digestion by following our previously published protocol (Sun T, et al., 2019, JCI Insight; June 18; 5(14): e128674). After washing, cells were blocked by purified rat anti-mouse CD16/CD32 antibody (Cat #553142; BD Biosciences) and stained with antibodies for CD45 (Cat #17-0451-82, eBioscience), EpCAM (Cat #11-5791-82, eBioscience), and CD31 (Cat #25-0311-82, eBioscience). Four cell populations from each mouse were sorted based on their cell surface markers: leukocytes ($CD45^+$; $EpCAM^-$); epithelial cells ($CD45^-$, $EpCAM^+$); endothelial cells ($CD45^-$; $EpCAM^-$; $CD31^+$) and fibroblasts (triple negatives). RNA was purified from the sorted cells using the RNeasy Mini Kit (Cat #74106; Qiagen). 0.5 μg of total RNA was used as an input material for library preparation using TruSeq RNA Sample Preparation Kit v2 (Illumina, San Diego Calif.), which was quality controlled with Fragment Analyzer and a Library quantification kit (KAPA Biosystems, Wilmington Mass.). The libraries were multiplexed and then sequenced on Illumina HiSeq2500 to generate 30M of single end 50 base pair reads. Sequencing reads were mapped to the reference mouse genome (GRCm38), using the GSNAP short read aligner (Wu and Nacu, 2010), and assigned to RefSeq gene models. Expression was measured in normalized reads per kilobase per million total reads (nRPKM).

Conditional Knockouts

Two targeting constructs were targeting the exon 6s in Tgfb2 or Tgfb3 locus respectively. Adeno-FLP was used to treat positive ES clones to remove the PGK neomycin selection marker at the ES cell stage. Two loxP sites were created to flank the exon 6 in the TGFβ2 or P3 loci in their respective cKO mice.

qPCR

Lung genomic DNAs were isolated from tamoxifen treated mice and evaluated by quantitative PCR (vs. Tert). Exon 3 is located outside of the floxed locus and was used as the experimental control.

Results:

Intratracheal (IT.) bleomycin challenge is a frequently used in vivo rodent model of lung fibrosis. Bleomycin selectively injures alveolar epithelial cells, triggering an innate immune response followed by fibroblast differentiation into myofibroblasts and ECM deposition. Unlike a chronic, progressive condition such as IPF, the bleomycin model has specific phases: injury, inflammation, fibrosis, and, in young animals, resolution. To determine whether TGFβ isoform expression was relevant in this model and during which phases, lung gene expression in mice was assessed at various time points after i.t. bleomycin instillation.

Figure 8A:
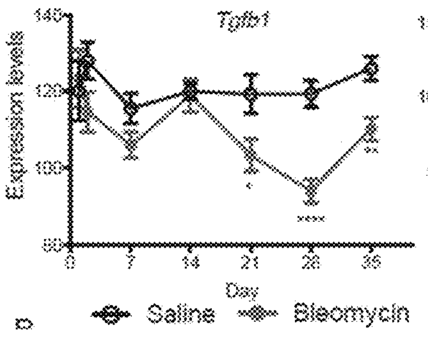
FIGS. 8A-F show expression derived from microarray at the indicated times after i.t. bleomycin installation of TGFβ1 (FIG. 8A), TGFβ2 (FIG. 8B), TGFβ3 (FIG. 8C), COL1A1 (FIG. 8D), Serpine1 (FIG. 8E), and Fn1 (FIG. 8F). Expression of TGFβ2, TGFβ3, COL1A1, Serpine1 and Fn1 followed similar kinetics, peaking between day 7-14 after bleomycin. *, P<0.05; , P<0.01; *, P<$10^{-3}$; **** P<104 by unpaired two-tailed Student's t-test. Data represent means±SEM.
Figure 8B:
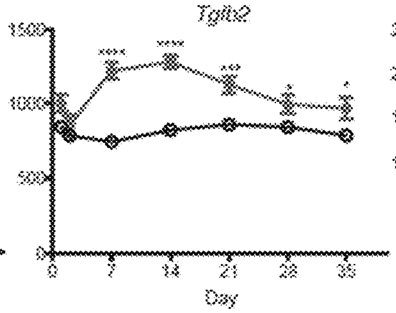
Figure 8C:
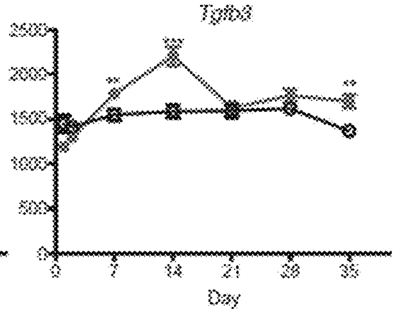
Figure 8D:
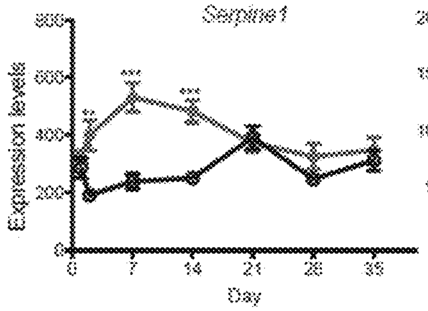
Figure 8E:
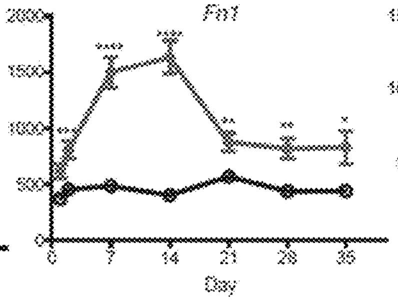
Figure 8F:
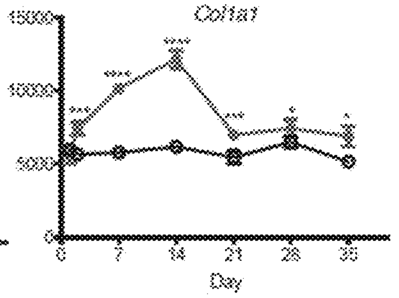

To assess the kinetics of TGFβ isoform expression in this model, lung gene expression was assessed in mice at various timepoints after i.t. bleomycin instillation based on a published transcriptomic dataset (Blaauboer, supra). While Tgfb1 expression was not substantially elevated in bleomycin-challenged mice at any time point, and was in fact slightly decreased at days 21 and 28, Tgfb2 and Tgfb3 expression were substantially increased after bleomycin installation at day 7 and day 14 after challenge (FIG. 8A, FIG. 8B, FIG. 8C). This pattern overlapped well with the induction of genes associated with fibrogenesis and TGFβ signaling, such as Serpine1, Fn1, and Col1a1 (FIG. 8D, FIG. 8E, FIG. 8F).

The significant upregulation of Tgfb2 and Tgfb3 during the fibrotic phase of the model concurred with expression pattern observed in IPF lung (FIG. 3A). To further characterize the specific cell types responsible for the expression of each TGFβ isoform in this model, RNAseq was performed on sorted lung cell populations day 14 after bleomycin administration when multiple fibrosis-associated genes peaked. Consistent with scRNAseq data from human IPF lung tissue (FIG. 4A), leukocytes ($CD45^+$) had the highest Tgfb1 expression levels. Tgfb2 and Tgfb3 were predominantly expressed in fibroblasts ($CD45^-$, $EpCAM^-$ $CD31^-$); Tgfb2 was also induced in epithelial cells and TGFβR-inducible genes Col1a1 and Serpine1 were induced mainly in fibroblasts after bleomycin treatment. While substantial upregulation of Tgfb3 was not observed in any individual cell populations after bleomycin treatment, the significant upregulation in Tgfb3 in bulk lung tissue (FIG. 8A, FIG. 8B, FIG. 8C) was attributed to increased proportions of Tgfb3-expressing fibroblasts at those timepoints.

As constitutive deletion of Tgfb2 or Tgfb3 results in embryonic or perinatal lethality, inducible knockouts of these genes were generated to investigate their roles in bleomycin-induced lung fibrosis in adult animals, by introducing loxP sites in Tgfb2 ($Tgfb2^{fl/fl}$) and Tgfb3 ($Tgb3^{fl/fl}$), respectively. $Tgfb2^{fl/fl}$, $Tgfb3^{fl/fl}$, and $Tgfb2^{fl/fl}$/$Tgfb3^{fl/fl}$ were crossed to ROSA-$CreER^{T2}$, and 12-16 week old mice were dosed with tamoxifen to delete the respective TGFβ alleles (single conditional KO mice will be referred to as TGFβ2.cKO and TGFβ3.cKO, and double targeted mice will be referred to as TGFβ2/3.cDKO). No gross abnormalities or morbidities were observed in cKO animals up to 6 weeks after tamoxifen treatment. To assess the roles of TGFβ2 and TGFβ3 in lung fibrosis, adult cKO animals were treated with tamoxifen starting 2 weeks before bleomycin administration. From days 9-24 after bleomycin administration, deuterated drinking water was administered to enable determination of new collagen synthesis in whole lungs by measuring deuterated hydroxyproline. In both TGFβ2.cKO and TGFβ3.cKO mice, new collagen synthesis was significantly reduced, as well as in TGFβ2/3.cDKO mice, suggesting that both TGFβ2 and TGFβ3 contribute to fibrogenesis in this model (FIG. 52A and FIG. 52B).

Figure 9A:
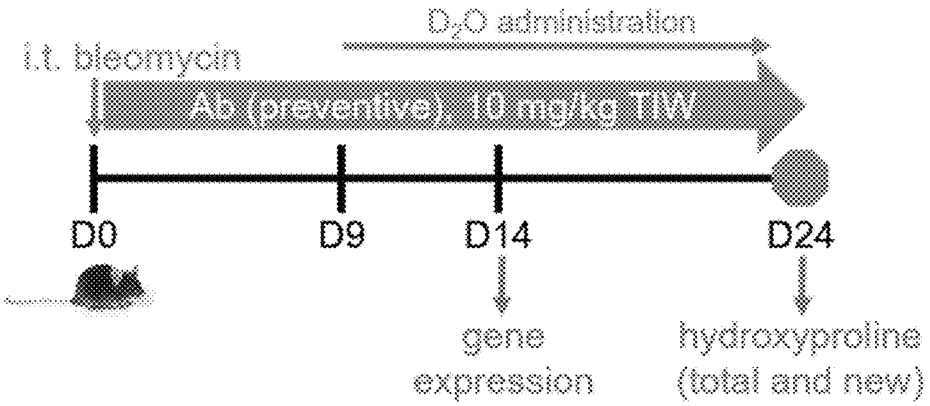
FIG. 9A is a schematic for in vivo I.T. bleomycin experiments to assess efficacy of TGFβ antibodies. Separate cohorts of animals were sacrificed at day 14 or day 24 to assess lung gene expression during peak TGFβ2/3 expression or lung collagen toward the end of the 'fibrotic' stage, respectively. Deuterated drinking water was provided to animals from day 9-23 to assess the fraction of new collagen production during that interval (deuterated hydroxyproline).

The significant upregulation of TGFβ2 and TGFβ3 during the "fibrotic" phase of the model mirrored the isoform distribution that was observed in IPF lung. Therefore, TGFβR-induced target gene expression at day 14 and collagen accumulation at day 24 were prioritized as key readouts in the context of preventive treatment with anti-TGFβ antibodies over the course of the study to assess their in vivo activity and potency (schematic, FIG. 9A).

Figure 9B:
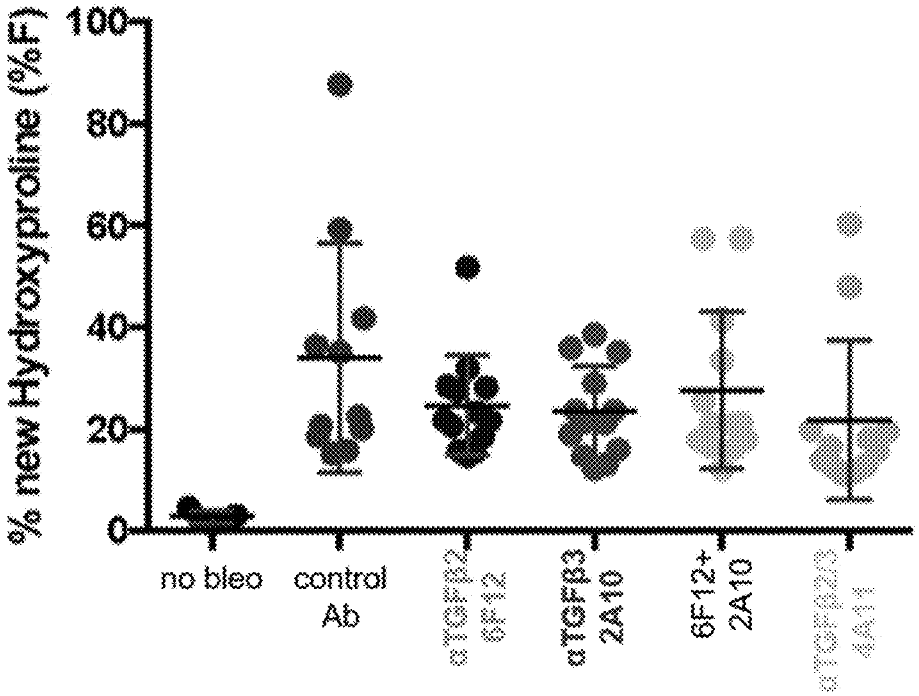
FIG. 9B is a plot showing reduced levels of the fraction of lung deuterated to total hydroxyproline at day 24 with preventive administration of anti-TGFβ2 and/or TGFβ3 antibodies (10 mpk, TIW). Each dot represents an individual animal.
Figure 9C:
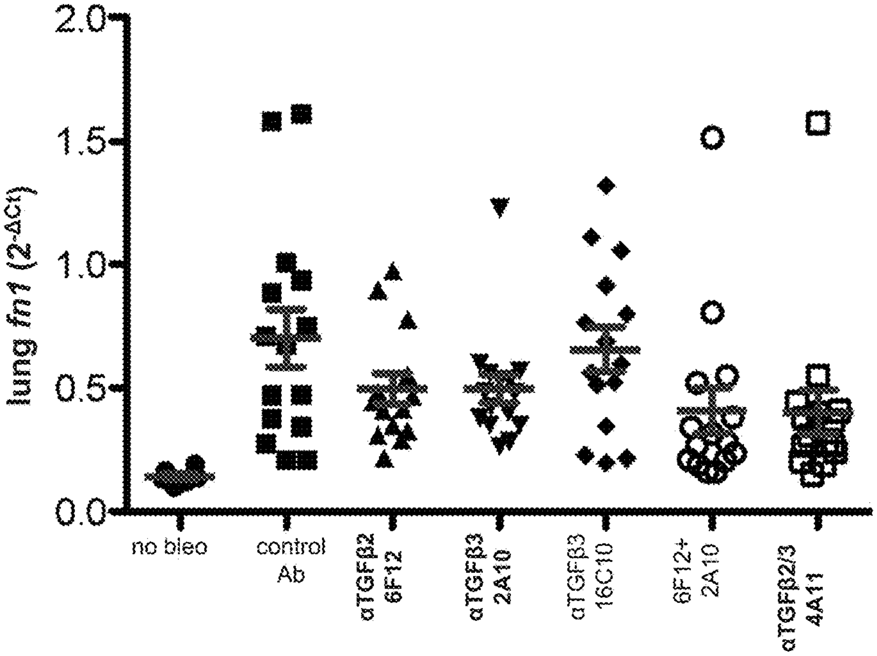
FIG. 9C is a plot showing reduced levels of lung gene expression of FN1 at day 14 after i.t. bleomycin instillation with preventive administration of anti-TGFβ2 and/or TGFβ3 antibodies (10 mpk, TIW). P<0.01; * P<0.001; ****P<0.0001 (One-way ANOVA with Dunnett's test).
Figure 9D:
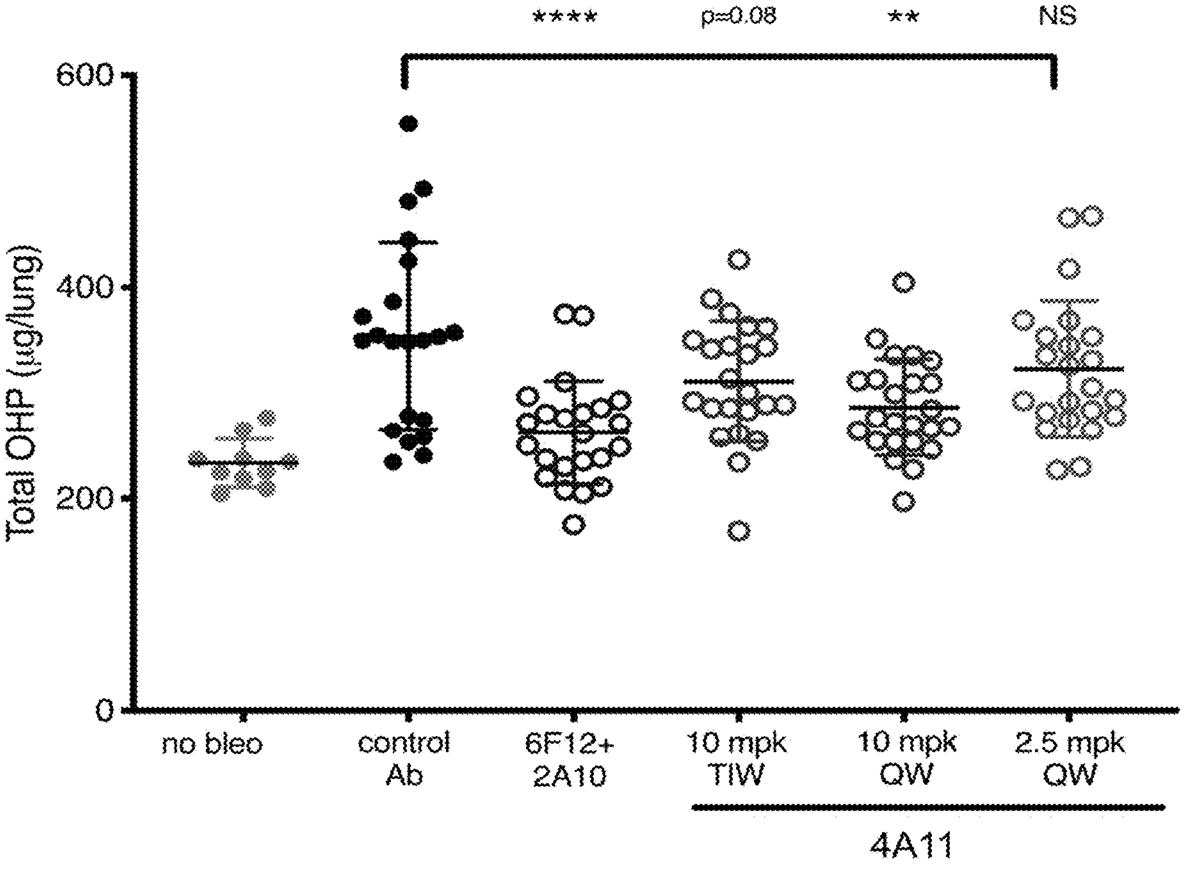
FIG. 9D and FIG. 9E are plots showing the effect of co-administration of 6F12 and 2A10 (10 mpk, TIW) or 4A11 at 10 mpk TIW, 10 mpk QW, or 2.5 mpk QW on total (FIG. 9D) and deuterated (FIG. 9E) hydroxyproline at day 24 after i.t. bleomycin. Similar reductions observed for 10 mpk of 4A11 QW vs. TIW, but decreased effect at 2.5 mpk QW. P<0.01; * P<0.001; ****P<0.0001 (One-way ANOVA with Dunnett's test).
Figure 9E:
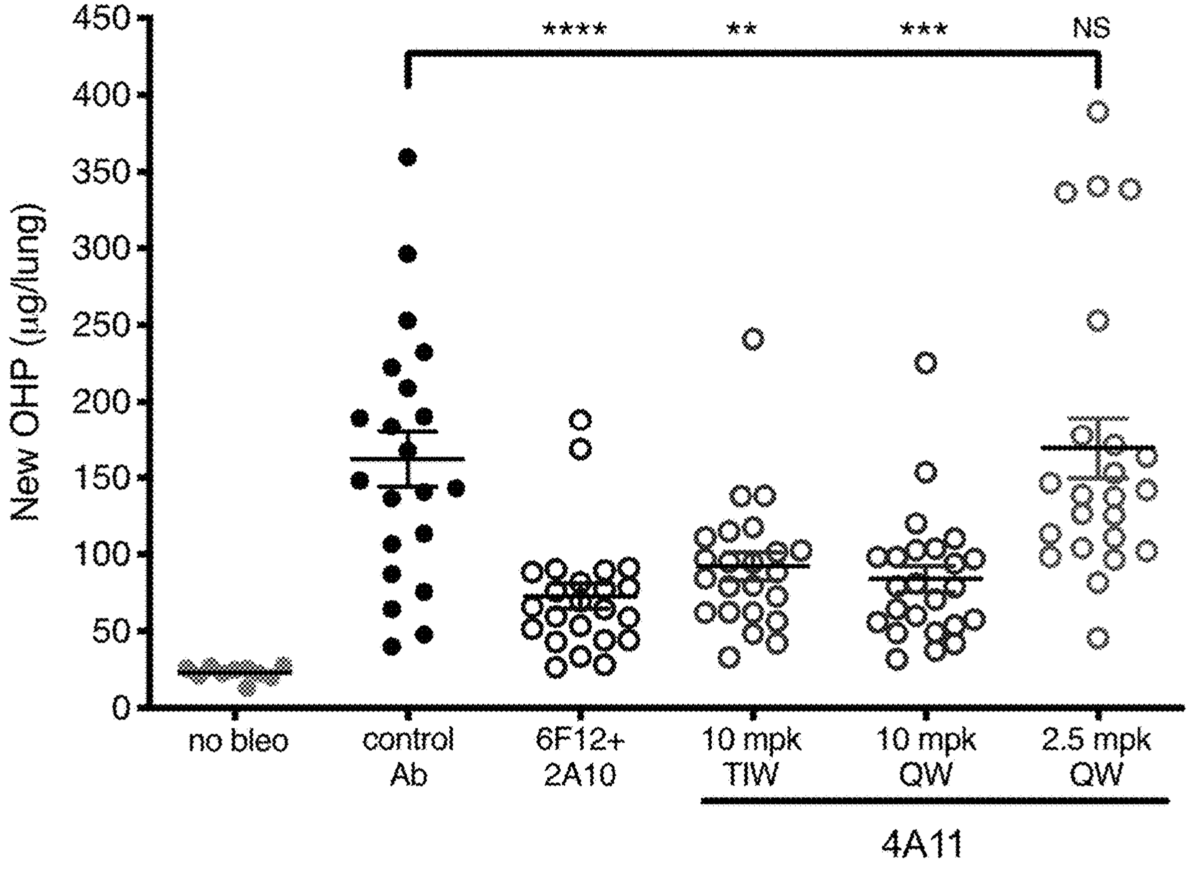

When dosed at 10 mg/kg three times per week, single inhibition of TGFβ2 with 6F12, TGFβ3 with 2A10, or both with either the combination of 6F12+2A10 or monotherapy with 4A11 reduced new collagen synthesis reflected in the incorporation of deuterium into lung hydroxyproline in animals administered $D_2O$ in drinking water from day 9-23 after bleomycin (FIG. 9B). As a more proximal pharmacodynamic readout, in a separate cohort of animals, lung gene expression of fibronectin-1 (fn1) at day 14 after bleomycin was significantly reduced by 6F12, 2A10, the combination of 6F12+2A10, or 4A11. However, 16C10, a less potent TGFβ3 antibody, had no effect on lung fn1 expression (FIG. 9C). Similar effects were observed on other TGFβ-inducible genes including serpine1, col1a1, col1a2, and col3a1. While single administration of either anti-TGFβ2 antibody or anti-TGFβ3 antibody reduced gene expression and collagen synthesis, the combination of both via co-administration of 6F12+2A10 or single administration of 4A11 was numerically superior across multiple experiments, suggesting that both TGFβ2 and TGFβ3 contribute to fibrogenesis in this model, and that the 6F12, 2A10, and 4A11 antibodies can inhibit TGFβ isoforms in vivo (FIG. 9D and FIG. 9E).

Example 6: Humanization of Anti-TGFβ3 mAb 2A10

Materials and Methods:

Antibody Affinity Measurement by BIAcore

For binding affinity determinations of all humanized 2A10 antibodies, Surface Plasmon Resonance (SPR) measurement with a BIAcore™-T200 instrument was used. Briefly, series S CM5 biosensor chip with protein A was first applied to capture each humanized 2A10 variant to achieve approximately 100 response units (RU) on each flow cell, following by injection of 3-fold serial dilutions of human TGFβ1, TGFβ2 or TGFβ3 (0.02 nM to 5 nM) in HBS-EP buffer (0.01M HEPES pH 7.4, 0.15M NaCl, 3 mM EDTA and 0.05% v/v surfactant P20) at 25° C. with a flow rate of 50 μl/min for kinetics measurement. Association rates ($k_{on}$) and dissociation rates ($k_{off}$) were calculated using a simple one-to-one Langmuir binding model (BIAcore T200 evaluation software version 2.0) to determine the equilibrium dissociation constant ($K_D$), which was calculated as the ratio $k_{off}/k_{on}$.

HEKBlue Cell-Based TGFβ Blocking Assay

HEK-Blue™ TGFβ cells (InvivoGen, San Diego, Calif.) stably expressing human TGFβRI, Smad3, Smad4 proteins and secreted alkaline phosphatase (SEAP) reporter gene under the control of the P-globin minimal promoter fused to three Smad3/4-binding elements (SBE) were used to evaluate the blocking potency of 2A10. 2A10 was incubated with each of the TGFβ isoforms (PeproTech, Rocky Hill, N.J.) at 25° C. for 1 h prior to the addition into 4.5×104 HEK-Blue™ TGF-β cells seeded in 96-well plate in 100 μL of assay buffer (DMEM high glucose with 10% heat inactivated FBS, 2 mM L-glutamine and 0.5% Penicillin Streptomycin). The final concentration of antibody and TGFβ was 0.001-200 nM and 20 pM respectively. The plate was incubated at 37° C. and 5% $CO_2$ for 18-22 h. The SEAP level in the cell supernatant was determined by QUANTI-Blue™ assay according to the manufacturer's instructions (InvivoGen). Pan-TGFβ mAb neutralizes TGFβ1, 2, and 3 at low cellular potencies (IC50) of 0.72, 2.2, and 0.026 nM, respectively.

Results:

Humanization of 2A10:

2A10 Humanization Step 1: Rat 2A10 CDRs Grafting into Human Frameworks:

Monoclonal antibody 2A10 was humanized as described below. Residue numbers are according to Kabat et al. (*Sequences of proteins of immunological interest, 5th Ed., Public Health Service*, National Institutes of Health, Bethesda, Md. (1991)). For 2A10 antibody humanization, hypervariable regions from the rat 2A10 (r2A10) antibody were engineered into human germline IGKV1D-39 and IGHV3-49 acceptor frameworks to generate humanized 2A10 version 1 (h2A10.v1) and human germline IGKV1D-39 and IGHV3-23 acceptor frameworks to generate humanized 2A10 version 2 (h2A10.v2). Specifically, from the r2A10 light chain variable domain (VL), positions 24-34 (L1), 50-56 (L2) and 89-97 (L3) were grafted into IGKV1D-39. From the r2A10 heavy chain variable domain (VH), positions 26-35 (H1), 50-65 (H2) and 95-102 (H3) were grafted into IGHV3-49 and IGHV3-23 respectively.

In addition, position 4 in framework I, position 38 and 43 in framework II, position 58 in framework III of VL, position 47 and 49 in framework II and position 78 in framework III of VH were retained from the rat sequence in h2A10.v1. Like h2A10.v1, two additional positions (73 and 76) in framework III of VH were also retained from the rat sequence in h2A10.v2. Those residues were found to be part of the framework residues acting as "Vernier" zone, which may adjust CDR structure and fine-tune the antigen fit. See, e.g., Foote and Winter, *J. Mol. Biol.* 224: 487-499 (1992). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. *J. Mol. Biol.* 262: 732-745 (1996)).

Both primary humanized versions were subject to human TGFβ isoforms binding in BIAcore and the results indicated h2A10.v2 is more comparable to r2A10 than h2A10.v1 in retaining human TGFβ3 binding (Table 9). Interestingly, after humanization, both humanized versions showed human TGFβ2 binding drop in comparison with r2A10.

2A10 Humanization Step 2: Framework Polishing:

In humanized 2A10 framework polishing, more humanized 2A10 variants were generated by substituting each rat residue of humanized 2A10 at Vernier zone with corresponding human residue from germline sequence. Each variant was then evaluated by human TGFβ isoforms binding in BIAcore and blocking potency in HEKBlue to elucidate its importance.

In h2A10.v1, these framework polishing variants are h2A10.v1. 1 (VL: L4M), h2A10.v1.2 (VL: H38Q), h2A10.v1.3 (VL: Q43A), h2A10.v1.4 (VL: I58V), h2A10.v1.5 (VH: L47W), h2A10.v1.6 (VH: A49G), h2A10.v1.7 (VH: V78A) (Table 9). In purification, some of the framework polishing variants in h2A10.v1 tend to have expression (h2A10.v1.1) and aggregation (Monomer<95% for h2A10.v1.3, h2A10.v1.4, h2A10.v1.6) issues. Therefore, it was decided to move on with h2A10.v2 variants.

In h2A10.v2, these framework polishing variants are h2A10.v2.1 (VL: L4M), h2A10.v2.2 (VL: H38Q), h2A10.v2.3 (VL: Q43A), h2A10.v2.4 (VL: I58V), h2A10.v2.5 (VH: L47W), h2A10.v2.6 (VH: A49S), h2A10.v2.7 (VH: D73N), h2A10.v2.8 (VH: S76N), h2A10.v2.9 (VH: V78L). Unlike h2A10.v1 variants, all h2A10.v2 variants were expressed and behaved well in purification (Monomer>99%). In BIAcore binding study, most of variants appeared to be the same as parental h2A10.v2, except for h2A10.v2.1 (VL: L4M) and h2A10.v2.7 (VH: D73N) variants with slightly drop in TGFβ3 binding (2-3 fold) and h2A10.v2.5 (VH: L47W) variant with more drastically drop in TGFβ3 binding (385 fold) (Table 9). Surprisingly, in the cellular HEKBlue TGFβ blocking study, both h2A10.v2.5 (VH: L47W) and h2A10.v2.7 (VH: D73N) showed significant loss of TGFβ3 blocking (>10-fold), but not for h2A10.v2.1I (VL: L4M) (Table 9). Overall, it was determined that all rat residues at Vernier zone of 2h2A10.v2 can be replaced with human germline residues, except for position 4 in framework I of VL, position 47 in framework II and position 73 in framework III of VH.

TABLE 9 h2A10.v1 and h2A10.v2 framework polishing variants characterization summary

| 2A10 | Human | Framework | BIAcore (pM) | | | HEKBIueTGFp blocking IC50 (nM) | | | SEC Monomer |
|---|---|---|---|---|---|---|---|---|---|
| variants | Framework | mutation | TGFβ1 | TGFβ2 | TGFβ3 | TGFβ1 | TGFβ2 | TGFβ3 | (%) |
| Rat 2A10 | — | — | >5000 | 62.8 | 1.2 | >200 | 70 | 0.01 | — |
| h2A10.v1 | $K_{1D\text{-}39}H_{3\text{-}49}$ | — | — | — | — | — | — | — | 88.9 |
| h2A10.v1.1 | $K_{1D\text{-}39}H_{3\text{-}49}$ | LC: L4M | | No expression | | | — | — | — |
| h2A10.v1.2 | $K_{1D\text{-}39}H_{3\text{-}49}$ | LC: H38Q | — | — | — | — | — | — | 97.7 |
| h2A10.v1.3 | $K_{1D\text{-}39}H_{3\text{-}49}$ | LC: Q43A | — | — | — | — | — | — | 92.0 |
| h2A10.v1.4 | $K_{1D\text{-}39}H_{3\text{-}49}$ | LC: I58V | — | — | — | — | — | — | 90.1 |
| h2A10.v1.5 | $K_{1D\text{-}39}H_{3\text{-}49}$ | HC: L47W | — | — | — | — | — | — | 98.6 |
| h2A10.vl.6 | $K_{1D\text{-}39}H_{3\text{-}49}$ | HC: A49G | — | — | — | — | — | — | 94.0 |
| h2A10.v1.7 | $K_{1D\text{-}39}H_{3\text{-}49}$ | HC: V78A | — | — | — | — | — | — | 96.5 |
| h2A10.v2 | $K_{1D\text{-}39}H_{3\text{-}23}$ | — | >5000 | 314 | 1.3 | >200 | >200 | 0.01 | 99.6 |

TABLE 9-continued h2A10.v1 and h2A10.v2 framework polishing variants characterization summary

| 2A10 variants | Human Framework | Framework mutation | BIAcore (pM) TGFβ1 | TGFβ2 | TGFβ3 | HEKBIueTGFp blocking IC50 (nM) TGFβ1 | TGFβ2 | TGFβ3 | SEC Monomer (%) |
|---|---|---|---|---|---|---|---|---|---|
| h2A10.v2.1 | $K_{1D-39}H_{3-23}$ | LC: L4M | >5000 | 238 | 3.1 | >200 | >200 | 0.01 | 99.4 |
| h2A10.v2.2 | $K_{1D-39}H_{3-23}$ | LC: H38Q | >5000 | 124 | 1.2 | >200 | >200 | 0.01 | 99.5 |
| h2A10.v2.3 | $K_{1D-39}H_{3-23}$ | LC: Q43A | >5000 | 242 | 1.5 | >200 | >200 | 0.01 | 99.5 |
| h2A10.v2.4 | $K_{1D-39}H_{3-23}$ | LC: I58V | >5000 | 190 | 2.1 | >200 | >200 | 0.01 | 99.5 |
| h2A10.v2.5 | $K_{1D-39}H_{3-23}$ | HC: L47W | >5000 | 2820 | 500 | >200 | >200 | 27.4 | 99.6 |
| h2A10.v2.6 | $K_{1D-39}H_{3-23}$ | HC: A49S | >5000 | 249 | 1.5 | >200 | >200 | 0.01 | 99.8 |
| h2A10.v2.7 | $K_{1D-39}H_{3-23}$ | HC: D73N | >5000 | 921 | 3.2 | >200 | >200 | 0.12 | 99.5 |
| h2A10.v2.8 | $K_{1D-39}H_{3-23}$ | HC: S76N | >5000 | 365 | 1.2 | >200 | >200 | 0.01 | 99.6 |
| h2A10.v2.9 | $K_{1D-39}H_{3-23}$ | HC: V78L | >5000 | 768 | 0.7 | >200 | >200 | 0.01 | 99.6 |

2A10 Humanization Step 3: Fix CDR-H2 N-Linked Glycosylation Site ($N^{54}Y^{55}T^{56}$)

In h2A10.v2, a potential N-linked glycosylation site ($N^{54}Y^{55}T^{56}$) in CDR-H-2 was identified as a potential liability. Two approaches were applied to address this issue, one of which was to substitute Asn at position 54 to nucleophilic Ser (h2A10.v2.N54S) or its homolog Gln (h2A10.v2.N54Q), the other of which was to keep Asn at position 54, but substitute Thr at position 56 to a smaller residue Ala (h2A10.v2.T56A). All three variants were expressed and behaved well in purification (Monomer >99%) (Table 10). In BIAcore analysis, however, only the h2A10.v2.T56A variant retained similar human TGFβ3 binding while the other two variants showed a slight drop (<2-fold) by comparison with parental h2A10.v2. Despite the differences in binding, however, no differences were observed with respect to human TGFβ3 blocking for all three variants.

TABLE 10 h2A10.v2 CDR-H2 $N^{54}Y^{55}T^{56}$ variants characterization summary

| 2A10 variants | Human Framework | Framework mutation | BIAcore (pM) TGFβ1 | TGFβ2 | TGFβ3 | HEKBlue TGFβ blocking IC50 (nM) TGFβ1 | TGFβ2 | TGFβ3 | SEC Monomer (%) |
|---|---|---|---|---|---|---|---|---|---|
| h2A10.v2 | $K_{1D-39}H_{3-23}$ | — | >5000 | 314 | 1.3 | >200 | >200 | 0.01 | 99.6 |
| h2A10.v2.N54S | $K_{1D-39}H_{3-23}$ | — | >5000 | 425 | 2.4 | >200 | >200 | 0.01 | 99.5 |
| h2A10.v2.N54Q | $K_{1D-39}H_{3-23}$ | — | >5000 | 378 | 2.5 | >200 | >200 | 0.01 | 99.6 |
| h2A10.v2.T56A | $K_{1D-39}H_{3-2}3$ | — | >5000 | 247 | 1.0 | >200 | >200 | 0.01 | 99.6 |

2A10 Humanization Step 4: Final Version Generation

By combining the results from framework polishing and CDR-H2 N-linked glycosylation site repair, the final two humanized 2A10 versions, h2A10.v3 and h2A10.v4, were generated based on further engineering of h2A10.v2. Both versions retained L at position 4 in framework I of VL and L at position 47 in framework II, D at position 73 in framework III of VH from r2A10. The other six framework residues derived from r2A10 at Vernier zone were changed to corresponding human germline residues, which were Q at position 38 and A at position 43 in framework II, V at position 58 in framework III of VL and S at position 49 in framework II, N at position 76 and L at position 78 in framework III of VH. The only difference between the two versions were at CDR-H2 N-linked glycosylation site, which were $\underline{S}^{54}Y^{55}T^{56}$ in h2A10.v3 and $N^{54}Y^{55}\underline{A}^{56}$ in h2A10.v4. This difference was significant functionally, however, because in BIAcore TGFβ3 binding and HEKBlue TGFβ3 blocking assays, h2A10.v4 appeared to be better than h2A10.v3 and comparable to parental r2A10 (Table 11).

Overall, the humanization process for 2A10 was quite challenging. The challenges in rat-derived 2A10 humanization included unexpected difficulty with antibody expression at the $1^{st}$ step (grafting 2A10 CDRs onto the closest human VH/VL frameworks pairing) and with stability issues of the variants in the $2^{nd}$ step of framework polishing (see FIG. 10, FIG. 11).

TABLE 11 h2A10.v3 and h2A10.v4 characterization summary

| 2A10 variants | Human Framework | Framework mutation | BIAcore (pM) TGFβ1 | TGFβ2 | TGFβ3 | HEKBlue TGFβ blocking IC50 (nM) TGFβ1 | TGFβ2 | TGFβ3 | SEC Monomer (%) |
|---|---|---|---|---|---|---|---|---|---|
| Rat2A10 | — | — | >5000 | 62.8 | 1.2 | >200 | 70 | 0.01 | — |
| h2A10.v3 | $K_{1D-39}H_{3-23}$ | LC: H38Q, Q43A I58V HC: A49S, S76N V78L | >5000 | 482 | 2.6 | >200 | >200 | 0.05 | 99.7 |
| h2A10.v4 | $K_{1D-39}H_{3-23}$ | LC: H38Q, Q43A I58V HC: A49S, S76N V78L | >5000 | 300 | 1.9 | >200 | >200 | 0.01 | 100 |

The sequences for humanized 2A10 antibody variants (CDRs of select variants, variable regions, and complete sequences) are shown in Table 12, Table 13, and Table 14, below, and sequence alignments are shown in FIG. 12, FIG. 13, FIG. 14, FIG. 15, and FIG. 16.

TABLE 12

Heavy and Light Chain CDR Amino Acid Sequences of Humanized 2A10 Variants

| | CDR-H1 | CDR-H2 | CDR-H3 | CDR-L1 | CDR-L2 | CDR-L3 |
|---|---|---|---|---|---|---|
| H2A10. v2.N54Q | SYGMS (SEQ ID NO: 4) | DIVSKTYQ YTTYYSDS VKD (SEQ ID NO: 159) | APGGSFD Y (SEQ ID NO: 6) | RASQSVS ISRFNLM H (SEQ ID NO: 7) | RASNLAS (SEQ ID NO: 8) | QHSRES PWT (SEQ ID NO: 9) |
| h2A10. v3 | SYGMS (SEQ ID NO: 4) | DIVSKTYS YTTYYSDS VKD (SEQ ID NO: 34) | APGGSFD Y (SEQ ID NO: 6) | RASQSVS ISRFNLM H (SEQ ID NO: 7) | RASNLAS (SEQ ID NO: 8) | QHSRES PWT (SEQ ID NO: 9) |
| h2A10. v4 | SYGMS (SEQ ID NO: 4) | DIVSKTYN YATYYSDS VKD (SEQ ID NO: 35) | APGGSFD Y (SEQ ID NO: 6) | RASQSVS ISRFNLM H (SEQ ID NO: 7) | RASNLAS (SEQ ID NO: 8) | QHSRES PWT (SEQ ID NO: 9) |

TABLE 13

Heavy and Light Chain Variable Region Amino Acid Sequences of Humanized 2A10 Variants

| | VH | VL |
|---|---|---|
| h2A10. v1 | EVQLVESGGGLVQPGPSLRLSCTAS GFDFNSYGMSWVRQAPGKGLELV ADIVSKTYNYTTYYSDSVKDRFTIS RDDSKSIVYLQMNSLKTEDTAVYY CTVAPGGSFDYWGQGTLVTVSS (SEQ ID NO: 37) | DIQLTQSPSSLSASVGDRVTITCRAS QSVSISRFNLMHWYQHKPGKQPKL LIYRASNLASGIPSRFSGSGSGTDFT LTISSLQPEDFATYYCQHSRESPWT FGGGTKVEIK (SEQ ID NO: 36) |
| h2A10. v1.1 | Same as v1 (SEQ ID NO: 37) | DIQMTQSPSSLSASVGDRVTITCRA SQSVSISRFNLMHWYQHKPGKQPK LLIYRASNLASGIPSRFSGSGSGTDF TLTISSLQPEDFATYYCQHSRESPW TFGGGTKVEIK (SEQ ID NO: 38) |
| h2A10. v1.2 | Same as v1 (SEQ ID NO: 37) | DIQLTQSPSSLSASVGDRVTITCRAS QSVSISRFNLMHWYQQKPGKQPKL LIYRASNLASGIPSRFSGSGSGTDFT LTISSLQPEDFATYYCQHSRESPWT FGGGTKVEIK (SEQ ID NO: 39) |

TABLE 13-continued

| Heavy and Light Chain Variable Region Amino Acid Sequences of Humanized 2A10 Variants | | |
|---|---|---|
| | VH | VL |
| h2A10. v1.3 | Same as v1 (SEQ ID NO: 37) | DIQLTQSPSSLSASVGDRVTITCRAS QSVSISRFNLMHWYQHKPGKAPKL LIYRASNLASGIPSRFSGSGSGTDFT LTISSLQPEDFATYYCQHSRESPWT FGGGTKVEIK (SEQ ID NO: 40) |
| h2A10. v1.4 | Same as v1 (SEQ ID NO: 37) | DIQLTQSPSSLSASVGDRVTITCRAS QSVSISRFNLMHWYQHKPGKQPKL LIYRASNLASGVPSRFSGSGSGTDFT LTISSLQPEDFATYYCQHSRESPWT FGGGTKVEIK (SEQ ID NO: 41) |
| h2A10. v1.5 | EVQLVESGGGLVQPGPSLRLSCTAS GFDFNSYGMSWVRQAPGKGLEWV ADIVSKTYNYTTYYSDSVKDRFTIS RDDSKSIVYLQMNSLKTEDTAVYY CTVAPGGSFDYWGQGTLVTVSS (SEQ ID NO: 42) | Same as v1 (SEQ ID NO: 36) |
| h2A10. v1.6 | EVQLVESGGGLVQPGPSLRLSCTAS GFDFNSYGMSWVRQAPGKGLELV GDIVSKTYNYTTYYSDSVKDRFTIS RDDSKSIVYLQMNSLKTEDTAVYY CTVAPGGSFDYWGQGTLVTVSS (SEQ ID NO: 43) | Same as v1 (SEQ ID NO: 36) |
| h2A10. v1.7 | EVQLVESGGGLVQPGPSLRLSCTAS GFDFNSYGMSWVRQAPGKGLELV ADIVSKTYNYTTYYSDSVKDRFTIS RDDSKSIAYLQMNSLKTEDTAVYY CTVAPGGSFDYWGQGTLVTVSS (SEQ ID NO: 44) | Same as v1 (SEQ ID NO: 36) |
| h2A10. v2 | EVQLLESGGGLVQPGGSLRLSCAAS GFDFNSYGMSWVRQAPGKGLELV ADIVSKTYNYTTYYSDSVKDRFTIS RDDSKSTVYLQMNSLRAEDTAVYY CTVAPGGSFDYWGQGTLVTVSS (SEQ ID NO: 45) | Same as v1 (SEQ ID NO: 36) |
| h2A10. v2.1 | Same as v2 (SEQ ID NO: 45) | Same as v1.1 (SEQ ID NO: 38) |
| h2A10. v2.2 | Same as v2 (SEQ ID NO: 45) | Same as v1.2 (SEQ ID NO: 39) |
| h2A10. v2.3 | Same as v2 (SEQ ID NO: 45) | Same as v1.3 (SEQ ID NO: 40) |
| h2A10. v2.4 | Same as v2 (SEQ ID NO: 45) | Same as v1.4 (SEQ ID NO: 41) |
| h2A10. v2.5 | EVQLLESGGGLVQPGGSLRLSCAAS GFDFNSYGMSWVRQAPGKGLEWV ADIVSKTYNYTTYYSDSVKDRFTIS RDDSKSTVYLQMNSLRAEDTAVYY CTVAPGGSFDYWGQGTLVTVSS (SEQ ID NO: 46) | Same as v1 (SEQ ID NO: 36) |
| h2A10. v2.6 | EVQLLESGGGLVQPGGSLRLSCAAS GFDFNSYGMSWVRQAPGKGLELVS DIVSKTYNYTTYYSDSVKDRFTISR DDSKSTVYLQMNSLRAEDTAVYYC TVAPGGSFDYWGQGTLVTVSS (SEQ ID NO: 47) | Same as v1 (SEQ ID NO: 36) |
| h2A10. v2.7 | EVQLLESGGGLVQPGGSLRLSCAAS GFDFNSYGMSWVRQAPGKGLELV ADIVSKTYNYTTYYSDSVKDRFTIS RDNSKSTVYLQMNSLRAEDTAVYY CTVAPGGSFDYWGQGTLVTVSS (SEQ ID NO: 48) | Same as v1 (SEQ ID NO: 36) |

TABLE 13-continued

Heavy and Light Chain Variable Region Amino Acid Sequences of Humanized 2A10 Variants

| | VH | VL |
|---|---|---|
| h2A10. v2.8 | EVQLLESGGGLVQPGGSLRLSCAAS GFDFNSYGMSWVRQAPGKGLELV ADIVSKTYNYTTYYSDSVKDRFTIS RDDSKNTVYLQMNSLRAEDTAVY YCTVAPGGSFDYWGQGTLVTVSS (SEQ ID NO: 49) | Same as v1 (SEQ ID NO: 36) |
| h2A10. v2.9 | EVQLLESGGGLVQPGGSLRLSCAAS GFDFNSYGMSWVRQAPGKGLELV ADIVSKTYNYTTYYSDSVKDRFTIS RDDSKSTLYLQMNSLRAEDTAVYY CTVAPGGSFDYWGQGTLVTVSS (SEQ ID NO: 50) | Same as v1 (SEQ ID NO: 36) |
| h2A10. v2.N54S | EVQLLESGGGLVQPGGSLRLSCAAS GFDFNSYGMSWVRQAPGKGLELV ADIVSKTYSYTTYYSDSVKDRFTIS RDDSKSTVYLQMNSLRAEDTAVYY CTVAPGGSFDYWGQGTLVTVSS (SEQ ID NO: 51) | Same as v1 (SEQ ID NO: 36) |
| h2A10. v2.N54Q | EVQLLESGGGLVQPGGSLRLSCAAS GFDFNSYGMSWVRQAPGKGLELV ADIVSKTYQYTTYYSDSVKDRFTIS RDDSKSTVYLQMNSLRAEDTAVYY CTVAPGGSFDYWGQGTLVTVSS (SEQ ID NO: 52) | Same as v1 (SEQ ID NO: 36) |
| h2A10. v2.T56A | EVQLLESGGGLVQPGGSLRLSCAAS GFDFNSYGMSWVRQAPGKGLELV ADIVSKTYNYATYYSDSVKDRFTIS RDDSKSTVYLQMNSLRAEDTAVYY CTVAPGGSFDYWGQGTLVTVSS (SEQ ID NO: 53) | Same as v1 (SEQ ID NO: 36) |
| h2A10. v3 | EVQLLESGGGLVQPGGSLRLSCAAS GFDFNSYGMSWVRQAPGKGLELVS DIVSKTYSYTTYYSDSVKDRFTISR DDSKNTLYLQMNSLRAEDTAVYY CTVAPGGSFDYWGQGTLVTVSS (SEQ ID NO: 55) | DIQLTQSPSSLSASVGDRVTITCRAS QSVSISRFNLMHWYQQKPGKAPKL LIYRASNLASGVPSRFSGSGSGTDFT LTISSLQPEDFATYYCQHSRESPWT FGGGTKVEIK (SEQ ID NO: 54) |
| h2A10. v4 | EVQLLESGGGLVQPGGSLRLSCAAS GFDFNSYGMSWVRQAPGKGLELVS DIVSKTYNYATYYSDSVKDRFTISR DDSKNTLYLQMNSLRAEDTAVYY CTVAPGGSFDYWGQGTLVTVSS (SEQ ID NO: 57) | DIQLTQSPSSLSASVGDRVTITCRAS QSVSISRFNLMHWYQQKPGKAPKL LIYRASNLASGVPSRFSGSGSGTDFT LTISSLQPEDFATYYCQHSRESPWT FGGGTKVEIK (SEQ ID NO: 56) |

TABLE 14

Complete Heavy and Light Chain Sequences for Humanized 2A10 Variants

| | Complete H Chain | Complete L Chain |
|---|---|---|
| h2A10. v1 | EVQLVESGGGLVQPGPSLRLSCTASGFDF NSYGMSWVRQAPGKGLELVADIVSKTYN YTTYYSDSVKDRFTISRDDSKSIVYLQMNS LKTEDTAVYYCTVAPGGSFDYWGQGTLV TVSSASTKGPSVFPLAPSSKSTSGGTAALG CLVKDYFPEPVTVSWNSGALTSGVHTFPA VLQSSGLYSLSSVVTVPSSSLGTQTYICNV NHKPSNTKVDKKVEPKSCDKTHTCPPCPA PELLGGPSVFLFPPKPKDTLMISRTPEVTC VVVDVSHEDPEVKFNWYVDGVEVHNAK TKPREEQYGSTYRVVSVLTVLHQDWLNG KEYKCKVSNKALPAPIEKTISKAKGQPREP QVYTLPPSREEMTKNQVSLTCLVKGFYPS DIAVEWESNGQPENNYKTTPPVLDSDGSF FLYSKLTVDKSRWQQGNVFSCSVMHEAL HNHYTQKSLSLSPGK (SEQ ID NO: 59) | DIQLTQSPSSLSASVGDRVTI TCRASQSVSISRFNLMHWYQ HKPGKQPKLLIYRASNLASG IPSRFSGSGSGTDFTLTISSLQ PEDFATYYCQHSRESPWTFG GGTKVEIKRTVAAPSVFIFPP SDEQLKSGTASVVCLLNNFY PREAKVQWKVDNALQSGNS QESVTEQDSKDSTYSLSSTL TLSKADYEKHKVYACEVTH QGLSSPVTKSFNRGEC (SEQ ID NO: 58) |

TABLE 14-continued

Complete Heavy and Light Chain Sequences for Humanized 2A10 Variants

| | Complete H Chain | Complete L Chain |
|---|---|---|
| h2A10. v1.1 | Same as v1 (SEQ ID NO: 59) | DIQMTQSPSSLSASVGDRVTI TCRASQSVSISRFNLMHWYQ HKPGKQPKLLIYRASNLASG IPSRFSGSGSGTDFTLTISSLQ PEDFATYYCQHSRESPWTFG GGTKVEIKRTVAAPSVFIFPP SDEQLKSGTASVVCLLNNFY PREAKVQWKVDNALQSGNS QESVTEQDSKDSTYSLSSTL TLSKADYEKHKVYACEVTH QGLSSPVTKSFNRGEC (SEQ ID NO: 60) |
| h2A10. v1.2 | Same as v1 (SEQ ID NO: 59) | DIQLTQSPSSLSASVGDRVTI TCRASQSVSISRFNLMHWYQ QKPGKQPKLLIYRASNLASG IPSRFSGSGSGTDFTLTISSLQ PEDFATYYCQHSRESPWTFG GGTKVEIKRTVAAPSVFIFPP SDEQLKSGTASVVCLLNNFY PREAKVQWKVDNALQSGNS QESVTEQDSKDSTYSLSSTL TLSKADYEKHKVYACEVTH QGLSSPVTKSFNRGEC (SEQ ID NO: 61) |
| h2A10. v1.3 | Same as v1 (SEQ ID NO: 59) | DIQLTQSPSSLSASVGDRVTI TCRASQSVSISRFNLMHWYQ HKPGKAPKLLIYRASNLASG IPSRFSGSGSGTDFTLTISSLQ PEDFATYYCQHSRESPWTFG GGTKVEIKRTVAAPSVFIFPP SDEQLKSGTASVVCLLNNFY PREAKVQWKVDNALQSGNS QESVTEQDSKDSTYSLSSTL TLSKADYEKHKVYACEVTH QGLSSPVTKSFNRGEC (SEQ ID NO: 62) |
| h2A10. v1.4 | Same as v1 (SEQ ID NO: 59) | DIQLTQSPSSLSASVGDRVTI TCRASQSVSISRFNLMHWYQ HKPGKQPKLLIYRASNLASG VPSRFSGSGSGTDFTLTISSL QPEDFATYYCQHSRESPWTF GGGTKVEIKRTVAAPSVFIFP PSDEQLKSGTASVVCLLNNF YPREAKVQWKVDNALQSG NSQESVTEQDSKDSTYSLSS TLTLSKADYEKHKVYACEV THQGLSSPVTKSFNRGEC (SEQ ID NO: 63) |
| h2A10. v1.5 | EVQLVESGGGLVQPGPSLRLSCTASGFDF NSYGMSWVRQAPGKGLEWVADIVSKTY NYTTYYSDSVKDRFTISRDDSKSIVYLQM NSLKTEDTAVYYCTVAPGGSFDYWGQGT LVTVSSASTKGPSVFPLAPSSKSTSGGTAA LGCLVKDYFPEPVTVSWNSGALTSGVHTF PAVLQSSGLYSLSSVVTVPSSSLGTQTYIC NVNHKPSNTKVDKKVEPKSCDKTHTCPPC PAPELLGGPSVFLFPPKPKDTLMISRTPEVT CVVVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 64) | Same as v1 (SEQ ID NO: 58) |
| h2A10. v1.6 | EVQLVESGGGLVQPGPSLRLSCTASGFDF NSYGMSWVRQAPGKGLELVGDIVSKTYN YTTYYSDSVKDRFTISRDDSKSIVYLQMNS LKTEDTAVYYCTVAPGGSFDYWGQGTLV TVSSASTKGPSVFPLAPSSKSTSGGTAALG CLVKDYFPEPVTVSWNSGALTSGVHTFPA VLQSSGLYSLSSVVTVPSSSLGTQTYICNV | Same as v1 (SEQ ID NO: 58) |

TABLE 14-continued

Complete Heavy and Light Chain Sequences for Humanized 2A10 Variants

| | Complete H Chain | Complete L Chain |
|---|---|---|
| | NHKPSNTKVDKKVEPKSCDKTHTCPPCPA PELLGGPSVFLFPPKPKDTLMISRTPEVTC VVVDVSHEDPEVKFNWYVDGVEVHNAK TKPREEQYGSTYRVVSVLTVLHQDWLNG KEYKCKVSNKALPAPIEKTISKAKGQPREP QVYTLPPSREEMTKNQVSLTCLVKGFYPS DIAVEWESNGQPENNYKTTPPVLDSDGSF FLYSKLTVDKSRWQQGNVFSCSVMHEAL HNHYTQKSLSLSPGK (SEQ ID NO: 65) | |
| h2A10. v1.7 | EVQLVESGGGLVQPGPSLRLSCTASGFDF NSYGMSWVRQAPGKGLELVADIVSKTYN YTTYYSDSVKDRFTISRDDSKSIAYLQMNS LKTEDTAVYYCTVAPGGSFDYWGQGTLV TVSSASTKGPSVFPLAPSSKSTSGGTAALG CLVKDYFPEPVTVSWNSGALTSGVHTFPA VLQSSGLYSLSSVVTVPSSSLGTQTYICNV NHKPSNTKVDKKVEPKSCDKTHTCPPCPA PELLGGPSVFLFPPKPKDTLMISRTPEVTC VVVDVSHEDPEVKFNWYVDGVEVHNAK TKPREEQYGSTYRVVSVLTVLHQDWLNG KEYKCKVSNKALPAPIEKTISKAKGQPREP QVYTLPPSREEMTKNQVSLTCLVKGFYPS DIAVEWESNGQPENNYKTTPPVLDSDGSF FLYSKLTVDKSRWQQGNVFSCSVMHEAL HNHYTQKSLSLSPGK (SEQ ID NO: 66) | Same as v1 (SEQ ID NO: 58) |
| h2A10. v2 | EVQLLESGGGLVQPGGSLRLSCAASGFDF NSYGMSWVRQAPGKGLELVADIVSKTYN YTTYYSDSVKDRFTISRDDSKSTVYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CVVVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 67) | Same as v1 (SEQ ID NO: 58) |
| h2A10. v2.1 | Same as v2 (SEQ ID NO: 67) | Same as v1.1 (SEQ ID NO: 60) |
| h2A10. v2.2 | Same as v2 (SEQ ID NO: 67) | Same as v1.2 (SEQ ID NO: 61) |
| h2A10. v2.3 | Same as v2 (SEQ ID NO: 67) | Same as v1.3 (SEQ ID NO: 62) |
| h2A10. v2.4 | Same as v2 (SEQ ID NO: 67) | Same as v1.4 (SEQ ID NO: 63) |
| h2A10. v2.5 | EVQLLESGGGLVQPGGSLRLSCAASGFDF NSYGMSWVRQAPGKGLEWVADIVSKTY NYTTYYSDSVKDRFTISRDDSKSTVYLQM NSLRAEDTAVYYCTVAPGGSFDYWGQGT LVTVSSASTKGPSVFPLAPSSKSTSGGTAA LGCLVKDYFPEPVTVSWNSGALTSGVHTF PAVLQSSGLYSLSSVVTVPSSSLGTQTYIC NVNHKPSNTKVDKKVEPKSCDKTHTCPPC PAPELLGGPSVFLFPPKPKDTLMISRTPEVT CVVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 68) | Same as v1 (SEQ ID NO: 58) |
| h2A10. v2.6 | EVQLLESGGGLVQPGGSLRLSCAASGFDF NSYGMSWVRQAPGKGLELVSDIVSKTYN YTTYYSDSVKDRFTISRDDSKSTVYLQMN | Same as v1 (SEQ ID NO: 58) |

TABLE 14-continued

Complete Heavy and Light Chain Sequences for Humanized 2A10 Variants

| | Complete H Chain | Complete L Chain |
|---|---|---|
| | SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 69) | |
| h2A10. v2.7 | EVQLLESGGGLVQPGGSLRLSCAASGFDF NSYGMSWVRQAPGKGLELVADIVSKTYN YTTYYSDSVKDRFTISRDNSKSTVYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 70) | Same as v1 (SEQ ID NO: 58) |
| h2A10. v2.8 | EVQLLESGGGLVQPGGSLRLSCAASGFDF NSYGMSWVRQAPGKGLELVADIVSKTYN YTTYYSDSVKDRFTISRDDSKNTVYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 71) | Same as v1 (SEQ ID NO: 58) |
| h2A10. v2.9 | EVQLLESGGGLVQPGGSLRLSCAASGFDF NSYGMSWVRQAPGKGLELVADIVSKTYN YTTYYSDSVKDRFTISRDDSKSTLYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 72) | Same as v1 (SEQ ID NO: 58) |
| h2A10. v2.N54S | EVQLLESGGGLVQPGGSLRLSCAASGFDF NSYGMSWVRQAPGKGLELVADIVSKTYS YTTYYSDSVKDRFTISRDDSKSTVYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN | Same as v1 (SEQ ID NO: 58) |

TABLE 14-continued

Complete Heavy and Light Chain Sequences for Humanized 2A10 Variants

| | Complete H Chain | Complete L Chain |
|---|---|---|
| | GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 73) | |
| h2A10. v2.N54Q | EVQLLESGGGLVQPGGSLRLSCAASGFDF NSYGMSWVRQAPGKGLELVADIVSKTYQ YTTYYSDSVKDRFTISRDDSKSTVYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 74) | Same as v1 (SEQ ID NO: 58) |
| h2A10. v2.T56A | EVQLLESGGGLVQPGGSLRLSCAASGFDF NSYGMSWVRQAPGKGLELVADIVSKTYN YATYYSDSVKDRFTISRDDSKSTVYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 75) | Same as v1 (SEQ ID NO: 58) |
| h2A10. v3 | EVQLLESGGGLVQPGGSLRLSCAASGFDF NSYGMSWVRQAPGKGLELVSDIVSKTYS YTTYYSDSVKDRFTISRDDSKNTLYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CWVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 77) | DIQLTQSPSSLSASVGDRVTI TCRASQSVSISRFNLMHWYQ QKPGKAPKLLIYRASNLASG VPSRFSGSGSGTDFTLTISSL QPEDFATYYCQHSRESPWTF GGGTKVEIKRTVAAPSVFIFP PSDEQLKSGTASVVCLLNNF YPREAKVQWKVDNALQSG NSQESVTEQDSKDSTYSLSS TLTLSKADYEKHKVYACEV THQGLSSPVTKSFNRGEC (SEQ ID NO: 76) |
| h2A10. v4 | EVQLLESGGGLVQPGGSLRLSCAASGFDF NSYGMSWVRQAPGKGLELVSDIVSKTYN YATYYSDSVKDRFTISRDDSKNTLYLQMN SLRAEDTAVYYCTVAPGGSFDYWGQGTL VTVSSASTKGPSVFPLAPSSKSTSGGTAAL GCLVKDYFPEPVTVSWNSGALTSGVHTFP AVLQSSGLYSLSSVVTVPSSSLGTQTYICN VNHKPSNTKVDKKVEPKSCDKTHTCPPCP APELLGGPSVFLFPPKPKDTLMISRTPEVT CVVVDVSHEDPEVKFNWYVDGVEVHNA KTKPREEQYGSTYRVVSVLTVLHQDWLN GKEYKCKVSNKALPAPIEKTISKAKGQPR EPQVYTLPPSREEMTKNQVSLTCLVKGFY PSDIAVEWESNGQPENNYKTTPPVLDSDG SFFLYSKLTVDKSRWQQGNVFSCSVMHE ALHNHYTQKSLSLSPGK (SEQ ID NO: 79) | DIQLTQSPSSLSASVGDRVTI TCRASQSVSISRFNLMHWYQ QKPGKAPKLLIYRASNLASG VPSRFSGSGSGTDFTLTISSL QPEDFATYYCQHSRESPWTF GGGTKVEIKRTVAAPSVFIFP PSDEQLKSGTASVVCLLNNF YPREAKVQWKVDNALQSG NSQESVTEQDSKDSTYSLSS TLTLSKADYEKHKVYACEV THQGLSSPVTKSFNRGEC (SEQ ID NO: 78) |

Example 7: Cynomolgus Monkey PK Study of 2A10 Humanized Variants

Materials and Methods:

Eight experimentally naïve female cynomolgus monkeys (*Macaca fascicularis*, Cambodian origin) were assigned to one of two groups (n=4/group). At the outset (Day −1) of the study, animals were approximately 4 years old and weighed approximately 2.5-4 kg, and only animals that appeared to be healthy and that were free of obvious abnormalities were used for the study. Animals in Groups 1 or 2 were given a single 10 mg/kg I.V. bolus dose of anti-TGFβ3 h2A10.v3 or h2A10.v4, respectively. Doses were administered via the cephalic vein in the forearm. At various timepoints up to 43 days post-dose, serum samples (n=4/timepoint) were collected and analyzed for serum test article concentrations by ELISA methods.

The serum concentrations of animals dosed with 10 mg/kg of anti-TGFβ3 variants h2A10.v3 and h2A10.v4 were determined by an ELISA method. 384-well plates were coated with 0.5 pg/mL sheep anti-human IgG antibody (Binding Site, San Diego, Calif., USA) diluted in coat buffer (0.05 M carbonate/bicarbonate buffer pH 9.6) and incubated overnight at 4° C. The plates were washed 3 times with wash buffer (0.5% Tween-20 in PBS buffer, pH 7.4) and treated with block buffer (PBS/0.5% BSA/15 ppm Proclin, pH 7.4) for 1 to 2 hours at room temperature (RT). The plates were again washed 3 times with wash buffer and then samples diluted in sample diluent (PBS/0.5% BSA/0.05% Tween 20/5 mM EDTA/0.25% CHAPS/0.35M NaCl/15 ppm Proclin, pH 7.4) were added to the wells and incubated for 2 hours at RT. The next day, the plates were washed 6 times with wash buffer. A detection antibody, goat anti-human IgG (H+L)-horseradish peroxidase (HRP) (Bethyl Laboratories, Inc., Montgomery, Tex., USA), diluted to 100 ng/mL in assay buffer (PBS/0.5% BSA/15 ppm Proclin/0.05% Tween 20, pH7.4) was added to the wells and incubated on a shaker for 1 hour at RT. The plates were washed 6 times with wash buffer and developed using TMB peroxidase substrate (Moss Inc., Pasadena, Md.) for 20 minutes followed by 1 M Phosphoric acid to stop the reaction. Absorbance was measured at 450 nm against a reference wavelength of 620 nm. The concentration of the samples was extrapolated from a 4-parameter fit of the standard curve. The reportable assay range was 0.156-10 ng/mL. The minimum required dilution was 1:100 with the Minimum Quantifiable Concentration at 16 ng/mL.

Figure 17:
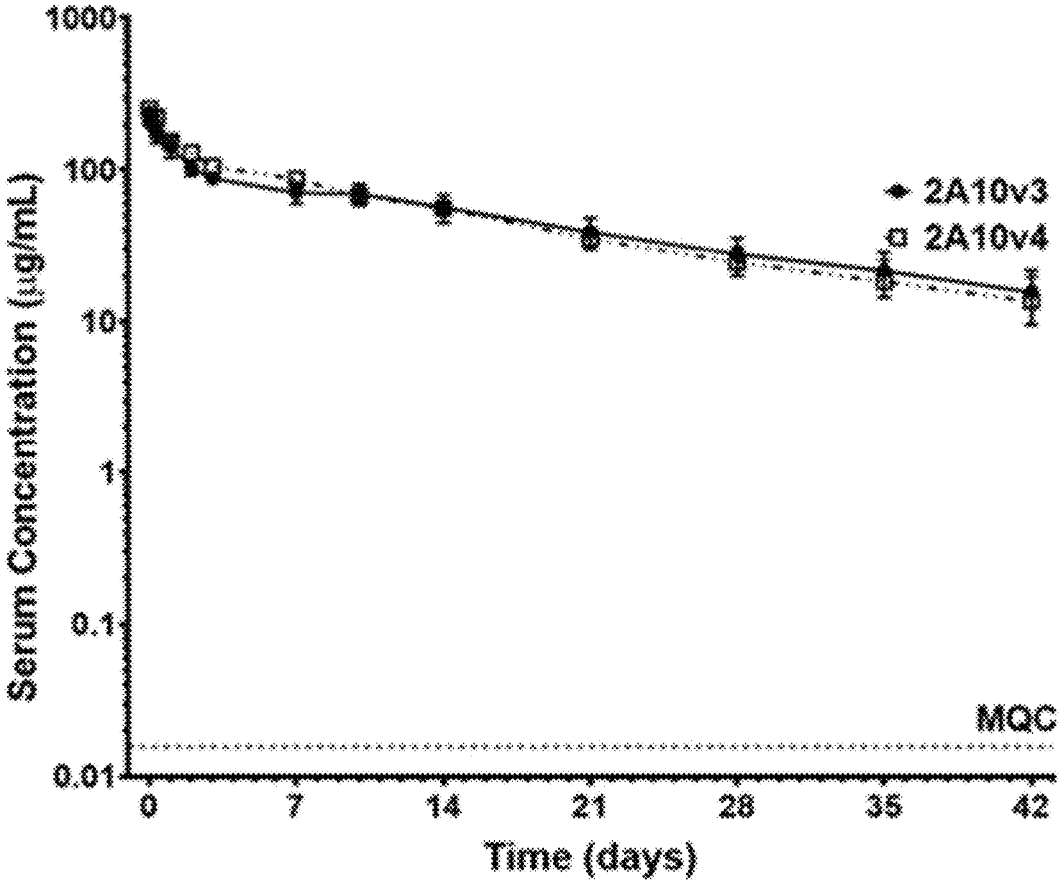
FIG. 17 is a line graph showing mean (±SD) serum concentration of h2A10v3 and h2A10v4 after a single I.V. dose of 10 mg/kg in a cynomolgus monkey PK study (n=4 per group).
Figure 18:
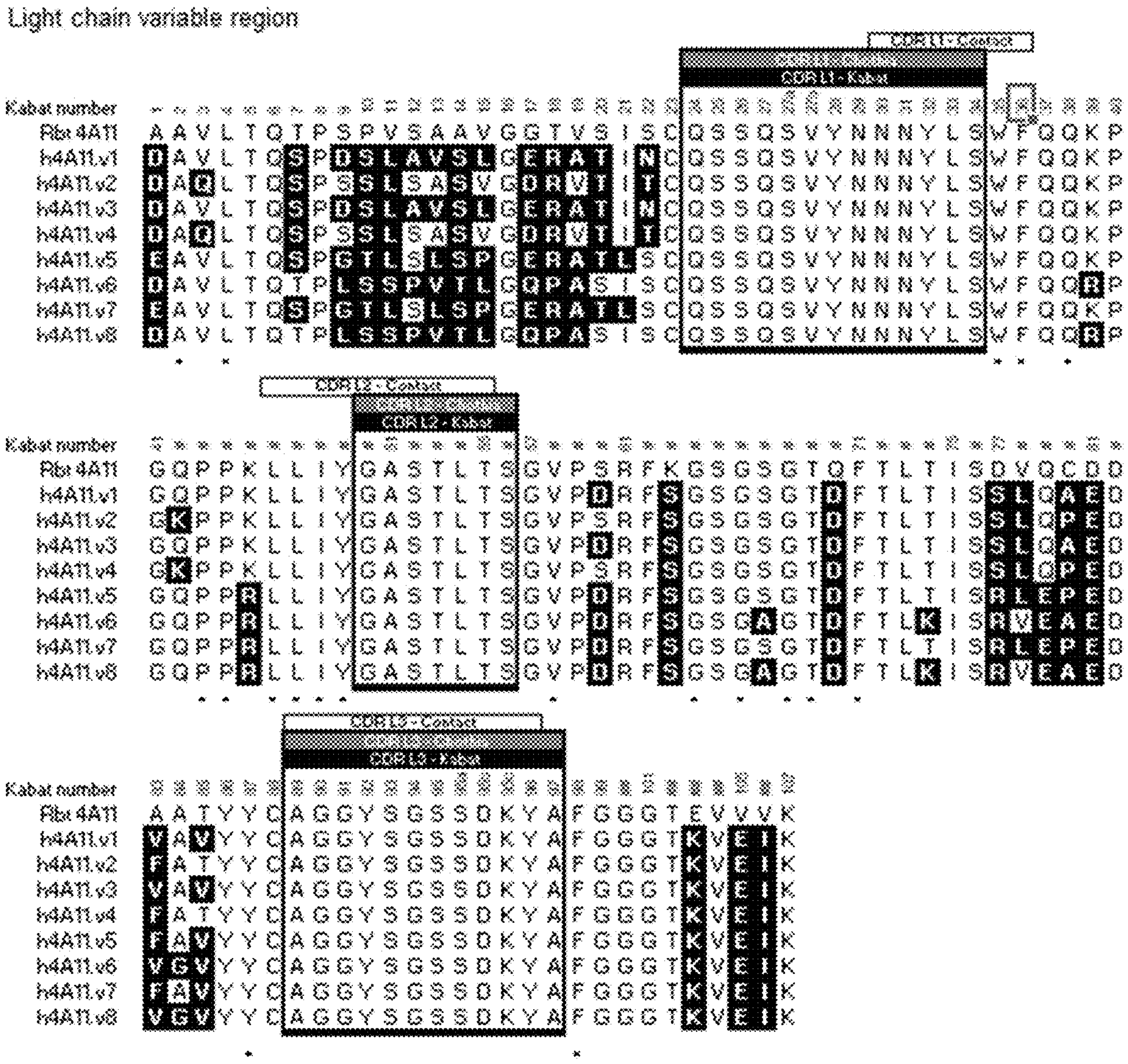
FIG. 18 contains an amino acid sequence alignment of the light chain variable region of rabbit 4A11 mAb and its humanized variants, v1-v8; the sequences shown correspond to SEQ ID NOs: 26, 80, 82, 80, 82, 84, 85, 84, and 84, from top sequence to bottom sequence in the alignment. Residue numbering is according to Kabat; "*" indicates Vernier zone. CDR regions according to Chothia or Kabat (as indicated) are boxed; mutated residues are highlighted.

Results:

Following a single I.V. bolus dose of anti-TGFβ3 h2A10.v3 at 10 mg/kg, mean clearance (CL) was 4.35 mL/day/kg, $C_{max}$ was 238 pg/mL, exposure (AUCinf) was 2400 day • μg/mL, terminal half-life ($t_{1/2}$, λz) was 15.1 days, volume of distribution at steady state ($V_{ss}$) was 88.2 mL/kg. h2A10.v3 demonstrated apparent biphasic distribution characterized by a rapid initial distribution phase followed by a slower elimination phase (FIG. 17).

Following a single I.V. bolus dose of anti-TGFβ3 h2A10.v4 at 10 mg/kg, mean clearance (CL) was 4.21 mL/day/kg, $C_{max}$ was 252 μg/mL, exposure (AUCinf) was 2470 day • μg/mL, terminal half-life ($t_{1/2}$, λz) was 16.0 days, volume of distribution at steady state ($V_{ss}$) was 79.1 mL/kg, respectively. 2A10.v4 demonstrated apparent biphasic distribution characterized by a rapid initial distribution phase followed by a slower elimination phase.

The pharmacokinetics of anti-TGFβ3 variants h2A10.v3 and h2A10.v4 following a single I.V. bolus administration at 10 mg/kg was as expected for a human IgG1 monoclonal antibody in cynomolgus monkeys and similar to that of typical IgG1 and IgG4 monoclonal antibodies.

The PK data are summarized in Table 15, below.

TABLE 15

Results of cyno PK study

| PK Parameter | 2A10.v3; 10 mg/kg IV; (n = 4) | 2A10.v4 10 mg/kg IV; (n = 4) |
|---|---|---|
| $C_{max}$ (μg/mL) | 238 ± 2.26 | 252 ± 6.96 |
| AUCinf (day · μg/mL) | 2400 ± 539 | 2470 ± 559 |
| CL (mL/kg/day) | 4.35 ± 1.05 | 4.21 ± 0.952 |
| $t_{1/2}$, λz (day) | 15.1 ± 2.26 | 16.0 ± 5.63 |
| $V_{SS}$ (mL/kg) | 88.2 ± 6.40 | 79.1 ± 9.63 |

Example 8: Humanization of 4A11 (Dual-Specific Anti-TGFβ2/3 Antibody)

Materials and Methods:

Antibody Affinity Measurement by BIAcore

Binding affinity determinations of all humanized 4A11 antibodies were performed using SPR measurement with a BIAcore™-T200 instrument, as described above in Example 6 (2A11 Ab example).

HEKBlue Cell-Based TGFβ Blocking Assay

HEKBlue cell-based TGFβ3 blocking assay was performed as described above in Example 6.

Results:

Humanization of 4A11:

4A11 Humanization Step 1: Grafting Rabbit 4A11 CDRs onto Human Frameworks:

Rabbit B-cell derived monoclonal antibody 4A11 was humanized as described below. Residue numbers are according to Kabat et al., *Sequences of proteins of immunological interest,* 5th Ed., Public Health Service, National Institutes of Health, Bethesda, Md. (1991).

The variable regions of the rabbit 4A11 (Rbt 4A11) antibody were first aligned with all human germlines. Four light chain human germlines (IGKV4-1, IGKV1D-39, IGKV3-20, IGKV2-24) and two heavy chain human germlines (IGHV3-48, IGHV4-59) were identified as the closest acceptor frameworks for grafting Rbt 4A11 light chain and heavy chain hypervariable regions (CDRs) respectively. Specifically, from Rbt 4A11 light chain variable domain (VL), positions 24-34 (L1), 50-56 (L2) and 89-97 (L3) were grafted into IGKV4-1, IGKV1D-39, IGKV3-20 and IGKV2-24. From Rbt 4A11 heavy chain variable domain (VH), positions 26-35 (H1), 50-65 (H2) and 95-102 (H3) were grafted into IGHV3-48 and IGHV4-59 respectively.

Eight humanized variants were generated by shuffling different grafting acceptor frameworks: Humanized 4A11 version 1 (h4A11.v1) is by IGKV4-1 and IGHV3-48; humanized 4A11 version 2 (h4A11.v2) is by IGKV1D-39 and IGHV3-48; humanized 4A11 version 3 (h4A11.v3) is by IGKV4-1 and IGHV4-59; humanized 4A11 version 4 (h4A11.v4) is by IGKV1D-39 and IGHV4-59; humanized 4A11 version 5 (h4A11.v5) is by IGKV3-20 and IGHV3-48; humanized 4A11 version 6 (h4A11.v6) is by IGKV2-24 and IGHV3-48; humanized 4A11 version 7 (h4A11.v7) is by IGKV3-20 and IGHV4-59; humanized 4A11 version 8 (h4A11.v8) is by IGKV2-24 and IGHV4-59 (Table 16).

In addition to CDRs grafted onto the closest acceptor frameworks described above, further modifications were made as follows:

Light Chain Framework:

h4A11.v1 and h4A11.v3 used the same IGKV4-1 acceptor framework, retained rabbit residues at position 2 and 4 in framework I and position 36 in framework II of VL from Rbt 4A11.

h4A11.v2 and h4A11.v4 used the same IGKV1D-39 acceptor framework, retained rabbit residues at position 2 and 4 in framework I and position 36 and 43 in framework II of VL from Rbt 4A11.

h4A11.v5 and h4A11.v7 used the same IGKV3-20 acceptor framework, retained rabbit residues at position 2 in framework I, position 36 and 43 in framework II and position 58 in framework III of VL from Rbt 4A11.

h4A11.v6 and h4A11.v8, used the same IGKV2-24 acceptor framework, retained rabbit residues at position 2 and 4 in framework I and position 36 in framework II of VL from Rbt 4A11.

Heavy Chain Framework:

h4A11.v1, h4A11.v2, h4A11.v5, h4A11.v6, used the same IGHV3-48 acceptor framework, retained rabbit residues at position 2 and 24 in framework I, position 48 and 49 in framework II, position 71, 73, 78 and 91 in framework III and position 105 in framework IV of VH from Rbt 4A11.

h4A11.v3, h4A11.v4, h4A11.v7, h4A11.v8, used the same IGHV4-59 acceptor framework, retained rabbit residues at position 2 in framework I, position 37 in framework II, position 67, 71, 73, 78 and 91 in framework III and position 105 in framework IV of VH from Rbt 4A11.

All of these residues were found to be the part of framework residues acting as "Vernier" zone, which may adjust CDR structure and fine-tune the antigen fit. See, e.g., Foote and Winter, *J. Mol. Biol.* 224: 487-499 (1992). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. *J. Mol. Biol.* 262: 732-745 (1996)).

All eight humanized 4A11 variants were further subjected to BIAcore for human TGFβ isoforms binding affinity determination and HEKBlue cell-based assay for human TGFβ isoforms blocking potency assessment. Although there was some drop (3-10 fold) in human TGFβ2&3 binding for most of the variants, the degree of drop in human TGFβ2&3 blocking were more pronounced and significant (Table 16). In all of the eight humanized versions, only h4A11.v7 retained comparable human TGFβ2&3 blocking compared to Rbt 4A11 despite a few fold drop in human TGFβ2&3 binding. Therefore, this clone was moved forward for the next step of humanization, framework polishing.

TABLE 16

4A11 humanization step 1 variants characterization summary

| 4A11 variants humanized | Human Framework | BIAcore (pM) TGFβ1 | TGFβ2 | TGFβ3 | HEKBlue TGFP blocking IC50 (nM) TGFβ1 | TGFβ2 | TGFβ3 |
|---|---|---|---|---|---|---|---|
| Rbt 4A11 | — | >5000 | 1.6 | ≤1.2 | >200 | 0.09 | 0.06 |
| h4A11.v1 | $K_{4-1}H_{3-48}$ | >5000 | 4.6 | 14.4 | >200 | >200 | >200 |
| h4A11.v2 | $K_{1D-39}H_{3-48}$ | >5000 | 1.4 | 13.3 | >200 | >200 | >200 |
| h4A11.v3 | $K_{4-1}H_{4-59}$ | >5000 | 9.6 | 12.1 | >200 | 3.9 | 0.23 |
| h4A11.v4 | $K_{1D-39}H_{4-59}$ | >5000 | 10.0 | 10.1 | >200 | 1.9 | 0.08 |
| h4A11.v5 | $K_{3-20}H_{3-48}$ | >5000 | 12.1 | 13.9 | >200 | >200 | 1.4 |
| h4A11.v6 | $K_{2-24}H_{3-48}$ | >5000 | 8.4 | 12.5 | >200 | >200 | 6.7 |
| h4A11.v7 | $K_{3-20}H_{4-59}$ | >5000 | 6.3 | 9.7 | >200 | 0.09 | 0.03 |
| h4A11.v8 | $K_{2-24}H_{4-59}$ | >5000 | 8.2 | 14.1 | >200 | >200 | 0.66 |

4A11 Humanization Step 2: h4A11.v7 Framework Polishing:

In framework polishing of h4A11.v7, three variants (v7.1-v7.3) were generated to delete the amino acid insertion being introduced from the step 1 humanization. Next, other humanized variants were generated by substituting each rabbit residue of h4A11.v7 at Vernier zone with the corresponding human germline residues (v7.4-v7.15). To determine which residues were necessary to be retained, binding to TGFβ isoforms of each variant was then evaluated by BIAcore and blocking potency was assessed in HEKBlue cell-based assay.

In h4A 11.v7, these framework polishing variants are h4A 11.v7.1 (VH: Delete E1), h4A11.v7.2 (VH: Delete K75 and N76), h4A11.v7.3 (VH: Delete E1, K75 and N76), h4A11.v7.4 (VL: A2I), h4A11.v7.5 (VL: F36Y), h4A11.v7.6 (VL: P43A), h4A11.v7.7 (VL: V581), h4A11.v7.8 (VH: Q2V), h4A11.v7.9 (VH: V37I), h4A11.v7.10 (VH: F67V), h4A11.v7.11 (VH: K71V), h4A11.v7.12 (VH: S73T), h4A11.v7.13 (VH: V78F), h4A11.v7.14 (VH: F91Y), h4A11.v7.15 (VH: P105Q) (Table 17).

Most of the variants appeared to be similar or slightly improved in comparison with parental h4A11.v7 in binding and potency assay, except for the major impact on h4A11.v7.11 (VH: K71V) with some drop in TGFβ2 binding (6-fold) and TGFβ3 binding (2-fold), and significantly, more loss in TGFβ2 blocking (>2000-fold) and TGFβ3 blocking (118-fold). There was one variant with minor impact: h4A11.v7.5 (VL: F36Y) with near 2-fold drop in both TGFβ2 binding and blocking, and two variants with sub-minor impact: h4A11.v7.13 (VH: V78F) with 2.5-fold drop in TGFβ2 binding; h4A11.v7.14 (VH: F91Y) with 4-fold drop in TGFβ2 blocking (Table 17). In summary, it was determined that all rabbit residues at Vernier zone of h4A11.v7 could be replaced with human germline residues, except for major position 71 in framework III of VH, minor position 36 in framework II of VL and/or sub-minor position 78 and 91 in framework III of VH.

TABLE 17

4A11 humanization step 2 variants characterization summary

| h4A11.v7 variants | Human Framework | Framework mutation | BIAcore (pM) TGFβ1 | BIAcore (pM) TGFβ2 | BIAcore (pM) TGFβ3 | HEKBlue TGFβ3 blocking IC50 (nM) TGFβ1 | HEKBlue TGFβ3 blocking IC50 (nM) TGFβ2 | HEKBlue TGFβ3 blocking IC50 (nM) TGFβ3 |
|---|---|---|---|---|---|---|---|---|
| Rbt 4A11 | | — | >5000 | 1.6 | ≤1.2 | >200 | 0.09 | 0.06 |
| h4A11.v7 | $K_{3-20}H_{4-59}$ | — | >5000 | 6.3 | 9.7 | >200 | 0.09 | 0.03 |
| h4A11.v7.1 | $K_{3-20}H_{4-59}$ | HC: Delete E1 | na | na | na | >33 | 0.09 | 0.03 |
| h4A11.v7.2 | $K_{3-20}H_{4-59}$ | HC: Delete K75 & N76 | na | na | na | >33 | 0.03 | 0.01 |
| h4A11.v7.3 | $K_{3-2}0H_{4-59}$ | HC: Delete E1, K75 & N76 | na | na | na | >33 | 0.03 | 0.03 |
| h4A11.v7.4 | $K_{3-20}H_{4-59}$ | LC: A2I | >5000 | 6.4 | 4.3 | >200 | 0.01 | 0.05 |
| h4A11.v7.5 | $K_{3-20}H_{4-59}$ | LC: F36Y | >5000 | 9.2 | 9.3 | >200 | 0.16 | 0.04 |
| h4A11.v7.6 | $K_{3-20}H_{4-59}$ | LC: P43A | >5000 | 5.8 | 6.5 | >200 | 0.01 | 0.01 |
| h4A11.v7.7 | $K_{3-20}H_{4-59}$ | LC: V58I | >5000 | 6.3 | 6.1 | >200 | 0.04 | 0.04 |
| h4A11.v7.8 | $K_{3-20}H_{4-59}$ | HC: Q2V | >5000 | 4.5 | 5.3 | >200 | 0.06 | 0.03 |
| h4A11.v7.9 | $K_{3-20}H_{4-59}$ | HC: V37I | >5000 | 4.9 | 5.7 | >200 | 0.08 | 0.02 |
| h4A11.v7.10 | $K_{3-20}H_{4-59}$ | HC: F67V | >5000 | 5.6 | 6.8 | >200 | 0.02 | 0.02 |
| h4A11.v7.11 | $K_{3-20}H_{4-59}$ | HC: K71V | >5000 | 40.1 | 21.4 | >200 | >200 | 3.53 |
| h4A11.v7.12 | $K_{3-20}H_{4-59}$ | HC: S73T | >5000 | 6.0 | 6.5 | >200 | 0.01 | 0.03 |
| h4A11.v7.13 | $K_{3-20}H_{4-59}$ | HC: V78F | >5000 | 15.9 | 8.9 | >200 | 0.03 | 0.05 |
| h4A11.v7.14 | $K_{3-20}H_{4-59}$ | HC: F91Y | >5000 | 4.9 | 5.5 | >200 | 0.35 | 0.04 |
| h4A11.v7.15 | $K_{3-20}H_{4-59}$ | HC: P105Q | >5000 | 4.7 | 4.8 | >200 | 0.09 | 0.02 |

4A11 Humanization Step 3: Final Version Generation and Selection

According to the results from h4A11.v7 framework polishing, h4A11.v7.18 was first generated by replacing h4A11.v7 non-crucial framework residues at Vernier zone with the corresponding human germline residues, which were A to I at position 2 in framework, P to A at position 43 in framework II and V to I at position 58 in framework III of VL, and Q to V at position 2 in framework I, V to I at position 37 in framework II, F to V at position 67 in framework III, S to T at position 73 in framework III, P to Q at position 105 in framework IV of VH (Table 18). Together with all the above substitutions, two other subminor framework residues in h4A11.v7, V78 or F91 in framework III of VH, were also replaced with the corresponding human germline residues to generate the other 2 humanized versions, h4A11.v7.16 (VH: V78F) and h4A11.v7.17 (VH: F91Y). One more humanized version, h4A11.v7.19, was generated by incorporating the deletion of K75 and N76 in framework III of VH, which was beneficial in improving TGFβ2 & 3 blocking in the framework polishing of h4A11.v7 (Table 17, above: h4A>1.v7.2 and h4A>1.v7.3).

By comparison of all 4 final humanized versions, interestingly, only h4A11.v7.19 appeared to be superior than h4A11.v7 and comparable to parental Rbt 4A11 not only in human TGFβ2 and TGFβ3 binding, but also in human TGFβ2 and TGFβ3 blocking.

TABLE 18

4A11 humanization step 3 variants characterization summary

| h4A11.v7 variants | Human Framework | Framework mutation | BIAcore (pM) TGFβ1 | BIAcore (pM) TGFβ2 | BIAcore (pM) TGFβ3 | HEKBlue TGFβ3 blocking IC50 (nM) TGFβ1 | HEKBlue TGFβ3 blocking IC50 (nM) TGFβ2 | HEKBlue TGFβ3 blocking IC50 (nM) TGFβ3 |
|---|---|---|---|---|---|---|---|---|
| Rbt 4A11 | | — | >5000 | 1.6 | ≤1.2 | >200 | 0.09 | 0.06 |
| h4A11.v7 | $K_{3-20}H_{4-59}$ | — | >5000 | 6.3 | 9.7 | >200 | 0.09 | 0.03 |
| h4A11.v7.16 | $K_{3-20}H_{4-59}$ | LC: A2I, P43A, V58I HC: Q2V, V37I, F67V, S73T, V78F, P105Q | >5000 | 4.9 | 6.6 | >200 | 0.09 | 0.13 |
| h4A11.v7.17 | $K_{3-20}H_{4-59}$ | LC:A2I, P43A, V58I HC: Q2V, V371, F67V, S73T, F91Y, P105Q | >5000 | ≤1.3 | 3.2 | >200 | 0.16 | 0.17 |
| h4A11.v7.18 | $K_{3-20}H_{4-59}$ | LC:A2I, P43A, V58I HC: Q2V, V37I, F67V, S73T, P105Q | >5000 | ≤1.1 | 4.6 | >200 | 0.09 | 0.11 |
| h4A11.v7.19 | $K_{3-20}H_{4-59}$ | LC: A2I, P43A, V58I HC: Q2V, V37I, F67V, S73T, Delete $K^{75}N^{76}$, P105Q | >5000 | ≤1.0 | ≤1.3 | >200 | 0.05 | 0.09 |

The amino acids sequences of the 4A11 variants are provided in Table 19 and Table 20, below, and sequence alignments are shown in FIG. 18, FIG. 19, FIG. 20, and FIG. 21.

TABLE 19

Heavy and Light Chain Variable Region Amino Acid Sequences of Humanized 4A11 Variants

| | VH | VL |
|---|---|---|
| h4A11.v1 | EQQLVESGGGLVQPGGSLRLSCAVS GFSLSSYTVNWVRQAPGKGLEWIG YISYGGSAYYASWANGRFTISKDSA KNSVYLQMNSLRAEDTAVYFCARH MQVGGAPTGSMAAFDPWGPGTLVT VSS (SEQ ID NO: 81) | DAVLTQSPDSLAVSLGERATINCQ SSQSVYNNNYLSWFQQKPGQPPK LLIYGASTLTSGVPDRFSGSGSGT DFTLTISSLQAEDVAVYYCAGGY SGSSDKYAFGGGTKVEIK (SEQ ID NO: 80) |
| h4A11.v2 | Same as v1 (SEQ ID NO: 81) | DAQLTQSPSSLSASVGDRVTITCQ SSQSVYNNNYLSWFQQKPGKPPK LLIYGASTLTSGVPSRFSGSGSGT DFTLTISSLQPEDFATYYCAGGYS GSSDKYAFGGGTKVEIK (SEQ ID NO: 82) |
| h4A11.v3 | EQQLQESGPGLVKPSETLSLTCTVTG FSLSSYTVNWVRQPAGKGLEWIGYI SYGGSAYYASWANGRFTISKDSSKN QVSLKLSSVTAADTAVYFCARHMQ VGGAPTGSMAAFDPWGPGTLVTVS S (SEQ ID NO: 83) | Same as v1 (SEQ ID NO: 80) |
| h4A11.v4 | Same as v3 (SEQ ID NO: 83) | Same as v2 (SEQ ID NO: 82) |
| h4A11.v5 | Same as v1 (SEQ ID NO: 81) | EAVLTQSPGTLSLSPGERATLSCQ SSQSVYNNNYLSWFQQKPGQPPR LLIYGASTLTSGVPDRFSGSGSGT DFTLTISRLEPEDFAVYYCAGGYS GSSDKYAFGGGTKVEIK (SEQ ID NO: 84) |
| h4A11.v6 | Same as v1 (SEQ ID NO: 81) | DAVLTQTPLSSPVTLGQPASISCQ SSQSVYNNNYLSWFQQKPGQPPR LLIYGASTLTSGVPDRFSGSGAGT DFTLKISRVEAEDVGVYYCAGGY SGSSDKYAFGGGTKVEIK (SEQ ID NO: 85) |
| h4A11.v7 | Same as V3 (SEQ ID NO: 83) | Same as v5 (SEQ ID NO: 84) |
| h4A11.v7. 1 | QQLQESGPGLVKPSETLSLTCTVTGF SLSSYTVNWVRQPAGKGLEWIGYIS YGGSAYYASWANGRFTISKDSSKNQ VSLKLSSVTAADTAVYFCARHMQV GGAPTGSMAAFDPWGPGTLVTVSS (SEQ ID NO: 86) | Same as v5 (SEQ ID NO: 84) |
| h4A11.v7. 2 | EQQLQESGPGLVKPSETLSLTCTVTG FSLSSYTVNWVRQPAGKGLEWIGYI SYGGSAYYASWANGRFTISKDSSQV SLKLSSVTAADTAVYFCARHMQVG GAPTGSMAAFDPWGPGTLVTVSS (SEQ ID NO: 87) | Same as v5 (SEQ ID NO: 84) |
| h4A11.v7. 3 | QQLQESGPGLVKPSETLSLTCTVTGF SLSSYTVNWVRQPAGKGLEWIGYIS YGGSAYYASWANGRFTISKDSSQVS LKLSSVTAADTAVYFCARHMQVGG APTGSMAAFDPWGPGTLVTVSS (SEQ ID NO: 88) | Same as v5 (SEQ ID NO: 84) |
| h4A11.v7. 4 | Same as v3 (SEQ ID NO: 83) | EIVLTQSPGTLSLSPGERATLSCQS SQSVYNNNYLSWFQQKPGQPPRL LIYGASTLTSGVPDRFSGSGSGTD FTLTISRLEPEDFAVYYCAGGYSG SSDKYAFGGGTKVEIK (SEQ ID NO: 89) |

TABLE 19-continued

| Heavy and Light Chain Variable Region Amino Acid Sequences of Humanized 4A11 Variants | | |
|---|---|---|
| | VH | VL |
| h4A11.v7.5 | Same as v3 (SEQ ID NO: 83) | EAVLTQSPGTLSLSPGERATLSCQSSQSVYNNNYLSWYQQKPGQPPRLLIYGASTLTSGVPDRFSGSGSGTDFTLTISRLEPEDFAVYYCAGGYSGSSDKYAFGGGTKVEIK (SEQ ID NO: 90) |
| h4A11.v7.6 | Same as v3 (SEQ ID NO: 83) | EAVLTQSPGTLSLSPGERATLSCQSSQSVYNNNYLSWFQQKPGQAPRLLIYGASTLTSGVPDRFSGSGSGTDFTLTISRLEPEDFAVYYCAGGYSGSSDKYAFGGGTKVEIK (SEQ ID NO: 91) |
| h4A11.v7.7 | Same as v3 (SEQ ID NO: 83) | EAVLTQSPGTLSLSPGERATLSCQSSQSVYNNNYLSWFQQKPGQPPRLLIYGASTLTSGIPDRFSGSGSGTDFTLTISRLEPEDFAVYYCAGGYSGSSDKYAFGGGTKVEIK (SEQ ID NO: 92) |
| h4A11.v7.8 | EVQLQESGPGLVKPSETLSLTCTVTGFSLSSYTVNWVRQPAGKGLEWIGYISYGGSAYYASWANGRFTISKDSSKNQVSLKLSSVTAADTAVYFCARHMQVGGAPTGSMAAFDPWGPGTLVTVSS (SEQ ID NO: 93) | Same as v5 (SEQ ID NO: 84) |
| h4A11.v7.9 | EQQLQESGPGLVKPSETLSLTCTVTGFSLSSYTVNWIRQPAGKGLEWIGYISYGGSAYYASWANGRFTISKDSSKNQVSLKLSSVTAADTAVYFCARHMQVGGAPTGSMAAFDPWGPGTLVTVSS (SEQ ID NO: 94) | Same as v5 (SEQ ID NO: 84) |
| h4A11.v7.10 | EQQLQESGPGLVKPSETLSLTCTVTGFSLSSYTVNWVRQPAGKGLEWIGYISYGGSAYYASWANGRVTISKDSSKNQVSLKLSSVTAADTAVYFCARHMQVGGAPTGSMAAFDPWGPGTLVTVSS (SEQ ID NO: 95) | Same as v5 (SEQ ID NO: 84) |
| h4A11.v7.11 | EQQLQESGPGLVKPSETLSLTCTVTGFSLSSYTVNWVRQPAGKGLEWIGYISYGGSAYYASWANGRFTISVDSSKNQVSLKLSSVTAADTAVYFCARHMQVGGAPTGSMAAFDPWGPGTLVTVSS (SEQ ID NO: 96) | Same as v5 (SEQ ID NO: 84) |
| h4A11.v7.12 | EQQLQESGPGLVKPSETLSLTCTVTGFSLSSYTVNWVRQPAGKGLEWIGYISYGGSAYYASWANGRFTISKDTSKNQVSLKLSSVTAADTAVYFCARHMQVGGAPTGSMAAFDPWGPGTLVTVSS (SEQ ID NO: 97) | Same as v5 (SEQ ID NO: 84) |
| h4A11.v7.13 | EQQLQESGPGLVKPSETLSLTCTVTGFSLSSYTVNWVRQPAGKGLEWIGYISYGGSAYYASWANGRFTISKDSSKNQFSLKLSSVTAADTAVYFCARHMQVGGAPTGSMAAFDPWGPGTLVTVSS (SEQ ID NO: 98) | Same as v5 (SEQ ID NO: 84) |
| h4A11.v7.14 | EQQLQESGPGLVKPSETLSLTCTVTGFSLSSYTVNWVRQPAGKGLEWIGYISYGGSAYYASWANGRFTISKDSSKNQVSLKLSSVTAADTAVYYCARHMQVGGAPTGSMAAFDPWGPGTLVTVSS (SEQ ID NO: 99) | Same as v5 (SEQ ID NO: 84) |

TABLE 19-continued

Heavy and Light Chain Variable Region Amino Acid Sequences of Humanized 4A11 Variants

| | VH | VL |
|---|---|---|
| h4A11.v7.15 | EQQLQESGPGLVKPSETLSLTCTVTGFSLSSYTVNWVRQPAGKGLEWIGYISYGGSAYYASWANGRFTISKDSSKNQVSLKLSSVTAADTAVYFCARHMQVGGAPTGSMAAFDPWGQGTLVTVSS (SEQ ID NO: 100) | Same as v5 (SEQ ID NO: 84) |
| h4A11.v7.16 | EVQLQESGPGLVKPSETLSLTCTVTGFSLSSYTVNWIRQPAGKGLEWIGYISYGGSAYYASWANGRVTISKDTSKNQFSLKLSSVTAADTAVYFCARHMQVGGAPTGSMAAFDPWGQGTLVTVSS (SEQ ID NO: 102) | EIVLTQSPGTLSLSPGERATLSCQSSQSVYNNNYLSWFQQKPGQAPRLLIYGASTLTSGIPDRFSGSGSGTDFTLTISRLEPEDFAVYYCAGGYSGSSDKYAFGGGTKVEIK (SEQ ID NO: 101) |
| h4A11.v7.17 | EVQLQESGPGLVKPSETLSLTCTVTGFSLSSYTVNWIRQPAGKGLEWIGYISYGGSAYYASWANGRVTISKDTSKNQVSLKLSSVTAADTAVYYCARHMQVGGAPTGSMAAFDPWGQGTLVTVSS (SEQ ID NO: 103) | Same as v7.16 (SEQ ID NO: 101) |
| h4A11.v7.18 | EVQLQESGPGLVKPSETLSLTCTVTGFSLSSYTVNWIRQPAGKGLEWIGYISYGGSAYYASWANGRVTISKDTSKNQVSLKLSSVTAADTAVYFCARHMQVGGAPTGSMAAFDPWGQGTLVTVSS (SEQ ID NO: 104) | Same as v7.16 (SEQ ID NO: 101) |
| h4A11.v7.19 | EVQLQESGPGLVKPSETLSLTCTVTGFSLSSYTVNWIRQPAGKGLEWIGYISYGGSAYYASWANGRVTISKDTSQVSLKLSSVTAADTAVYFCARHMQVGGAPTGSMAAFDPWGQGTLVTVSS (SEQ ID NO: 105) | Same as v7.16 (SEQ ID NO: 101) |
| h4A11.v8 | Same as v3 (SEQ ID NO: 83) | Same as v6 (SEQ ID NO: 85) |

TABLE 20

Complete Heavy and Light Chain Sequences of Humanized 4A11 Variants

| | Complete H Chain | Complete L Chain |
|---|---|---|
| h4A11.v1 | EQQLVESGGGLVQPGGSLRLSCAVSGFSLSSYTVNWVRQAPGKGLEWIGYISYGGSAYYASWANGRFTISKDSAKNSVYLQMNSLRAEDTAVYFCARHMQVGGAPTGSMAAFDPWGPGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYGSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 107) | DAVLTQSPDSLAVSLGERATINCQSSQSVYNNNYLSWFQQKPGQPPKLLIYGASTLTSGVPDRFSGSGSGTDFTLTISSLQAEDVAVYYCAGGYSGSSDKYAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 106) |
| h4A11.v2 | Same as v1 (SEQ ID NO: 107) | DAQLTQSPSSLSASVGDRVTITCQSSQSVYNNNYLSWFQQKPGKPPKLLIYGASTLTSGVPSRFSGSGSGTDFTLTISSLQPEDFATYYCAGGYSGSSDKYAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 108) |

TABLE 20-continued

| Complete Heavy and Light Chain Sequences of Humanized 4A11 Variants | | |
|---|---|---|
| | Complete H Chain | Complete L Chain |
| h4A11. v3 | EQQLQESGPGLVKPSETLSLTCTVTGFSLSSY TVNWVRQPAGKGLEWIGYISYGGSAYYAS WANGRFTISKDSSKNQVSLKLSSVTAADTAV YFCARHMQVGGAPTGSMAAFDPWGPGTLV TVSSASTKGPSVFPLAPSSKSTSGGTAALGCL VKDYFPEPVTVSWNSGALTSGVHTFPAVLQS SGLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYGST YRVVSVLTVLHQDWLNGKEYKCKVSNKAL PAPIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK (SEQ ID NO: 109) | Same as v1 (SEQ ID NO: 106) |
| h4A11. v4 | Same as v3 (SEQ ID NO: 109) | Same as v2 (SEQ ID NO: 108) |
| h4A11. v5 | Same as v1 (SEQ ID NO: 107) | EAVLTQSPGTLSLSPGERATL SCQSSQSVYNNNYLSWFQQ KPGQPPRLLIYGASTLTSGVP DRFSGSGSGTDFTLTISRLEP EDFAVYYCAGGYSGSSDKY AFGGGTKVEIKRTVAAPSVFI FPPSDEQLKSGTASVVCLLN NFYPREAKVQWKVDNALQS GNSQESVTEQDSKDSTYSLS STLTLSKADYEKHKVYACE VTHQGLSSPVTKSFNRGEC (SEQ ID NO: 110) |
| h4A11. v6 | Same as v1 (SEQ ID NO: 107) | DAVLTQTPLSSPVTLGQPASI SCQSSQSVYNNNYLSWFQQ RPGQPPRLLIYGASTLTSGVP DRFSGSGAGTDFTLKISRVE AEDVGVYYCAGGYSGSSDK YAFGGGTKVEIKRTVAAPSV FIFPPSDEQLKSGTASVVCLL NNFYPREAKVQWKVDNALQ SGNSQESVTEQDSKDSTYSL SSTLTLSKADYEKHKVYACE VTHQGLSSPVTKSFNRGEC (SEQ ID NO: 111) |
| h4A11. v7 | Same as v3 (SEQ ID NO: 109) | Same as v5 (SEQ ID NO: 110) |
| h4A11. v7.1 | QQLQESGPGLVKPSETLSLTCTVTGFSLSSYT VNWVRQPAGKGLEWIGYISYGGSAYYASW ANGRFTISKDSSKNQVSLKLSSVTAADTAVY FCARHMQVGGAPTGSMAAFDPWGPGTLVT VSSASTKGPSVFPLAPSSKSTSGGTAALGCLV KDYFPEPVTVSWNSGALTSGVHTFPAVLQSS GLYSLSSVVTVPSSSLGTQTYICNVNHKPSNT KVDKKVEPKSCDKTHTCPPCPAPELLGGPSV FLFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 112) | Same as v5 (SEQ ID NO: 110) |
| h4A11. v7.2 | EQQLQESGPGLVKPSETLSLTCTVTGFSLSSY TVNWVRQPAGKGLEWIGYISYGGSAYYAS WANGRFTISKDSSQVSLKLSSVTAADTAVYF CARHMQVGGAPTGSMAAFDPWGPGTLVTV SSASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPELLGGPSVF LFPPKPKDTLMISRTPEVTCVVVDVSHEDPE | Same as v5 (SEQ ID NO: 110) |

TABLE 20-continued

Complete Heavy and Light Chain Sequences of Humanized 4A11 Variants

| | Complete H Chain | Complete L Chain |
|---|---|---|
| | VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 113) | |
| h4A11. v7.3 | QQLQESGPGLVKPSETLSLTCTVTGFSLSSYT VNWVRQPAGKGLEWIGYISYGGSAYYASW ANGRFTISKDSSQVSLKLSSVTAADTAVYFC ARHMQVGGAPTGSMAAFDPWGPGTLVTVS SASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 114) | Same as v5 (SEQ ID NO: 110) |
| h4A11. v7.4 | Same as v7.3 (SEQ ID NO: 114) | EIVLTQSPGTLSLSPGERATL SCQSSQSVYNNNYLSWFQQ KPGQPPRLLIYGASTLTSGVP DRFSGSGSGTDFTLTISRLEP EDFAVYYCAGGYSGSSDKY AFGGGTKVEIKRTVAAPSVFI FPPSDEQLKSGTASVVCLLN NFYPREAKVQWKVDNALQS GNSQESVTEQDSKDSTYSLS STLTLSKADYEKHKVYACE VTHQGLSSPVTKSFNRGEC (SEQ ID NO: 115) |
| h4A11. v7.5 | Same as v7.3 (SEQ ID NO: 114) | EAVLTQSPGTLSLSPGERATL SCQSSQSVYNNNYLSWYQQ KPGQPPRLLIYGASTLTSGVP DRFSGSGSGTDFTLTISRLEP EDFAVYYCAGGYSGSSDKY AFGGGTKVEIKRTVAAPSVFI FPPSDEQLKSGTASVVCLLN NFYPREAKVQWKVDNALQS GNSQESVTEQDSKDSTYSLS STLTLSKADYEKHKVYACE VTHQGLSSPVTKSFNRGEC (SEQ ID NO: 116) |
| h4A11. v7.6 | Same as v7.3 (SEQ ID NO: 114) | EAVLTQSPGTLSLSPGERATL SCQSSQSVYNNNYLSWFQQ KPGQAPRLLIYGASTLTSGVP DRFSGSGSGTDFTLTISRLEP EDFAVYYCAGGYSGSSDKY AFGGGTKVEIKRTVAAPSVFI FPPSDEQLKSGTASVVCLLN NFYPREAKVQWKVDNALQS GNSQESVTEQDSKDSTYSLS STLTLSKADYEKHKVYACE VTHQGLSSPVTKSFNRGEC (SEQ ID NO: 117) |
| h4A11. v7.7 | Same as v7.3 (SEQ ID NO: 114) | EAVLTQSPGTLSLSPGERATL SCQSSQSVYNNNYLSWFQQ KPGQPPRLLIYGASTLTSGIP DRFSGSGSGTDFTLTISRLEP EDFAVYYCAGGYSGSSDKY AFGGGTKVEIKRTVAAPSVFI FPPSDEQLKSGTASVVCLLN NFYPREAKVQWKVDNALQS GNSQESVTEQDSKDSTYSLS STLTLSKADYEKHKVYACE VTHQGLSSPVTKSFNRGEC (SEQ ID NO: 118) |

TABLE 20-continued

Complete Heavy and Light Chain Sequences of Humanized 4A11 Variants

| | Complete H Chain | Complete L Chain |
|---|---|---|
| h4A11. v7.8 | EVQLQESGPGLVKPSETLSLTCTVTGFSLSSY TVNWVRQPAGKGLEWIGYISYGGSAYYAS WANGRFTISKDSSKNQVSLKLSSVTAADTAV YFCARHMQVGGAPTGSMAAFDPWGPGTLV TVSSASTKGPSVFPLAPSSKSTSGGTAALGCL VKDYFPEPVTVSWNSGALTSGVHTFPAVLQS SGLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYGST YRVVSVLTVLHQDWLNGKEYKCKVSNKAL PAPIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK (SEQ ID NO: 119) | Same as v5 (SEQ ID NO: 110) |
| h4A11. v7.9 | EQQLQESGPGLVKPSETLSLTCTVTGFSLSSY TVNWIRQPAGKGLEWIGYISYGGSAYYASW ANGRFTISKDSSKNQVSLKLSSVTAADTAVY FCARHMQVGGAPTGSMAAFDPWGPGTLVT VSSASTKGPSVFPLAPSSKSTSGGTAALGCLV KDYFPEPVTVSWNSGALTSGVHTFPAVLQSS GLYSLSSVVTVPSSSLGTQTYICNVNHKPSNT KVDKKVEPKSCDKTHTCPPCPAPELLGGPSV FLFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 120) | Same as v5 (SEQ ID NO: 110) |
| h4A11. v7.10 | EQQLQESGPGLVKPSETLSLTCTVTGFSLSSY TVNWVRQPAGKGLEWIGYISYGGSAYYAS WANGRVTISKDSSKNQVSLKLSSVTAADTA VYFCARHMQVGGAPTGSMAAFDPWGPGTL VTVSSASTKGPSVFPLAPSSKSTSGGTAALGC LVKDYFPEPVTVSWNSGALTSGVHTFPAVL QSSGLYSLSSVVTVPSSSLGTQTYICNVNHKP SNTKVDKKVEPKSCDKTHTCPPCPAPELLGG PSVFLFPPKPKDTLMISRTPEVTCVVVDVSHE DPEVKFNWYVDGVEVHNAKTKPREEQYGS TYRVVSVLTVLHQDWLNGKEYKCKVSNKA LPAPIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMHEALHNHYTQKSLSLSPGK (SEQ ID NO: 121) | Same as v5 (SEQ ID NO: 110) |
| h4A11. v7.11 | EQQLQESGPGLVKPSETLSLTCTVTGFSLSSY TVNWVRQPAGKGLEWIGYISYGGSAYYAS WANGRFTISVDSSKNQVSLKLSSVTAADTAV YFCARHMQVGGAPTGSMAAFDPWGPGTLV TVSSASTKGPSVFPLAPSSKSTSGGTAALGCL VKDYFPEPVTVSWNSGALTSGVHTFPAVLQS SGLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYGST YRVVSVLTVLHQDWLNGKEYKCKVSNKAL PAPIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK (SEQ ID NO: 122) | Same as v5 (SEQ ID NO: 110) |
| h4A11. v7.12 | EQQLQESGPGLVKPSETLSLTCTVTGFSLSSY TVNWVRQPAGKGLEWIGYISYGGSAYYAS WANGRFTISKDTSKNQVSLKLSSVTAADTA VYFCARHMQVGGAPTGSMAAFDPWGPGTL VTVSSASTKGPSVFPLAPSSKSTSGGTAALGC LVKDYFPEPVTVSWNSGALTSGVHTFPAVL QSSGLYSLSSVVTVPSSSLGTQTYICNVNHKP | Same as v5 (SEQ ID NO: 110) |

TABLE 20-continued

Complete Heavy and Light Chain Sequences of Humanized 4A11 Variants

| | Complete H Chain | Complete L Chain |
|---|---|---|
| | SNTKVDKKVEPKSCDKTHTCPPCPAPELLGG PSVFLFPPKPKDTLMISRTPEVTCVVVDVSHE DPEVKFNWYVDGVEVHNAKTKPREEQYGS TYRVVSVLTVLHQDWLNGKEYKCKVSNKA LPAPIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMHEALHNHYTQKSLSLSPGK (SEQ ID NO: 123) | |
| h4A11. v7.13 | EQQLQESGPGLVKPSETLSLTCTVTGFSLSSY TVNWVRQPAGKGLEWIGYISYGGSAYYAS WANGRFTISKDSSKNQFSLKLSSVTAADTAV YFCARHMQVGGAPTGSMAAFDPWGPGTLV TVSSASTKGPSVFPLAPSSKSTSGGTAALGCL VKDYFPEPVTVSWNSGALTSGVHTFPAVLQS SGLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYGST YRVVSVLTVLHQDWLNGKEYKCKVSNKAL PAPIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK (SEQ ID NO: 124) | Same as v5 (SEQ ID NO: 110) |
| h4A11. v7.14 | EQQLQESGPGLVKPSETLSLTCTVTGFSLSSY TVNWVRQPAGKGLEWIGYISYGGSAYYAS WANGRFTISKDSSKNQVSLKLSSVTAADTAV YYCARHMQVGGAPTGSMAAFDPWGPGTLV TVSSASTKGPSVFPLAPSSKSTSGGTAALGCL VKDYFPEPVTVSWNSGALTSGVHTFPAVLQS SGLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYGST YRVVSVLTVLHQDWLNGKEYKCKVSNKAL PAPIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK (SEQ ID NO: 125) | Same as v5 (SEQ ID NO: 110) |
| h4A11. v7.15 | EQQLQESGPGLVKPSETLSLTCTVTGFSLSSY TVNWVRQPAGKGLEWIGYISYGGSAYYAS WANGRFTISKDSSKNQVSLKLSSVTAADTAV YFCARHMQVGGAPTGSMAAFDPWGQGTLV TVSSASTKGPSVFPLAPSSKSTSGGTAALGCL VKDYFPEPVTVSWNSGALTSGVHTFPAVLQS SGLYSLSSVVTVPSSSLGTQTYICNVNHKPSN TKVDKKVEPKSCDKTHTCPPCPAPELLGGPS VFLFPPKPKDTLMISRTPEVTCVVVDVSHED PEVKFNWYVDGVEVHNAKTKPREEQYGST YRVVSVLTVLHQDWLNGKEYKCKVSNKAL PAPIEKTISKAKGQPREPQVYTLPPSREEMTK NQVSLTCLVKGFYPSDIAVEWESNGQPENN YKTTPPVLDSDGSFFLYSKLTVDKSRWQQG NVFSCSVMHEALHNHYTQKSLSLSPGK (SEQ ID NO: 126) | Same as v5 (SEQ ID NO: 110) |
| h4A11. v7.16 | EVQLQESGPGLVKPSETLSLTCTVTGFSLSSY TVNWIRQPAGKGLEWIGYISYGGSAYYASW ANGRVTISKDTSKNQFSLKLSSVTAADTAVY FCARHMQVGGAPTGSMAAFDPWGQGTLVT VSSASTKGPSVFPLAPSSKSTSGGTAALGCLV KDYFPEPVTVSWNSGALTSGVHTFPAVLQSS GLYSLSSVVTVPSSSLGTQTYICNVNHKPSNT KVDKKVEPKSCDKTHTCPPCPAPELLGGPSV | EIVLTQSPGTLSLSPGERATL SCQSSQSVYNNNYLSWFQQ KPGQAPRLLIYGASTLTSGIP DRFSGSGSGTDFTLTISRLEP EDFAVYYCAGGYSGSSDKY AFGGGTKVEIKRTVAAPSVFI FPPSDEQLKSGTASVVCLLN NFYPREAKVQWKVDNALQS |

TABLE 20-continued

| Complete Heavy and Light Chain Sequences of Humanized 4A11 Variants | | |
|---|---|---|
| | Complete H Chain | Complete L Chain |
| | FLFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 127) | GNSQESVTEQDSKDSTYSLS STLTLSKADYEKHKVYACE VTHQGLSSPVTKSFNRGEC (SEQ ID NO: 186) |
| h4A11. v7.17 | EVQLQESGPGLVKPSETLSLTCTVTGFSLSSY TVNWIRQPAGKGLEWIGYISYGGSAYYASW ANGRVTISKDTSKNQVSLKLSSVTAADTAVY YCARHMQVGGAPTGSMAAFDPWGQGTLVT VSSASTKGPSVFPLAPSSKSTSGGTAALGCLV KDYFPEPVTVSWNSGALTSGVHTFPAVLQSS GLYSLSSVVTVPSSSLGTQTYICNVNHKPSNT KVDKKVEPKSCDKTHTCPPCPAPELLGGPSV FLFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 128) | Same as v7.16 (SEQ ID NO: 186) |
| h4A11. v7.18 | EVQLQESGPGLVKPSETLSLTCTVTGFSLSSY TVNWIRQPAGKGLEWIGYISYGGSAYYASW ANGRVTISKDTSKNQVSLKLSSVTAADTAVY FCARHMQVGGAPTGSMAAFDPWGQGTLVT VSSASTKGPSVFPLAPSSKSTSGGTAALGCLV KDYFPEPVTVSWNSGALTSGVHTFPAVLQSS GLYSLSSVVTVPSSSLGTQTYICNVNHKPSNT KVDKKVEPKSCDKTHTCPPCPAPELLGGPSV FLFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 129) | Same as v7.16 (SEQ ID NO: 186) |
| h4A11. v7.19 | EVQLQESGPGLVKPSETLSLTCTVTGFSLSSY TVNWIRQPAGKGLEWIGYISYGGSAYYASW ANGRVTISKDTSQVSLKLSSVTAADTAVYFC ARHMQVGGAPTGSMAAFDPWGQGTLVTVS SASTKGPSVFPLAPSSKSTSGGTAALGCLVK DYFPEPVTVSWNSGALTSGVHTFPAVLQSSG LYSLSSVVTVPSSSLGTQTYICNVNHKPSNTK VDKKVEPKSCDKTHTCPPCPAPELLGGPSVF LFPPKPKDTLMISRTPEVTCVVVDVSHEDPE VKFNWYVDGVEVHNAKTKPREEQYGSTYR VVSVLTVLHQDWLNGKEYKCKVSNKALPA PIEKTISKAKGQPREPQVYTLPPSREEMTKNQ VSLTCLVKGFYPSDIAVEWESNGQPENNYKT TPPVLDSDGSFFLYSKLTVDKSRWQQGNVFS CSVMHEALHNHYTQKSLSLSPGK (SEQ ID NO: 130) | Same as v7.16 (SEQ ID NO: 186) |
| h4A11. v8 | Same as v7.3 (SEQ ID NO: 114) | Same as v6 (SEQ ID NO: 111) |

Example 9: Humanization of 6F12 (anti-TGFβ2)

Materials and Methods:

Antibody Affinity Measurement by BIAcore

Binding affinity determinations of all humanized 4A11 antibodies were performed using SPR measurement with a BIAcore™-T200 instrument, as described above in Example 6 (2A11 Ab example).

HEKBlue Cell-Based TGFβ Blocking Assay

HEKBlue cell-based TGFβ3 blocking assay was performed as described above in Example 6.

Results:

6F12 Humanization Step 1: Rat 6F12 CDRs Grafting into Human Frameworks

Monoclonal antibody 6F12 was humanized as described below. Residue numbers are according to Kabat et al. supra.

The variable regions of the rat 6F12 (r6F12) antibody were first aligned with all human germlines. Two light chain human germlines (IGKV1-5, IGKV3-15) and two heavy chain human germlines (IGHV2-26, IGHV4-59) were identified as the closest acceptor frameworks for grafting r6F12 light chain and heavy chain hypervariable regions (CDRs) respectively. Specifically, from r6F12 light chain variable domain (VL), positions 24-34 (L1), 50-56 (L2) and 89-97 (L3) were grafted into IGKV1-5 and IGKV3-15. From r6F12 heavy chain variable domain (VH), positions 26-35 (H1), 50-65 (H2) and 95-102 (H3) were grafted into IGHV2-26 and IGHV4-59 respectively.

Furthermore, total four humanized variants were generated by shuffling different grafting acceptor frameworks: Humanized 6F12 version 1 (h6F12.v1) is by IGKV1-5 and IGHV2-26; humanized 6F12 version 2 (h6F12.v2) is by IGKV1-5 and IGHV4-59; humanized 6F12 version 3 (h6F12.v3) is by IGKV3-15 and IGHV2-26; humanized 6F12 version 4 (h6F12.v4) is by IGKV3-15 and IGHV4-59. In addition to CDRs graft onto the closest acceptor frameworks described above, for light chain framework, h6F12.v1 and h6F12.v2, used the same IGKV1-5 acceptor framework, retained rat residues at position 43 in framework II and position 66, 69, 71 and 87 in framework III of VL from r6F12; h6F12.v3 and h6F12.v4, used the same IGKV3-15 acceptor framework, retained rat residues at position 43 in framework II and position 58, 66, 69, 71 and 87 in framework III of VL from r6F12. For heavy chain framework, h6F12.v1 and h6F12.v3, used the same IGHV2-26 acceptor framework, retained rat residues at position 37, 48 and 49 in framework II and position 105 in framework IV of VH from r6F12; h6F12.v2 and h6F12.v4, used the same IGHV4-59 acceptor framework, retained rat residues at position 37 and 48 in framework II, position 67, 71 and 78 in framework III and position 105 in framework IV of VH from r6F12. All of these residues were found to be the part of framework residues acting as "Vernier" zone, which may adjust CDR structure and fine-tune the antigen fit. See, e.g., Foote and Winter, *J. Mol. Biol.* 224: 487-499 (1992). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. J. Mol. Biol. 262: 732-745 (1996)).

All 4 humanized 6F12 variants were further subject to BIAcore for human TGFβ isoforms binding affinity determination and HEKBlue cell-based assay for human TGFβ isoforms blocking potency assessment. In BIAcore analysis, although all 4 humanized 6F12 variants showed selective and similar binding to human TGFβ2 comparable to parental r6F12, the binding affinities were beyond the instrument detection limit, and therefore the results could not be used to determine which variant to move forward. Interestingly, in HEKBlue cell-based potency assay, the results indicated there were about 2.5-5 fold drop in blocking human TGFβ2 for all variants, except for h6F12.v3 (Table 21).

TABLE 21

6F12 humanization step 1 variants characterization summary

| 6F12 humanized variants | Human Framework | BIAcore (pM) | | | HEKBlue TGFP blocking IC50 (nM) | | |
|---|---|---|---|---|---|---|---|
| | | TGFβ1 | TGFβ2 | TGFβ3 | TGFβ1 | TGFβ2 | TGFβ3 |
| r6F12 | — | >5000 | <0.5 | >5000 | >200 | 0.004 | >200 |
| h6F12.v1 | $K_{1\text{-}5}H_{2\text{-}26}$ | >5000 | <0.5 | >5000 | >200 | 0.02 | >200 |
| h6F12.v2 | $K_{1\text{-}5}H_{4\text{-}59}$ | >5000 | <0.5 | >5000 | >200 | 0.01 | >200 |
| h6F12.v3 | $K_{3\text{-}15}H_{2\text{-}26}$ | >5000 | <0.5 | >5000 | >200 | 0.005 | >200 |
| h6F12.v4 | $K_{3\text{-}15}H_{4\text{-}59}$ | >5000 | <0.5 | >5000 | >200 | 0.02 | >200 |

6F12 Humanization Step 2: h6F12.v1 Framework Polishing

In humanized 6F12 framework polishing, more humanized 6F12 variants were generated by substituting each rat residue of h6F12.v1 at Vernier zone with corresponding human residue from germline sequence. Each variant was not evaluated by BIAcore due to instrument limitations, but by HEKBlue cell-based assay to determine human TGFβ isoform blocking potency.

These framework polishing variants are h6F12.v1.1 (VL: S43A), h6F12.v1.2 (VL: E66G), h6F12.v1.3 (VL: P69T), h6F12.v1.4 (VL: Y71F), h6F12.v1.5 (VL: F87Y), h6F12.v1.6 (VH: V37I), h6F12.v1.7 (VH: M48L), h6F12.v1.8 (VH: G49A) and h6F12.v1.9 (VH: P105R). Most of the variants appeared to be similar or slightly improved in comparison with parental h6F12.v1 in the potency assay, except for the major impact on h6F12.v1.6 (VH: V37I) and h6F12.v1.9 (VH: P105R) with some drop in TGFβ2 blocking about 5-8 fold. There were two variants with minor impact: h6F12.v1.5 (VL: F87Y) with 2-fold drop and h6F12.v1.8 (VH: G49A) with 4-fold drop in TGFβ2 blocking respectively (Table 22). In summary, we determined that all rat residues at Vernier zone of h6F12.v1 can be replaced with human germline residues, except for major position 37 in framework II and position 105 in framework IV of VH, and minor position 87 in framework III of VL and position 49 in framework II of VH.

TABLE 22

| 6F12 humanization step 2 variants characterization summary | | | | | |
|---|---|---|---|---|---|
| h6F12.v1 | Human | Framework | HEKBlue TGFβ blocking IC50 (nM) | | |
| variants | Framework | mutation | TGFβ1 | TGFβ2 | TGFβ3 |
| Rat 6F12 | | | >200 | 0.004 | >200 |
| h6F12.v1 | $K_{1-5}$ $H_{2-26}$ | | >200 | 0.02 | >200 |
| h6F12.v1.1 | $K_{1-5}$ $H_{2-26}$ | LC:S43A | >200 | 0.02 | >200 |
| h6F12.v1.2 | $K_{1-5}$ $H_{2-26}$ | LC:E66G | >200 | 0.02 | >200 |
| h6F12.v1.3 | $K_{1-5}$ $H_{2-26}$ | LC:P69T | >200 | 0.01 | >200 |
| h6F12.v1.4 | $K_{1-5}$ $H_{2-26}$ | LC:Y71F | >200 | 0.02 | >200 |
| h6F12.v1.5 | $K_{1-5}$ $H_{2-26}$ | LC:F87Y | >200 | 0.04 | >200 |
| h6F12.v1.6 | $K_{1-5}$ $H_{2-26}$ | HC:V37I | >200 | 0.11 | >200 |
| h6F12.v1.7 | $K_{1-5}$ $H_{2-26}$ | HC:M48L | >200 | 0.03 | >200 |
| h6F12.v1.8 | $K_{1-5}$ $H_{2-26}$ | HC:G49A | >200 | 0.08 | >200 |
| h6F12.v1.9 | $K_{1-5}$ $H_{2-26}$ | HC:P105R | >200 | 0.16 | >200 |

Figure 22:
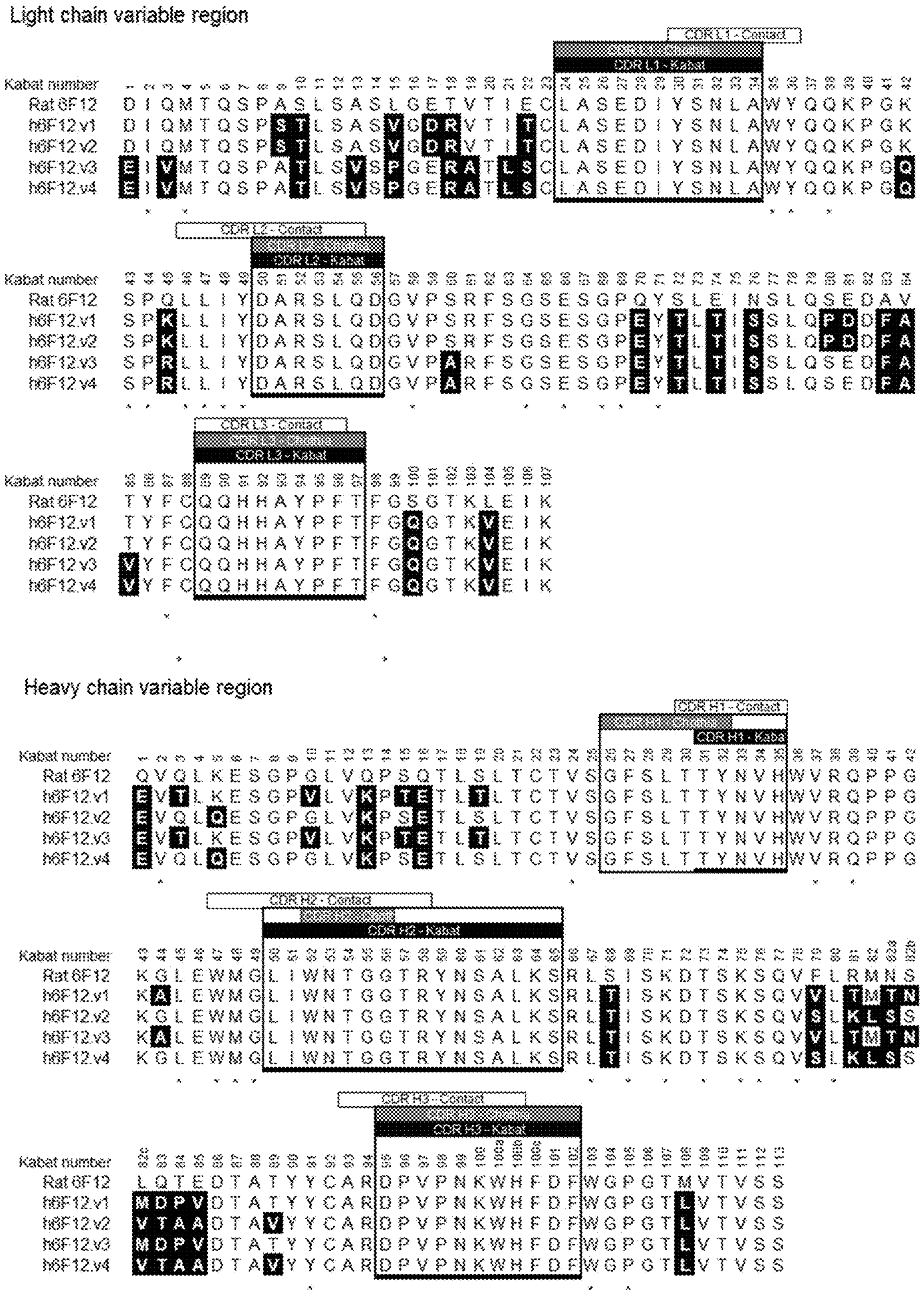
FIG. 22 contains amino acid sequence alignments of the light chain (upper panel) and heavy chain (lower panel) variable region sequences of the rabbit 6F12 antibody and humanized variants v1-v4; the amino acid sequences shown in the figure are SEQ ID NOs: 24, 131, 131, 143, and 144 (upper panel, from top sequence to bottom sequence in the alignment) and SEQ ID NOs: 25, 132, 142, 132, and 142 (lower panel, from top sequence to bottom sequence in the alignment). Residue numbering is according to Kabat; "*" indicates Vernier zone. CDR regions according to Chothia or Kabat (as indicated) are boxed; mutated residues are highlighted.

The sequences of the 6F12 variants are provided in Table 23 and Table 24, below, and sequence alignments are shown in FIG. 22, FIG. 23, and FIG. 24.

TABLE 23

| Heavy and Light Chain Variable Region Amino Acid Sequences of Humanized 6F12 Variants | | |
|---|---|---|
| | VH | VL |
| h6F12. v1 | EVTLKESGPVLVKPTETLTLTCTV SGFSLTTYNVHWVRQPPGKALE WMGLIWNTGGTRYNSALKSRLTI SKDTSKSQVVLTMTNMDPVDTA TYYCARDPVPNKWHFDFWGPGT LVTVSS (SEQ ID NO: 132) | DIQMTQSPSTLSASVGDRVTITCL ASEDIYSNLAWYQQKPGKSPKLLI YDARSLQDGVPSRFSGSESGPEYT LTISSLQPDDFATYFCQQHHAYPF TFGQGTKVEIK (SEQ ID NO: 131) |
| h6F12. v1.1 | Same as v1 (SEQ ID NO: 132) | DIQMTQSPSTLSASVGDRVTITCL ASEDIYSNLAWYQQKPGKAPKLL IYDARSLQDGVPSRFSGSESGPEY TLTISSLQPDDFATYFCQQHHAYP FTFGQGTKVEIK (SEQ ID NO: 133) |
| h6F12. v1.2 | Same as v1 (SEQ ID NO: 132) | DIQMTQSPSTLSASVGDRVTITCL ASEDIYSNLAWYQQKPGKSPKLLI YDARSLQDGVPSRFSGSGSGPEYT LTISSLQPDDFATYFCQQHHAYPF TFGQGTKVEIK (SEQ ID NO: 134) |
| h6F12. v1.3 | Same as v1 (SEQ ID NO: 132) | DIQMTQSPSTLSASVGDRVTITCL ASEDIYSNLAWYQQKPGKSPKLLI YDARSLQDGVPSRFSGSESGTEYT LTISSLQPDDFATYFCQQHHAYPF TFGQGTKVEIK (SEQ ID NO: 135) |
| h6F12. v1.4 | Same as v1 (SEQ ID NO: 132) | DIQMTQSPSTLSASVGDRVTITCL ASEDIYSNLAWYQQKPGKSPKLLI YDARSLQDGVPSRFSGSESGPEFT LTISSLQPDDFATYFCQQHHAYPF TFGQGTKVEIK (SEQ ID NO: 136) |
| h6F12. v1.5 | Same as v1 (SEQ ID NO: 132) | DIQMTQSPSTLSASVGDRVTITCL ASEDIYSNLAWYQQKPGKSPKLLI YDARSLQDGVPSRFSGSESGPEYT LTISSLQPDDFATYYCQQHHAYPF TFGQGTKVEIK (SEQ ID NO: 137) |
| h6F12. v1.6 | EVTLKESGPVLVKPTETLTLTCTV SGFSLTTYNVHWIRQPPGKALEW MGLIWNTGGTRYNSALKSRLTIS KDTSKSQVVLTMTNMDPVDTAT YYCARDPVPNKWHFDFWGPGTL VTVSS (SEQ ID NO: 138) | Same as v1 (SEQ ID NO: 131) |
| h6F12. v1.7 | EVTLKESGPVLVKPTETLTLTCTV SGFSLTTYNVHWVRQPPGKALE WLGLIWNTGGTRYNSALKSRLTI SKDTSKSQVVLTMTNMDPVDTA TYYCARDPVPNKWHFDFWGPGT LVTVSS (SEQ ID NO: 139) | Same as v1 (SEQ ID NO: 131) |

TABLE 23-continued

| Heavy and Light Chain Variable Region Amino Acid Sequences of Humanized 6F12 Variants | | |
|---|---|---|
| | VH | VL |
| h6F12. v1.8 | EVTLKESGPVLVKPTETLTLTCTV SGFSLTTYNVHWVRQPPGKALE WMALIWNTGGTRYNSALKSRLTI SKDTSKSQVVLTMTNMDPVDTA TYYCARDPVPNKWHFDFWGPGT LVTVSS (SEQ ID NO: 140) | Same as v1 (SEQ ID NO: 131) |
| h6F12. v1.9 | EVTLKESGPVLVKPTETLTLTCTV SGFSLTTYNVHWVRQPPGKALE WMGLIWNTGGTRYNSALKSRLTI SKDTSKSQVVLTMTNMDPVDTA TYYCARDPVPNKWHFDFWGRGT LVTVSS (SEQ ID NO: 141) | Same as v1 (SEQ ID NO: 131) |
| h6F12. v2 | EVQLQESGPGLVKPSETLSLTCTV SGFSLTTYNVHWVRQPPGKGLE WMGLIWNTGGTRYNSALKSRLTI SKDTSKSQVSLKLSSVTAADTAV YYCARDPVPNKWHFDFWGPGTL VTVSS (SEQ ID NO: 142) | Same as v1 (SEQ ID NO: 131) |
| h6F12. v3 | Same as v1 (SEQ ID NO: 132) | EIVMTQSPATLSVSPGERATLSCL ASEDIYSNLAWYQQKPGQSPRLLI YDARSLQDGVPARFSGSESGPEY TLTISSLQSEDFAVYFCQQHHAYP FTFGQGTKVEIK (SEQ ID NO: 143) |
| h6F12. v4 | Same as v2 (SEQ ID NO: 142) | EIVMTQSPATLSVSPGERATLSCL ASEDIYSNLAWYQQKPGQSPRLLI YDARSLQDGVPARFSGSESGPEY TLTISSLQSEDFAVYFCQQHHAYP FTFGQGTKVEIK (SEQ ID NO: 144) |

TABLE 24

| Complete Heavy and Light Chain Sequences for Humanized 6F12 Variants | | |
|---|---|---|
| | Complete H Chain | Complete L Chain |
| h6F12. v1 | EVTLKESGPVLVKPTETLTLTC TVSGFSLTTYNVHWVRQPPGK ALEWMGLIWNTGGTRYNSAL KSRLTISKDTSKSQVVLTMTNM DPVDTATYYCARDPVPNKWHF DFWGPGTLVTVSSASTKGPSVF PLAPSSKSTSGGTAALGCLVKD YFPEPVTVSWNSGALTSGVHTF PAVLQSSGLYSLSSVVTVPSSSL GTQTYICNVNHKPSNTKVDKK VEPKSCDKTHTCPPCPAPELLG GPSVFLFPPKPKDTLMISRTPEV TCVVVDVSHEDPEVKFNWYV DGVEVHNAKTKPREEQYGSTY RVVSVLTVLHQDWLNGKEYK CKVSNKALPAPIEKTISKAKGQ PREPQVYTLPPSREEMTKNQVS LTCLVKGFYPSDIAVEWESNGQ PENNYKTTPPVLDSDGSFFLYS KLTVDKSRWQQGNVFSCSVM HEALHNHYTQKSLSLSPGK (SEQ ID NO: 146) | DIQMTQSPSTLSASVGDRVTITCLA SEDIYSNLAWYQQKPGKSPKLLIYD ARSLQDGVPSRFSGSESGPEYTLTIS SLQPDDFATYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 145) |
| h6F12. v1.1 | Same as v1 (SEQ ID NO: 146) | DIQMTQSPSTLSASVGDRVTITCLA SEDIYSNLAWYQQKPGKAPKLLIY DARSLQDGVPSRFSGSESGPEYTLTI SSLQPDDFATYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 147) |

TABLE 24-continued

Complete Heavy and Light Chain Sequences for Humanized 6F12 Variants

| | Complete H Chain | Complete L Chain |
|---|---|---|
| h6F12. v1.2 | Same as v1 (SEQ ID NO: 146) | DIQMTQSPSTLSASVGDRVTITCLA SEDIYSNLAWYQQKPGKSPKLLIYD ARSLQDGVPSRFSGSGSGPEYTLTIS SLQPDDFATYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 148) |
| h6F12. v1.3 | Same as v1 (SEQ ID NO: 146) | DIQMTQSPSTLSASVGDRVTITCLA SEDIYSNLAWYQQKPGKSPKLLIYD ARSLQDGVPSRFSGSESGTEYTLTIS SLQPDDFATYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 149) |
| h6F12. v1.4 | Same as v1 (SEQ ID NO: 146) | DIQMTQSPSTLSASVGDRVTITCLA SEDIYSNLAWYQQKPGKSPKLLIYD ARSLQDGVPSRFSGSESGPEFTLTIS SLQPDDFATYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 150) |
| h6F12. v1.5 | Same as v1 (SEQ ID NO: 146) | DIQMTQSPSTLSASVGDRVTITCLA SEDIYSNLAWYQQKPGKSPKLLIYD ARSLQDGVPSRFSGSESGPEYTLTIS SLQPDDFATYYCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 151) |
| h6F12. v1.6 | EVTLKESGPVLVKPTETLTLTC TVSGFSLTTYNVHWIRQPPGKA LEWMGLIWNTGGTRYNSALKS RLTISKDTSKSQVVLTMTNMDP VDTATYYCARDPVPNKWHFDF WGPGTLVTVSSASTKGPSVFPL APSSKSTSGGTAALGCLVKDYF PEPVTVSWNSGALTSGVHTFPA VLQSSGLYSLSSVVTVPSSSLGT QTYICNVNHKPSNTKVDKKVE PKSCDKTHTCPPCPAPELLGGP SVFLFPPKPKDTLMISRTPEVTC VVVDVSHEDPEVKFNWYVDG VEVHNAKTKPREEQYGSTYRV VSVLTVLHQDWLNGKEYKCK VSNKALPAPIEKTISKAKGQPR EPQVYTLPPSREEMTKNQVSLT CLVKGFYPSDIAVEWESNGQPE NNYKTTPPVLDSDGSFFLYSKL TVDKSRWQQGNVFSCSVMHE ALHNHYTQKSLSLSPGK (SEQ ID NO: 152) | Same as v1 (SEQ ID NO: 145) |
| h6F12. v1.7 | EVTLKESGPVLVKPTETLTLTC TVSGFSLTTYNVHWVRQPPGK ALEWLGLIWNTGGTRYNSALK SRLTISKDTSKSQVVLTMTNMD PVDTATYYCARDPVPNKWHFD FWGPGTLVTVSSASTKGPSVFP LAPSSKSTSGGTAALGCLVKDY FPEPVTVSWNSGALTSGVHTFP | Same as v1 (SEQ ID NO: 145) |

TABLE 24-continued

Complete Heavy and Light Chain Sequences for Humanized 6F12 Variants

| | Complete H Chain | Complete L Chain |
|---|---|---|
| | AVLQSSGLYSLSSVVTVPSSSL GTQTYICNVNHKPSNTKVDKK VEPKSCDKTHTCPPCPAPELLG GPSVFLFPPKPKDTLMISRTPEV TCVVVDVSHEDPEVKFNWYV DGVEVHNAKTKPREEQYGSTY RVVSVLTVLHQDWLNGKEYK CKVSNKALPAPIEKTISKAKGQ PREPQVYTLPPSREEMTKNQVS LTCLVKGFYPSDIAVEWESNGQ PENNYKTTPPVLDSDGSFFLYS KLTVDKSRWQQGNVFSCSVM HEALHNHYTQKSLSLSPGK (SEQ ID NO: 153) | |
| h6F12. v1.8 | EVTLKESGPVLVKPTETLTLTC TVSGFSLTTYNVHWVRQPPGK ALEWMALIWNTGGTRYNSAL KSRLTISKDTSKSQVVLTMTNM DPVDTATYYCARDPVPNKWHF DFWGPGTLVTVSSASTKGPSVF PLAPSSKSTSGGTAALGCLVKD YFPEPVTVSWNSGALTSGVHTF PAVLQSSGLYSLSSVVTVPSSSL GTQTYICNVNHKPSNTKVDKK VEPKSCDKTHTCPPCPAPELLG GPSVFLFPPKPKDTLMISRTPEV TCVVVDVSHEDPEVKFNWYV DGVEVHNAKTKPREEQYGSTY RVVSVLTVLHQDWLNGKEYK CKVSNKALPAPIEKTISKAKGQ PREPQVYTLPPSREEMTKNQVS LTCLVKGFYPSDIAVEWESNGQ PENNYKTTPPVLDSDGSFFLYS KLTVDKSRWQQGNVFSCSVM HEALHNHYTQKSLSLSPGK (SEQ ID NO: 154) | Same as v1 (SEQ ID NO: 145) |
| h6F12. v1.9 | DIQMTQSPSTLSASVGDRVTIT CLASEDIYSNLAWYQQKPGKS PKLLIYDARSLQDGVPSRFSGS ESGPEYTLTISSLQPDDFATYFC QQHHAYPFTFGQGTKVEIKRT VAAPSVFIFPPSDEQLKSGTASV VCLLNNFYPREAKVQWKVDN ALQSGNSQESVTEQDSKDSTYS LSSTLTLSKADYEKHKVYACE VTHQGLSSPVTKSFNRGEC (SEQ ID NO: 155) | Same as v1 (SEQ ID NO: 145) |
| h6F12. v2 | EVQLQESGPGLVKPSETLSLTC TVSGFSLTTYNVHWVRQPPGK GLEWMGLIWNTGGTRYNSAL KSRLTISKDTSKSQVSLKLSSVT AADTAVYYCARDPVPNKWHF DFWGPGTLVTVSSASTKGPSVF PLAPSSKSTSGGTAALGCLVKD YFPEPVTVSWNSGALTSGVHTF PAVLQSSGLYSLSSVVTVPSSSL GTQTYICNVNHKPSNTKVDKK VEPKSCDKTHTCPPCPAPELLG GPSVFLFPPKPKDTLMISRTPEV TCVVVDVSHEDPEVKFNWYV DGVEVHNAKTKPREEQYGSTY RVVSVLTVLHQDWLNGKEYK CKVSNKALPAPIEKTISKAKGQ PREPQVYTLPPSREEMTKNQVS LTCLVKGFYPSDIAVEWESNGQ PENNYKTTPPVLDSDGSFFLYS KLTVDKSRWQQGNVFSCSVM HEALHNHYTQKSLSLSPGK (SEQ ID NO: 156) | Same as v1 (SEQ ID NO: 145) |
| h6F12. v3 | Same as v1 (SEQ ID NO: 146) | EIVMTQSPATLSVSPGERATLSCLA SEDIYSNLAWYQQKPGQSPRLLIYD ARSLQDGVPARFSGSESGPEYTLTIS |

TABLE 24-continued

| Complete Heavy and Light Chain Sequences for Humanized 6F12 Variants | | |
|---|---|---|
| | Complete H Chain | Complete L Chain |
| | | SLQSEDFAVYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 157) |
| h6F12. v4 | Same as v2 (SEQ ID NO: 156) | EIVMTQSPATLSVSPGERATLSCLA SEDIYSNLAWYQQKPGQSPRLLIYD ARSLQDGVPARFSGSESGPEYTLTIS SLQSEDFAVYFCQQHHAYPFTFGQ GTKVEIKRTVAAPSVFIFPPSDEQLK SGTASVVCLLNNFYPREAKVQWKV DNALQSGNSQESVTEQDSKDSTYS LSSTLTLSKADYEKHKVYACEVTH QGLSSPVTKSFNRGEC (SEQ ID NO: 158) |

Example 10: Structural Characterization of Isoform-Selective Anti-TGFβ Antibodies Materials and Methods Fabs were expressed from CHO cells. Human TGFβ2 and TGFβ3 were purchased from Peprotech (Rocky Hill, N.J.). Fabs and TGFβ2/3 were mixed at 1:1.5 ratio on ice for 30 minutes, complexes were isolated from HiLoad Superdex S200 16/600 column (GE healthcare life science) in 25 mM Tris pH7.5, and 50 mM NaCl. Samples were concentrated to 10 mg/ml for crystallization. Vapor diffusion method was used for growing crystals. 1 μl of protein was mixed with 1 μl mother liquid over 500 μl well solution. 2A10 TGFβ3 was crystallized in 25% PEG 1000, and 0.1M Hepes pH 7.5. The 4A11v2/TGFβ2 complex was crystallized in 15% PEG 4000, and 0.1 M sodium cacodylate pH 6. 4A11v7 and TGFβ2 complex was crystallized in 30% PEG 1000, and 0.1M Tris pH8.5. Crystals were cryo-protected with 20% glycerol and frozen in liquid nitrogen before data collection.

Results:

2A10/β3

The crystal structure of the 2A10v4 Fab (expressed in CHO) and mature dimeric form of human TGFβ3 (A301-S412, expressed in *E. coli*, purchased from Peprotech (Rocky Hill, N.J.)) was solved at 2.5 Å with R/Rfree refinement statistics of 22.6% and 27.1% respectively (Table 25).

TABLE 25

| Data collection and refinement statistics for TGFβ3/2A10v4 structure | |
|---|---|
| | TGFβ3/2A10v4 |
| Data collection | APS 24-IDC |
| Space group | I2 |
| Cell dimensions | |
| a, b, c (Å) | 133.94, 47.20, 200.83 |
| α, β γ (°) | 90, 101.68, 90 |
| Resolution (Å) | 49.17-2.50 (2.59-2.50) |
| $R_{sym}$ or $R_{merge}$ | 0.109 (1.367) |
| I/σI | 11.0 (1.1) |
| Completeness (%) | 99.3 (98.9) |
| Redundancy | 5.6 (5.4) |
| CC½ | 0.996 (0.514) |

TABLE 25-continued

| Data collection and refinement statistics for TGFβ3/2A10v4 structure | |
|---|---|
| | TGFβ3/2A10v4 |
| Refinement | |
| Resolution (Å) | 49.17-2.50 |
| No. reflections (total/test) | 42938/2096 |
| $R_{work}/R_{free}$ | 22.3/26.9% |
| No. atoms | |
| Protein | 7869 |
| Water | 161 |
| B-factors | |
| Protein | 62.6 |
| Water | 47.8 |
| R.m.s. deviations | |
| Bond lengths (Å) | 0.010 |
| Bond angles (°) | 1.22 |

*Values in parentheses are for highest-resolution shell.

Figure 25:
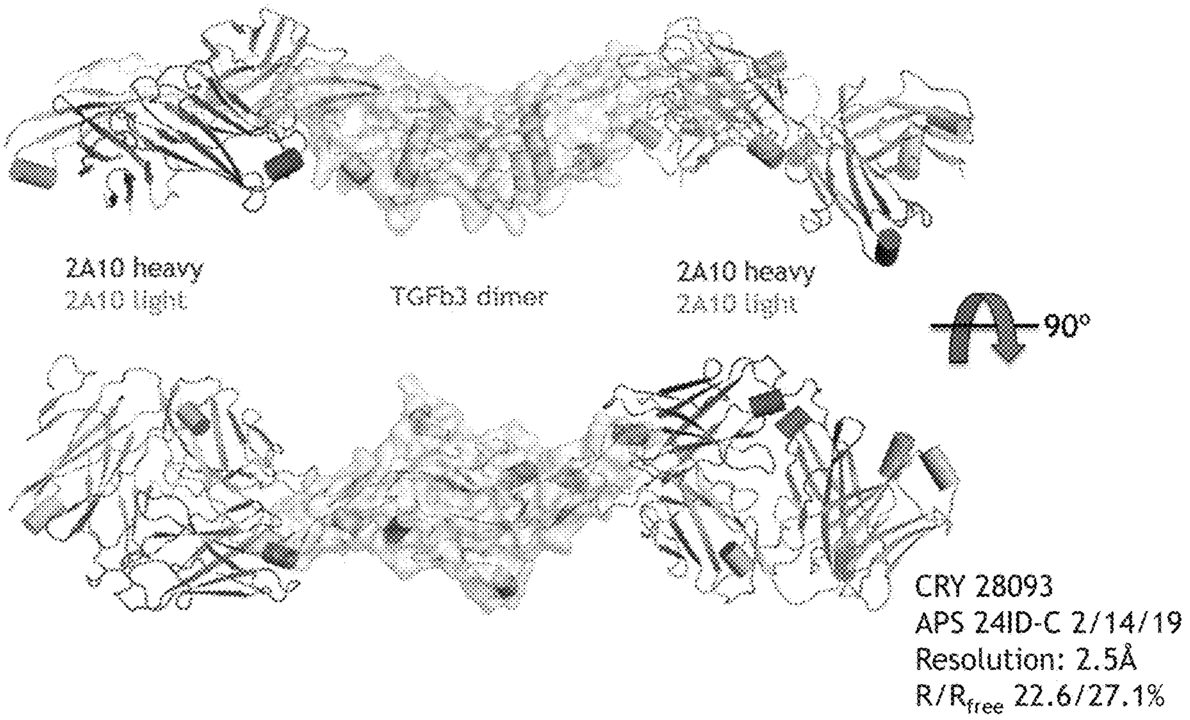
FIG. 25 is an image of the crystal structure of 2A10 in complex with human TGFβ3.
Figure 26:
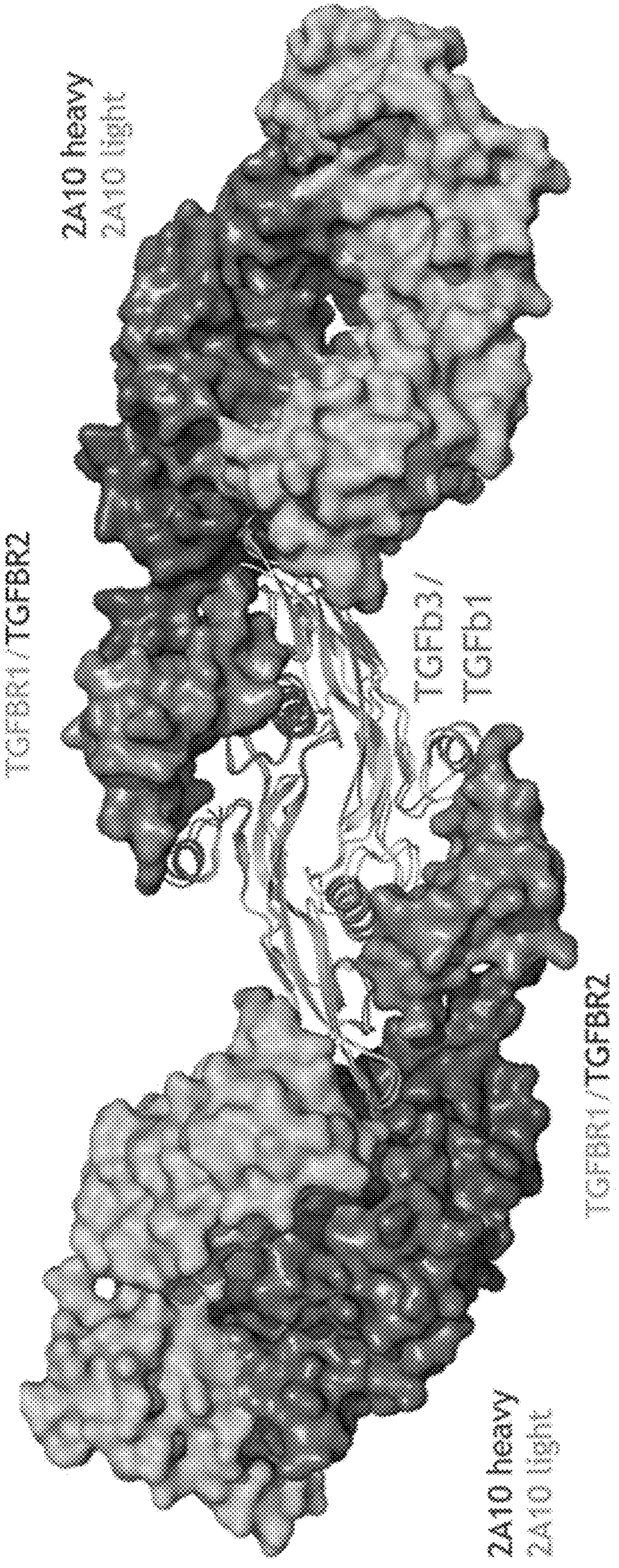
FIG. 26 is an image of TGFβ3 bound to 2A10, and comparing to TGFβ1 with TGFBR1/TGFBR2 complex. It indicates that 2A10 would sterically block TGFBR2 recruitment, but likely not TGFBR1.
Figure 27:
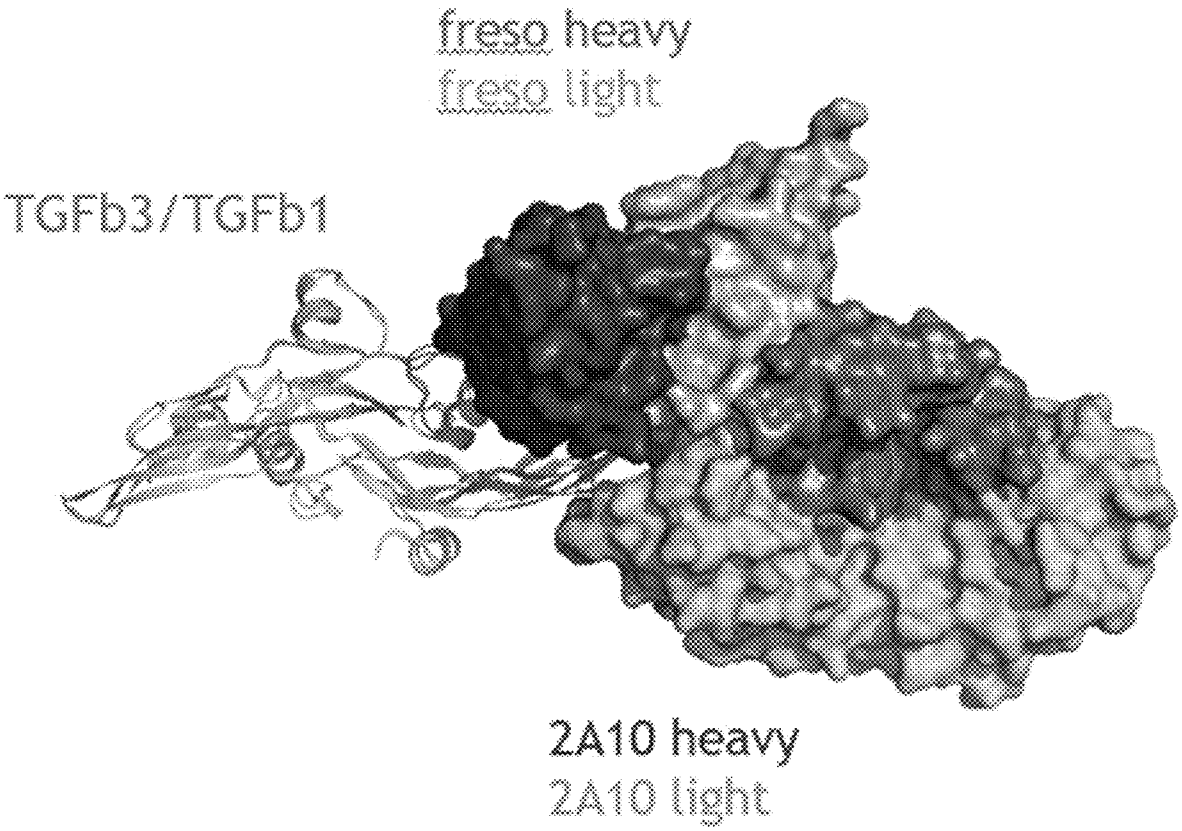
FIG. 27 is an image of fresolimumab ("freso"), a pan-TGFβ antibody, compared with 2A10. Fresolimumab blocks TGFβ3 binding to both TGFBR1/TGFBR2, but 2A10 only blocks binding to TGFBR2 due to a different binding angle.

The structure in FIG. 25 shows that each dimer of TGFβ3 is bound by two 2A10 Fabs. 2A10 binds to the beta6/beta7 hairpin region of TGFβ3. Comparison of the 2A10/TGFβ3 structure with the structure of TGFβ1 bound to TGFBR1 and TGFBR2 (FIG. 26) (see also, Radaev JBC 2011, PDB 3KFD) indicates that the 2A10 Fab would sterically block the ability of TGFBR2, but not TGFBR1, to bind TGFβ3. Since the signaling complex of TGFβ with TGFBR1 and TGFBR2 is known to cooperatively assemble, first by TGFβ binding to TGFBR2 followed by recruitment of TGFBR1, it is expected that blocking TGFBR2 binding is sufficient to completely prevent the R1/R2 signaling receptors from binding to TGFβ3. The binding mode of 2A10 is different from the pan-TGFβ antibody fresolimumab, which binds to all TGFβ isoforms via an epitope that blocks both TGFBR1 and TGFBR2 binding (PDB ID 4KV5, 4KXZ, 3EO1, 3KFD).

Figure 28:
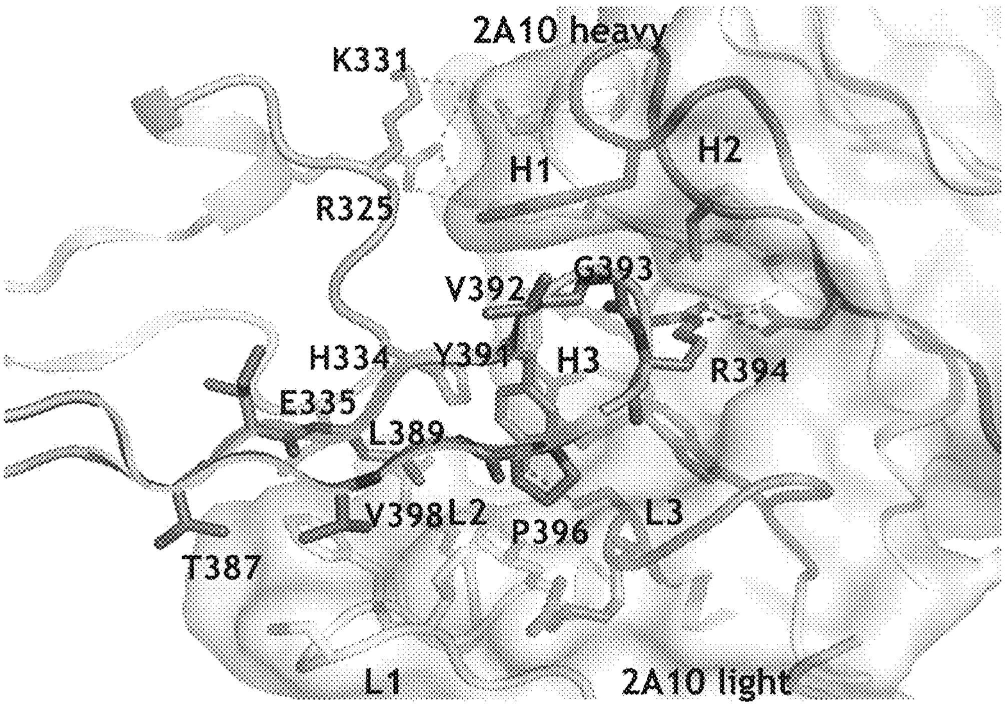
FIG. 28 shows the epitope on TGFβ3 bound by 2A10. 2A10 binds the beta-hairpin at the tip of beta 6-beta7 "finger" of TGFβ3 through R394. Polar contacts are also made between R325 and K331.
Figure 29:
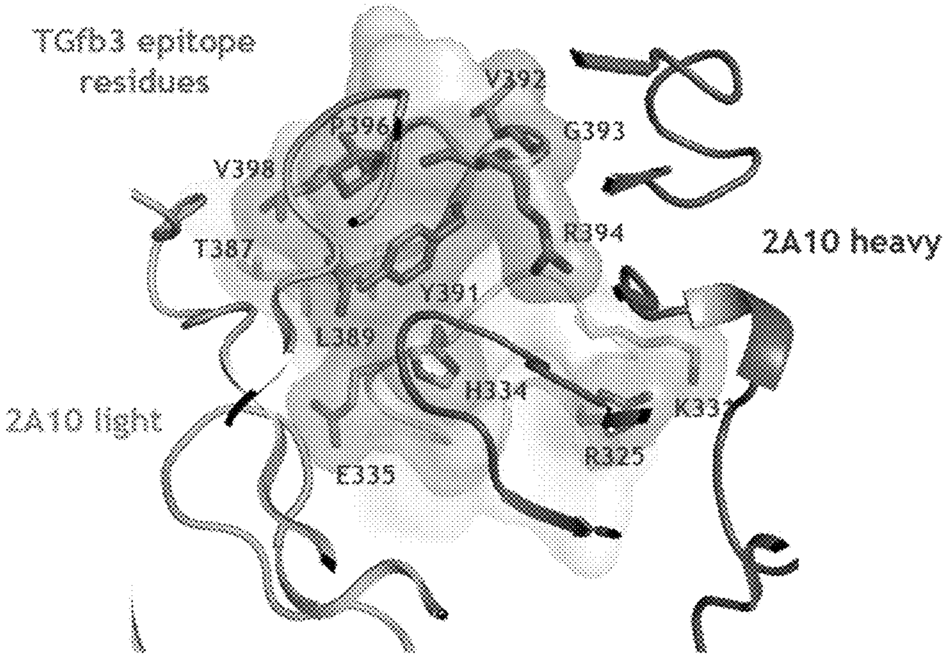
FIG. 29 shows the epitope on TGFβ3 bound by 2A10; residues involved in binding of TGFβ3 by 2A10 within 5.0 Å are labeled.

The epitope on TGFβ3 bound by 2A10 is shown in FIG. 28 and FIG. 29, and summarized in a list of contacts found in Table 26. TGFB3 residues contacted by 2A10 (within 5.0 Å) are R325, K331, W332, H334, E335, T387, I388, L389, Y391, V392, G393, R394, P396, K397, and V398. As one can see from FIG. 28, the bulk of the epitope is contributed by the beta6 and beta7 strands of TGFβ3, including the beta hairpin region. This beta hairpin contains R394, which makes the largest number of contacts with 2A10 (see Table 26) and also makes an ionic salt bridge with Asp50 in the 2A10 heavy chain CDR2. The TGFβ3 epitope is shown from another angle in FIG. 29, which better highlights the contacts between 2A10 and the 325-335 loop in TGFβ3.

TABLE 26

Contact Residues on TGFβ3 and anti-TGFβ3 mAb 2A10

| TGFβ3 Amino Acid Residue | Light Chain | Heavy Chain |
|---|---|---|
| R325 | | Y32 |
| K331 | | D28 |
| | | S31 |
| W332 | | Y53 |
| H334 | R50 | P96 |
| | | G97 |
| | | G98 |
| E335 | F30 | |
| | R50 | |
| | N53 | |
| T387 | S28 | |
| | R29 | |
| | F30 | |
| I388 | F30 | |
| L389 | 127d | |
| | F30 | |
| | L32 | |
| Y391 | L32 | Y53 |
| | H34 | P96 |
| | S91 | G97 |
| | W96 | G98 |
| V392 | | Y53 |
| G393 | | V52 |
| | | Y53 |
| R394 | S91 | G33 |
| | S94 | M34 |
| | W96 | S35 |
| | | D50 |
| | | I51 |
| | | V52 |
| | | Y58 |
| | | A95 |
| | | G97 |
| P396 | I27d | |
| | L32 | |
| | S91 | |
| | R92 | |
| | E93 | |
| K397 | I27d | |
| V398 | I27d | |
| | S28 | |
| | F30 | |

Figure 30:
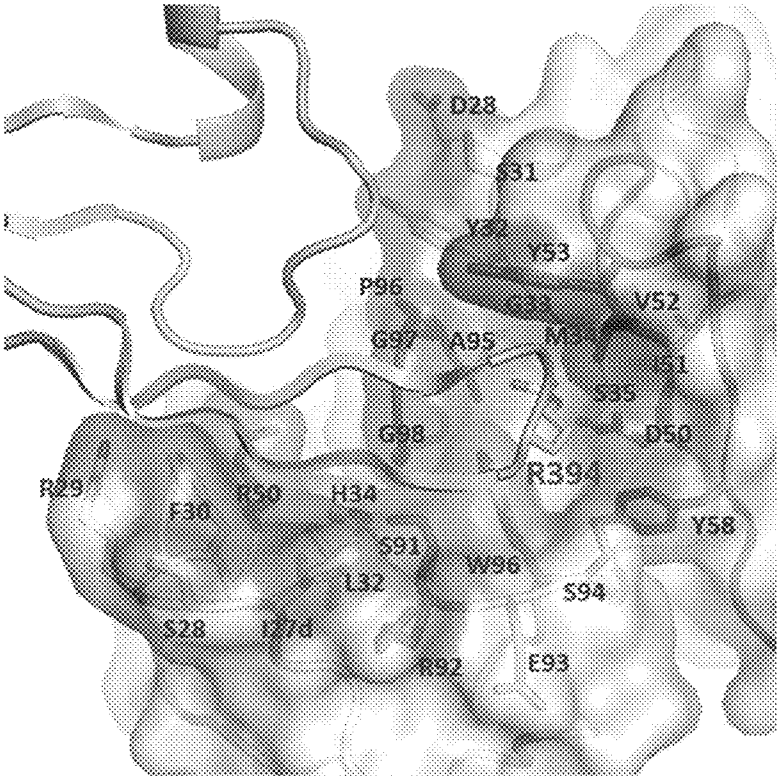
FIG. 30 shows the 2A10 antibody paratope (residue numbering according to Kabat). R394 on TGFβ3 is in contact with D50 of 2A10.

The 2A10 paratope is shown in FIG. 30. Both the heavy and light chains contribute relatively equal surface area to binding of TGFβ3. -885 Å2 of buried surface area (BSA) is contributed by the light chain, and -805 A2 of BSA is contributed by the heavy chain, for a total of ~1690A2 in the interface between 2A10 and TGFβ3 (an average of the two Fabs bound to the dimer in the structure). Given the concave surface of the antibody paratope combined with extended beta6/beta7 epitope on TGFβ3, all six CDRs contact TGFβ3 (FIG. 30 and Table 26). TGFβ3 Arg394, which makes a key contact with Asp50 in the 2A10 heavy chain, is almost completely buried in the center of the antibody paratope, contacting 2A10 light chain CDR H3, and all three CDRs from the heavy chain. An extended 15 residue light chain CDR L1 is a key contributor to interactions with the beta6/beta7 strands, and short glycine rich CDR H3 helps create the space for the beta6/beta7 hairpin to approach and interact with CDR H2 D50. These unique interactions help explain the fact that the light chain BSA is larger than the heavy chain BSA, which is somewhat unusual for antibody antigen interactions.

Figure 31:
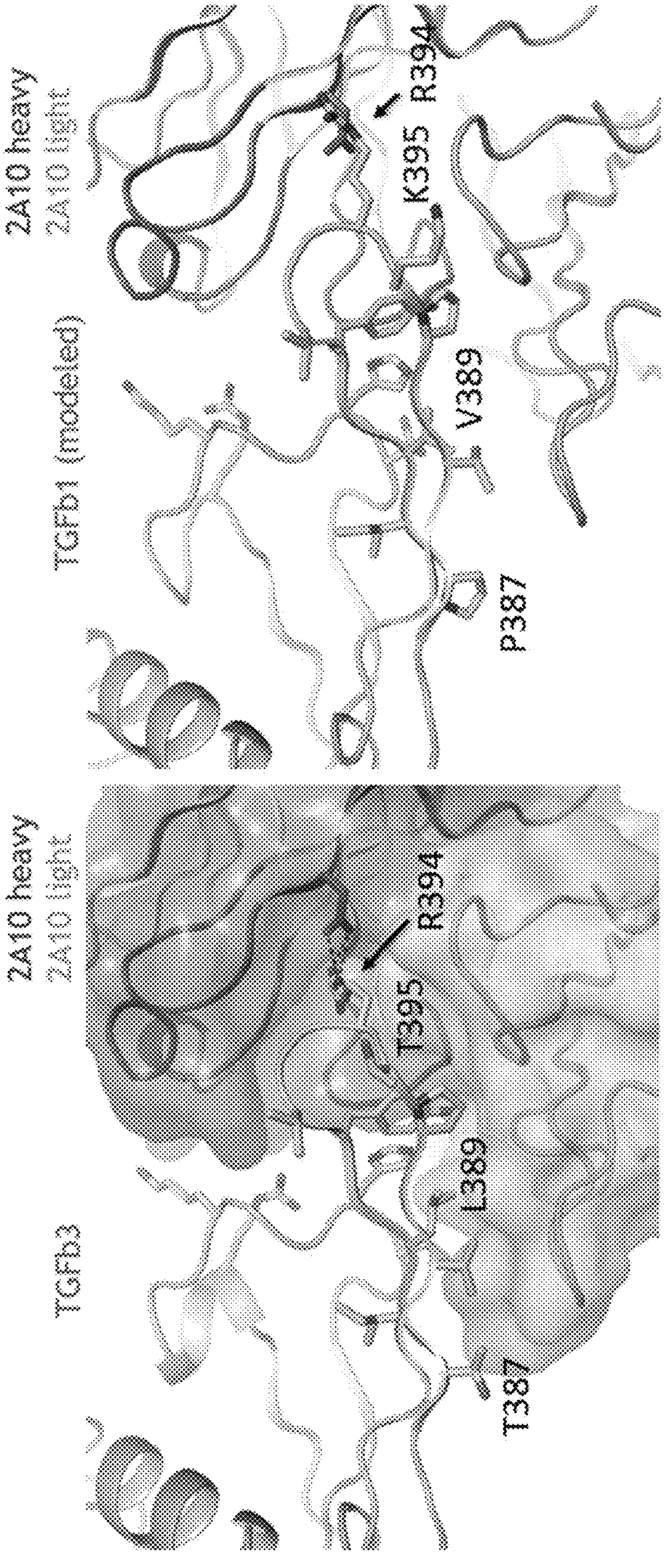
FIG. 31 shows the TGFβ3/2A10 epitope and a comparison to TGFβ1. TGβF1 has three changes in epitopic residues, when compared to TGFβ3. The P387T, L389V and T395K substitutions may subtly change the conformation of the beta-hairpin and 06-07 fingers of TGFβ2 and remove some beneficial contacts with 2A10.

Selectivity for TGFβ3 over TGFβ1 and TGFβ2 is likely achieved in different ways for each of these isoforms. For human TGFβ1, there are three amino acid differences between TGFβ1 and TGFβ3 near or within the 2A10 epitope. These residues, T387P (meaning the residue is a "T" in TGFβ3 (human TGFβ3 numbering) and a P in TGFβ1 (P365 in TGFβ1)), L389V, and T395K suggest that residues along the beta6 strands (T387P, L389V) play a large role in 2A10 binding (FIG. 31). In TGFβ3, T395 does not make a direct interaction with 2A10 in the crystal structure, so the effect of the change to lysine in this residue is unclear.

Figure 32:
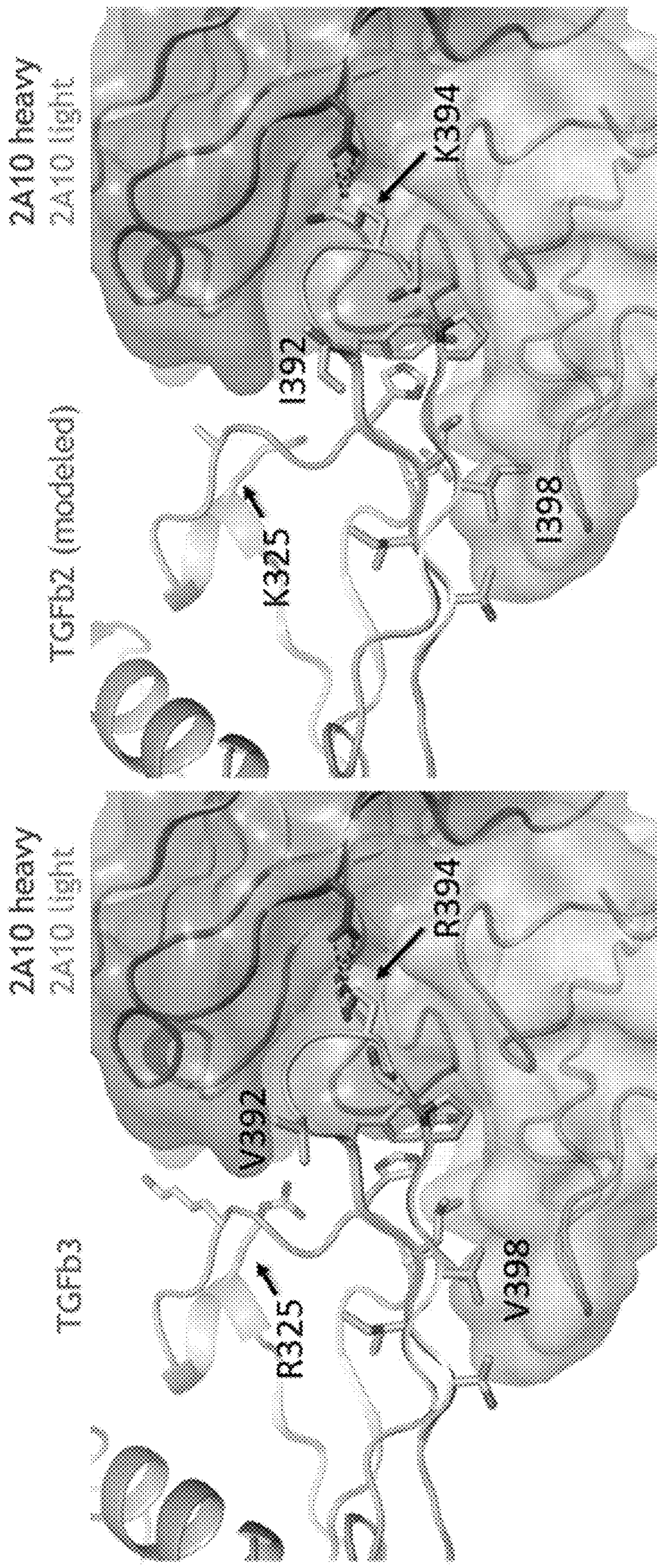
FIG. 32 shows the TGFβ3/2A10 epitope and a comparison to TGFβ2. TGFβ2 has four changes in epitopic residues when compared to TGFβ3. The primary reasons for TGFβ3 vs. TGFβ2 specificity are likely to be based on the R394K change, which removes an optimized salt bridge in epitope R394-D50, and V398I, adding a potential steric clash.

For TGFβ2, there are four amino acid changes between TGFβ2 and TGFβ3 that lie within or near the 2A10 epitope. Of these four residues (R325K (meaning the residue is a "R" in TGFβ3 and a K in TGFβ2 (human TGFβ3 numbering), V392I, R394K, V398I), three could disrupt productive contact with 2A10 (FIG. 32). TGFβ3 R325 makes a hydrogen bond with heavy chain residue Y32, which would be altered when changed to a lysine. A change to isoleucine at position V398 could introduce a steric clash with 2A10. Most importantly, a change in the highly contacted R394 residue (to lysine in TGFβ2) would also likely change the chemistry of the interaction with 2A10 in an unfavorable manner. The substitution of isoleucine for valine at position 392 would not be expected to have a large effect on binding, given its position in the epitope and the conservative nature of the change. Overall, the structure of 2A10 bound to TGFβ3 provides a strong indication of how 2A10 achieves high selectivity between TGFβ isoforms.

4A11/TGFβ2

Figure 33:
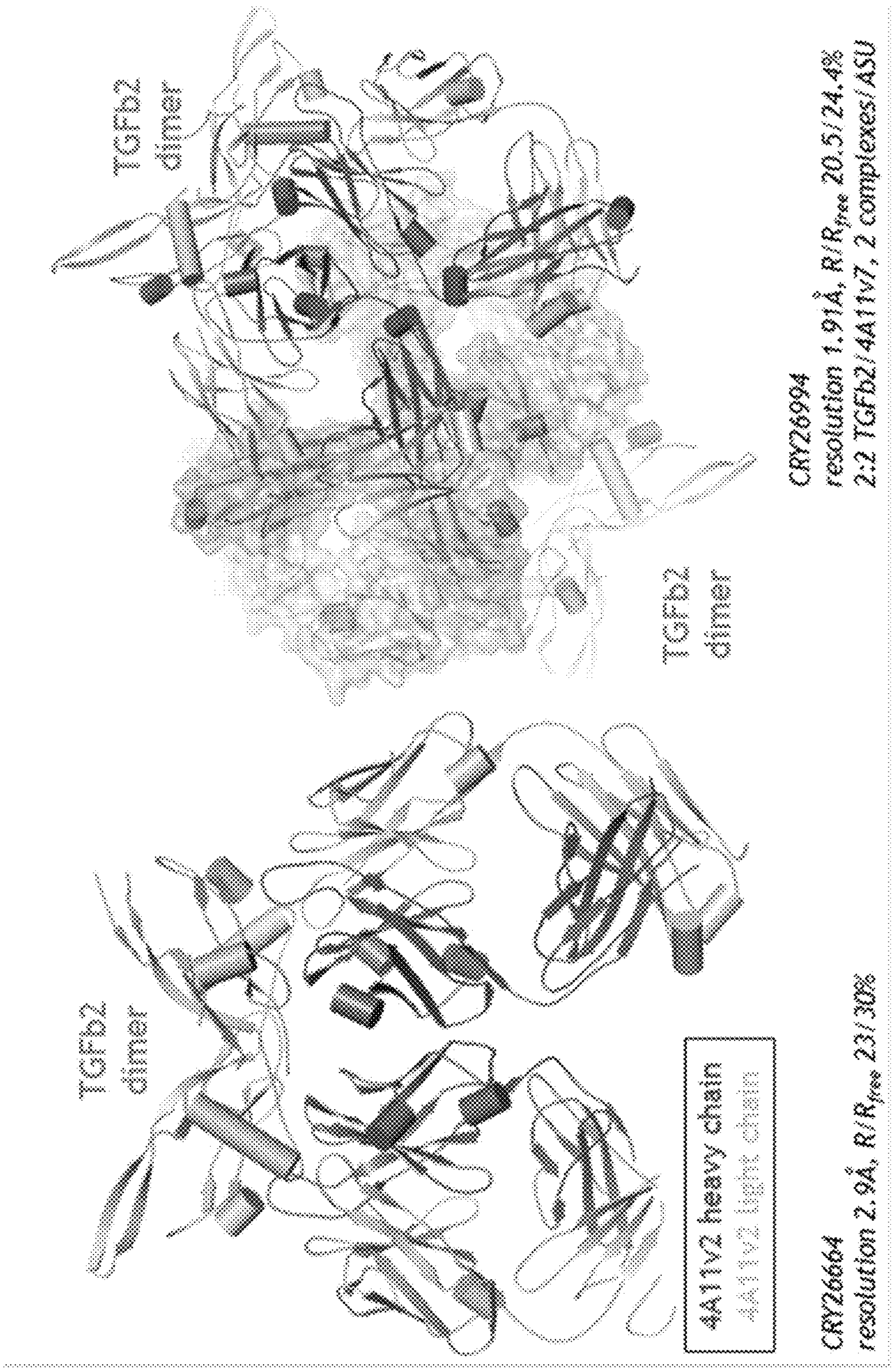
FIG. 33 shows a comparison of TGFβ2 binding to 4A11v2 (left cartoon) and 4A11v7 (right cartoon). The antigen-antibody complex is very similar. The heavy chains come close to each other upon binding, but the binding elbow angle of the second Fab is different.

In order to better understand the reasons for functional differences between the humanized 4A11 clones, the structures of two versions of 4A11, v2 and v7, bound to the mature form of human TGFβ2 were solved using methods as described above with respect to 2A10. V2 and v7 were humanized to the VL1VH3 and VL3VH4 frameworks respectively. FIG. 33 shows the two structures. 4A11v2/TGFβ2 was solved at 2.9 Å resolution, to R/Rfree statistics of 23/30%, while 4A11v7/TGFβ2 was solved at 1.91A with R/Rfree statistics of 20.5/24.4% (Table 27). Each TGFβ2 dimer is bound by two 4A11 Fabs that share a nearly identical epitope. While the overall architecture of the complexes was very similar, 4A11v7 crystallized in a different spacegroup and there were some small differences in elbow angle for the second Fab bound to TGFβ2.

TABLE 27

Data collection and refinement statistics for TGFβ2/4A11 structures

| | TGFβ2/4A11v2 | TGFβ2/4A11v7 |
|---|---|---|
| Data collection | ALS 5.0.2 | APS 22ID |
| Space group | P2 21 21 | P1 |
| Cell dimensions | | |
| a, b, c (Å) | 60.15, 103.48, 196.25 | 64.42, 85.11, 112.73 |
| a, β, γ (°) | 90, 90, 90 | 112.73, 99.15, 97.32 |
| Resolution (Å) | 49.06-2.90 (30.8-2.90) | 82.97-1.91 (20.1-1.91) |
| $R_{sym}$ or $R_{merge}$ | 0.075 (0.640) | 0.073 (0.494) |
| I/σI | 11.6 (1.9) | 8.5 (2.5) |
| Completeness (%) | 98.8 (99.7) | 90.5 (88.7) |

TABLE 27-continued

Data collection and refinement statistics for TGFβ2/4A11 structures

| | TGFβ2/4A11v2 | TGFβ2/4A11v7 |
|---|---|---|
| Redundancy | 4.0 (4.3) | 2.8 (2.9) |
| CC½ | 0.998 (0.663) | 0.997 (0.877) |
| Refinement | | |
| Resolution (Å) | 45.95-2.90 | 82.97-1.91 |
| No. reflections (total/test) | 27587/1335 | 161613/8036 |
| $R_{work}/R_{free}$ | 25.6/29.5% | 20.5/24.4% |
| No. atoms | | |
| Protein | 7597 | 16444 |
| Water | — | 708 |
| B-factors | | |
| Protein | 79.0 | 41.7 |
| Water | — | 42.4 |
| R.m.s. deviations | | |
| Bond lengths (Å) | 0.008 | 0.10 |
| Bond angles (°) | 1.05 | 1.19 |

*Values in parentheses are for highest-resolution shell.

Figure 34:
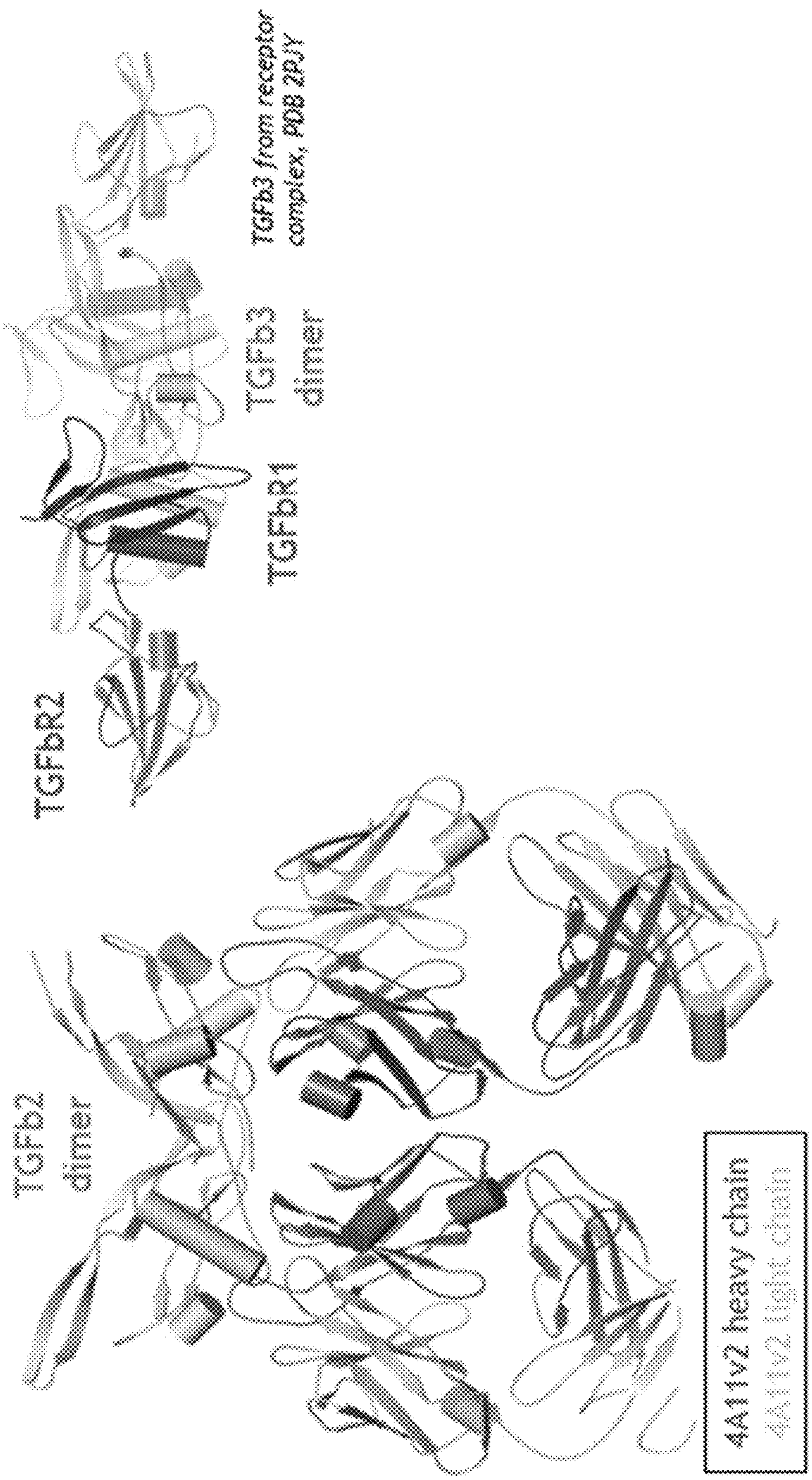
FIG. 34 shows a comparison of 4A11v2/TGFβ2 to the TGFβ3/receptor complex. 4A11v2 does not directly compete with the TGFBR1/2 binding sites; rather, 4A11v2 slightly alters structure of TGFβ2, causing the fingers to "pinch" together. This may be a result of a steric clash between 4A11v2 Fabs.
Figure 35:
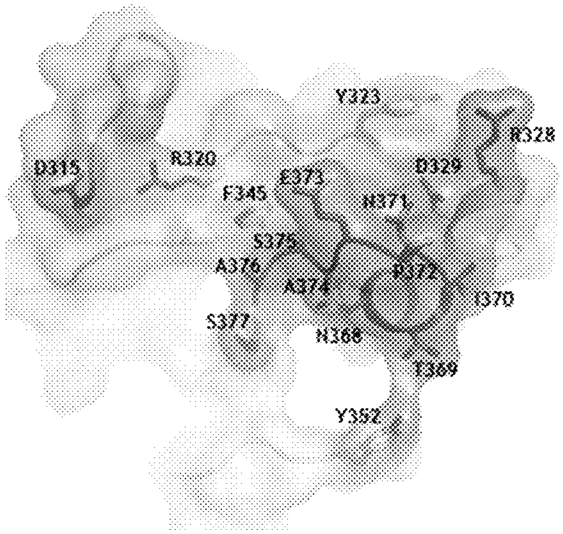
FIG. 35 shows the TGFβ2 epitope bound by 4A11. Glutamic acid at position E373 of the TGFβ2 amino acid sequence (TGFβ2 numbering) is at the center of the contact interface. TGFβ3 also has glutamic acid at this position, similar to TGFβ2, whereas TGFβ1 has a glycine.

The epitope for 4A11 is found on the underside of the TGFβ2 dimer, with the two Fabs bound to two identical epitopes as expected for a symmetric homodimer (FIG. 34). The epitope for 4A11 encompasses TGFβ2 residues V313, Q314, D315, R320, L322, Y323, R328, D329, F345, and A347 in one TGFβ2 monomer, and N368, T369, I370, N371, P372, E373, A374, 5375, A376, and S377 in the second TGFβ2 monomer (FIG. 35 and Tables 28 and 29). For the 4A11v2/TGFβ2 structure, ~1760A2 of surface area is buried, and for 4A11v7/TGFβ2 structure, ~1950 Å2 of surface area is buried. The 4A11 epitope is centered on the cap of an alpha helix (residue 359-372). Within the epitope, there is significant conservation of sequence between TGFβ1/2/3, but one major difference found in TGFβ1 but not TGFβ2/3 is a change from glutamic acid to glycine at position 373 (human TGFβ2 numbering) (FIG. 35). This glutamic acid residue lies at the center of the 4A11 epitope, and makes a polar contact with CDR-H1 T33. A change from glutamic acid to glycine would disrupt this polar interaction as well as remove a large amount of sidechain introduced surface area.

TABLE 28

Contact Residues on TGFβ2 chain A and 4A11 Mab

| TGFβ2 chain A | 4A11 Light Chain | 4A11 Heavy Chain |
|---|---|---|
| V313 | | S28 |
| | | S30 |
| | | S31 |
| Q314 | | S28 |
| | | S30 |
| D315 | | S28 |
| | | L29 |
| | | S30 |
| | | S73 |
| R320 | | S30 |
| P321 | | Y53 |
| | | G102 |
| | | G103 |
| L322 | | Y53 |
| | | G103 |
| Y323 | | G103 |
| | | A104 |
| | | P105 |

TABLE 28-continued

Contact Residues on TGFβ2 chain A and 4A11 Mab

| TGFβ2 chain A | 4A11 Light Chain | 4A11 Heavy Chain |
|---|---|---|
| R328 | Y30 | P105 |
| | N31 | |
| D329 | Y30 | |
| F345 | | Y53 |
| | | G54 |
| A347 | | G54 |

TABLE 29

Contact Residues on TGFβ2 chain B and 4A11 Mab

| TGFβ2 chain B | Light Chain | Heavy Chain |
|---|---|---|
| N368 | G96 | S56 |
| | K100 | Y58 |
| T369 | S95 | Y58 |
| | G96 | |
| | S97 | |
| | K100 | |
| I370 | Y30 | |
| | Y94 | |
| | S95 | |
| | G96 | |
| | K100 | |
| N371 | Y30 | Y50 |
| | Y94 | |
| | S95 | |
| | K100 | |
| P372 | A30 | Y50 |
| | A34 | |
| | G93 | |
| | Y94 | |
| | S95 | |
| | K100 | |
| | Y101 | |
| E373 | Y101 | T33 |
| | | Y50 |
| | | Y53 |
| | | H98 |
| | | Q100 |
| | | V101 |
| | | G102 |
| | | G103 |
| | | G107 |
| | | S108 |
| A374 | K100 | S52 |
| | | Y53 |
| | | G54 |
| | | S56 |
| | | Y58 |
| | | S52 |
| S375 | | Y53 |
| | | G54 |
| | | G55 |
| | | S56 |
| | | G54 |
| A376 | | G55 |
| | | S56 |
| | | G55 |
| S377 | | S56 |

Figure 36:
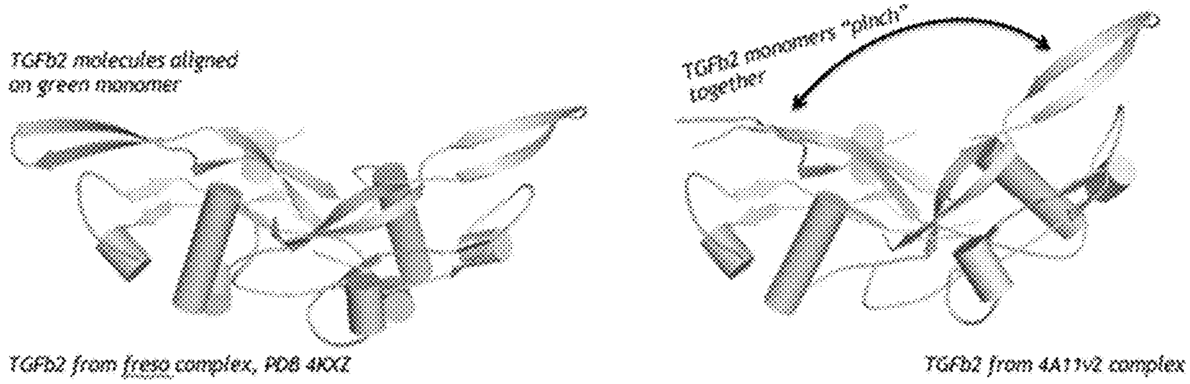
FIG. 36 contains cartoons showing the conformational changes in TGFβ2 induced by 4A11v2 (right cartoon) and the TGFβ2 from fresolimumab ("freso") complex (left cartoon). Conformational changes in TGFβ2 structure may alter the ability of the signaling receptors to bind TGFβ2. 4A11 may also block access of the membrane tethered receptors, by binding the membrane proximal side of TGFβ2 or TGFβ3.
Figure 37:
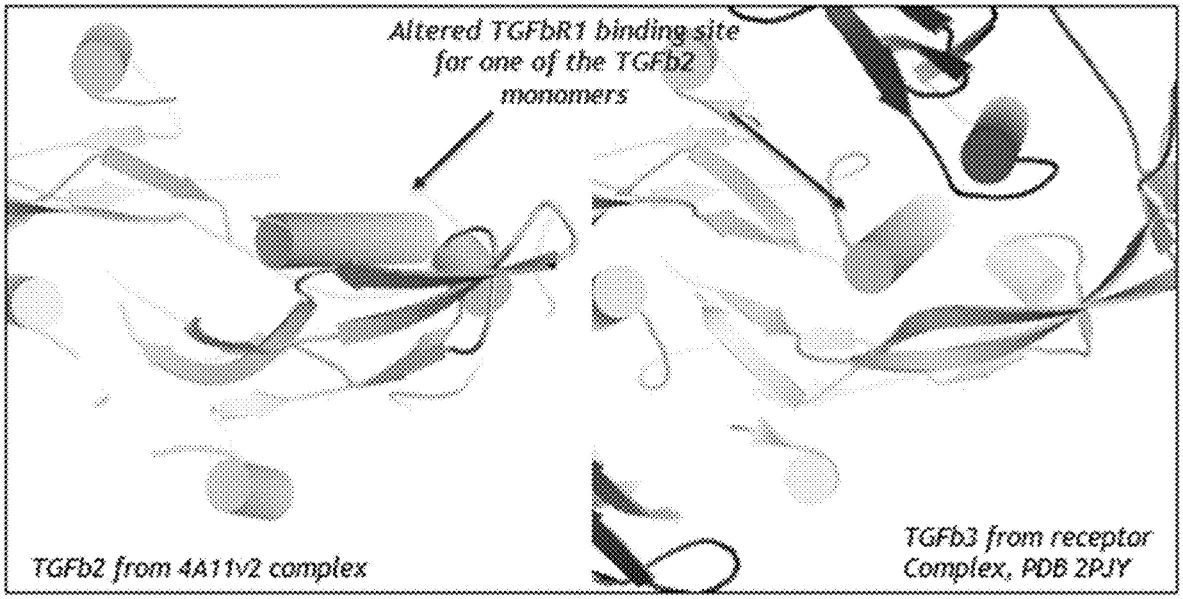
FIG. 37 is a cartoon showing TGFβ2 from the 4A11v2 complex (left image) and TGFβ3 from TGFβR1/TGFβR2 complex. Conformation changes in the TGFβ2 structure may alter the ability of TGFBR1 to bind on one monomer.

As shown in FIG. 34, the 4A11 epitope is away from the TGFBR1/TGFBR2 binding sites, and neither 4A11 molecule sterically competes for receptor binding. Instead, the 4A11 Fabs appear to induce a conformational change in TGFβ2, causing the two monomers to "pinch" together by several degrees (FIG. 36). Comparison of the 4A11 bound TGFβ2 to TGFβ3 bound to TGFBR1 and TGFBR2 suggests that the receptor binding site for at least one of the TGFβ2 monomers is compromised by this conformational change (FIG. 37). These changes apparent in the crystal structure indicate that 4A11 uses an allosteric mechanism to inhibit TGFβ2/3 signaling, by conformational disruption of one or both of the receptor binding sites. Importantly, bivalent binding of a 4A11 IgG molecule would be required to induce this conformational change in TGFβ2/3, and therefore inhibit TGFβ2/3 signaling. Unlike a receptor blocking antibody, where blocking one R1/R2 receptor binding site on the TGFβ dimer can block signaling, single arm binding of 4A11 is unlikely to be sufficient to inhibit signaling. Given the location of the epitopes, divalent binding of a full 4A11 IgG molecule may also sterically prevent an IgG bound TGFβ2/3 molecule from getting close enough to the membrane to any of the TGFB receptors.

Figure 38:
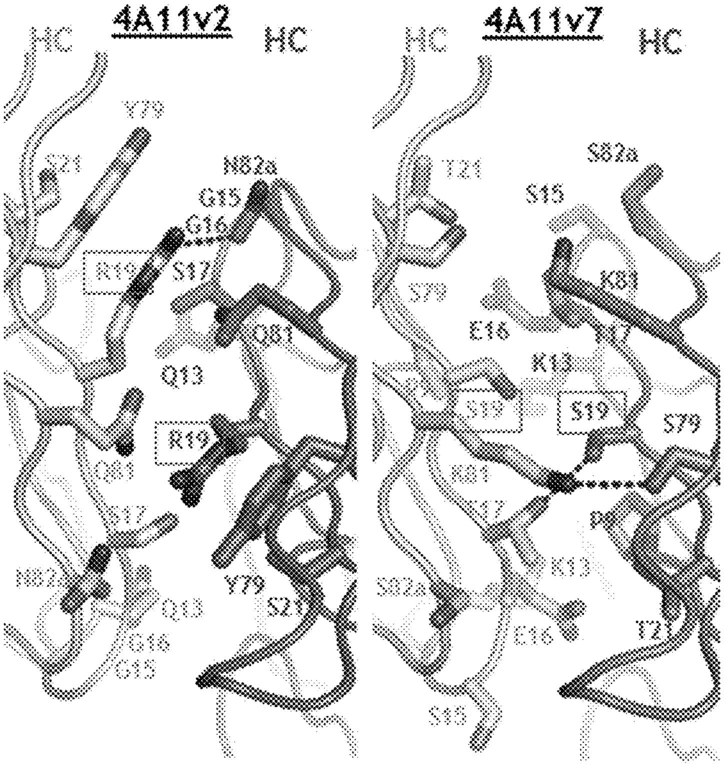
FIG. 38 shows the interaction of heavy chain of 4A11v2 (left structure) and 4A11v7 (right structure) residues; VH framework interaction are complementary in both structures.

During the humanization process for 4A11, it was noted that a number of antibody framework sequences caused a disconnect between antibody affinity and $IC_{50}$ in a cell based assay. For example, 4A11v2 had picomolar affinity for TGFβ2, but lost all activity in cell based assays, while 4A11v7 had similar in vitro affinity to v2, but retained very potent activity in cell based assays. As previously mentioned, V2 and v7 were humanized to the VL1VH3 and VL3VH4 frameworks respectively, which have significant sequence differences. It was therefore investigated more closely how framework residues may influence the ability of 4A11 to form a divalent complex with the TGFβ2 dimer (FIG. 38).

Figure 39:
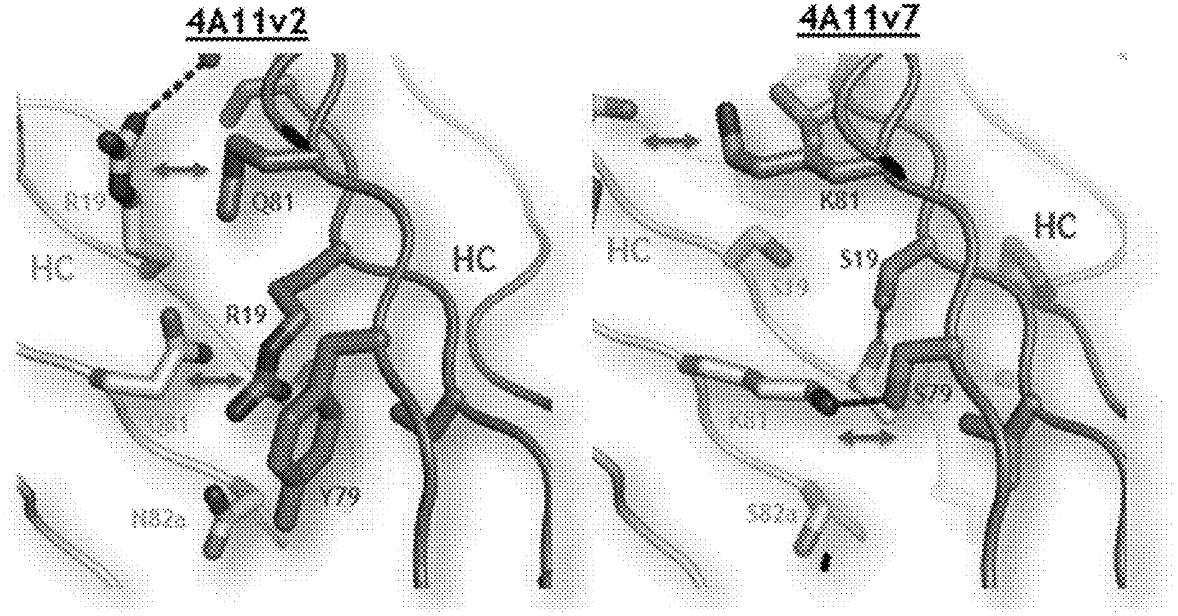
FIG. 39 shows 4A11v2 and 4A11v7 VH framework comparisons. In 4A11v2, Q81 is packed against R19 in a high-energy rotamer and awkward position. In 4A11v7, K81 forms a weak H bond to S79, therefore framework residues in v2 are likely repulsive, while v7 residues are more permissive.

The structures of 4A11v2 and v7 with TGFβ2 show that the heavy chain frameworks come close together in the structure, and actually do interact to form an interface. The residues within those framework regions could therefore have an effect on the ability of a 4A11 IgG molecule to form a divalent complex. A close examination of this HC/HC framework interface suggests that the v2 framework residues are a less permissive interface than that seen for v7 (FIG. 39). For example, HC position 19 is an Arginine in v2 and a serine in v7, and HC position 81 is a Glutamine in v2 and a Lysine in v7. In v2, the R19 and Q81 push close together, forming what looks to be an entropically unfavorable contact, with no stabilizing polar interaction. In v7, the S19 residue makes space for K81 to reach out and form a H-bond with Ser79. In addition, v2 has two large bulky residues (Y79 and N82a) that do not form obvious productive contacts. Importantly, these positions are smaller residues in v7 (S79 and S82a), which likely allows the HC framework interface to come together in a more permissive fashion. While these HC framework contacts in v7 do not appear to be particularly complementary, they do seem to be more permissive (less unfavorable) than the framework contacts between the two v2 heavy chains. These interactions appear to be unfavorable, due to both steric bulkiness and potential entropic penalty of burying large flexible sidechains.

Further corroborating the above analysis, calculation of the buried surface area for the HC/HC framework interactions in the v2 and v7 structures suggest the v7 HC/HC contact is more complementary. In the 4A11v2/TGFβ2 structure, the HC/HC interface (chain D and chain F) buries approximately 660A2 of surface area. For the 4A11v7/TGFβ2 structure, there are two of the 2:2 complexes in the asymmetric unit of the crystal, and between the two sets of HC/HC framework interactions, 1050 A2 (chain D/F) and 730A2 (chain B/H) are buried. The large difference here between the two 2:2 complexes is likely caused by crystal packing artifacts, but the overall trend suggests the v7 HC/HC interface is larger, suggesting a more complementary contact area. It is also important to mention that in the context of a crystallization experiment, the protein concentrations are very high (>10 mg/mL) and at those concentrations repulsive effects of non-complementary HC/HC framework interactions can be overcome and the divalent complex formed. In the context of a lower-concentration solution-based experiment (such as cell based assay, or in vivo) repulsive effects induced by the framework could cause monovalent binding to be preferred over divalent binding.

Figure 40:
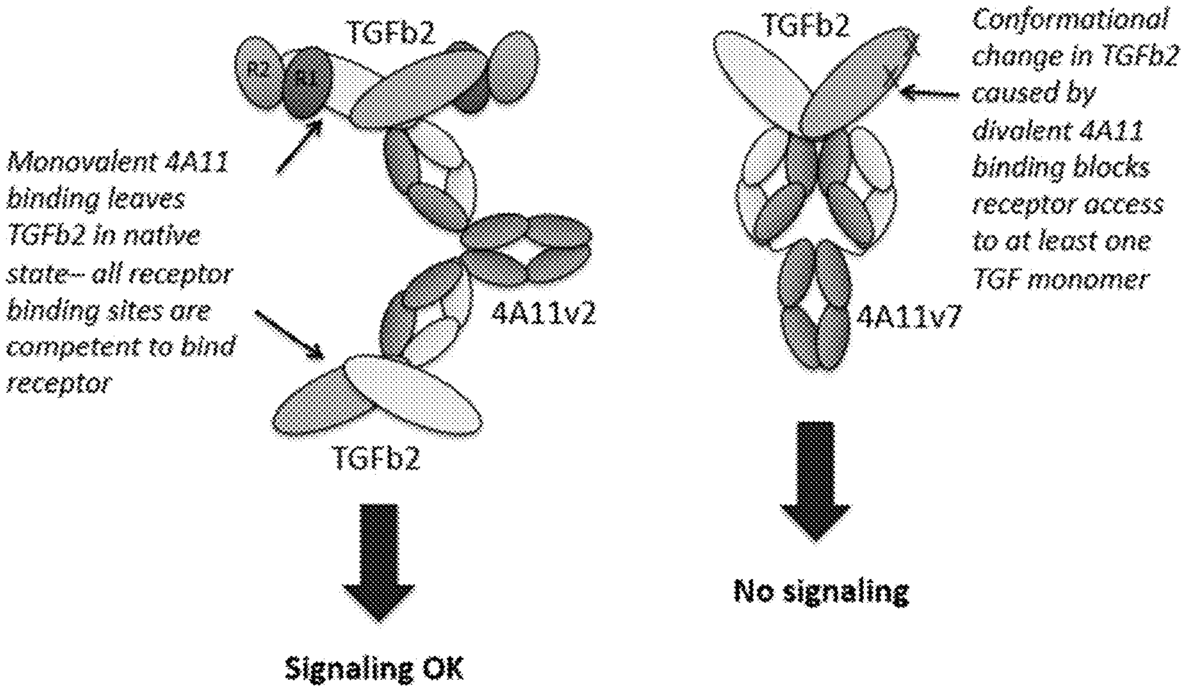
FIG. 40 contains cartoons illustrating monovalent (left cartoon) and divalent (right cartoon) 4A11 binding to TGFβ2.

The implications of these framework differences are important to explain the differences in cell-based activity of 4A11v2 vs v7 (FIG. 40). If at a low concentration, v2 cannot divalently bind to the TGFβ2/3 dimer, this antibody will not induce the necessary conformational change in TGFβ to block the second receptor site and inhibit signaling. For v7, the framework contacts are permissive for divalent binding to TGFβ2/3 dimer, and therefore this antibody can induce the conformational change that blocks receptor tetramer formation, and therefore can inhibit signaling. This data all points to a novel mechanism of allosteric inhibition of TGFβ2/3 by the 4A11 antibody, that does not rely on steric block of (interference with) the receptor, but instead requires divalent binding to the TGFβ dimer to block signaling.

Example 11: Safety Comparison to Pan TGFβ 1D11 Antibody

In this example, 2A10 mAb, an antibody having the 2A10.v4 variable region with a murine IgG1 Fc region, or the pan-TGFβ antibody 1D11, is administered thrice weekly (TIW) for 4 weeks (12 total doses) to CD-1 mice at doses of 0 (control), 10 and 50 mg/kg I.P. TIW, and 50 mg/kg I.V. TIW in a vehicle consisting of phosphate buffered saline. Males and females are assigned to the toxicity groups at all dose levels and are scheduled for necropsy at the end of the dosing period (Day 29). Blood for toxicokinetic evaluation is collected from additional mice in the control and 2A10/2A10v4 mAb treated groups (n=9 males/group). Criteria for evaluations include the following parameters: clinical observations, body weight, clinical pathology (hematology and clinical chemistry), anatomic pathology, and toxicokinetics.

The AUC exposures are determined, and expected to increase approximately dose-proportionally with an increase in dose from 10 to 50 mg/kg.

No 2A10- or 2A10.v4-related clinical observations, effects on body weight, or clinical pathology changes are expected, whereas such related clinical observations, effects on body weight, or clinical pathology changes indicating increased toxicity are expected for mice treated with 1D11 antibody, e.g., histologic lesions, weight loss, nonneoplastic cystic epithelial hyperplasia and inflammation of the tongue and dental dysplasia and epithelial hyperplasia of the gingiva and esophagus, as described in Lonning et al. (2011) Current Pharmaceutical Biotechnology, 12, 2176-2189.

Example 12: Safety Comparison to Anti-TGFβ1 Selective Antibodies

In this example, 2A10 mAb, an antibody having the 2A10.v4 variable region fused to a murine IgG1 Fc region, the variable region of the anti-TGFβ1 antibody CAT-192 (metelimumab) fused to murine IgG1 Fc, are each administered thrice weekly (TIW) for 4 weeks (12 total doses) to CD-1 mice at doses of 0 (control), 10 and 50 mg/kg I.P. TIW, and 50 mg/kg I.V. TIW in a vehicle consisting of phosphate buffered saline. Males and females are assigned to the toxicity groups at all dose levels and are scheduled for necropsy at the end of the dosing period (Day 29). Blood for toxicokinetic evaluation is collected from additional mice in the control and 2A10/2A10v4 mAb treated groups (n=9 males/group). Criteria for evaluations include the following parameters: clinical observations, body weight, clinical pathology (hematology and clinical chemistry), anatomic pathology, and toxicokinetics.

The AUC exposures are determined, and expected to increase approximately dose-proportionally with an increase in dose from 10 to 50 mg/kg.

No 2A10- or 2A10.v4-related clinical observations, effects on body weight, or clinical pathology changes are expected, whereas such related clinical observations, effects on body weight, or clinical pathology changes indicating increased toxicity are expected for mice treated with CAT-192, e.g., as described in Denton *A&R* 56:323 (2007).

Example 13: Full-Length TGFβ3 Conditioned Media Inhibits Alveolosphere Formation In Vitro Materials and Methods Lung Cell Isolation Lung cells were isolated following a previously published protocol (see, Rock et al., 2011 Proceedings of the National Academy of Sciences of the United States of America 108, E1475-1483). Tissues were disrupted and single cells were collected after lungs were inflated and digested with a protease solution cocktail (5 U/ml Dispase, 450 U/ml Collagenase Type I, 4 U/ml Elastase and 0.33 U/ml DNaseI in DMEM/F12) for 45 minutes at 37° C. with frequent agitation. Cells were then washed by DMEM with 10% Fetal Bovine Serum (FBS, Invitrogen) and resuspended in ACK lysis buffer for 3 minutes to lyse red blood cells. After washing, cells were blocked by purified rat anti-mouse CD16/CD32 antibody (Cat #553142; BD Biosciences) and stained with antibodies for CD45 (Cat #17-0451-82, eBioscience), EpCAM (Cat #11-5791-82, eBioscience). AEC2 cells were sorted on a BD FACSAria Fusion cell sorter (BD Biosciences), based on the following markers: CD45-; $EpCAM^+$; and $tdTomato^+$. Data was analyzed by Flowjo software.

AEC 3-D Organoid Culture

AEC organoid culture was performed by following a previously published protocol with minor modifications (see, Barkauskas, 2013 JCI 123, 3025-3036; Sun T, et al, 2019, JCI Insight; June 18; 5(14):e128674). Sorted AEC2 cells were mixed with human stromal cell NHLF (Cat #CC-2512; Lonza Walkersville Inc. USA) at a 1:10 ratio. The cells were resuspended in pre-chilled 1:1 mixed media of MTEC/Plus and growth factor-reduced Matrigel (Cat #356231; BD Biosciences). $10^4$ AEC2 cells and 105 NHLF cells were placed in 90 μl mixed media in a 24-well 0.4-μm transwell insert (Cat #3470; Costar). 500 μl MTEC/Plus media was added to the lower chamber. Media were changed every other day. Organoids were assessed after 12-14 days of culture by inverted fluorescence microscope.

Microscopy

The whole organoid culture images were captured on a Nikon Ti-E Perfect Focus inverted microscope. Large images were generated by automatically stitching multiple adjacent frames from a multipoint acquisition using a motorized stage. Images were analyzed by ImageJ software.

Secretome Library Screening

The Secretome library is a collection of plasmids expressing individual human cDNA on mammalian expression vectors, containing ~1,700 individual full-length genes that encode secreted proteins. To identify factors that may be involved in AEC biology in the alveolar organoid system, the library was first divided into 96 sub-libraries, with each containing around 10-20 individual plasmids. Each sub-library plasmid pool was transiently transfected into 293T cells using Lipofectamine 2000 (Cat #11668019, ThermoFisher) by following the manufacturer's recommendations. Conditioned media were collected two days later, kept at 4° C. until used in the alveolosphere culture. Positive sub-libraries were identified at the end of the culture. During the second round of screening, conditioned media from individual plasmids in each positive sub-library were generated and tested. Positive single genes responsible for the organoid culture phenotypes were eventually identified.

Results

The lung alveolar epithelium is maintained and repaired by proliferation and hyperplasia of type 2 alveolar epithelial cells (AEC2), followed by differentiation into type 1 alveolar epithelial cells (AEC1). To investigate AEC biology, a 3-D alveolosphere organoid culture system was employed, in which fate-mapped AEC2s were isolated from Sftpc-$CreER^{72}$; Rosa26R-tdTm mice after tamoxifen induction and co-cultured with lung fibroblasts in Matrigel. After ~14 days, spheroids derived from individual AEC2s form, with an outer layer of AEC2s and an inner lumen with AEC1s that have differentiated from AEC2 progenitors. This system was previously employed to identify TAZ as a regulator of AEC2-AEC1 differentiation during alveolar repair (see, Sun, T. et al. (2019). JCI Insight; June 18; 5(14):e128674). To identify potential secreted factors that affect alveolar epithelial cell proliferation, a screen was performed using an expression plasmid library carrying approximately 1,700 individual human genes encoding secreted proteins. This plasmid library was transiently transfected into 293T cells, first in pools (10-20 individual plasmids/pool) and subsequently individually, harvested the conditioned media two days later, and added conditioned media to alveolosphere cultures. Conditioned media from cells transfected with a construct encoding full-length TGFβ3 completely inhibited alveolosphere formation. In contrast, conditioned media from cells transfected with full-length TGFβ1 had no effect, despite using the same transfection conditions and expression vectors. Prior studies have shown that the receptor-binding domain ("mature" form) of TGFβ1 can promote apoptosis of primary type 2 alveolar epithelial cells (AEC2) in vitro and in vivo. Indeed, recombinant mature forms of TGFβ 1 or TGFβ3 inhibited alveolosphere formation in these experiments. Therefore, under the culture conditions used, full length LAP-associated TGFβ1 is inactive, but full length LAP-associated TGFβ3 is active, suggesting that "latent" TGFβ3 has intrinsic activity and/or it can be activated by a unique mechanism presented in this culture system, distinct from those described for TGFβ1.

Figure 41:
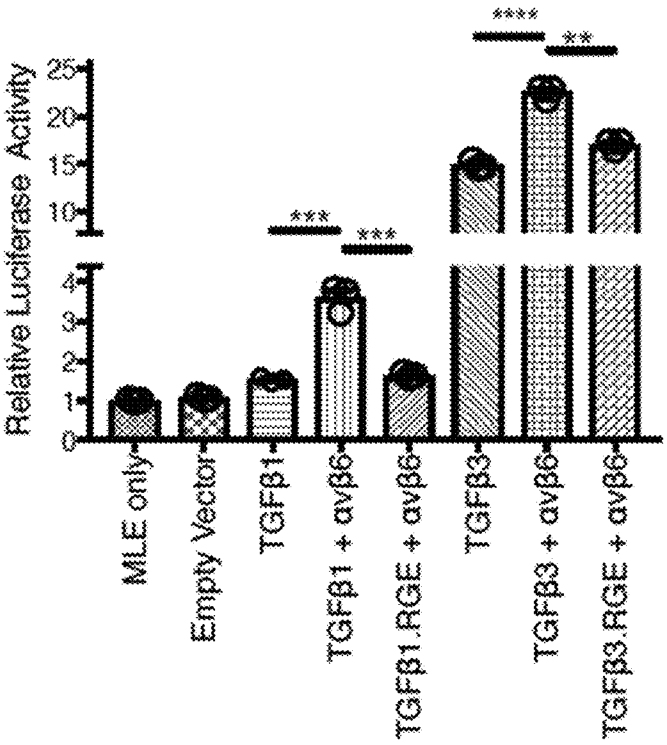
FIG. 41 is a graph plotting the relative luciferase activity of MLEC reporter cells following coculture with 293T cells transfected with a plasmid encoding FL-TGFβ1 or FL-TGFβ3 (wild-type or RGE mutants) with or without plasmids encoding integrins αv and β6. , $P<0.01$; *, $P<10^{-3}$; ****, $P<10^{-4}$; NS, $P>0.05$ by unpaired two-tailed Student's t-test.

Example 14: Full-Length TGFβ2 and TGFβ3 can Activate TGFβR-Dependent Signaling Independent of Integrin Binding In Vitro As integrin binding is an established mechanism of TGFβ1 activation, and differential activity of TGFβ 1 and TGFβ3 was observed in the alveolosphere model, it was next sought to determine the integrin dependence of TGFβ3 activation. A 2-cell in vitro reporter system was used, in which expression vectors encoding full-length TGFβ1 or TGFβ3 were cotransfected into 293T cells with expression vectors encoding αv and β6 integrins, and co-cultured with a reporter cell line driving luciferase expression downstream of a SMAD-dependent promoter element ("MLEC") (see, Abe et al., 1994; Anal Biochem, 216, 276-284). While full-length TGFβ1 required co-expression of αvβ6 integrin to induce reporter activity, it was found that full-length TGFβ3 robustly induced reporter activity without co-transfection of αv and β6 integrin constructs. Co-expression of αvβ6 further increased full-length TGFβ3 dependent reporter activity, and this further increase was attenuated by mutation of the RGD integrin-binding motif in the LAP of TGFβ3 to RGE (FIG. 41).

Figure 42:
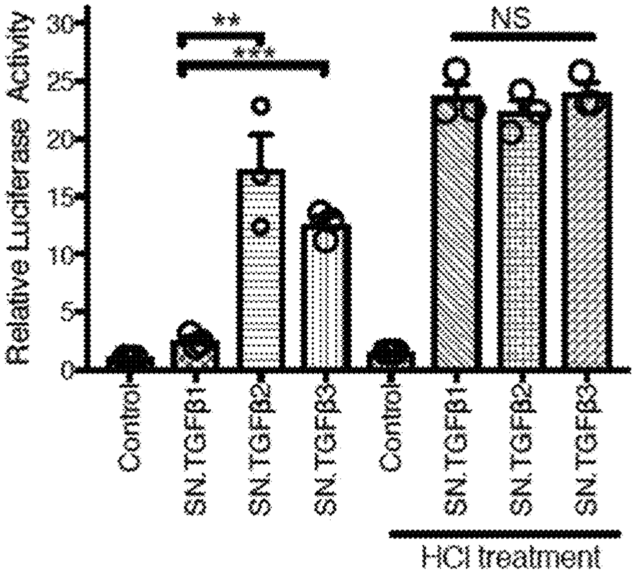
FIG. 42 is a graph plotting the relative luciferase activity in supernatants (SN) from MLEC reporter cells (measuring TGFβ activity). SN were collected from cells transfected with a plasmid encoding FL-TGFβ1, FL-TGFβ2, FL-TGFβ3 or an empty vector (control). Supernatants were acidified as indicated (HCl treatment). , $P<0.01$; *, $P<10^{-3}$; **** $P<10^{-4}$; NS, $P>0.05$ by unpaired two-tailed Student's t-test.
Figure 43A:
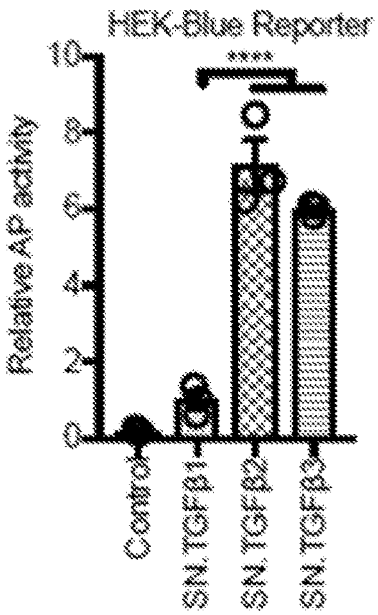
FIG. 43A and FIG. 43B are graphs plotting the TGFβ activity assessed by alkaline phosphatase released by HEK-Blue TGFβ reporter cells (FIG. 43A) or with MLEC reporter cell assay (relative luciferase activity) (FIG. 43B).
Figure 43B:
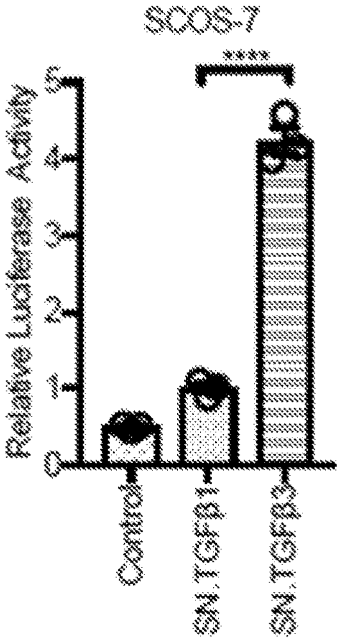

Consistent with the observed effects from the alveolosphere experiment described above, supernatants from cells transfected with full-length TGFβ3, but not TGFβ1, robustly induced reporter activity (FIG. 42). Similar reporter induction was observed with supernatants from full-length TGFβ2-transfected cells; as TGFβ2 lacks an RGD motif (FIG. 1), its activation is likely integrin-independent (FIG. 42). Total TGFβ activities from these three supernatants were comparable after an acidification step, which releases the receptor-binding domain of TGFβ from its latent complex (FIG. 42). To rule out the possibility that these effects were specific to the reporter cell lines we used, HEK-Blue (InvivoGen) and SCOS-7 cells were assessed as alternative TGFβ reporter and transfection recipient cell lines, respectively. High "intrinsic" activities of TGFβ2 and/or TGFβ3 were observed in both cases (FIG. 43A and FIG. 43B).

Figure 44:
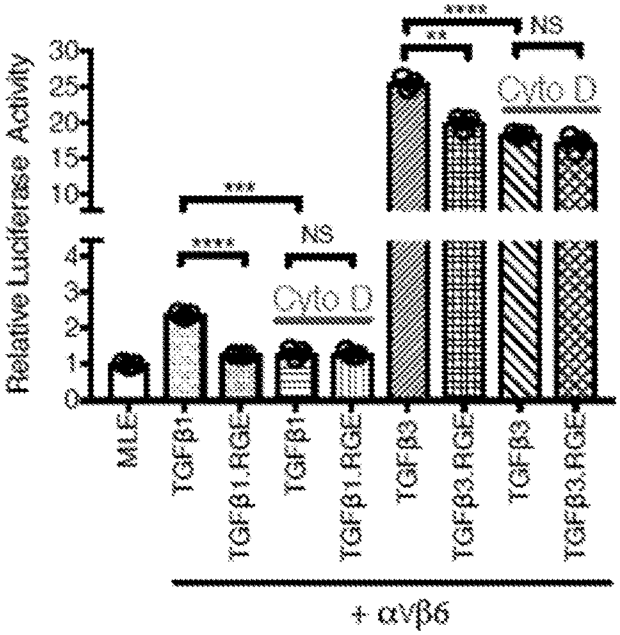
FIG. 44 is a graph plotting the TGFβ activity assessed by MLEC reporter cell assay (relative luciferase activity). 293T cells were transfected with plasmids encoding various forms of FL-TGFβ and integrins αv and 06. TGFβ activities were measured with MLEC reporter cells after co-culture. Cytochalasin D (30 μM) was added at the beginning of the co-culture where indicated ("Cyto D"). "MLE" is control. , $P<0.01$; *, $P<0.001$; ****, $P<10^{-4}$; NS, $P>0.05$ by unpaired two-tailed Student's t-test.

Cytoskeletal tension is required to transduce forces during integrin αvβ6-mediated activation of latent TGFβ1. To discount the possible involvement of other cytoskeleton dependent integrin activities, this culture system was treated with cytochalasin D to inhibit actin polymerization, which reduced the integrin αvβ6-mediated activation of TGFβ 1 and TGFβ3. However, the "intrinsic" activity of TGFβ3 remained unaffected (FIGS. 44A-44C), suggesting that this activity is integrin independent.

Figure 45:
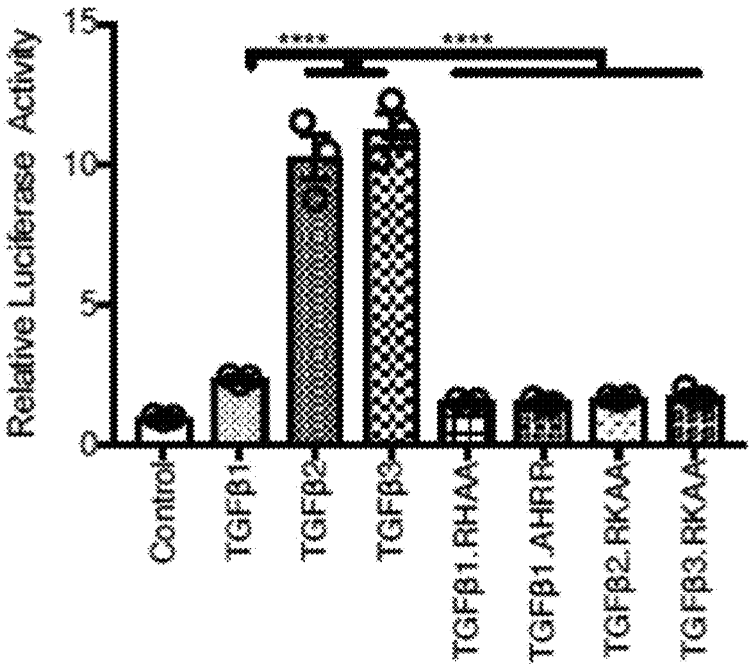
FIG. 45 is a graph plotting the TGFβ activity assessed by MLEC reporter cell assay (relative luciferase activity) in supernatants collected from 293T cells transfected with plasmids encoding wild-type or furin site mutant FL-TGFβ proteins, showing the loss of TGFβ activities with the mutated proteins. , $P<0.01$; *, $P<0.001$; ****, $P<104$; NS, $P>0.05$ by unpaired two-tailed Student's t-test. Data are averages±SEM from experiments run in triplicate. Error bars are not shown when they are shorter than sizes of their corresponding symbols.
Figure 46:
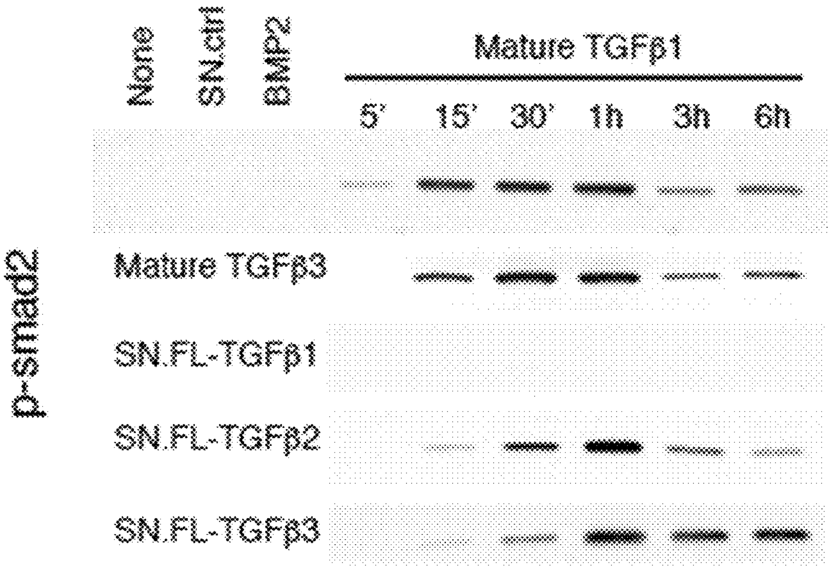
FIG. 46 is an image of a Western blot showing the kinetics of smad2 phosphorylation in NHLF cells treated with recombinant proteins or supernatants. As controls, NHLF cells were also treated with supernatant from non-transfected cells (SN.ctrl) or the recombinant BMP2 for 1 hour. To control the loadings among different samples, protein concentrations of supernatants were measured by BCA and 20 μg protein was loaded in each lane.

In the Golgi apparatus, the pro-peptide of TGFβ1 (pro-TGFβ1) is proteolytically cleaved by furin, leading to the formation of the SLC. This proteolytic digestion is essential to generate functional TGFβ1. All three TGFβ isoforms have conserved furin cleavage sites (RKKR or RHRR, FIG. 1). To assess the requirement for this protease cleavage for TGFβ2/3 activity in our system, the furin cleavage sites in each TGFβ isoform were mutated. Mutated full-length TGFβ2 and P3 completely lost their intrinsic activities (FIG. 45). Thus, like TGFβ1, furin cleavage is required for TGFβ2/3 activity, despite distinct extracellular activation mechanisms of the SLCs. To evaluate the kinetics of "intrinsic" TGFβ2 and TGFβ3 activity, phospho-SMAD2 was assessed in normal human lung fibroblasts (NHLF) after treatment with transfection supernatants and observed similar kinetics to cells treated with recombinant TGFβ receptor-binding domains, with pSMAD2 peaking about 1 h after stimulation (FIG. 46).

Figure 47:
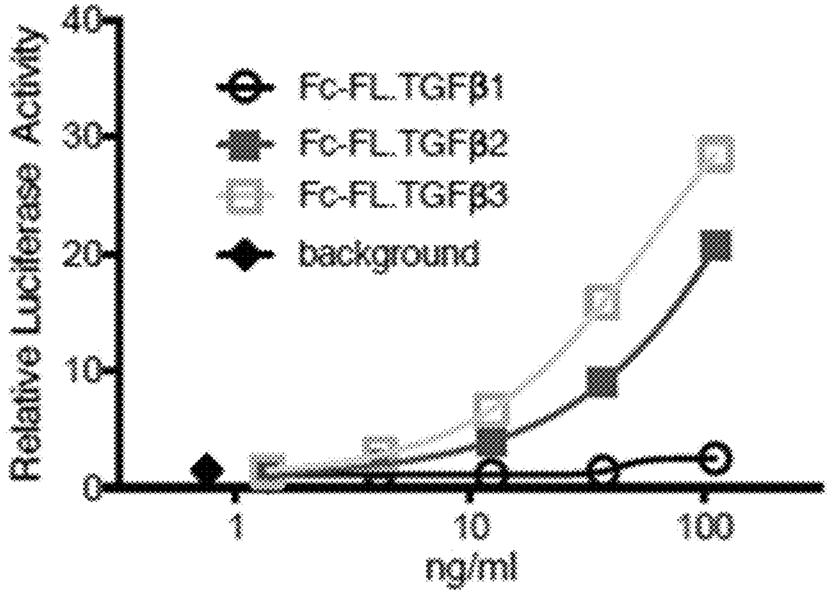
FIG. 47 is a graph plotting TGFβ activity measured in MLEC reporter cells (relative luciferase activity) after incubation with a series of concentrations of human Fc-FL-TGFβ isoform fusion proteins. "Background" means no fusion protein was added. Data are averages±SEM from experiments run in triplicate and error bars are not shown when they are shorter than sizes of their corresponding symbols.
Figure 48:
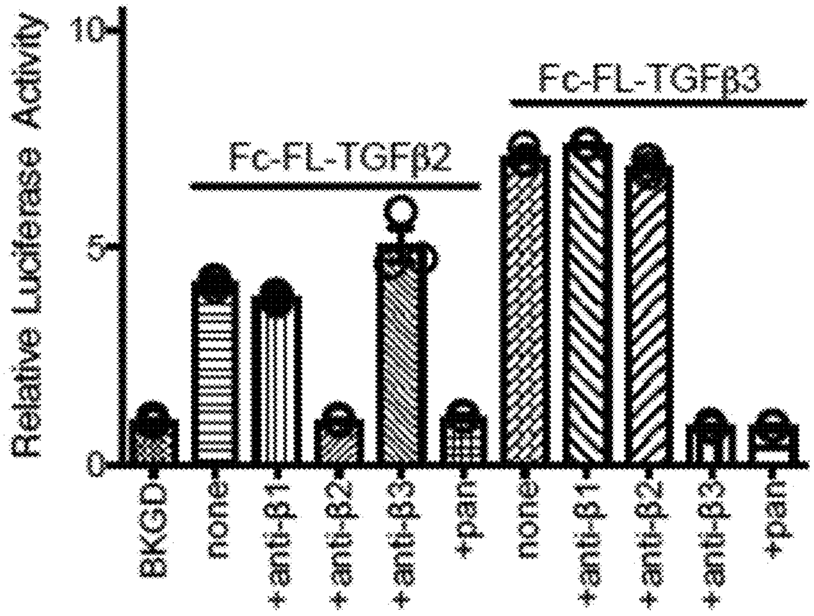
FIG. 48 is a graph plotting TGFβ activity measured in MLEC reporter cells (relative luciferase activity) after incubation with human Fc-FL-TGFβ2 or Fc-FL-TGFβ3 fusion proteins (30 ng/ml) and isoform specific antibodies: 19D8 (anti-TGFβ1); 6F12 (anti-TGFβ2); 2A10 (anti-TGFβ3); and 1D11 (pan-anti-TGFβ) at 3 g/ml. "Background" means no fusion protein was added. "None" means no antibody added. Data are averages±SEM from experiments run in triplicate and error bars are not shown when they are shorter than sizes of their corresponding symbols.

To discount the possibility that other factors present in the conditioned media of transfected cells could contribute to TGFβ2 and TGFβ3 activation, recombinant full-length TGFβ isoforms were generated. To improve expression and stability and to facilitate purification, in-frame N-terminal fusions were made of the constant domain of human IgG1 ("Fc") to each isoform (Fc-FL-TGFβ1, 2, and 3). Consistent with the effects observed in conditioned media, purified recombinant Fc-FL-TGFβ1 did not activate reporter activity in MLEC. However, Fc-FL-TGFβ2 and Fc-FL-TGFβ3 robustly induced reporter activities (FIG. 47), which were inhibited by their respective isoform-specific antibodies (FIG. 48).

Figures 49, 50A, 50B, 50C:
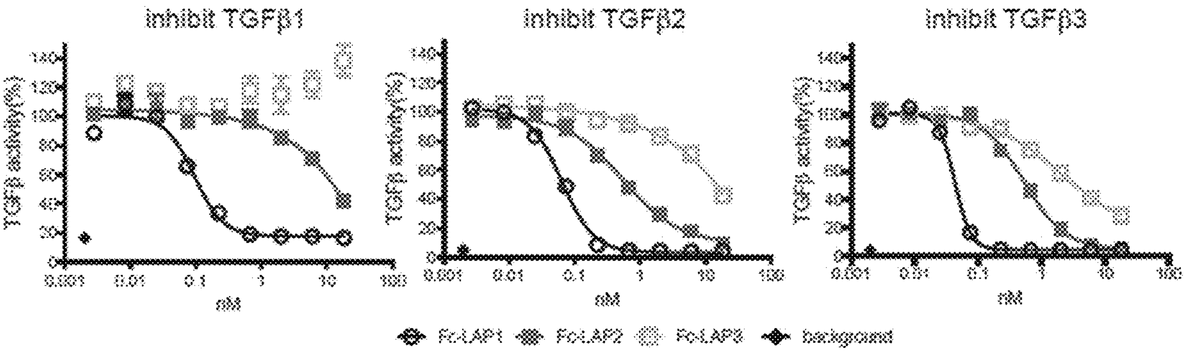
FIG. 49 is a table showing the primary amino acid sequence similarities (%) among human TGFβ isoforms of the latency associated peptides (LAPs) and mature domains (active).
FIG. 50A, FIG. 50B, and FIG. 50C are graphs showing titration curves from MLEC reporter cell assay (TGFβ activity) following incubation of mature peptide (1 ng/ml) of TGFβ1, TGFβ2 or TGFβ3 (left to right graphs) with a series of concentrations of human Fc-LAP fusion proteins as indicated. Data are averages±SEM from experiments run in triplicate and error bars are not shown when they are shorter than sizes of their corresponding symbols.

Previous studies showed that recombinant LAP from TGFβ1 (LAP1) can strongly inhibit the receptor-binding domains of TGFβ1, 2, and 3 in vitro and in vivo, presumably by reconstituting them into SLCs. While the receptor-binding domains of TGFβ isoforms are highly homologous, the LAP domains are more diverse (FIG. 49). Thus, it was postulated that the LAPs from TGFβ1, 2, and 3 (LAP1, 2 and 3, respectively) might have differential inhibitory capacities. Recombinant N-terminal fusion proteins of human IgG1 with human LAP1, 2, and 3 (Fc-LAP1, 2, and 3) were generated. Substantially different neutralization capabilities were observed for each Fc-LAP. Consistent with observations with conditioned media and recombinant full-length TGFβ proteins, Fc-LAP1 more potently inhibited the receptor-binding domains of all three TGFβ isoforms than Fc-LAP2 or Fc-LAP3 (FIGS. 50A, 50B and 50C and FIG. 51). Taken together, these data show that the relative potencies of LAP1, 2, and 3 to inhibit TGFβ activity are divergent and may explain the "intrinsic" activities of full-length TGFβ2 and TGFβ3 not observed for TGFβ1.

Taken together, these data show that FL-TGFβ2 and TGFβ3 may have distinct activation mechanisms and thresholds from those of TGFβ1. Although FL-TGFβ1 can be activated by ectopic expression of αvβ6 integrin, and the activity of FL-TGFβ3 can be increased by αvβ6 integrin binding, both FL-TGFβ2 and FL-TGFβ3 appear to have "intrinsic" activities, and/or are activated by as-yet unidentified mechanisms. The biochemical inhibitory potencies of LAP1, 2, and 3 are divergent, with the biochemical IC50 of LAP1 against each receptor-binding isoform being several orders of magnitude lower than those of LAP2 and LAP3. Given that latent TGFβ 1 has a much higher threshold for activation than latent TGFβ2 or TGFβ3, these mechanistic observations suggest that TGFβ2 and TGFβ3 gene expression are more likely than TGFβ1 gene expression to reflect their activities in tissue.

The receptor-binding domains of TGFβ1, 2, and 3 are highly homologous, with 83-90% amino acid similarity. Dimeric receptor-binding domains of all three isoforms bind to pairs of heterodimeric receptor complexes of TGFβR1 and TGFβR2; the tetrameric receptor complex then activates intracellular signaling via receptor tyrosine kinase (RTK) activity of TGFβR1, also known as ALK5. In canonical TGFβR signaling, ALK5 phosphorylates SMAD2 and SMAD3, which then associate with SMAD4, translocate to the nucleus, and direct gene transcription. Additional non-SMAD dependent signaling pathways such as MAP kinases, AKT, JAK-STAT, and NFκB may be activated downstream of TGFβRs in certain contexts (Derynck, 2019 Science signaling 12). Biochemical and structural studies have shown that the assembly of TGFβ-TGFβR signaling complexes have subtle isoform-specific differences: TGFβ1 and TGFβ3 bind more strongly to TGFβR2 and only form strong interactions with TGFβR1 when in complex with TGFβR2, whereas TGFβ2 binds weakly to both TGFβR1 and TGFβR2 alone, and avidity may drive full complex formation (Radaev, 2010, JBC 285, 14806-14814). TGFβ1 and TGFβ2 crystallize in "closed" structures that facilitate binding to TGFβR1 and TGFβR2, while TGFβ3 can adopt a similar "closed" or less ordered "open" structure in crystal form, which may lead to differences in the avidity of ligand-receptor complex assembly. In addition, TGFβR3 (betaglycan), a non-signaling receptor, can facilitate TGFβ2 binding to TGFβR1/2 complexes, but does not appear to play a similar role in TGFβ 1 or TGFβ3 receptor binding (del Re, 2004 JBC 279, 22765-22772). The structural analyses of the allosteric inhibitory mechanism of 4A11 demonstrated herein suggest that bivalent antibody binding to a TGFβ2 or TGFβ3 dimer constrains TGFβ in a form that precludes simultaneous binding to two sets of receptor heterodimers (FIG. 7). Ultimately, despite these differences in signaling complex assembly, recombinant receptor-binding domains of TGFβ1, 2, and 3 are all able to induce TGFβR-dependent SMAD signaling to a similar degree in cell-based in vitro assays. Hence, any differences in the in vivo activity of endogenous TGFβ isoforms are more likely due to differences in their patterns of expression and mechanisms of release from SLC or LLC than to differences in their receptor-binding domains.

Discussion

The LAP domains of TGFβ 1, 2, and 3 are substantially less homologous than the receptor-binding domains, with only 42-56% amino acid similarity. All three isoforms have conserved furin cleavage sites (RKKR or RHRR) between the LAP and receptor-binding domains, and a conserved "fastener" sequence (YYAKE). TGFβ1 and TGFβ3 have an RGD integrin-binding sequence but TGFβ2 has an R-S substitution at that site and has not been shown to be activated via integrin binding. Structures of the SLC including the LAP and receptor-binding domain have been solved for TGFβ1 but not for TGFβ2 or 3. The "finger" region of the receptor-binding domain of TGFβ 1 that interacts with TGFβR2 is shielded by a "latency lasso", a loop between the α1 and α2 helices of the LAP that is associated with the fastener sequence. In all three isoforms, the C-terminal sequence of the LAP α1 helix is highly conserved, with a lysine residue (GQILSKL) that interacts with two conserved tyrosines (YYAKE) in the fastener of TGFβ1; in addition, the alanine (YYAKE) interacts with an arginine in the α5 helix near the C-terminus of the LAP that is conserved across the three isoforms (Shi et al. 2011; Nature 474, 343-349).

The latency lassos of the three TGFβ LAP isoforms show some sequence diversity, with 6 prolines in TGFβ 1, 5 in TGFβ2, and 4 in TGFβ3, and the length of the lasso is 1 and 2 residues shorter in TGFβ2 and TGFβ3, respectively, than in TGFβ1. There are substantial sequence differences between the three isoforms around the RGD integrin binding site: TGFβ2 has an SGD sequence, does not likely bind integrins, and is 9 residues longer than TGFβ1 between the β9 and β10 strands; TGFβ3 has an RGD and is 3 residues longer than TGFβ1I between the β9 and β10 strands; and the loops between the β4 and β5 strands and β7 and β8 strands are substantially longer in TGFβ2 and TGFβ3 than they are in TGFβ1. While structure-function relationships have not yet been elucidated for these regions, it is possible that they may contribute to different modes of activation and/or inhibitory potency of the LAP domains of TGFβ2 and TGFβ3 as compared to TGFβ1. Heterozygous loss-of-function mutations have been described in TGFβ2 and TGFβ3 genes associated with Loeys-Dietz syndrome (see, Lindsay, 2012 Nature Genetics; 44, 922-927; Bertoli-Avella, 2015 J Am Coll Cardiol 65, 1324-1336; Schepers, 2018 Human Mutation 39, 621-634) in key residues in the LAP domains, implicating the furin cleavage site in both, the fastener in TGFβ2, and the RGD integrin-binding site in TGFβ3, suggesting that these conserved motifs are important for at least some functions of TGFβ2 and TGFβ3. While it is shown herein that full-length TGFβ2 and TGFβ3 carry "intrinsic" activity, this activity remains dependent on furin cleavage, and in the case of TGFβ3, can be augmented by integrin binding. Consistent with the notion that the LAP, rather than the receptor-binding domain, confers activation specificity, it is shown herein that the LAP of TGFβ1 can potently inhibit all three isoforms, whereas the LAPs of TGFβ2 and TGFβ3 are significantly less inhibitory.

Example 15: Pharmacokinetics of Anti-TGFβ Isoform-Specific Antibodies in C57BL/6 Mice Pharmacokinetics (PK) of three chimeric antibodies (6F2, 2A10, and 4A11) were characterized following a single intravenous (IV) dose of 1 or 10 mg/kg, or intraperitoneal (IP) dose of 10 mg/kg in female C57BL/6 mice. All three antibodies demonstrated favorable PK profiles, with apparent biphasic distribution characterized by a short distribution phase followed by a longer elimination phase. Linear and dose-proportional ($C_{max}$ and AUC; area under the concentration-time curve) PK were observed between 1 and 10 mg/kg, with clearance ranging from 3.5 to 4.9 mL/day/kg in all cohorts. Following single IP administration of 6F2 and 4A11 at 10 mg/kg, the $AUC_{last}$ was ≥97% and $C_{max}$ was ~50-60% when comparing the $AUC_{last}$ and $C_{max}$ after IV administration at 10 mg/kg. The data are shown in the Table 30, below.

TABLE 30

PK of anti-TGFβ isoform-specific antibodies in C57BL/6 mice

| Antibodies | Specificity | Route | Dose (mg/kg) | $C_{max}$ (μg/mL) | $AUC_{last}$ (day · μg/mL) | CL (mL/day/kg) | $T_{1/2,\lambda z}$ (day) |
|---|---|---|---|---|---|---|---|
| 6F12 | TGFβ2 | IV | 1 | 23.3 | 104 | 4.89 | 10.2 |
| | | IV | 10 | 273 | 1163 | 3.88 | 15.5 |
| | | IP | 10 | 134 | 1197 | 3.58 | 17.5 |
| 2A10 | TGFβ3 | IV | 10 | 305 | 1910 | 3.56 | 13.1 |
| 4A11 | TGFβ2/3 | IV | 1 | 18.1 | 118 | 4.58 | 10.6 |
| | | IV | 10 | 233 | 1486 | 4.16 | 9.2 |
| | | IP | 10 | 133 | 1456 | 4.39 | 5.5 |

$C_{max}$ = maximum observed concentration; $AUC_{last}$ = area under the serum concentration versus time curve from time = 0 to time of the last measurable concentration; CL = clearance; $T_{1/2,\lambda z}$ = terminal half-life

Example 16: In Vivo Activity of Isoform-Selective Anti-TGFβ2 and TGFβ3 Antibodies in a Lung Fibrosis Model Materials and Methods Lung Genomic DNA Isolation and Quantitative PCR Genomic DNA was isolated from mouse whole lungs using the DNeasy Blood & Tissue Kit (Cat #69506; Qiagen). TGFβ DNA levels were quantified by qPCR using Taqman Copy Number Assays (Applied Biosystems). Threshold cycle values (Ct) were normalized to an internal reference, Tert (ΔCT). The genomic DNA levels were calculated by the 2-ΔΔCT method. The following Taqman assays from Applied Biosystems were used:

Tgfb2 Exon3 (Mm00035180_cn)
Tgfb2 Exon6 (Mm00035822_cn)
Tgfb3 Exon3 (Mm00381025_cn)
Tgfb3 Exon6 (Mm00381036_cn)
and Tert (4458373).

Histological Analysis of Mouse Lung Fibrosis in the Bleomycin Induced Model

Formalin fixed samples of mouse lungs (5 lobes) were embedded as a whole and processed to 1 slide per animal, stained with H&E or Masson's Trichrome. Alternatively, fibrosis was evaluated by immunohistochemistry using anti-collagen III antibody (Cat #ab7778, Abcam). The extent of pulmonary fibrosis was scored according to the following criteria:

(A) Interstitial fibrosis pattern—number of foci: 0, none detected; 1, ≤10; 2, ≤15; 3, >15/all sections, but distinct; 4, multifocally coalescent or locally extensive; 5, diffused (B) Interstitial fibrosis—size of foci: 0, none detected; 1, largest focus ≤area of ~2 alveolar spaces; 2, largest focus ≤area of ~4 alveolar spaces; 3, coalescent (>4 patent alveolar spaces); 4, locally extensive (60-90% of an entire lobe); 5, diffuse (>90% of an entire lobe);

(C) Total scores: number of foci×size of foci

Results

Figure 53A:
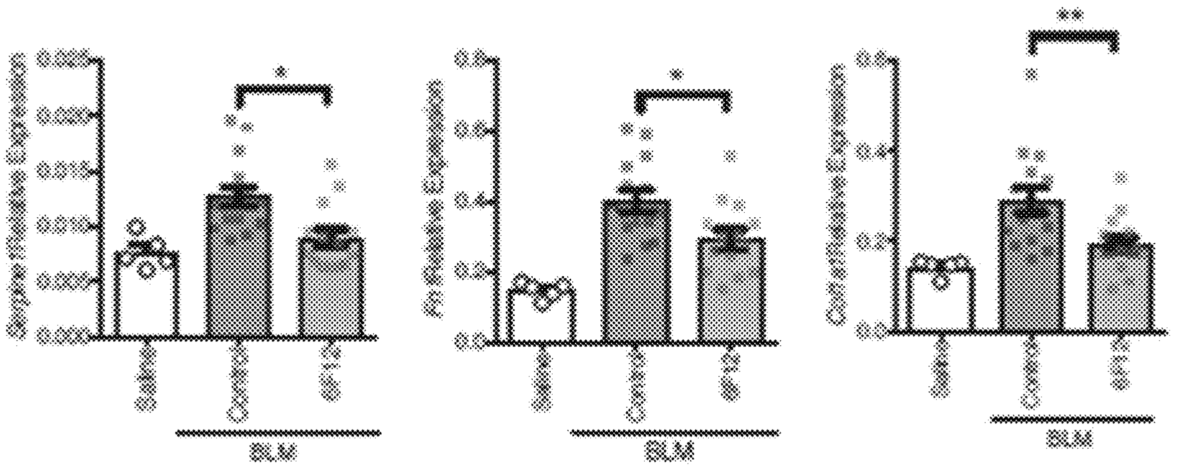
FIG. 53A and FIG. 53B are bar graphs plotting whole lung gene expression of Serpine1, Fn1 and Col1a1 as determined by quantitative RT-PCR 14 days after I.T. saline or bleomycin instillation and treatment with isotype control antibody, anti-TGFβ2 antibody (6F12) (FIG. 53A) or anti-TGFβ3 antibody (2A10) (FIG. 53B).
Figure 53B:
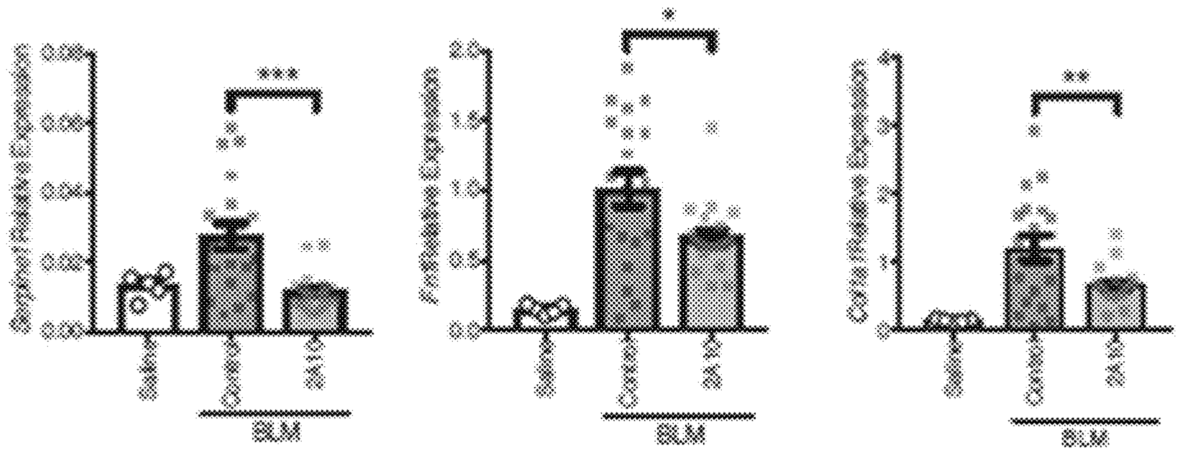
Figure 53C:
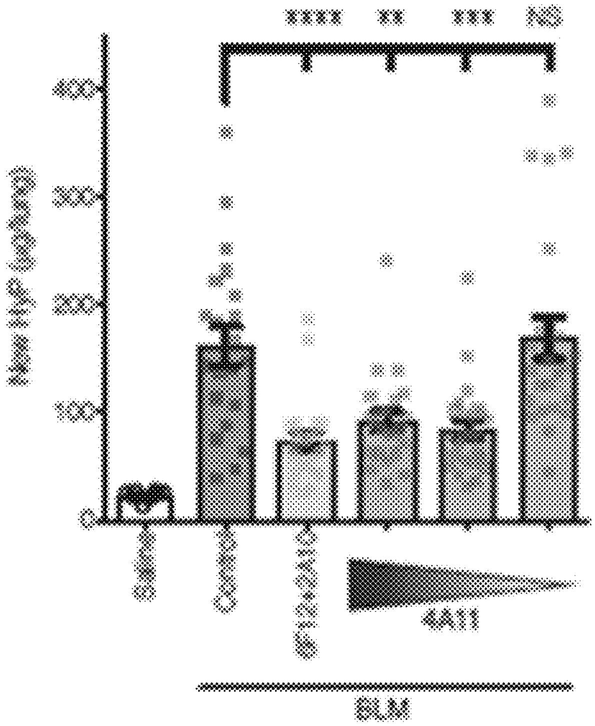
FIG. 53C is a bar graph plotting the newly synthesized collagen levels as determined at day 24 after saline (n=10) or bleomycin ("BLM") installation. Animals were treated with either an isotype control (n=21), the combination (n=23) of 6F12 and 2A10, or anti-TGFβ2/3 antibody (4A11). Dose levels of 4A11 were high (10 mg/kg; 3 times/week, n=23); middle (10 mg/kg; 1 time/week, n=24), or the low (2.5 mg/kg; 1 time/week, n=23), respectively. *P<0.05, P<0.01, * P<0.001, **** P<0.0001, NS, P>0.05 by One-way ANOVA with Dunnett's test.
Figure 53D:
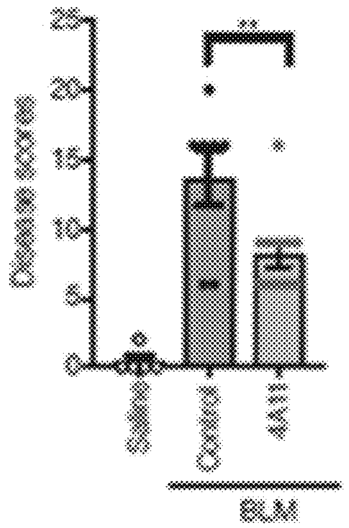
FIG. 53D is a bar graph plotting the disease scores as determined by pathology analyses. Mouse lungs were harvested 24 days after either saline (n=5) or bleomycin ("BLM") instillation, with treatment by either isotype control (n=7) or 4A11 (high dose, n=12). *P<0.05, P<0.01, * P<0.001, **** P<0.0001, NS, P>0.05 by One-way ANOVA with Dunnett's test.
Figure 53E:
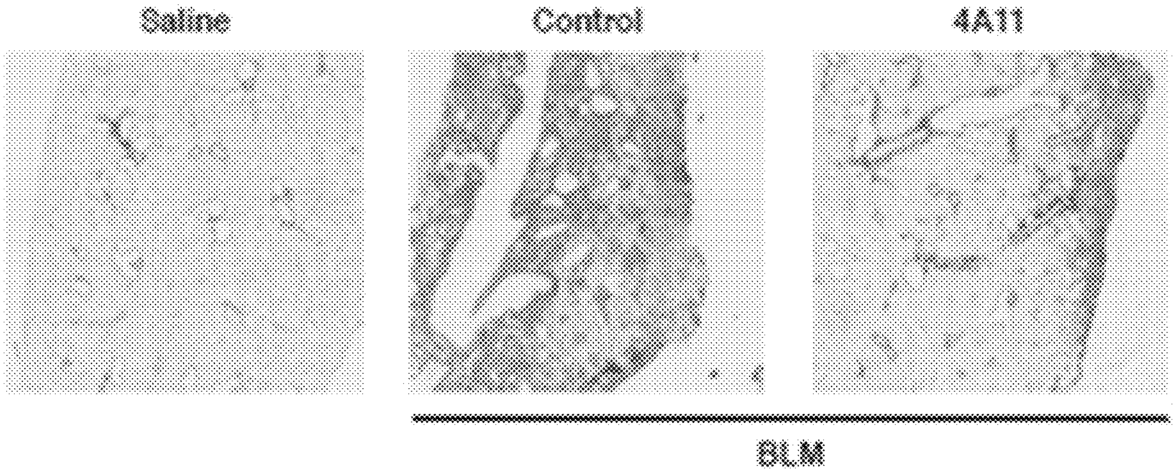
FIG. 53E contains representative mouse lung images of immunohistochemistry staining for collagen III.

To assess the in vivo anti-fibrogenic effects of anti-TGFβ2 (6F12) and anti-TGFβ3(2A10) antibodies, mice were treated preventively and examined for TGFβ induced gene expression in lungs at day 14 after bleomycin administration, when the expression of those genes peaked. Serpine1, Fn1, and Col1a1 expression were all significantly reduced in mice treated with either antibody (FIGS. 53A and 53B). The antibody 4A11 potently inhibited the activities of both TGFβ2 and TGFβ3 isoforms in vitro (Table 30, above). In vivo, 4A11 treatment reduced new collagen accumulation at day 24 comparably to the combination of both 6F12 and 2A10 (FIG. 53C). A dose titration of 4A11 was performed and comparable efficacy at doses of 10 mg/kg thrice or once weekly, but not at 3 mg/kg/week were observed (FIG. 53C). Pathologic examination of lungs at day 24 showed significantly attenuated disease scores and collagen accumulation in the high-dose 4A11 treated group compared to the control group (FIGS. 53D and 53E). Taken together, these data show that treatment with neutralizing antibodies to TGFβ2 and TGFβ3 can reduce lung fibrosis in vivo.

Example 17: TGFβ2 and TGFβ3 Contribute to Hepatic Fibrosis

Materials and Methods

CCl4 Model 8-10 week-old male C57BL/6J mice (Jackson West) were IP injected with 0.5 ml/kg body weight carbon tetrachloride (Sigma-Aldrich, #319961, 1:6 v/v diluted in corn oil) or corn oil (Sigma-Aldrich) three times per week for 6 weeks. Mice received anti-TGFb2/3 (4A11)-mIgG2a-LALAPG antibody or control (anti-gp120-mIgG2a-DANA) three times per week at 10 mg/kg for 6 weeks. The animals were terminated 72 hours after the final $CCl_4$ injection and whole livers and serum were collected for histological and molecular analysis.

RNA Isolation and Quantitative RT-PCR from Mouse Tissues

Whole mouse lungs (bleomycin studies) or mouse liver lobes ($CCl_4$ studies) were isolated. Tissues were processed using a gentleMACS Dissociator (Miltenyi Biotec) for tissue homogenization. RNA was extracted from the tissue homogenates using RNeasy Mini Kit (Cat #74106; Qiagen). Gene expression levels were quantified by RT-qPCR using Taqman RNA-to-CT 1-Step Kit (Cat #4392938; Applied Biosystems). The reactions were run on a QuantStudio 6 Flex Real-Time PCR System (ThermoFisher). Threshold cycle values (Ct) were normalized to a house keeping gene, GAPDH (ΔCT). The relative gene expression levels were calculated by the $2^{-\Delta\Delta CT}$ method.

The following Taqman gene expression assay kits from Applied Biosystems were used:

Serpine (Mm00435858_m1)
Fn1 (Mm01256744_m1)
Col1a1 (Mm00801666_g1)
Col3a1 (Mm01254476_m1)
Tgfb1 (Mm01178820_m1)
Tgfb2 (Mm00436955_m1)
Tgfb3 (Mm00436960_m1)
Gapdh mouse (Cat #4352661).

Histological Analysis of Mouse Liver Fibrosis in the CCl4 Model

Formalin fixed samples of mouse livers were processed. For each animal, one section was stained with H&E and one section was stained with Trichorme. Lesions are scored blinded to group identities for degrees of architectural disruption and extent of fibrosis based on a previous published method (Zhao et al, 2008 Pathol Int 58, 580-588).

Results

Figure 54A:
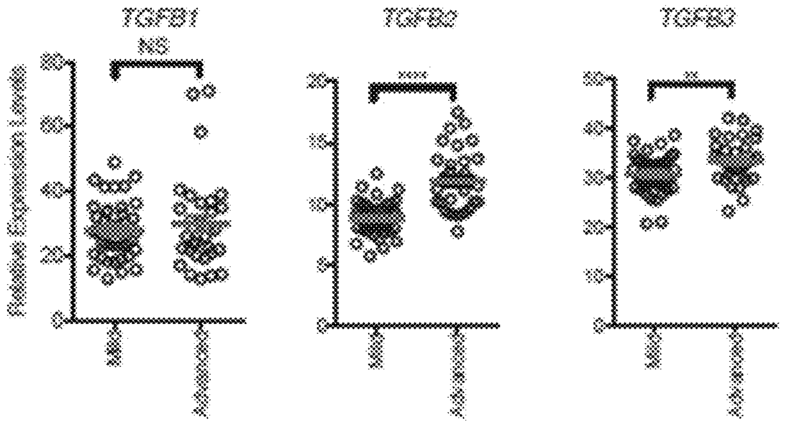
FIG. 54A contains bar graphs plotting relative gene expression levels of TGFβ isoforms in livers from NASH patients with mild fibrosis (F0 and F1) (N=40) vs. severe fibrosis (F3 and F4) (N=32).
Figure 54B:
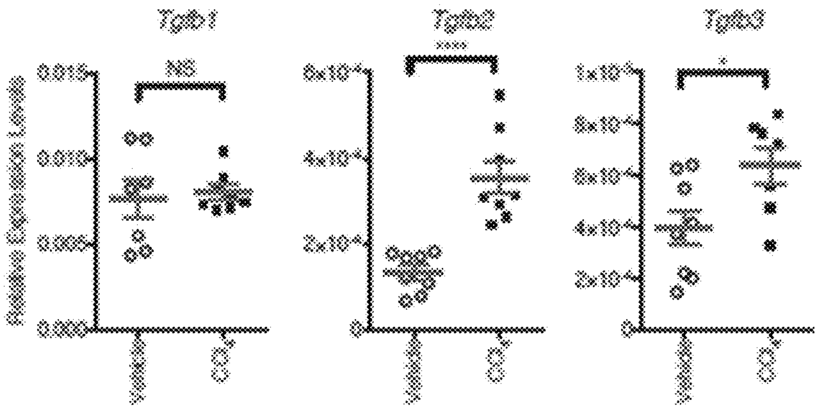
FIG. 54B contains dot plots showing relative gene expression levels of TGFβ isoforms in mouse livers as determined by quantitative RT-PCR at 6 weeks after the initiation of vehicle or $CCl_4$ treatment; n=8 for both groups.
Figure 54C:
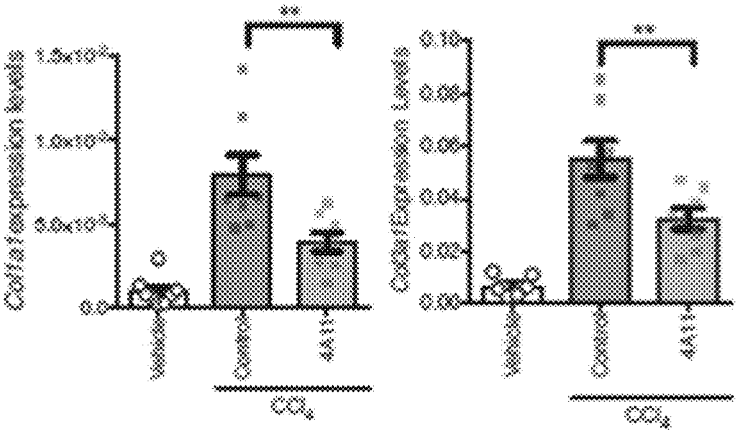
FIG. 54C contains bar graphs plotting the liver gene expression of Col1a1 and Col3a1 as determined by quantitative RT-PCR 6 weeks after the initiation of vehicle or $CCl_4$ treatment; animals were preventively treated with either isotype control or 4A11; n=8 for all groups. *, P<0.05; , P<0.01; , P<$10^{-4}$; NS, P>0.05 by unpaired two-tailed Student's t-test (A and B); P<0.01 by One-way ANOVA with Dunnett's test.
Figure 54D:
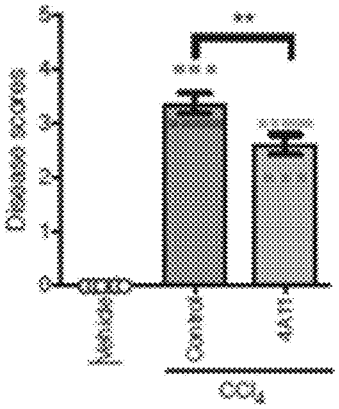
FIG. 54D is a bar graph plotting the liver pathology scores as determined by histopathological analysis; mouse livers were harvested 6 weeks after either vehicle or $CCl_4$ treatment; n=8 for all groups. *, P<0.05; , P<0.01; , P<$10^{-4}$; NS, P>0.05 by unpaired two-tailed Student's t-test (A and B); P<0.01 by One-way ANOVA with Dunnett's test.

To extend the observations of Example 16, above, beyond pulmonary fibrosis, TGFβ isoform gene expression in human NAFLD/NASH patient samples were assessed from a published dataset comparing mild to advanced fibrosis (GSE49541, (Murphy et al., 2013 Gastroenterology 145, 1076-1087; Moylan et al., 2014 Hepatology 59, 471-482)). Similar to IPF lung tissue, the expression levels of TGFB1 were comparable across disease severity, while both TGFB2 and TGFB3 were significantly increased in livers from patients with more advanced fibrosis disease (FIG. 54A). In the carbon tetracholoride ($CCl_4$)-induced liver injury and fibrosis model in mice, upregulation of Tgfb2 and Tgfb3, but not Tgfb1 expression was observed after 6 weeks of $CCl_4$ challenge (FIG. 54B). Anti-TGFβ2/3 antibody (4A11) treatment significantly attenuated collagen gene expression and histological disease scores in $CCl_4$-challenged mice (FIGS. 54C and 54D). Histological examination showed a modest reduction of fibrosis in the 4A11 treated group when compared to controls. Taken together, these data suggest that TGFβ2 and TGFβ3 inhibition can reduce hepatic fibrosis in vivo.

Example 18: TGFβ2 and TGFβ3 Blockade does not Promote the Enhanced Immune Responses Associated with Pan Anti-TGFβ Blockade in a Colitis Model Materials and Methods 8-10-week-old C57BL/6 mice (Envigo) were inoculated orally with 0.2 ml $1\times10^9$ cfu/ml *Helicobacter hepaticus* suspension for two consecutive days. Mice were treated with anti-IL10R antibody (Cat #BE0050, BioXCell) weekly at 1 mg/mouse to induce colitis. To test the effects of anti-TGFβ antibodies, mice were received pan anti-TGFβ (1D11), anti-TGFβ2/3 (4A11) or control antibody three times per week at 10 mg/kg until the end of the study. The animals were euthanized at day 24, and mouse intestines were isolated, weighed and proceeded as indicated.

Mouse intestine lamina propria were isolated from cecums and proximal colons by following to the manufacturer's recommendation (Cat #130-097-410, Miltenyi).

Total cell numbers were determined and cells were stained with antibodies for CD3e (Cat #553064, BD Biosciences), CD4 (Cat #553729, BD Biosciences), CD8 (Cat #553036, BD Biosciences), CD11b (Cat #553312, BD Biosciences,), Ly6G (Cat #551460, BD Biosciences), Ly6C (Cat #1760-09, Southern Biotech). Data was analyzed by Flowjo software.

Figure 56A:
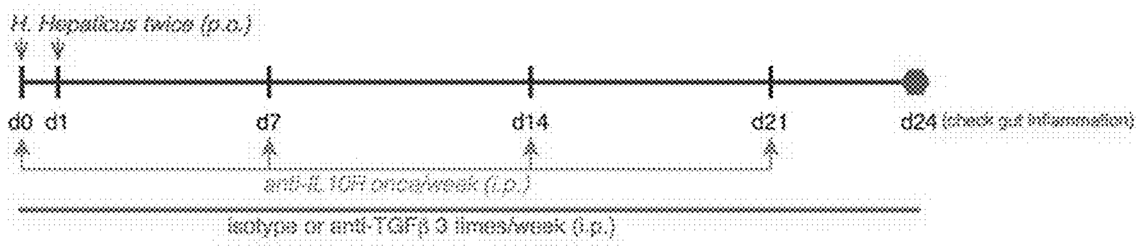
FIG. 56A is a schematic for a colitis model to assess the enhanced inflammatory responses associated with anti-TGFβ antibodies.
Figure 56B:
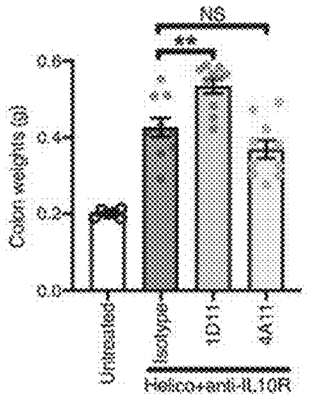
FIG. 56B provides colon weights (grams) measured at day 24 in the colitis model of FIG. 56A. N=10 for all groups except the untreated group (n=6).
Figure 56C:
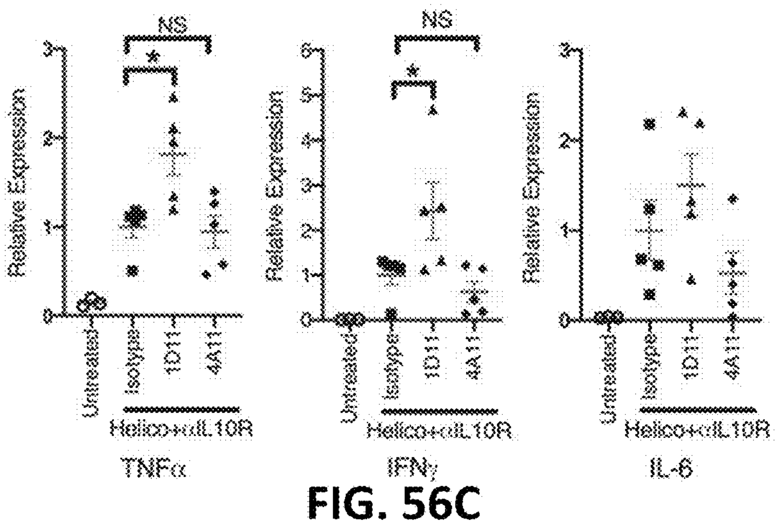
FIG. 56C provides the relative expression of inflammatory genes (analyzed from colon RNA) in the colitis model of FIG. 56A. Three to five mice from each group were analyzed as indicated.
Figure 56D:
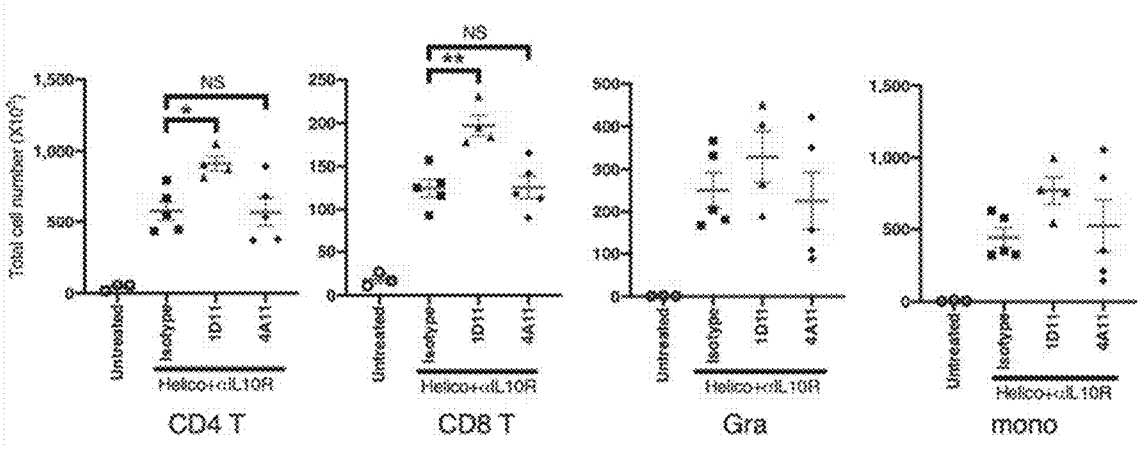
FIG. 56D summarizes the immune cell numbers in lamina propria from the remaining mice in each group (3-5/group), as determined by flow cytometry using their surface markers, in the colitis model of FIG. 56A.

FIG. 56D provides immune cell numbers in lamina propria from the remaining mice in each group (3-5/group) as determined by flow cytometry using their surface markers: T cells (CD3+; CD4+ or CD8+); Granulocytes ("Gra," CD11b+; Ly6G+); monocytes ("mono," CD11b+; Ly6C+). *P<0.05, **P<0.01, NS, P>0.05 by One-way ANOVA with Dunnett's test. Data represent means±SEM. For clarity, stats bars are not shown in graphs lacking nominally significant differences between experimental groups.

Results

TGFβ signaling plays pivotal roles in the regulation of immune responses. Previous studies with genetic or pharmacological blockade of TGFβ signaling showed excessive inflammation and leukocyte infiltration in multiple organs, resulting in serious adverse toxicities (M. J. Anderton et al., *Toxicol Pathol* 39, 916-924 (2011); M. S. Mitra et al., *Tox Sci,* 175, 24-34 (2020); J. C. Marie, et al., *Immunity* 25, 441-454 (2006); M. O. Li, et al., *Immunity* 25, 455-471 (2006). To assess the contribution of TGFβ2 and TGFβ3 blockade to systemic immune responses, *Helicobacter hepaticus* infected IL-10R blockade colitis model was employed (FIG. 56A). This model is often used to assess the involvement of dysregulated immune responses and intestinal microbiota, two major components of human inflammatory bowel diseases (IBD) (M. C. Kullberg et al., *Infection and immunity* 66, 5157-5166 (1998); M. C. Kullberg et al., *Infection and immunity* 69, 4232-4241 (2001); M. C. Kullberg et al., JEM 203, 2485-2494 (2006)). In agreement with previous findings, *H. hepaticus* infected mice treated with the anti-IL10R antibody developed colitis. Treatment with a pan-anti-TGFβ antibody (1D11) promoted increased inflammation, as evidenced by increased colon weights, inflammatory cytokine expression, and immune cell infiltration (FIGS. 56B-56D). Mice treated with the TGFβ1-sparing anti-TGFβ2/3 antibody (4A11) exhibited no increases in inflammation on those parameters. These results suggest that selective TGFβ2/3 blockade will not induce toxic inflammatory responses as observed with pan-TGFβ blockade.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated anti-TGFβ3 antibody, wherein the antibody comprises:

(i) heavy chain CDRs comprising CDR-H1, CDR-H2 and CDR-H3, wherein CDR-H1 has the amino acid sequence of SEQ ID NO: 4; CDR-H2 has the amino acid sequence of one of SEQ ID NOs: 5, 34, 35, and 159; and CDR-H3 has the amino acid sequence of SEQ ID NO: 6; and (ii) light chain CDRs comprising CDR-L1, CDR-L2 and CDR-L3, wherein CDR-L1 has the amino acid sequence of SEQ ID NO: 7; CDR-L2 has the amino acid sequence of SEQ ID NO: 8; and CDR-L3 has the amino acid sequence of SEQ ID NO: 9.

2. The isolated anti-TGFβ3 antibody of claim 1, wherein the antibody comprises a heavy chain variable region (VH) amino acid sequence having at least 95% sequence identity to an amino acid sequence selected from the group consisting of SEQ ID NOs: 23, 37, 42-53, 55 and 57.

3. The isolated anti-TGFβ3 antibody of claim 1, wherein the antibody comprises a light chain variable region (VL) amino acid sequence having at least 95% sequence identity to an amino acid sequence selected from the group consisting of SEQ ID NOs: 22, 36, 38-41, 54, and 56.

4. The isolated anti-TGFβ3 antibody of claim 1, wherein the antibody comprises a heavy (H) chain and a light (L) chain, wherein the heavy chain and the light chain comprise amino acid sequences (respectively) selected from the group consisting of SEQ ID NOs: 29/28 (rat 2A10), SEQ ID NOs: 59/58 (v1), SEQ ID NOs: 59/60 (v1.1), SEQ ID NOs: 59/61 (v1.2), SEQ ID NOs: 59/62 (v1.3), SEQ ID NOs: 59/63 (v1.4), SEQ ID NOs: 64/58 (v1.5), SEQ ID NOs: 65/58 (v1.6), SEQ ID NOs: 66/58 (v1.7), SEQ ID NOs: 67/58 (v2), SEQ ID NOs: 67/60 (v2.1), SEQ ID NOs: 67/61 (v2.2), SEQ ID NOs: 67/62 (v2.3), SEQ ID NOs: 67/63 (v2.4), SEQ ID NOs: 68/58 (v2.5), SEQ ID NOs: 69/58 (v2.6), SEQ ID NOs: 70/58 (v2.7), SEQ ID NOs: 71/58 (v2.8), SEQ ID NOs: 72/58 (v2.9), SEQ ID NOs: 73/58 (h2A10.v2.N54S), SEQ ID NOs: 74/58 (h2A10.v2.N54Q), SEQ ID NOs: 75/58 (h2A10.v2.T56A), SEQ ID NOs: 77/76 (v3), and SEQ ID NOs: 79/78 (v4).

5. A pharmaceutical formulation comprising the antibody of claim 1, and a pharmaceutically acceptable carrier.

6. An isolated anti-TGFβ3 antibody, wherein the antibody comprises a heavy chain variable region (VH) comprising (a) CDR-H1 comprising the amino acid sequence of SEQ ID NO: 4, (b) CDR-H2 comprising the amino acid sequence of SEQ ID NO: 35, and (c) CDR-H3 comprising the amino acid sequence of SEQ ID NO: 6; and a light chain variable region (VL) comprising (d) CDR-L1 comprising the amino acid sequence of SEQ ID NO: 7, (e) CDR-L2 comprising the amino acid sequence of SEQ ID NO: 8, and (f) CDR-L3 comprising the amino acid sequence of SEQ ID NO: 9.

7. The isolated anti-TGFβ3 antibody of claim 6, wherein (a) the heavy chain variable region (VH) of the antibody has at least 95% sequence identity to the amino acid sequence of SEQ ID NO: 57, and (b) the light chain variable region (VL) of the antibody has at least 95% sequence identity to the amino acid sequence of SEQ ID NO: 56; or wherein the antibody comprises (c) a heavy (H) chain having at least 95% sequence identity to the amino acid sequence of SEQ ID NO: 79, and (d) the antibody comprises a light (L) chain having at least 95% sequence identity to the amino acid sequence of SEQ ID NO: 78.

8. The isolated anti-TGFβ3 antibody of claim 6, wherein the antibody is a monoclonal antibody.

9. The isolated anti-TGFβ3 antibody of claim 6, wherein the antibody is an IgG1 or IgG4 isotype.

10. The isolated anti-TGFβ3 antibody of claim 6, wherein the antibody is a humanized or chimeric antibody.

11. The isolated anti-TGFβ3 antibody of claim 6, wherein the antibody is a humanized antibody.

12. The isolated anti-TGFβ3 antibody of claim 6, wherein the antibody is a full length antibody.

13. The isolated anti-TGFβ3 antibody of claim 6, wherein the antibody is a humanized monoclonal IgG1 antibody.

14. The isolated anti-TGFβ3 antibody of claim 6, wherein the antibody is an antibody fragment that binds to TGFβ3.

15. The isolated anti-TGFβ3 antibody of claim 6, wherein the antibody is an antibody fragment that binds to TGFβ3 selected from the group consisting of Fab, Fab', Fab'-SH, Fv, single-chain Fv (scFv), diabody, and $F(ab')_2$ fragments.

16. The isolated anti-TGFβ3 antibody of claim 6, wherein the antibody comprises a human Fc region that comprises a modification to remove a glycosylation site at amino acid residue position N297 (EU numbering as in Kabat) and wherein the modification is a mutation N297G.

17. A pharmaceutical formulation comprising the antibody of claim 6, and a pharmaceutically acceptable carrier.

18. An isolated anti-TGFβ3 antibody, wherein the antibody comprises (a) a heavy chain variable region (VH) comprising the amino acid sequence of SEQ ID NO: 57; and (b) a light chain variable region (VL) comprising the amino acid sequence of SEQ ID NO: 56.

19. The isolated anti-TGFβ3 antibody of claim 18, wherein the antibody is a monoclonal antibody.

20. The isolated anti-TGFβ3 antibody of claim 18, wherein the antibody is an IgG1 isotype.

21. The isolated anti-TGFβ3 antibody of claim 18, wherein the antibody is a full length antibody.

22. The isolated anti-TGFβ3 antibody of claim 18, wherein the antibody is a humanized monoclonal IgG1 antibody.

23. The isolated anti-TGFβ3 antibody of claim 18, wherein the antibody is an antibody fragment that binds to TGFβ3 selected from the group consisting of Fab, Fab', Fab'-SH, Fv, single-chain Fv (scFv), diabody, and $F(ab')_2$ fragments.

24. The isolated anti-TGFβ3 antibody of claim 18, wherein the antibody comprises a human Fc region that comprises a modification to remove a glycosylation site at amino acid residue position N297 (EU numbering as in Kabat) and wherein the modification is a mutation N297G.

25. A pharmaceutical formulation comprising the antibody of claim 18, and a pharmaceutically acceptable carrier.

26. An isolated monoclonal anti-TGFβ3 antibody, wherein the antibody comprises a heavy (H) chain comprising the amino acid sequence of SEQ ID NO: 79 and a light (L) chain comprising the amino acid sequence of SEQ ID NO: 78.

27. A pharmaceutical formulation comprising the antibody of claim 26, and a pharmaceutically acceptable carrier.

* * * * *